US007273605B2

(12) United States Patent
Laidlaw et al.

(10) Patent No.: US 7,273,605 B2

(45) Date of Patent: Sep. 25, 2007

(54) VACCINE

(75) Inventors: Stephen Laidlaw, Grove Wantage (GB); Mike Skinner, Wantage (GB); Adrian V. S. Hill, Oxford (GB); Sarah C. Gilbert, Horspath (GB); Richard Anderson, Headington (GB)

(73) Assignee: Isis Innovation Limited, Oxford (GB)

( * ) Notice: Subject to any disclaimer, the term of this patent is extended or adjusted under 35 U.S.C. 154(b) by 0 days.

(21) Appl. No.: 10/856,118

(22) Filed: May 27, 2004

(65) Prior Publication Data

US 2005/0025747 A1 Feb. 3, 2005

Related U.S. Application Data

(63) Continuation of application No. PCT/GB02/05411, filed on Dec. 2, 2002.

(60) Provisional application No. 60/334,649, filed on Nov. 30, 2001.

(30) Foreign Application Priority Data

Nov. 30, 2001 (GB) ................................ 0128733.3

(51) Int. Cl.

*A61K 48/00* (2006.01)
*A61K 39/02* (2006.01)
*A61K 39/12* (2006.01)
*A61K 39/275* (2006.01)
*A61K 39/015* (2006.01)
*A01N 63/00* (2006.01)
*C12N 15/863* (2006.01)
*C12N 15/00* (2006.01)
*C12N 15/09* (2006.01)

(52) U.S. Cl. ............... 424/93.2; 424/190.1; 424/199.1; 424/232.1; 424/272.1; 424/93.3; 424/184.1; 435/456; 435/69.3; 435/320.1; 435/455

(58) Field of Classification Search ................ 424/93.2
See application file for complete search history.

(56) References Cited

U.S. PATENT DOCUMENTS

| | | | |
|---|---|---|---|
| 4,053,582 | A | 10/1977 | Stickl |
| 4,748,019 | A | 5/1988 | Lysons |
| 5,110,587 | A | 5/1992 | Paoletti et al. |
| 5,185,146 | A | 2/1993 | Altenburger |
| 5,225,336 | A | 7/1993 | Paoletti |
| 5,453,364 | A | 9/1995 | Paoletti |
| 5,462,734 | A | 10/1995 | Letchworth, III et al. |
| 5,766,597 | A | 6/1998 | Paoletti et al. |
| 5,846,546 | A | 12/1998 | Hurwitz et al. |
| 6,103,244 | A | 8/2000 | Dorner et al. |
| 6,663,871 | B1 | 12/2003 | McMichael et al. |
| 2003/0138454 | A1 | 7/2003 | Hill et al. |
| 2004/0018177 | A1 | 1/2004 | Hill et al. |
| 2004/0131594 | A1 | 7/2004 | McMichael et al. |
| 2004/0175365 | A1 | 9/2004 | McMichael et al. |
| 2004/0191272 | A1 | 9/2004 | McMichael et al. |
| 2004/0197349 | A1 | 10/2004 | McMichael et al. |
| 2004/0213799 | A1 | 10/2004 | McMichael et al. |
| 2005/0175627 | A1 | 8/2005 | Schneider |

FOREIGN PATENT DOCUMENTS

| | | | |
|---|---|---|---|
| EP | 0 638 316 | A1 | 2/1995 |
| EP | 0 753 581 | A1 | 1/1997 |
| EP | 0517292 | B1 | 2/2000 |
| WO | WO92/22641 | A1 | 12/1992 |
| WO | WO93/03145 | | 2/1993 |
| WO | WO96/26271 | | 8/1996 |
| WO | WO97/39771 | A1 | 10/1997 |
| WO | WO98/04728 | A1 | 2/1998 |
| WO | WO98/56919 | A2 | 12/1998 |
| WO | WO9856919 | A2 * | 12/1998 |
| WO | WO 01/02607 | A1 | 1/2001 |
| WO | WO 01/14416 | A2 | 3/2001 |
| WO | WO 01/85932 | A2 | 11/2001 |
| WO | WO 01/85932 | A3 | 11/2001 |
| WO | WO 02/068654 | A2 | 9/2002 |
| WO | WO 02/068654 | A3 | 9/2002 |
| WO | WO 2005/030964 | A1 | 4/2005 |

OTHER PUBLICATIONS

Laidlaw, S.M. et al., "Comparison of the genome sequence of FP9, and attenuated, tissue culture-adapted European strain of Fowlpox virus, with those of virulent American and European viruses", 2004, J. Gen. Virol., vol. 85: pp. 305-322.*

(Continued)

*Primary Examiner*—Sumesh Kaushal
*Assistant Examiner*—Michael Burkhart
(74) *Attorney, Agent, or Firm*—Hamilton, Brook, Smith & Reynolds, P.C.

(57) ABSTRACT

The present invention relates to a fowlpox virus genome which has modifications in one or more wild-type FPV genes. The present invention also relates to a viral particle comprising such a genome and its use to deliver a nucleotide of interest (NOI) to a target cell. The present invention also relates to vaccination methods, particularly a method which comprises administering a priming composition (which comprises a first non-replicating viral vector) and a boosting composition (which comprises a second non-replicating viral vector) to a subject to treat and/or prevent a disease.

20 Claims, 95 Drawing Sheets

OTHER PUBLICATIONS

Schneider, J. et al., "Induction of CD8+ T cells using heterologous prime-boost immunisation strategies", 1999, Immunological Rev., vol. 170: pp. 29-38.*

Skinner, M.A. et al., "Fowlpox virus as a recombinant vaccine vector for use in mammals and poultry", 2005, Expert Rev. Vaccines, vol. 4: pp. 63-76.*

Carvalho, L.J.M. et al., "Malaria Vaccine: Candidate Antigens, Mechanisms, Constraints and Prospects", 2002, Scand. J. Immunol., vol. 56: pp. 327-343.*

Carter, B., "Gene Therapy as Drug Development", 2000, Mol. Therapy, vol. 1: pp. 211-212.*

Holder, A. et al., "Faliciparum Malaria MSP1 Workshop Progress toward MSP1 Vaccine Development and Testing", 2000, Malaria Vaccine Initiative, pp. 1-30.*

Niewiesk, S. et al., "Measles Virus-Induced Immune Suppression in the Cotton Rat (*Sigmodon hispidus*) Model Depends on Viral Glycoproteins", 1997, J. Virol., vol. 71: pp. 7214-7219.*

Afonso, et al., NCBI Accession No. AF198100, *J. Virology 74*(8):3815-3831 (2000).

Anderson, et al., "Enhanced CD8 T Cell Response and Protective Efficacy Against Malaria Using Recombinant Fowlpox Virus In Heterologous Prime/Boost Immunisation Regimes," Abstract, *Immunology 101*(Supplement 1):32 (2000).

Hodge, James W., et al., "Diversified Prime and Boost Protocols Using Recombinant Vaccinia Virus and Recombinant Non-Replicating Avian Pox Virus to Enhance T-Cell Immunity and Antitumor Responses," *Vaccine 15*(6-7):759-768 (1997).

Tsukamoto, Kenji, et al., "Dual-Viral Vector Approach Induced Strong and Long-Lasting Protective Immunity Against Very Virulent Infectious Bursal Disease Virus," *Virology 269*(2):257-267 (2000).

Irvine, K.R., et al., "Enhancing Efficacy of Recombinant Anticancer Vaccines with Prime/Boost Regiments That Use Two Different Vectors," *J. Natl. Cancer Institute 89*(21):1595-1601 (1997).

Taylor, J. And Paoletti, E., "Fowlpox Virus As A Vector in Non-Avian Species," *Vaccine 6*:466-468 (1988).

Taylor, J., et al., "Recombinant Fowlpox Virus Inducing Protective Immunity in Non-Avian Species," *Vaccine 6*(6):497-503 (1988).

Afonso, C.L., et al., "The Genome of Fowlpox Virus," *J. Virology 74*(8):3815-3831 (2000).

Shaw, I., and Davison, T.F., "Protection From IBDV-Induced Bursal Damage By A Recombinant Fowlpox Vaccine, fpIBD1, Is Dependent ON the Titre of Challenge Virus and Chicken Genotype," *Vaccine* 18:3230-3241 (2000).

Boulanger, D., et al., "The 131-Amino-Acid Repeat Region of the Essential 39-Kilodalton Core Protein of Fowlpox Virus FP9, Equivilant to Vaccinia Virus A4L Protein, Is Nonessential and Highly Immunogenic," *J. Virol 72*(1):170-179 (1998).

Boulanger, D., et al., "Morphogenesis and Release of Fowlpox Virus," *J. of Gen. Virol. 81*:675-687 (2000).

Laidlaw, S. M., et al., "Fowlpox Virus Encodes Nonessential Homologs of Cellular Alpha-SNAP, PC-1, and an Orphan Human Homolog of a Secreted Nematode Protein," *J. Virol. 72*(8):6742-6751 (1998).

Dale, C. J., et al., "Induction of HIV-1-Specific T-Helper Responses and Type 1 Cytokine Secretion Following Therapeutic Vaccination of Macaques with A Recombinant Fowlpoxvirus Co-expressing Interferon-Gamma," *J. Med. Primatol. 29*:240-247 (2000).

Kent, S. J., et al., "Enhanced T-Cell Immunogenicity and Protective Efficacy of a Human Immunodeficiency Virus Type 1 Vaccine Regimen Consisting of Consecutive Priming with DNA and Boosting with Recombinant Fowlpox Virus," *J. Virol. 72*(12):10180-10188 (1998).

Boursnell, M. E. G., et al., "a Fowlpox Virus Vaccine Vector with Insertion Sites in the Terminal Repeats: Demonstration of its Efficacy Using the Fusion Gene of Newcastle Disease Virus," *Veterin. Microbiology 23*:305-316 (1990).

Boursnell, M. E. G., et al., "Insertion of the Fusion Gene from Newcastle Disease Virus into a Non-essential Region in the Terminal Repeats of Fowlpox Virus and Demonstration of Protective Immunity Induced by the Recombinant," *J. Gen. Virology 71*:621-628 (1990).

Boyle, D. B. And Heine, H. G., "Recombinant Fowlpox Virus Vaccines for Poultry," *Immunol and Cell Biol. 71*:391-397 (1993).

Boyle, D. B., et al., "Comparison of Field and Vaccine Strains of Australian Folwpox Viruses," *Arch Virol 142*:737-748 (1997).

Brooks, J. V., et al., "Boosting Vaccine for Tuberculosis," *Infection and Immunity 69*(4): 2714-2717 (2001).

Campbell, J. I. A., et al., "Tandem Repeated Sequences Within the Terminal Region of the Fowlpox Virus Genome," *J. Gen. Virol. 70*:145-154 (1989).

Grosenbach, D. W., et al., "Synergy of Vaccine Strategies to Amplify Antigen-specific Immune Responses and Antitumor Effects," *Cancer Res 61*:4497-4505 (2001).

Hertig, C., et al., "Field and Vaccine Strains of Fowlpox Virus Carry Integrated Sequences from the Avian Retrovirus, Reticuloendotheliosis Virus," *Virol. 235*:367-376 (1997).

Irvine, K. R., et al., "Route of Immunization and the Therapeutic Impact of Recombinant Anticancer Vaccines," *J. of the Natl. Cancer Inst. 89*(5):390-392 (1997).

Kent, S. J., et al., A Recombinant Avipoxvirus HIV-1 Vaccine Expressing Interferon-gamma is Safe and Immunogenic in Macaques, *Vaccine 18*:2250-2256 (1999).

Gilbert, S. C., et al., "A Protein Particle Vaccine Containing Multiple Malaria Epitopes," *Nature Biotechnology 15*:1280-1284 (1997).

Mahnel, et al., "Experiences with Immunization Against Orthopox Viruses of Humans and Animals Using Vaccine Strains MVA," *Berliner Und Munchener Tierarztliche Wochenschrift 107*(8):253-256 (1994) Abstract Only.

Meyer, H., et al., "Mapping of Deletions in the Genome of the Highly Attenuated Vaccinia Virus MVA and their Influence on Virulence," *J. of Gen. Virol. 72*:1031-1038 (1991).

Moss, B., "Genetically Engineered Poxviruses for Recombinant Gene Expression, Vaccination, and Safety," *Proc. Natl. Acad. Sci. USA 93*:11341-11348 (1996).

Paoletti, E., "Applications of Pox Virus Vectors to Vaccination: An Update," *Proc. Natl. Acad. Sci. USA 93*:11349-11353 (1996).

Piebanski, M., et al., "Protection from *Plasmodium berghei* Infection by Priming and Boosting T Cells to a Single Class L-restricted Epitope with Recombinant Carriers Suitable for Human Use," *Eur. J. Immunol. 28*:4345-4355 (1998).

Pollitt, E., et al., "Nucleotide Sequence of the 4.3 kbp BamHI-N Fragment of Folwpox Virus FP9," *Virus Genes 17*(1):5-9 (1998).

Qingzhong, Y., et al., "Protection Against Turkey Rhinotracheitis Pneumovirus (TRTV) Induced by a Fowlpox Virus Recombinant Expressing the TRTV Fusion Glycoprotein (F)," *Vaccine 12*(6):569-573 (1994).

Robinson, H. L., et al., "Neutralizing Antibody-independent Containment of Immunodeficiency Virus Challenges by DNA Priming and Recombinant Pox Virus Booster Immunizations," *Nature Medicine 5*(5):526-534 (1999).

Schneider, J., et al., "Enhanced Immunogenicity for CD8+ T Cell Induction and Complete Protective Efficacy of Malaria DNA Vaccination by Boosting with Modified Vaccinia Virus Ankara," *Nature Medicine 4*(4):397-402 (1998).

Somogyi, P., et al., "Fowlpox Virus Host Range Restriction: Gene Expression, DNA Replication, and Morphogenesis in Nonpermissive Mammalian Cells," *Virology 197*:439-444 (1993).

Sutter, G. and Moss, B., "Nonreplicating Vaccinia Vector Efficiently Expresses Recombinant Genes," *Proc. Natl. Acad. Sci. USA*, 89:10847-10851 (1992).

Tanghe, A., et al., "Improved Immunogenicity and Protective Efficacy of a Tuberculosis DNA Vaccine Encoding Ag85 by Protein Boosting," *Infection and Immunity 69*(5):3041-3047 (2001).

Taylor, J., et al., "Protective Immunity Against Avian Influenza Induced by Fowlpox Virus Recombinant," *Vaccine 6*:504-508 (1988).

Wang, M., et al., "Active Immunotherapy of Cancer with a Nonreplicating Recombinant Folwpox Virus Encoding a Model Tumor-Associated Antigen," *J. Immunol. 154*:4685-4692 (1995).

Coupar, B.E.H., et al., "Restriction Endonuclease Mapping of the Fowlpox Virus Genome," *Virology 179*:159-167 (1990).
Mayr, A., et al., "Attenuierung von virulentem Hühnerpockenvirus in Zellkulturen und Eigenschaften des attenuierten Virus," *Zbl Vet Med B* B13, 1-13 (1966).
Ada, G., "Do Cytotoxic T Lymphocytes Clear Some HIV/SIV Infections?," *J. Med. Primatol. 25*(3):158-162 (1996).
Aidoo, M., et al., "Recombinant Vaccinia Viruses for the Characterization of *Plasmodium falciparum*-specific Cytotoxic T Lymphocytes: Recognition of Processed Antigen Despite Limited Re-Stimulation Efficacy," *Intl. Immunol. 9*(5):731-737 (1997).
Aidoo, M., et al., "Identification of Conserved Antigenic Components For a Cytotoxic T Lymphocyte-Inducing Vaccine Against Malaria," *Lancet 345*(8956):1003-1007 (1995).
Allsopp, C.E.M., et al., "Comparison of Numerous Delivery Systems for the Induction of Cytotoxic T Lymphocytes by Immunization," *Eur. J. Immunol. 26*:1951-1959 (1996).
Berkner, K.L., "Development of Adenovirus Vectors for the Expression of Heterologous Genes," *BioTechniques 6*(7): 616-629 (1988).
Blanchard, T.J. et al., "Modified Vaccinia Virus Ankara Undergoes Limited Replication in Human Cells and Lacks Several Immunomodulatory Proteins: Implications for Use as a Human Vaccine," *J. Gen. Virol. 79*:1159-1167 (1998).
Blanchard, T., et al., "Future Vaccines for HIV," *Lancet 348*(9043):1741 (1996).
Brossart, P., et al, "Virus-Mediated Delivery of Antigenic Epitopes into Dendritic Cells as Means to Induce CTL," *J. Immunol. 158*:3270-3276 (1997).
Buge, S.L., et al., "Factors Associated with Slow Disease Progression in Macaques Immunized with an Adenovirus-Simian Immunodeficiency Virus (SIV) Envelope Priming-gp120 Boosting Regimen and Challenged Vaginally with SIVmac251," *J. Virol. 73*(9):7430-7440 (1999).
Carroll, M.W., et al., "Highly Attenuated Modified Vaccinia Virus Ankara (MVA) as an Effective Recombinant Vector: A Murine Tumor Model," *Vaccine 15*(4):387-394 (1997).
Castelli, C., et al. "Mass Spectrometric Identification of a Naturally Processed Melanoma Peptide Recognized by $CD8^+$ Cytotoxic T Lymphocytes," *J. Exp. Med. 181*:363-368 (1995).
Conry, R.M., et al., "Safety and Immunogenicity of a DNA Vaccine Encoding Carcinoembryonic Antigen and Hepatitis B Surface Antigen in Colorectral Carcinoma Patients," *Clin. Cancer Res. 8*:2782-2787 (2002).
Davis, H.L., et al., "DNA-Mediated Immunization to Hepatitis B Surface Antigen: Longevity of Primary Response and Effect of Boost," *Vaccine 14*(9):910-915 (1996).
Denis, O., et al., "Vaccination with Plasmid DNA Encoding Mycobacterial Antigen 85A Stimulates a $CD4^+$ and $CD8^+$ T-Cell Epitopic Repertoire Broader than that Stimulated by *Mycobacterium tuberculosis* H37Rv Infection," *Infect. Immun. 66*(4):1527-1533 (1998).
Doolan, D.L. et al., "Circumventing Genetic Restriction of Protection against Malaria with Multigene DNA Immunization: $CD8^+$ T Cell-, Interferon γ-, and Nitric Oxide-Dependent Immunity," *J. Exp. Med. 183*(4):1739-1746 (1996).
Doolan, D.L. and Hoffman, S.L., "The Complexity of Protective Immunity Against Liver-Stage Malaria," *J. Immunol. 165*(3):1453-1462 (2000).
Drexler, I., et al., "Highly Attenuated Modified Vaccinia Virus Ankara Replicates in Baby Hamster Kidney Cells, a Potential Host for Virus Propagation, but not in Various Human Transformed and Primary Cells," *J. Gen. Virol. 79*:347-352 (1998).
Egan, M.A., et al., "Induction of Human Immunodeficiency VirusType 1 (HIV-1)-Specific Cytolytic T Lymphocyte Responses in Seronegative Adults by a Nonreplicating, Host-Range-Restricted Canarypox Vector (ALVAC) Carrying the HIV-$1_{MN}$env Gene," *J. Infectious Diseases 171*:1623-1627.
E-mail dated Jan. 5, 2006 from American Society for Microbiology re: Date of Disclosure of Buge's Document.
Franchini, G., et al., "Highly Attenuated HIV Type 2 Recombinant Poxviruses, but not HIB-2 Recombinant *Salmonella* Vaccines, Induce Long-lasting Protection in *Rhesus macaques*," *AIDS Res. Hum. Retroviruses 11*(8):909-920 (1995).
Fuller, D.H., et al., "Enhancement of Immunodeficiency Virus-Specific Immune Responses in DNA-immunized *Rhesus macaques*," *Vaccine 15*(8):924-926 (1997).
Fuller, D.H., et al., "Gene Gun-Based Nucleic Acid Immunization Alone or in Combination with Recombinant Vaccinia Vectors Suppresses Virus Burden in *Rhesus macaques* Challenged with a Heterologous SIV," *Immunol. Cell Biol. 75*(4):389-396 (1997).
Gallimore, A., et al., "Early Suppression of SIV Replication by $CD8^+$ *nef*-specific Cytotoxic T Cells in Vaccinated Macaques," *Nature Med. 1*(11):1167-1173 (1995).
Greenspan, N.S. and DiCera, E., "Defining Epitopes: It's not as Easy as it Seems," *Nature Biotechnol. 17*:936-937 (1999).
Hanke, T., et al., "Immunogenicities of Intravenous and Intramuscular Administrations of Modified Vaccinia Virus Ankara-based Multi-CTL Epitope Vaccine for Human Immunodeficiency Virus Type 1 in Mice," *J. Gen. Virol. 79*:83-90 (1998).
Hanke, T., et al., "DNA Multi-CTL Epitope Vaccines for HIV and *Plasmodium falciparum*: Immunogenicity in Mice," *Vaccine 16*(4):426-435 (1998).
Hanke, T., et al., "Enhancement of MHC Class I-Restricted Peptide-Specific T Cell Induction by a DNA Prime-MVA Boost Vaccination Regime," *Vaccine 16*(5):439-445 (1998).
Hill, A.V.S., et al., "Common West African HLA Antigens are Associated with Protection from Severe Malaria," *Nature 352*(6336):595-600 (1991).
Hill, A.V.S., et al., "DNA-Based Vaccines for Malaria: a Heterologous Prime-Boost Immunisation Strategy," *Dev. Biol. 104*:171-179 (2000).
Hirsch, V.M., et al., "Patterns of Viral Replication Correlate with Outcome in Simian Immunodeficiency Virus (SIV)-Infected Macaques: Effect of Prior Immunization with a Trivalent SIV Vaccine in Modified Vaccinia Virus Ankara," *J. Virol. 70*(60):3741-3752 (1996).
HIV CTL Epitopes Table 2 p24. [online], Dec. 1996. Retrieved from the Internet <URL:http://hiv-web.lanl.gov/content/immunology/pdf/1996/CTL/TABLES/p24.pdf>.
HIV CTL Epitopes Table 3: p24 [online], Dec. 1999. Retrieved from the Internet <URL:http://hiv-web.lanl.gov/content/immunology/pdf/1999/1/tables/p24.pdf>.
HIV CTL Epitopes Table 4: POL [online], Dec. 1997. Retrieved from the Internet <URL:http://hiv-web.lanl.gov/content/hiv-db/immunology/PDF/1997/CTL/tables/pol.pdf>.
HIV CTL Epitopes Table 6 gp120. [online], Dec. 1996. Retrieved from the Internet <URL:http://hiv-web-lanl.gov/content/immunology/pdf/1996/CTL/TABLES/gp120.pdf>.
HIV CTL Epitopes Table 7 gp41. [online], Dec. 1996. Retrieved from the Internet <URL:http://hiv-web.lanl.gov/content/immunology/pdf/1996/CTL/TABLES/gp41.pdf>.
HIV CTL Epitopes Table 8 Nef. [online], Dec. 1996. Retrieved from the Internet <URL:http://hiv-web.lanl.gov/content/immunology/pdf/1996/CTL/TABLES/nef.pdf>.
Huygen, K., et al., "Immunogenicity and Protective Efficacy of a Tuberculosis DNA Vaccine," *Nat. Med. 2*(8): 893-898 (1996).
Irvine, K., et al., "Comparison of a CEA-Recombinant Vaccinia Virus, Purified CEA, and an Anti-Idiotype Antibody Bearing the Image of a CEA Epitope in the Treatment and Prevention of CEA-Expressing Tumors," *Vaccine Res. 2*(2):79-94 (1993).
Johnson, R.P., et al., "Induction of a Major Histocompatibility Complex Class I-Restricted Cytotoxic T-Lymphocyte Response to a Highly Conserved Region of Human Immunodeficiency Virus Type 1 (HIV-1) gp120 in Seronegative Humans Immunized with a Candidate HIV-1 Vaccine," *J. Virol. 68*(5):3145-3153 (1994).
Kent, S.J., et al., "Analysis of Cytotoxic T Lymphocyte Responses to SIV Proteins in SIV-Infected Macaques Using Antigen-Specific Stimulation with Recombinant Vaccinia and Fowl Poxviruses," *AIDS Res. Hum. Retroviruses 10*(5):551-560 (1994).
Lalvani, A., et al., "An HLA-based Approach to the Design of a CTL-Inducing Vaccine Against *Plasmodium falciparum*," *Res. Immunol. 145*(6):461-468 (1994).
Lanar, D.E., et al., "Attenuated Vaccinia Virus-Circumsporozoite Protein Recombinants Confer Protection against Rodent Malaria," *Infec. Immun. 64*(5):1666-1671 (1996).

Layton, G.T., et al., "Induction of Single and Dual Cytotoxic T-Lymphocyte Responses to Viral Proteins in Mice Using Recombinant Hybrid Ty-Virus-Like Particles," *Immunology 87*(2):171-178 (1996).
Leong, K.H., et al., "Selective Induction of Immune Responses by Cytokines Coexpressed in Recombinant Fowlpox Virus," *J. Virol. 68*(12):8125-8130 (1994).
Leong, K.H., et al., "Generation of Enhanced Immune Responses by Consecutive Immunization with DNA and Recombinant Fowl Pox Vectors," *Vaccines 95*:327-331 (1995).
Li, S., et al., "Priming with Recombinant Influenza Virus Followed by Administration of Recombinant Vaccinia Virus Induces $CD8^+$ T-Cell-Mediated Protective Immunity against Malaria," *Proc. Natl. Acad. Sci. USA 90*(11):5214-5218 (1993).
Limbach, K.J. and Paoletti, E., "Non-Replicating Expression Vectors: Application in Vaccine Development and Gene Therapy," *Epidemiol. Infect. 116*:241-256 (1996).
McShane, H., et al., "Enhanced Immunogenicity of $CD4^+$ T-Cell Responses and Protective Efficacy of a DNA-Modified Vaccinia Virus Ankara Prime-Boost Vaccination Regimen for Murine Tuberculosis," *Infect. Imm. 69*(2):681-686 (2001).
Moorthy, M.S., et al., "Safety of DNA and Modified Vaccina Virus Ankara Vaccines Against Liver-Stage *P. falciparum* Malaria in Non-Immune Volunteers," *Vaccine 21*(17-18):1995-2002 (2003).
Moorthy, V. and Hill, A.V.S., "Malaria Vaccines," *Br. Med. Bull. 62*:59-72 (2002).
Pialoux, G., et al., "A Prime-Boost Approach to HIV Preventive Vaccine Using a Recombinant Canarypox Virus Expressing Glycoprotein 160 (MN) Followed by a Recombinant Glycoprotein 160(MN/LAI)," *AIDS Res. Hum. Retroviruses 11*(3):373-381 (1995).
Ramarathinam, L., et al., "Multiple Lineages of Tumors Express a Common Tumor Antigen, P1A, but they are not Cross-protected," *J. Immunol. 155*: 5323-5329 (1995).
Reece, W.H.H., et al., "A DNA/MVA Prime-Boost Vaccination Regime Induces Strong Immune Responses and Partial Protection Against *Plasmodium falciparum* in Humans," *Poster at the British Society for Immunology* (Dec. 2001).
Richmond, J.F.L., et al., "Screening of HIV-1 Env Glycoproteins for the Ability to Raise Neutralizing Antibody Using DNA Immunization and Recombinant Vaccinia Virus Boosting," *Virology 230*:265-274 (1997).
Rimoldi, D., et al., "Efficient Simulataneous Presentation of NY-ESO-1/LAGE-1 Primary and Nonprimary Open Reading Frame-Derived CTL Epitopes in Melanoma," *J. Immunol. 165*:7253-7261 (2000).
Robert-Guroff, M., et al., "Vaccine Protection Against a Heterologous, Non-Syncytium-Inducing, Primary Human Immunodeficiency Virus," *J. Virol. 72*(12):10275-10280 (1998).
Rodrigues, E.G., et al., "Single Immunizing Dose of Recombinant Adenovirus Efficiently Induces $CD8^+$ T Cell-Mediated Protective Immunity Against Malaris," *J. Immunol. 158*(3):1268-1274 (1997).
Rodrigues, M., et al., "Influenza and Vaccinia Viruses Expressing Malaria $CD8^+$T and B Cell Epitopes," *J. Immunol. 153*(10):4636-4648 (1994).
Rodriguez, D., et al., "Regulated Expression of Nuclear Genes by T3 RNA Polymerase and lac Repressor, Using Recombinant Vaccinia Virus Vectors," *J. Virol. 64*(10):4851-4857 (1990).
Schneider, J., et al., "A Prime-Boost Immunisation Regimen Using DNA Followed By Recombinant Modified Vaccinia Virus Ankara Induces Strong Cellular Immune Responses Against the *Plasmodium falciparum* TRAP Antigen in Chimpanzees," *Vaccine 19*(32):4595-4602 (2001).
Schödel, F., et al., "Immunity to Malaria Elicited by Hybrid Hepatitis B Virus Core Particles Carrying Circumsporozoite Protein Epitopes," *J. Exp. Med. 180*(3):1037-1046 (1994).
Sedegah, M., et al., "Protection against Malaria by Immunization with Plasmid DNA Encoding Circumsporozoite Protein," *Proc. Natl. Acad. Sci. USA 91*(21):9866-9870 (1994).
Seguin, M.C., et al., "Induction of Nitric Oxide Synthase Protects against Malaria in Mice Exposed to Irradiated *Plasmodium berghei* Infected Mosquitoes: Involvement of Interferon $\gamma$ and $CD8^+$ T Cells," *J. Exp. MEd. 180*(1):353-358 (1994).
Sequence Alignment of SEQ ID No. 4 with Geneseq database ID No. AAR43245 from WO 93/201103-A. Entry date: May 1994 Inventor: Elvin, et al.
Sequence Alignment of SEQ ID No. 2 with Geneseq database ID No. AAR43244 from WO 93/201103-A. Entry date: May 1994 Inventor: Elvin, et al.
Sequence Alignment of SEQ ID No. 6 with Geneseq database ID No. AAR43243 from WO 93/201103-A. Entry date: May 1994 Inventor: Elvin, et al.
Shah, K.V. and Howley, P.M., "Papillomaviruses." In *Fields Virology*, B.N. Fields, et al., eds. (PA: Lippincott-Raven Publishers) pp. 2077-2109 (1996).
Stoute, J.A., et al., "A Preliminary Evaluation of a Recombinant Circumsporozoite Protein Vaccine Against *Plasmodium falciparum* Malaria," *N. Engl. J. Med. 336*(2):86-91 (1997).
Tsang, K.Y, et al., "Generation of Human Cytotoxic T Cells Specific for Human Carcinoembryonic Antigen Epitopes from Patients Immunized with Recombinant Vaccinia-CEA Vaccine," *J. Natl. Cancer Inst. 87*(13):982-990 (1995).
Tsuji, M., et al., "CD4+ Cytolytic T Cell Clone Confers Protection Against Murine Malaria," *J. Exp. Med. 172*(5):1353-1357 (1990).
Walker, B.D., et al., "Long-term Culture and Fine Specificity of Human Cytotoxic T-Lymphocyte Clones Reactive with Human Immunodeficiency Virus Type 1," *Proc. Natl. Acad. Sci. USA 86*:9514-9518 (1989).
Wang, R., et al., "Induction of $CD4^+$ T Cell-Dependent $CD8^+$ Type 1 Responses in Humans by a Malaria DNA Vaccine," *Proc. Natl. Acad. Sci. USA 98*(19):10817-10822 (2001).
Watson, J.C. and Peter, G., "General Immunization Practices," in *Vaccines*, Plotkin, S.A. and Orenstein, eds., (W.B. Saunders) pp. 47-73 (1999).
Wizel, B., et al., "Irradiated Sporozoite Vaccine Induces HLA-B8-restricted Cytotoxic T Lymphocyte Responses against Two Overlapping Epitopes of the *Plasmodium falciparum* Sporozoite Surface Protein 2," *J. Exp. Med. 182*(5):1435-1445 (1995).
Xiang, Z.Q., et al., "Induction of Genital Immunity by DNA Priming and Intranasal Booster Immunization with a Replication-Defective Adenoviral Recombinant," *J. Immunol. 162*:6716-6723 (1999).
Zhu, X., et al., "Functions and Specificity of T Cells Following Nucleic Acid Vaccination of Mice Against *Mycobacterium tuberculosis* Infection," *J. Immunol. 158*:5921-5926 (1997).
Zorn, E. and Hercend, T., "A Natural Cytotoxic T Cell Response in a Spontaneously Regressing Human Melanoma Targets a Neoantigen Resulting from a Somatic Point Mutation," *Eur. J. Immunol. 29*:592-601 (1999).
Ahlers, J.D. et al., "Cytokine-in-Adjuvant Steering of the Immune Response Phenotype to HIV-1 Vaccine Constructs," *The Journal of Immunology*, 158(8):3947-3958 (1997).
"AIDS Vaccine Trials Dangerous," Isis News No. 11/12, Ho, M., ed., *Institute of Science in Society* [online], Oct. 2001. Retrieved from the Internet, [retrieved on 2006.
Allen, T.M. and Watkins, D.I., SIV and SHIV CTL Epitopes Identified in Macaques [online], Dec. 1998: Retrieved from the Internet <URL:http://hiv-web.lanl.gov/content/hiv-db/COMPENDIUM/1998/III/Allen98.pdf>.
Altman, J.D., and Feinberg, M.B., "HIV Escape: There and Back Again," *Nature Med. 10*(3): 229-230 (2004).
An, L.-L., and Whitton, J.L., "A Multivalent Minigene Vaccine, Containing B-Cell, Cytotoxic T-Lymphocyte, and $T_h$ Epitopes from Several Microbes, Induces Appropriate Responses In Vivo and Confers Protection against More than One Pathogen," *Journal of Virology*, 71(3): 2292-2302 (1997).
Austyn, J.M. and Wood, K.J., "An Overview of Immune Responses," In *Principles of Cellular and Molecular Immunology*, (NY: Oxford University Press Inc.), pp. 42-44 (1993).
Bakker, A.B.H., et al., "Identification of a Novel Peptide Derived from the Melanocyte-Specific GP100 Antigen as the Dominant Epitope Recognized by an HLA-A2.1-Restricted Anti-Melanoma CTL Line," *Int. J. Cancer*, 62: 97-102 (1995).
Bergmann, C.C., et al., "Flanking Residues Alter Antigenicity and Immunogenicity of Multi-Unit CTL Epitopes," *The Journal of Immunology*, 157(8): 3242-3249 (1996).

Bukowski, J.F., et al., "Natural Killer Cell Depletion Enhances Virus Synthesis and Virus-Induced Hepatitis In Vivo," *The Journal of Immunology*, 131(3): 1531-1538 (1983).
Casares, N., et al., "$CD4^+/CD25^+$ Regulatory Cells Inhibit Activation of Tumor-Primed $CD4^+$ T Cells with IFN-γ-Dependent Antiangiogenic Activity, as well as Long-Lasting Tumor Immunity Elicited By Peptide Vaccination," *The Journal of Immunology*, 171(11): 5931-5939 (2003).
Chamberlain, R.S., Poster Presentation presented at the Meeting of the American Association of Cancer Research, Apr. 20 through Apr. 24, 1996.
Cox, W.I., et al., Induction of Cytotoxic T Lymphocytes by Recombinant Canarypox (ALVAC) and Attenuated Vaccinia (NYVAC) Viruses Expressing the HIV-1 Envelope Glycoprotein, *Virology*, 195: 845-850 (1993).
Desrosiers, R.C., "Prospects for an AIDS Vaccine," *Nature Med. 10*(3):221-223 (2004).
Egan, M.A., et al., "Use of Major Histocompatibility Complex Class I/Peptide/β2M Tetramers To Quantitate $CD8^+$ Cytotoxic T Lymphocytes Specific for Dominant and Nondominant Viral Epitopes in Simian-Human Immunodeficiency Virus-Infected Rhesus Monkeys," *Journal of Virology*, 73(7): 5466-5472 (1999).
Eisenlohr, L.C., et al., "Flanking Sequences Influence the Presentation of an Edogenously Sythesized Peptide to Cytotoxic T Lymphocytes," *The Journal of Experimental Medicine*, 175: 481-487 (1992).
'Epitope Maps', HIV Molecular Immunology Database, [online] [Retrieved from the Internet on Jun. 23, 2003]. <URL:http://hiv-web.lanl.gov/content/immunology/maps/maps.html.>.
Fang, Z.-Y., et al., "Expression of Vaccina E3L and K3L Genes by a Novel Recombinant Canarypox HIV Vaccine Vector Enhances HIV-1 Pseudovirion Production and Inhibits Apoptosis in Human Cells," *Virology 291*:272-284 (2001).
Feng, C.G., et al., "Induction of $CD8^+$ T-lymphocyte Responses to a Secreted Antigen of *Mycobacterium Tuberculosis* by an Attenuated Vaccinia Virus," *Immunol. Cell Biol. 79*:569-575 (2001).
Friedrich, T.C., et al., "Reversion of CTL Escape—Variant Immunodeficiency Viruses in vivo," *Nature Med. 10*(3):275-281 (2004).
Gherardi, M.M., et al., "Prime Boost Immunization Schedules Based on Influenza Virus and Vaccinia Virus Vectors Potentiate Cellular Immune Responses Against Human Immunodeficiency Virus Env Protein Systemically and in the Genitorectal Draining Lymph Nodes," *The Journal of Virology*, 77(12): 7048-7057 (2003).
Gilbert, S.C., et al., "DNA Immunisation of Mice with *Plasmodium berghei* Antigene: Use of Whole Antigens or Multi-epitope Strings, Boosting with Vaccinia and Protection Against Challenge," *Immunol. Lett.*, 56/1-3: 28 (1997) (From *Malaria and Other Tropical Diseases Abstracts*, 1997, Abstract No. 0.4.05.7).
Gönczöl, E., et al., "Preclinical Evaluation of an ALVAC (Canarypox)-human Cytomegalovirus Glycoprotein B Vaccine Candidate," *Vaccine*, 13(12): 1080-1085 (1995).
Hanke, T., et al., "DNA and MVA-based Multi-CTL Epitope Vaccines for HIV and *Plasmodium falciparum*: Immunogenicity in Mice and Macaques," *Immunol. Lett.*, 56/1-3:291 (1997) (From *Poster Presentations Abstracts*, 1997, Abstract No. P.4.01.22).
Hu, S.-L., "Non-Human Primate Models for AIDS Vaccine Research," *Curr. Drug Targets Infect. Disord.*, 5(2):193-201 (2005).
Hu, S.-L., et al., "Protection of Macaques Against SIV Infection by Subunit Vaccines of SIV Envelope Glycoprotein gp160," *Science*, 225: 456-459 (1992).
Hunter, C.A., "How are NK Cell Responses Regulated During Infection!," *Experimental Parasitology*, 84: 444-448 (1996).
Janeway, C.A., et al., "General Properties of Armed Effector T Cells," In *Immuno Biology*, (NY: Garland Publishing a member of the Taylor & Francis Group) p. 319 (2001).
Kazanji, M., et al., "Expression and Immunogenicity in Rats of Recombinant Adenovirus 5 DNA Plasmids and Vaccinia Virus Containing the HTLV-I, inv Gene," *Int. J. Cancer 71*:300-307 (1997).
Koziel, M.J., "The Role of Immune Responses in the Pathogenesis of Hepatitis C Virus Infection," *J. Viral Hepatitus* 4(2):31-41 (1997). Abstract only provided.
Koziel, M.J. and Walker, B.D., "Characteristics of the Intrahepatic Cytotoxic T Lymphocyte Response in Chronic Hepatitis C Virus Infection," *Spriner Seminars in Immunopathology*, 19(1):69-83 (1997). Abstract only provided.
Konishi, E., et al., "Induction of Japanese Encephalitis Virus-specific Cytotoxic T Lymphocytes in Humans by Poxvirus-based JE Vaccine Candidates," *Vaccine*, 16(8): 842-849 (1998).
Konishi, E., et al., "Poxvirus-Based Japanese Encephalitis Vaccine Candidates Induce JE Virus-Specific $CD8^+$ Cytotoxic T Lymphocytes in Mice," *Virology*, 227: 353-360 (1997).
Kuby, J., "Cell-Mediated and Humoral Effector Responses," In *Immunology*, (NY: W. H. Freeman and Company) pp. 379-412 (1997).
Leslie, A.J., et al., "HIV Evolution: CTL Escape Mutation and Reversion After Transmission," *Nature Med. 10*(3):282-289 (2004).
Letvin, N.L., "Progress Toward an HIV Vaccine," *Annu. Rev. Med. 56*:213-223 (2005).
Linnemeyer, P.A., "The Immune System—An Overview," [online] Nov. 1993 [retrieved on Apr. 12, 2006]. Retrieved from the Internet <URL:http://www.thebody.com/step/immune.html>.
Malcherek, G., et al., "Supermotifs Enable Natural Invariant Chain-derived Peptides to Interact with Many Major Histocompatibility Complex-Class II Molecules," *J. Exp. Med.*, 181: 527-536 (1995).
Martin, R.M. and Lew, A.M., "Is IgG2a a Good Th1 Marker in Mice?" *Immunology Today*, 19:49 (1998).
Müller, H.-M., et al., "Thrombospondin Related Anonymous Protein (TRAP) of *Plasmodium falciparum* Binds Specifically to Sulfated Glycoconjugates and to HepG2 Hepatoma Cells Suggesting a Role for this Molecule in Sporozoite Invasion of Hepatocytes," *EMBO J. 12*(7):2881-2889 (1993).
Narvaiza, I., et al., Intratumoral Coinjection of Two Adenoviruses, One Encoding the Chemokine IFN-γ-Inducible Protein-10 and Another Encoding IL-12, Results in Marked Antitumoral Synergy, *The Journal of Immunology*, 164(6): 3112-3122 (2000).
Natuk, R.J., et al., "Immunogenicity of Recombinant Human Adenovirus-Human Immunodeficiency Virus Vaccines in Chimpanzees," *Aids Res. Hum. Retroviruses*(9):395-404 (1993).
Ojcius, D. M., et al., "Is Antigen Processing Guided by Major Histocompatibility Complex Molecules?," *FASEB J.*, 8: 974-978 (1994).
Okuda, K., et al., "Induction of Potent Humoral and Cell-Mediated Immune Responses Following Direct Injection of DNA Encoding the HIV Type 1 env and rev Gene Products," *Aids and Research and Human Retroviruses*, 11(8): 933-943 (1995).
Picard, O., et al., "Complication of Intramuscular/Subcutaneous Immune Therapy in Severely Immune-compromised Individuals," *J. Acquir. Immune Defic. Syndr.*, 4(6):641-643 (1991).
Plebanski, M., et al., "Protection from *Plasmodium berghei* Infection by Priming to a Single CTL epitope with Vaccine Carriers that do not Require Adjuvants," *Immunol. Lett.*, 56/1-3: 425 (1997) (From *Poster Presentations Abstracts*, 1997, Abstracts, 1997, Abstract No. P.4.05.08).
Puig, M., et al., "CD4+ Immune Escape and Subsequent T-Cell Failure Following Chimpanzee Immunization Against Hepatitis C Virus," *Hepatology*, 44:736-745 (2006).
Puls, R.L. and Emery, S., "Therapeutic Vaccination against HIV: Current Progress and Future Possibilities," *Clin. Sci.*, 110(1):59-71 (2006).
Ramirez, J.C., et al., "Biology of Attenuated Modified Vaccinia Virus Ankara Recombinant Vector in Mice: Virus Fate and Activation of B- and T-Cell Immune Responses in Comparison with the Western Reserve Strain and Advantages as a Vaccine," *Journal of Virology*, 74(2): 923-933 (2000).
Reusser, P., et al., "Cytomegalovirus-Specific T-Cell Immunity in Recipients of Autologous Peripheral Blood Stem Cell or Bone Marrow Transplants," *Blood*, 89(10): 3873-3879 (1997).
Rodrigeuz, D., et al., "Regulated Expression of Nuclear Genes by T3 RNA Polymerase and lac Repressor, Using Recombinant Vaccinia Virus Vectors," *J. Virol. 64*(10):4851-4857 (1990).
Rodrigues, E.G., et al., "Efficient Induction of Protective Anti-Malaria Immunity By Recombinant Adenovirus,"*Vaccine*, 16(19):1812-1817, (1998).

Romero, P., et al., "Cloned Cytotoxic T Cells Recognize an Eptitope in the Circumsporozoite Protein and Protect Against Malaria," *Nature*, 341: 323-326 (1989).
Rothel, J.S., et al., "Sequential Nucleic Acid and Recombinant Adenovirus Vaccination Induces Host-protective Immune Responses Against *Taenia ovis* infection in Sheep," *Parasite Immunology 19*:221-227 (1997).
Schneider, J., et al., "DNA Followed by Recombinant Vaccinia Induces Cellular and Humoral Immune Responses Against a pre-erythrocytic Antigen of *Plasmodium falciparum* in Chimpanzees," *Immunol. Lett.*, 56/1-3:291 (1997) (From *Poster Presentations Abstracts*, 1997, Abstract No. P.4.01.18).
Smith, C.L., et al., "Recombinant Modified Vaccinia Ankara Primes Functionally Activated CTL Specific for a Melanoma Tumor Antigen Epitope in Melanoma Patients with a High Risk of Disease Recurrence," *Int. J. Cancer 113*:259-266 (2005).
Takada, K., et al., "Definition of an Epitope on Japanese Encephalitis Virus (JEV) Envelope Protein Recognized by JEV-specific Murine CD8+ Cytotoxic T Lymphocytes," *Arch. Virol.*, 145: 523-534 (2000).
Thompson, S.A., et al., "Recombinant Polyepitope Vaccines for the Delivery of Multiple CD8 Cytotoxic T Cell Epitopes," *J. Immunol.*, 157(2):822-826 (1996).
Tonini, T., et al., "Current Approaches to Developing a Preventative HIV Vaccine," *Curr. Opin. Investig. Drugs*, 6(2):155-162 (2005).
Vasmatzis, G., et al., "Computational Determination of Side Chain Specificity for Pockets in Class 1 MHC Molecules," *Molecular Immunology*, 33(16): 1231-1239 (1996).
Warnier, G., et al., "Induction of a Cytolytic T-cell Response in Mice with a Recombinant Adenovirus Coding for Tumor Antigen P815A" *Int. J. Cancer 67*(2):303-310 (1996). (Abstract only).
Whitton, J.L., et al., "A "String-of-Beads" Vaccine, Comprising Linked Minigenes, Confers Protection from Lethal-Dose Virus Challenge," *Journal of Virology*, 67(1): 348-352 (1993).
Wiley, J.A., et al., "Production of Interferon-γ by Influenza Hemagglutinin-Specific CD8 Effector T Cells Influences the Development of Pulmonary Immunopathology," *Am. J. Pathol. 158*(1): 119-130 (2001).
Yang, Y., et al., "Upregulation of Class 1 Major Histocompatibility Complex Antigens by Interferon γ is Necessary for T-cell-mediated Elimination of Recombinant Adenovirus-infected Hepatocytes In Vivo," *Proc. Natl. Acad. Sci. USA*, 92: 7257-7261 (1995).
Yellen-Shaw, A.J., et al., "Point Mutation Flanking a CTL Epitope Ablates In Vitro and In Vivo Recognition of a Full-Length Viral Protein," *J. Immunol.*, 158(7): 3227-3234 (1997).
Zhu, M., et al., "Specific Cytoltic T-Cell Responses to Human CEA from Patients Immunized with Recombinant Avipox-CEA Vaccine," *Clin. Cancer Res.*, 6: 24-33 (2000).
Moreno, A., et al., "Cytotoxic CD4+ T Cells From a Sporozoite-Immunized Volunteer Recognize the *Plamodium falciparum* CS Protein," *Int. Immunol. 3*(10):997-1003 (1991).
Moss, B., et al., "Host Range Restricted, Non-Relicating Vaccinia Virus Vectors as Vaccine Candidates," *Adv. Exp. Med. Biol. 397*:7-13 (1996).
Müller, H-M., et al., "Thrombospondin Related Anonymous Protein (TRAP) of *Plasmodium falciparum* Binds Specifically to Sulfated Glycoconjugates and to HepG2 Hepatoma Cells Suggesting a Role for this Molecule in Sporozoite Invasion of Hepatocytes," *EMBO J. 12*(7):2881-2889 (1993).
Murata, K., et al., "Characterization of in Vivo Primary and Secondary $CD8^+$ T Cell Responses Induced by Recombinant Influenza and Vaccinia Viruses," *Cell. Immunol. 173*(1):96-107 (1996).
Nardin, E.H. and Nussenzweig, R.S., "T Cell Responses to Pre-Erythrocytic Stages of Malaria: Role in Protection and Vaccine Development Against Pre-Erythrocytic Stages," *Annu. Rev. Immunol. 11*:687-727 (1993).
Notice of Opposition to a European Patent. Patent No. EP 1 214 416. Opponent: Transgene S.A. (English translation attached.), 2006.
Notice of Opposition to a European Patent. Patent No. EP 1 214 416 B1. Opponent: Merck & Co., Inc., 2006.
Notice Of Opposition to a European Patent. Patent No. EP 1 214 416 B1. Opponent: Crucell Halland B.V, 2006.
Ohminami, H., et al., "HLA Class I-Restricted Lysis of Leukemia Cells by a $CD8^+$ Cytotoxic T-Lymphocyte Clone Specific for WT1 Peptide," *Blood 95*(1):286-293 (2000).
Van den Eynde, B. and Van der Bruggen, P., "Peptide Database," *Cancer Immunity*, Mar. 2001, online, retrieved from the Internet on Jun. 23, 2003, <URL:http://cancerimmunity.org/peptidedatabase/tcellepitopes.htm>.
Sutter, G., et al., "A Recombinant Vector Derived from the Host Range-Restricted and Highly Attenuated MVA Strain of Vaccinia Virus Stimulates Protective Immunity in Mice to Influenza Virus," *Vaccine 12*(11):1032-1040 (1994).
Syfpeithi Database, "Find Your Motif," [online], [retrieved on Sep. 1, 2006]. Retrieved from the Internet <URL:http://www.syfpeithi.de/Scripts/MHCServer.d11/FindYourMotif.htm>.
Tartaglia, J., et al., "NYVAC: A Highly Attenuated Strain of Vaccinia Virus," *Virology 188*(1):217-232 (1992).
Tartaglia, J., et al., "Protection of Cats against Feline Leukemia Virus by Vaccination with a Canarypox Virus Recombinant, ALVAC-FL," *J. Virol. 67*(4):2370-2375 (1993).
Tascon, et al., "Vaccination Against Tuberculosis by DNA Injection," *Nature Med. 2*(8): 888-892 (1996).
The Chamberlain Declaration cited in the opposition proceedings of European Patent Application No. EP0979284, 2006.
The Gritz Declaration cited in the opposition proceedings of European Patent Application No. EP0979284, 1996.
The Schlom Declaration cited in the opposition proceedings of European Patent Application No. EP0979284, 2006.
Thomson, S.A., et al., "Delivery of Multiple CD8 Cytotoxic T Cell Epitopes by DNA Vaccination," *J. Immunol. 160*:1717-1723 (1998).
Timofeev, A.V., et al., "Immunological Basis for Protection in a Murine Model of Tick-Borne Encephalitis by a Recombinant Adenovirus Carrying the Gene Encoding the NS1 Non-Structural Protein," *J. Gen. Virol. 79*:689-695 (1998).
Timofeyev, A.V., et al., "Recombinant Adenovirus Expressing the NS1 Nonstructural Protein of Tick-Borne Encephalitis Virus: Characteristics of Immunological Basis of Antiviral Effect," *Vopr. Virusol. 42*:219-222 (1997). (English Abstract attached).

* cited by examiner

| | | | | |
|---|---|---|---|---|
| FEATURES | | | | |
| LTR | 1 | 10158 | | left ITR |
| misc_feature | 21 | 39 | | telomere resolution sequence |
| repeat_region | 230 | 3982 | c | 3753 bp repeat region |
| repeat_unit | 101431 | 101477 | | ID to FPV US 100799-100845 & 106630-106676; |
| recomb site between B22Rs FPV097 & 098 | | | | |
| LTR | 221735 | 221933 | | REV LTR partial U3 |
| LTR | 255988 | 266145 | | ITR right |
| repeat_region | 262164 | 265916 | c | 3753 bp repeat region |
| ORFs | | | | |
| misc_feature | 266107 | 266125 | c | telomere resolution sequenceFP9.000.1 |
| 1 155 c (?) No STOP. Absent from FPV US | | | | |
| FP9.002 | 4004 | 4672 | | FP9 EF1 100% |
| FP9.003 | 5137 | 5508 | c | FP9 EF2 100%, C-type lectin family |
| FP9.004 | 5762 | 6067 | | FP9 EF3 100% |
| FP9.005 | 5858 | 6226 | c | EFc family |
| FP9.006 | 6568 | 7824 | | FP9 BamHI-orf1 Q385->E, C4L/C10L-like |
| FP9.007 | 8236 | 8454 | | FP9 BamHI-orfA 100% |
| FP9.008 | 8318 | 8821 | | FP9 BamHI-orf2 100%, C-type lectin family |
| FP9.009 | 8685 | 8885 | | FP9 BamHI-orfB 100% |
| FP9.010 | 9760 | 10827 | c | Serpin family |
| FP9.011 | 10913 | 11794 | c | alpha-SNAP family |
| FP9.012 | 12674 | 13669 | c | ANK family |
| FP9.013 | 14344 | 14526 | c | (?) |
| FP9.014 | 14552 | 15865 | c | ANK family |
| FP9.015 | 16286 | 16819 | c | (?) |
| FP9.016 | 16995 | 17711 | c | (?) |
| FP9.017 | 17819 | 18556 | c | V-type Ig domain family |
| FP9.018 | 18632 | 20734 | c | ANK family |
| FP9.019 | 20816 | 21130 | c | (?) |
| FP9.020 | 21665 | 22945 | c | C4L/C10L-like |
| FP9.021 | 23036 | 23998 | | GPCR family |
| FP9.022 | 24018 | 25754 | c | ANK family |
| FP9.023 | 25835 | 27139 | c | ANK family |
| FP9.024 | 27205 | 28995 | c | ANK family |
| FP9.025 | 29098 | 29709 | c | (?) |
| FP9.026 | 30087 | 31397 | c | ANK family |
| FP9.027 | 31439 | 32434 | | GPCR family |
| FP9.028 | 32485 | 33027 | | (?) |
| FP9.029 | 33674 | 34024 | c | CGI-147 |
| FP9.030 | 34125 | 36578 | c | FP9 PC1 O90761 100% |
| FP9.031 | 36703 | 37728 | c | FP9 ANK3 100% |
| FP9.032 | 37788 | 38915 | c | FP9 DNaseII O90759 100% |
| FP9.033 | 39310 | 40173 | c | FP9 SNAP |
| FP9.034 | 40214 | 41461 | c | FP9 ANK2 |
| FP9.035 | 41645 | 42052 | c | (?) |
| FP9.036 | 42090 | 42551 | c | (?) |
| FP9.037 | 42556 | 43044 | c | (?) |
| FP9.038 | 43041 | 43478 | c | VV F2L dUTPase |
| FP9.039 | 43529 | 44056 | c | EAT/MCL-1 (BCL-2 rel) |
| FP9.040 | 44101 | 45114 | c | Serpin family |
| FP9.041 | 45196 | 45816 | c | (?) |
| FP9.042 | 45860 | 46117 | | (?) |
| FP9.043 | 45901 | 47595 | c | FP9 DNA ligase Q67480 281N->K |
| FP9.044 | 47629 | 48705 | c | Serpin family |
| FP9.046 | 48754 | 49866 | c | FP9 Q67477 beta-SDH 37LDRPM->IRIDQW |

FIG. 1A

| | | | | |
|---|---|---|---|---|
| FP9.045 | 49811 | 50032 | | (?) |
| FP9.047 | 49918 | 51756 | c | Semaphorin |
| FP9.048 | 52206 | 52991 | | GNS1/SUR4 |
| FP9.049 | 53067 | 53531 | | FP-A1 |
| FP9.050 | 53552 | 55210 | | FP-D13 |
| FP9.051 | 55242 | 56111 | | FP-D12 mRNA capping enz small subunit |
| FP9.052 | 56186 | 58099 | | NPH-I/NTP-I |
| FP9.053 | 58103 | 58780 | c | FP-D10 mutT motif |
| CDS | 59371 | 59454 | c | D9R 054 N-term remnant |
| FP9.055 | 59704 | 60531 | c | FP-(D8)/Y V-type Ig domain |
| FP9.056 | 60695 | 61180 | c | FP-D7 RPO18 |
| FP9.057 | 61167 | 63068 | c | Viral early transcription factor small subunit |
| FP9.058 | 63049 | 65424 | c | NTPase |
| FP9.059 | 66365 | 67024 | | Deoxycytidine kinase family |
| FP9.060 | 67069 | 67635 | c | CC chemokine family |
| FP9.061 | 68009 | 68398 | c | CC chemokine family, AITR-ligand |
| FP9.062 | 68494 | 69150 | c | Uracil DNA glycosylase FP-1 |
| FP9.063 | 69198 | 70400 | c | (?) |
| FP9.064 | 70572 | 71174 | | Phospholipid hydroperoxide glutathione peroxidase (selenoprotein ) |
| FP9.065 | 71178 | 71513 | | (?) |
| FP9.066 | 71722 | 71856 | c | (MSV047) |
| FP9.067 | 71972 | 72244 | c | HT motif family |
| FP9.068 | 72614 | 73015 | c | (?) |
| FP9.069 | 73089 | 73901 | c | Virion structural protein |
| FP9.070 | 74027 | 74203 | | Murine T10 gene |
| FP9.071 | 75363 | 75869 | c | (?) |
| FP9.071.1 | 75909 | 76121 | c | Conserved - DNA/pantothenate metabolism? |
| FP9.072 | 76308 | 76868 | c | beta-nerve growth factor family |
| FP9.073 | 76890 | 77414 | c | Tyrosine protein kinase (Afonso et al., IL-18bp) |
| FP9.074 | 77669 | 77983 | c | (?) |
| FP9.075 | 77987 | 78586 | c | N1R/p28 family |
| FP9.076 | 78655 | 79089 | c | beta-nerve growth factor family |
| FP9.077 | 79201 | 79578 | | Glutaredoxin |
| FP9.078 | 79551 | 80228 | | (?) |
| FP9.079 | 80222 | 80533 | c | Elongation factor (IBT-dependence) |
| FP9.080 | 80560 | 81651 | c | Transforming growth factor-beta |
| FP9.081 | 81723 | 83503 | | Metalloprotease |
| FP9.082 | 83587 | 85635 | c | fpI8R RNA helicase/NPH-II |
| FP9.083 | 85668 | 86933 | | fpI7L Virion core protein |
| FP9.084 | 86936 | 88108 | | fpI6L |
| FP9.085 | 88109 | 88354 | | fpI5L |
| FP9.086 | 88364 | 88915 | | fpTK thymidine kinase |
| FP9.087 | 88992 | 89267 | | FP9 11.2k, HT motif family |
| FP9.088 | 89300 | 90172 | | fpI3L DNA-binding phosphoprotein |
| FP9.089 | 90173 | 90370 | | fpI2L |
| FP9.090 | 90377 | 91312 | | FPI1L O72898 277L->Y,278C->S |
| FP9.091 | 91477 | 93447 | | FPO1L malaria rpoD |
| FP9.092 | 93389 | 93784 | | fpE11L O72894 100% |
| FP9.093 | 93781 | 94065 | c | fpE10R |
| FP9.094 | 94092 | 97058 | | fpE9 DNA pol 100% |
| FP9.095 | 97050 | 97868 | c | vv E8R |
| FP9.096 | 97861 | 99576 | c | vv E6R |
| FP9.097/098 | 98702 | 105086 | c | VAR B22R family FPV097/098 Hybrid |
| FP9.099 | 105327 | 111176 | c | VAR B22R family |
| FP9.100 | 111243 | 111791 | | RNA polymerase subunit RPO30 |
| FP9.101 | 111844 | 113997 | | (?) |
| FP9.102 | 113984 | 115402 | | Poly(A) polymerase catalytic subunit |

FIG. 1B

| | | | | |
|---|---|---|---|---|
| FP9.103 | 115396 | 115740 | c | DNA-binding virion core phosphoprotein |
| FP9.104 | 115817 | 116239 | | (?) |
| FP9.105 | 116576 | 117022 | | (?) |
| FP9.106 | 117314 | 117529 | | (?) |
| FP9.107 | 117577 | 122910 | c | VAR B22R family |
| FP9.108 | 123092 | 124225 | | Major envelope antigen p43K |
| FP9.109 | 124263 | 126155 | | Virion release protein |
| FP9.110 | 126195 | 127550 | | (?) |
| FP9.111 | 127628 | 128962 | | Serine/threonine protein kinase-2 |
| FP9.112 | 128937 | 129578 | | Myristylated IMV membrane protein |
| FP9.113 | 129669 | 129869 | | (?) |
| FP9.114 | 130239 | 130790 | | HAL3, DNA/pantothenate metab. flavoprotein |
| FP9.115 | 131957 | 132682 | | ANK family |
| FP9.115.1 | 132648 | 133568 | | ANK family |
| FP9.116 | 133590 | 133952 | | CC chemokine family, MCP-1 |
| FP9.117 | 134498 | 135820 | | (?) |
| FP9.118 | 135822 | 136013 | | RNA polymerase subunit unit RPO7 |
| FP9.119 | 136013 | 136579 | | (?) |
| FP9.120 | 136544 | 137575 | c | Virion core protein, (zetal-cop) |
| FP9.121 | 137979 | 138344 | | CC chemokine family |
| FP9.122 | 139246 | 144858 | c | VAR B22R |
| FP9.123 | 144889 | 150189 | c | VAR B22R |
| FP9.126 | 150968 | 151750 | | VLTF-1 |
| FP9.127 | 151763 | 152773 | | fp1 100% Myristylated protein |
| FP9.128 | 152774 | 153505 | | fp2 25K myristylated IMV membrane protein |
| FP9.129 | 153540 | 153830 | | fp3 100% |
| FP9.130 | 153820 | 154725 | c | fp4 100% |
| FP9.131 | 154751 | 155512 | | fp5 25K 100% VP8 DNA-binding core protein |
| FP9.132 | 155513 | 155902 | | fp6 100% membrane protein |
| FP9.133 | 155853 | 156299 | | fp7 100% |
| FP9.134 | 156332 | 157258 | | Poly(A) polymerase small subunit |
| FP9.135 | 157255 | 157815 | | RNA polymerase subunit RPO22 |
| FP9.136 | 157805 | 158218 | c | Membrane protein |
| FP9.137 | 158259 | 162122 | | RNA polymerase subunit RPO147 |
| FP9.138 | 162131 | 162631 | c | H1 protein-tyrosine phophatase |
| FP9.139 | 162647 | 163219 | | vvH2R |
| FP9.140 | 163377 | 164360 | c | p32K envelope antigen vv H3L (30-35K) |
| FP9.141 | 164361 | 166757 | c | RAP94 |
| FP9.142 | 166901 | 167425 | | Virus late transcription factor 4 |
| FP9.143 | 167426 | 168376 | | DNA topoisomerase |
| FP9.144 | 168381 | 168839 | | (?) |
| FP9.145 | 168802 | 169113 | c | (?) |
| FP9.146 | 169121 | 171676 | | Large subunit mRNA capping enzyme |
| FP9.147 | 171735 | 172049 | | HT motif family |
| FP9.148 | 172046 | 172465 | c | vv D2L virion protein |
| FP9.149 | 172733 | 173293 | | (?) |
| FP9.150 | 173360 | 174190 | | N1R/p28 family, Makorin 1 |
| FP9.151 | 174230 | 174937 | | Deoxycytidine kinase family |
| FP9.152 | 174947 | 175330 | c | HT motif family |
| FP9.153 | 175429 | 176055 | | (?) |
| FP9.154 | 176280 | 176732 | | (?) |
| FP9.155 | 176761 | 177987 | | N1R/p28 family |
| FP9.156 | 178243 | 178641 | | HT motif family |
| FP9.157 | 178687 | 179622 | | N1R/p28 family |
| FP9.158 | 179712 | 180314 | | Photolyase |
| FP9.161 | 180382 | 180855 | | N1R/p28 family |
| FP9.162 | 182233 | 184044 | | ANK family |
| FP9.163 | 184277 | 185068 | | N1R/p28 family |
| FP9.164 | 185560 | 186729 | | (?) |
| FP9.165 | 187796 | 188473 | c | VLTF-3 vv A2L |

FIG. 1C

| | | | | |
|---|---|---|---|---|
| FP9.166 | 188470 | 188688 | c | MC105L M91L vv A2.5L |
| FP9.167 | 188703 | 190676 | c | Virion core protein p4b vv A3L |
| FP9.168 | 190739 | 191713 | c | 39K immunodominant core protein vv A4L |
| FP9.169 | 191752 | 192255 | | rpo19 vv A5R |
| FP9.170 | 192250 | 193374 | c | vv A6L |
| FP9.171 | 193378 | 195504 | c | Viral early transcription factor large subunit |
| FP9.172 | 195570 | 196475 | | 34K Viral intermediate transcription factor 3 |
| FP9.173 | 196437 | 196667 | c | (?) |
| FP9.174 | 196668 | 199343 | c | Virion core protein p4A |
| FP9.175 | 199361 | 200185 | | (?) |
| FP9.176 | 200186 | 200701 | c | Virion protein |
| FP9.177 | 200716 | 200922 | | (?) |
| FP9.178 | 200912 | 201127 | c | (?) |
| FP9.179 | 201194 | 201469 | c | Virion envelope protein vv A14L MC118L M103L |
| FP9.179.1 | 201487 | 201647 | c | Virulence factor; not annot. in FPV US |
| FP9.180 | 201662 | 201955 | c | (?) |
| FP9.181 | 201939 | 203048 | c | Putative myristylated membrane protein |
| FP9.182 | 203064 | 203660 | c | Virion IMV membrane phosphoprotein, morphogenesis factor |
| FP9.183 | 203675 | 205063 | | DNA helicase, transcriptional elongation |
| FP9.184 | 205031 | 205297 | c | (?) |
| FP9.186 | 205305 | 205646 | c | (?) |
| FP9.185 | 205645 | 206946 | | Processivity factor |
| FP9.187 | 206946 | 207416 | | (?) |
| FP9.188 | 207427 | 208578 | | 45K Viral intermediate transcription factor 3 |
| FP9.189 | 208605 | 212078 | | RNA polymerase subunit RPO132 |
| FP9.190 | 212329 | 212619 | c | ATI |
| FP9.190 | 212634 | 213884 | c | ATI |
| FP9.191 | 213920 | 215341 | c | Homologue of variola Bangladesh A30L, p4c, virion occlusion protein |
| FP9.192 | 215342 | 215767 | c | (?) |
| FP9.193 | 215782 | 216690 | c | RNA polymerase subunit RPO35 |
| FP9.194 | 216665 | 216889 | c | (?) |
| FP9.195 | 217069 | 217410 | | (?) |
| FP9.196 | 217411 | 217773 | | (?) |
| FP9.197 | 217762 | 218667 | c | Virion assembly protein |
| FP9.198 | 218854 | 219375 | | C-type lectin family |
| FP9.199 | 219430 | 220089 | | V-type Ig domain FAMILY |
| FP9.200 | 220064 | 220861 | | V-type Ig domain |
| FP9.201 | 220882 | 221733 | | MC144R from 355/642 |
| FP9.202 | 221617 | 221919 | c | (?) |
| FP9.203 | 222056 | 222913 | | Tyrosine protein kinase |
| FP9.204 | 222949 | 223977 | | Serpin FAMILY |
| FP9.205 | 223980 | 224636 | c | (?) |
| FP9.206 | 224751 | 225677 | | GPCR family |
| FP9.207 | 225687 | 225941 | | Remnant |
| FP9.208 | 226876 | 227079 | | (?) |
| FP9.209 | 227345 | 227737 | c | HT motif family |
| FP9.210 | 228241 | 228441 | | (?) |
| FP9.211 | 228380 | 228757 | | Epiregulin EGF domain |
| FP9.212 | 228760 | 229671 | | Serine/threonine protein kinase |
| FP9.213 | 229722 | 230228 | | (?) |
| FP9.214 | 230548 | 230922 | | IL-18bp MVA 13.7K 057169 |
| FP9.215 | 231035 | 231259 | | (?) |
| FP9.216 | 231627 | 232517 | | ANK family |
| FP9.217 | 232946 | 233932 | | Xestia c-nigrum GV ORF147, LdOrf-109 |
| FP9.218 | 233972 | 235357 | | ANK family |
| FP9.219 | 235387 | 236340 | | ANK family |
| FP9.222 | 236361 | 236633 | | ANK family |

FIG. 1D

```
FP9.223      236845  237270     ANK family
FP9.224      237275  237715     ANK family
FP9.225      238092  238406     ANK family
FP9.226      238409  239287     Serine/threonine protein kinase
FP9.227      239340  240425     ANK family
FP9.228      240516  242093     ANK family
FP9.229      243385  243810  c  Similar to FPV221 vv A47L(26% over 121 aa)
FP9.230      243942  244508     ANK family
FP9.231      244472  245242     ANK family
FP9.232      245509  246957     ANK family
FP9.233      247000  248538     ANK family
FP9.234      248569  249855     FP9 BamHI-orf12 ANK
FP9.235      249874  250305     FP9 BamHI-orf11 C-type lectin family
FP9.236      250308  251150     FP9 BamHI-orf10 N1R/p28 family
FP9.237      251159  251362  c  FP9 BamHI-orf9
FP9.239      251619  251969  c  FP9 BamHI-orf8 100% C-type lectin family
FP9.238      251915  252100     FP9 BamHI-orfF
FP9.240      252088  253320     FP9 BamHI-orf7  ANK
FP9.248      254020  254475     FP9 BamHI-orf6 N1R/p28 family
FP9.249      254856  255173     FP9 BamHI-orf5
FP9.250      255402  255824  c  FP9 BamHI-orf4 (MDV US orf2)
FP9.251      255940  256386     FP9 BamHI-orf3 (FPV010  224-355/355) serpin family
FP9.252      257261  257461  c  (?)
FP9.253      257325  257828  c  FP9 BamHI-orf2 C-type lectin family
FP9.254      257692  257910  c  BamHI-orfA 100%
FP9.255      258322  259578  c  FP9 bam-orf1 P14361 384Q->E, C41/C10L-like
FP9.256      259920  260288     EFc family
FP9.257      260079  260384  c  (?)
FP9.258      260638  261009     C-type lectin family
FP9.259      261474  262142  c  (?)
FP9.260.1    265991  266145     (?) No STOP  Absent from FPV US
```

FIG. 1E

| FPV001 | Deleted | C-type lectin family |
|---|---|---|
| FPV124 | Deleted | N1R/p28 ring finger motif family, virulence protein? |
| FPV125 | Deleted | V-type Ig domain family |
| FPV159 | Deleted | N1R/p28 ring finger motif family, virulence protein? |
| FPV160 | Deleted | Unknown |
| FPV220 | Deleted | Unknown |
| FPV221 | Deleted | Vaccinia A47L homologue |
| FPV241 | Deleted | Ankyrin repeat family protein |
| FPV242 | Deleted | Ankyrin repeat family protein |
| FPV243 | Deleted | Ankyrin repeat family protein |
| FPV244 | Deleted | Ankyrin repeat family protein |
| FPV245 | Deleted | Ankyrin repeat family protein |
| FPV246 | Deleted | Ankyrin repeat family protein |
| FPV247 | Deleted | Fowlpox EFc family |
| FPV260 | Deleted | C-type lectin family |
| FPV158 | Deleted (partially) | Photolyase |
| FPV219 | Deleted (partially) | Ankyrin repeat family protein |
| FPV222 | Deleted (partially) | Ankyrin repeat family protein |
| FPV054 | Frame-shifted | MutT motif, Nudix hydrolase |
| FPV070 | Frame-shifted | Murine T10 homologue |
| FPV071 | Frame-shift & terminating mutations | DNA/pantothenate metabolism flavoprotein |
| FPV115 | Frame-shifted | Ankyrin repeat family protein |
| FPV190 | Frame-shifted | A-type inclusion protein |
| FPV207 | Frame-shifted | Unknown |
| FPV239 | Terminating | C-type lectin family |
| FPV097/098 | Fused (by deletion) to form chimaeric gene | Variola B22R homologue family |
| FPV018 | Non-conservative amino acid subsitutions (x2) | Ankyrin repeat family protein |
| FPV063 | Non-conservative amino acid subsitution | Unknown |
| FPV066 | Non-conservative amino acid subsitution | Unknown |
| FPV093 | Non-conservative amino acid subsitution | Vaccinia E10R homologue; redox protein erv1 homologue |
| FPV127 | Non-conservative amino acid subsitution | Vaccinia G9R homologue, myristylated |
| FPV191 | Non-conservative amino acid subsitutions (x3) | A-type inclusion protein homologue |
| FPV207 | Non-conservative amino acid subsitution | Unknown |

Gene nomenclature according to Afonso et al., (2000) J. Virol. 74: 3815-3831

FIG. 2

Gambian Volunteers
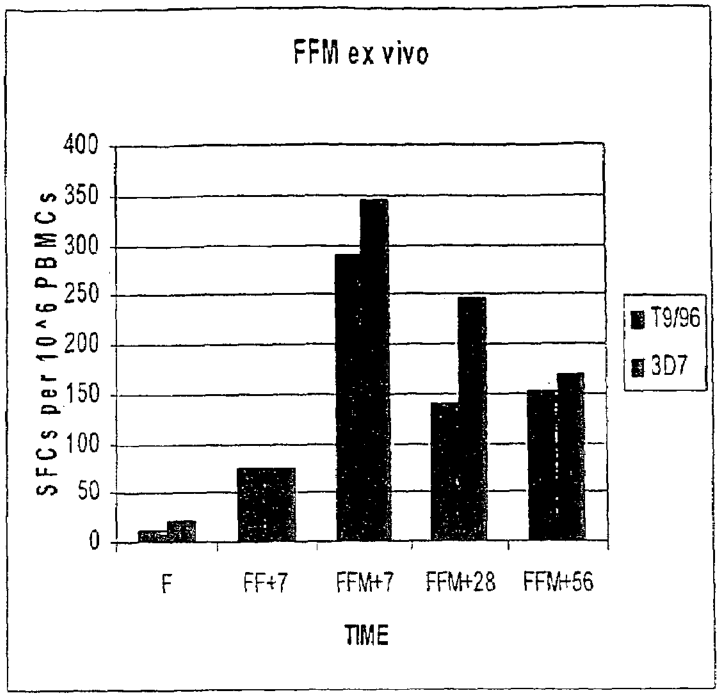
*Gambian Volunteers*
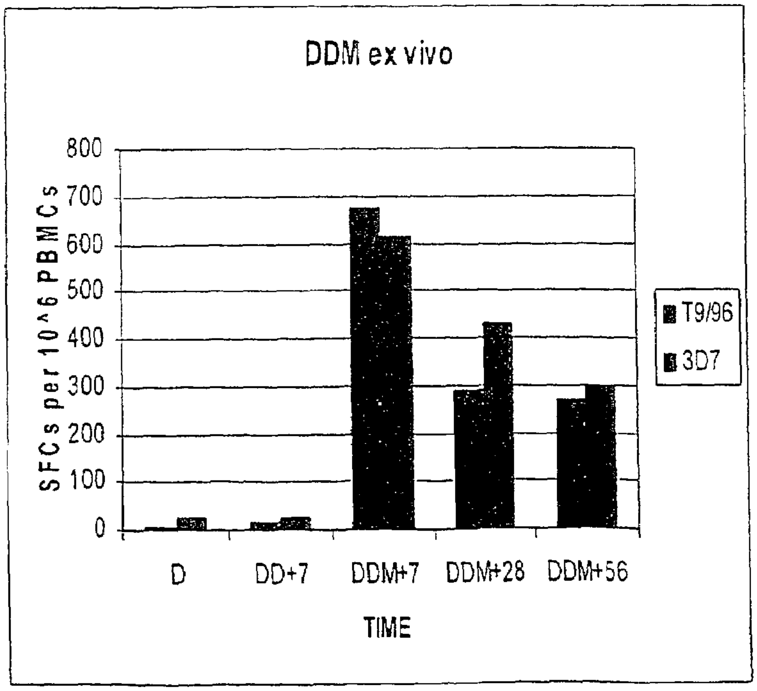
FIG. 13

Figure 15. Antigen-specific immune responses following heterologous prime/boost immunisation with FP9PbCSP, FPV-MPbCSP and MVAPbCSP.

SEQ ID NO. 1

```
1 acccttatct tacgatgagt atttatatag taaaaaaaat gtataaacag taccttccaa
61 aaccctaata tacacattct tttacccctt aatttgttaa ggtgtaaaat acccccctatt
121 aaaatatata ttattgtttt aataaaaaaa accatacggt tttacataaa ataatactat
181 atctaatttc cttccggaaa atattttata aagctaccca acgttagcga aaaacttttt
241 tatcgagagc tcgagttata gaaaaagttt ttatcgagat ttcgaaaagc tttttttatcg
301 agagctcgag ttatagaaaa actttttttat cgagagctag agttatagaa aaagtttttta
361 tcgagatttc gaaaagcttt tttatcgaga gctcgagtta tagaaaaact ttttttatcga
421 gagctcgagt tatagaaaaa ctttttttatc gagatttcga aaagcttttt tttatcgaga
481 gctcgagtta tagaaaaact ttttatcgag agctcgagtt atagaaaaac tttttttatcg
541 agagctcgag ttatagaaaa agtttttatc gagatttcga aaagcttttt tatcgagagc
601 tcgagttata gaaaaacttt tttatcgaga gctcgagtta tagaaaaagt ttttatcgag
661 atttcgaaaa gctttttttat cgagagctcg agttatagaa aaactttttt atcgagagct
721 cgagttatag aaaaagtttt tatcgagatt tcgaaaagct tttttttatcg agagctcgag
781 ttatagaaaa agttttttat cgagagctcg agttatagaa aaactttttt atcgagagct
841 cgagttatag aaaaactttt ttatcgagag ctcgagttat agaaaaactt ttttatcgag
901 agctcgagtt atagaaaaac tttttttatcg agagctagag ttatagaaaa agtttttatc
961 gagatttcga aaagcttttt tatcgagagc tcgagttata gaaaaacttt tttatcgaga
1021 gctcgagtta tagaaaaact tttttatcga gatttcgaaa agcttttttt tatcgagagc
1081 tcgagttata gaaaaagttt ttatcgagat ttcgaaaagc tttttttatc gagagctcga
1141 gttatagaaa aagtttttta tcgagagctc gagttataga aaaacttttt tatcgagagc
1201 tcgagttata gaaaaacttt tttatcgaga gctcgagtta tagaaaaact tttttatcga
1261 gagctcgagt tatagaaaaa ctttttttatc gagagctaga gttatagaaa aagtttttat
1321 cgagatttcg aaaagctttt ttatcgagag ctcgagttat agaaaaactt ttttatcgag
1381 agctcgagtt atagaaaaac tttttttatcg agatttcgaa aagctttttt ttatcgagag
1441 ctcgagttat agaaaaactt ttttatcgaga gctcgagtta tagaaaaact tttttatcga
1501 gagctcgagt tatagaaaaa gtttttatcg agatttcgaa aagcttttttt atcgagagct
1561 cgagttatag aaaaactttt ttatcgagag ctcgagttat agaaaaactt ttttatcgag
1621 atttcgaaaa gctttttttt atcgagagct cgagttatag aaaaactttt tatcgagagc
1681 tcgagttata gaaaaacttt tttatcgaga gctcgagtta tagaaaaagt ttttatcgag
1741 atttcgaaaa gctttttttat cgagagctcg agttatagaa aaactttttt atcgagagct
1801 cgagttatag aaaaagtttt tatcgagatt tcgaaaagct tttttatcga gagctcgagt
1861 tatagaaaaa ctttttttatc gagagctcga gttatagaaa aagtttttat cgagatttcg
1921 aaaagctttt tttatcgaga gctcgagtta tagaaaaagt tttttatcga gagctcgagt
1981 tatagaaaaa ctttttttatc gagagctcga gttatagaaa aacttttttta tcgagagctc
2041 gagttataga aaaacttttt tatcgagagc tcgagttata gaaaaacttt tttatcgaga
2101 gctagagtta tagaaaaagt ttttatcgag atttcgaaaa gctttttttat cgagagctcg
2161 agttatagaa aaactttttt atcgagagct cgagttatag aaaaactttt ttatcgagat
2221 ttcgaaaagc ttttttttat cgagagctcg agttatagaa aaacttttta tcgagagctc
2281 gagttataga aaaacttttt tatcgagagc tcgagttata gaaaaagttt ttatcgagat
2341 ttcgaaaagc tttttttatcg agagctcgag ttatagaaaa actttttttat cgagagctcg
2401 agttatagaa aaagtttttta tcgagatttc gaaaagcttt tttatcgaga gctcgagtta
2461 tagaaaaact tttttatcga gagctcgagt tatagaaaaa gtttttatcg agatttcgaa
2521 aagctttttt atcgagagct cgagttatag aaaaactttt ttatcgagag ctcgagttat
2581 agaaaaagtt tttatcgaga tttcgaaaag ctttttttat cgagagctcg agttatagaa
2641 aaagtttttt atcgagagct cgagttatag aaaaactttt ttatcgagag ctcgagttat
2701 agaaaaactt ttttatcgag agctcgagtt atagaaaaac tttttttatcg agagctcgag
2761 ttatagaaaa actttttttat cgagagctag agttatagaa aaagtttttta tcgagatttc
2821 gaaaagcttt tttatcgaga gctcgagtta tagaaaaact tttttatcga gagctcgagt
2881 tatagaaaaa ctttttttatc gagatttcga aaagcttttt tttatcgaga gctcgagtta
2941 tagaaaaact ttttatcgag agctcgagtt atagaaaaac tttttttatcg agagctcgag
3001 ttatagaaaa agtttttatc gagatttcga aaagcttttt tatcgagagc tcgagttata
3061 gaaaaacttt tttatcgaga gctcgagtta tagaaaaagt ttttatcgag atttcgaaaa
3121 gctttttttat cgagagctcg agttatagaa aaactttttt atcgagagct cgagttatag
3181 aaaaagtttt tatcgagatt tcgaaaagct tttttttatcg agagctcgag ttatagaaaa
3241 agttttttat cgagagctcg agttatagaa aaagtttttt atcgagagct cgagttatag
3301 aaaaactttt ttatcgagag ctcgagttat agaaaaactt ttttatcgag agctcgagtt
3361 atagaaaaac tttttttatcg agagctagag ttatagaaaa agtttttatc gagatttcga
```

FIG. 19A

```
3421 aaagcttttt tatcgagagc tcgagttata gaaaaacttt tttatcgaga gctcgagtta
3481 tagaaaaact tttttatcga gatttcgaaa agcttttttt tatcgagagc tcgagttata
3541 gaaaaacttt ttatcgagag ctcgagttat agaaaaactt ttttatcgag agctcgagtt
3601 atagaaaaag tttttatcga gatttcgaaa agcttttta tcgagagctc gagttataga
3661 aaaacttttt tatcgagagc tcgagttata gaaaaagttt ttatcgagat ttcgaaaagc
3721 tttttatcg agagctcgag ttatagaaaa actttttat cgagagctcg agttatagaa
3781 aaagttttta tcgagatttc gaaaagcttt ttttatcgag agctcgagtt atagaaaaag
3841 tttttatcg agagctcgag ttatagaaaa actttttat cgagagctcg agttatagaa
3901 aaactttttt atcgagagct cgagttatag aaaaactttt ttatcgagat ttcgaaaagc
3961 tttttttat cgagagctcg agaagttaaa tcgagacgcc gatatgatcg tagagaaaat
4021 agcggcgtgg ttattgtatc cgctatgcct tctacgatgt ttcctctgta actcggtaag
4081 gcccgccact tgcaaatgcg tccactgtct cttgtatccc ttcgaagtat gttgcgaatg
4141 catgagcgag acgttagact ctctggaaca cagttgttgt tactgttgcg tgcttcctct
4201 attgattatc agagagttct ggagacgcgt gatattacct actctaaaag cgacttgcga
4261 ctgtattagg ctaccgtgcg ttctcaccag aagattctgt aaaagaacca tctgcccgtt
4321 agctaaatct tggtgtcgtt gtttctgttg cccttgcgag gttttcttga ggtgtctcct
4381 ctttccttgc atgatgttga gaagaatgca tagaggcaga ctgaccggag taagagaacc
4441 gggagcgttt agagattcaa gagatcccgc cagacgggga acctgggtca acgactggtg
4501 cgaagatctc tgcgtatgga tatggtctcc gtgttgttac gtcaagagat gtattcgcac
4561 gatgtgcgac accttcacta aaaaaatttt ctactggttc atcgcccccg caggatcgcc
4621 gagaatgccc gaggaacctt ctccgctatc gagaaaggtc ttttcgtcgt gaagcatcgc
4681 gacgtgtaga tgaaagagat tggacgccaa aaggtatacg ctcgtattat tacgaatcgc
4741 gctcgtcgtc gtgcctcgaa gatgataaag agaacgcgag taaggaaata caagataaaa
4801 acaaactgtc gattctacgt aatacgattt ctaaaacggc gtctaccgca atctttttca
4861 tcagagtaag ggataggtta agattcttaa ggacctttat caaaactatc ggagaaaaac
4921 tttacgctaa agccgctctc atgctctttc acagactggt gacctatagg cttcctatcg
4981 ttagggatat agtcccgttt tattacgcga ggaaaaattt ttggaggttc gcttttctat
5041 atctcatgaa gaaagtcgct gttcgtccta ctaaaaacta atgctaaaaa aaaatctatc
5101 gttaataaat taaaagttat cgggttttga atattattaa tctatgcata cgaaaccgta
5161 cgtcgcgtta cacggggaga atccgaacgt tttcccgtcc gtataggcac acttacccac
5221 ttctggtttc ttgtcatccc ttatccacaa actctgcccc ataccgaatt tgcttatgaa
5281 tttcatgtct ttttcattgt ctattagact acgtctagct aacgtaccca tgggaaacgt
5341 tatcaaacac gtagtcgacg cttcgctgta agttttttg tgatgcattt tatctaatcg
5401 gtttacccag atacacttat tgttgtaaga ggtgtacggt cctctgcaat ttagagagtt
5461 agcgcaatcc aacattaaca acatcgctat caagattaat gatttcattt tgatacacgg
5521 atcaatttta atagtctata gagatatacc ccaccaatag ttacgcgatt aattttcaat
5581 tatacataat aaaaatctag aggagttgcc atgtgattct ctgtcgacga cgttacctcg
5641 ttagttttat taattcttct ttaagttctg acgacggtta tataccaaaa cagcttttac
5701 ttttcgtaag acgataatta cgttataaaa gattaagaaa ttttattttt actaaagtat
5761 catgaataat gacacgatat ttactttgtt ttattgtaaa aataaaaaat atgttcgtgg
5821 ggaggggga aggaggagag ggaagacggg tatcctttta ttccatccaa taaaccaccg
5881 tgttatagga actagtgcac atcagtgtta taaaacacga agaatcggtt tcaaactcta
5941 cgcagttgcc cctcgtcacg tatccactat ccgctgtggg agatcccact cggctcaccg
6001 agtagataag ttctccttct ccttccaaaa agtagatttt cactgtatcg ccggcagcgg
6061 cgcataggta tctggcccta cagaattcca tattcctgat agctcgcgcg acgaagcctc
6121 cgtcgcccgt gtgatcattt tcataattca agggatccga cgcggctgcc aagaccttta
6181 tacccgactc ttgttctact ggacgaacgc ggagatttaa agccatggct gacgtatagt
6241 cgaggacgcc ctcggtaata aattgattat attttcagtt ttaaaaaatt aatttatatg
6301 tactcaatat ccttatatag aattatttta tctcttctga tatacgttag gtagatgccg
6361 ttcaaataat aaaatatctg atgacgtttt tatgcgcgtg ttacgttatt ataatagata
6421 atagaaataa acgttaaaat aataattaat tatcttttca gttgttaaat atattctagt
6481 tttataagcg ttattcatat ataaaaaata taaaaactaa atcgtattta ttatgatgct
6541 acggcggtca tttaacaaat ttacgcgatg gagttcggtt gtacgggaac taataaccag
6601 ttggccgttc acagatttac agaaacgcgt tttacatctt tcaaaaaaga acttttagtt
6661 aatttaggaa taagtgactt aaatgatata aaaaacatat gcgaggattc taaaatattc
6721 tttccggaaa agagaacgga gctcttaagt attaaagatc gtaaatctaa acaaatagtt
6781 ttcgaaaact ccctaaacga tgacttgctt aaaaaattac acgccttgat ctatgatgaa
6841 ttaagtacgg tagtagattc cgttaccgta gagaataccg ttacattgat tatgtatgaa
6901 aaaggagatt actttgccag gcatagagat tttagtaccg tcttttctaa aaacataata
6961 tgcgttcacc tgcttctata tttggaacaa ccagaaacgg gaggtgaaac ggttatatat
7021 atcgataata atacgtcagt gaaattaaaa acagatcatc tatttgataa aactatagaa
```

FIG. 19B 7081 catgaaagta ttaccgttga aagcggtaga aaatgcgtgg cgttattcga tgtcttacta
7141 gaaaaaaagt tatccgcgtc aacaaacgta ataggtagca tagaatactt aggtaaaaaa
7201 ataaatttat atgacagaga aaatgatctt cagttgtgtt attgtgatat ggtaatagaa
7261 agaatgacag aagataaaga atatagccta ggaatgatat ctgatagatc aggtagatgt
7321 ataaaatctc atcataacgg tagtattgtt agataccgta aagaagaata tggatctttc
7381 gatgctctat gtatatataa catgaatgaa gtggatgaaa tttggactgg tgataagaaa
7441 catattatat ggtctactat tgataaaaaa acaggaacgt ctttatacc tatagatcct
7501 gtactttacg aaaagttaaa agctatttct tctaaagagc ataaagaata caaagatttg
7561 agagggtttt gtaatagcag aacggagtat atttgttgtt cggtatctaa gtactatttc
7621 gacttaccta caaaaacaga tttaatacac gaggtgatta attctatcga ttatgatact
7681 aagtcagtgg gtacacccga ctggtatact ctgcctatag aagttaaaca aactatccta
7741 ggtaatatgt cttacgaaga gttatttaat atagtaagag gtaatatagc tcttgaagaa
7801 gacaatgaat atggctgtga ttaacattaa tggtaatact tttctaaaaa ctaatctcaa
7861 gtattgttta caagcgactg aagtaatagt tttagcaaaa taatacctt actgttagtt
7921 ctacaatcga aattatgctg taacatgagg taaggatata tttattaata cgttacatct
7981 ttcgaaagac tttgatcgta gtataatatt atacatctgc tctacttatt atacataaga
8041 aaatttgtat tttatttagt gcgctgataa atcgtgttta aagtatacaa cggacgtcta
8101 tttccaaaaa atctgcgcgt gttaacggat taaaatctac atgaaaatat ctcttaaact
8161 ttatttctac gtataacaaa caacagactg attttatata ttacgaataa ctatttttctt
8221 aggtttttta tatagatgct atacagtgtt tttacgcgta tatacaaaat acggaaaaat
8281 aataaaacag aaatgattct ggcaatatac gaccgcaatg cctatattgt taaaaaaaca
8341 ggtatcggaa gtatcttgct acgcgataac ggtactagga atactatgct taatattatt
8401 tacgatacta gtagtcgtaa catgcaaatg gtattacgcg tttccgtact ttagcaaggt
8461 atgtcctgat gagtggatag gatataatag taaatgctac tactttacta tcaatgaaac
8521 taattggaat gatagcaaaa aactatgcga tgttatggat tcttcattga taaggttcga
8581 taacatagaa actctaaatt tcgtgtcgcg atacggtaag ggtagttact ggatagacat
8641 aaatcaaaat agaaaaattc cgggtattaa tttctcacta tattatgaac aaggcgttaa
8701 tgatatttgt ctattatttg acacgagtaa cattatcgaa atgtcttgta tatttcacga
8761 aagaacgata tgtgttaaag aagatagata cacccattgg tataccgaat acatgcgtta
8821 gatttactac ctctttttta tacaatagta ttttgtacgt tcttgtaaac agaaaatccg
8881 tatagtttat atttttaatc aaagtaataa cgaatatctc gatgtcacgt ataaacgcag
8941 attctagata ttaaattctc aacgtacgtc atttgcattc cctgagatga tactttgcta
9001 ttttattata ccgtagtcta tacaaccact acaaagttaa acgaagtaaa attattgatt
9061 cgttgttatt atttcagcac agtagtactc gctatcttcg tttaaatcta ataacacgcc
9121 ctttgaaaca tttttgtgct agataataat acgttattat tacactaacc tgtatttctt
9181 ctaatcttta aggtgtgcta acgatatatc acgggattaa aaggttatta gtagtcgtat
9241 aacaacataa taatagcaca tctgtatatt tatatacctc tcgagtacat aaaaataata
9301 tgttttgata aaacgtaaat caataagtgt ataaggtatt atttctttta atgaagaaat
9361 aggacgtaat gtctaaatca gatttatatt cccgaaaata tttttcttag atgtatatgt
9421 tagttaaatt acgtgattat attataagtt atctgcttac tttaacatta tatagtaatt
9481 atatactaac cgatcttaac acttccgtac aaagaggtat gcccgcatct gcgagatatt
9541 gtgattttcg tatttagata tgtgaatata gttatctact aacgcgactt tcctccaatt
9601 tacaaagctc taaggaaaaa aaataaaata atactaccac gttcctcttt taagagttaa
9661 ctatttactc ggaggtatcg gtatacatac aattctatat aatttagtta atcgcttttt
9721 acgcgcataa gtctacgtat aatgtctttg tttaagtaac tatccctgga atattcctaa
9781 aaatagcgga atttttgttt gtacgtcggc tactaggaac atgaaaggta cgttcgcttt
9841 tacgatagga attttcttta ttccgtctgt agtgcataat tcggtaacac tagctgcttc
9901 agttccgtat tcatctactt ttatcacaga tttttgcctg atattaccta tcctcaaagt
9961 ttttgtatcg gatataccta ctaattcacc tgacttgaat agatcattac atcccatatg
10021 gattagcgcg tctttcaagt ctacgtcatc ttctaattcg aatttaggta aataaagaac
10081 tatttctttc aaagtcatat ctttttttaga tattatttta ttgatattct taccgttatt
10141 gagagaatca actactccat ctatacctgt aactgaatca ggtatgatta taaacataac
10201 aaatctataa tcttcgtatt ctaacataac tacctgactt cttatatctt catcatgctt
10251 atagtaaaac gcaacgtctt gtatcatcat cgtatctatc ataacatctg tcccgttata
10321 tttttgaaa ggatgtttag aagttaattc tgtatcgaaa ggatatttcc atttagattt
10381 aaagtataat acgtttatga ttgccagtct tatatcatct gctagtgaaa tgctaaaatc
10441 tttaataagt cctctcgtag atagttctac ccatttattt atagtttccg atatagtatc
10501 atctgtaaaa ctgactacct ttgcgttgaa tatatcgtaa ctagagttta taaaatctct
10561 ttttataggg tatccttctt ctattaacat aatactctta tttatgagtt cgtccttgtc
10621 gtcgtaatac tctacgtaat attctgactt atcaggtata ggaacgtagt taccaaatat
10681 tcctaataga tcttttattt tatccctcgt ctctttttta catcctatca tgatgttcat

FIG. 19C

```
10741 tagtatagta tataccccctc taggggaaat acatatgtct tttccaggga catatagttc
10801 ttttaataat cttactaagg aacccatcgt caactaatta tttaacaaac atatacttat
10861 atttccattt ctatgtaata tgtatatacg aagagtcaat aaaaacatta ttttactcta
10921 cctcatcttc aaatgtagct tttcttattg ttaacaacat agacattagt gcttcatcta
10981 tagtatttcc gtgatcatac tcctcgatag cacttgtaaa agtttcaatg tttttagttt
11041 cgcacgctgc taatatcttc tctatgaact tacattcctt aaaatctttg aacgcgggaa
11101 aaatatcttt atatttatct agagaacgtt tagcacgtga tacgtcagaa cacagataac
11161 acatgatagc ataaagtaat tgatgtctgg attcgtattt tgacaacata gtgttcattc
11221 tattatatcc cacttgttca aaaattttac cagccctgtc aaaatcttct ttttgtatag
11281 ataacctagc aattagcaac atacaatcat ccgatagttt attatatcct tcaccgccat
11341 aatatccaga tgcattctca tagtgaaata ttgctttatc tagttctaat atatcattct
11401 cataaatcgc ggctatattc atgtgacatc tcgcaactgt ataaaacttt cctaaacaag
11461 tatatacctc tatagcttta gatagacagt ttatagcttc ataactatct atcttcttaa
11521 atgcgtttgc ggcatctaca aaactcgaag ccgcggcaat agaattttta ttcttttgca
11581 atagcatatc acctgattta aaaaatgctt tacccgcaca ctcccataac tgtacggacg
11641 caaaaagatt agcagcgtga cttaccatgc cggcggcttc ttctatttct ataggtggcc
11701 caaatagatt cttaaaaaag gacttacctt taattttatt ttctgcatct tctaaaatct
11761 tggttgcttt ttgttctact tctttgcgat ccatctatac taactactat aacctcattt
11821 atatttacat attatacata tgcgataatc tgtataaaaa taaatctctg ttatcgagta
11881 ctgtatttct ataggaaaaa atctccaata actgagtcga aggacatcgt gtaattaatt
11941 tatttaggga tatttctatg gaatttagta tctcgtctat acctgatatt acttttatct
12001 tctctatata ttttaaaatc tgccgtgtct agtctcgtta ttacaggatt cctcgcagtt
12061 tagaatttaa aatctccatt accgaacatt agtaaaccat agcttgaatt aagttttatt
12121 tcgtatatag ttttcagttc tttctcacag gtgtgtcata aatgttctta gcagtgcaga
12181 agaatttatc ttattcatat taagttcaaa accttgtact tattttcttc cgaacctacc
12241 ttttcttata gtaattatta atattggtaa taggaacatc gtatccagaa catacgtatc
12301 acatatgttc gttattttat aaagcatgta catatcgttg tttctatgtc tagtggaata
12361 catggtggat tacatactat taataccata tactttatca acaatttatc tagagtgtga
12421 caaccgcaag gtcattttat tattcctgta atattagata acaagaaagt atctagatca
12481 tgacctctct tttaccttat cgaatatatc gtataagttc taagtaaact cggcattaat
12541 gactctataa tgttggcaag aaacctcgaa cgggtattaa tatgaaatgc agtcatatta
12601 acgcgataat aaaaattaca ttctcaaact atcatccatc gcttactata ttatttctac
12661 tttataaaat cggttaacca gtcttattat taactttaat agcgtcattc aagatcaatt
12721 tttttatatt atcgttatta agtttactta atatattcaa tttacccttt aatggaagta
12781 aacaccattc tgtatttaac gatgataaat tacaactatt aacacgtacc gcggaacaca
12841 gcaactcttt cctatatctg cccatttcta taatcttatt catcgtataa ccgtaaatac
12901 gtaagttgct ttgagattct ataagcttat ctagaaaggc gacaaaactg ttatggtcta
12961 tgtctttaat atcttccaag atacatattt caaaaaggct tttatcacct atccctctag
13021 tagtcatgaa agctatttcg gatttacatt tcagcgcaac ttctagtaat ctactatttt
13081 ttgcaatagc cgctatattc ctattaaaac cttctatatt aaccgttata gatgctttaa
13141 attttgaaat aattatataa ggtacaagat taaggatagg tatcttgtat tcgtcaaata
13201 agttaataaa atattccatg attgtataag ttacctgacc tatgttaata atctggttac
13261 agttagcccc tctatccatc aataacttaa gaatagtagg tctatagtaa ctaattattc
13321 ttacaagagg agtaataccg tatttgttaa catagttagg attagcaccc tcatctaaca
13381 aaacattaca cgttttaata tctccagtac atatcgctat taatagagcc gtataaccat
13441 cattagtctc tttatctaca ttagctccgt atcttatcaa tcgtcttatt atttttatat
13501 tgcccgtttt agcggcaata tgtaacggag tgtaggaatc tacgttcggt gtattaggat
13561 ttacaccttt atacaataac tcaaccacct tttttatatt acctttagca gtttccttat
13621 ataaagaagt atatccatcg ttattgacac cgtccatttc tgtatccatg aatacaatag
13681 attagttata ttctatgtaa taataacgat tacatgtata taacatatac tatttctatt
13741 ttcttatgtt atataaaaaa gttatttatt tacataataa gacttttcat atcagtattt
13801 tctagtcttg agaatatata gtgttttatt ttagagtaat ctattaccca tacacggcct
13861 tccgaatctt aaatatttat ctgttaaggg tattgcattt tgtagtttca ttttttcttgt
13921 tgacgctatt ttaataatac gaggcatggt gtatttatat gattttgcgt tttactatcc
13981 tattatagga tcttgcgaac gcatttttac cgtattgtag ttttagtgta tagatattat
14041 acagatttga tttatctatt atatcgcttt ccatgtgtat aagctattta ctattattcc
14101 acggctattc tcagaagtgg ttcacgccct ttctttaaca ggaccttgca catttccggg
14161 tttaataact aatactaaag acgtattaac ttttccatct tctatattag gattagttgt
14221 tttatacttt cttctattat aattgagttg ttgtttttac gtcaagaagg agctagtata
14281 tccatggtga gaatatcgga gtctgcaccg ctttgtagta atagtcttat tattttagcg
14341 ccgttaaagt ttacatctaa gtggggtagt attattatct agagttatag cattgtgtaa
```

FIG. 19D 14401 ttcttttttc cgccgtgatt tatcctgatc cgggtaggaa ttgagcaact ctatagcttc
14461 attgcttttg attataacca aatccatatg agaaggatac cagtcagtcg taactcttgt
14521 tttcattttt catggataat ataaaaatat tctaacaata agggagatct tcttcatcta
14581 tttttctaa gatatcatac ttaatcccta atggaagatc tgaccaatct ttcaatccat
14641 tatcctttac attccgattt ttttcaaacg ccttttccat gacatcaaga gccttgtcca
14701 gagattcgtg tctcagcaat cctctttcga tggtatattc tattagttgc ctgtaaatga
14761 agaatccttc acaagatata caatttaagc attttgctat ggcattgtca tcgcaattga
14821 gacataagtc taatagggaa cgtctatcag aacctaaagt agtttttctc attttctcta
14881 cttcttctat acaggaatct ttccaatctt tcatttcatt gttagattct attatctcga
14941 gatcatttct tctagcttct tcgttaatca ctttgtggta cttatattct gtgtttataa
15001 ccattgttga tattatttgt ttagctattt ctattcctgt gtcggagttt aaatcacaaa
15061 ctgaaagagg tgtatttctc cctgatgaaa cagaagtatc tgcccagaag tccaacaaaa
15121 cttttacgat atcgagttca gatgcgttag ctgcgaggaa taaaggtgtt cttccgcaaa
15181 agtcttgaac ttctacgcta gcgccgtgtt ccaacagcgt aagtaccata tctgcagaac
15241 cttccattac cgcgtgatga agggaactaa atgaaagttc atcttcgaca tcaggtaacg
15301 cacccctgga gagcaattca actactaatt cataattgcc agatcttata gcatgatgga
15361 tggtgtaaac agatcccata ctccttgaat taatcctggc tccggcatct attagaagct
15421 tacagatttc aagatttcca ttagcggctg cgtcgtttat agggcaatta aacctataga
15481 tatcttctgc atcagcgcca taatctaata acgtttttagt catctttaca tcattgagct
15541 taacagcata ttccagggga gtacgacttt cgtggttttc ataattatca ggatcaacat
15601 tgaattccat taacaggtta actatatcat aatgtcttaa tataacagct ctatgtaatg
15661 ctgtaggcgt agactcggtg tacagatcag gatttgcacc ttcgagtaac agaattctag
15721 ctatttcagt atttccattt tctacggcgc agtgcaaaag ggaacatcca tattcattaa
15781 ccatattcgg gtccgagtca ttgcctttta aagctttaat aacatcagaa acacagccag
15841 attcgatagc ctcaaatacc tccatgttgt ataatattgg tagtatccgt gtagatacac
15901 cggatgtacc aagcgatata aaaataatta aaatttcaat ttatttaaca ttagtatgtt
15961 tatttcataa tgtcattatt agtatttagt agttagcaag tgccatatta caactaataa
16021 gatcaaaaat aaaactgctg atgtataatt tatacccata aagaaattat ttataaaatc
16081 ctccgccata gaaataataa aatgacataa ccaattcatt tacaatgttt atttattcat
16141 ttatttatag gtatctatta ataagttaaa tatttttaca agagtaaaca cgatttaata
16201 aaatctaata taatataaat atatttcaaa taatataaaa tgtatatagt tagtaattgt
16261 cttttaattt ataacaaaat aaaatctaat agagtaatat ctttttagtt tcatatacat
16321 cattaggatt tacacattta actaggtttt caggttcata acttctataa tctctatagt
16381 ctctataatt atcataagta ggcttaaaca tttcttcttt attgacattc ttacatttgt
16441 tggtatcggt catgttggat ttcaaatctt cattatatac taaaggtgcc attgccaaac
16501 agaactctga cataggagac agtttttcta cataaaattt accttcaccg tctaccatat
16561 taaggatttc atctcttgta gtatattgag tacatccaga aacatattcg gtatcaggat
16621 gtagacatcc tatgaatata ttgaatatta tacatgatgt cataaactta catttagtat
16681 cgtaatcgaa agcctttaat atcgattctg gagtaggtct agttccattt acctgcatga
16741 ataccatgct attagtaatc ggagttactt cattaaagca tgatttgatt tcactactta
16801 tttcgcgtag tataaccatt attgtaaatt ttagtagtta tatattactc aaaagaaatt
16861 accatttact agttaattta taaaacagag agtattaata attcacttat atattactca
16921 aaagaaatta ctatggttca atgtatagac atatagaagg aataattaat tcaaaatatt
16981 tataaaatag tattctacca tcttccgtaa acatctttgt attctgttac tatgtattcc
17041 tttccttgtt cttttccgac gtaatgtact ggaaattctc tagcgtgtgt attattaatc
17101 caatatctgc aatatggcgt ttcaacatga ccgactacac tttcgtttac ctttatactc
17161 gtgtatctgt aatactctac attttgtgta aaaccccgag gtatctcgta tgacataaca
17221 cctcccgtta ctataccggt tactatccat ctaggatcgc cgtgtttact tcctacaaaa
17281 caagttattg ttgtttcatt tctatgcttt tctactacat acgttatatc ttctttttga
17341 atttcggtac atctttgata cgtttcctct tttccagaag ccgtacgtag tacacaggta
17401 aagcacaaac tttgaggatc tggtttttttg accgtaaaag tagaagtact tccactaaca
17461 gttacttcat acatatcttt ataaggacca ggaacataat tgaaagcgtt caacccgtaa
17521 ccgcctactt gttcttgagc taccatgata ttatcatcgc ctctccaagt agctctcgat
17581 atttcgtctc catctttggt tctacattgc aattttacag ggctatccgg taaatcttct
17641 tccccgtaga tatttttttaa gataaatgat attataatag cgattgctat aaccatatag
17701 ttcattttca tattgattgt tttatatca aacgctgaac aatatacgag gatgacatac
17761 tagatactat acttattcac ttttattaaa aatatgttaa tcttaaaaaa atcaaaaatt
17821 attccaacca cctcttataa cgggatttct ctccgtattc caaaaatgat cccgaaatca
17881 gaaccacgga aaggtcttga cgaggttctt tatcatcaca agatataata gatgctatat
17941 aatctctact tagaccttg taacttacgg tgaatatcac ttcggtagtg aaatcagtat
18001 aatttttatt ggcgactact ttttcacatt catgatattt cttgtattct actaattgag

FIG. 19E 18061 tatcttcgct taacaccaca ccacccgctc tagcatccac ttttacttcg ctatcttcca
18121 tagttctagt cctgtttatt ataaaatcaa tcaaacctct acccacatca tctaccgcat
18181 aagcgtctac tcgaggcatt actctaagtt ctataatgtg tctgtaactc tctgtcttgt
18241 tgtaatagaa gatacatcta tagcgacctt cgtcatttct ggatgatctt ctcggaagct
18301 cgacgttata ttctttatct ggatcgttac aatagcagat actatcttct ccggcattat
18361 gtatgtcaat agttacctta aatgtgttgt ttttcaggtt tccttttata actaccagtt
18421 tagtcgcgtg tatgtcaggg ggtagaatac aagtcaaatt aactcttaca tcgttatgta
18481 ctaccattgt ataggaatta cattgtataa acgtagtcaa taagaataga gaaaatgagt
18541 atatctttcc gtacatgatt atctccagta atttttttac caagcactag tgattcaaca
18601 atagtgttag tgttatactt tatgtttttt tctaataata tccggaaatc gttttaagat
18661 cttccataga taaattcgat acaattactc tatgtatctc aggagataaa agccaccatc
18721 tactaagatg atctttacta gtgtattcat tgatgatcga taataccgac tctatagccg
18781 aatttctttt ttccatgtat tttatatgtt ttttaataaa acgacgaaat attattatct
18841 gtttaagatc tatccgtcgt atacgtttta tagtgttagc cagatcatcc agtttatcta
18901 atatcagaac atcgtacaag gatattttct tatcacccgt ataaaataca ttgtctttca
18961 taatagacaa ttcgttctct atttcgtctt ttaatgattt ggtttcttta tgattgttta
19021 cgaatctcat attacgtaca aacccttgtt tattccttat agaagaatcg tttattacag
19081 aaaagtatag gtatatcgca gctaggaata cagcaggatt atcatgagtt ttatgaatgg
19141 taatgggagt atgaaatcta ttcataaaac acatatccgc tccgtgttct agaagtactc
19201 gagtacactc tttactctta ttgcgtatag cgtatgttaa tgcggtattt ttatcataat
19261 ctgtttgatt aacgtcggca ccattagcta ataagtattc catattactt actttaccct
19321 ctctagaaca aatcattaaa ggtgttatac cgtaattatc cctttcgtta acattagctc
19381 cgttcttgat taatactttt atattaccga tcttagaata catacaggct aaatgtattg
19441 gtgttttacc gtatctattt cttacgttta catcggcacc tttattaata agtagtctag
19501 taagccttga ggtatttata gaaacagccg cgtgtatagg atacatatta caagcatcgc
19561 acgatacgtt tatatcattt atctttttta atagttttct tgtaattggc aaattcctta
19621 attcgtatat acacatacaa agtatagaaa taggtagata attaacaggc aaactaagta
19681 tgtatgagat aatgctataa taccgtttac atattgcttc tattagtata tcgttacaac
19741 accttattcg agctccgttc ttaaccagaa tattgaataa ttttacaccg tgtttactag
19801 acattatagc gtattttaac atcgaatata tatctcctat atccggatct gcaccatgat
19861 ttaataatag cattaccagg gtaacgtttt cttgttctac agcatgatat agtgcagtat
19921 gcgagttttc acatattgta gaattaatat caataccaga atcaaggaat agtttcacca
19981 ttttagggct attggtttta acagcttcta gaaaataatc ttctaacgct gtatccgtgt
20041 ccgctaataa gttattagat ataaagtgtt tcaccagttc tatatttact tctctaatag
20101 cacacttaat agtaattctt ctcatataat ataaactggg atgtttagtt tcttcccata
20161 gaatttggca tagaggtata gtactaaaat atgaatatcc tatagcgtaa ccggttttaa
20221 tgcaatacga accacccttg taaaaatcta atacgtaaga tctacatacc attttcaagt
20281 ctgctccgtg ttttatcaga agttttacta ttttggtgta tttttctgta ttattaaccg
20341 ttaatagacg tcttattctt ttactaggtt ttacgggctt gttatcatta tataacatca
20401 ttctacctcc cgctaatatc atagctatgt tgatgggatg tgtttttatt gtttctcctc
20461 cgttgataac ggcattgttg tctagtagca tttctactat ttctatgtct gaatgttcta
20521 tagcgatgtg taaaggaagt agtctattgc tgtcgtacat gtttattaca tctttatctg
20581 attctatcaa ttctcgaagt ctgtctacat tattttcttt taagatgtta tgtaatgata
20641 acaaacgatc catagtgctg tatttgtacg ttaacgtcat tatttttct tgcgttatgc
20701 aaagataaca gtgattttta atatatgaat tcatttattt tagaactaag ctattataat
20761 aatatatttt aagaataaat tacttattat ataataaaac acaattctca ttactttatt
20821 tatctgttaa tttttgttta taaggatttt gaataaaaga cgtcataccc gtattaataa
20881 cactcttgac gatcatatgt gtaatttttt gcattatgtt tgtaaggcat tttccgttta
20941 tatgcgatct atatttgcaa attgatgttt tacatttagt taaataataa aatattgtat
21001 ccttgttatt ttcataagca ttatatatat gtaaacctat aatatttagg tactttataa
21061 aaattttgca acatgtattt ctcctttttc ttcttttata tgtccttttt cctttttatag
21121 agtattccat ttttattcat aaaaaacatt tgtagcgtgg gtgatggtaa gtatataacg
21181 agttacttat agatatattt aatatcttat cgacggaagg acgaagatcc atggtatgtg
21241 ttatgatgtt tctgtccata aagggtaatg atcaatacta taatgttttt acgatcccta
21301 aaatctaaat atacgaatct agatattgat ataaaagcgt attggataaa tacggttatt
21361 catataaaga taatatgact gttactaaat ctggtgttat agaagagtta gaaaactaat
21421 ataaaataac taattgatgc aatacactac tttgacaata gcactgaaga cttctacaaa
21481 ataagcgata cgtataaaat aagatttata tctgaatagt agctttatgg taaaccggta
21541 aatacgaatc catctactta tgaaatacgc ggaaaaatat ttcatagcta aaggtattta
21601 taacgattat accaagtcat aaaaatctat actatagaga gaacgaatct tcttttttta
21661 tacactaatc gttatcgatt gtaatgtcgc tatcgctttc gtcagactga aggtcatact

FIG. 19F 21721 cttgtttact taaaactatt ttgaatagtt gatcgcgttc ataactagaa agcaaatcac
21781 gctttttgga atcttctagt tctttccaat ctgtagaaat agcttcaaga gaatcacctt
21841 gttttataat atagttaata atactttctt tatccggtaa tttaaaatag tatttgctta
21901 ccatacaata cgcgtaatac ggttctgcat cttcattact ttcatcaata tattctattt
21961 catagcattt agcgtgttct ttactagata ttttcattaa tttgtcaaat agttctttat
22021 cgttaggcaa gtagttgtcg ttttcgttac tatctatact agaccaagct atatcgttaa
22081 ttgtattttt ctctagatac gctactgtat attctctatt aaatttagaa acgctaacat
22141 cctgaaaaga agaaaataca ataggatgtt ctatgctatg tattttgttg tttatatgcg
22201 ttaatagaca ttttcccttt ctatttatca aaataccagc acgcacaagt tttttattac
22261 agggcggtgc tatatatata acttcacaat aacataatgt attattgttt tcgcggtcgt
22321 ataaattaat agaaacatcc aagtattcta ttgtatctac tatacctttt tctgctttta
22381 atttcatcgt gacgtcaagt aacgctacgt acgttacacc ggattcaact atagttgttt
22441 catgatatac ggatttatca aacagaacat cggatgaaat atctaatgaa tttattcctt
22501 taagatagaa ttttgttttt cctccttctg tagctttctg aagtagtaat aatatgtaca
22561 tgcatagtgt atttttttgat ttttttttac agggtttatt atttgttttt tttaaatagt
22621 cccctacacc gtaaacaaca aaagttacct tgttttctac gcgtacttcg ctaactatgt
22681 attttaactg cgatactata agattctcga gtttagtagt taagtcttta cagagggatt
22741 cataaacaat ttgcttagat ttacaatgtt ctaagtcgag tatctcgtat ccagtatgtt
22801 catctaaaat tcttgactcg ctaaagtcat agtccatata gttagtttct atttcttcta
22861 ttaacaattt cttgaaatca gaaaagtaat catctgaaaa tatatgcatt tttggaatac
22921 catctcttat atacgtgaat gacatattta caaaaaaata tattatttat gttttatatg
22981 aatctatata agtaataaat gaaattaaag ttatcaacta ttatagtata caaaaatgga
23041 taccgattac gggacggttc atacacagca gtctgtaaag ggaaatactt tgattctctt
23101 aatatatttt atatcgttta tagtaggatt tcctggtaat tgtacggtta tatggtttac
23161 gggatataga tggaaaaaat ctgttacgac tatatggttt cttaatctgg caatagctga
23221 tacattgttt gtaatattta ttcctttcga gattacttat atattaatgg gacactactg
23281 gccgtttggt ttattcgtgt gtagaatagg atctcttatg tttaatacag gcatgtacgc
23341 tagtatattt ttccttacat ttataagcat agacagatat tgtctcgcat ttcgtaggga
23401 tatatgcaac aaatataggt atagaattaa cataatggtt atgataatca ttagttggat
23461 aatatctata ctgctatcta ctccttacat gtattttaaa aacactaacg aaaaataccg
23521 taataacaga gactgcttgg aagattacca ttcggataat aatacttatt tactgcgtcg
23581 tgtagtattt tgtatatcgt tagtaatgag atatttagta ccctccgtag tcatgttatt
23641 ctgttattgc ttattacttt tcaaacacag tttatttcta tctaagggac agacttacac
23701 catagtgatt atgataactt catttatggt tttatggacg ccttacaata tattatattt
23761 tatagatgtt ataggtagtc attactacaa cgcagatacg ataatagatg ctgctcctat
23821 atctatctct ttgatatttt taagtagttc aatcaatccc atgatttaca tgctggttgg
23881 tagatatgta tcttttgaaa attattctat gcgcgaatcg ctaaaattaa tattatctga
23941 agaaagagac aatcaaacaa atcatgaaaa cgagattaaa atggaaaata ttaattaata
24001 aaaataatat aagtatatca taatttttct agttcattat ttgataaaaa acaacatata
24061 attgatctta tttctaaagg cagcatatgc agatatggtt ctgtagtcag tacagccctt
24121 tctagtagag tatatctagt tagtgacatg cctatgtttt tatcagctag ttctttgtac
24181 acgttagctg tttgttttag tacctttaat tttggatgat tcacaaatct ggctattacg
24241 ttataatctt tttctattac aaaatcgaat aaactatatc ccctaactag tttttggtta
24301 atcagttcgt ttagttcatt ttcacattgt aacattatat ttttataata ttcaattccg
24361 ttaatgaaag acacgcttct tatcactaat ggatctttta ttaactcttt attcttctta
24421 atcataataa ttaggtgaga tattaatgtt cttatagttt ttttacacgg acacgcttct
24481 tctataggag ttcttccatt tgtattaacg ctattgatat ccgatcctaa atctaatacg
24541 agttttattt tcttatattt acaacacgct gctaaagtgt gtaatatagt attcccgtca
24601 gagtttttag cgtttacatc cgctcctttt tgtaataata aattaaacac gttatcagtt
24661 tggtaaatga tagccgtttg taacggtatg ttaccgtaaa ggtcgcgctt gtttatattc
24721 gctcctagac cgaggatgag tgatacaatt tcaggattat ttgtttttat agattcatac
24781 agtaactccg ataagtaatc ttctgataat gcaatatctt ttattccgtg cattaaattc
24841 tttaactcgt ctatactgca atagtacatg gctaaaggta atgttctttt atccatgtta
24901 accataaact ctacggtata aaatttttata agttcatcta atataatttt attctttctc
24961 ttaatagcgt aatacaaagg agatacagag tgttcgtcta atactttagg atcgcatcct
25021 atatccagta agtatcttac agcttccaac ctttctgctt ctacggcgta gtgtaaagcg
25081 gtggttcctt cggtacctaa tatatctctg tctaacgata atatctttag tacttctata
25141 ttgtaatgag ttactataca tctccgcaat atttttattc tttctatatt atccgtaatt
25201 gctttgtttt ctaccaataa tttgattaat gataagttac ctttcttaac cgcataatat
25261 aaggcagtat gtccgtagcg atcaggtata tctaatctaa tattattctt tattagtaac
25321 gaacatgatt ctaatgttag tttgtcatat atcatatcat gaccaggata tggaccgcta

FIG. 19G 25381 ggttctaaag acagtaaata atctataatt tctatataac ccgtctttat agccgttaat
25441 aggggtgttt ctcctttgta acaaacatct acagaagcac cgtaagaaac caatattttt
25501 gccatcgtaa gatctttgtt tctaacagat attattagag gaggtacttt acaagcggac
25561 attttgatc cgttactaag aagaaattca gctactttat gggatttcat acttaccgcc
25621 ctacataata tagtgcggtt tttactacct ggtttattaa gatctatagg tttgtaagaa
25681 agtaatttcc ttattatatc tacatcatct tcatctatag cgcgtttaaa cgcgcttttt
25741 cttctatagg ccattatgtg tggtataatt agcctatgca cataaattta cgctatatat
25801 tttcaataat tgttagttaa atatagttat tcattcaact aatagaacaa gatgtggatc
25861 tccacccatc taaatcgtat tcttcatcca acaattccga cgatattcta tcaggaacta
25921 tatccttact ctttttattc tttataagtt tttcacatct tttagccatg ttcatgagat
25981 tttcatgaga ttctatacat tcgagatttt ttattaaacc ggccggataa tacattttat
26041 cattaaacag ttttctaatt aacattatct gtaatattat tatagagttc agcttttcgt
26101 tgtcgtaaga cattagatta gtaaaaggag tatttccttg gttatcaatt atatttatgt
26161 cagcgccgta cataaaaagt aatttaactc tattgtagtt atgcattgct tggaatagag
26221 gagttgttcc attagaacat ttgatattcg gatctgctcc attatccaat aatagttcta
26281 atagcgcgta gctgtcttca tctatagccg ctacgtgtaa cggcgtaaca cccgctttat
26341 cgcctatatt aggatcggct cccgattcta ttagttcctt agctatatta aagtttccgg
26401 agcctaccgc cgtatggagt actttggtgc ctatagaaga agacgatgaa gaatttggat
26461 cagcgccgct atctaatagt atacttacta attctatatt acgagtacta acggcacatg
26521 ctaaaggcgt agttccataa tcgttttcta tatttatatc cgctccgttt ttaattaaat
26581 gtcttaccat atttaatccg ttcctgtaat cacaggcata gtgtaatgcg gtattaccta
26641 tatcgtcttt gaaattaata tctatccctt tagacaacag tatatccatg atctgaattt
26701 cttctatttg cctgctaggt tccattcgcg atatagttaa gcatttacta atttcatcgt
26761 ctttacaata atccattatc attctcataa gttcaactct ttgaaatgaa taactagttt
26821 ttgatttatt caatctattg ataacttcta gcaattctgt atatgtattt gagcaccaat
26881 tatcgagttc gataaatgat gaattcggag gcatagttaa agtatgaagt gaggtaatac
26941 cgtgtgtatc tatagctaca ggatctacat cgttattcag taatagtctt actgcctcta
27001 tatttcttag ttcaatagcc ttatgaagga gaatctttaa tctgtaagtt gtaggtctta
27061 gatctataca gttctctatt agtttataca gtatactatc tattccagtt gtatatctag
27121 ttattttagt atagtccatt atacaggtaa ataataattt aagtttaata tcgtaattga
27181 ataagatata aaaattggtt atatttattt gttaactgaa tcaattatag atttaaatc
27241 tttattatct aacatttcca ttatcatata ttttacgtta ataggtactg aatttatcat
27301 acttatatta ttactgtatt ctatagcatc gtgaatcagt ttatatcgta tacttgaaga
27361 taatttagtt ttttgaatgt atttttata tatactaata caagaagata atttctcgac
27421 cttggggtgg ttcaagaatc taattagaat attattgtta ttatccgaat gaagaaatat
27481 cgatagcgaa tatcggtgat tcaactttat attccttata ctttttaatt catcctcaca
27541 atttttcta ataactttaa atctatcatt ttggtctata cattctatat ttgctttgaa
27601 tccatccaat aaaaatagat tactatcttt ttctaaatct aatactatct tagagattat
27661 gattgtagct attttatcgg atatgtaatt aatacaggat agaggcgtgt gacctaattt
27721 gttaatagag tgtacatcga cgttgtaaga catgagtaat tctacgctat ctagtctatt
27781 cgataagata gcgccatgga gaggtgtatt ttcattgctt tcatttttca tattagggtt
27841 agatccgtac cgtaatagta acttagcaaa ttttatttgc ataaacgtaa taatggctat
27901 gtataaagga gtgtaacctt ctctgttata tatatttact tccgccccat gattcagaat
27961 ttcagaaagt atatttatgt ctttggtttc taaagcttta tgtatcaaag gatttctact
28021 ttttaggcga gtgtttgcgc cgtacattag gagtaagttt attaaaatct tgttcctgtt
28081 acctacagct atattaagaa cggtatctat agtatcgtta tgtatattta cgtttgcacc
28141 tttttctata agtaatgtag tagcgattat atcgttcctc gatacagcgt aatgtaaagg
28201 agtgcctaga cacgaatctg ttatattagg atctgcgtca taatctagta atagtttaag
28261 tatgtcgtgt tttccagcac taacacaata atgtaacgaa gtcctttcta agtcatcttg
28321 ttcgtttacg ggtacgccat attttatcaa taaacgtaaa atagaaatat cacagttatg
28381 tttcacagcc gtaattaaat aatgattatt atatccttcc ggtattgtta aagaagcgtt
28441 attttccaaa agaagcttaa taagtggata atttgtgcat tttatagcat aatatatagg
28501 ggttttaaaa tgactatttt gaatatttag acttacttta tactttatca gtattttgaa
28561 aatatctata ggtattttat tatatatagc atcacaatag tttatgaata aagtattagg
28621 atcagcgcct ctttccaaaa gatatttagt aatatttgta ttacgtttac acaaagctag
28681 atataaagga ctattaccta aatatacttg ttcgatatcg gcaccgtgat ctactaatag
28741 ttttaccatt tctacattac ctaagttaat agccttatga aggggaggag atttacattt
28801 atttatatct gcgccgttat ctagtaaaaa tttaacaata tctatatcgg aattacttac
28861 cgctaaatat aagggtgtcg ataacgcatt tttgttagaa aatgtatact tcttaaggat
28921 aatatgtttt accgcgttta aatctctagt tctaatagtt ctatgtaaat cttttctaag
28981 tttttcattg cccatgttat ataatcatta tttactctaa tataatatgt ggtcgtatga

FIG. 19H 29041 acgttaataa atataagttt tcctcttttt tgttatatta cctatattga taaaaaatca
29101 ctcgtaccaa ccagttactt taattttga accccctgaat gcttccgcca attcgatgaa
29161 acgattttta ttgtcttcat catccgcgct cacgtagcct atggtaacgt gcggacacca
29221 tacaggatct gataacacag agccgaaaat ttctctaggt gtcggcacaa cgttaaatag
29281 tacgtttctc aaggctttca catcatcaga tgcctccagc ttcataacca ctgctctacc
29341 gttcgctcct aattctttag acgcacgact ttgaggaaag caaatcactt ccttgcacgt
29401 gaaggaaagc gatgtcaaat ctatattttt tgttaactct ttaaatcttt tgaagtttga
29451 ttcttggtct ttgtttgcta ttcccaacgt tacgtgggga ggtatatcac atcccgtcat
29521 gtatttgact gctatgcttt ccaggtctga tattcccttt tctaatctaa tatcgtagaa
29581 tgaaatggag gcccaattac agtaatccca aggaacttct acttctaatc ccattaatat
29641 agcatccttt ttattttgct tttcttttac cacgatttc tctaactcct tctgtatagt
29701 agtagccatt ttggttagag taccaatggc tctccaataa taaaaagatt aaaatttcac
29761 ttattttgaa cacgctgcta taaataatat aatttttaag tagttcgaat atatattttt
29821 attaatttta aagtaatata cggaaaaaag tatcctttat atttaccagt ttgatgtttt
29881 taatgtatag aatgtttttg tctctgtctt ctgagtaggt gacatataat tgatatattt
29941 ttgattatcg ctgtataaga tagaaatctg cgtttgtaaa tagtatcgat atcgtatgag
30001 aacatcaggt tatatccaat atatttatgt ttagttctat acagtaatat atgtaatact
30061 ccattaagta ttatttatcg aagttattat cttatttcgc ataattcttt attagtcatc
30121 ttttctacaa taatatatat aacttcataa ggtaggttag tgatggtact cgtcaagcta
30181 ttaacaacac gatctaattg ttcttttcta tataaaccaa tctttatata ctgatctata
30241 atatcaccgt atatctgaaa ttcgttttta ttaactccta cgagtaatag ttctatacat
30301 cttgctagcg tgttatgatc atcttgtttt ccagctttta taaaatcaaa taccgtcaat
30361 ttatatccag ctctgcgaat tttcatattt ctaatttctt cctcgcataa attttataa
30421 tagttaaacc ggtagatact attagtaaag tcttcgttta ttttgaatcc tggtgttaat
30481 ttaactttat cacgaatatg agatatcata acagccgatg atataagatc cttgacggtc
30541 atggatagag aatttccatg gcagtaacaa taccatgtta gcggtatgtg attgagtttt
30601 atattcaaga agaaaggatt agcgcctcta tggagtagca ttttattat aaaggggtcc
30661 gttctgttta cactagatag aagaatggta taccccttcta tacattttga atccactaga
30721 gctccgttct ctagcaatag tgatacgatg tttatatttt tgtctaaaac agcattatgt
30781 agtaccgtac gtccgttata atcagctatc tcgagatttg gagaatattg gagtaaaatc
30841 tttaccatct tttcatcgtt atatgttaca gctatctgaa tcgggatatt accgttttcg
30901 ttagtaatat tttgatcagc accggaatct agtaacagtt ttgcaatatc agtatttttt
30961 tgttgaatcg ctaaatgtag aggagtatta cgtaaataac atctggtatt gttaacgtcg
31021 gctcccgcgt acaatagtat acttacaata tctttgttac ctatatctac agcaaagtgc
31081 aataccgaat aacatgttaa ttcttcttca tagtattcat tttcattaac attcaccccg
31141 tattccagta atatttttat gatatctatt ctttcgaact ttatagccat tcttagtacc
31201 cgtattcctt catctttcgt attaccttcc attaatcttc ttactaagtt tatactataa
31261 ggttgtactg tagattcttc atgcggtgta tcatcatcta aaaacatagt tgtaatagtc
31321 aaataacatt ctatgtaaaa actaattaat agattttcat ttttcaaata atatacccgt
31381 tctggaaata gccacataac tgaaaataaa atacttaagt atatattata ggataacaat
31441 gtctatgaat aatattacga gtaaaatgaa tcaagatagt tatggatatt ttcaattaca
31501 tatgagcgat tttacacgtg tgtcgctatc gattgtattt acactagtat ttttggtagg
31561 tataataggt aatgctgtta tcatttggtt tataggattc aaatggacaa aaactatttc
31621 tacgctatta tttatcaacc tagctttagc agactcgtta tttttaatat tcattccagt
31681 atatactgtt tatgtattat ctaactttca ttggtatctc ggagaattct tatgtagggt
31741 tagttctttc ttctttacta ctaatatgta cgccagtatg tttttactta cgtttatatc
31801 tatagataaa tacttaacac taaccagtca ccgtttagtg tataaatacc gaaaatatag
31861 aaactactac gtgtgtatag gtgctatttg gtgtatttct atagctttag gtgttccaac
31921 tttatattat aagagggtta tattatcatc atctagaaac gagacacggt gtattagtta
31981 ttacggcgat gataaacaca cggctattac tatttataga attattgtgt gtattagatt
32041 tattatagga tacgtgtttc caatgacagt aatattgcta tcttatgcat taatagtata
32101 taaggtaaaa ttcataaata aaccaccgaa tagaagtttc atgataacaa cggcatctat
32161 atttgtattt ctcgcttgtt ggacccctca tcatgtatta aatattatat cgttgtatgg
32221 attaaaatcg acatctatgt ataattatat aaaagaatct attccgttcg taaatgctat
32281 tgcgtttgtt tatagcgcta taaatcctat tatctatata tttgttatta ggttaacgag
32341 tacttacgat tccgatacca tggatgaact aagaagtgcg ttattagatg aagaaactac
32401 gtctacagaa gattgtagcg atatatctag atagatttaa tttttgtaaa cataaaaaaa
32461 agtatatagt atcaaaaaac taccatggaa gaaaatattt tagtaaaaac ctttgacgaa
32521 ttatacaaaa atagattcgt agatgagatc tatcataacg ataaactcat tacgtttaat
32581 aaaaagaagg gtaaaggaaa caacttgtgt tattctataa ttgaatacat taatcccatt
32641 tatgattctt gttattctgt ggctaaagtt gtatatataa ctaacggagt tatgtatgct

FIG. 19I

```
32701 actttaaact atatgggaaa acctgtagaa aatcgtgagc tcgttcctat taataaatta
32761 ctatcggatt cagaaatctt atctatggga gtaaacgcta aagatctatc tactaaacat
32821 tacgaatata aatataaggt atctactaac cacgataaaa aaagggactc gtcattagtt
32881 aatataatta aagatgatag tttgttagaa aaattagatt atttcttga aggttacggt
32941 gattggaaga ttaccactat aagacccagg cagtttccta ataagttttg taaatacagg
33001 atatctaaat actacttttc attgtaatgt ttattatatt tttatagtag atgccgcata
33061 gtgaatcatt atcataaact tagtttagac taactataca agatagattc aaaccgattg
33121 attagctagt atcgaagaat caatcatctc tctatgctcc tgaaatttat tatagcatta
33181 tgattatcga atttatatgt tagctcgtga ttagtagtga tattgtagtt tagtaaatcc
33241 taatagatta ttacgtttat ctttaactat ataataaata tctgtttctt ctataattaa
33301 gcctatggct tctgatcata ttacatagta ttatctacta ctataggcct ttatttagta
33361 taagtatagt ctaacaactg ttacatccga atgtataata aaaataatac taatggcgtg
33421 ttcacgaggg taaataaatt tcggccatag ttacctctat ataataaaaa ttttattaat
33481 tttttattct tgtttttac agaatgttta aatctcgaat gtataccaac gagattttc
33541 actctgtttt agtagtaact agcgtattat atagcatgta tgtggatatt ttctggtata
33601 tacaataatt cataattcta taaagtatca aggttatttt ataaaaatat taataatggt
33661 tttaaagatc tcgtcaaaga ttcaaacata taattaggag caggacctta actaaaacag
33721 tattacattt ttgtctttta tcgttttgta caatataata gttaacgcct atagctgtag
33781 cgttttctct aatatccatc atttcattt cgttatctac tttgacagtt tctttaacct
33841 ggccattttt taaccatctt ttaagataat caggagaata tttttagat ttctcgtagg
33901 cacttatagc accatggcag cattgagaaa ctatttcacc tttagtcatt tttaaatcat
33961 ctctaataac gaataccatt tttaacatat ctctgtaaga agagttatca aaaacattag
34021 ccattattag cacaatatga taatctgtat tatttattta tgttttcagt atttacttaa
34081 tacaagttac ataaaatata tccttctttt tacaggtaca tatactacat gtaagttttt
34141 aagtaagcta cattagaaga tgttttgtaa acattacgat agaaactcat actcgttact
34201 gtttctatat ctttattcct tactctatga agactgaata ttttcctcac ataacttacg
34261 gaagttatat tctctctaga acacgattcg ttataatagg tatcgctatt gggtactaca
34321 aatgactctg ttttaatatt agagtaacaa tcatttaagg aagaatcttt atccttacag
34381 tatgttagta taacgaaata atccgaaggt atataaactt tgttattata accgcttgac
34441 atagatatta accaatcact atctcttata ccgttgctgt tgctatcgaa tacagggcct
34501 accataacgt taacgacatg atgttttgt acatattcga taagaataga tgacataaat
34561 acttcccata tcttttgaa attacgatac ataggtacag tatttgtctc caataggctt
34621 tgaaagtcag ttgccccttgc ggggtaaaga tatccataag taacatcttt ttgagtacta
34681 tagtatctac atggttcttt ataatacata actctcatat cctgaagata gcaggtcttg
34741 ttatatatat ttgtactatt atatgtaata tcgatactaa aagacgtcca aaggggaagt
34801 ctatttacct tactgtaggc agtaacgtaa ttatcatttt taataataca atgatggtgg
34861 cgattgagta gaacagcggg tttaccaaac ggtagattat atatgtaaga tgatgaacgt
34921 gttctggaac tgtcttcttt atttccttta gaagagaatc tgtctatgtt cttacaagta
34981 caacctttca gatgatctcc aacatacgcg tgtctatcgc actcagattc tattgttatt
35041 atatctagag aagaaacgtg agtatatcta ctatttctaa gaatattatt caaagatcct
35101 acagtaccgt tgttgttagc gggatttatg cctaatattt cacacatcat attatagagt
35161 tcgatgttat cgaagatcgg gactcttaca tcatcgagaa aagcaggtcc ataacctaag
35221 aataccgcgg tcatatcttg gaaactatta tcagatccgt ggaatccacc cgatcgatgt
35281 tttaagttgc cgttttcatc ggttgactgc catccttctt ctagatatac tcccagtatc
35341 tccgttctga accctgatcc gtaatgcaat cttttaggta gcctgctcct ataacttacg
35401 atgaaaggtt gatcgtccat cacacaacta gtagaagata taattccgtc ataatcgaat
35461 aatcttatat ggtttaaatt ttgaggcttt attactggag tagctcctgg ttttataact
35521 acgtcattat ttgttatgta atctttcaga tttactatct ttttgggatc tacattagac
35581 ataccatgat ccgatactag tattaggtta gcgcatccta ttaattgcaa atctttttaaa
35641 cctttcatca gtaaagcgat tgctttgtca actttttcta aagctttcc tactctttca
35701 tcatctgtac cgtattcata cccagaagac ccgggttctt caaggtatag cgcatagaag
35761 tagggtctat atcccgtatc cattttaac cacctcaata cggtatttat tctttcttca
35821 taaggaaccg atttattata gcttctatac atggtagggc gttttctagg aacaactttg
35881 tcagatcctg gccaaaagaa ggttgctgat ttaaatccgt tcttcatgat agtagtccat
35941 atgggttcac ctccaaacca ttctacttct tcagtttctt ccgaagctat cgtaaactcg
36001 atatcggttc ccctatctat gaattcatta tccgttatac cgtgagatat gggatacaat
36061 ccggtaacta tactgtacaa gtttgggaat gtattcgtag gatatacggg cctcataggt
36121 gccgtaactc cgtgttccat taaatctttt atcgtaggaa tatacttctc ccatttatta
36181 agataatcat atctaaatcc attcatcgct attagtatga gaggcggcct ttcaaattca
36241 ggaggacagg ttacctggaa tgatatacaa ccccctaacc tcgaatctct atatccgaat
36301 aacaaacaca aaggtatcat tattacggat attgcagcga tagtagctag tgaatacaat
```

FIG. 19J 36361 aagatatctc tagtttcaca cttacgcttt tttattggta tagtgtaaaa tatatccacc
36421 ttttttttctt tgtcgataat agaactatta tcttcatcgc ttatgcattc tttagattct
36481 tcttttacag gatacaatgt ataattatca ctgtgtatag acatatcttc atcggactga
36541 tatccatgat ccatagtggt actatttttc atagacattc gtataaacta attacttaat
36601 ccatcatttt tattatatat tattgtttga aagaaaaaaa tacgcgataa aataacaatt
36661 attatacttg atacgagttt gaattcttat ttttcaacaa tatcacgttt tacttcctgt
36721 catgatcttt aattcatcat tatttatata ggtaaagata tgatccttaa tttcattagg
36781 taaattgttc caagaggatg tattactgtc attatctaga aataaatctt ctaatacttt
36841 acttgcttta ttaagaagta cgtgtcttga cataaaagta tctataaaat ctgtatataa
36901 aatattaaac acggtaagtt ttttatcaaa atttactata aatctattat ccttatttat
36961 gcatcttagt aataaatcaa cattattatt aacgaataaa tcaaaaagtg taaatctcga
37021 gtttatactt acctgtttca ttttctcaat atcttttaaa caatgtatcg ctatacgttg
37081 taatctttta ttatctttaa ctagtttctt attatggtcg aatcctttag ttttattact
37141 catacaagta gaataatcta atctaataac gtgtgacact aataatgata ttatttcgta
37201 gttattacaa ctcatggcga tatctaaagg agttaaccct gtattttctt cttcgttatc
37261 tcttatatta acatctgctt tataacgtaa tagttttttt atgatatcta tactagcgtt
37321 ataaattact gctttatgta atggtgtaaa tccatcatta ttagtaatat tagtattagc
37381 accgtgaaat agtaatatat caactgttat gcggttatcg ttttttacag ctaaatgaag
37441 agctgtattt ccacatgtaa gactacgttg atttatgatc gctccgttat ttaatagtaa
37501 ttctaccaat tggtggctat taaatctaga tgctatcatt aaaggtgtaa gattatctct
37561 tatagtttcc tgaaagttaa tatcaacgcc ttttttaaca agatatctta caacatctat
37621 ataattacgt ttagtagcta ctaatagtaa actgtttcta tcaagtctat atttttggaca
37681 taaagttact attccagtaa tgcgtaataa ctctattaga aaaggcatag ttttagttat
37741 ataatcaaaa ttataaaact ttaaaatcaa tttagatttt tattaaacta catgtttata
37801 acacaacctt cgtactcaat gactgtttct tttagtaatt taaacagata tccattccta
37861 gtacaggcgt atccacctcc tctatgacgt tgagtaggac tcctattaat atcacctata
37921 catacccatc ctttttttatc gtaaagtgaa acaatccatt tagaatgatc ataataatta
37981 ataaacgatg ttccatttac gtttatcgat tttatgttat gtacatggta ttttgacgag
38041 caattggtta tcatactctc tcctctacgt tgccatgttt ctgatagtag gtcagattcc
38101 aaagtcggac ctatccatgc actcattata tcatggcgaa aatattttga cttagcaaat
38161 gttaaaaact tttctccttt tctagattcc atccacctag aaacattttt atataaagtc
38221 gtatagtttt tatcgttaca tagatggtat agattattca gattcttatt tgttactgaa
38281 cagttataca cgtttgggtt attaacaggt agtgtattgt ctaaggccgt aagacctcct
38341 ttgtaatcca agttaataca taacatagat tgcccgtata cataaccaga gtaaggataa
38401 ttgtatccca acacaggaga aggtggaaat ctaggtacag aatgtatcaa ccaaaatcct
38461 gttacgctat cactattcca tgccataaca cctttagtat gacctacctt cgatgaataa
38521 tttttgcttc ctgggatgcc atcattataa aaaatgtatt ctatatattt actatcatat
38581 aggtcataaa taggatatag tgttttccct attatactgt atctagagtt tataggtact
38641 ttacctcgtt tccatttagg attattacta tctatgtata aatattcatt acctttagtg
38701 cctaattttt ggagcttagg gagcttgtat acgaaatacc agtctactac ttcgccttct
38761 tcatttacac aatttacttt acctttatca tattcgttaa agtttgaacc gatggaattc
38821 agtatcttag agatatttga gatatctata ttattaccga tataatatgt aatacatatg
38881 catacggaca atgtaattgc cgtaggtgat atcattttat tgtatttatt atacttatta
38941 tacttatcta tatttcatta ataaacaact tgtatttata gtattatata gtgatatctt
39001 tctactataa acatataaag taataattga aaggtagtag tcttagttac gtactataaa
39061 aagtatatca tatggatttt attccctaac aactagaatt agttttaata ttattgtatt
39121 ttggaactaa caagataata ggaatagtcg ctaccatagc aataaatatt acgaccatta
39181 ttaaaacata tggatctatg aatttattaa tttctttttt tataatttct aaaattagta
39241 ccatcttaat attaatttaa ttatatcacc atattctaat attgtattat ttttatgtta
39301 tttattatat cattgtgttt gtatattctt cttaatttct aataacatga tcgttaagat
39361 ataatccaat ctagtaaccg aaccgtattc tcttaatgca tctactaata tatctaaatt
39421 gcatgtatca caagattcta cgactttcat tattaacgtg tactctctat aatcaataaa
39481 ttgagcataa agttctgtat agtatcccac tatcaatctc atatctttat ctcctataca
39541 gaaatggcaa agtatagctt tgagaaattg atctttaata cgatgtttaa gaataggtag
39601 tctcatgcat atgataccta tttgttcgta tacagacgcg gctttatcga attgtttcat
39661 tcgtgtaaaa cagtcagcta cttttatcat acaatcgtta gctgatttta tggatccttc
39721 ttctctatag tattcggtag catattcgta atgcatacat gctttttcta aatccataat
39781 acacgattca tatatttcag ctaccgtcat ttggtgtttt gccgccgtgg tgaaattatt
39841 tatcgattta tagacttcta tcgcttgtaa caggcattct atagattttt taggatctat
39901 ctttctatac atattactcg catttacaaa atttatagca gtatctaata cgaaatcaga
39961 ttcctgagat tgtaacacag cagctttaag aaatgaatat ccagctaact cccagttctt

FIG. 19K 40021 gaccgcttta aaaagtatag ctgaacgaat caataagttt ccaacttctt taacgttatt
40081 tacgtttctt aagaacttcc aagaaaataa aaatcccaca tcctttagtc tacgattggc
40141 ttccgatatt agtctatacg cttcttgttc catgtcaaaa taatatcgta tcttaattgg
40201 taatattgta tatttattga atgagtgtat tattataatt ataacgtttc ttatacggaa
40261 gaaatctgga ctcgttatga gatactttgg attgtatttt actataattt ataggcttat
40321 catcggttaa aacggagtat ggtagatgcc attcatagat gtctcctatg tattccataa
40381 agagcctcgg cgatccataa tttatcctat gtattagatt catattttgt ttatacgcac
40441 aaaagtcatt tagtacgatg ttgtcaactt ttagtgaaat cagatatgat acagtatatt
40501 gtgtaacttc tttcgaacca cctgttataa ccatattaac gggtgtttca ccaaatacat
40561 ttctgacatt tatatccgcg ccgttgtcta ataataattt cataaatctt acatcttgta
40621 aactggctgc aataaagata ggagtattac ctacatcgtc aaagctatcg acattagctc
40681 cattattaat taatacaaaa gcggcttcat aattacgttc ttttatggct aaatgtaacg
40741 atgttctacc accgtgtaat tctttaatgt ttacgtctgc gtttctgttt ataagtaaca
40801 tggtgccgta aatattatta cgttcgacag ctacgtgaat aggcgctttt acatgattta
40861 ttatatttac gtctattcct ttatctaata gaactgccat aacattatgg tatttattgg
40921 aagtagatag aaaatgcaac atactatact tgtttactat ggatatatca gcattttttt
40981 ctaaaagaaa gcataccata tcgtaattat tgttacaaat tgtatagtat aatgctgtat
41041 atcctttatc gtcttttaca tttatgttaa ttccgtgtaa gcatagtagt tctatcattt
41101 ttttattttc atgtgttata gcactatgta gtaacctata atcattttta tttattatag
41161 atccagcatc taataatatc ttagctatgt tgacgtcatc tacttctacg gcgtatctta
41221 ataaagtata tcctacggaa tcagctatat ttatgttaaa atttttatct ataaagatgt
41281 ttactaaatt gtgatcgtgg tttaaaaccg ccttccttaa catgttaaaa tgtttataag
41341 tattaatatt ttcttgttga tttaaaatca tacgtactac gatatagtct tttaattcta
41401 tagcctgttc taatagcttt atacagatag gttcgtgtaa tccaaacatt ttagttttca
41461 tatttgtatg ctaaatatat ctatatagta aaaatagtcc attaaatttc tattttaatc
41521 aataatttac ctcgcattcg tagcttatta gacaaaaagt acatacctac caccagtcta
41581 acaaattaaa tagcacctct agtattactt ccccgaagat aagacattga tatgttaata
41641 tccttcatat aatcttacgt attccgaata taaccacttc aaaatcattg ttagttatgc
41701 attctataag gtagtctgta ttacatttta tagctataat agacagcatg tcaatgtatg
41761 taaatttagt actagtggat gtagatactc ttatagtaag tccactagaa tctatataag
41821 atccatagat tattatttca tctccagatt ttatatgatg aatacaatta tttattttat
41881 ttagtctaaa cattcctata atgttactag tatctcttaa gtttaatagt tttctcatta
41941 taaaatttat agaatttggg aacatggtat gacaagaaca taaatctttt atcttgttta
42001 tatagttaat cacatcctta tcatgttcta attcttttat gtttatatcc attgtgctta
42061 tataagattt taaattgtat tttcattaat tacgtacgag aaataaaaaa tacgataata
42121 ttatacttgc tatctgtagc aatactattt tttatatcta tactgttata cggataagat
42181 acaaatctta ccatattatt tggatataac actatacatt ttccatcgtt atgtaataat
42241 aatccacagt cttccgaatc tatacataat attataaaat ttgaatagtt tcccacttct
42301 aaagtataat cattaatatc cattacaagc atgacgtgag ctaaatattc attattaaga
42361 agatactgag atagaatgtt agttaatgtt tccgatacaa atatattaat aacttagta
42421 ttattgatta atctgtaaaa atctgttatc cttgaacatt ccgtatatag atctatatca
42481 tcaataaaag atatcatgtg ataattcata ctgtatatat acgtataata tttattatat
42541 ttcattttca tgccattatt gtgacttttc agacttttta ctcaagctta ttacgttata
42601 gttaagcaat aagtgtagag aagaaacgac cataaagggc gatatacaag cacctattac
42661 agcgctcata ctattccaag ttagaaagtt atacacggat aacaagacat taagcgcgga
42721 aatgatagca cttgtcctta acatactcat gatgtagaat actaaaaacc atgacatatc
42781 cagaaataat tgcaagaaat aaaaaataat gatatgtcga ctgatctttt cgccagaggt
42841 catcaaatac atcgcatgcc ccatacaagc ataacttata gctgatagca cacatctaaa
42901 gtagtattct tttactacgt ggtatttatt atatcctatg taattgtaaa aactgtattt
42961 ttctattatc tttacgacta ttaaccataa cgtaagagat attagagaat aagaatgatc
43021 gcatatatat tcgaatagcg tcattttaat cctgtagatc caaatcctga attgcctcta
43081 tccgttatat tgatttcctc taaagtagtt acttctatta tttttgggta tgctattttt
43141 tcgaatataa tttgagctat cctatcaccc ttacatacat taaattgagt tgatccgaag
43201 ttaaataata aaacgcccac gtttcctcta tagtctgagt caattacgcc agcacctacg
43261 tctataaaat aattataagc aagccccgat ctaggagcta ttctaccgta gtatccgtta
43321 ggtattttta gaattatatc tgtttttatc agttctttat tcataggctc tatttacataa
43381 tcatacgcgc tatataagtc ataacccgct gaataactag tctgtttata tggtaacttg
43441 gccctatcag aaattttata tactgttact tcctccattt acgccgataa cttatacttt
43501 caatttcgta ataaagtata aaaagttatt acatataaaa ggaacatatt ttaaaaactg
43561 ctagtgaagc aatgatcaac gaggctgtaa aaatacaata tgaagctgta ttgaaaatat
43621 acgaatagtt tttatatata cgaattccat tccaataatc ttggtctatg aaccaagatc

FIG. 19L 43681 tatatttaga tagtatggca tcagttatcg cttctgatat tattccatcg tagtactgag
43741 gtgaagtatc ttgtttaact tttttagaat agtatgcaca aaaggcaata atagttatta
43801 ttctacccca attaatttta tcttctaata cttgcgttac tataacgtta aaatcaatat
43861 tcctagatat aattatatca aattcattat aattggtttt tattactgat ttacacgctg
43921 cctttagaac atcataggat atagaatcta ttacaaaact ttttcttggt ttatttgtgt
43981 tatattctat gatatagttc tgtatcatat tcaaagcgat ataataagtt tcgtctttca
44041 tattactact agccattatg tatattatga ttgatactat cttgttatag cttcaatttt
44101 ttagaatgaa tctctaagta ccccaaagta tatacaattt cctgtcactc tgcattgtaa
44161 tatgaaaata aatggtttc caactacagt ttcgctacat gaagaacagt ttatttttgg
44221 gtattcgtta ttagtaaact caagttctat atctgtattt aaactaatgg attcagcctt
44281 aatttccata atagaagatt gtgctattct ttcaacaaat aaagtagttt ctgggaatac
44341 atttgaaaac ttaatttcca taaggttcag gcctaaggat ttaagtaatt ctacgatatc
44401 ataagacgat gacatcttta ttttaggaat tttaagcctg tgttgagctt ttttcatctt
44461 actattatct atccaatcta ataagctatc tacgttgata ctattttcca ataaattgaa
44521 tatctcttct ttatcttcat taggagatat cgtagtaagg atatatctgt tgctagctaa
44581 tgaagttctt acgacgctac atcctatatt gtccaatctt cttaacatat gaagacgcct
44641 cttagcgtcg acgagaatgg atacaatttc caccgagtta tgccgtttcc ttatttgttc
44701 ttcggtagga gcggtaaacg gtctattcca tagagcttca aattctaaca cgttcttgaa
44761 tttaatactg caaccttctg tttcatctac ggtacatgtt ttatagcagt tgtagagtat
44821 gttttttgta cgttgattga tacatacatt atttaatcct agtttacaga aataatctat
44881 atcggaacta ttcatattat catttatttt tttcatgtat agatctatgt ttgggcattc
44941 tatgtttaat atatcatata ttttatcagc tgttgagtga tcagttagtt tactcaacgc
45001 gcataaagaa gaaattatac tacaaggtgc tattattata ttttcagtac ctgtagattt
45061 tatataattg tatatcttga tagctacatc taactgtatt tttatgatat ccataccgat
45121 aataatttgt attaatagat attatttcag tttatatatc tataatatag atgtatatat
45181 aaaataccgt aatttttatg aattttcctc atccaaagag tcatagtctt caatatctcc
45241 catttttaaaa agattatata gtataatcaa aggcataagc gatataaata ttactagtag
45301 tgctaatata taaattatca tatgacctat cgtaaatgcc cacgtatgtt ctttttctat
45361 taaacacact actacaccgg tagtatatac cgtctttaca ccgtatgtta tatcgtagta
45421 tactgaattg ggatatataa cttttttatg tgagttctta gtagattttc tacataccat
45481 aacttttaac gagttatata tatcgctatg agtaacatta tggccagcgt atttgcaatt
45541 atttagataa ggtaagtttt ctttatgttt atttatatca catatatagc acttataatt
45601 atcggtgtct aataatgtaa cagatacgtc ttttcctagc ctgatcactt tccatgcttt
45661 attactgggt atcatatatt cagatctttg atatcccaaa gtatactcgt ctatgtcagt
45721 tatcctacca aaacgacata caatattcgg agaaataggt ttagcatcga catggtacaa
45781 tacataaagt ataacattaa taattattat acgcatgatg gtcgcgggta attaactacg
45841 tatagtattc tacggtttta tgaaattatt tttctattta ttaattgtgt ataaaaagta
45901 ttattcttca ggaggagata tagaaaccgc gtataactgc ttaatatcat ttagattatt
45961 agccgtttca tacgttttgt cttctcttat cctagaacat ctaggaaacc gtatagatat
46021 attagaagcc gtatgggtag aagatctggt gaattcagat ccaattattt cccatacagg
46081 tgctaatgaa atatctgaga ttatcacgtc ggggtagtgt attttattaa tagataacca
46141 atcgggaatt gcatttctat cgaaaggaac tacagaaaga ttatcgttaa tttcctgaag
46201 ctctagatca gtatgcccac cagaacactt tgtaacagtg caccattttt cagattttgt
46261 atcgtagcat cccataagaa aactggataa aataccagac ttgttacccct ttccgtaata
46321 agcacccaaa actactagat cagctttatc cgccataaca catccatcta agtagtcttt
46381 ttttattttc agccatctac gcataccacg ttcgtataca ccttttgcat ctttgagtac
46441 aaacccttct atatttttac ttaatactat gtgtaataat ttagataatt cttcatcggt
46501 actaatattc tttacttctg aaagtaaaat tctattaggt atttccttta tattagcatg
46561 aataatattt cgtctttcaa ttagtggttt atcctataagt acggtatcgt taaaatacag
46621 acagtcgaat atgaagatac atacacaagc gttatggtac atactttttt tgttaatacc
46681 tagagtaccg aacggtagag gttgattagt ttctgtatct attagtataa tttcaccatc
46741 tagaatcatg ttcttagcgg aaggaaaagc tctatcgagt aattcttcaa agtcagtaac
46801 cttatgaggt gtaataggtt taagacttct actaaaatat ttaaaatttt tatcatgttt
46861 atgtatttgt attctttctc catcgtactt aaactctaca attataccat tagggcattt
46921 ttttaccgct tccgaaaatg tcttacacgc ggatgctaac atcggctgta aaggcaccat
46981 taattctatt agtggtttaa tattatcttc caaagatcgt tgtactacct gttctaaatt
47041 attacataat ttgaatattc cataagcgtc tttatggagc cctgataaca catgttttgg
47101 accaatgttc attcgtaaat catgttttat taatcttatg atatgtcgaa gatcattagg
47161 tgtacatctg ggtattattt tttttatttc tttgatttga tcattttctc tagttactgt
47221 agataatctt gttagaaaac aatcaacttc atgtaacgtt aatgtacttt ctgtggcata
47281 atctaccaca gatttactct ttttaagaaa tgaacctatc acataagcta catctcctat

FIG. 19M 47341 attaattaca tatttataca tttcatcagc atcatgacaa aatattttac taaataactt
47401 tactaactgt ttatcgttta tattataaat tagtttaccc gttcccggta gtaataactt
47461 tgtaataata tatacatcat tataatcacg accgcgatgt ataaattctg atattagttt
47521 tgttttcttt acatagcttg attctgtgga tatagatgta catagttctc taaattcttt
47581 caatgttact tccatgtctt tataataagc caggtatttt ttacgttttt attcagggtc
47641 ttttattttg cccatgaaaa ccacagaacc tgttttatta tattttatta cgaatataaa
47701 aggtctattt atatggtagt tgttattaga tatttttcc catttctttt ggtcacctag
47761 tacaatctta ttatttataa aatctacttg tgatttaaca aacaaactgg taatagaaaa
47821 cttgtctgga ctaactgatt tcatggaaca attttcatca aaaatatcag ttatacctag
47881 ttctacaaag acagacttga tgttatgttg tgtttgtata gaaaattttg ggatactaac
47941 tgatatttct gaatatttca tgttacttac tcctatctta gacgataata aaattcgagg
48001 cgtaatatgt ttttccaaat atttgaaatt cttatacgta tcggcgaaga aaagtaacat
48061 actataagtg ttatgcaagt aaggtatgtt aatgatattg gatttaattt catgacaata
48121 catatgtcca aacattccac tcgtaattat gtacggaacg actttagtta aatacttagt
48181 cacaaaaaac ttatgactgt cattatctga aaacggtgat tcccataaat cagaatactt
48241 aatattaaat agaatgctcg cttctggagg tttccggata ctagataaca tatcttctgt
48301 attatagttt aattcactca ttttattaca taatacagta acatctcccg aaaccaatga
48361 tgttatatta gatttactta catacttctt gtaactatca tgaatacgtt tgttatgatc
48421 tataaagaag atggatgtat attctgttct agatagcagt tctttaagta tcttgtctgt
48481 attactatca tcgtcttcat catcgtctaa aggtagcata tataataaat ctaatagttg
48541 atttctcgat ctatcagtac tcgctttcaa taacattttt actataagca taatagaagg
48601 cggtgatatc actatatttt tatcggtat tcttttagta attagttcgt agaatttcgt
48661 agagataaaa gccaatttgt tgttgatact gcttacgtta ctcatgtttc ttgtttctgt
48721 taattaacag gtataccctt acaataagtt taattaactt ttaggttttt gtgaagaact
48781 tttagcttct agttccctta tccataattg ggtcttagat ctagattctt cccatgtata
48841 aagggggaca tacccaaaat ctttaaatgc tttgtccgtt tctatagtaa atgtcgtaca
48901 ttccttaatc aaagtataag gatttagtaa aggcgtgtaa gaacaaatag gtgatagtaa
48961 tactcttaaa cctttattaa tattagcgat aaaccttaaa caccataaag gaagacatgt
49021 attccgtaga tccatcccta attgattaaa gaaatgcatg ttaaaatcat gataatgttc
49081 agtaggagag gtatcgtaac agtaatacac gttcttgcag agaggactat gttgaccatt
49141 ttctatcata tttcttgctg ctaaaatatg catccaagct acgtttcctg catagactct
49201 gctatgaaat actttatcat ccgcatattt atacattttc ctgcttttat acgatcttct
49261 gtataaagtt tctagtactg gacagtattc tccgaaaaca cctaatgggc gtagcgcaca
49321 agtgcataat ctaagtccta tattagacat agtaccgtta gcttctagta tatatttctc
49381 agataactgt ttactaagag gataagcctc tttatggtta gattgataat acgtattctc
49441 gtttcctctt atcatcgcat ctccgagaaa gttaggacct accgcagaat aactactcgt
49501 atatactaag actcttacgc cgttatacag acaagaatct actacgttct tcgttccgtt
49561 gatattaacg tccattatag agtcgttagt aaacttaccc gctacatcat ttatcgaagc
49621 aatatgaatg accacatctg ctgatctaag cgcttcgtcc aaagtacttt tatttctaac
49681 atctccaatc acgggaacta tctttattat attacatttt tctacaagat ctagtaacca
49741 ttggtcgatt ctaatatcgt aaacacgaac ttcttttaaa gaggattcga acaagataag
49801 attatttata atgtgtctac ctaaaaatcc acaccctccg gttaccacgt atactagtgt
49861 acgcattttg agtattaact atataagacc aaaattatat tttcattttc tgttatatta
49921 tactataata aaaacaaata aatatacgaa tattataaga aatttagaac acgttattaa
49981 agtattgcct tttttattaa cggcgtgttc ttgtaattgc cgtttagaat agtctttatt
50041 tactttagat aactcttcta tcataaccgt ctccttattc caaccttctt cagaagtaca
50101 tgtgtactta ccgaagttat catcatagag attatatatg aagaaatagc acatatcatt
50161 attatcaggt ccacaatcga cgatagtttt gttatgttta tttacccaga cgtaattggc
50221 ttgatgagat tctatgggac aacttaaaac atgataggat gatgaactta aatacacctt
50281 tctactaaaa ggttctctct ttattaaact accggaacat atatttttag gaacatcgta
50341 tatatctttt tgtaggagtt tctttctcc accgtaaacg cagtcaatat ttgtccatcc
50401 gcaatgaggg tctctactca ggagacaact atcgcacgta ccgccgtata aatggcaaaa
50461 tgctaaaggt agttcgatag tactatcgtt gtaagataca aataattttt ccgaacgttc
50521 gtccgacact agagcgagca caggagatgg atattgtttt agagttaatt ctatgacatt
50581 tataactcca tcttcgtaaa ctactacttt gtgtatttta ccatcggacg tagaaagata
50641 gaacgtggta accctgtagt ctttatgttg gtagtttata acagctgtat taattactat
50701 atgtgtatac gtatattttg ttttaaatat aaaatctcct tttacaccat ataatgtttc
50761 aggatataaa tcgattactt caaaagtatc tctgggagtt gatgtgttta aacaagtacc
50821 tggcctaacc gacagaactt taccaccgct ataccctttc agtggagaag tattaaagtt
50881 attctgtatt ttatcgaact taaacataca tacggcagaa tagttccatt cattaaagaa
50941 tagtccatat ataatagttt catttggact tttacctttg attacgacaa catcttttag

FIG. 19N 51001 ataattaaat cgtacattca gatcttcgca gatcattatc gatttcagga aggtagacca
51061 ttttgaaccc gataatgacc ccgatcctcc ctgatcgtgt ttacatactc tagatacttt
51121 tgccattcct tcttcctgga agaatatata tattgtatca tttatactgt ttgtttcttg
51181 tagcgatact aaatgtacaa atttaggatt tttcattgta gaactagatg tatataatac
51241 aggcttacct acgattctac taaatcctgt acttagatga ctatattttt ttatagttga
51301 gtatatttct ttaccatcta ttaataccag tcctgtcata tcataactct ccggagagag
51361 tcctctaccg taaggcgtgg gttcttttat ggtaccgttg atataccagc atgtgggtga
51421 actagaattc gttccacaca ctagaatttt gtcatcatat ccacctataa atgtaatata
51481 attagcgcct gattgtgtcg atacattatc gggtgaaaag tccaccgtaa tattgctttt
51541 atcggttgta tttaccacgt atacagtatt tgttactcct ataattagtc gggtattaca
51601 atccgtgcga tatataacca catcttccat ataagtttta tacctaaact cgatattatt
51661 ttcagtcaac ttgctcttaa cacggggaga tattatttta gcgatattac acggtattac
51721 caaaagtata acgatgatga tacttatata aaacattatg gttggtatac tgttatattt
51781 tataatacta ttgatatttt gtgtatcgta tagattatat attcatatat tacgtcatat
51841 taatacatat ctattttta tgttttacga tatagataaa aatgaatata ataatttaat
51901 tacttattag tatcttgggt tttgtaagga cattctggct cacaacaacc cccatcagaa
51961 ggtttaggtc cggtatttac gcctttatca tcggtagatg gaggttgtac attccccttct
52021 gggggagaat cgattgttgg tttttcagct ggagattcca tggctttagg gttcaataat
52081 attaatgttt ctttttcatt tttaatgtac gttatttgt aataatgttt atataaatta
52141 ccatacttta gatattataa atattgaagt aaaagaatag tctaaattac ctaacataga
52201 acatcatgtc cacgagttta atagaattct ataattggtc tcttaccata cgtgataagc
52261 gtgtagacaa ttggctgtta atgaattctc ctattcccac aatatgtata agtactttat
52321 atctaattat agtctggtta ggacctaaat ggataaaaac tagaaacgcg tttaacatta
52381 gatggttact agtttgtat aatttttcta tggtatttct taatttctat attctgaaag
52441 aattatttgt atcgtcggca gcaaaaggtt atagttatgt ttgccagcct atagattatt
52501 cagataacgt tcacgaggtt aggatagcca gagcattatg gttgtactat atatccaaag
52561 ggatagaata cttggatacg gtatttttca tacttaggaa aaaatttaat caggttagtt
52621 ttctacacgt atatcatcat tttactatgt ttactctagg atggataggt attaaatggt
52681 ttgctggagg tcaggcattt tttggagctc agctaaattc ttttatccat gttattatgt
52741 acacttatta tggtatggcc gcttgtggtc ctatgttcag aaagtatcta tggtggaaac
52801 gttatcttac tataatgcag ttggtacagt tccatatagc tataggacat actgctatgt
52861 ccatttacat agattgcccg tttccaaaat ggatacagtg gtcagttatt atctattcta
52921 ttagtttcat attactgttt ggtaacttct atttagaac atacaagaat tctagtaaga
52981 aggttaaata agcatatatc taaaatgaca tacggttatc acaaatagaa atttatataa
53041 atagcaaatt ggtaatataa ataataatgt ataaaaaagt caacctttct ggtatagtta
53101 tatcagaacc aaaatcggta aaaaaattta agacaaaaga ttctatagtt aatgtattgc
53161 cagaatacta ccatactatt gctgacaaaa gactcgaaat acgtaaagat aaagataatt
53221 gctggttctg taaacaagat atgaatacat ataatcccta ttttatagag actctatacg
53281 gtgatcatat aggggtattt tgttccaaaa tttgtaggga ttctttcgct aacatgataa
53341 aaagtgtaat agctttacga gaagaaccta aaatatctct tctgccgttg gaactatatg
53401 aaaagccgga agaagtatta gaagtaatca acgatctaag acacaaagaa ggaatatatg
53461 gaagctgtat acttgaatcc gacaaaaata tcattaaatt aacactaaga tgccattgta
53521 atactaatta aataattttc acttactata aatgaataat tctataataa gttcggtaat
53581 taactctata gattctagca gcaagcgaac taacatattt agcttcgatg tacaacagcc
53641 cacggcttat atgccacaat atatatccgt taacggatat cataataaaa aagacaatga
53701 cgctaatcaa gtatgcagcg tgtcattcga tattagggat cagcatatag cagctataaa
53761 ttatttcttt atatcaatac aattgccaga agtatcggga gaaggtaagt ttgcttacgt
53821 accatacgta ggctataaat gcattcaaca cgtagctatt acctgcgggg atattactat
53881 atgggaaaca gatggagaag aacttttcga taagtgtgta gatgataaga tagcgagttt
53941 atccggttat tctccagagt taaacgatat ctccacagga tatactccta acgatacgat
54001 aaaagatcct actactctat atgtatatat aaaatctcct tttgatgcgg ataaaactat
54061 tagtagtttg aaactagtta ataataagat aaccgttaca ataacattca gaagtattaa
54121 tgatgtaata gtttatgatt ctaagtttca agtagagagg tttgttaaag actttgttta
54181 ttctactgaa ttacatctaa tcgcttacgc ggttagtgat ataaaaccta agtctgctta
54241 tatagagttg gatcgtagag tagtctcgtg ttctagtacg cctaccccta tacccgttat
54301 ttcagatgta tacgcgtgta ctgctatgtc tgtttatgtt aagccctatt acggaatgat
54361 ggaaaacaaa tttatatctt accccggata taaacaaacc gaatctgact atgtaagatg
54421 tatggtaaat cgcttgctag acgatcttgt tgttgtggca gatacagtac caaaaggttt
54481 tccgagcacg gcaacatttg taaaagttcc tgttgatgga cagataaatc tacaagatgt
54541 tgatataata gttaaaatag acaacgtacc cgatgataaa gatatatact accatactaa
54601 tctattaata ttcggaacaa ggaaaaactc tttcgtttat aatatatcca agaagttttc

FIG. 19O

```
54661 atctataata ggtatgtatt ctcctaatac agatagtatc aacttttcta aagtaaacca
54721 taccatcagt attacggatg cttctatacc tgttagcttc tgggtatcac aaaagaacgt
54781 ctatcaggga gataacagat ctaactattc taaatctaaa gacttagtag taaacgatcc
54841 cttcaggaaa ggaatagata tggttaataa aacggatgta atttctagac tagaagtacg
54901 ttttggaaat gatcctatat attcagaaat ctctcctatt acaaaagtat ttaacatgct
54961 acttactggg agtagcataa atatgaggaa gattattttt aatatgaatc cggctaatat
55021 atttagacct accactctca atgctaatac taagagaggg aaagataaac tcacagttag
55081 gatatcttat atcgatacag atcctaataa tcctatacat tatgtagcta aacaactagt
55141 agttatatgt acagatctat acaggataga ttatgatggg aatattaata taactaaaat
55201 tactgaataa aaaatgattt tataaataag gtattaataa aatgaatacg gacaggataa
55261 ccgctttcat taaaaatggc atttcagcaa gaatgccttt ttatgatact ttgccagata
55321 tggatcttgt ttttggtaaa aaccatttgc ctagtctaga atacggtgct aattatttc
55381 ttcagctttc aaaaattaac gatattaatc gtttatctac tgaaatgtta tctctatata
55441 cacacgatct taacaaagaa tctgatatta gtaaactttt tgaaccttat aacataaaga
55501 ccataaaatc ttacggaaga tctattcaag cagatgctgt agttgtagac ctgagaccta
55561 gcaactcgct ttataagaac gaacatcctt actataaatc taataactac ttaaaagaaa
55621 ataatctata tatatgcgat tatactatga taacttttga gatatatcgt ccgatatttg
55681 aattatccac agagaaaaca tgtattatta aggtaccaac tctttttgga aaaacaatcg
55741 taaacgcagt gcgcgtttac tgcagtctat ttagatatgt caagctttac aaactatcgg
55801 ccgatagttg gttaaaagat agtgctatta tagtgtgtca acaaccccat gccgcaaaca
55861 taaataaatt tataacttat attagaaaag ttactaaatc acaaacttgg ctagacagca
55921 acaatgtaaa ttttatatta atccacgatt ctgtagaaag agtatttata gaaaaattct
55981 tatcatttc atataaaata tatgaatctt tatattacgt tcattcgtta ctctacagta
56041 gcatgacatc tgatctccaa tctctagata acgaatatca aaaaaagttg attaagttgt
56101 tacgcggtta atcgtattaa taatatcata gctgttacca atactttact aatgataatt
56161 tgttcaacaa attacatata gttaaatgaa cacgtacgct gcgtatattg attatgcgct
56221 taagaaatta gatacctttc ctgtagatat gactggcggg aacgataata cggtttttatt
56281 gaaggattac caattatttg tagcaaaagt tttttagga ctcaatagta tgaactctat
56341 actattattc caggaaacag gtgttggaaa aacaattact acggtatata tgctcaagaa
56401 ccttaaaaaa atatatagtg aatggactat tatcatcttg gtaaaaaagg cattaataga
56461 tgatccatgg acgcatacta tcttagatta tgcaccagaa gtaatgaaag attgtattat
56521 catgaattat gatgatcaaa attttcataa taagtttttt acaaatataa aatctataaa
56581 cgtaaaaagt agaattttca tcatcataga cgaatgccac aactttatat ctaaatcact
56641 gaccaaagaa gataataaaa aacgtaatac taaacttgtt tataactaca tagcgaaaaa
56701 tcttatgcaa aaaaacaata aacttatatg tttgtcggct acacctattg taaacgatgt
56761 tagggaattt cagatgcttg ttaatcttct tagacctggt atattaactc ctgataagtc
56821 tttgttttat aataaaaagc taatagatga aaaagagatc atttcaaaac tgggatgtat
56881 atgttcctat atcgttaaca atgaagcatc tatattcgag gacgtagaaa atactactct
56941 ttttgctaaa aaaactgtac atattaagca cgtgtttatg tctaaaaaac aagaagaact
57001 atatctaaaa gccagatatt tagaacgtaa actcggcata tcggtattca aaatatatca
57061 acgtatggcg tctacttttg tatttgatga tattccagat aagaaaaagt taaccgaaga
57121 agaatatgaa aaatttgtag attcgttatc tatagatttt aaaaatacct tatacggtaa
57181 aaaaatatct aaacagtcgt tagatatatt atcagctgga ggtacaatta atgatatcaa
57241 agacgttaaa gatatagaat tatataacta tttgtacgag catagttgta aattcacatt
57301 cgtatgtgtt tcaataatac aatctaaagg aaaatgtctc gtatttgaac cttttataag
57361 atcgtcagga atagaaatat tgctacaata ctttaacgta tttggtataa catatataga
57421 gttctcttct aggacgaagg atattagatc taaaagcgta tccgatttca ataaagtaga
57481 taataccgat ggtgaaataa cgaaagtatg cgtattttcc caaagtggaa acgaaggtat
57541 aagtttttctt tctataaacg atatttttat actggatatg acgtggaacg aagcatcttt
57601 aaaacaaatt ataggacgtg ctatacgcct taacagtcac gttaataacc cgccagaacg
57661 tagatacgta aacgtgtatt tcgtggtagc taaactatcg tctggtagat ctagcgtgga
57721 cgatattttg ttagatatta ttcaatctaa gtctaaagaa ttttcacagc tctataaggt
57781 atttaaacat tcgtctatag aatggatcta ttctaactat acagattttc agacagtgga
57841 cgatgaaaag ggtttaaaa aattaatttc taggaatatc atactagatg aaaatacaat
57901 aacaaataaa aaaaagttaa ctatgggtga aaatatatgg tattcatttt cttcttcttt
57961 agtatccatt cacagaggtt tcaaatccat ggataataaa atttacgact ctgaaggatt
58021 tttcatcaca gtattacccg ataagcctac tataaaaata tatgaaggaa aattaattta
58081 tatattaaca gttagataga tgttaactat tgctagcgga tgttcttaca gcgtttatta
58141 tatatttaat tacattagta tacaaataat ctttgttaat atctcttgcg tctataaatg
58201 atattccttt aatttctcta ttagggatga atctattcaa tatttgtcta ctcgtaagat
58261 ctgtttctac gtaaagggct ataacttcaa aatctttatc tatcaatctg tcgtatatag
```

FIG. 19P 58321 aaccgtatac aaaacagttc ttacagatag cgagataaga ggaatcgata tttaattctt
58381 cttttatttc tcttactaga caattagtta tactttccaa gtcttttatt ttaccacctg
58441 ggaagattat atctatatgg tttgtattat agttattagg aagcgatagc ttataactta
58501 atatatcacg ttcgatgtta ctcatatact ttgaatattt cttaaagagt cttattttcc
58561 gtcgtttatc ttttgtaaat gctatttctg aaaacaagaa actattgtat ctatggcata
58621 aaacaaactt gtcatctatt gttttcatta tacctattac ggatagtgga tatttagcat
58681 gtagtttgcc atattcatat gctaccagtt tgattttttg tatattatca gaatatacag
58741 acggcctaag gagcaattta tttttataat actccccccat atttatatgt taataaggta
58801 ttataaataa aatgcaagta ttcgtatttt tcattacttg atcgatcaaa taatgatcct
58861 aattctttga tttctatgtt atataaaggt ttaatgattt ctgaatagag ttggtctata
58921 aaacacacta tacaataccc ataaaatgtt ctacgaagta tcttatcttc tatggtaagt
58981 tttaatattt tattaccaaa tgtttttata gtaagtattc catcgctttc ttccgatagt
59041 tctctactca ggcattgata tattgattct ttatttttaa ctcttcctcc taataatact
59101 aactcttcaa agttgttgaa tccgctatat gtgaatggta ctattgatct aatgatattt
59161 ctttaatttc gttattatac atatacttta gatggtttat atcgacggct aatatttctg
59221 aaaagcttct tctttttgat ataaccgatt gatacataaa agacgttctt cttataccga
59281 ttataggtat attatctgat gtaatacata acgcgaatat gtgaattcgt ctatcgctaa
59341 gtatatcttt tatgttagtg ttttctatag ttattcttta tttgtttcga aagtaataac
59401 acaatcttta tttttttcta atatatttg ttgttctctg gatatatcga acatgatctt
59461 agtttttata gttgtttatt tttcacttat gtttgataaa ctatatatag tgaaatagca
59521 tatcgtaaac tatataaaaa aatactagtg tatcccattt atgaatatat tttttaatt
59581 aagatataaa ggaatatatg atataattaa actaataagt taacgattat atcgttaaag
59641 tagaaaaatg tattgagaaa ttattttact ttatagcaat atataccgcg tccctgagat
59701 gatctattct actatccatc caccgtacgg actttttttg actttgcatc tttccataaa
59761 atgtgatcct tcctctgaag tataactatg atcagattct gtatctgata aaggagataa
59821 tgattttacc agtctaaatc caacatttcc aatatctcca caggtaacta cgcacatata
59881 cttacctgtt gattctcctg ttgtaggatt tgggatactt agcgatccta tccctccata
59941 agtatgtaac agtaagttaa ctcccgaagt ctgttgttcc cattttcgtg taataccgtc
60001 aatcttccac catttatgt tgacttggct tctaccatat attcgtcggg tactaaaagc
60061 acattcaatt tttagcggcc gaccatccga catatctact ctcgatcttc gaggggttat
60121 acttacttcg ttatgcatgt aggtttttt tgaaacagta aacactccta gattcatttt
60181 tttataatca gcgtcgccgt ttatccatac aacacacata tatgaacctt ctgcttcttt
60241 agataccttg gatatatgta gcatggtttg gcccacttgt cgtgtcgtat cccaagttgt
60301 ttttattcct tgagtaactt ctccgtcacc ctgttgccac gctacaatta ctttatcttc
60361 tccagcaccc tgatcatctt taataaaaca agtaagattt atatcactac cttccggtac
60421 gagtacatag ggaggtgctt ttacttctac aaaagttttt gatagatata taaagcagag
60481 aaatattatc aacgtcaatt ctttatgtcg aatactattt ttacatatca ttgtgtgtat
60541 aactaatatc tttctacatg ataaagaatt caatatacta ttaaaatatt tatagttatt
60601 tttgatttta caaatattac taaatgctat ccatgtttaa taagctatac gttacatgat
60661 gtaggtatta tgtaaattaa tctttattaa agtattattt ttcaattatg ttacctaaga
60721 aaacaaaaga tgattccatt ccagattggg cttcttttaa cataacagta actgtacttt
60781 cattagcgta gactttaccg ttctttatga aacagtattt tgaattatca tatgaaacag
60841 taccggagtc gcttctgatt ttacaaatta gatcactaca aactaccgaa atatcagatt
60901 cgtctgtaat agttagtata ccagaaacta tatcacctac cttatagtat ttataatcta
60961 tgttacatgt cacatgaaca actatttcat tattaactaa ctccgctaat ggcatggggg
61021 tatcttctac tatctgtatc ttttggccca taaacccaga tgtttccttg tgtaaatact
61081 tatttataac tgcctttttt atattatcca ttagatctaa atttaattca tggggttgta
61141 taactacggg taaatacgcg tttgtattaa acaacgacat ttagttcctt tctaaaatta
61201 atcatccaag aatattctgt aaacaataga ttgaaaggta ctactataat atcattttta
61261 tgtttatata acaatgattt ttcaaatact ttattagtaa cgaagaaatg gtcgtctgtt
61321 atcttctcta tatatttttg tgttttttct ttggatttaa aaatactatt taccatttta
61381 aaaagtttag catcgtttat acttactcta gaattgtggt aaaaaaattg tctaaccagc
61441 tcgcctaata caacatccgt tatataagga tggggtgatg atctatagtt tatagatata
61501 tcttttagta tggaataaat tcgttttgtt tctttcgttt taaactttag ataaagtagt
61561 tttttgatat cgaatggtaa agtatttata tcatctatac tataatcatc tagagaagtt
61621 attgtatcgt taaaatctga ataaaccgta gctaataggt atacgttaac aggtttcgaa
61681 acatctttat acgagaactt tctaatagat ctacccaaaa tctgattgta ttgtgaaaaa
61741 gtatcaggta tagtcataaa ccagatgttt cttacttcct tcaaagtata tgattctgac
61801 ataatattgg aggaaaataa aaacataatc ttttctccgt tatcattccc tggggaatta
61861 tacacttcca ataaatcttc taaggatgac ttcattttac tcgtgactat agcaaatgtt
61921 ttaagatgtc cgtttatcat ttttggattg gtaccttgcg aaccggcgta ttcagaatat

FIG. 19Q

```
61981 ccgttgttaa gcatgatata cttgatgact aatccaccgt atgtagaatt agaaaaatag
62041 ataaaatttt tacccgtaag attcccgata gtatctataa aatatttaaa ttttgagctt
62101 atattaagtt tagttaattc gtctccgtat aagacaccgt cgtttatttt caaattagga
62161 taaagttctt tatcctgttc tacgaataac agttctaaac tattagccaa attcaaaggt
62221 cctaatacag ctaaagaaac atttgtcatg ttttttttcaa acatttcatt attgcacaat
62281 ttccgtacgt ttatgtagtc agtttcctgt agtttagaca ttttacaata aactactttc
62341 gtatctaaaa actctttacc gtgaaagatg atactcggta gttccgtatc acataattca
62401 tagtaggata tcttattctt cagaatattt tttaatacgc ctacaccttt ttcgttttaat
62461 attatctgaa atactttctt tccctggatt ataatatcgt taaagtttat accttcatcc
62521 gacataatac taataatatt agatagtgta ataggtgtat tagtgatagg agaccctgat
62581 agtaaaagaa aaggtacctt attcttattt ttaataatag tcattaattc acctgtattg
62641 tttccgaata tgttatgagc ctcgtctatg atgaaaatag agtcgttgta cttagataaa
62701 gcattgtagt tcactacatt atcgttgtag ttaagactat agaaattaat cgtcgaataa
62761 atatgaatat tttcaataac atattctgta ttgatgagat tagttgccaa atctaaatta
62821 tacgtaaata tattaagtat attaatatta ggtaccaata tgtaaacctt tttaaacttt
62881 gacacgataa gtgcaaatag cagtgctata atagttttcc ctgaccccat aatatgaaac
62941 aacaaaacac tttcattatg atctagtata gtccttaaaa gataatccaa ggtagctaat
63001 tgatgaggta agatattagg aatgttatct atgtgcccat taaagagttc aagtatttct
63061 aggttcattt atagtattca aatcttctat gaatataaaa gacatgtatt catcggccaa
63121 gttcatatat tttttatttct tcatgataaa actgtcaatg tcttgcccgt atagttttac
63181 attaaaatgg agacttaatt tctgttgaaa tatgtttaat tgtagtacag gtattccatc
63241 atcgtctgtt atatatccta atttcattaa tttatctaca tatttcacat gcgtagaatt
63301 actaggaata atgagagatt ctacttttaa tctgaactta aagtctggta ttttatctgg
63361 tgttggtaat attcttaagt taggaacatg atatttacta aaccatccta aaagtatttt
63421 cagaaacgcg tatctaaaat aattagattg aattttttgaa tcaagacttt cgtttaacgg
63481 tttaataaaa tcatactttg agttatgcac cttctttttt gtattagtaa agtgagtttt
63541 aaaattaact agagctatcc ttctcattat agcgttatct actttatcga atacgggttt
63601 atagttggta tctattatga tagtagcatg attcctgtta ttgattttat tagaataaca
63661 agatcttcct actacacagg gttctgttaa cttcttgata ttgtcggatc ttattttttt
63721 ggacgtatta caactaaaat caggaagttc gctacaaaat actactctct tcaagtgcat
63781 gttagcgata aagggattag gacctttatc catttgttct gttagaataa cctgaccggt
63841 ttctagaaac atattatgca tgacagattt tagtaatttt ttagtcgtcg attttccagt
63901 agctgtttct ccataaaaga agaatatgca ttgttttgta gtacccatga gacaactcga
63961 aagtatctgt tcgtagagtt ctctattttc aaaattttcc tttgtctttg gttggatatc
64021 gtctagtata gacattagtt ctgtagttat atcatcaaca tttatacctt cttcgtattt
64081 atacccagtt gatacagtac aaacaaattt ctttgcgtca ttaccttgat agaatataga
64141 atcttttata tcatacacac cgttaagaaa ttgtaatttt tctggataag tgtcggtttc
64201 tatcgtatct atcaacatat ctttaaggtt atgttctatg actttccgat ttctaggaca
64261 tagtaacaaa tcggtacagt cggatgataa gtgatctctc atatatagta ttaatttggt
64321 tatattatta tcatcttcac acattctcca cacgtttttc aaccaaacta gatattctcc
64381 tctatctgaa acattaatta cattaagatc tattatttgc tgtgaaatac tgaataattt
64441 attaccttct aaggaaatag ttttaatctt acagctattg ggatttccgg atttatatat
64501 tcttatacaa tcgttactaa tcagtaagtg atgaggatgt ttatgagata cttttttaca
64561 tagattacaa ggcgtggcat agtaaatatc taaaggagtt actgtaaagt tttcagctgt
64621 aatatccttt agattaatta tgctattacc tatagcttta gatatttttt tgatagcgtc
64681 gtgaaaaggt atatattcct ctttccagtt taagagatct ggagattgat gttgttgctc
64741 gctgacgaaa taataacagt cttcttcatt ataatctaca taggtgaata gataattttt
64801 aaaatgaata ttttgtttag tctttttatg aacgtgaatg ttaatcgaat ctttcttagt
64861 tcccactatc ctaagagatg gcttatgtct gtaaactgat gtatctatag cttttactaa
64921 acggttattt gattcttttg tcaatacaat taattttta cgcatattta tgagagtatc
64981 cagggtagta tagcaattga aaaatataag atgaaaactt gtttttcctt tatcggtaga
65041 ctcggttatt gaaaaattcg atttcatatc agttatcatt ttatctttat ctctatgatt
65101 acttatcatc ttacaatcgt tataggcgta atctgctaca aactttgtaa tgatgtttac
65161 aaaattatga gtagcctgat atttatcatc taacctccca tccatatcca catcaaaaaa
65221 caccctgaca tttgaataat actcttcatc ttttagcgtt tcgaataacg tacaatctgg
65281 attgctatag atatatcttt ccagttcatc gcatgtaaat gattctacat atttgctgtt
65341 attattttct ctatgttttg tacgtacacc tatctgctta agtacaaaaa taatgtgatt
65401 gtttcttatc acagaaaggg ccatttaaat cattaattaa aatttcacta aaaggatata
65461 gtttcttcta taagtattta ctatttttaa agttagatat aatgtaaata ttgtttgata
65521 atgataacgt ggttacaaac acaaacatac agtataaaca aatatgactc tttgtattaa
65581 tataaattga ttttctattt taaatctcgt tatcgttata cgatttaaat attatgtaac
```

FIG. 19R

```
65641 tctgtattta ttcgacacta ttaatctagt acatacagaa tttctttcgt atcttttaaa
65701 caatataaac ttcaatactc gtcgccgaag taaggcaatc ctagtacact tctactattt
65761 gaaatatcac aaaatgtatt attggaagca atagcgggaa tactttggtt tttacacgaa
65821 tgtagaatgt tctatagttt ataacagcat aagctgatat actatttata ttaagatctc
65881 tatgattatg acaagattta ttgtctgtat ctacgttgaa ttatatttct ttgataaaga
65941 tattatttat aaaaagtatt attattttta ggaatacaca gtagagatat ataagactat
66001 gattagatat ctcttaaccc caatactcat ctccttcaat gaaattatag ctacgtctat
66061 ctacagacgc acgaattaca taacttaaac ggaaagatag tgcggttact agatatcccc
66121 atctctccag aacagcagca tagtgttagg acaatcatct aatgcaatat catatatgaa
66181 tctcactccg ataggatact ttaccacagc tattataatc ttaatgtatg ttctatcata
66241 ttttaaaaac agaaacaaac ggctataagt ttatatgatg tctatattat agtgagtata
66301 ttataagtat gcgggaatat ctttgattta acagcgtacg attcgtgata agtaaatata
66361 ggcaatggat agcataaatg aattcacatc taaaaaacta tccatagaag gaaatatatc
66421 ttctggaaag acagacgtcc taaatatact aagaaatatt aataacgttg tttctttcca
66481 cgacgtagaa gatagatata ctcctataga aaaagaatta ataagaaaat tccatgaaaa
66541 tccttcaaga tggagttacg cgttacaaac gcattactgt atgaagagag tcagaatgca
66601 cttagaatgt tttgtaccta gccgcgtaaa tatattagaa agatctatat ttagcgatag
66661 gtatgttttt gccgaagcag ccacagccct aggatatatg gatgacccag aatgggcact
66721 ctactgtaaa cagcacgatt ggtatacgga taaattagag atccagtttg atggtattat
66781 ttatttaaga actataccgg agtcgtgtaa agaacgtatt aatgaaaaat ctataacgga
66841 gaaaaactat ccaaatataa gtatagacta tttaaagaca cttcatgaaa aacacgaatt
66901 atggctgacg caatgtaaaa aagttccggt attaataatc gatggagaag aagattttat
66961 attcgatcca tgtgcaaaaa aaaaattaat aaacgaggtt acggaattca taaattctat
67021 ataaactatt atattaaata aaattgtcag ttaacggtac aaataccgtt aacctttttct
67081 ggataaatct gaacattcac taccaaaata gaatcctata ttatcgtttt tactgttttc
67141 tggtatgcaa accgccgaac cgttatttct caccagtaag tatcctctat cttcacagga
67201 agcatctgat ttcctgcagt ctataacatc atcttcgttg agtgaactag atgaaacttt
67261 tgtatagtca ttgcagcatc ctagcggatt gttggctcta agactatcta cattttctct
67321 taaatcacag cactctccgg tacatcctcg atccggcaga ggcgggcatt tagcgatgca
67381 attacggagg tcttctcttg tttttgaagt atagttactg gataggcaac actgtaaaat
67441 ttcacctata ccttcattgc tgcttgccag atattgaaga ttacatagta acacgcatag
67501 gtctctatca atagcagcat catcgtattt tttacccgcc atacagcact ctgtttcgca
67561 tgataacggc atacagagta tattatagaa atttattaca aaaaataata tacttaattt
67621 gtaacgcgta tacatttgt aatcctttta tttatattta aaaaaaatta ttttagaata
67681 atcttgaaat tggtatatac ttaagagata gaggatagct ctgcgcagct ataccccact
67741 taataaatta taccgcgcag agtataaaag attatattat ccattactat ttataataga
67801 gataacagaa cagtataata tttcatatac taactcatta gtacgagaga tgtttttaac
67861 catctatcgt attattaaat tattagtact accgacgtac aagtattatc cattttacct
67921 attttaaat gtatcgtacg tagtatacga tactcgtata gcaaaactta ccatactata
67981 gcatataatg tcgttattat atgttatttt agcaacttat ttttatgtta ttaatactgt
68041 tattactagg tgatttacca cgcggatatt cttccaacat cctagttata agtctgccgg
68101 caccaacgtt cataccgcta caatttggaa atatggcacc aattgtttgt ggataattac
68161 ctttatccgt ctcattccct gttatgcaat aagttttatt ttcactagtt gttaataggt
68221 agccactgtc cgggcatccg ggcccagttt tggtacaatt taaaactttc caaggagcgg
68281 gaactggtcc gtatctgcca ttacagcaat catctctaca ctcgtacgtt agtataaaag
68341 gattgtaaaa acaggatcct attacagtta acacgtatat agaaatatta ctctgcatat
68401 ctgcgttaat taagatactt gtaaacactt aatagtaatt catctgttaa tggctatatt
68461 atttttaaat ttttttaacc ttttataaaa acattatatt tcaaatcctt gtacccaatt
68521 tattctgggt tcgttcttga gttctaataa cgtgttaaca atttcgaaag tttcgtctgt
68581 atcgaattga cgattcctag ccgctggatg atagcctact actacagtag ttggagagtt
68641 taatatagat ctaaaattcg agaaatcgct tttacctaaa aagtaaaaca cggatacgta
68701 ggccgctata tggttgatga aaacatccgc taacctttcc cagaaaatct tgtgactttt
68761 tgtttcgcct tctctgcaac ttaagtaata gttccacgct aatacacctt ctacaaacaa
68821 aaaattgtag ttcttgaaga gtctgacgtt atatcttcta gaaatatttt ctgctatagc
68881 cttaatagtt ttttttgaaa aatccggaga ttcgaaaggc acgccggtag catccgtggg
68941 gtaaggatct ataccgacta tacatactct tttatctttt agtgattgtt taagttgttt
69001 aaaaatattt tcatgagacg gtgatgtatt ttcttctagc agccaaggtc ctgtctcttc
69061 tataacatca gatatatggt taataatatt ttcccaatcc tcgtggtatt ctataggata
69121 cggccaatta tttaacttta acgtcttcat tatagattac aattattcat atttattttg
69181 ttttcaattt cgctgtatca tgcacgtgat agaacaggcc agtcattata ccacttattt
69241 ttatctagta aattcaattt taaatcatcc cacagttcga cttctttact gatatctaac
```

FIG. 19S

```
69301 atccaaggat taaatggaag atatttatat tgattattat caggtgatat tactttatta
69361 ttttgtttat ttttattatc catagaagat ttatacttat tatacctaat aagttgtatc
69421 gatgctactt ctttccaaaa atttctaaat gtaatacgtt tacaatctaa tcctagttta
69481 ttagcttgtt ttcttactat accaaaagcg tatattagta tatctcctaa accgcaatta
69541 ttagttattt ttctacccgt cattcgtttt agaatacgta cgatggtgtc caaattaatg
69601 ttatgtgtac cgtattctcc tataatccat agtctaaaaa acgttatact gggctttccg
69661 aggggccatc ttaaagcttg tattaaactt ttatttttac tttttagaat atctgaaatc
69721 ttgtatttat aatgatatat aggattacaa atccagtaag cgtttataga actaatatca
69781 gtaactttta tattagttct atccaggtaa tattcactcg taatacattt cttagttatt
69841 ctagatatac tgtgttttac aacacgtgtt ttcttttttt ctatatacca tttaccgatg
69901 ataaatccac aaccaactag taatgctttt ttattattct gttctataga tttatatctt
69961 aacatgttag agtcgtagta acatattaat atcttatatt ttttaccaag agttaattta
70021 tattgttctt cttcgttgtt atttatttta acagttgtaa taactatatg gttagtatgt
70081 tctgaagaat ttatcaccat atggtatcta gcggacagtc ttttcaagaa cagctttaac
70141 ctatctattc ctaccttcag tttaatatta tcgggtaaat ccaaaaccag tattaataaa
70201 tgggaattat gtaattttaa tgatattgtt gtgtatttgt taactattat tccgttaagc
70261 attctaatat taataatatt accaaatttt gatagaaacc tatcgaatct aaatctattt
70321 acgcttatat tcttttcatc tatcataaat ctatccaatg aataattatt gcttaatata
70381 ttagtgtatg tagagatcat gattgtatat attatagaca agtaaatttt tatttttttt
70441 tcaatatttg atgcgataac atatttata ggagattaaa taaagtacaa ttattgccta
70501 tagttgataa caattaatat attattacgt gcttttaaca gttaaataac atacgtttta
70561 taataaatta aatgaatgat gattggatat tgcatcatac catttataat tttaacctca
70621 atctattaaa tggggagagt tttgacttta aaacatataa agataagata tgtatatttg
70681 taaacgtagc atcggaatga cgactagctg acaggaatta taaggaactt acaaaattat
70741 acgacaggta tttttgtgat ggattacgta taatggcatt tccttgtaac cagtttggtg
70801 gacaagaacc aggtggtgtc aaagaaataa tggaaaccat aaagaaatat tcggtattat
70861 ttgatgtgtc cgaaaaggta atagtaaata ccatatacgc gcatccttta tggaagtggt
70921 tacaaacaag gcctatactg ggagatgtgc ccggtcctat aaaatggaat ttttgtaagt
70981 ttctaataag tccttttggt tacgttatta agagattcga tcctgaagtc aacccctatgt
71041 cgatacaaaa agatatagaa catgttatag aacaacgtgc taatgaagaa atgactataa
71101 atagatgggt catgcctgac acgcattgtt ctgaggaaga atctctttct aaagatgtgt
71161 taaatgacgt ataataaatg gtatctaact actgtgttgt attcatgtta aataattatt
71221 catcggatga ttataaaaaa ataaaatctc tagattatca ctatctaata cttgataaac
71281 attcagatag ttctcataaa acaatatctg gatacgtaga gttaaaagat ggtatatctt
71341 gctcgataat agaaaacata aattctcgaa tattatataa aaaactacaa ggaaacaagg
71401 atttttaag aattaataaa aagaatatag tagacagttt taaatctaaa ggttgttacg
71461 aagaatacag atcgagaaga ttagatctta gtatttttga ttactataag taaattcatt
71521 tctaagttta cggcttttag ttttttata catgtctttg tttaatattc ttttacatat
71581 tgtcttctca cttaataccg tattttttag catagatagg tattccgtaa agtgatacat
71641 tatatggtct aatgaattat cgtctagttt aaaagtatct atggaatcga gataattatc
71701 ctttaaaaac cgagtatata attattttat ttcgtatatg ttgtaaaggt tatattcaga
71761 aacatctagg tttaatatat cttctctgca ttctccgaag taacacggac ttataccatc
71821 gtgtttaaga atatcattta cttcatctat actcatttct tgatattctt gcacgctatc
71881 acatctgcag gccttgcttt taatgtataa ttatatttat gtttttgtt tttttccctt
71941 attatattaa atctaaaaag caaataagtt gttatgtttc ttcaggctga atagttatct
72001 tgtaaacagt aaatcctctt atcctttta tcaattcctt gattttaggt tctatagtgt
72061 ttctaaatgt aacggttttg tgatatttac ccattctgct acattgtagt ctataacaga
72121 aacgttgata aaccgattta aatgcataat tagtcatttc atgaaatcga cataatatta
72181 catctatgtc ctttcttgaa ttcatcacaa acactatttt taccatgatt ggtgatataa
72241 acatatagta tggtatttat ttttatatat tacagatcac gatattattt ttgggtgcgg
72301 gtaatcctta atacatgtat tgtatatcac agaagtaatt aaatcctgct gtgatactat
72361 ttactatcat tacaaaaagt aatgataaaa acatccataa ctacctacca cgtacgataa
72421 cgtgataaag aacggatgtg acaataaata ttttataaat taattattaa gttaaaacat
72481 taatatataa taatcattat tttttgctaa tttcctattt cggactagag caaaatatat
72541 gtaaaaagtt attacattaa ctcaattgat ttaaattaaa taataatatt ggataaatgc
72601 tccaacagtt ctttcaaaaa ttaatttctt tattacgtaa accactaaag atatctgtac
72661 ggggtttgct agaagagcct ttttcgggtt cgggagtagg ttgatctgat ggtttactag
72721 aagagtcttt ttcgggttcg ggagagggtt gctcgggtgg tttactttcg ctaggttggg
72781 gctgtggctc agaaccagca tcattagaag gaggcatcgt atcaatatcc gacttctcgg
72841 tgggtgcttt gctactacct ccagccaatg ttctaaatac gtcactaatt aacttagtca
72901 tgttgtccat tctgccacgc atatcttcgt ggcagataag tagctgcctg gtaaagacat
```

FIG. 19T

```
72961 ctttggcctc ttggcctttg agtttttcat actcttgaat cagtttcttt tccatgattt
73021 ataggctata aaaaatagta ttttctactc attattttac tgttacttaa actaaaatac
73081 aggattattt atattctttt ttctatcatt tcataaacgg ttttgatagt ttcgttttct
73141 tctttacaat tacttagttg tccgctatac caagctctaa caaatgcatg aaacttatct
73201 ctatcgtaat cgaattttac taatttttct atatcactac tatcgaataa ttcatcagaa
73261 ataattactt tccaaatgtc agtatcgctt aatgatacta tatgtttatt taatatacag
73321 taaaggttag atgattcctg ttttcttatc aagcaattta tctcttttct caataaaatg
73381 tttttataaa acaaatctga tttatccata tttatttgtt ttataagatt gggagatgta
73441 taaaaaaatg aactgtcgtt gacttgataa ccatctataa ctatctcttt ttcgggtttt
73501 aataattgat gacatttgat catcgttata gttttgatat ctccgttaca tctgtaacat
73561 aatacataaa catggagttt atccggttga gaatacatct ttatatttcc ctcgttgttg
73621 attacacatg aacctattac ttttttatat tctttatata acattaaatt gattctttgt
73681 ttgataggac agacaacgtt ggatgtaata aaagaatggt ataactcatc ttcatcgtta
73741 acacttattt cataaacata ataaagttct atgttgttca tcaataatat tattctttta
73801 tttataaatt catccgtatc tcctagtaaa atgtatacat tattactact attacataaa
73861 tagtctactg atgtataact atttaaccta tgtatttcca tctaaatatg atatttaatt
73921 tatatataaa atatagataa aatatcacat ataaaagagg tttttataa tattataata
73981 gtagtatata atttttata ttatatatga ttcaaatatt tatataatgt gtatattgtt
74041 tttattcttc gatccccata atatatatgg gagatttaaa tatataatag cgtctaatag
74101 agatgaaatt tattctcgtg aagcaatacc tgctaaattt tggaattcta acggctatga
74161 tgtactcagc ggtatagacg taaaatccgg ggtacctggt taggcataaa tactgacggc
74221 aagttttccg tagtcactaa ttacttacaa ccttacgaag atcctaattt tataagtagg
74281 ggaaatttag tatctgatta tttaacatct aatatatctt ctcgtgaata tctatgctat
74341 ttatcaaaga gagggcattt atacaacgga tttaatctta ttacggcgtc tttttctaaa
74401 gaatccgatg atttatatta ctactctaat agatcaggta ctgcaccaga aaggctagga
74461 accgggatat acggattatc taattctttg ttagatatat catggcctaa agtttgtgtc
74521 ggtaagaaag tattcacaga tataattcat gcccataaga atgatttaaa ccaagaatca
74581 ttaatcacgg aattactaga aatgttaaac gataccagtc cgctaccgat agatcctaga
74641 atacaggaac agggccaaga tttcataaga ccgatgataa aagaattttc atctatatgc
74701 gttagagccg atggttacgg tacaagaaca aatacgatag taactataga tagtcattat
74761 agtgttaatt ttattgaaaa aaccataacg gatatggaca caaaagagtt taaaatatcg
74821 agatatacat ttagtttatt atcttagaaa aagtaagtgt atcaaagttc tttatttata
74881 taataacata ctgtaacttt atttaatata tgtataatct tataggttaa aataacacta
74941 actatcagat ttatcattaa tattattatt actattatac ttaacctctc catctacatc
75001 ctcctttcaa gagaataacc aattacgtag tggattcttt ctgtattata atcagataga
75061 gttctataca gtccttgtta gtcgggaggt attcctttct tattttgggt ctttaatttt
75121 aaattttcaa ccgtattact aggttcagct aaataaatga ttatctttac aaatatctgc
75181 attactgtat ttttatacta aacgcgtatt atatacgaga aataattata tttttatatt
75241 ctagatattt attaactact tttatctata tgttcatcat gcatttcctt tatagattta
75301 attatcttat cttctattac tattccttct ttgctatctt tatcgctaag tactatattt
75361 gattaagaat gattagtaat tagtaatacg ttagttcttc tggtatctag agaattagct
75421 attacaacat ggtgattata tttatatagc gcttgcctag ctttagttac taacatgttt
75481 ttatcggtct ctaatttgaa tgacactaca aaagcatttg gacaccattc gtctactaaa
75541 tgaaataaca tcttagggac ggtttttaac tctaaagtaa tatctgtaga cgaatctatt
75601 ttatgttcat acatttcgtc ttctggaata tagaaatcag aaacggccgc tgcaagatat
75661 acaacggcat gactaccgag tatagataaa gatttagaaa tcatttctaa gaaatttaga
75721 tactgatgta tacaagtata actaatagcg agtaatttat tttgttctat agcttcatta
75781 tattttttta aagcagatac aagttgtgta tttagagcgt cgttaaagta aacagtattt
75841 ccttctacat ttaatgaact caataacata tttcccgaag gtaataatct tgaccaaggg
75901 aaaatagatt attcacggta taagaaacat acagaataac cattttctat taactttca
75961 acagaaatag ctcctctcat acccgtacta aaattctcta aaaatctgac tggtttttt
76021 tctaaagata ctctagtccc tccagatgtg actaaagcta cacgcctgtt tttctctttt
76081 tgtaatttta cccaattatt aatgttagta gtcgtgtcca ttttttaat ataagaattt
76141 atattaggtt aatttataag aaaccaatac tttaaatctc taattcgttg ttctaaacaa
76201 cagttatggt ttcttaaatt gttgattcat gataatatta tcgtaataat tctattattg
76261 aaatatctag tctcgttttt gagataaata ttacgaataa agcatattca tatcaaagca
76321 acattagctt tacatttaag ttgtactacg catacgcacg aagtacctat tcttatatat
76381 tcccaggaag gcattccatt tttaataact atagagttaa caaaagaatg agacgtagaa
76441 caataagagg accaaaatcg tgtatctatt cctaaacagc cactaatagc cggatattcc
76501 ttacacttgg tttcgaatag gtactgatag taaacttgtt tattatgtac tatttgatcc
76561 aatagttcta gtttattacc tctgtgatca aagactgtag ttttgttagc gacccatgta
```

FIG. 19U

```
76621 gaactacttt cacaagataa gtatattcct tcactggtat tacctacaga caataattca
76681 tctatgcttc gtttaccacg atgttctata ttcggagtac gagtactaaa aacaacttta
76741 gatgtatcta atttatcgtt tataagataa ggattagtaa attggagtaa cgatcccttg
76801 catactatac ctaatacaca tataaagatt agccttctaa aattacaggg gtgcgtatgg
76861 tatgccattc ttatttatat atgaacttac taattaagta atagaatatg tctcagtaat
76921 aattgacggt acactgtagt atttgattcc actagtaaac acataaattc cttaccatta
76981 tgtttattat ccactaatag ttctctaata aaaaatgtag agttttgtaa cggaattgtt
77041 acaggacttt tatgaattac cgattccatt tcgctaatgg gtttaccacc gggaccggcc
77101 caaaacattc tcgctgacga acctttccta ccacacccta cacatattaa gctagtagta
77161 tttatatctt caggcagtct agtaatatta acgtaggtac aatcttcgcg tgttacagga
77221 cagcattctc gcacaccgtc ggaatttttt cttgcgtttt ccggaagata tccttctagg
77281 tctagaaaaa tagtttcgtc actatcatct tcctcataac taactgtact gtaatctcct
77341 tcatcgccat agtctatcgg attcaagagt acgggtatta tcaaacatag aataaaaata
77401 gttctataca tcatgttaat ttagatattt cttctggaca cgatatctat cctactaagt
77461 atgtatggta tttatttatc aattaatctg cgtatgtagt aactactaca gcgtttctaa
77521 gatcatcatg tcctacaatt ttatttcttt gacgtcgtgt ttatatcatt ttctgttttg
77581 ggataataat tttctctaat ataaaattat atattaattc tttttctata ttgaagtgat
77641 ttaattaaag aaaatatgta atctttatct aattaggttt ttccttatct aataatagaa
77701 ctgtatacct ggtgatcttc ctacttgatt tacgtgacct aatataatta tttagatatt
77761 tacctgtttt tcgcataaat ataattccta aaaatattat tattaagata ttaatatcta
77821 ttatccatga taatatatag agaaacatta tattaatcgc caatcgaata tgaataacat
77881 acatagtaat aataaagata gcagttaatg gcaaactaat attattcatg ataactgcta
77941 taaaagaaga taatatagca agatatattg aagtgtctat catatcttat tttatggata
78001 aacctttaac ggcaacttct aagttactta tttttggtt tattaaacta ttggtttttt
78061 cgtacttttc ttccaatttt tttgtatttt tctttaattt taatatctca ttatcatgaa
78121 tgtcgtatag tattttactt ataccctcag agaagaagcc gcttcgtatc tgatcttcat
78181 tatcagaacc ttttttaagc ctcgtgcaat aggagttaga aagataggag ttaagtatct
78241 tggaaaaatt aagtgcaata ctaggaaaaa cccaacagat aatatgaggc acgagatcga
78301 tatgcacata tgttcctaca agttcgtatt tataggcact atttgatgct aatccgattt
78361 ctaaaacggc tttattatag ataccgtttt tatagttcaa tgtttttatg agtttttttag
78421 atgactctag tctacaccac tgcctaaagt tcttatttcc aagatcacat atttagtag
78481 catttatata tccgttgtat tttaacatga ttacttctat gttcgcatag ttgataaagc
78541 aaaagttctc atctatatgt ttaacggtgt taggtacaaa ctccatattg taatactttc
78601 attcagaata gtattgtttt tacatttttt attataagga aaaaactggt ttattcattt
78661 tcttttaacc atgcatacac aatttacagg aactgataca tgtttagtca ttacagcatt
78721 attttcacca agatacatta ttttttaat ttctgtgacc gtagaacagt aagattccca
78781 tcttgactca tcaatgccct tacaaggaga tgtagaatta gggaatccca tgcagctaat
78841 catttgaatg tattgtgtgt atccatctcc tttctcagaa tatctgccca aaaattctat
78901 tttactgaca ccagttccat taacagggct tacttctcta atatctaccc atgtagttac
78961 taattcacaa gcgggttcgt ataaataaac agtagtatta tcattactag atgtctgggt
79021 atcgtataat acagctgcat gatagtactg aaaacatgtt agtaacacaa gtatatgtgt
79081 aacgtacata atagaaaaaa gtataattta tgccttattt ttacattata gttaaaacca
79141 taaaactatc ttaattacaa ataaaatact atgtagttcc attattttttg atcgcattaa
79201 atgaaaggaa ctattatatt gtttggtaaa ccaaattgcc cgttatgtaa atttcaaac
79261 gaaatacttt cgaataaaaa gatagctagt aaatatgaaa tcgttagaat aaatatagct
79321 acattcttcg ataaatcaaa ggtcgtagaa atactcggta tggataagtc ttacgatcta
79381 ttaaattcta ttggagaaaa attaggaaac gaatatgttc ttgtatttag gtatgatgat
79441 actagtaagc aaatggcgta tattccattt aagaaataca tagtaatagg acaaatatca
79501 caagattcta tagatttcga taagctgctt aatgaattag aaacaacacc ttacaatata
79561 cttcttaagg ataagtagat atcgtttagt gtactggata taatattatt aggtttattg
79621 ctaaagaccg tatctaacat atcagtattg gattcattca aaagatggtc tatacattgg
79681 tctgttactt ttatttttat atccttgtta gataacactt ttttagctaa catgtaagta
79741 aagtagtcta agtaatcttt accaaaaatc agaacaatag attctttggg tatatcttct
79801 gttttaatac catctgggta ttctgtatat ctatatatag atggaatata cttgagttta
79861 gagtaagcta tagtattatt atcggcgttg tattttattt catttccatt aataactatt
79921 atacctatac cttcgttagg aagtttataa ctacgtttaa ttgttttagt aaatttgcct
79981 aactttatgg ttacgagttc cttaagtatg ttgtctggat aagataattc tatttctttt
80041 aaatacgtat cacagtttaa tgctttactt ataagctttg tatttttaga attataatac
80101 ttagttaata cctttactct gtctacgttg aaagaattac ataacgatat aaatttttcc
80161 atatatgctt catcaccact gtctaaatac tttaatagat tataagatat aagggttcta
80221 aatgacatta ttcttagtta tattctttat actattcttg ttattatgtt atttttttag
```

FIG. 19V 80281 ttttaaacga actaataaaa tggaaattgg gataaatcct attaagaaaa ttccatggag
80341 tgataacgag catatatttg tatcatcttt atttactaat aaggacaaat atctcaccgg
80401 tcctatgagg ttaacctata gacccgatag taaaacagca gttttagatt ttaaaggtac
80461 caactatacc tattatctag acaatttga tgatgttagg aaattagtac ctacgttgct
80521 actgagtaaa tagtatattt aataatactt gatttatttt caaatacatt tacagctttt
80581 tacagaaacc ttacgaagaa tcgcggtttt aggtgtcctt cctaacctat aatgcactac
80641 taaatcatcc atactctgaa tgctacaaca ctgttttaat tctataccat ctatatagtg
80701 gaatgctagt aaactatata aaaaactatc agtatataca aacgactggc attcgcccat
80761 gcaatagcca taatctatac ccggaggatg taatatccat ttaagaccta tactcctgaa
80821 atttatatac tttctatata ctttacaatt atcggacgga gatgagtagt ctacccccact
80881 atcagattca acatattttt tagaacctac actcatttta ttagttgact cggtagggcg
80941 gtccgtgctt ttaatacttc tttttcttat atcgaatgaa taatctacgt gatcatccga
81001 gtagagttct tcttcatcgg taatacttaa aagcttcttt attaacccct caacagatat
81061 atatctatgt ctgttattag tagagactgt atagtatcta tcatctttag gttctgtttc
81121 atttacgtag tattctagaa aaacatgcct ggttctgtta ataataccat caggagctaa
81181 tagagtataa ttacaatgtc tattatagat agattgttta gccatattct cagtaagtaa
81241 gatacaatac catttatcag caggtagtac atgataatca ccagttccgc atatttttatt
81301 aatgctacaa ttacaaatga ctttcaaaac tacttcttcg tgttgagtat taagatatat
81361 acaaatacta acgtttagta ttctgttaac aaaatataca tcatgagtat taaaatatgc
81421 agtattcatg tatttaccac ttccgtacat accgtgtaaa tctatggatg gtttgttctt
81481 atggtttca ggaacttcta ctatggtatc atagtattcg tcttgcaagt tttcttcatt
81541 ctctcctatc atagaaagta ttaaatcttt tatagacggc aagttaccat atcctattac
81601 acagtatact aaacatgaac tgataaaaat tattatatta cgacatacca ttttaacgct
81661 tgacgcatat acaaaattcg aacgaatgaa agaaaactac ttcttatttt aactgtactt
81721 aaatgattca actaaataat ggtatacgta tatttgttaa tcattctatg aaaaaagata
81781 tatatatagg tatttcagat tttgggttcg aaaaagatat aaacgatgga attctaggga
81841 tagcgcattt actagaacac atattaatat cattcgataa caagtatttt aatgctaacg
81901 ccagtacttc gcgtacgtat atgagtttct ggtgtgttgc tttacaaaag cgtcattatg
81961 aagatgctat tagaacagct ataagctggt tttttgataa aaagtatata ctaaaaacag
82021 atttttctag aattgtatta gaaaattata ttaccgaact agaaaatgaa tactattatc
82081 gtacagaaat gtatcattgt atggatgtat tggcgtatct atatggagga gatctttata
82141 acggaggccg tataactatg ttagaaaggt tgccagaaat acgtaatatg ttaagtaacc
82201 gaatgaaatt tctatccggt aagaacatag ttatctttgt taaaagacta actaataaca
82261 tactaacgtt actaacaaac acattcggta gtataccaaa gtatcctatt ataatacctc
82321 tagatcctca gattcaggat gctaggagaa agattatcat gatgccttgc ccgttttata
82381 ctcttcttat ccaagtagat aatacaatga ataatttact agctattatc tgtttagtag
82441 aaaactataa ccttatagac tatgaaacaa taagcgataa attatatgtg tgtatttcat
82501 tcgctaacga ggatcaatac gaatatcttt tgtataacat aaaggatatg gatttaaca
82561 taaatagaat agaactagat ctcggagagg attatattat gaatctatat atcaactttc
82621 cttggctgaa gaatgatata ttcgaatata tacataccat gaataccaaa agcgcgatgc
82681 tgttagccga tttaaagaaa aatatgcata acagtatact agaacataag tttatgatta
82741 tatatcctag ttttacgaag ctattatata atataaccga taaacaaaat cacggtatat
82801 tagttgtagg agatgttagt tttacaccag aaaaagatcc aagtatgcat cattctaaca
82861 aagaaaataa taacaattat tctaaaactg taaccaaacg caagagtaaa tatgttatgt
82921 atagaaagac accgacgact aataatatag ttattgatta tacagacagt agttttttg
82981 attacgcgac tttttaccat gttatgaaat caaaatatga aaagacaaat ttattttcta
83041 ggcttaagac ttcaacaggc atgtgttata aacattgttt tgataatgat gatcttaatg
83101 aattaataaa ttcagatacg tttatacggt ataatagttc taaaccagct gtattatacc
83161 aatatatact tttagcatat tttgttaccg aacgagatat aaaagagtta gtagattata
83221 aagacgctat agaattagac atgaaatatt atagtaaaaa taaaatactc tttggaaaga
83281 atactagata tgatatacgt accaaatcaa tgtttgtatg tggattaatc aaaggacgta
83341 aattaagtga aaaagtcatt accgattata tgtggaagct aaaaagttta ggattaatat
83401 attatcttac ttctattaaa ctaggaatat caaatacttt ttatattttt gcatttacta
83461 tatttccaga aaaagtatat aattttttttg ttgggttaaa agagataacc aatcgttgtc
83521 tcatagtttc aaataaaaat acaaaaatag aagaagatga ctattcctct ttaaacaagc
83581 agatagttat cggtataaag taaaacttct ttctgttaac atataaacat aatttctata
83641 tagttgttta ctagataatc ttataactgt attcatgtag ggaccgaaca aaatttctcc
83701 tttgtaacaa tacatctttt tgcgtctagt agttgtattg atttaacta aaagctgaag
83761 attctttatg tccttaagag tttctccggt tagaatatca ttcctttcaa acatgtctag
83821 gttttcggct ttcttaccac ccttgttata aattttgacg tattctacca tattaacgaa
83881 ataattaaca taaatttcga ataatctatc aaacgatata ttaaaagact tgatatactc

FIG. 19W

```
83941 ttctgatttt tttaacatat ccttatcact aggaattact aataaatcgt taggtagtga
84001 taatttgaat ttttttgcat atactatgta ttcgtataaa aattcatggt ctatgctttt
84061 aatcggtttt aaaagacaca tatcataaaa gtatacgtaa atacctttg atacccctacc
84121 tacacggcct tttctttgcg tcatcataga cttggatata aacagttgat cacctccgaa
84181 gggttttggg acgtatacac gtcccgtgtc gtatacgtga gtagccgtac gaatagtaat
84241 actggattca aggtaaggag tagaaaccaa gatacatgga cgttctctac caggtctctg
84301 aacggcgtta agaacctctg taatatcagg tattttaccg tgtattatta taaagtccat
84361 atcggagtta cttttctcta ggtatttttt ataacttata cactgagaaa cggatgctaa
84421 aaatagtatt ccacacatgc cgtttctagg tctacaccag ttaagagtgg tcgatatatt
84481 cttttttctt tcctctgtat acgctttgga atcgtaagag tacttgtttt tgacatatat
84541 ctctttaatg gagtagagta cgggaccttc tatatggtaa aattctacat ctggtaagaa
84601 ttcttgtaat ctgtccctat cgtcttctaa agtagccgac attaatacca gagaatgtat
84661 agtatcgata tttttctta gaacggatat aataatatct gctattctat catgctcgtg
84721 gatttcatca actataataa tattataatt agataaagaa taactagtaa gcttgttcgt
84781 agataatact ataccatcgt gttgtcgtgt agtatgttct gtttttcctc cgtatcttag
84841 ttctacaggc gaaccttcaa aatctgaaaa ccctaatgac tgtaaaaaat taataccgtt
84901 acttttaact aaagctactc taggtaatga taaaactatt ggtctagata tgtaatcaaa
84961 tcttacacga tctaaattat cccatcctcc gaataaatag ttataccaca taatcacttt
85021 tggtaactga gatgtttcc ctattcctgt acttcctgta acgactattt gtttgcgctt
85081 tctaagtagt tcgaagattt gtaattgtgt aattaagctt aaagacttaa atttaattac
85141 agtaaatggt tttggatttt tgagtatgcc tattgaagat ttttcaggca tctgtttatt
85201 ggaagaaaaa atagataata tatttcctgc agataataga cctcttttat catctagagt
85261 tatatcgtaa atactgttat accccttaca ctttagatag ctgtaacatt cgaacgtaat
85321 aaatgtttta tctgaaatct tgtatatttc tttttttata tcggtactta taggacgtat
85381 atcgataaga tgttggatag gtactctatc gtaaggtttt gaagtatcta attcgatatt
85441 tagcatatag acattattct gaaaacatat ataagctttg gaccatcggt gctttataac
85501 cggaaatata gtatacgaga aaaataaagg atttttcgg tgatattctt ctagttcttt
85561 ttgactatac ttcctaggaa atatatcata catattagaa aatgcataaa tagaaaatag
85621 atcgtttgtt gtcatgtcac agatgttata tatttagtta gtaataaatg gacaagtata
85681 cagaactcgt tatcaataaa ataccagaat tgggattcgt taatttactt tctcatattt
85741 atcaaacagt gggattatgt tcatctatag atatatcaaa atttaaaaca aactgtaatg
85801 gttatgtagt agaaagattt gataaatcag aaactgcggg aaaagtatca tgcgttccaa
85861 tatccatact aatggaatta gtagaaaggg gaatgttatc caagcccgat aatagtaaat
85921 cacaattaga agttaaaaca gacttagtaa acgaactaat cagtaagaat aacggatttg
85981 aagatataat gactattcct actagtatcc cgatgaaata tttttttaaa cctgttctta
86041 aagaaaaggt atctaaagct atcgattttt cagttatgga tattaaagga gacgatgtta
86101 gtcgaatggg tatacgctac ggagaaaatg ataaagttgt taaaattaaa attgctccag
86161 agagggatgc ctggatgacc aatactagca ttcaccagtt tcttatcccc atgtgttacg
86221 gtacggaagt aatttatata ggacagttta attttaactt catgaataga cacgctattt
86281 acgaaaaatc atccgtgttt aacaaaaata cggaagtgtt taaattaaaa gataggataa
86341 gggataacag atcctcaaga tttattatgt ttggattctg ctatttacat cattggaaat
86401 gtgctatata cgataagaat agagacttta tctgttttta tgattccgga ggtaataatc
86461 ctaacgagtt taaccattat agaaacttct tcttttatag taattcagac ggactaaaca
86521 gaaattcata tttatctagt ttagcgaatg aaaatgccga tatagatata ttatttaact
86581 tctttataga taattacggt gtaaccgctg gttgtataaa cgtagaagtc aatcagttac
86641 tggaatcaga atgcggtatg ttcacgtgtt tatttatggc cgtatgttgt ctaaacccac
86701 caaagggatt caaaggaata cgaaaaatat acacctactt taaattctta gctgataaga
86761 aagtaacgat gttaaaatct atattattta atgttggaaa aatggagttc actataaaag
86821 aagtagatgg agaaggtatg caacagtata aaaaaatgga gaaatggtgc gccaacacta
86881 taaatatatt ggctaataag ataacctcaa gagtagaaga tattataaat tgataatgga
86941 taacttttta aagcaaattt cttctaacgt gaaaaaacct atagcagaac ttgaagatcc
87001 ggatgccgtg ataaaattcc attacatgaa tatatctttt aatttcccgg atctgtatta
87061 ttgtaataat aatttgtttg ataaacccga aaacaactta ttagatatat caaaatcgct
87121 actgatgctt aactcatttt cacacgaatg ttttatatta caagatatat tgagagtcat
87181 tcgccgttac ggccatgtat acgatgttta ctttttacct attggttggt tggtaggaca
87241 tggtgaagcg cctaaatatc atgcatcgat aaaattaata aggagcaata cacaagaaat
87301 aatagacggg atcatacgca gacagttatc ccaatacggt atacaaggag acaatttatc
87361 aatttttgta gattcttcca atgaagttgc tataaacagg cactctatta taggagctag
87421 acagttgaat cctatatgcg tagtatcttt ttatcccttt gatccagaac ataaagtttt
87481 tttcgttata tatgttggta gatataaaga taagtattgt ggaatttcct acgtagctga
87541 tagagaagat atgtacaaag ttatcaacag gatatacccg tacgttagtt gtttttacct
```

FIG. 19X 87601 cgtatcagat ggtataataa attttcatac tactcccgta gctaatcaca ctagaaatat
87661 taaacccctt ccagttaatt attgtaatac tttatgtgaa atagtatatg attttgaata
87721 tttaaagttt gaacaaggtg ttatgtctat tccggtgttc atgccttttg taccaaaaca
87781 gtttgtatct attatcaatt taccagatga tattctcata acatgtacag cgtccagtaa
87841 catagaatac ataacacata tagataataa aaagctaaaa agaatactta taataataaa
87901 agataaattt ctaaagggta ctatcatgca aggtactttt aaaaaagtaa atatcataag
87961 acacaagaag tatacatata ctataacgta ttcttctttt gattgcccta aactagaaga
88021 tactaagtca tcgctgccaa gtacgtgcaa taaagccata ttagatgggc gtagatatgt
88081 tacaaaaact tttaatgata caatataaat ggaaatagct agagaaacgc taataacgat
88141 aggccttact atattagtag tgttattgat aataactgga ttctcgctag tgctaagatt
88201 aataccgggt gtttatagtt cagtatcgag gtcatcattt acagcaggaa gaatacttcg
88261 ttttatggaa atattttcta ctattatgtt tattcctgga ataattatat tgtacgctgc
88321 ttatataaga aaaattaaaa tgaaaaataa ttagaatctg aaaatgtctt ctggaagcat
88381 ccatgttatt acaggcccta tgttttccgg taaaacatcg gagctagtaa gaagaataaa
88441 aagatttatg ctatctaact ttaaatgtat tattattaaa cattgtggag ataatagata
88501 taatgaggat gatataaaca aagtatatac tcatgatcta ttgtttatgg aggctacggc
88561 atcttctaat ctatctgtat tagtacctac gctattaaat gatggagttc aggtaatagg
88621 tatagacgag gctcaattct ttctagacat agtagaattt agtgaatcca tggctaattt
88681 aggtaaaaca gttattgtgg ccgcgcttaa cggtgatttt aaacgcgaat tattcggtaa
88741 cgtatataag ttattatcat tagctgaaac agtgtccagt ttgacagcta tttgcgtgaa
88801 atgctattgc gacgcttcgt tttctaaacg agttacagaa aataaagaag taatggatat
88861 aggtggtaaa gataaataca tagccgtgtg taggaaatgt ttttttagta attaaggggt
88921 ttagtgtaat aaatttaata aaatattgac aaaatagtta aatgaatata tgaaagtaca
88981 ttatacacgg aatggagttc gatattagtt cttgcagaat gatatattct gttctcgaac
89041 aatatcactt tgttactgat aatcgttata acaaccataa tcaaaaattt agaattatat
89101 tatactgttt aaaagattct acgataaaga aatatccgta caggtttgtt tctgaaattc
89161 actttgtaag atacataatt aacaaattca gggggaaaaa tctttacaaa attagtatag
89221 aagctataga tatatcaaaa ggtagacaac aaataatcag aacctaattt ttttatcaaa
89281 aaattaaaat ataaataaaa tgaaaaataa cttgtatgaa gaaaaaatga acatgagtaa
89341 gaaacaagta aaaactcaaa gtaaatgtaa taataacgca tctagattta catgcctgga
89401 tgcggtgcaa tacgctaaag ctttgtgtac taaagatact aaaatagtta aatcagtgaa
89461 attaactcct tctcatcata atctatgcag taatatttct gtgacattag aacctaaata
89521 taatgaaaaa cttgtatctc cgtttatttt ggtggaagga gaaggaaaaa tatatcaaac
89581 tagaagtgac aatttcagtc gtgaggaatc atacttccta aaaatacgcc cgagtgtaat
89641 tagtcctatt ttacatcaga tgatggaatg catttatagt gacttgggct atctggatcc
89701 ggaaaatact atggatgaaa aaacatttaa agatggttat atatacatta ataaaaataa
89761 aatgtcatct actataatag aatatacgag aaacaacaag gaagtagctg gtagaaaaac
89821 tctatccagc gaagtagaac atctatcgaa gaaagatcct cagatggtta aagctgtact
89881 agttgcttct atatttttcg aaaatgcggt aatgtgtaaa ataagcttta gcttgaaaaa
89941 gcttattatg gaaaaagttt gtaggaaaac tctgatagat actaacggag aagtaatcag
90001 cgtcgtaacc tccggagacg atgatataga ggatgaatcg ggagagtttg aatatgaatc
90061 agacggtgta tctggaattt tagaagaaag atctgatggt aacaggagag gtggttacaa
90121 aataaaagaa acagatgaat atgatgaacg atcattattt aacgtaaact aaatggaaaa
90181 gctatttaca ggtacatacg gtgtttttct ggaatcaaat gattctgatt ttgaggattt
90241 tatcaataca ataatgacag tgctaactgg taaaaaagaa agcaaacaat tatcatggct
90301 aacaattttt attatatttg tagtatgcat agtggtcttt acgtttcttt atttaaagtt
90361 aatgtgttaa gattaaatgg agcaatttga tcaacttgtt cttaatagta ttagcgctaa
90421 agctttaaag tcatatctga ctacgaaaat agctgaagct atagatgaac tagccgctaa
90481 aaagaattct cctaaaaaga aggcacaaac taaaaaaccc gagaatagaa ttcctctaga
90541 tctcataaat aagaactttg tgtctaagtt tgggctaaag ggatataaag atggtgtact
90601 gaatagtttg atatgtagtt tagtagaaaa taattacttt gaaaatggca aacttaaaag
90661 gggtaaacac gatgaactag ttcttctaga tatagaaaaa gaaatattgg ccagaataga
90721 tgaaaattct agtctcaata tagacgtact agacgttaag gttttagcaa atagattgag
90781 aacaaatgcc gatagatttg agtttaaagg tcatacttat tacttagaac aaaataaaac
90841 agaggatatt atcaatcagc ttattaagaa ttcagctata tctatggata tgaaaaatac
90901 tattaaagat acattttata tgatatccga tgaacttctg gatgtattta aaaatagact
90961 atttaaatgt cctcaagtta aagataatat tatatcacgt gctcgattgt acgaatattt
91021 tattaaagct acgaaacccg acgattcaaa aatatacgtt attctaaaag atgataatat
91081 cgctaaaata ctgaacatag aaactatagt tatagaccat tttatctata cgaaacacag
91141 tcttttggta tcgtcgattt ctaatcaaat agataagtat tctaaaaagt ttaacgacca
91201 gttttatagc tccatatcag agtatatcaa agataacgag aaaattaatt tatctaaggt

FIG. 19Y

```
91261 aatagaatac ctaactatat ctactgtgaa aatagaaaat actgtagaat aaatgatagt
91321 aacagtactt tttttaatta tgttcttcat ttgcacgtta tacagctatc actatttgaa
91381 accatggatc ttctatgtcg aacgtgaagt cacgtagata cgaaatggaa atataaattt
91441 ataattatat aatcactact tgtcatcttg tctgagatgg cgaatctcta ttctaagaaa
91501 gttagaaaat ccatacgcaa atttattcgt tcaggtttaa acttcgactt attacatgag
91561 aaacacggac gccgattaat aattaacaat atattcgtta aattaccccc aaaatattat
91621 aactttgcta aaggtctgga tttaaacaat atactagcgt ttgatagcga aataatacaa
91681 cttaatgact taaaaaaact gattatgaga ctacctcttt taccagactg ttttaccgat
91741 gtaatatcgt gtcataaaaa atacttatta tcggatgctg ctattgtgaa taaacttatt
91801 aactctaata tggtatctct ttcagatata cgtaatataa tagataacag aataaaaaca
91861 cctgttgaaa tagcattgct taacagctct ttagttatac cgggtactcc atttttctcta
91921 gatgaagtaa aatatatttt tgaaaacact agtgcagaaa acgtgaaaga gctatacaag
91981 agaatagaaa cacctattca cagcgttctc tatatggaag aaaaatttc tatatcaccg
92041 gttcattcat ccctatatca agtaactgat gttgataaaa ttatatattt gataaagaag
92101 tatcccgatg atgatattat tgattatgtc aatggaatag taaaatcaaa aaaagatttt
92161 atagaatcaa taattactat cattaaggat agattacccg atatatcacc ttgcttgaat
92221 aaatggatat caacacaatt accacccgat aaacttagag atgaatttgg tatatacttt
92281 tatgcgttgt ttgaatggat agatatacct ctatacatag ataagtactt gtttctaaac
92341 ataacggagg atgaaactaa atttatctgc cgttatatag atatatacaa aaaaaagtca
92401 gagttgtttg taaatgcgtt tagatggcat ctatattatt gtaatagtat gtatcctcaa
92461 aaagtatttc ccgttattac ttataaacaa gattctaaag aaaaatatgt tgtaaaagaa
92521 tcattcaagt atttagataa taaacaaact atgaaagtac tattaaatga ttttaaatat
92581 aactatgcta tagggaaata catacttgac tcgtcatcgt ccaatgaggt aaagatggat
92641 gctctaaaca tgttacagaa acaagtagtt tgtttagaaa atgctaagtg ttttgatcta
92701 ggtaatttat attctgtatt aataaagttt caatatcacc cggtagatta tgtaatgtat
92761 agcgataaac tgttagatta tatgtctaaa aatagtactt tcgataataa tgatatagga
92821 ttattgactc tagcaagttt cttatttttct accgccaaga aaggtattat agatatcaat
92881 tttctgaata ctaactcgct atggagtcct ttgatgtatc ttatagatga ttcgtgtaaa
92941 gtagatttca cgaggtttat gatggctaca aagaatataa aagccgataa cataaattat
93001 ctcaaaaaca aggacgaaaa tattaataat aattttgaac atatagataa tatagatata
93061 tataaactat tagactatag tcgaataaaa ctttatggaa taaacttcat taaaaaagta
93121 atactagcta atgttatttt cgaatatatt tttactttga taattatcag atatcaaaaa
93181 acaagctata atttaagatc gtttttagaa atgttattat atagatgctt aaaaggattt
93241 ggtatatcac caaaactgta taaaaatgta tacgttaatg aaatgaatat ttgttgtgaa
93301 ttagaaaacc taatcaataa ctatgttgta cctttcaaaa cctacggaat attaatgaaa
93361 ctattaataa ccatttttaa taacttaaat ggaattagta aacattcttt tagaatcaga
93421 gtcagaaaga gtaaaactct attatgatat tccaccaaaa aaatctttaa gaaccaagtg
93481 tgaggtagat agagcggtta aatatttcat atcggttata aagaaatata taaaactaaa
93541 agaatctacg ttctatgtag tagttaagga tacaacatta tttacatata aatacgataa
93601 aggagaacta actccagtag ataatactta ttatacattc agtaaagaac tagctagcac
93661 ggactatact tcctcagaaa taacttctat ttgttttact attactgacg atatgagtat
93721 ttctgtaaag ccaaaaaacgg gttacattgt taaagttaga tctgataatt ctaggtatta
93781 ctaaattagt ttttttactt tttttatatc tatacatctt tctggattaa acactagatt
93841 gttgtaaaga cttatgaaaa agaagtatat ataattaata tcgttgcttg acataatatt
93901 atttcttctgt attgcctgta gagcatggtc cttacattca gcacacggta atgctttaca
93961 tatgttatac aagtgacgtt tgcaagtttc tatatcgtgt ttaaacttgg taattataat
94021 aaatataact atccaaaagc tgcgtcccca gtatctagga tccataactg aaatttaacg
94081 tatctaaaaa aatggatata aggtgcgtaa actggtttga gaataaagga gaaacaaaat
94141 atatttactt aaaagctatt aaccgagaat cgaatgttat atttataaga ttcaattatt
94201 actatcacta tgtatacgat gcttccaaag aactagaata taaacctaat gagtgtatag
94261 atttaggacc gttcaaaatt attaatatag acgaaaagct aagtaccgat ataaggtatg
94321 tcgaacctcg aaattactat acttcggaat tggtactcgt aaaggatcta aaaagaaata
94381 gggaaaaaca atatctgcaa gaatatttag atataacttg gttttatcta cttaataata
94441 taacaccgga cgggtgttat aaaatagata tagaacatct aactcctata aaaaaagatt
94501 gttaccattg tgatgatgtt agcaaagtat tcattcaaga aatacctatc ttcgaagtta
94561 aatttactta cttactgttt gacatagaat gtcaatttga taaaaagttt ccttctgtat
94621 ttgtaaaccc tatttcacat atcagttgtt ggattataga caaggtcacc gaatataagt
94681 ttactttaat taatacagat atcttacccg ataaagaacc tagtatatta catcacaaag
94741 acttctctcc aaaagatagg ataacctatt gtacagaaat tgtgatgttg cttataatga
94801 aaaaaattct agaacataga ttcgattttg taataacttt taacggaaat aatttgata
94861 tcaggtatat atctggaagg ctagaaattc tcgagaaatc ttttatatat ttcctctctc
```

FIG. 19Z 94921 ctgatgcgac ggaaacagtt aaacttaaaa tatttgaaag attcgttaca ggaggaacat
94981 tcactaataa aacataccac ataaacaata ataatggtgt tatgtttttt gatttgtatg
95041 cgttcataca aaaaacagaa cgattagatt cttacaaact agatagcata tcaaaaaata
95101 tatttaattg taacgttgct ataaaagaaa tagatgatac aattttaaca ttggaagcca
95161 cggtaaaaga taattctaaa gataaattat ctatatttc tagagtatta gaaaccggta
95221 attatatcac tataggagat aacaatgtaa gcaaaatagt atacaaagat ataaaccaag
95281 atagtttcat aattaaagtc atatctaaca gggattacga aataggatcg gtacataata
95341 taagttttgg aaaggacgat gtagacttaa aagacatgta taaaaactat aatctggaaa
95401 tagcgttaga tatggaaaga tattgtattc acgacgcttg tctctgtaaa tatatatggg
95461 attattacag ggtgcccagt aagattaacg ccgcatcatc tacttatctt ttaccacaaa
95521 gcttagcgct agaatatagg gccagtactc ttattaaagg accattactg aagttactat
95581 tagaagaacg agtaatctat actagaaaaa tcacaaaagt aagatatccg tatataggtg
95641 ggaaggtatt tcttccttct cagaaaactt tcgagaataa tgtaatgata tttgattata
95701 atagtctgta tccaaatgta tgcatctacg gtaatctatc accagaaaaa ctagtatgta
95761 tattattaaa tagtaataag ctagaatcag aaataaatat gagaactatc aaaagtaagt
95821 atccatatcc tgaatatgtt tgtgtttctt gtgaatctag actttcagat tattatagcg
95881 aaattattgt ttacgataga agagaaaaag gtataatacc taaacttttg gagatgttta
95941 tagggaagag aaaagaatat aaaaaccttt taaagacagc atcgacgact atagaaagta
96001 ctttgtatga ctctttgcaa tatatctata agataatagc aaactctgtt tacggtttaa
96061 tgggattcag taatagtact ctatattctt attcgtcagc aaagacgtgt actactatag
96121 gtagaaatat gattacctat ctagattcta taatgaatgg cgctgtgtgg gaaaacgata
96181 agcttattct agcagatttt cctagaaaca tattttcagg agaaacaatg ttcaacaaag
96241 aactagaagt tcctaacatg aatgaatctt ttaagtttag gagcgtatac ggcgatacag
96301 attctatatt ttcagagata tctaccaaag atatagagaa aacagccaag atagcaaaac
96361 acctagaaca tataataaac acaaaaatat tacacgctaa ctttaaaata gaatttgaag
96421 caatttatac gcaattgata ttacagtcaa agaagaaata tactacaata aagtatttag
96481 cgaactacaa accaggggac aaacctataa gagtaaacaa aggaaccagc gaaacacgta
96541 gagacgtggc attgttccat aaacacatga tacaaagata taaagatatg ttaatgaagc
96601 tgttaatgca aagcaaagga cagcaagaga taaccagatt aattcttcaa agtttagaaa
96661 cagatatgat atccgaattt acacacaaca gagaatttga aaagtatttg ttgagtagga
96721 aacatcacaa taattacaaa tcagcgactc actcaaattt tgaacttgtt aaaagataca
96781 atttagagaa tacagaaaaa atagaaatag gagaaagata ctattatatc tatatatgtg
96841 atattagttt gccatggcaa aaaaagctat gcaatatatt atcctatgaa gtaatcgccg
96901 atagcaagtt ttatctgcct aaagacaaaa gaatattcta cgaaatatac tttaaaagaa
96961 tagcatctga agtagtaaat ctgctaacgg ataaaacaca gtgtatgtta tttttcagta
97021 gacttttcgg tactaagcct gtattttcat cagactaata tcacatttc tttttttagt
97081 cctaatttat tcattagata ttctacagcg ggtgtaattt ttgtagttac tgataaacct
97141 ggaaggtaga atatcaaaaa aatcaataca ggatcctgct ttgtattaga aataataaca
97201 gacaagtttt ccaatgtttc aatattcaat agatacagat ttggagatgt tgcaggaatt
97261 tgtaacgtgg ccatattaac aggaaataaa gttccatcgt atagaccctg ccggtccagt
97321 ttaccaaaga taggtttgta atcaccgcct cgtataagat atttagctag ttctatatgc
97381 ttagcatcat ctatatagaa actacccgta aggctgtgga ttctaggatt aaaagttgta
97441 tttttaaaga agaataatat attatatatt ggaatgctcg taagcaataa gaaacttatt
97501 aactgatcaa cgggtaatat agaaaatttc ttaaagtaat cgtttagatt aacagtagaa
97561 atctggttca aatactgtat atttatttta ggagtatatt gcggaggcgg accttgatga
97621 agacctagca tgaactcaaa tttgtttaat agacctaatg ttataggata atagcttctt
97681 atatctagtt tttcatactg ggtgttccat aatgctgttt caggtatcca tccataagca
97741 taatcgtgat acaaaaacgt attattaagt ataggggta aattcatacg attaaacgtc
97801 ttttgatcat ctgtgcgttc atgagcgttt cctataatat ctcttatacc acgattagcg
97861 ttagtcataa ttgccgttga ttatttgtaa tataaatttt ttatcatttt tagataaatg
97921 tttagtattg tctagatatt cattaacata atatatgttt tcttgtagaa actgtttaaa
97981 taatataata atagctactt taaaatgatt aataattgta cgcacaactg atttaagtat
98041 agatttatca ttacaggttg cataaactat aaaagaagta aagttttgta aacaactaga
98101 tcccgttatg attttaagga ttatatcatc cttatagttt tctattatta accctaacga
98161 tgctaattta gaatcaagat agtatttcaa aagactttta ctaaataaag aaaaaacaat
98221 agagggtgaa ttaagatcta aatcagatag ttttttagc tctcctttat aaatgactat
98281 gggattatcc tcatttaagt ataaataagt attatactct tttatagcat attctgtatc
98341 tttattatat atctgacaaa gttttttatt ttctaacgct agcaagtcta cattttgtgt
98401 ttggtatatc atttgagaaa catatgtaga atttattttc atatcatcaa atctctttac
98461 taaagtagcg tctgttctga atatagattc tatgtctctt cttatatcaa acttttccgg
98521 gtctatttta gcaatcacgt taaacaaatc gtcgtagaat ctattagcgg atgtaaatgt

FIG. 19A2

98581 tttatcatct ataaagttat catgataaaa atcaacaaaa tatgatttcc aggtttcatc
98641 cctttcgtct ataatagaaa ggatatcacc tggtatacca tatattaatt ccaacataaa
98701 tttcttaatt tcgctatcgc tatccaacat atatacaact tttaacatat tcttattaac
98761 acgagcttgt ttaatttctg agtagatata acttaatacc ttttcgtaaa tcgtgatcgc
98821 gggttcattc gtatatactt tctcatcatt atagattctt tcttcataa acaaccaata
98881 actcgtagta ctattttttg gaaatacaaa ttctttaaat gtttctgtca ttatactgct
98941 gactacaggt cccgtttct gtaatatagt atacagatcg tgactatcat tatcatcaaa
99001 tttcatccct gtatccattt ttagcgaata ggcccatatt agaagtcgta acacacttat
99061 cctgtctact ttgataaatc tagtttcctt aaagagtttg gaatatatta tctctaagtc
99121 tttaataggc tcattcaagt gaaataaagg atttaactca gtactaaagt taacgcttat
99181 aatatcttga aagtaaggtg aaagttttgt tacgaataag aaacgtttgt catccaggag
99241 tgtattagac tgttgtttat aaatatcaat aaaatctgta aaagatgtat agttttttac
99301 taactggttt aggtataaaa gagttacatc gaaagacgac ttaagaacta tatcgtatgt
99361 ttcacagtct cttatgaaat gcaaaaatat ataaaaattg gtattattaa aaatgtcctt
99421 agtcagcact gatttatgat actttttaat aatatagtta atagctacga cgtgattaag
99481 acaaaagttt gatatcttat ccgctagttc ttgcgtaaag aaattaatat tgttttctac
99541 agtatatata agatatttcc ttcttataaa atccatacta atactatctt atattaatcg
99601 atatttataa aatgtttaaa tgatatatat tataacgata aacaacagta acttaatgac
99661 atattttact atatctttat atttatattt aattattact gttatgaaag tgatgtaata
99721 ttatttttta ttaacgaagt actaattgta gcgtccaaat catatattag atcttgcata
99781 gcatcttcta tggcatgtaa cagtaaattc ttttctatgt ctttgatcac actttgtttt
99841 aacggtacta tagtaggata gaaacaagtt aatataggta taccagtaac acctactaga
99901 tcataatcta cgaaacttcc gttcactaac aaccatgtat tttcatcatc tgtatacatg
99961 aaatctttca atacaccaca tgtataatgt tcatcaggat ataacttaat agatgaatta
100021 tttactacgt ctaacagaca gcatttttca tcactctctt tatagaatat ttcctctacg
100081 tcttcgtctg ataatgtgtt gatgagaaca tctctagtag tctgtactat agattcttct
100141 agttctaata ttttttcttt atctgcttcg taagctattt ctagaacttc actatccact
100201 actacgtcag atatgcttct tccatcattc gttaacgcac tagctaatct atttatagca
100261 ttaggtaaag acccgtctct atattccata agccttgtat aatctttata tagcttttcg
100321 agtttatccg aaagttcttt atccacatat tcgttagtac ttttcttatc atatttaaaa
100381 tcaaatacat aaggcggttt atctaatacc tcagattcta tccacgtatc cctataatgt
100441 attaatatat tagctctgca agcttcatat ttaggatggg tataaggaac atgatttagg
100501 ttactaatat atccgcaata gtgtccagga tctcgttcat ctggccatac gtgcgaaccg
100561 cagtatctaa ccttatcagc ggttgtctta ggataaccgt atttctttata atcatcagat
100621 tgtatagcgc agtgatctct agaagtgatt gttacaaaac atagaccctc atacttattt
100681 atagttctag gtattgtaaa catgggacat ttcaacctca ttaatttagt ctttagatct
100741 agttctgcca tacattctcc tccttcaata tgtttaaaag tatatttctt accgtctcca
100801 taatcgttag tcattgactg tatatatcct aaaacagata ttatctcttc cgctttataa
100861 gtaagaatat tagctctcga cgtacacggt aatacaacca gtaagatact actgtacgtt
100921 ctaaattgtt tctccgcatc caaccaaaat ctatcagggt cgtcgtatgc catacctaga
100981 tttcctacag aaaattcaac atccaattcg taagggaatt ttaaattcgc ttttctctata
101041 ttatagatat ccacagtatt aggatcgtac ttttctgtaa ctagtaattc actacctaca
101101 tctacctgta acaagaaatc aggagtccaa acttctactt tcccgtaata tcctatacag
101161 gtcctacctt gcttccatgt aacgcacgtt cttgatctcc aaggcattct atgattacca
101221 gttagatcat caaatattct atttttacct tcgtacgtat caatcagtac tgattcatta
101281 tcgtattttg gatttatgaa acttaccatt atcatatcag atttatatct tttatcgtaa
101341 ttattaacac agaatacacc tatagtacgc ggtttaatag aagaaaacat tttaaccgta
101401 tagaagtcgg ccaaaggtaa ttctattatg ccatctttat cacctacggc tacaggagtg
101461 gacccagaag gacacgttaa tacgaaacta gtgaaacctc ttccatttcc aaaagtgtag
101521 agctctaaat atatagttct agatctagaa gcacaggaag gtgatgtatc gtctagtacc
101581 attaattctg cccaataaca ttctgtggcg tgtctattgg tacagaattt agaatgaccg
101641 ggtatttcat taggttttat aacagtttcg ttaaaatcgt atttctgaaa cgtaaacaat
101701 tgacgtaatc taccattctg ttcaaaagga ttttcgagta cccatctctg atataaaggt
101761 tcccaagtag ccagtctcaa gagaacacta caagtagtat aaactacaga taccatagaa
101821 ttgtcaaacg ggcatcctct taccgtaagg taaaacctct ttaaaggaaa tatatcacat
101881 acgttactag gaatactctt agtttcttca ggctccccgg gcgtagacat ttttagtaac
101941 tgcatttcgt ttaatgctat ttcaaaaggc cgtagagtta gtgtaatatc tcttccacaa
102001 gttaagagca ctacaggaaa ctttgaaagc atagcaccga gtctagtaaa tgtatagaat
102061 ctagcaccgt cttcgctagt aaatttaaga acagtatacg cgttaatatc caatgtaggc
102121 gatcttaaat agccaatagg acacgctacc gtcaatgaaa agtcgagtat aatattactg
102181 gtattaagat agtaaagaac actgtctata gaatcgacga aaaacaatga caattttct

FIG. 19B2

```
102241 aaagacggta taactataga atcgttcctg tatgacatgt aaactatagt ctcagtaccc
102301 ggcatcatac attttcggac gccagatttt gaagtatcgg taacataatc cctataagca
102361 ttaaaagtct taagtacagg atcttgaggt cgttgttttc ctgataatat ataataaata
102421 tctctcccag catccaataa tccagatatc gcggataaac ccattccagc aaaagcaacc
102481 tgcggagacg cgataatacc cgatgctgta acgacgcttc ctatagtacc tatagctgta
102541 ctaactacat caaatacaac ctccgcgtca tctctatcat cgtcttgtat cataaatgat
102601 cgtagatttc tgtccattaa tccctgagta ataaattggg cggctaggcc tactgctaaa
102661 gtcttgtcaa aagatcttga tattcttctc attctagctc cgtagtcatt gtcactagca
102721 tgattattat taccatcacc actagaatac ccacttgaac ttatactgtt accacctcct
102781 ccaccaccac cactacctcc acttctcctt ccgttattcc tactgctact actgctacta
102841 cttacatgta acgaactatc atctctagaa cttagtcttt ggctgctagg acccgctccg
102901 gcattaacat cagactctgt atcgctagaa gataaccaat aagatgtaag atccacggaa
102961 ccaataaggc tactactgga cgaatctaaa gcaaaactac ccattggaga aacactaact
103021 agactatccg acgaagaact gtcgctttgt acaggaggaa ccggccttct agtacgcggt
103081 aaaggagtga gcattagtaa tccacacatc gcactcgtta aacctctttt acatcgtcga
103141 ttagagtgtg taacgggttt agtattatga tataatatac tattaggtaa cgaagacggt
103201 aaactagggc gggtgctact agaatgcata gattgttctg gttggaaaat agatttaccg
103261 ggtttagtaa taacgcttcc tatatttata cccactactg gattttgta tactatcgaa
103321 gataatactt tactaccacc tgatttacta tatttatcta tactatcttt atagtgttct
103381 actacttttc tagttttcgt attcttatgg tttaacatat ctttatctcc taattgtttt
103441 tctcttaact ctagatgagt aaggcgtctt tttatgtcgt ctaactcttc ttctatagat
103501 gtactaagac tttgtgttgt tagtgcctct ttaatagatt gttgtttttg gtaactaata
103561 gatgatatta atcctggtgt aaaaccaccg tcagaattta ttatattttt acttattgta
103621 gacattatgc tatttggtgg tgtttcaaca ggaactaaag taaccatttt ttctaactta
103681 gatttcatag aatcttttaa tgtagatatt atatcgtcgt ctcctaatac attatcttca
103741 ctaccgctta tacctacttg gatataagat gccttacgag gtattacttc ttccaaccca
103801 aagtattctt ttaaattgtt catcttgtgt tcatctaatg atcttttagg tctgttttta
103861 taagactgtt tacgcaattt attagtatcg tggtactttc tattaggctt tcttttttta
103921 tactttttat tcttatcagg atttttatg cagttatcgt atctatcatc gttgtcattg
103981 tcgttatcgt aagacaaata catacattct aagtcggtat catctatatt tgttgtttca
104041 tcagtatctt ctgaatcacc cgcgtttctt ctaggccttg atttcttcg ctttctacta
104101 gatcccgtat acgcacttaa cactttaaat gaactatcct ttattttatc agtaagcggt
104161 atataattta tacaattatc gccaccagtt acttcgcaaa ggtaaaacaa attaactaaa
104221 tcgctatacc ctataccacc acattctttt aaagaaatat taaattcatt aggtacttca
104281 gtaacttcag ccattaaacc catgcggcaa tcactgcaat gcccagttag tattttcttt
104341 actcttactt tatccttttg atcgttatat tcttcacagg ttgttatcat ctctgttaca
104401 cactcttcaa aaatatctga agattcgtac ggtggactgg atgaaatacc gtcaaacgta
104461 atgaatatat cggtatgtgc attctcgtta ttattgtcag taagaacact ataattccca
104521 acagtaactt tgtctactgt aatattccta catttattac ctgtatatgt aatactagac
104581 acgctgggta aagaacaagt aagtttatta tccgatgttt tacatattag atactgaaca
104641 tctttctttg ataatgatag tgcactagct actatacacg atgtaacttt tctttctcgcg
104701 ctagtattat cgcctctttt aggcttttta ggagcataaa tcgatacatc taatacatat
104761 gtataattat actgatatct agtatgatct ttatctgtcg ataattcaca ctgttttaca
104821 aatctgtttt ttacagtttg ttgaatgtta gtccagttaa aacattccga gaatctctgt
104881 tcttcctttt ttcttacgga actaaggtac ttaactgtcg cagaagcttt atgatcggat
104941 aattctttcg gacttattgt tttagaaaga ctatggtact ttgcatgttt ccttaaacac
105001 gtgttttcgt cttcatcttc atcttcataa tctgaataaa ctaatgaaaa caataacaca
105061 attaacataa atattatgtt tttcatatta ctagtggcta tgatggttat aataatagta
105121 cattacttaa tatccgtaag tctttttagt tcatttttaa tcaactaacc aagtaataaa
105181 aatgtcatta atgctcgcgt atatgaatga aatgtattgg acaacgttag ttttatacta
105241 actatagtaa atactatgca tattcttgta tttcgtagtt aaactattag taaaatacct
105301 acatcttagg gttaatctac agtaatttaa ctagaaaagc tagaataaga ttcattgtct
105361 agttcgatat gttcctgcat ataaaatctt tttaggatat tatatttctt tgctctttta
105421 agccagaaac agatacaaat tattatcaac aatacggata ctgaacttat agctacgggt
105481 actaaagacg cgattagaat gttgcttgaa gaagattcta tgtagtcatt ttcggaggct
105541 attagagcta gactgatatt agcgtccatc tcatcaaata catcatttaa cgcgtctgat
105601 acggcattat atattatagc atcctctact atcttccttg attcttttgt gtctaacggt
105661 ataatactaa cgttataaca agtagttact accgctcccg atcgatttaa atactcgtat
105721 gttatataag tgtcattaat cagtacgtac ttcgtttctt cttcatccgt gtacacgtag
105781 tcactaactt ctccacatat atatttatct atcggataat acttcactgt aagattgttg
105841 cgaacgtcta taatacaaca cctatcattt tctgcagctt ccataatctc ttttaaatct
```

FIG. 19C2

105901 tgatctgtta gagtatgaat gaatatgtca ttggttattt cagatatttt atcttgaatt
105961 tccattatct tttctttatc agcctgataa gccagctcca agatatttcc gtctacgttc
106021 acgctcgtaa tttctctacc ttctttggtc aatgccgttg ctaatctgtt aatggactta
106081 ggaagtgttc catccgtata ttctattagt tttttgtatt cttcatatag ttcgttcatt
106141 ctatcgctta gttccttgct gacatactcg ttattcctat cgtgtgtgaa ctcaaaggta
106201 taaggaggtg actgtattac ttcggattct atccaaagat ccttgtattc tatgtggata
106261 taggatttgc acgagtcata atctgggaag taatcatata tatctccgtt atatccgcag
106321 taatagtctg taggtgtata gtaaaacgcg gttcgtttta tacatgttct agaatgacta
106381 gaatatttag aggtataccc gtgattcttc atccattctt tttcagtagc gcaatgatct
106441 tttgatgtta ctacagcaaa gcataatcct tcataattta ctacattggc tctaggaata
106501 ctaaatggat cacaacttac agttatatct cgagaattaa ggtctaattc agcacggcaa
106561 ttgccttcgg aagtatctat tttcttgaaa taatagtgtt taccatcgcc ataatcttca
106621 gtctctgatt gcagatatcc catggttgac actatatacc cgagttttat gtctttattt
106681 cttgaagtgc aaggtactaa actaattaat atggcactat aagtacgttt cttattaatg
106741 gcatcttccc aaaatctgga aggattctta tacgcgttac ctaaattgtt tacggtaaat
106801 gttactttta tagacgtggg aaagcttgtt ttgctttttct tgacaatatc cggatctata
106861 ctttccattt cataactttc ctttagcata atttcttgac tactgtgatg tatgtctagt
106921 tctacatcgg gattagtgaa atcaacatct ccaaagtaac attcttgtct cctgttgtcg
106981 caatatcgcg atctgaaagg cattccagat gatagaccag taaacaattt atccctatcg
107041 ttatagttgg atttatgtat tcccctagga tttgaatttt tatcgaataa tattactata
107101 atgtctgatt tgtacctagt atcgtaatta tgcatacaga acactcctat tcttttcttt
107161 tctgtggagg cgaataattt ggacgtccca taatcaccta caggcaattc tattatttta
107221 tcgtttccat ctatagatac cggagtagaa ccgctagggc acgtaagtac aaaactatca
107281 aatcctctat ctccgaacag agcaattttt acgtatatct ttctaactct agtctggcac
107341 gatgttacat cttctaacat catcgattcg gtccaataac attgactact ctgtttgtta
107401 gtgcagaaat ctgaatgccc cggaactcca tttggatcta ttattgtgtc gttaaaatcg
107461 tacttagaaa aggtgaatag ttgtttaaat tcaccttctt gcctgaaagg atttttaagt
107521 acccatctgt tcctgaaagg atcccaggta gacattttaa gcaagatact gcaagtggtg
107581 tgtactatca tagtttgaga agtatcgtat ggacaaccgt ccgccaataa gtagaacttc
107641 tttagaggat atttatcaca cacgtctgat ggaatagatc tcgtcgattt aggttctcca
107701 ggagtagcca tttttagcaa ctgcatacta ctcataggaa cttcataagg cctgatggtt
107761 aatgtagtaa ctctgccaca tgttaaacgt actaccggtg ttctagatag taatatccct
107821 aagcgtgtaa atacatattt cttgacttct ccatcatcgt acataatcgt gtatgctgta
107881 atgtctgtat ctggggatct caagactcct ataggacagg caactcgtag ctgataatcc
107941 aggataatat ctgaagtatt catgtaaagt aactcagaat tgatagtatc tagaaaatat
108001 agttctgtat tttccttttc gggtttaaat gactttgtat cattctggta agccatgtat
108061 atcatcatac tatctccagg aaccatacat ttcctcactc ctgatttttc gcggtcgttt
108121 ataagtccag aatatgtatc caataactta attaaaggat ctttaggcct ttcgataccg
108181 gaaaacaagt agaatacatc tttaacagta tctataattc cagttatagc agtaacggcc
108241 attccagcta tcataagttt tggacctccc gccaaacccg ctgatgtcag agtagttcct
108301 agagttgata agctcatcgt aactgcctcg aataccttct cttctttagt catagaatct
108361 tttctttgta taaccgattg cctggcttga tgttgagccg cttgctgtcc ggccattaac
108421 atggcacctc caaaaataag agatttatca agagatgaag atatttttttt cattgatcct
108481 ttataaccac cagaagattt tgaatttcca gatgggtctg ttccacgagt tatcgtagac
108541 ttgtcaacta cattgacttt atctttaggt atacctccta tttcttcgta gatcggagat
108601 tctggtttctc cggctagaga ataagatgat tctggtgatc cggctagcga ataagtacct
108661 tctagtttctg gcttgctctg taacatgccg catattactc cgtctagact tcttctacat
108721 cttctatgta gattcttagg tatagcaccg ctttttggat ttgcttcttc cggaatagca
108781 tgcaaaggtc ttctagaccc atcacgagga gatagtggag gtggaccgtg tgtaacagaa
108841 ggcgatggtc tattaggagg aaacaagtta ctaggttttc catctgtagg tccttccgtg
108901 tatatttcat tgtctagctg cggtgttcta gcgggtgaaa attgtatacc gttacttaaa
108961 tgtgtagtac cactatcggg ccgctttcta atagctgctc ttctagtaag aggagtagtt
109021 attacagttc ctgtatcaac acctttgatc atactgggtg aataaggaga cggtggttgt
109081 tttataatgt ctacaccttt aagtactttg gctgtatttt ctaatttttt tgttatagcg
109141 ttacccgctg gatctaaacc ttcagttcct ttcttcattt ttatgatatc ttttggtgga
109201 ggtggatatt caaaatcact actatcgctg cttagtcgtc tacgaggagg tggtggatat
109261 tcaaaatcgc tactggtact agatctacga ggaggtggat attcgaaatc actactatcg
109321 ctacttagtc gtctacgagg aggtggtgga tattcaaaat cgccgctact gctactactg
109381 tgccttcgtg actgctgcac gttacctagt ctcatctctt gtagttgcct tttaacatct
109441 tcaatatcca cgaaatcggg ttcagaatct atgctgctaa cagattcttt cctagaaaat
109501 tcgattctag tataaaccgg caaaccatgt ttacttttag acggtagatt attactaatc

FIG. 19D2

```
109561 tctaattccg tgaacaatac ctccgatatt gatttttgtt tttgacctat agtttcgcgt
109621 accgcttctg tgaaaacatc agatttaat tttggaggta gtttaggtgg ttttcttact
109681 ttggtgtata ggtcttcggg ttttccggta gatggtaaac taggagctat actagataca
109741 agatcttag ctctttttt tacgtcgttg tagatagccc catcacccgt aacaccagat
109801 tccctttct gttggatgcc tacctgaagg tgcgatgctt ttggaggaag tactggttta
109861 tttcctaaat gttttctagc attagctgta aatcctgtat ctttttcctt ttttggttct
109921 ttatcagatc tcctatttct gatttttgct tcacaaccat ccatgttact tacatcagga
109981 tagtacaagt atctgcaatc aaattcttct atactggagg attctgtttt taatgcaata
110041 ctccttctat gtctagaatg ggaggtgttg tttaaattgc tatgttttaa catttctgct
110101 gttttaccaa ccgttatcga actaagatct ataaattcca tacaatcgtc gtcatctatc
110161 aaattacaca aatagaaact atcagtagaa ttatccatct ctattcctaa ttctttcatg
110221 gtgttattaa aatcttcagg aacagatgtt acactcgcca taaatttcat ggaacatttc
110281 tcacatccac taattacttc atgggtataa acggtatcat tattaatgtt tatggaaatg
110341 cattttatca gttcgtcaga atttacgtta ctaccgtcgt cggtattaat attcgataga
110401 gatactctga ctttcacccc atttgtagta ttaattatag aaaagtttac cttattagct
110461 gtcacattat tacaattact gtattgtaat atttttgtgc ttccttttag tatattaggg
110521 tcattttctt cggatgtatt tttcgtagag ttgatatttc ctgccatgat taacgattcg
110581 tttgaataca taaatgcttc aacagttgtt tcgttaacgt ctagtactga tatcaagaat
110641 ttcatagcgt tatcgtaatc agaagaacca tcatttatag gaatggaagt agtttctacg
110701 gatgattgaa ttgtagttgg gatgatggtg gtaaaagttc cattatctgt aacggtataa
110761 taactgttag tagttaagac tacagtagta gttatttctt gtgttgtaga ttctatagtg
110821 ctattttac ctatagttgc ctcaaatacg atagtatagt tatacgcgta tgtatcgtta
110881 ccgagattac aagatctatt aaactccgat ctaatatctt cctttatttt tgtccaatta
110941 aacgaactaa gaagacgaga ttgttctttc ttttcagcaa tttgtaaata tctgaaagta
111001 gccgatgatt tacggtcgat ggtatcatcc tgtacaagca taccggtgtc gtggtataaa
111061 gaggatttc tcgcgcatgt tttgtatcct tcagaaacgg aaattaaaat taatataggg
111121 gtaatatacc acgagaatat tttgatattc attgttacat aaccgcgtac aggcatcgcg
111181 ataattatac taattattca ctttatctgt acgctattaa atagtaacat tataattata
111241 taatggatat gatgaagatc ataaaaaaat acataaattc ggaagaagaa gcgcaaaaat
111301 tgctaaaatg ggctatagat aatgcaaata tatattactt aagaaatatc gttaatacaa
111361 aagttaatat tgaagaaact aagtttaaaa cagtccataa tataggaata gagtattcta
111421 aagataataa gtataagcta tcttatagaa acaagccgtc tatcgctact aacgagaaat
111481 acaaagaact atgtaatctt atcaggtcca ccaatggtat agaaaaggaa acccttaggt
111541 atcttttatt cggtataaag tgtgttcacg ccaaagtaga atatgatata gaaaaagtac
111601 ccgattacga ttatagtaac tactttgatg tacttaaaga aaaatctact ataagatgcg
111661 tagcgtgtaa gtctaataat acgattccta tgatactcca aactagatca tctgacgaag
111721 aacctactgt acgcgtagta tgcaaagatt gtggcaaaaa cttcgcacct cctaggttga
111781 agtttaatta aatagcgtat ggttgtaatt atttactaat aaataattga tatactataa
111841 atcatgtttg atatcactaa tctgatagaa ttatacgagt ctaacgatta tgtatccggc
111901 gactacaagc attctcagct tcagaaagct tttttaaaac taccgataac agaagttgta
111961 atgttagtta aatctggatt ctatccatct aaattatcta aaaagttcta caagccaata
112021 gctaaattct gtgttgataa gatatattta tttaaacctg aatacgtatc gttaaaagac
112081 ttatttacag taatttatac attcgatgac ttaagcaaat ataaagaaat tataagatat
112141 tattattacg agctatctgt ttctaacagc tatcaagtat ataaaaaatg taaaaacatc
112201 ttaggataca aggatgaata cgataatgat attatagaag aactttctga aaatgattta
112261 gtagaaaaaa tggtaaactt tccaggtttt agaaaaatag tatataaaaa gaaaatttta
112321 tctataagaa tactaaaaga gatgtattac aaacataagg tattacctat caacaagggt
112381 ataactccta tcagagaaga agatatatgc tttttatag acgcgttgta tgatgcacac
112441 gatgatgacg acgttctata tttgttacta gagattaacg agcaaatact agattctgac
112501 gaggttaaag aaacaataat aagaaaaata tgtaaaggcg aaaatataga tgtattgcgt
112561 tattatgtat ctcattacct aatagatcat gcaaagttgg gcgtatacta taatatcttt
112621 ttctcagaac gcgatattat ttcagagtat ggtttaaccg acgaatcatt aaaagtaatt
112681 tgtaagtata tagacagata ttccagttct attccttcta taataaaatt actattggat
112741 aattctaatt atacattatt agcatcagta atagactata taccagaaga aagactcaat
112801 gaaaatctat atatgcaaat agttagacat tcaaacgata acaaacctaa aatcaagagc
112861 ttcaaagcag aatttttatc agaatgtttg atggtaatgt gttatctgag aggatacgaa
112921 gatattgtag atttccttat cgctttagat gtagaaacta ttgtacgaaa tagaataaat
112981 cctttaacg attatacgtt tacaacggat tggtttaata aaaacactga attagtacgt
113041 ctttatatat cctttattg tatagatcct gttatgatgc gtaagctact attcgaatat
113101 ccccttgtg agacttctac tacagtagcg atagaagaac ttaagaaata cagatcgtca
113161 ataaataata actataatat agactatcac gaagaattca aaattgtaga tttgcctaga
```

FIG. 19E2

```
113221 tcatttaaca taccgataag cgaggtagtt tcaactaaag aatataattc tattatttca
113281 tttatttcag acaaaagtta taaatttaag ataacttcac agttactaaa atataacata
113341 ttacaaacta taaaagtaga aaacttatgt tactctcata tcaataacct acattccttt
113401 tattttaata ttactaaacc aagtggtata atcgataata tatctagact tatatatcag
113461 ataggtgatt taggcagact acttagacac gggtttttat cgtttactga taactatttt
113521 ggaaaatgga taccctcatt aaattattct aaaatactgg atcattatca gtataatgga
113581 cctgattatg tattatcttg gcaaataggt aaactagatc taaaggcgtt cgtaaagtat
113641 aaagattttc ctaaattctt tttaacaaaa tataatatcg atttcctgtt agaaaaagag
113701 gtactattat actactgtat atattcttat ttattgctgt atatactagt gggttcggta
113761 acgtacgtag aacaggaaaa catatattat tttattacaa atataataaa ttcgttcatt
113821 caaggattgg gtatacgtaa ttctatagat tcactatcag aagaggtagt aaaagagtta
113881 ataattatac aaaaattacc agaaaataaa cgtaaactat catctatcag acccgtaagt
113941 ctgttaaact tatgtaaaag agtttgtgct tttatatcta gagatggaaa gaagtagaca
114001 agtatactat attattaacg agtatttagg tagacatcca tcatctaccg aataccaagt
114061 attaaaacac caagtagaga agatttcaaa aattaataat tttaataaag aaactttctt
114121 ttttctgcta aaaaaaaata aaaacaaatt ttttaaggat ctagaactat cagatgattt
114181 gctcaaaaag agaatagacg aatatttttc aaaacagaaa cacgcgaaaa ggttaggcaa
114241 cttattcgct atcatggaat tacagaagat attaatttct agttttacta agactatagg
114301 tatcctaaca accaaagtac cagaatatta tcattccact ataaaactgg aatattcgtc
114361 tatggaaaaa atagcggatg atattttaga ttcttataat gttgttgaac ctagtaaaga
114421 agtaaaaggt agacacaagg tatccgatct agtaggtcat gtttataaaa taatggaaga
114481 ataccttaga agacatagca acagttgttt atgttacgga tcttattctt tacacttctt
114541 aaacaataaa atagaatacg gggatataga tgttttacaa acaaatgcta gaacattttt
114601 gattaatata gcctttctaa taaaatttat aactggaaga cgtatagtcc ttctaaaagt
114661 tccctttttg aagaactacg taataatgca cgatgaagaa actaatcacg ttatggatac
114721 attcaatata cgtgaaaaaa ccatgaatat gatacctaag ataatgatcg ataatatgta
114781 tatagtggat ccgtgtatac aattacttaa tatgattaaa atgttatctc agattgatag
114841 attggaggaa cttcaagcca aattcgaaaa attgagcgta cgactaggaa cgttgttaga
114901 atatacgagg tatagatatt ctataccact ggatagcgaa agtatattag aggtacgcgc
114961 taaacttgat aaagataaaa gaaaaataac agttgacttc aagaaataca aactcaatta
115021 tataaaatgt tatttctatt tagatgaagt cgaactaaag aaatttataa gtaaaaattc
115081 tggtttagac gaatacgaag attttgaggc ggtaacaaat tcagagtacg ctatacgtaa
115141 taaaacgatg tacacgtact tttcaaatac cgcccttatg agatcggaaa acgaaataca
115201 tcccataacg ataaacgcgt taactagtca cgcactttta tatcatgtta tcacaaggaa
115261 gttttacgat gatttattag gcgatctagt tagatctctt atgatcgtgg aaaaagttcc
115321 tgtatttaaa atcataccta gagataaaaa acaaggtagg cacacgatca ttgatattga
115381 aaaggatatc atatttcact gatttattac tctcgctgct ttatctgttg tattggcaaa
115441 caaattagat aatgcacctg tattaataaa tctcaattgc ggagcttgac gttgctgctg
115501 aggcgatgtt tgttgcatat aacatttttgg tgctgaatcc gaagaactaa tagggcaagg
115561 tgattggggc ttatctactt tcagtacgca actcgtttct tgtttcatgc aatctatagt
115621 tctcacattg catagtttta tagcttttag aactaaatat cttccttcat ccgtgtttag
115681 aatgaaagga ctaacaaagt attttggatc gtgaaatggg gttccagcac tttcttccat
115741 ttatagtatg aatatttctt cttcttgtat tggcaaaaac gtataagtca gatacaaaaa
115801 taaaataatt atataaatgt ttaaaaatta caagtatact ctgttatctg aagatactaa
115861 taatatgaaa ctacttattc cgggattgga agatgatatg gaagcaggaa caatagaaaa
115921 ttccggatac agaaatatat ctacgaagat gtttaaagat caagtaaaag acatagttaa
115981 gaaaacttac aatcagactt acttacagtt attacaactt cttgaaaggt ctaatgtaga
116041 ctgtaacgaa ttagaattgt tatatagaat aatcaatatt aatccaagaa tttgtcatag
116101 attctatata aatagatacg atagtatatt tgggtctttt aataaattac atgaatttat
116161 aagcaacgtt atgattaaaa tatttaaaat aggtaattct atatatatat tacgtttatc
116221 agtgataata ctagtctaga aattaatgta gataacgata cagaaggaag actaatgaat
116281 atagattaca ctattaaatt tggtgatgta attatactac aattaggtag aatatctata
116341 aaatttagcg gtaattttgt gataatgaaa gacatacttt tcttagtcac ggattctaac
116401 aaaatagtat ataacgaaga tgagttttta ttagagatat ataatacata aaattgataa
116461 aataatcaga tatcgtagat tgggatatct gtcgcgcaca tatgttagtc aatttatttt
116521 aaatataaaa tatacgaata caatctattt attgctattt ttaaataaga taacaatgaa
116581 cgtatcaaga ttagaagagt taatttctat gaatccattt agcgatatgg aaaatatagt
116641 catcaacgaa aaagaaaaat gtatattagg aaacaggtgt tttgtcaaac tttcagaggt
116701 atataatatg cctatgtgtt gtatagatac caatcaatgt ttaactatga atagatttaa
116761 atttagctta aatgaactac tctacacacc ttttttactat aaacaactac aatatcagta
116821 tctaacaccc cagttcatat ttagatgtat acaagaagct aatgaaaaca atatgagttg
```

FIG. 19F2

116881 ctattactgt tatactaaga aaaaggaaca taacggatta aatattgata ttttcattcc
116941 aactgcaaat tcaaagtctt atatagttat aggactacgt ataaaagatt tttggaaaca
117001 atcttttaaa gtaaataagt aaataaacat taacatggta aaaatctata tatttatgtg
117061 catttataac ttatgtacgt tagtacacaa tggtgttata aatcactttt tgttattaac
117121 ttaatcaata aaattatatt tttatataca tatttcccaa aactgaaaaa aaataaaatc
117181 ttgaagataa acaggtgttt attgataaat tatatatatc aataaatatt ttattatacc
117241 atggcgatat ttaaaaggct aagaagattt ctaggaatcg aaaaaaaata gacttaagaa
117301 aagaatacct agcatgtatg tatcagaact agacttatct aaaggcttta tggtcatatc
117361 cgacataaaa accaacgaga taataaatat agatctatac aatcaaaaag gtttttcaac
117421 tataaacaac aatcatgaac aaaatcatct gaatagatta tctaaaagct gttttgatat
117481 acataacaag ataatgtgca aggcagagat gagaaaatta tgctactaag acactaactt
117541 tttttaggaa aaacactaca tatttatttt aacaaatcag tctatatatg taatattgtt
117601 actcaacatt atgctactaa tattataatc taattcttcc attaatgagc ccaaaccaag
117661 ttctattgaa tataataata tattttttc tacttcggat ctcgcggatc ctatagacag
117721 aggtatcacg ttatcgtcta agcaggttac gacgctagct tctgataccg aaaacatgtc
117781 gtagtccata tgagttccgt taataagtac agtgatttct gttgtgttgc cggtgtcttc
117841 ttcgtatata aaatcatcta gagtaccgca tgtataatta caattaggat acaccttagt
117901 actggtgttg agtttaaaat ctaaaaggca acacatgccg tattgctctt tcattattat
117961 ctcataaaga tcattatctg ataacgtgct tatcaatact tctttagata aatcttttat
118021 tttttcctct aattgagcca tcttttccat atcagctaaa tacgctactt ctaatacact
118081 gctatctatg ttaacacttg ctatatctct acctttatca gataacgcac cggctaatct
118141 attaatagac tttggtagag tcccgtcggt gtattcgtac aactctttgt aagcttgata
118201 taagccgcgt aacttacctg atatggtact atctatatat tcgtttttgc tagtatcgta
118261 tttgaaatta aaagcgtaag gaggttcgtc taatatttct ttttctatcc atgtatcact
118321 gtagtatatg tgtatgtatg acttacacgc ttcatactgt ggaggataat aagttccgta
118381 cagagaaccg taaccgcaat agttatctgg aacgtacatg ctgatactag gatatttata
118441 catgtcacat cctcgtggag tattagcatg cgaagaagaa tagcctctat actttgaaga
118501 atctaaagta gtaccacaat gatccttaga cgatatagtg atagaacata taccttcata
118561 ctgaggcaga gtagacctag gcaaagaaaa ctcttcgcac tgtaaggata ataatttagt
118621 agtcaagtct aactcggcgg tgcatttgct cccgcttagc gtagtaaaca catacttttt
118681 accatctcca tatttattag taagggcttg ctgatattgt aatatagata ttctctgact
118741 atgatatttt atgatattct gtatcatatt gcaaggtact aatacaataa gcatagaact
118801 gaaagttctg aatttctttt tcgcgtcttg ccaaaatcta tccgctgtat catacacttt
118861 tcctagaccc gataatgaat acttaagttg taacttgtaa ggaaaataat ggctggattt
118921 actgatactg gataacgtag caatatcggg gtcatacttt tcagttatca taatctcgct
118981 acctatttct gtatctacta catagttagg attccatata tctattcttc cgtgaaagct
119041 aatacacgac ttactaccca ctatattaga acacgtccta gaacgccacg gcatgtgatt
119101 gtataccaat tcgttaaata gtttattttg tccatcgtag gtatctagag gcaatacatc
119161 ctttggaaaa ttaggttcta caaattttag tattatcatg tctgatctat atcttgtatc
119221 gtaatcgttt acacaaaata ctcctatgtt tgtttcttta accgaggcaa acatctttac
119281 agtaaaaaga tcagagaatg gtaattctat aatcccatct ttattaccta cagcaacagg
119341 agtagatcca gaaggacacg tcaacacaaa actagtaaat cctctactcc cggaaaacaa
119401 gtatatttct acgtatattt ttctaacacg attttcacag gatgaaatat catccagcac
119461 catgacgtcg aaccagtgac aatggttgga ctgtctattg gcgcaaaact tcgcatggcc
119521 tgatatttcg ttaggtttta tgaccgtatc attaaaatta aatctattaa aagtaaataa
119581 ttgtttaaat ctgtttttat tatcaaatgg attttctaat aaccatcgtc tattttcttc
119641 ctcccaaatg gacattctta ataatacact gcacgtagta taagctatag ctactttaga
119701 attatcaaag ggacatcctt ttactagtag gtaaaagttc ttgagaggga aaagatcaca
119761 aacgttagaa ggcatcgact tggactcttc gggttcaccc ggagtagcca ttttcagtaa
119821 ttgcatatta gatagaggta tctcaaatgg ttttaaagtt agagtaactt ctctcccaca
119881 tgtaaaccgt actataggtg acttagaaag catcgcccct agcctagtca cttgataaaa
119941 tctaacttct tcagtaacat cttttaaagt aacaaacgca tttacatcta aatcaggaga
120001 tcttaaatat cctataggac acgcgatagt caaggaataa tccattatta tattactagt
120061 attgaggtag taaactatac tttcaggtac atctataaaa tgtaaattaa gtttctccaa
120121 tgatggttta aatgaggaat catttctata agctaaataa ataactagat cagatcccgg
120181 cataagacag gttcttacac ccattctggt agaatcagaa actagttcgt tatactgatt
120241 aaattttttt actagtggat cctcggtttt tggtttaccc gtgattaact gataaagatg
120301 atttcctaga tctaataatc cagatatgaa tgataatccc atgcccgcaa aagctacagt
120361 aggagatgct ataattcctg cagaaagcat agcgttacct acactactaa aagaagcact
120421 aactgcttcg aatatagtct cggcttcgtt aaagtcaacg tttttaaaat tttcattcct
120481 aattctggca ctaatcatac cttgaactat caactgtgta gcagatgtca gagcagccgt

FIG. 19G2

```
120541 cttatcgaac tttttagcag tttctatcat tttctctctg tatactttct tgcttttaat
120601 atctagctct ttaattgatg gttgatatac agatccttcc atatcagatc tggatgtatc
120661 tccttgatat ccgctttccg accgtaaacg attactacga gttccacctg aataagttct
120721 agatcttcca tataagctgc tatcgatatc atctatatca ctgttcgata tccaacttac
120781 cctactacga gtcgatcctt gtcttacgta ctgtctactt ctttcatggt tatctatctt
120841 agattcatcc gagaatgtta catgggatac cgtatgtttt atacccgatc tgcctaatat
120901 actagtactt atgggaattt ttggtactct taatggtgtc ttagaatttc ttaatttatc
120961 aatcaagata ttaacagccg tgttatgttt tacgttatta ttattatttt tacccatatc
121021 aggcacgcgt cctaatagtg cacaagccgc ggtattgccg aactttccgc aatcttcaat
121081 actatttgtg ctcttagtcc ttctcaatga atcgaaatta ttttcttgta ttgtttccat
121141 agttaggcta tctatacgac gaccaaattc cttcattgaa ctctcgatgc tatgacgtct
121201 aggttttacg atactcgtac tagtgtctac attaaacatc aaactgctct gtctttgatt
121261 gtacttagta agtaatactt caccgcctgt gtccctaaag tctctaattt tttctttcat
121321 agtgtcaaat attgaactag atacaatctt tttggaacta taactagttt tgacatctcc
121381 gtgtaaggct tttgattgtt ttgttattcc atctccttcc gtgagatatt cttttatcac
121441 cgttttatgt ctgttatcgt cggataaagc agataatacg ctattcactt tattggtagc
121501 cacgctgtat actccagcaa taacgggatt tttactagga ggaggaaggt ttgaagtcga
121561 tgtccttaag acatcccgaa tactataggg gtctgtatcc agaggtactg aaggcatata
121621 aggcgcgaaa gcttgtctag cttgtaaaga tagtctggat atgagctgac cgtcgcctat
121681 tattccatca ttttcactcc ctccatggat tcctgtttgt atatgcgata ctcgatccgg
121741 tattacctgg ccatctacac ctagataacg agccatcatt ttagtttcat catctgtatc
121801 tgtatttata gagggtacta ttgtcctttt ctttctggat ttagcaattt ctgctttctt
121861 actattaaca cattcggtat attcagttcc ttctctgtaa ggttcgtaag cttcatacat
121921 acattcaaga tcttcgctgt ctaaaggtat ctcgcccgta tctcttttat gtctgttacc
121981 ctttgtatac atataagagg ataaaatttt tgttgcttgt gcagcggtat ccgctgctaa
122041 cgaaacgtag ttcgagcaat cgggattatt ttccaacata cactcataaa acaaacgggt
122101 attaacatca tccttaatgg agaaatttcc aataatatta agatatgaat taggaggggt
122161 tacaacttct gccatcaaag acatactagc atgatcgcaa ttaccagtta gtgtttttct
122221 aatagtactt ataaaagaat tagatgtttt acatgattct actatcttat taatacagtc
122281 aggaaactta tcagaatcca tatacggatg ttggacagat acaccgttaa aatttataat
122341 aatatcttcg gcagcgctgc gtgaatcggt aacagagaaa ttacctattg ataccgtact
122401 tatagtaacg ttattacact taggattttc atattttacg tagtctatat ccggtatttt
122461 gaaactgtat ccggatccgc tggttgttac gtactcgtct atactattag cagtagttaa
122521 ttgttgaatt aaagacataa gtgtcttttt cttgctgtct ccgatcttgg ttcccttagt
122581 tacttgtacc attaccctta agacatattt gtaagagtag tcatacttat agtgcgtact
122641 cccgttggat tttttaatac acttagtctt gtaggcatct tttacttctt ttcttatttt
122701 ttcccagtca aactttccca tgaacaacga tttttctttt tcttcagcga gttctagata
122761 tttatgtaac gcttctgctt tagtatccgt tgattgtttg ttctcgactg agttttgtgc
122821 agaatgatac ataggtaaat ttttcataca tgttttgaa tccgttttat gtatatatat
122881 gaatgcatat atcattatgt atttgtacat tattgtaatt tataacatac tatattaaag
122941 ctataaagtt tttagttcaa ttttgatttt ttgtatattt atatacataa cttaaagaag
123001 taagttatta acatttttgc acattaaaaa tagcattcat catattttac agtaataaaa
123061 taacatacat tactcttaat tcgtttcaaa aatgggaaat atttttaagc ctattccaaa
123121 ggccgattat cagattgtgg aaacagtacc acaaagctta acagctatta attctactaa
123181 tcttttctact tatgaatgtt ttaaacgttt aatagatcta gcaaaaaaag agatctacat
123241 agctacgttt tgttgtaacc taagtactaa tcctgagggt actgacatac taaacagatt
123301 aatcgatgtt tcgagtaaag tttctgtata tattttagta gatgagagca gtcctcataa
123361 agattatgaa aagattaagt cttcccatat tagttatatt aaagtagata taggtgtgct
123421 taataatgaa tcagtaggaa acttgttagg taatttctgg gtagtggata agcttcactt
123481 ttatataggt agtgcgtctc ttatgggaaa tgcgctaaca actattaaaa atatgggcat
123541 atattccgaa aataattctt tagcaatgga tttatatttc agatcgttgg actataaaat
123601 tataagcaag aaaaaatgtt tattctttac cagaatggcc acaaagtacc atttcttcaa
123661 aaaccataac ggtatattct tttcagattc tccagaacat atggtaggta gaaaaagaac
123721 ttttgacttg gattgtgtta ttcattatat agacgcggcg aagtctacta tagatctagc
123781 gatagtatct cttcttccta caaagagaac aaaagattct atcgtctatt ggcctataat
123841 aaaagatgca ttaatacggg ccgtattaga acgaggtgtc aaactacgag tgctattagg
123901 attttggaaa aaaacggatg ttatatcaaa agcatctata aaaagcctta acgaactagg
123961 agttgaccat atagatatct ctactaaagt atttaggttt cccgttaatt ctaaagtaga
124021 tgatattaat aattctaaaa tgatgattat agatggaagg tatgctcatg ttatgactgc
124081 taacctagac gggtctcatt ttaatcacca tgcttttgtt agctttaact gtatggatca
124141 acaatttaca aagaaaatag ctgaagtgtt tgaaaggac tggatatctc cttacgcaaa
```

FIG. 19H2

124201 agaaatagat atgtctcaaa tatagtatat atgataaaaa gatcctaata aataaatata
124261 gcatggcact aatagaacag ttacaatctt ctgaacaatc aatactttca ccgtttagat
124321 attatggttt taaagatttt cataatgtaa tttttaccac aatagatgac gaaacattaa
124381 tagtaattac agtcaacaat gtaccattag taactaggtt aataacgttt gaaaaaataa
124441 catttttttag atcgtttaat agtacttgta ttataacttc caacaataat tcggatattg
124501 atacagatac ttattttata ccaaattcgt tatcactact agatattttg aagaaaagag
124561 catatgatgt agaactaaga gatctatcat ttgctataat gtcggaaatg aataacgatg
124621 aattgagaaa tagtgatatt gtatctctaa acaaatggct acataagcat aatttactag
124681 actacaaatt agtactaata agtgatatcg atagaagata taaattatac aataaaaaaa
124741 atacaataat tgatgttata tccgtaaatg gtagaaatta taatatatgg gttaaagatg
124801 ttatagaata ttattcaccg gaatacttaa gatggtctat agatattaaa agagccacag
124861 aaagtaataa ctggttaccg tatagccagt ctataaaccc tttgaatgaa aatatatacg
124921 cttttgaatt tatagctact ttagaaagat ccaatgagcg cttaaatatc ggagcgatat
124981 tcctgtatcc ggatataata attacaggta gaaacaacga agatataata gaaaagtttt
125041 tagatcagtt agaagaagta atatataaaa aaaattctga tagtattgtt ttaacaggtt
125101 atcatctaac atttttagag aatactattt tagagagata tatcagtaag tataaagact
125161 ggattttttac atgtaatcgt ctagtacatt gtaaaaccgg cactgaagta ttcttatttg
125221 atgccgctat attttttcca tcctctaata agaaaggata tgtaaaacat tggacaggta
125281 aaaaattaaa ttttaaaaac tttttccaaa aagatagtca gctagaaaaa tacataaata
125341 ataacagtgt agcagaacgt atatattatt tacagtcttc tttacacaag catatatcct
125401 gtctaataga aattttcgag ttaaatggat ttgattttaa ttttcctggg ttgttagata
125461 tacttatttt cagtattcgt gttaagaata ataatggtaa ttactattac cctaaacatt
125521 cttcagctgt gaatttgatg ttgtcatcta tttacacgga ctattatgct attgatgata
125581 tagataaaga tagtaagaaa cttgttttta actctatttt tcctttaata atggaaggat
125641 attaccctga aggaaaacct tattatacga aaacacccaa agaagggtat ttgtcaatat
125701 gtttatgtga tgtagaaata tctaatgata taaagaatcc tatattgtat tgtaaagaaa
125761 acaagtcagc taggaagttt acaggagtat tcacatctgt agatatagat accgctgtaa
125821 aactaagagg atataaaatt aaaatattag aatgtattga atggcctaat aaaataaaat
125881 tattcgacaa tatatgttat ctgaataaat tatttataga acatcaggat tacacacacg
125941 atgaaaaatc tttacaaggc tatctttttt cttatttact taaaggcaac gttaccgaag
126001 atgttttagc tatgaaaagt tgtagaaata atctttctat aatatcattt ataataagtt
126061 actgcagaaa ctatacttac aaactattag aatgtccagt atacgaatca agtaatatag
126121 ttaaatgtaa atataatcaa gttatatata agtaaacaat ataattgaaa ataaaaatat
126181 aatataccag cagcatggat actaatagaa aaagatcact agatgaacat gacaccggtg
126241 aagaatcacc cggtaaatta caaatagttg aaattaacga tgaagaagat atcacattta
126301 cagataaccc atattataaa ctagtgaaat ctcgcgataa tagtattaat ctcgtacctt
126361 tagtcggatg tgttatgatt aagataaatg atattaaggg tgtaacagat aaagtaaata
126421 aactattacc taaaacatct agtaagacaa attctactag ttgtataaat attcctatag
126481 atagtattcc tttgaatttt ctggatgatg gtaataaata tttcaatgtt tccgaagtga
126541 gtatacttca ggtaagtcat ggaaatgata tgatgaacat agataaatat gtcgatggta
126601 gctttgatta catagccgta ttatgtttaa aaaattctgg tagatctgtg attatgttaa
126661 atcattgcaa caaacaacac gtaatgcaag ataatttctg cttaatattc agatcttttct
126721 atggtataaa catattgact caaataattg gagaatctgt atatttatta gttaaattat
126781 cacctagtga tttatttaaa ataagatggt cgtctgttat cgactctaat agattcatgg
126841 ggaagaaatt ctatatccga aatttacaag aagacgcgtg tatagaaaaa atgaaaaata
126901 tggaaaaaga tatctacaaa aacatagagt ttataataat taatagcgtt ttattggaag
126961 atttaaaatc tcgtcttgat ataacaagag agttaaatca caccatagat aaaatgttta
127021 atcataataa taatacactg tttagtgata taataaaatt atcagaagaa attatagata
127081 aagactttaa aaacatggaa aaaatgtctg atagtgtatt agcagatgta aaacaaatat
127141 ctaaaacgaa gaataaatta cgtgaaagac ttttaaaagc agcgatttcc tctaaagaag
127201 tagaagaaat attatccgat atacccgtta tagaagaagg tacaataaaa caattttctt
127261 taaatcaacg agctgtatac gatcactaca aaaaagtaat ctacaaaaat aacagtagct
127321 tggacttagg atgtatgaat atagaaaaga gttatatgtt caacctatac aaggtatacg
127381 gacaaaacga gtacatgatt acatatatac taaacttaat aaatagagta aaaaagggta
127441 tggatgctat aaaaagtaac ctaggtgata tatacaaata taatattgat aatattaatt
127501 tagttgtatc agaaagaata aacaaagtta tatcagggga atctctgtaa atattagata
127561 tataaaaata ctgttagtta cgtatataaa atcactttcc gtatagttgt atttgcttct
127621 acattaaatg gaatttccgg acatacatgc ttataattct accaagtatt tagaagatgg
127681 agacactacg atattaggag atactattca gtttcagttt atatacgaaa atatagacaa
127741 taaggagcat atctccttac caaaataaa gattttcaag tattttagag ataagatatc
127801 ttttgaaaca ctagatagaa ttattaaaaa tgattacata aatccttcct atttcagtt

FIG. 19I2

```
127861 aaaagataaa aagttttgtg cgcacaatag ggatttttac catctatcta ccgggggata
127921 tggtattatt tttaggatgg aaaaatatgt agttaaattt gttttcgaag acgggagtaa
127981 aaaatataaa cctatggaag taacatctga atttacaatt cctagatttt tatataataa
128041 tcttaaaggt gatgaaagga agtttatagt ttgtgcaatc gcgatgggga ttaattttaa
128101 gatagatttc ttacgtacaa tctattataa cacgatgagt ttaatgtctg cgttatttaa
128161 catcatggaa ggagaacctc tagaaaacaa atattctcat agaaaagtat tacgttattt
128221 cgctaagtac aaacaatcta atgattttgt aaaattgata tcacagtttt atccgtatgt
128281 tgttaactct aatatcaatg taattaataa ctttaattat ctaattaatt tttttgaacg
128341 tagtaggaga tcaaacggtt attttaacag aggtaacata ataatattcc ctttagcaaa
128401 atgttccgca gaaaaaataa ctccggataa ctatgcacaa tatggatttt ctagtatagt
128461 agaatatact aaatttatgt ttttacaaat agctttattg tacataaaaa tttatgaatt
128521 gccatgcagt aactttgttc atttagactt gaaaccggat aacatattaa tttttgattc
128581 caaagaacct ataaatatat acgtaggtga tatgcattat gtgtttaaag aacctataag
128641 atgtacatta aacgactttg acttttcaca gatatcggaa attattccta ataagaaagc
128701 tgtaaccgct attaacaaag aacagaattg gtattacgac ttccactttt tctcgcatgt
128761 actatttaaa gtatatccag aaatatctaa agacgaagat tttacttctt tgcttaacga
128821 atttactatc tgtgataaat atatctgtga aaactttaga ctacaagtaa ataaattacc
128881 ttctatatcg tttttaataa atatagtttc tagagatatt ttttcaaagt ggatagatgg
128941 aaaatcaaca agtcatcagt aatctatact atttattttc tgaaaagtac ctagagaaat
129001 tgaatcaaca cccagacact agtaacgtta gatgcggaat acatataggt tatttaagcg
129061 gtgaagcaaa aaactgtata gttagtataa taaacgcgtg taacagtaat gaacaaaaaa
129121 gctttcaact tctgatagaa tcattaattg aaacaataga aaatcttcca gaaaaacaac
129181 aaaaagaaat agctaaaagt ataggaatca acatagatga ttacaaagcg ggtaaaaaga
129241 cagaattaca gcagcattgt gaagcctatg ctaatctgac gcagcacata gatatacaac
129301 acttcaacat aggtacgtgc tattctccta acgataaata cactgatata aaaattataa
129361 atacaggatc tgctttatca aactgcggag tagaaattat tctaaataaa attaaaacaa
129421 ataatcctat agtacctata gataataaac tatccatgga gtctttttca ataaaaatggt
129481 ttattatata tatagtttta tgtgtgttaa tattattatt gctgggttat atatatagaa
129541 ctgtcaggat aaaatatacc tacggtgtat atatttaaat ctaaaataat aagaaaataa
129601 caaaaataaa atagaaaatt aagtccaaga atatcttatt caatcagtat tcgggtacgt
129661 gcagtacaat ggctgatagg aatgttaagt cttctaataa tcttacaaag aagcgtatca
129721 agaaagttag aataaagcag cctgatccta ctaccgaaga aatagatact tacggcgccg
129781 atataaatgt taaacttatt caacctaata taagtataga acaagatgac ggtgaaatac
129841 aaactattca tatagatgac tttaattagt tgataataat tacaaaaatg tccggagaca
129901 tttcattgat ataaatttaa attctatcaa gtcatgatat gaaggataca tactgtgaat
129961 aagttatact actggttatg ggttatacta cgataaactg acaatatcca taatgtgtaa
130021 atggtataga aaggaataac ttcactagat gttgttctac atggcgattg ttataccaca
130081 tattacatat ttgtattcta aacttgttat gtatatccta cctacttttg gatattttca
130141 tgcgttatta tatattatac tataccttaa cagtattatt acttatttta ttaagatagt
130201 aaaataacgt catctttttt ttctaataaa tagtaattat gtctagaata aaaatactaa
130261 taggtataac aggtagcgta gctgcggtta agttacctga cctgataaaa gaattaacgc
130321 gtttggaaaa catagaatta agaatagtcg ctacagaaaa ttctatgaag ttcacagacc
130381 aaaaaactat aggtattcct atttatacag ataaagacga gtggactacg tggaaaaaaa
130441 tacccgatcc tgttttgcat atagaactta ggagatgggc ggatgttttt attatagcgc
130501 ccttaacggc aaatacgtta gcaaaaatag ctaatggtat atgcgataat ttactgacgt
130561 ctattgtaag agcctgggat acaaacaaac cactcatttt ctgtcctgca atgaatactc
130621 ttatgtggga acatcctatt acagaaaaac atatagatac gttaaaatat atgggtttca
130681 tagaaataga atgcatagaa aaaaaactag catgtggaga cgtaggaaat ggtgctatgg
130741 cagaagttgc agaaatctat agggttgtta gagatataat gagagtttaa atatataaaa
130801 aatattatgt ataactaaag catacttcct ttaattaagg gcatgtacaa gtttacaaag
130861 acggatgaaa agatagagtt tagtagagaa atttcttccc gtaagataaa actacggtaa
130921 tatctaaaca tttcgttttg acgtaacatg aatacgtcaa aacatataga gattatcagt
130981 atccaagaca ctaataaaca cgtagcttgt ataactatta ctataagata aaatacttct
131041 atcttacgta taacaaaaat gctaatagat aacggcacta atattaactt atctaaaggg
131101 ctaacacctt tacatatagc gcccaaatcg ttataatata taattaatta acaaagtact
131161 caaagtaaac actttgtaaa gaaacataac agagatataa tactagactc ttttattatg
131221 cacgatgaga caggtttact ttagatagcg gtactgatgt ccacacgcgt tagataaata
131281 taataaatct catctacatt atgctgtgtt tacgtaatat ctataaaata gcagagatat
131341 aaatataaga gatgaatcaa cgatacgccg atattctacg tttttcattc ttctagaaac
131401 atttgaacta ttattagaca atggagaaaa gtgaatatac gtaataaaaa taaaactata
131461 ctattgatta aatatgtcaa taccttaggt gcctatactt catacttgct atataatcaa
```

FIG. 19J2

131521 tctacatata atgctataat tagactattg gtaaaatata tacgttgatt tagatgagtt
131581 atcatataat aaaaatattg aatacataaa cagaaaaaag aaataacaaa atataaaatc
131641 tggtactcta gttattgcct ggaccgtttc tttcatttta taaacggtta atttgttaac
131701 caagttaata gcttttgtaa ataatataga tatagaggaa tattccctac gtataaaaac
131761 aaaactagcg gtgaacagag caaatctata caatatatgt ttaaataaga ttaacggact
131821 cttatcacgt aacgataact gtgttcattg cctgtagaaa ttaggtgtta tatagtatct
131881 ttttctaggt actatgaatt acttgtaata ttgaaataaa agactacatt aagtacttgt
131941 ataataattt tacattatgg acggacgatg tctccataat attatgtata cgggtactta
132001 tgatgaaatc atgagagcta taaatatata cgaacaccgt aactattctt ctttcagaaa
132061 tctaccgtta cactacgcga tttattctag aaggaaagat atagtagaaa ccttgctaaa
132121 gtcgggttat gatcctaatt ctgtagatat cacggataat aattgtcttc aattattatc
132181 aatgcctttt gatataacta tgcttcccgt tgatgaagaa gtacaagact atgctatttc
132241 gttctattta tctaaaaata tgaaacacac atccatgtta atacctatta ctaaagaagc
132301 tttacgcggg aataggtatc cttcagagcc ttattttagt agcatgtgta gaaaatttaa
132361 agataatgag ttatgtataa tggatctttt attacggtac ggggctttac ctaattctag
132421 aaaggatgga ttattacccc tatatcatgc cgcggcggct ggtaatacag agatggtaga
132481 attactttta agttacggcg ctaagactaa tctacatacg cgttatgaag attctatttt
132541 catgtgcgct ataaagtcta acaatgtaaa aactgctaaa attattagcg atctatataa
132601 ttacaaaaac gatataaaca atatattaaa aacaatacag ttatataatg ctgatagaga
132661 taggcttaga tataaacact aaagacaaaa aaggaaaaac agctttacac tatgcttgta
132721 attcgattaa ctgtatagaa actgttaaag aaattatgaa atacggtgcg gatataaatg
132781 taaaagatcg tgaaggacta acaccgttac attcggcgtg taaatacggt gatctaaaat
132841 tatccaaatt attaatcgag tatggtgctg atgttaaagt aaaaacaaca tctaccgtac
132901 taaacttagc ggtagaatcg ggtaatgtag aactagtaaa atttcttata gagaagaatc
132961 ccgaatttat tacatcagac tacttatcgt tgtcactggc gattagatgt aaagatatta
133021 atatagtctt acttcttttg gacgctggaa tggatgtaaa ctctagtaag tgtatatcga
133081 caccccttca tttaggagtt attttaggca attcaaatat cgtcaagttg cttttagatc
133141 atggtgctaa tattaacgct atagataagt acggcgaaac acctttagag gcagctaata
133201 aacgcataaa tatagattat gcggaattat ataaatctaa tagatttatt ataaagtatc
133261 tagtattcct atcacgatat gactataaaa taaagaataa tataggtttc attaaaaata
133321 tgtatataat agataaagat gaaacgctaa gttgttttag aaatatgtgt gagacagaat
133381 tagataagat atcatctata aaaataggtc agtattctct atatagtctg ttagcatcag
133441 ataatgatgt aaaagaatat atatgtaaaa acagacagga aataacacaa aaaattattg
133501 ataatctaaa agatattatt atatatcgtt cttttataga gaaatatatt tctagaataa
133561 atatataaaa cttttttttaa catattagta tggaaaaatt aattatatat agttttatac
133621 tagttgtatt aaaccacgtt tacggacaat atctatactt aggaggacta tttagttcac
133681 cgcgtaaaac tattatcatg aagttatgtt gtccatccgt agatggagat atgttaccag
133741 cggataaaat cggtagtaat ataagagcta cagattgccg atgtaaagt aaaccgtcta
133801 taatagtatc taccaccaaa gaagaagaga agtgtttcc tcctaatact ccgtggttgg
133861 aacaagctat aaaagaaaaa aatttaaaaa taccgaagtg cgtatactat cctaacaaga
133921 taggcgctcc taaaggattt ggttataagt agtttttaaa acactcgaaa ttcttcgaat
133981 acagattaca agtaatgtta tgctttttaat agttttgaaa tatctatgta ataaagcaaa
134041 attaaaccta ttatctaata atacattact cgcgttacat aattactcta gctttaccta
134101 tgtcaagact gtagctatcg gtattaattt catgatccgt tatagaatta gtgtatctcc
134161 atgagatacg ttatatagtt catacctata gcacatccaa aacatatgtg tatgaactta
134221 tctcctgcct tatcagttat cgtataagat gagaaattgt aacaaagact tcttccttga
134281 caacagtgga agttctaaac ttgtaacgtt aattaaaccg gaggaaacta taaatataga
134341 ccagcatata cttatatagt aatacccaca tatttataaa aatcgttttc gcgataaaac
134401 acatacagtt atatttatac taactagtag ttagttgctt tatcaaaaaa aatcataaaa
134461 ataaatctat acacattaat ttaatcaggt atctataatg ggtattaaaa acctaaaatc
134521 cgtattgcta ttaaagcaca gcttgaaagt acttgattcc gctgtaaaaa gtaaagaaat
134581 atacgttgat tttctaggat tatttatggc aatcgcatac tcggttacat ctacagcaat
134641 gttacatcat attataaaag aaaaatttaa gtttatacat tctatagctg ataatgttac
134701 tgtgtttgta gatagaggaa gtatttctct aaaaacatca ttaagagaga agagaaaaca
134761 atcgttaaag aatcaatata aaaggaagca agaagaactg aaaaacttgg aaatagcgat
134821 agacaatctc tctgtagacg atgaaatgta tgaagaacaa aaagagagct tgttttctaa
134881 aatagataaa aatagctatt atatgttctt ggcggataag aaaaatatgg aagctattat
134941 aacagatgta ctagctctctc taaaaaatac agaaatctat tactgtgatc atatagatgc
135001 ggaatttatg atgtgttgta gagcaaggga atattatact aataacggta catggccttc
135061 tatactaagt agtgatcagg atactatttg tctagtatgc gttgacacgc aagaaaaaat
135121 attatacgat actaaaagcg tatacaaatt atctcccaac aagtacacat cttatcttac

FIG. 19K2

135181 aaaattaata gtattaacta acggttgtga tttctttaga ggactttacg gaatttctat
135241 aaataaagat aattatatga gatacgaatt atttacagaa tttaatagag agaatgcatt
135301 cagaagcata gctcataaaa actatagctt aaataattct aataccgatg aaaatataga
135361 tgaaatttct actaacatag atgtgatttt tgattttata aaccactata catcgttaaa
135421 tgaagatgct tacaaatttg aagatttgcc ggatatacgt gttaaggatt tcttggacgt
135481 tatggtccgt agtaaatggt acgaagctaa aaacaagtac gatcttggat cggatatatt
135541 acaaaacatt tacaacgttt ataaagtaca tagacgtaat tatgaaaagg aaaaagaaac
135601 gaatatacta aaaatgatag aatcttataa atatagaaac ataaaaataa atactataac
135661 tacatttata aaacttctag gaatagaaac ttctgattct atatgcgtat tgggtatatt
135721 ggcgccttca gaattatata taggtttcga aggaagattc tattttaata aaacatctat
135781 tattaaaagt tctccgaaat taattaatat aaatatctag aatggtattc ccgttagtat
135841 gttctacttg cggtagggat ctcagcgaag ctagatatag attattagtc gaacaaatgg
135901 aattaaaaaa agtagtaatt acttattctc gtaaatgttg tagattaaaa ttgtctactc
135961 aaatagaacc ttatcgaaat ctaacagttc aaccttccct agatatcaac taatggatat
136021 ctcattattt gattatgtag cgccaggagc tgttatatta agtcaatcta atcactctat
136081 cgtaaatttt ttcaatccat cagaagaaaa acattcttct ttatatttcg gttatggtat
136141 agtagatttc atcattaaaa atgatatcaa cttttctatt aacggattaa ataattttac
136201 aaattatatt atagaattca acacatctgg ttttgctata ataccttaa gggaattcat
136261 gttagatagg aagtatgcaa aagtatacta ctatatggaa ggaatatttc caaattatag
136321 attgatggaa gatactgtaa aacaagcatt tttacacgct aacaaagaat atggtttcgg
136381 gaaagataaa acttactgtt tcaagatgat agccgactgt tatctagata taggtataaa
136441 tgttaaatcg tataaaattt taggtaaata tatttatctt agtcaatctt tttgtaccga
136501 tgatagatgg actaaagtat tagatacttt aacgggagaa aatctaatta ctaggaacag
136561 ttactatttt ataaggtgaa ttaatggtta acgtagttcc tggctttttt gttttaaatg
136621 atttcttctt tttaatgcaa ttagctagta ctctaatggt atatagataa tccagtatag
136681 caaatttttct taagtcatta ttagtaagtc ttattctatc ttctgtgata ggactgatga
136741 cagcaccgtc aagatcatgt cctttagaat atttgtaagc catgtctaaa actttattgt
136801 tgttggctat gtaggtagcc aattgattct tgacggtatt ttcagcttct tcaccaactt
136861 cttctatttt taatccagct atatattctg gataagtatc cttacacagc cctatctcgc
136921 atatggtctt atacatttta tctagttttg gagactttaa gggtaaatcg ataattatat
136981 ctatttcttc cgaaaaagac atcactttac ctccggctat agtctctatg tcttgctggc
137041 cagtgagtat aggaaatatc ttatactgcg cgaatttaag tatggcatac ttcatatcta
137101 gtagatcgga tacctcactt gacggtcgtt ttttgaatc gaataggtaa ttttctatct
137161 ccatgactat cttcgccgca tgaatgagtt gattggcaag aattaaggtt aaaagtgtag
137221 cagctgtagt atttatgaga tagttacaag ttataaaaaa agacttatta tgagtcaatc
137281 tagtaagaat gtttcttaac tcattaaatt ctatttcgtc ttgcacgtgt ctttcataat
137341 ttctagtttt atcaactagg gattttacac ccgctatagt aggaatagat atatcggact
137401 cgcattttttg atatatgcta tttataatgc tatctctatt agaggagtta tatatatatt
137461 tagctctagc tactataccg gctattgctt tatcgtctaa gtagtctttt aacagtgttt
137521 ctattaaaga tttagacacc atgttaaaaa tcctcgattg tttctggtct tccatttaaa
137581 tcaaatattt ttaaaaatat aaaagtaatt tattacaact agttaatatc actaaaaaga
137641 catatagtag taggttacct attatcctta aggctcatca tgtatgacct acgtttatta
137701 taatctcgcc gagtgtgtag ttaatatttt tcttctttcg acatagaaga agctaataacc
137761 atcgtagtgg actttcgctt tgaagagtta atgttaatat atttactcca tagattcgat
137821 ataatttatt acgggaagct aaagaattaa gaaaacagta tcgcgatacg caagaactat
137881 taccatttta atcggagagc tttctatgga tatagggtta gcgtctcaag aaatacataa
137941 aaataagtat tatattacgt atatattata tatacagcat ggatacaact aaaagaatgt
138001 ggcctctaca actttgtgcg ttaattgcta tctgctttac atctactact gtatctgctg
138061 ctagtggtga tggatgttgt ccatacggat ttctcccaga tggtactgac gtgcctgtat
138121 ggaatctgtt aaactgtacc aaaataccgg ataattgtga gaaaaaggga ttttattcc
138181 attacaaaag cggtggtgga acatgcggaa ccggcgatga agactggttt agtcctcata
138241 gtcttatgaa tgatctctgt aataatggac taaccgcgat tgttaaacgt actatgtccg
138301 gagactgtaa ttgcaaatgt acttgcgata tggaggataa gtagcgtgta taaaaaataa
138361 atttttgcta gtctcgtata gtacttaact gtagatgtag atttgatgac actcactact
138421 agtcgttttg aaataggtga tttagaatat tggatttttc tactctatac tagataatag
138481 agttgcatac aatattttag ctatcgtatg gataaatata ttctagaata caaaaatatg
138541 gtctaatctc gctactggat aaatcgaaaa atacttttta ttatatacat atagtctatt
138601 aaacaaaatg atagctcgta acctataaaa ggaagcagtg tgtctgcatc gcttgctctg
138661 aagatgtcaa atattataaa ctgctacatt tctgctgggg acaatactaa aattggcgac
138721 attgttatgc aggtttaaca atgggatata gatgacacta aagaatacta ttgtgaacaa
138781 catggtatga attatctaac tccgttagac gtgtgggata gaaaccaagt taaggttaaa

FIG. 19L2

```
138841 gaaattggag aactcaagag atatcccggc attatttttt cctaaaagtt atatacccaa
138901 cagaaatgtg cgttatttca cgagtaacga tatcgaagaa gtcaataatg ttattactag
138961 ttacttaagt gaagcctatt attgttcata aaaatgcata atgagataaa gtgattaacc
139021 cggtgatatt gtaaaagaag attgatccta ttcttaagac tttacgatta caagcaaagg
139081 taaaggagag actttaaact agaacgcgta aaaatcaatt acagagattt tacgttatgc
139141 aatatagaat agccactatt taatacggca ataatggttt tgggaatata ttaatagtaa
139201 agtcgaatac cggtttatta taacatgctt ttcaagtatc caaatctact gagtataaga
139261 taactcacta gttaataatg ctatactaat attataatcc agttcgtata ataattcctg
139321 gataccctct tctatcgcgt gtagtattat agcatcttct acttcttttt ttgtagctga
139381 aactaatggt acgataattg gatagataca agtcaatact ggcattccga taacattaac
139441 tagttcgtaa tccataaagg tgtcattaac taataataaa atttgatcat tgtgttcata
139501 aacgaaatct tctagtaaac cacatgagta attctcttct ggatatacct ttatagataa
139561 tttcttttct agatccagta aacagcactt ctcgtaatcg tttttgtaaa atatttcttc
139621 taagtcttcg tctgataaag tgctcgttag tacttcttga gtagtttctt taatcttttc
139681 ttctagttct aatatctttt cttgatcagc cgcataagat atttctataa gatcagtatc
139741 taccaataca tcagtaatac tccgcgcctc tttcgtaagt gcttcagata atctattaat
139801 agacttagct aaagatccgt ctctatattc gattagtttt atgttatcgt cgtataatgt
139861 tttaagctta tccgaaagtt ctttatccac atattcgtta gtacttttct tatcatattt
139921 aaaatcaaat acataaggcg gtttatctaa tacctcagat tctatccacg tatccctata
139981 atgtattaat atattagctt tacacgcttc gtattcagga tgggtataag gaacatgatt
140041 taggttacta atatatccgc aatagtgtcc aggatcttct tcatttggcc aagtatacac
140101 tccacagtgc ctaacttcat ttgccttatt actgggatag ccgtatttct tatattcgtc
140161 tcccttaatg gcacaatgat cttttgatgt aatagtaacg aagcaaagtc cttcgtattt
140221 acttatattc ctaggtatag taaacatggg acatttcata gatatagatt ttaacgtaag
140281 atctaacgta gcggtgcatt cgccccccctc catatgtcta aaagtatatt ttttgccgtc
140341 cccgtaatcg tttatctgtg attgcatgta tcctaaaaca gatataacaa cattagcgtc
140401 gtatattaat atatttgctc tggaagtaca cggtaataac aaaagtaaaa tactactata
140461 agtccttaat tgttttttag catcatccca aaaccgatta ggatcatcat acgctctacc
140521 taactcgctt acagaaaatt caatatcgag ttcataagga aatctagtaa ttgccttttt
140581 tagattcatc gcatcaaccg tactaggatc atatttttca gtaattaaca gttcagtacc
140641 aatatctata tttagtatat aatccggtgg ccatacagcg acttttccat aatatcctat
140701 acacgttcta ccctgcctcc aagtaacgca cgttctggac cgccaaggca tcctcaccgc
140761 ttttaccaaa tcgtcgaata gttttttttt acctttgtaa gtatctacta agacagcgtc
140821 ttccggatat acgggtttga cgaaagatac cattagtata tcggatttat atcggctatc
140881 ttcgttgtga acacaaaaca ccgctacact acgctcttct gtagaaccga acatttttaac
140941 gctaaagaaa tctgacaacg gtagttctat cagtcctaaa gtattaccta cggctacagg
141001 agtagaccct gagggacaag ataatacaaa actattaaaa cccgcgttgc tattaaacgt
141061 ataaacttct acgtataaga ttctaactct actattgcaa gaagttatat catctaatat
141121 cataacatca ttccagaaac attcttttat atgtctattt gtacaatact tcgcatgtcc
141181 tggaatagta ttaggtttta taatagtatc gttaaaatcg tacttatcga aagtaaataa
141241 ctgacgatgt ttattactat cttcaaaagg attttccagt atccaacgtt gggtttttatc
141301 atcccatatc gtcattttca ttagtatact acacgtcgtc cgcgttatag aagtttgtga
141361 agcgtcgtac ggacaccctt tcaataaaag ataaaagttc ttcatgggga atagatcgca
141421 tacattagat ggaaatgttt tagtatcggg tggttcaccg gacgtagaca tctttaaaag
141481 ttgcatgtct gtcattttaa cttcgaacgg tttcagagtg agcgttatat ctttcccaca
141541 tgtaagttct acgatcggaa actttgaaag catcgccgcc agcccaacaa actgataaaa
141601 cttaactccc tcatccgtgg tgaattttaa tgtggtgtac gccgtaatat ctaaagtggt
141661 agatcttaga tgtcctattg ggcatgcgac ggttaaccca aaatctacta taataccgct
141721 agtgttaaga tagtataaaa cactatcgat ggtatctatg aaatgcgtcg ctaactttttc
141781 tgactgcggc ataaaactag tatcagatct gtaacttaag aatatagtca aatctgaacc
141841 aggcattaaa catttcctaa caccggtgtg ctcggtatct gcaactatct ctctatacat
141901 gttaaatttt agaactaatg gatctgaagg ttttttaata ccggagagtg aatagtatat
141961 atctttttccg atatctatta agccggtaat taatgttaac cccattccag ctagggcaag
142021 atgaggagat ataactatac ccgctgtcga catagatgtt cctatactac ttaaagcggt
142081 actaacagat tcaataacgg cttccgcatc atctctaaat ccttcatgta ttcgttgtaa
142141 cctagactgt ctattgatca tattcataga cattgtttgt atggctagac taaataccat
142201 ggctttgtct gtagaagatg atagtttctt catcttttca ctatacttag agatagcagt
142261 agatttataa ctatcatcat cattagccga taaccgagaa cttacgctaa ctacgctacc
142321 tcttctacca ccactactac tgccaccgac atcgcctatc actgaatata tgtcatcgat
142381 atctaaatta ctgtataacg aatcgtaata agacgatgaa tgcgatcttg aacttcctgg
142441 aattcttggg agaggacggc gggcgagatt ataagaatcc ctcatacggt catagtcatt
```

FIG. 19M2

```
142501 atagctagtc agtctcgccg aatttactac atcataatat gcgtaaggtg ttactaggtt
142561 cacaaaaggt ctggcagccc gctgttgcgt atttctaaa aaccccatat tagggctaga
142621 catatagata agttcttgtg attgtgcggt agagggatgc ctacgtcttc cttgtaaaga
142681 gtgcttttcg ggtactatta ttcccatagc tcttgcggcc tctatatgtc gttggtacgg
142741 atcttgaaaa gattcctgat gtacttgtgc gtgaccttgt cttcctgtcg ctattcccat
142801 agctcttgcg gcctctatat gtctttggta cggatcctgt gaaaaacctc ttgctgatga
142861 actacgcgcg gagttcatag cgcttgaagc cgtatgagcg tccacataaa catcgttagg
142921 attaccttcc ggtctagatc gttgacctaa catcgcacac actacatcgt tagtacctcg
142981 cttacatctt ctgcgcgacg tcgatgaatt ttctggttca tttcttgaaa agagttctga
143041 caccgatgtc actggtgaac ctactaattc tcgtacgttt ttatatttac ccatcgtgtt
143101 cctgatgata gtggttcctt ttcttgttaa cggacttacc actaccgtag atgtatcgac
143161 gtcgaataaa ccggtaggtg tatctgatac agtagatact acgtgtattc ctttgccgcc
143221 tttttttctg tacgctgcga tgttttctac gagattatct cctgttctgt accgcgcacg
143281 tcctcgtctt atatggttct ctactattcg gatatcctct tcctcagatt cgtacctcga
143341 caccataaat tgtaattctg cgtaaccagc atcttcagta ctactactat acccgattct
143401 agactctagt actcccctaa cagattctat ttttctagct gttatcgccg ctaatcttct
143461 agaaagtata ttttgtgaat cttcagggac tttatttata ggcctaggcc tatttatctt
143521 atcgtatatc tcgtcagtgc gtgtatcagc cgggatattt ggtaagaaac tttgtaacgt
143581 tttcttagct ctatctttta cttttgcacg tatatcgata tcaccggcta cttgtgtagt
143641 agatccttta gaataagaag tacttgttcc taattgtaaa tgggtggctt ctttaggaat
143701 aatgtctctt atttcatga tcttcttcaa gtattgtgcc atgtctatat taccatgacc
143761 atcctctgaa gtttctctct tagatctact tttagatgta atcatacact gtgtaaaatc
143821 atcttttta cgagtatcgt acatattata aatacattta atatcttcca tagatatctc
143881 gccgtgggta tcgatatcgc gttttactcg atgtttatat tgttttatat aactagatag
143941 agataacaag gtatcagatt gaaacttttc agtaggcgcg acgtaatcta tacaatcttt
144001 accgtttgtc atcatacaag cgtataataa ttcggataac gtatcagatg tagctccgtt
144061 ctttttaaa gtagtgtaaa attcttccgg aatatctgtt acttccacca ttaaacctac
144121 cgtacacgtc tcgcaattat taattaccga tttatctatt ttcgccttgc ctttaggga
144181 caggcatcct tcgttgactt tcttcgtgat gcattctata aattgatctg aatcggtata
144241 aggttcatgc gtagagactc ctttaaagat tatcggtata atagatttag attgtggtaa
144301 ccttgcttta tctccgtcta ttacactaaa tttagatatt atcactttat ctatggttac
144361 attgttacag ccgctatcgg agtaggaaat gtgttccata actggtaatt cgaaatacgt
144421 tctatcattt gtctcgttta taaattgatc cgtaacacta ttgttgtgca atagtagagt
144481 attgattata tttttattta tatccttata ttgcttataa ctcgttcctc gaactccgtc
144541 ttcagtatcg gcggatacgg taatattcat catgacggta taattatatt ttataactcc
144601 tctatcatta gaacatttat ctagaaacat tttcttaacg gacgccaaaa tgctatccca
144661 attaaaagat tctatgaaag tctctttgtg aattctttcc gcgattgaca gataaccgta
144721 tgttgcggta gcggcataat cggtcttttc tttgggattt aaatcttttc tagtatcatg
144781 atatattggt aactttcttc tacaaaattc tgatcgcgtt atcgcaacaa aaataataag
144841 tatagtaatt atatccataa taactatgtt aataaccttt tagttcattt attctaagtt
144901 tgttaacgaa ctgacgttat gtctcattaa tatagtactt atattcatgt cgaattcata
144961 catcaattct tctaaccctt cttaaaagc gcgtaataac attatctctt ctacctcgtg
145021 tctaatactt tttgttctaa gaggtattac ggtggcttct atacaggtaa ctactggttc
145081 tcctattagg tataataact cgaagtcttg taacgtcccg tttataagta tcataggtct
145141 gatctgatcg ttagacatat tactatattc tataaaatca tcatacatat aatcggttaa
145201 ctcaccgcag taataactgg ataaatcatc tacctttgta atactattgt ctctgaaatt
145261 aattagacaa catttatctt tattcccaat tatatcgttg atatcttcag ccgacaaaga
145321 attcgctata acttcttgag aagttatact aatagcatgt tctaattcgg ttaaacgttc
145381 agaatcggct ttataagccg tttcaagtat tctaccgttt acaatgattt cagtaatgct
145441 acgtccgtta gaagtaagac tttccgataa cctgtttata gcagatggta gcgaccctg
145501 cttatattct gatatcgaac ggtactcttc gtataatctt ttcaacgaat ttgataattt
145561 tggattaaca tattcattat ttttatcgta tgtgaacttg aacgcgtacg gaggtttaga
145621 aagtacttcc ttctctatcc aagtatcttt atagtaaacg tgaatataag acctacaagc
145681 ctcgtattta ggatagcgat atcctatatg cctaaactta ctaaaataac cacagtaatg
145741 atcaggatct tcccaaacag ccggaacaat atacgtctcg cagtatctag cagtattagc
145801 ttgctcttta gagtatccgc tcgttttaat atcgtcttct aaggtagcac aatgatctct
145861 agacgtaacg gttatcgaac atatgccttc atatttgtgt atcgtcctcg gaatagaaaa
145921 tggatcgcaa gtaactttca tcattcttga ggttaattct aattctgcaa aacaattact
145981 accagacact ctagtcagta tatacttttt accgttaccg taatcttgag tcatagactg
146041 gtggtacgct aaactagaaa tagtatcgct agtattatat attagcatgt tagctctcat
146101 cgtacacggt attaaaatta aaacgataga actatacgtt ctatacatat ttttagcatc
```

FIG. 19N2

146161 tgaccaaaat ctattagaat cgtcgtatgc ttttcctaga tctttgatgt agtaatgtat
146221 ttttaggtcg caaggaaacc ataccttaga tttttctacg ctattaatat ctatggtacc
146281 agcgtcgtat tttctgtga tcattatttc atctcctata tctgtttcta tgatatagtc
146341 ctccgtccat atatctatct ttccgtgata actaacgcac gatctcttgt gtttccaggt
146401 tacacatttc ctagaccgcc aaggcatagt ccctagtttt gccatgtctt caaatactcg
146461 ttctctaccc gtgaactcgt ctatgaatat aacagactcg ttgtacgctt gggatacaaa
146521 gttaatatgg atgagatcgg atttaaaatc actatcataa ttatctatac aaaacacgcc
146581 tattttattt tcttctgtag aagcaaacat tttactcgtc gcaaaatcac ctataggtag
146641 ttctattact ccatctttat tacctacggc tacgggagta gatcctgaag gacacgataa
146701 tacaaaactc gtaaaccccc taccatatcc aaaagtatat atttctacat atatatttct
146761 agatctggat tcgcaggaag aagtgtcgtc caataacatt gtgtctttcc aataacattc
146821 agtagtatgt ttattagcgc aaaatttaga atgtccttga acagtattag gttttattac
146881 tatatcactg aaattacggt tttgaaacac aaataattgt ttgagttcag gatctttacc
146941 gaacggattt tctaatatcc atcgcttacc tgcaggatcc caacttgaaa tccttaatag
147001 aatactacat gtagtatgaa tgatgtaagt tatggaacta tcaaacggac aaccccgtac
147061 caacagatta aaactttta gaggaaatat atcgcacacg ttagaaggca tagtcttagt
147121 ttcttctggt tctcctggtg tagccatttt aagtagctgc atgtttctta gctctacttc
147181 gaaaggtttt aaagtaagag ttatatcttt tccacatgtt aatctaaccg taggaaaact
147241 agaaagcata gttcctagat ttaaaaactt ataaaaccgt actccgtctt cattagtata
147301 tttaagagta gtatatgctg ttatatcaac atctatggat ctgagatatc ctagaggaca
147361 ggctactgtc aacgaaaaat ctagtataac gttactcgta ttaaggtaca tgaggacact
147421 atctatagta tctataaaat gtaacgataa tttatccaat ggttgtttaa agctagtatc
147481 gtttctgtag gacatataaa cgagagtttc tgttcctggt atcatacact ttctaacgcc
147541 agttctttca gtatcagata tatattcttc atacgtatta aacatcttga taacaggatc
147601 tggagatcta ggtttcctg ttagtatatg atatatatct acaccagcat ctattaatcc
147661 ggctatagtg gataaaccca ttcctgaaaa ggctagtcta gtagacataa acgaccccgc
147721 tatagacatg actcctccca tgctttccaa acaagtactt actgtttcag caacagcggt
147781 agccacagaa ttatcatcgt tatatcttag ctgtaaatct attaacctat gtacgagcaa
147841 ttgtgaagct aagttaaaat ttactgcttt atctaattgt ttggctatct tgtccatatt
147901 agacccataa tcggtcatcg gataaccgct gcctataatg taattactac tttctgtagt
147961 ataactggtt ccgctaatac ttcctgtact gtatccactg agtatgctat taacgctctc
148021 gctatacatg ccgtaaacac tatgcgtatc acctctaccg gatgtgtgta tgctattatc
148081 gctatatcta ccgctagaat cataataccc gtataaatct tgcgacgtgt ctagactacc
148141 tccccgtactt aaactcggcg tcgatcgtct acgtgaagaa tcactatggc gagtaagaga
148201 taacaatcca caaacagcgc ctattcctcg cttacaccgg atagatggtt tatgattttg
148261 ggacgtatag atttctgtat caagaactcg ctttacgtcg cgcgatgagt ccacggagcg
148321 aactcttctt tgaaggacgt cctgactctc atccgaggtg gttggtttag aaatgatact
148381 ccttacttct acgcctaata ctgatttact cggagtagcc acgacagaaa cagtacgtcc
148441 tccatattct ttataagcgt ttattccgtc tttaaaacac gatattatgt ttttatgttg
148501 tttgttattt aactcgatat gatttaaccg tctctctaat ttatccaaat cttcttcgaa
148561 tatatggtaa ctatgtttat tatttgttat cacgctcttt atggattcta tttttgtaaa
148621 agctatgtaa tatagactcg ctgaaacgat attcctacca tctaatctag gcacaggaat
148681 atcgagtata tttaatacat ctttaggtaa tatatttgat gaaatttctg gcatgtatgt
148741 tctgaacgtt gactttacca tgtcctttaa cgtattcact aactcgccgt ctccactaat
148801 acctttttgc ttcttataca tacctatctg cagatgagta atatcttcta atattacgct
148861 atctatacct agatagtttt taagaagagt cctaatatcc ttcgaagaag agttcgttcc
148921 gattacgtcc tctacactat catcttctaa gatagatctt ttacgtctgt gtctataact
148981 acgatacgcg ttatttagtt tacgtttatt tttatagtcg ccagaatgtt ctatgcactt
149041 ttcgtattct tcgccgtcgt ctaagtcgta catattatac atacaattta aatgctcgtg
149101 gttaatcgac gaatctttca gttcttcttt aaaggacatc tgtggagtga gcgtatctct
149161 tttagttttt gttcttctct ttttacctgt ataagcacgt aaagttttta tggaattgga
149221 ttttatctta tcatttatat agatatagtt ggtacaatct gtacctcccg taacttcaca
149281 agtataataa agactagcca ttttatcata aggtaatcct ccgcaagtcg ctagagatgt
149341 cttaaattca tcaggtacgc ttaccacatc taccattaaa ctcatctgac agtcgtgaca
149401 attactagtt agttttgtgt ctataataac ttgacctata cgtccaaagg ttggtgcctt
149461 ttggcaatta gataatatat gttttacgca ttcagcaaat acgttagacg gctcataagg
149521 aggactagac gatacaccgt taaaagtaac ggttatagta ctattatttt tactttattt
149581 catagtaaag tttttaacaa tcaccgtatc ggctgtaatg ttttacatt tatcattatt
149641 gtaggtaacg gcatacatgg gtggtacact acacgttagt acgttatcgt gagtttcaca
149701 gttagtatat tcaatatctt ctttagataa agataaagca gcggctgata tacacgagaa
149761 tagtttcaaa ccttcacgca aataattatg tctatttctt gctttattat gaatatataa

FIG. 19O2

149821 tgatacgcta taagtatagt tatatctata aactgcgtca agacgatctt ggttactacg
149881 tgtatcgcac atactaataa aactgcgctt gatttcttct ctaatacttt tccagtcgaa
149941 gcaattatga agacgttctc tttctcgagt tctaattatc gacaagtatc tcatagcggc
150001 gatagcttta tggtctgtca gttctttggg ttttatgttg ttaacgatgc gatgatatct
150061 agactctttt cttaagcatg attcattttc agagtcatct gcataatatg cgaatgttaa
150121 tgaatagaat aaaatactta taataattcc cttcaaagaa gaactctctc cgcgtacgtc
150181 cttcgacatc ctttcatcct atggtgtata tagtattata ataatatata gctagtttgc
150241 cttttagttc atttttaata catggaaaac atgaagcata attacctact gtaggtgata
150301 tatatcaaat cctacttgta tgattagtga gaaaacattt agttattggg tattctagat
150361 atcacgacct tgaaaaatgc gataaatacg ataaagatat tttggagctt gagatttacc
150421 gagaacaacg taaagagaaa gaagaatata aaaaagcaaa gtaaatgggt agctaaagac
150481 gggtcgtggg atgctgcgtc agttaatgta tacattacag aggaagacat tgatggttca
150541 acgtaaaaca agatcgctat aaactagtaa attctattat atcgttatct tggatttgct
150601 tgtacggtaa aggtattgtt ggtctatggc atgggataat gcttttgtgc tacaatgtgt
150661 attttatatt actaatgtga gtgatgttat agcaagactt tagttgttac tagaaaacta
150721 atgcgtttgc ttgcatacaa agtgtataaa taacttctaa tagaactaac ccgcttatac
150781 atgcatagct aagtcacata tctctgtata ctgtgaaaac agactctggg gactagtgtt
150841 tcctatctca aggaacttaa atgaagagtt gtagacaaac ttagtaatct tatagaaagt
150901 ttatgaagat ttataagata cgtgaaataa tataccatat caagtttaaa taacaaatga
150961 aaaataaatg agtttgcgta taaaaatcga taagcttcgt caacttgtaa cctatttttc
151021 agaatttagt gaagaagtat ctataaatat agatgtaaaa agcaacgttt tatatatatt
151081 tgccactcta ggtggatcta taaatatatg gaccattgtc cctctaaatt ccaacgtttt
151141 ttataacggt gtggaaaaca ccgtgttcaa tctacccgtt ttaaaagtaa agaactgtct
151201 atgtagtttt cataatgatg cagttgtatc aataacagcg gatcatgata ataataccgt
151261 cacgctatct agtcattata ccgtaagcat agactgtaac aacgaacaaa taccccatag
151321 tacaggaacg agtatttctt taggtataga tcagaagaag tcctatatct ttaactttca
151381 taaatatgaa gaaaagtgct gcggaagaac ggtgtttcat cttgatatgc tacttggatt
151441 tattaaatgt attagccagt atcaatacct caatatatgt tttgatgata aaaaattgtt
151501 gcttaaaaca ccgggtacta gggatacgtt tgtaagaagt tattctatga ctgaatggtc
151561 tcctactctt cagaattatt ctttcaaaat agcaatttte tcgttgaata agctaagagg
151621 gtttaagaaa agagtattag tattcgagtc aaagatagtt atggatacgg aagggaacat
151681 actaggattg ctgtttagag atagaatagg tacttataaa gtcaatgttt ttatggcgtt
151741 tcaggattaa tcagtaaaat aaatgggggg tggtttagtt ctacctacta gggatccgcc
151801 caaagaacaa gatacttcgg agacagctac taatattcct aaactattaa aatctattcc
151861 tggtgtaaag ttaggacaac agataagaat aggttacaaa cctggtcctg aaactgccaa
151921 ggcatttcca gaatttgata tcaaagaagt aagtaatgga ttatacgaac ttagcagaaa
151981 atcgtatctc ggtgatacta aaacgtgttg tataaatcct tctctaagtt actattggga
152041 agactccaaa aataaaatat ttgacgagta cgctacaggt agaagtctta aaacatgcga
152101 tcctttaaca aaaactatat ctggttctac attatgtgat aatatattaa cgagcttatg
152161 tctggacgaa aaatctggag tagatagaac tatgtgtaac gaatggatgg gatatgctct
152221 taatagaccc gatctttcca ttccgaaatc aattaacgat agatatacga agctatgctc
152281 caagggagcc aataatatag tatgtgaaga ttggttgcat catttaagaa ttataggagg
152341 aaaagaaaat gatgaagtta tagacaacgt attaatgcaa caaacgcctg aatttaaaga
152401 aaaatatatg aagtgtagtt ttcctagcca taatacagta tttctggcat atagagtaat
152461 agaacctaga gaatgctggg accaagaatg tattacgtct aacgtccatt ttcttctaag
152521 taaaaactat cataatttaa cattatgtca catctataga tgtaacatta gtatcaataa
152581 ccttttgata gatggtaaat catctgttaa aatatcttgt catgacgaga atataagtaa
152641 taaagataag ccaaaagcac gtaataaagc aaaatttata gacgatatac tagggtcctc
152701 gtttaatata aatttggat tctttttgt gatttttatt atgatagcgt taatattaat
152761 tgttttactt taaatggggg cagcggctag tatccaaact acagttacaa ccattaataa
152821 aaaaatatct gaaaaactag aacaaactgc ttccgcgtca gctactgcta attgtgatat
152881 taatatagga aatataattt ttaaaaagaa taaaggatgc aatgttttag taaaaaatat
152941 gtgttctgcg aatgcgtctg cacaattaga cgctatagta tccgctgtga gagaagtata
153001 tgatcaacta acagaacaac agaaggctta cgcacctagc cttcttaccg cggcgcttaa
153061 cattcaaact aacgtgagta cgataacgca agactttgaa acctatataa agcaaaaatg
153121 taattcggat gctgttatca ataatatcat taacgtacag agtttagaag tggatgaatg
153181 ctcggcgccg cctgggcaga ttatgacgtt tgaattcatt aatactggta cagctactgg
153241 aaattgcgct atgaaatcag tattggacgt tcttacaaaa agcagtgata gagtatcagg
153301 taatcaatca acgggtaacg atttctctaa atatctatat ataataggag gcataaatatg
153361 ttttttgatt ttactatatt atgctaaaaa gttatttttt atgtccacca atgataaagt
153421 aaaagttcta ttggctaaaa aaccagacgt gcattggacg acgtatatag atacatactt

FIG. 19P2

153481 tagatcgtca ccggtgttgg tttagagaat taaattcaac ttaacataat atacattaaa
153541 tgcatacctt tttaacagct cgtctacaag caatagaaga tgtatcaaat aggaatttga
153601 gtatgttgga actaatattg acgagagcta tagttactca ttggataata ctagacttgg
153661 tactaaatct aattttcgat agtctaataa catcattcgt cattatatat tctttatatt
153721 catttgtagc cagaaataat aaggtattat tatttttact gatgtcttat gctatattcc
153781 gatttatcgt catgtattta ttgtatatag tatccgagtc tatagattga tattagttga
153841 tcgtgttatt aattctttcg ctgtaaatac atcattagta gaaaaatcat ctatttcaaa
153901 aatatttccc ccatcgatag aataaattac acgaactatg ttattcagcg atacatcgga
153961 taaagttata cccataatta aagcatcgtt atacattaca taaaccaatg atccgggttc
154021 tgtgagcctg tgtatttggg gtgtattaat atagttcttt tttatcttaa atatatccaa
154081 atactgccta gatatgtttt caaagtgatt tcttataaac cattcaaaaa aatagtttgt
154141 agatttcaag tttcttctag tcatcaagtc ttgatgggca gtcatataat ctaaatagca
154201 cgattgtgat aattcagact tatagagatg agtatttgta gacaatagta ttaaagattc
154261 tgtattaaac aataatacta gatggttaat cgacatagat atagtactcc taggtataga
154321 aactaaatcg aatttaaaat catctgagaa tatgttgttt ttataaagag aatataatat
154381 agcgactatt tgcagtatta tgtctttagt taggcataca gtatttatat tcagattagt
154441 acgtttcata ttcttgaaat actcgaagta gatagttctt ccgtatgtat gatctttaac
154501 actatatact agtggaaatc ctagagcttt accggctttt actaaagcag ataatgttac
154561 ccaataatta gcttcgtcta tacatacttg cttacgaata ttaaaatatt ctcctatata
154621 acaagaaatt tcgtatctct ttctttcttg gtagtaatcg cataatctct gttctgtaaa
154681 aggtatttgc ctattagact ctgtagttgc attattttta ctcatttaat cttaaaaaaa
154741 acttatctaa atgaacgatc ttctattaga aaatctgttt ggagaaaaag cattatgcgc
154801 gcaagtaacg agagatcaac tgttagaaat aatagcggcg ggagcgagat caaagtttcc
154861 taaatcttta ctatctatgt acagagtaac tcctagagta atgactcgct atcctctgaa
154921 acttataact aacgaatcta ttaccggagt ggttatcact acagtatata atcttaaaaa
154981 gaatttgaat attcctcaga ataataaact tacaacacaa gatatcgaac gttattattt
155041 agataaaagt gtagaagtta ttaatcttat ggttggtaat acgtctctcg gagatttggc
155101 atgtgggaga cccaggagaa caaaatcttc aaagaagaaa gatcccgtta tattcttggg
155161 tatatcagca cctcttatat tggttatgaa ttctaagaag tcgataaata catacataca
155221 agataagaag tctgatccca gtagcgatta tgttaatata aatccaggca tcggagtact
155281 agagaactat ggaaatacgt atctactaga catccataat ccgtcatcgg tattaactat
155341 ttctactata tacgggctcg ataataatat ggaactgaaa aaattaagta cagccagtga
155401 aatagatgct taccaagatg taaacatagg taaatcagta gatctaaaaa agtttaatga
155461 aatatttaat acgatgaaaa aacatttgtc tttgtcaaat tttagtatct aaatggatag
155521 aaatatcaat tttagtcctg tatttataga acctaggttt aaacacgagt ttctattatc
155581 tcctcaaagg tatttttata tattagtttt tgaagtaata gtagctttga ttatattgaa
155641 tttttttctt aaggaagaaa tattatatac atttttttcg ttagctaagc cttctaaaaa
155701 ttcaataaat agtctgctgg atagaactat gttaaaatgt gaagaagatg gatctttgat
155761 gatttcgaga ccttccggta tctattcggc cttgagttta gatggttcac cggtaaggat
155821 ttccgattgt agtttgcttt tatcgtcaat aaatggcgca tcctcatcaa catctcctta
155881 ctctattttt aacagacgat aacggatttt attctatctt atccgaaaaa agtgatgatg
155941 aagctcttga agacataaat actattaaga aatatatgga ctttattcta agcgttctta
156001 tacgttctaa agagaaacta gaaaatatag gatgttctta cgagcctatg agtgaatcgt
156061 ttaaggctct tattaaagta aaggatgatg gtactttagt aaaagcattt accaagccat
156121 tgttaaatcc tcattccgaa aagatagttt tagatagagg ttatacttcg gatttgcta
156181 taagcgtaat aagactatcc agtaaaagca gttatatact tcccgcaaat acaaaataca
156241 taaatccaaa cgagaatatg tatataaaca acctaatatc attgttaaaa aggaattgaa
156301 agaaaatatt ttatatcgta ataaattaaa tatgcatgaa ggacatcagg agtcttttaa
156361 agaacttgaa atgacaaaac cttatatgtt cttcaatgaa ctagtaggtg aagaagacta
156421 taacaaagag ttagaaaatt ctaatactaa gtttcaagga cagggccagc ttaagctgtt
156481 attaggagaa ctttatttct taaatacatt aatcaagaat aaaacgttat gttcagatac
156541 agttatcgtg tatatagggt cagcaccagg aagccatata aatttttat atcattatat
156601 ggatgatctt aaaatagatt taaaatggat attaatagat ggtagagatc atgatcgatc
156661 tctagaaagt cttaaaaatg tgtctataat acataggttt gtagatgaac aatacttgtt
156721 taagctacgt aatatgatta ggaaaaacca taaaattgta ctgatatcag atattagatc
156781 gctaagagga aaagaaccta ctagccagga cctattacac gattacgcgt tgcagaatca
156841 aatggtaagc attcttaaac caatagcatc gagcctgaaa tggagatgtc cgttttccgga
156901 tcagtggata agagactttt acattccttg tggagatgag tttctgcagc cgttcgcgcc
156961 tcctttttca gcggaaatga gattgctaag ttgttactca cgggcaccca ttcgtctaat
157021 acgtatagat aagaatgcag ctatagaata tgaaaaaaaa atgttttatt taaataccaa
157081 aatcagacct aaaatagttc ttgattttga ttatccaaac caaaatacg attactttta

FIG. 19Q2

157141 tatgttttat atccttaaag acatcgtgtt gcctacttat aaagagtttt caacatataa
157201 acaaaaggtt atatttctac aggaggcaat ctttaacgcg ttaaatataa aaccatgatg
157261 aaccaatata atgtcacata tttatcaaaa atattgtgtc taaaaacaga aatactatac
157321 aagccttttt ccataattaa taggagtata gttaatcagt ataatataga tgttaagtac
157381 gacgatatta caagtatcgt aaagattaga cataaaacag aaaatactat tttagtattc
157441 caaatattta acgaatctaa tgtaaaatat tctcctatag aatatgatta tggtgatccc
157501 atcattataa cgtctaactt acaacacggt cataatagaa tccctattaa catgttgtat
157561 atagatgtcg tagaatcaga catgtttcca acgtttttcca ggttagacag tgaaacaatt
157621 aaaattataa ctagtatatt acaatctgat aataaaaagg aacaatctat taagctacct
157681 aaagtttcag aaaacgaact atctgtaaaa atattatatc ataaagacta tccgctgaaa
157741 tacgttagat attataaaaa caatatggta actggtatag aagtcataga tagatcggtg
157801 gcgattacca gttaataaga acgattaacg ctaatatcgc taaacctaat attaaatatt
157861 ttggatcgat aataggaagg tgtatctcct gttcaagagg tttaactgaa taacccgcgt
157921 atatagcatg actagataaa caatcattat ttactttttaa aataccatct aataagttga
157981 tctcgcccaa agatacgcta caatctataa gattacatct tttcatgtta tcccttaaag
158041 cggtaggtat tttagcggtt ttcctttttac atggttcata ccaacaataa taaggcaata
158101 ataggtcttc tccaattttt tctatagtag gttctggatg aatacataga cagtctctat
158161 ctttagggtt agattcacaa tacttaaata ttgcttcatc gtttataacg ttgtccatat
158221 taaaatttaa aatctaaaaa taatagttat aatcaaaaat gtctgtgata tctaaagtaa
158281 gttatagttt atattctcaa aacgaaataa atgctacaga tattaatatc aattatgtta
158341 agaacgacga cgaagtcggc accgtcaagg acagtaggct aggagcaacc gatggagtat
158401 tatgtagaac gtgcaaccgt actgaattag aatgtttcgg tcactggggg aaagttagga
158461 tatacgaaaa tattattatt aaaccagaat atataagcga agtaatacgc attctaggcc
158521 atatttgttt aacgtgcggt cttctcagat ctcgagaacc ttatactgtt aatatttctt
158581 ctcttactag cggtgaatta aaaaaactaa aggacaaaat atcgtccaaa aagaaatctt
158641 gttggaatag tcgttgtatg caaccttacc aaaaagtaaa cttctcaaaa aagaaagtat
158701 gcttggttaa taaaacagat gaattctgtg tgcctaatgc tttagtatac gaaaaaataa
158761 catctattca ccataaattt tggccggtat tagatattca tcaagatcca gctacttttat
158821 tttatagagg ctatttttcg atacctccat tattgattag acccgtaatc agcttttgga
158881 tagataacgt acctaaagat accaacgaac ttacctacct tctaggagtt attgttaaac
158941 attgtaacgc aaatgcggat gaaccaacta ttcaaaaagc tattatcgaa tatgataata
159001 ttaagttaat atctactaat agtactacta ataatctttc ttatattact tctggtaaaa
159061 ctaatatgtt gagaagtttc gtagttgcta ggagaaaaga tcaaacagct agatccgtct
159121 taggactcga ttcttcatta gatattacag aagtaggtat acctgactac gtaagaaata
159181 ctctaacaga aaaaatattt ataaacgcat ttacaataga taaagtcaaa gatatgtttc
159241 agcgcggtga gattaagtat tactttaaca aacaattaca ccaattgacg aaaataaaac
159301 aaaataaatt tattaagaat aagatacatc ttcttcccgg agattgggta gaaactaaca
159361 ttcaagaatt tactaatatc attttcggta gacaaccttc tttgcatagg tataacgtta
159421 tatcgtcttc tgtaagaaaa acagaagaag ataccattaa aataccacca ggtatcgcta
159481 attcacaaaa tgcggatttt gatggagatg aagaatggac tatagtcgaa caaaatccaa
159541 aaagcgtgat agaacaaagt attctaatgt atccaactac tctattaaaa cacgatgtac
159601 acggaatgcc cgtatacggt tctatacaag acgagatctt agctgcttac aatctatttc
159661 gtgaatacga tctaacccaa gacgaagtac ttaatatctt aggaaagtac ggattggaat
159721 tcctaaccga ttatgaaagg aaagataaat ataccggtaa agatattttt aaattttttga
159781 tcaacgaacc agaaattaat tatcccggta taatatgtaa tggagaaatt atagccgaaa
159841 acatagatag taattttata gtatcgatga aacacatgtc catatccggt cttataacgg
159901 attataaatc tagcgtagaa ggtataaaat ttataaacaa agcatcctat gtgtttaaaa
159961 gatatttaaa gatatatgga tttagtatca ctttcagaaa tttatgcccg gattttgagt
160021 ttacaaaaaa actcagagaa caaaatataa aaaagattaa cgatattaaa cattcttatg
160081 ttaagtattt gtacgacgtt gctaacggtg atattatacc attatctaga tccgatgaga
160141 tggatgctgt cgattctatt ctttccggcc ttaccaactt taatattcag gagattgaga
160201 aatacatgaa agaagttata tcaaaggacc cagataatag cttgatgaaa atgtcttgcg
160261 cgggatataa ggtaaatcca acagaactca tgtatatctt aggtacatac ggacaacaac
160321 gtatagatgg agaacctatt gatacaaaaa tatatggaag agtactaccc tatttcttac
160381 ccgattctaa ggaccctgaa ggaaagggtt acatactcaa ttctctcata caaggattga
160441 cgggttccca atattattat gccatgttaa tagctagatc tcaatctact gatatagttt
160501 gtgagacatc aaggacgggt actctagcta gaaagattat caaaaagatg gaagatatgg
160561 tggtggacag ttacggacag attgtgtacg gtaatactct agtcaaatac gccgctaatt
160621 acacaaagat acaaggatct gtttgtaaat ctgtagagtt aatatatccc gatgaatctt
160681 taacctggtt tctagaaata agcgctttgt gggataagct aaaaaatggc tttatatata
160741 atcaaggtca gaaaatagct aaatatattt tagctccttt taacttcaaa gtatttatga

FIG. 19R2

```
160801 agttggacga aactaatccc atgaagtcta aagacttata tgacaagata caactagtaa
160861 ttaaagatgt aagagaaaat tatttcttcg atgtcactag tatagacttc atagaatacg
160921 tatttctaac tcatttaaac ccgtctagag taaaagtttc tgaagataca gcaaatttaa
160981 ttttcgaaaa actgtatgaa aaattaaatt acacgttagg aggaggaact cccatcggca
161041 ttatatctgc acaagtgcta agtgaaaagt tcactcaaca ggctttatct agttttcata
161101 ccactgagaa aagcggtggt ataaaacgca aactcggatt taacgaattc aaccagttaa
161161 caaatcttag caaaaacaaa acagagatta tcactctcat atctgatgat atcacaaaac
161221 tacaaactat taagatgaat tttgagtttg tatatttagg agaactattt ccagagatta
161281 caatagaaga agacaaaaac tattaccgta tagatataaa tgttaataga ctttacataa
161341 aacgtaatca actaacagaa ctgatcgtcg aatacatgtt agaaaagttt gtttcctata
161401 gtgtgttggt taaaaactgg ggaatggaaa cgaacataat taacgaacat atcattagat
161461 ttagcttatt cattgtattt acagagccgg taaatctcaa taaaaataaa tttatgatga
161521 tgttaccagg agcggcaaat aaaggcaaaa ttagtaaata caagatacct atatctgaat
161581 atcagtcata taccgattat aacaaaacag taaagttata taggcttact gtagaattaa
161641 tgggccttaa agagcttgga accttttgatc tagttaatgt caatgttata cctggtgtat
161701 ggaatactta cgagatattc ggtatagaat ctgcaaagag ttatctttgt gaagctctgc
161761 tcagtactta tggagaaggg ttggattact tatatcaacc gtgtgattta ctagctagct
161821 tgatatgttt aaactatgaa ccggaatcta taaacaagtt taaatttggt cctgtaagtg
161881 ctttaaagcg cgctacattt ggcgataaca aagccatcat taacgcagca ttatacaaga
161941 aaacagaacc cgtaaatgat aacagtagtt gccacttttt tagtaaagta ccgaaaatag
162001 gtacaggata ttacaaatat ttcatagatt tggaaaagtt tcttcgcatt aaaaagacta
162061 tctcagagaa acttatagat aaaaagttag tagatatagg tgataatatt actgattttt
162121 agtacatcag tcatatatac ttatctatta tttggttcaa gaatgattta ttttctataa
162181 aagctccccct tatagatttt agttcatgat atatatacaa aaagtatatt acaaatggta
162241 tatttttgtc tctaatctcc ataagataac ccataatcat agccgaactt ctgttaatac
162301 ctgccataca gtgtaccaat acgggaatct ttaaagattc acattttta agtacatatg
162361 taaccgcgtc gatatgtttt gatatactaa cagtgtcatt gtcttctaat ggaaagtgta
162421 ataccgttat atctgttctc ttgagtttat atttaacat cgatacgttt actatatatt
162481 tgaagaatgt tttattaggt aattcgatta catttctata atttcctaga tatacataat
162541 cggtaatttt agttatatct ctaggcgtaa atttacaca tgtgttagta gatttagtaa
162601 taatatgctt atatagttgt ttttcatcca tttatatagg ttacaaatgg gaaacgaagt
162661 agagttatcg gttcatggaa tagaacttaa ctatgctaga aataatatta ctaaaaatat
162721 acgatatgct agagtatcta ctttaatatt tttcttttta cttttagtaa ttagcgttgt
162781 tttattcttt ttccagatat ccaataatag tatattctca acactgagta aatatactcg
162841 tataaaaaac aatttaagct cctggaaacc actagtaata caaaaatcta aaataaatag
162901 cgagttagga aagcacgcgg ctcttaacag acaggattta atgagattta aatgtgttga
162961 ctttggtagt tactttctac ctgtaagatt gaataataat aacttcttac cggaagcggt
163021 tagaagagga gatggagatg gatggatgat aaaaaaggcg gggaagtacg atcctgctgc
163081 tgagcagtat tgtgatttta tactggacag atataaagat acaatcacat gcggtgacca
163141 aatgtttaat agcctagggt atagcggtta tttcgaatct gggcactggt gtcagacctt
163201 tctagattta gttaaataac tatgatgtta ataagcattc taacttcaat aacagtttta
163261 tagtaaacat cactcaagat tacttacttc tattttaatg tatagattaa aaggttattt
163321 cgtatgatta tgttatatta aacaattaat ttagcactat tatagttctg aatgtattac
163381 atagaatacg ctaaaaatac tccagatagt aaccataata gcttgttatt gatatcgaat
163441 atagcgagtc ctatgataat aactattgcg attaaaaaca tcatagtgat atcgtatttc
163501 ccaaatacgg aaaatagagg atagtacatg cgatgataaa atgacggcca gttatccata
163561 atccagccat ctatacgaga tttaatagac aatctatttt tcttgttctt catgaattcg
163621 tttgctagtt tatagtcgtg ataaacgtat ctatcgttat ccacgacgta tctagttata
163681 cccagagtat tctcaattct aagaatttct aaagatatat caaagctcgg tttattattc
163741 gtaaaatagc tatataattt ccttaccgct tcctgtctaa taatataagc agataacgat
163801 acatcaaaac taccctttaaa agcttctaaa tctggaagta gcataaggtg ttgagagttt
163861 ctatctttta gcaatttggt atgtgttact aattgcagta tatctacgtt gttatcgtta
163921 agtaccttgg ttatgttatc taaatttgta ataaaacctt ccccggttat tgtattatcg
163981 tcttccataa tgacaacata attcggtaat ttttctgcat tatccataat atacctccat
164041 agacttatgt ggtccgcgat gaagatttta gtatcttccg tacatgttag tctacagacg
164101 tcagaataat aaccatctct aacagaaacc atttcatcgt attctatgtc acctacctta
164161 tcgtccgcat ttggttcttg tttgcttttt ggaagtggtt taggagacgg cgggtctctg
164221 taatcatcgt atccattttt aataccccttt ttataactcc attcggatac ctccaaattc
164281 ttaaagggta ctacggtaga tgaaggtcta cctatcgtag ttattacaaa tataatttgt
164341 ttcttgtcgc ccggcgccat ttaattgtta aaattaatta tgtatagttc cttgatcttt
164401 ttgctatttt cttctatcca ttctgttaca ttgacgtagc tagccaaaaa catgtaaaaa
```

FIG. 19S2

164461 ctaaattcaa gttcttgtct attcaaacta tcgctaaaat acgtaaacac gttactatta
164521 ggtaataatt cctgcctaag catattatat ccggtgattt tatggttagt atgttcttga
164581 ctaatcaagt cataatgaaa tggaaatgga tcaccaaatt tgaaaacata aaaatctaca
164641 ttagatgaat aatacttgag aacattatat acaaaaagac tagtcaatgg aataattatt
164701 ttttcttttt ccacttctaa tttgatatga gttgtaaaaa atgaggcgtt gtacgcgttt
164761 gtatcattca cccttataag aactttagta gttttcttca ttatatcttc aaaaatttct
164821 ttatcttcat cagtgccttc ttttattctt acaggatgtt ttatcgttat gatttctgta
164881 ttctcggcta ctaccttttc gtaagtaatg aacaacttag tacttgttat acaactagga
164941 aaaaaagcta tttcatctgt tctctgtatc tgcctataga tactaatatc atagttaggt
165001 gtttttctat ctttcttaat ggctattaaa cgttccattt cgagttttat tctattatag
165061 tggactataa gttcttcggt tgctattttc atgtatgttt ccgtaaatag ttctatagta
165121 ttgaactgct tggagtcaac tgtcctggtt ttcttcagaa aatcaaatac gataactgat
165181 ataatatgat ttagatccga atagttagtt tcttcctttt tgttagtcat ataatacata
165241 ataaagtccg caccactgtt aagtactata actagggcta ctataaaatg gatattcaat
165301 atcttagcag aatagaataa ctccatagaa gacatctgaa tgtcaaaaag attagcggaa
165361 agccttagga agaatatacc tttcttaatt tctgtagcaa actgtttttc gtattcgtgt
165421 cttttgctgt taatgtctat taggaaattc agaataagac gatttatatt atacttcata
165481 ttccacattt gagacttcat aatagtatcg aacgacataa tcgtattaaa tataaacctt
165541 tggctatgtg agaaataatt atagggttcc gacataaata tagatttatt ataagtaacg
165601 ttaataagag atattttcgt gacatcggta gcatccaagt ttagttcctg tatgtttatt
165661 ccgcatagat tacagtacgc tagtccatct tcataatata tatatttagc tataaactta
165721 ttaatgttct cgtagtattc tagactaact tttttagcat cgataatatc tatctcatgt
165781 tcacagggta caaaatctac gctacctcct tcttcccaga atttcaattc ggatacgtat
165841 atgtactcta taggattctt cctaggttcg aaggtgactt gttttatatt aattaactcc
165901 ataaacaaat cacacaaacc atagttagac aaaaagaagt aactatataa acgaggattt
165961 ttaaacttag gtataataac cttaccccat tcgtaaaagt acttattgtc atcatcaaaa
166021 ttattcctgt aggctttatt agtttcttcc aagtatacgt attttacatc gaggtagtct
166081 ttaataacta taggtatagt tagttcgtct ataacgtagt taaaaatgta cctaacgtta
166141 tattttcgtt tagatatttt tatacctatg tttctacaca aatatgcaaa gtctaaatac
166201 tttttagaaa aacgtaactg atctaaattc tttgatacgt acgataataa ctccttcatg
166261 ttaaaaggga tttcgtttac tacctgttca tatttatctt ctttgtatga taaactcgta
166321 gtaaaacttc tgtaattgat attaaagtcg ttattacctt cgtcattcac gagaatgttg
166381 acatgttttt gccttattat gaaatctaaa gtagaaaaga aggtatcata catattataa
166441 ttcatatcac ctgtcatcct atcacctaaa tcgatactag aattgtcatc gtggatgttc
166501 ttttcaaaat tatatcctat ataagaaaat atagctacca aagatttatc atctatatct
166561 atgttttgtt ctatagtaat gtaaagtagt tttatatctt catccgtaat catattaacg
166621 ttatatagat tacagataaa taattctttg tttttgcta taaaatcttg ataagatttt
166681 tcctttaccg tatcatcttt tatatacgcc tttatcttag gcactaactc taataataca
166741 gattccttgt tctccattta atgtatagaa ctaatttata ataaacatag taaatatggg
166801 taacttctta atagccataa ttaaaattga aaaaaaaata tcattataaa acgtaaacga
166861 acaaaaaaca ttaatttaaa tttgccaata acaaaccaat atgtcttgga caaattctga
166921 agataaatcg tttaaaacaa tagatgagct taaagccaag gtaaaggcgg atagcagtca
166981 tcatgtttcc aactctgctt ctgatacaga accggaaatg attccggaag tagtaaaaaa
167041 gcctaccaaa aaaactgcta aaaaaacaaa aaaacaagaa cttgcatctt gtaattctag
167101 taatccaaat acagatccat ttactaagga tctagatctt tacgatcttg atgttcttag
167161 cgatggaaag tgtgcggaag aaaacaaacc gtcgtctata gatcttgtag agactagatt
167221 ggtaataaag actatctcta aatcaataaa agatatagca catagaatag cggcattgag
167281 gtcagtaata catgatttgg accttactga tatcccgaag aatacgggtc aagctatcaa
167341 ggaagtagac aaattaaaag aagcgttatg taatctaggt gttagcgtac caccacctaa
167401 acaacaaagg aaaaaagcta agtaaatggt aaagaaagtt ttttttcatt ataaagatga
167461 taaactatat tacgatgccg catataaaaa tctagttcct gctagtaata aaacatacga
167521 aataattaaa gcgtatagag ttcctcctca tttgaaagaa gtaatcgtat acgagcaatc
167581 tctagaagag gcgtctaaca gcttaatatt tatcggagta gattctaaag gacgaaagca
167641 atatttttat ggcaaaaatc atgtaatatt aagaaataag aatcgagata aagtttttcat
167701 taaagtacat aaaataataa aaaaaattaa taattatata gacaagaata tatgttccga
167761 atcaaatact ctagaatttc aactagcagt attcatgtta atggaaacta gctttttatat
167821 acggatagga aaagtaaaat actataaaca aaacgatact gttgggttat tgacgctaca
167881 aaataagcac ctgactgtta cggacgagaa tattactata aaattcacag gtaaagataa
167941 agttgttcac gcgtttaacg tcaagaaaga aaacagatta tatgagccct tattaagaat
168001 acatgacttt tcgaaaccag attccgtatt attttcttta ttatcagaaa agaaagttta
168061 ttcatttatt aagcaatatt caataaaaat aaaagacttg cgtacttacg gtgtaaatat

FIG. 19T2

168121 cacattttta tataatatat ggaataacgt aatttctatg ttgaaattac ctagtatcaa
168181 aaaactaata gtattatcta taaaacaaac tgcggatact ataggccaca cccctaatat
168241 ttctaagcaa gcgtatatgg ctattactat actagaacta atgaaagaag aaaatataac
168301 agaaactatt aaacaaaaga cattcgacga gtttcttaat tttgtgatta attatgtaaa
168361 taaaaaaaag atataattaa atggaccata aatctagaat gcttttagat accatattta
168421 aagatatgct aaatacgaaa gacgtatatg cattaataaa atatattttt aaaaaagatc
168481 ctgtagaaac tatatttctc aaaaaagacg atgatatatt tatagatttt gtctataacg
168541 ataatgttct agcatctgat tacctgggta tgaaaactac taaagtagag gattgttgca
168601 gttgtagaaa agtagtagct gtagaatata tgaatacatc tattatagat aatgacttag
168661 aaggatatat aaagcaatcc gataaactaa aaagatttat taaactatat aataaaaata
168721 atgctattaa aaaagcgaga aacataaaat cacgccagaa aatgctaaaa gatgctggta
168781 tagatgatat aggatatgaa tttataaaag acgccattgg tctaataagt cgtaagtaaa
168841 tttcatagcc gtgtatgggt ccatacgctt tatatcttta tgtttattca attcattaga
168901 tgatgttaaa tcgtaccaag cactataatt agtctttttc tcagataact cttcttgtaa
168961 tttcactagt gtattttgag cggttatttt atctttgtat aatccactta gtatcatatt
169021 atctttatct aaccgaacag atgttgcttt cttagttaac ataaatagaa aaaaaacgat
169081 aactataata taaataacca atataactat catttaataa atggataaat atatatcaaa
169141 aacccccactt agctgttatt ttgaagaact agtagataca tttatttctg tagttaacag
169201 tataaacaaa gtagatgaat ctaagcatca tgaagtcgaa cttatcttat ttaaaccacc
169261 tattattacc ctcactaacc tatataacat ggcaactacc acagaatctt atatagagtt
169321 taccatgtta cccgtagata aaccaaacac taagtttaga aacagaatac cttatctaa
169381 gattcatgga ctagatgtaa aaaataatca actagtagaa agtttggatg gttttatttg
169441 ggaagaaaaa tctcttttgt taaaaaaaga catatcggat aattcttccg cgattataaa
169501 atattctatt gaagaaaaaa ctttattcgt ggattacaaa agacgtaacg cgtctattaa
169561 actagaactt gtaagtgtag tacgagctaa acttagaaac atagttatag attttaaaat
169621 gaaatacttt ctaggttcag gcgcacaatc agcaaattct agttctctat tatgtgcttt
169681 aaaccatcct aaaaataaac ccagtctgta tatagagttc gagatcatga tgcaagacaa
169741 aaacatatct aaaaagaagc tactcgaaga actaaatatg tcagctagtg ctttatttct
169801 aagtcatcca aagtacatta gactgtgtcc tagtataaac cctatactta gaactcactt
169861 actcaaaaaa caggatatta ttaatataaa tacagacgac ttatatatta caagcaagac
169921 ggatggtata ttttcacacg tctatataga aaagaagtct atattctgct attttagcca
169981 tctagggtat ataaaagagt atacagcgtc tagggaaata gaagaaacta tatatctata
170041 tgctgaaatg cgtaaagaag aatctatatt atatcttaca gttattaaag tattaaaacc
170101 gtgtatggaa gatcggttgt cagaactagc attcgtaaaa aatcacctta ccggtatcca
170161 tgatagattg gtatttgtta caaaatgtta cgatggacct tttgaatcta gttctgatct
170221 tgtggtgtct atagaagaaa tgttaaaaac agaacaagaa ggtattatac tttttactc
170281 caagggagaa gattctacaa cagattataa agttaagaaa gataatacta tagatcagtg
170341 cgttaatgtt atatatagat atatgtctag tgaacccata gtatttaacg ataaaggttc
170401 gttcttggaa tataaaagat acagtaatga taagggtttt cctaaagaat tctctacagg
170461 gaaattagat ctcaacggaa gcgttgaata tataaataac atatattgta tagaaattaa
170521 acaccttaat ccatgtaccg gtattactaa tcttgtatta cctataaaat tcatagcaga
170581 attctctcat aacgatgaat taatacaacc cagaatagat aaaactatga aatatctata
170641 tgaaagcgga tactacggga atcaactatc cgttattatg gatcatttga acgatcaaaa
170701 actgagaata ggagatgttt ttgaggaaga aaaattagca gatatagcag cacacatgaa
170761 attaaaagat tctatgcgtc taaatccgga cggtaactac ttcctatcga acagagtgag
170821 aggagcgtta ggtattttat ctaatttgt taagacgtta cttatatcgt tatattgttc
170881 gaaaacatac ctagataatc attccaagag aaaagttcta gccatagact ttggtaacgg
170941 agctgactta gaaaaatact tttatggtga gatagcattg atggtagcta cagatccaga
171001 cgataatgct atcgaaacgg gtaaaaaaag gtataacgaa cgtaacgcag gtgataaatc
171061 caagtactat aagtttaatt atataaaaga aactattcga tctgaaactt acgtttctag
171121 tatcagacaa gtgttatatt ttgaaaagtt cagtttggta gattggcagt tcgcgataca
171181 ttattcgttt catcccaaac attatagtac catcatgact aacctacagg aattaacaga
171241 atcaggatgt aaagtcctta ttactactat ggatggggat tatctggata ctcttaagga
171301 aaaaaagaaa tttattattc gcaaattatt acccgaaacc gaaaactatt tatcgataga
171361 aaaaatagac gatgataaag tgcttgtgta taatccttcg agtatgtcta aacccatggc
171421 ggaatacata gttagacgcg acacgctgat acgtgtattc agggagtaca agtttaagtt
171481 aatagattca tgtaatttta aaactatcat tgatagaaac ataagtttta ttaacggggt
171541 ttcgaggttg gaatctaggg gatcgacaaa aaatttcttc gagttaaaca ggaaagcttt
171601 agaagaatgc aacgacactg atgttcttga attattgagt cattatatgg tatatgtgtt
171661 ttctaaagag gtatagtgta ttacattgtt tttatatata gtttctagtt atttaaatta
171721 tatcagggtt aaatatggga cccgaattat atcataccga tgctatgaca ttttcattaa

FIG. 19U2

171781 gcgataagta cgatatatat ggcatattca gaacgtttca tattaacact gacggtaagt
171841 attctaaacc cggatcatta tacgattatt acataactta taatactgac ggagtagaaa
171901 gttatttcct cttcgaacgt gctacagaag aacaattata taaaatatta aaatcatata
171961 actatttact tataaccaag gtaactgttt atcctaatga taattcctac gatagaaggt
172021 ataaacatag aagagatcgt aggtactaag gacgtgtata ataataacaa catcctaata
172081 ctttatttgt tttaaagcta ttaaagagtt ctaacaatat catttttgga tgtttatttg
172141 cggacggtat acgtagggta ctactttcct ttctaatagg aaattcttca ttaaatgatt
172201 ctaatatatt ttgactggga aatataacag gaaggtaatc atgtctatct ttgtatacgt
172261 tttttatttg ttgatatata attccattat caaatctggc tactttatca aagttatata
172321 tttcaaacag tttaccatta tcacaaaacg atacaattat ataatctgat tttaatatat
172381 tatttatatc ttgttggaac ctgatgactt tattaaacaa cgtatgtatg tttattaatc
172441 ctatactctt caattctagt tccattttga ttgaacgtta tatttatagc tagctacagg
172501 tttacctatt ttatcacgat tgatatctga ttatattgtg tacaagtaaa ataattacta
172561 cctttgtaac tatcgagtat aatctatgcc ttgtagatgg tgtgacgaat tataaaaaaa
172621 tctcaatatg ttgtattact atattagaaa attagaatat tattgtgaaa attggtgata
172681 tactttttat attaatgaaa aataataatt aaaagtttgg acaatataaa aaatgaatat
172741 ttgtattaac cccgagagta ctaattgcgt tcactcgact aatgatgtta aagcccggac
172801 tcccataaaa aataaatatt tacctgatta cgcgttaata agatttatga ttaaaaagtt
172861 taataaacta ttcatcgaaa aaggtttacc tataacagct gtatatagtt ggaccgtgtt
172921 tcgtgaagct gctatatgta gaggtcaata cagaagttgg ataatgtcat ttatacatac
172981 tatttctggt aataatattg ctaattttag attagataga gcttactcag attccagata
173041 taattctata ataatagact ccacatcagg aaagattata tgtgaaggaa ttggcatcat
173101 ggagaagttg agattacacg gggtagattt tattaacgac aagttattca ccgaagaaga
173161 aataataaca catgtatacg gagttcaacc gcttcaggat atatgtatta ggatgatacg
173221 taatacggta agtagagacg attatgataa gctagaactt ccaagatcat tactaaaaga
173281 aattaagaaa taaggcagta aatatttatg tcaaaattga agtataatag caaataatac
173341 gctataaatg taggtgatta tgtcacatct tcatcttaat aatggagata cagagtatag
173401 agttattgaa gataatggat tttccattat attgcttaaa catacagaat atataaatgt
173461 tacaaaatta tgcaagatac ataacaaaga gttctataga tggaaaagac tgatctctgc
173521 gggacgtatt atcgaaactg tttcacgaga tatatcgaat caaggttttg aatctcctct
173581 agtatacgta aataggaaag gcaataaaga attttatgga ttttatgccc atcctcaatt
173641 agcgttgtat atagctaaat ggatatctga agatatattt aacaagatta agcatttaat
173701 aaactcctat acgatatcag ataaaaccgt agtaataaaa gatttttcat attgtgacga
173761 actatgtccc gacgctataa taggaaagtg ttgtaaaacc aaatcatcat gcgagtacgt
173821 ccatggagat atatgcgata tatgtgggtt tgaggcttta catccaaccg atattgataa
173881 aagattgact cacgaaaagg tatgtatgca actactatgc aaagaagata taaaatacga
173941 taaatgcggt atttgtttgg atgctataaa aggaaataag aaaccttatg gtattttatc
174001 agactgtaat catatgtttt gtattaactg tattaaaaca tggatgacta ctattaattc
174061 taagaagcaa tgccctgaat gcagagtacc ttctaagtat atcatacaaa gtcctatctg
174121 gacagtggat aaggttagta agaatcagtt aagtgtttcg tacaagactg tatatataaa
174181 atcatgttaa cgttttgtag aagttgaaaa aataatatac tgatacaaaa tggcttttca
174241 agaactttgt tgtagtaatt tgttaaaatt cgagaactgt tcactactcg aaacgcataa
174301 aaagatatct atagaaggaa atatttctgc cggaaagtct acgttgataa atatattatc
174361 tgataatggg tataacgttg ttcaagaacc tttagaacaa tggagaggta ataatttact
174421 ggacaaatta tacaaagatc catctagatg ggcatatact ttccaatctc acgcttttttg
174481 gactcgaact aaaacttata tagatgctct aaacaaaaat aaaggtaata taattttaga
174541 aagatctgta tttagtgata agtatatatt tgcgacagcg ttacacgata taggatatat
174601 agatgataca gaatggaata tttataacga atacagtaag tggatgaccg aatttatgga
174661 tataaagata gatggaatta tatatttaaa gacatcaccg gatatatgtt ataaacgaat
174721 gttaaataga gcccgtcatg aagaaaatac cgttaaaata gattatttga atctgctcca
174781 tgataagcac gaaaagtggt tgtccgagaa taacgagcac gaatttaaag ttccggtatt
174841 agaaataaac ggagacggcg acttcatcga cgatagtaac agacaatcaa gcatacttag
174901 taacatttat gattttatat cggaattata catataagta aaacttttat aggttataga
174961 atttgtcttc tatttcctta ttcgttaatt ctcttatagg cattatgctt atcttatata
175021 agtcacataa tgatgcatta tttacaagtt cagcatattc tgattccgta gtataataag
175081 tatattcata tttttattc ttagaatata atcctatttg gaaatgttga tcttgatttc
175141 tatatttatc gtcagtgatt acatgatagc attcgaaaat tctaggtata tcgcacgtat
175201 tacttatttg tagtgaaata agatctccta ctgcaaattc tttccaaaaa aattgctcgt
175261 cgtaagatac ggtatttaca tcgttatcgt gaacagttaa gattaatgat ttacaattgc
175321 cattctccat aatttggtt ttaatatatt tataacacaa tttataataa taaatcttat
175381 agattaaata gaggtttaat aaacgcgtag ttatatatca ttataaaaat gatacttgct

FIG. 19V2

175441 tggaaaatta tatatctagc tattctcttg tatataccga cagaaagact agttttaagt
175501 cataccgtga ttacgcgtag taagctttcc acagaagata acgaaataga tgacgttcca
175561 acatgtccgt acagaatgtt caataaaaag aagattatgg gtcctatcgt gtctgtaaag
175621 tcacctgata atccgacggg ccctatcatg gctttggatg cttatcataa ctatacgtcg
175681 tgtaagtata atcaatattg tactttttt gatttctgta tggcgggtaa cactactatt
175741 cggtttggaa ggcagaaaat aaacttaata tactttgtat ttatagaagc tgtaaccaga
175801 gatgattata caaaaattac acaagaagtt accttgaagc atctagatga tgttagattt
175861 aaaccagtat ccgttacttt tgcagcatta tataaacaat ttgtgaaaat gtctgcatat
175921 cacgaatgta ataaaacagg ttttaaaaaa ccagttagag attcatgtag aaaagatagt
175981 aactctgcta tacaatatag taatgaacaa aaatcacatt acaatttctt gttaaaaagt
176041 agtaaaaaaa tataaaatga aaataaaaca atattttata atagcttaga taatatagat
176101 tttgattcac tcataaacat tattaaatta gaaaataaga ctataatatt tggaaaaaga
176161 ttgcagatat atatcaggtt gctgcttatg tattgactta tacatcatag ggtagcgtta
176221 aaatacacaa gttgttcaga cactacatga aaatataata gtacgggacc tgtaatgata
176281 tgtccggtaa taaaaatata atatttagtg aaatattgga aattcttaat agtaagtaca
176341 agaaggatat gaagctttta aatatagtct atgaaaaata tagagctatt atattctggg
176401 aattagacga cattaaatca gagagcaaaa aattgagaac acaatatcaa gaagaactta
176461 gtaaaaactt aatgccggat ttactaaaaa ataaatatca aagggatatt aggtatttca
176521 ggagtaaatt aatagagtta aaaactagac tagatgatat tgaaagaaag ttaatagata
176581 ggtctaatag tcttatgctt aaatacgtat cagatctaca aaaaatacaa tcatacctat
176641 cgagtaaaac aagcgactct gtaatcatcg atcttgttac tcagttaata gcttatagga
176701 tagtagatgg atataaagaa gctgaaaaat aatctatttt ttattacaaa ctaaacaagt
176761 atgatgttta atagtatgat aaccggttat atagatgaag aattttgcta tatacaatat
176821 tctggatttc atcttgttat gatgatttcc aattgttata ttaacgctag taagttatgc
176881 gatacaaagg attttaaaaa atggttgcgt ttagatagtt cgttatcgct tttacaagaa
176941 atagaaaaca caaactttcc atcggagaaa aagttttcta tcaaaaattc aaaatcggtt
177001 attattctag aaaagtatta tcacgaagaa gtagaaggat attacattca tcctgatata
177061 ctaccgcata ttgtaggatg gttatctcct acattcgcta ttagtatgtc taaattcatt
177121 aatgggtata tatctaatag ttttacaatt accgaaaaag atgacaaaaa atacaacacg
177181 ttaccaccat cttcatcata caaacaagga gatagaaatt gtttcataga tatgcttaac
177241 gaaatgacaa ataaacatct caatgatata acagaactaa aaactcatta tagagagcag
177301 aaaagagaac taaaatatca aaataccgta cttagctcaa aaataacaga attaaagaac
177361 gtcaatgacg aatttagata caggataaaa cattttgatg atagtattaa agaaataaaa
177421 gatgaaaata acactttaaa atcaaatatc aaaattacag aaaacataa caaagaatta
177481 caaagagata acaatagatt aaagacttta ttgagagaac tatacgaaaa gaatacttct
177541 ttgcaaaaca atataacaga acttagagaa acaatagcca gagaaacaaa agaattacat
177601 aatcaagtaa ttgaactttc caaagacaag gggatagaac ctatagaaga ataccgcgtt
177661 gacagatgct ttgtaaggaa tagattacac cgatctaata aaaataatta tataattatc
177721 tttcaacata aaaaggactt gtttactttc aaatacttta aactacatat aagaaaagta
177781 tgcatagaac tatttaatta tagagagagc cataatttat ttttaattat ttacgaacct
177841 actaataaat ctataatccg attcaagaat atgcttgaaa ataacgaaca tatagaacta
177901 aaagataaca actttaaaat aacagatact agatataccg ttataaatat attaaaggat
177961 ataaataaaa tattttcaga taactaatat aactttttcgt accgtgtaaa ttgcataatt
178021 ttttatacta taaatatgga tggtaacacc aataaccaac agaagaaagt ccctgacggg
178081 gtgattcccc agggccaaca aaagcttcct ccaaaagcac cgccgactaa cggcggtagt
178141 acaggagatg taaaaagtag tgatcaaaat acagaaccat cacagaaaag tgtataatat
178201 aaaattacgt cttatatcag taatactgat ataagtgaag ttatgtgttt taaggacgtt
178261 aggacccttt acaagaataa aagaagaaac aactgtgaaa tagtttataa atgtaattcg
178321 tatgcagaaa acgataatat attttggtat gagaaatcta aaggagacat agtttgtata
178381 gacatgcgct cttccgatga gatattcgat gcttttctaa tgtatcatat agctacaaga
178441 tatgcctatc atgatgatga tatatatcta caaatagtgt tatattattc taataataaa
178501 aatgttatat cttatattac gaaaaataaa tacgttaagt atataagaaa taaaactaga
178561 gacgatattc ataaagtaaa aatattagct ctagaagact ttacaacgga agaaatatat
178621 tgttggatta gtaatatata acagcgtagc tgcacggttt tgatcatttt ccaacaatat
178681 aaaccaatga aggaggacga ctcatcaaac ataaataaca ttcacggaaa atattcagta
178741 tcagatttat cacaagatga ttatgttatt gaatgtatag acggatcttt tgattcgatc
178801 aagtatagag atataaaggt tataataatg aagaataacg gttacgttaa ttgtagtaaa
178861 ttatgtaaaa tgcggaataa atactttttct agatggttgc gtctttctac ttctaaagca
178921 ttattagaca tttacaataa taagtcagta gataatgcta ttgttaaagt ctatggtaaa
178981 ggtaagaaac ttattataac aggattttat ctcaaacaaa atatgatacg ttatgttatt
179041 gagtggatag gggatgattt tacaaacgat atatacaaaa tgattaattt ctataatgcg

FIG. 19W2

179101 ttattcggta acgatgaatt aaaaatagta tcctgtgaaa acactctatg cccgtttata
179161 gaacttggta gatgctatta tggtaaaaaa tgtaagtata tacacggaga tcaatgtgat
179221 atctgtggtc tatatatact acaccctacc gatattaacc aacgagtttc tcacaagaaa
179281 acttgtttag tagatagaga ttctttgatt gtgtttaaaa gaagtaccag taaaaagtgt
179341 ggcatatgca tagaagaaat aaacaaaaaa catatttccg aacagtattt tggaattctc
179401 ccaagttgta aacatatttt ttgcctatca tgtataagac gttgggcaga tactaccaga
179461 aatacagata ctgaaaatac gtgtcctgaa tgtagaatag tttttccttt cataataccc
179521 agtaggtatt ggatagataa taaatatgat aaaaaaatat tatataatag atataagaaa
179581 atgattttta caaaaatacc tataagaaca ataaaaatat aattacattt acggaaaata
179641 gctggtttta gtttaccaac ttagagtaat tatcatattg aatctatatt gttttttagt
179701 tatataaaaa catgattagc cccaatcgg atgaaaatat aaaagatgtt gagaatttcg
179761 aatacaacaa aaagaggaat cgtacgttgt ccatatccaa acatataaat aaaaattcaa
179821 aagtagtatt atactggatg tttagagatc aacgtgtaca agataattgg gctttaattt
179881 acgcacaacg attagcgtta aaactcaaaa tacctctaag aatatgcttt tgtgtcgtgc
179941 caaaatttca cactactact tctagacact ttatgttttt aatatccggt cttaaagaag
180001 tcgcggaaga atgtaaaaga ctatgtatag ggttttcatt gatatatggc gtaccaaaag
180061 taataattcc gtgtatagta aaaaaataca gagtcggagt aatcataacg gatttctttc
180121 cattacgtgt tcccgaaaga ttaatgaaac agactgtaat atctcttcca gataacatac
180181 cttttataca agtagacgct cataatatag taccttgttg ggaagcttct gataaagaag
180241 aatacggtgc acgaacaaag acaaacgtgg ttataaacaa aagccattac ccggattgga
180301 aactaaaata ctagatagta ttataagatt ttaaaaacat aaaattaata ggtttttata
180361 gattgactta ttatatacaa tatggataaa agatatatat caactagaaa gttgaatgac
180421 ggattcttaa ttttatatta tgattcaata gaaattattg tcatgtcgtg taatcatttt
180481 ataaatatat cagcgttact agctaagaaa aacaaggact ttaatgaatg gctaaagata
180541 gaatcattta gagaaataat agatacttta gataaaatta attacgatct aggacaacga
180601 tattgtgaag aaccttacgg cgcatcacat tccagtgtaa ttattgaggt caaagctagt
180661 aacttaatag atgacaggac agctggattt tatgtacata aagatttgat accttatata
180721 ctgacatgca tatctatacc ttttagtctt aaagttgtcc gtgtattaga tacttatata
180781 ggtgaaaaac tagaaaacag aattaagcta agtcagagta tggatttgga aacgaacaat
180841 tcatacaaca tgtagaaaag aaaaaataat gttcttataa taatactata actccatatt
180901 gttatgtaaa cctagtagta acagctatga gagagattct aattatatta atgctaaaaa
180961 atatgtagta tcatcgataa taaaaaattt ataaatggca tagattagaa tattctaaag
181021 aactaatagc ttacaataga tacgatcgtt aatacaaaaa atctaagata aaaataagta
181081 gtaccataat taatagtgct cctagtaata tagatatact aggttattac gtccatccgc
181141 tgctagtacc tcataccata taccatcttg gaggtcagcg gaataagaat taaaaatttc
181201 aaagatagta aaggttatct attctaagat gtatcataac aatggaaaaa tctaaaaatt
181261 aaaaaaacaa ctaatataat tataactata atgcatgatt atatataaca gaatggtaat
181321 aacagtaaga tataccattt ttaacaatat aaagttattt gtaattacta taggattgtt
181381 atgtagtgta ttattattac gtaatatagt gtacttgtac aatagaatat tacagttaat
181441 aattgattaa ataaaagaaa ttaccatgat tttaaatgta taagttctaa acatattaat
181501 agtaaattct gttatataca gcataattat ttagaactaa taaagatgag agataattct
181561 tttataaatg ccatacattt atgtttatca ggaggaaagg atttttctac gtggttatca
181621 ttatatacac ctaggtgtct actagatacg ttagctaaaa caatcttcaa tggaacgtcg
181681 atgttgacta gtcagaagga ataattaaag aaaagtctta tgatactgat gaagagtata
181741 aatgttacta tattctcact atgaccatat agccgtgggt atttagttat tttgctgtaa
181801 acttatacga gctcgttagt aacatctata tcatatgcaa aaacagatga catgttttaa
181861 actatatttt gcgttcatat tagactacaa acctaatgat aataacaaaa atcattcata
181921 ttttacaagt tttaacaata ttgaacgcgt aattagataa accaaaatgg ttttatatta
181981 gtgtaaatat aatatcgagt ttatgtaatt aaatatcatg gttatagtgt aataaagtta
182041 aggataatta tgctaaatag cccgtattat aatacacgat aaattaataa attgaagcta
182101 tttatatcac aaggagatat aataccgtcg taaagtaaat ataaaatatt atcagaatac
182161 acgtatttat ctaaaatcat taaatggact tgtatgataa taattgaaaa acaattatct
182221 caatacattt gaatggtgat atattgtaac ctacatacag taattatgaa tatattctat
182281 aacaatattc atcgatgttt taaagacacg cctttacata aagccgtaat gttacctgat
182341 gcggtagaaa gaataagaat gtttgtatct aaaggcgcgg acataaacgt aatatcagat
182401 tttaaaaaga cggcattgca ttatgcggca aagaaattgg ctactccaga agtacttaaa
182461 acactcatat atttaggtac taacgtaaac gtcaccgaca tgtttgaatc aactcctttg
182521 cattacgccg tacaagaaaa tggattagaa gcaacaaaaa agttattaga cctaggtgca
182581 gatcccaaca ccaaatacat gaacggtcag actccgttac attgcgcagc gatggttata
182641 cccgatggtc ctgaactggt aagaattctg gtcgagtacg gtgctaatgt taatgcgcta
182701 gacaataaac ataatacacc gctagctcta gccgcagaat tatctaatac aaacaaaaca

FIG. 19X2

182761 atagaaacgc ttatcgagct cggcgcggac gtaaaaataa aaaataatga cggtataaca
182821 cccttacatt tagccgctaa atcatcgtct gattccaaaa cagtggaaac acttatcctt
182881 cacggagctg atgtcaacgc tacatgctcg gaagggaaca cgcctttaca tgatgcggct
182941 acttcatacg agttatctaa tacaatagaa atgctgatag aatacggagc tgaagtaaac
183001 gccgcgaatt cggtaggtga tacaccttta cattgcgctg ctcgttctcg taatcctgtt
183061 cataagctga aaacactcat agcacacggt tctaacgtaa acgctgttaa cgggatatcg
183121 gtaactcctt tacatcttgc gacttattca gataatgcaa cggaagcatt aaaggtatta
183181 atagagcacg gcgctgaagt aaactccgta gatatctacg gaagaacacc catgcattat
183241 atctctaggt cttattcttc acaatcatta aaaaccgctg ttgagttact ggtagaacac
183301 ggtgccgata tagaagctaa aaatgtaata ggtggtacac ctttatccag cgcgtgtaat
183361 aatatagagt atgatctaag acttatagaa tgttttatag aatacggagc ggatataaat
183421 actagagata tacgtgatga aacaccttta tattcggcaa taaagtatcc ggagatagtt
183481 aatttattaa tgaattatag cgctagtaca aacataacaa ataaaagtaa tattactcct
183541 ctggaatcag ctatcgccaa ttgtataggt tctgcagaaa ttatagtaac tcaaattata
183601 ttagacgcgt ttagatttcc tgatataaaa aatgatgcga tatttatcag aaacatgaaa
183661 accatagaag aatgtaccat gcttatcgat gtaaaagaat cctgtgaata tgacataaat
183721 aaaatgcgat ctattaaatt taataatatg tacggactgg atatattcat tcgctcaaat
183781 aatataaatt tgttgtcaag tttggtatct aatgtagaag atatatactt agaaccaggt
183841 tgtttttttag tatatggaaa taaattaaga aaatctgtat atgccgctag gaagcgatta
183901 tcgttactaa aaaactctat atctattctg agtaatatca ctacagatgg ttactggaat
183961 gctttaccta tagaacttaa atataatata ttagctatgt taggagataa tgatttgttt
184021 aatattgtaa gaaactgttc gtaaagaacg tgataagata cagccacgtt tactagcggg
184081 acttataagt gaaatcattt tattgttcta tattagatta cgtaaatgta gatttttttc
184141 attatgttgg aaggaaatat tataatattt taatggcttg ttaatagtta ttatcttaaa
184201 aacatacatc atataaataa actcagttaa aaagttaaaa ataatctcat agtttcgagt
184261 aaagactatt acaatcatga ataccttacc gtatattatt caggatattg attcgcattt
184321 ctgttatata aaatacgatg gaattacact tactatgatg aaagacaacg gctacataaa
184381 tgctacacaa ctgtgtatgc ttggaaataa agactttaaa gaatggataa agttagatca
184441 cagtatagaa ctaataaaag aaatagaaaa aaatatcaat aaagaaacta ccaaatatgt
184501 aaaagctgtt atatcagtta gatcagatta ttataattca gagacctcca atgacataaa
184561 aggattttat atacacggta atataatgcc acatatctgt gcctggatat catctaagtt
184621 tgctataaaa gtatctaata ttgttcataa ctatctaaac gatagatatg tacaaaatga
184681 taaagaggaa atacaccaag aacccgataa ggatattaaa tatataaaga aacaatgtaa
184741 gttaatgcga gaaataagaa ttctatttaa aaaaaactat actcgcgagt tagacgaact
184801 caaaaaagta agggagcttt attacgaaaa aaataaagga cttgaagaat atattgataa
184861 attagaatat agttacactc agagaatgaa agaattaacc ctatctatag atgaattaaa
184921 aaatagtaac aagcaattaa agaacaagtt agaaaatata gagaaacgta taaaatgtat
184981 taatccacct actgaaagta gtaaaaatgt gatctatgat aggttcaaaa agttatatca
185041 cattctaaca ttcagaaaat ctaaataatc aattaattat tataaccatt aatagctatt
185101 attttgaata tattcaaaaa cagacataca tcatgtaata taacactata taatacettt
185161 acaccacgca actacatata ttgctttgta tatgttgtat gaaaggtaat tacgtaaaca
185221 taataggtcg ccttactaac gatcctaaaa gaagttatag cttcacatga tatagatata
185281 aaactaggta atctatacac actaaaaagt ttttatacat tacgatagat attatggata
185341 aaagtagaga aactcgcatt tgcgattatg cttctaggac tatactgtaa agtgtctcga
185401 tcttagcata tagataaatg tttgaactaa tatcctaaag gctgtatgta acagttggtg
185461 actattgaaa gatactgatt atcaaggaga agaataatat aaatcgtaaa aataatactt
185521 attatataat ataatgtata ataatataca aaaacagcca tgatacgtat tataatatta
185581 tcgttattat ttattaacgt aacaacagat agtcaagaat cttcaaaaaa tatacaaaat
185641 gtattgcacg ttacagaata tagtagaact ggtgtaacag cttgctcgtt acattgtttt
185701 gatcgttcca aaggtttaga tcaaccaaaa acatttatcc tgcctggtaa atatagcaat
185761 aacagtataa aactagaagt agctattgat acatataaaa aagatagcga cttcagttat
185821 tctcacccat gtcaaatatt ccagttctgt gtgtctggta attttagtgg taaacggttc
185881 gatcattatc tatatgggta tacaatttcc ggatttatag atattgctcc aaaatattat
185941 agcggtatgt ctataagtac tattactgtt atgccattac aagaaggatc attaaagcat
186001 gatgatgccg atgactatga ctacgatgat gattgtgttc cttataaaga aacccagcct
186061 cgacatatgc cagaatcggt aataaaagaa ggatgtaaac ccattccact accaaggtat
186121 gatgaaaatg acgatcctac ttgtattatg tattgggatc actcgtggga taattactgt
186181 aatgttggat tttttaattc tctacagagt gatcacaatc ctctggtttt tccgttaaca
186241 agttattctg atataaacaa tgcatttcat gcttttcaat catcttattg tagatcacta
186301 ggctttaacc aatcatacag tgtatgcgta tctataggtg atacaccatt tgaggttacg
186361 tatcatagtt atgaaagtgt tactgttgat cagttattac aagaaattaa aacactatat

FIG. 19Y2

```
186421 ggagaagatg ctgtatatgg attaccgttt agaaatataa ctataatggc gcgtacacgg
186481 attcaaagtt tacctcttac taacaatacc tgtatcccta aacaagacga tgctgatgat
186541 gttgacgatg ctgatgatgt tgacgatgct gatgatgttg acgatgctga tgatgctgac
186601 gatgatgatg attacgagtt atatgtagaa actacaccaa gagtgccaac agcgagaaaa
186661 aaacccgtta cagaagaata taatgatata tttagtagtt ttgataattt tgacatgaaa
186721 aagaaataag acatatttta ttaaatcaaa aagtctgtcg aacttttagt gtttaaccta
186781 tatcgattta tgattttcca tgatgatcca ggctatgact gactatggca aatgtataaa
186841 aagcagtaat ctgtatacga cttaatagat tctaaaaatc aagaaaacct taatttctat
186901 ctcacgttct tgagaatttt tgatgtatag ttgactacga cctagtagaa agattttgaa
186961 aagaagtttc tatgtttttc aaataggtat agaaaaataa tcattctgaa gcacgtgctc
187021 caataaaatg aaactatttt tgctactgag gtagactttt aatgtaataa caataagcat
187081 gactacctat tatctgcttt aaaatatact atgttgatgt gatagatcct tggttattat
187141 attccttata ctagtagaat agttacttag ttaatgatgt aattctaaca agaaatctgt
187201 gatacgtgat tatgatgatt cataaaaaag aataatatat agcgttattt agaaaatgta
187261 tctaaaataa tcatatcatc tggctctgtt attgtacccg atataacggt aatactaatt
187321 tatctaaata tgatgtataa gagttagata atggtttaat tccttagtat catattctcc
187381 agagactgta agattgttac cagattattg ttctaatact accgttatag ataaactaga
187441 cttcactttt tatggaatta taacattagt agaggtgaaa tattatagac gatatagaac
187501 attatactat ctgaagaata tataataact gatatagtat tatcagctat atcatacaag
187561 gattgttata tattttctaa aaatgtatac ctatacacaa taattgatac attaaaagaa
187621 acaacgaata actatgaatt aacattagct aactcattga ttattaataa gaacacagag
187681 cgataaaagt aatagaaaac actataccat gtctaccgat aatatgaaga ttatattcat
187741 aaagtcgtag ataattaaag agaagtttaa atttattata aattatccta cgttactaca
187801 cttctaaaga acatgttgta aaaccataat ctacaaatac gtattcgtgt ccgtaatcgt
187861 atacagatgt attaattttt ttctttttca tgtaatctag aaagtttccc catactagtt
187921 gattactatt gttcttcgtg tagtttttaa ccgtttgggg tttaaggtta ttcgttacag
187981 atgtaagact aaatatttta tccaaaaaaa acgaataatt aatagttttc gaagcggtat
188041 tttcttgaca gaaaaatact aagtgtttaa aaatttctat aacttcgttt atttacttg
188101 tatctaaatt taattttttct tctttatat gatttattat ttcgaatact agtttataat
188161 cttttttatt tatttttttca ttcgctttta aaaacgatga tacaaaatta gcgtctatat
188221 ctgtagaaga tatattattt tttgtcatta cagactttaa ttcgacaatg acgtctgaag
188281 aacattgatt agaaagtaat ctacgtagaa cgtttctcaa gtgtatcaat ttattagata
188341 catgaaaatt tgattttttta gatactttgt tagaaagttg gaatatagat tgacagaaaa
188401 tacagaattc atgattagat tctgttatca atccgttatg cttacaatta ctacaatgtt
188461 ttagattact catgttaaaa ctcttcttat ttccggatct agtatttag ttaacagagt
188521 tttatttcta ctaaatatta gaaattgttt taatatattt ttcttatatt cgttattatt
188581 taacattaat tttatcaatt gtctatctga ttttagatat tcaactaaat tattactaca
188641 gttactacac ctaactggag gatctatact atatttatac tccgacattt actttacgta
188701 aattaaacaa atatttctgt tatgctttta gttgctaagt aaggtagata gtcttgagca
188761 tacactaaaa tacaacaatt tctagaaata aggttcatag cttcttcgtg ggacaataaa
188821 tcatcttcaa acataacagt atgatgcatc agttgctgtt gctttatatc gcatagtttc
188881 ttagtggatt cttctttcaa ccaatcgtag aacattccgt cgtcatttcc atgttcttta
188941 taatattgat tcttcatcac tctcattaat cttgactctc ttgactgttt gctataaata
189001 gatagaggat cgtacatcca aggacccatt tccgtgaata gaatagtata gtatcctttg
189061 agaaatacat ctccgccgtc gcaacttccg gacatggtag ataacaaatc gtgtgtcttg
189121 taacaaactg ctgattttag tagatatgta ataccgttga tatttagttc attagctata
189181 tccattggac gatcgttaat tactgatcta aagcctgtaa aacactcacc tgatactata
189241 tttttatttt gtcgacgttc tatgtagtag ataagagtcc cgtttactat tactggggaa
189301 tttataatcc tatcatgaga aatagaattc aatacaggta gagcgtctac agtcctacaa
189361 gaaatagtac cttggtatct catattagca ggcatgaaca ttactctacc cgtagtatta
189421 tcgaaactta gagaataaat tgaattagag ttaatggata taggattgtt tatagtggta
189481 atcatttttg aagggcttac aactatataa gatacgggtt taagaactac gttaagcggt
189541 tggtaaggat ctgtgataga tactagcgcc ggtctgaatc ctacaataga tagaatcgaa
189601 gctagcattt gttcttcgtc ggccatcatc tgagagctgt ttatgtgaat aatcttcata
189661 agatggttgt cgacaagatc acaatccttg ctgtagaata tacctaatct caaattcaat
189721 attgtttttc tcagcatagt atgaatactg gctctatgta tttcactaga tacagaatca
189781 ttaatacccg taaagataat aggagaatct tcagtaagcc tattaatcaa caacatatag
189841 ttttctggct ttactttctt cgagttatac aattgtttca taagactata actatcacct
189901 aataccatag cgttttctag agccggtagc ttaacgccga ataaagcaac taatatagga
189961 tgaacgtagc ctatggaatc ctggtctttg aatctaaata acatatcact agatgttgac
190021 atgtcaacaa agtttgttga ttgaaaccta gtcgtatcta tcaacgcttg atatctggat
```

FIG. 19Z2

```
190081 ggatcatatg tattttctag tagttttaac tgttctccta tcttattatc tgagtgcgaa
190141 taaataacca ttagaggatg actcgttttt accgaaacgc tattactaga aagtgatcct
190201 ttgacatgag atagtaactc gaataactct tgtctttcat ttctaataat atttaattcc
190261 ctcataacgc gaataaggtc ttgtatcgta aagttattta tatcacattt tctatccatg
190321 agatatctta ctatagcatc tgcgtctttt ctaagattat attgccagtc atgagtagat
190381 gtaatttcat ctatgttgat aattgtgttt ttttgtttta cagaatctga aactccttta
190441 catatatcag gttttggttt actacgaaga cgcataggtc gttgttgttt agcacctgct
190501 gatataacat cttcttcagt aattttattc aagacatcac atacgttaca taaattattt
190561 ttatccggtt tatgtaaatg agatcctatt acttctaggt tattatagta aacaggttct
190621 aataaaatat taggatattt aacttcttca atcgctatat tagaatcaga ttccatttat
190681 atttgatagt tttttacttg taacgtatca aaataagtac ctaaagagac gtaactagtt
190741 aaggaataat agcatctctg agttctctta tatcatctgg taacataata ccctttttcct
190801 gaagatatat atttatccac gtaataactt catcaaaaaa catttgttta tctatcttat
190861 tgctattaga taatggtact ttaataggtg gtaggatatc aatatattta tcatgcagat
190921 ttcttatcca aagtggagta ctactaggca atgttaatac ttgtgactgc tgaatattag
190981 aagacggtac taaagtacta ctactgctag atgaagaagg tgtttgaggg ccaaaactac
191041 taccactaga tgaggttgtt tgaggtccaa aactactatt gctagacaat gacgatggtc
191101 cttgtaaacc aatattgcta gacaatgacg atagtccttg tggggctaat ccactaacgg
191161 aagacgaagt tccttgtggg gctaatccac taacggaaga cgaagttcct tgtggggcta
191221 atccactaac ggaagacgaa gttccttgtg gggctaatcc actaacggaa gacgaagttc
191281 cttgtggggc taatccacta acggaagacg aagttccttg tggggctaat ccactaacgg
191341 aagacgaagt tccttgtggg gctaatccac taacggaaga cgaagttcct tgattgccgc
191401 tagtcgaggg tagagtagta cttgaattat aggaaggagg tcctaaattt tgtggataag
191461 gcaaattact gctttgttga ttgttaaatc tattaagaaa actggtaaaa ataccagcag
191521 tatcgttact acgtaatata gatatcattc tatcctgaat agacctacta tcgtctgtat
191581 tgtattcgtc tactatagat tccttctcat ttctactatc atcttcatct agcttttctg
191641 aaaatatctc tggattatta ctaacattac gtttgattct agaaataaaa tctttgtgga
191701 agttctcagc catttagtat cctaaaattg aattgtaatt atcgataata aatggacaat
191761 tctatggata ttaacgatat actactgtca gatgataacg attataagag ttacgatgaa
191821 gatgatgact ctatatccga tataggagaa acaagtgatg attgttgtac gactaaacaa
191881 tcggattcca ggatagaatc tttcaagttc gatgaaacta ctcaatcacc tcatccaaaa
191941 caattgagcg aaaggataaa ggctataaaa caacgataca ctagacgtat aagcctattt
192001 gaaataactg gaattttatc cgaaagttat aatttattac aacgtggaag aattccatta
192061 cttaatgacc tgacagaaga aacgtttaaa gattcaatta ttaatattat gtttaaagaa
192121 atagaacaag gaaattgtcc tatagttata caaaagaatg gagaactttt atccttaacc
192181 gactttgata aaaaaggagt acagtatcat ctggactaca ttaaaactat atggcgtaac
192241 caacgtaaat tataatttag atatataatg ttcttgaata aaatcgaata tgaattctat
192301 atctacagca ttttctttat agttaatgtt gtaattatcg gttatacatt gaacaattga
192361 tataagtgtt gttttgtgct tttcatattc ttccacaaat atgtttttat acatttcacg
192421 gttatttgat atctcactta tcaatccctg aatgttatta acctttcttt tctttaaatc
192481 ttctacggaa actttagtct taaatgatgc cattatttca ctaaaaagaa cgtgtaagcg
192541 ttcgttagta agtatttcag aatacactat actagagagt ttagaaaata tgttaacaaa
192601 ttgtgttgtt ttgacacagc tagtttgaaa taaaataata ttaggtaata ccttttttaaa
192661 gaagcttacg tatttattat ttatctggtc tataccgtct atcgttatat cgcagaaaca
192721 cttaatacca aatattacgt tttctttaga gaaagaaaat acatctttat attcttcaag
192781 ttttatctta tcagatacta catctgtatt aaaaagtgca attatcttta tgatataatt
192841 gctatccgct aggactttat ttattgttct gataatgaaa ctattgtttt ccattaatat
192901 tttgtaagct tgatgttcgt tattagcact tttaattaac gacacaattc ctagtatctt
192961 ttttaaatcc tgcactattt catttgtatc tttttcata ttagagtaca tattgtttat
193021 agatgtaata acttttgcat atactaacat atctttaaat attctgataa actgttcttt
193081 tgtttcttta tctgttattt tgttgagcat agattttacg tttgccgctg atcgcatata
193141 ccaaaatgta aacatcttga attctacttg ctgcatggct agaataacag tctcgtcaga
193201 cattgcgcag ttaatatcac cgcctatctt actttctaga ataggaaaaa ccgttaaaaa
193261 tgaatcgata tcattatcat aatttacttc atacactttt tgacctgtac tattctctaa
193321 atacttctta cttaattcat aaaattcaat aaatgcattc ctgaactttt ccatgattta
193381 tagcttgtag tatttttcta atattgattt gatttgtata tgtgtataat ctttaccgat
193441 acctaattta agcatagtat taataaccca agtttttata aatatttctt tgttatcggt
193501 taccacatat ttaaatactg aattaaagta tttaactata ggattattct gagtagatat
193561 attatccata aatacagacc gttttgtaga tagaggttct gtaaataatt caccgtcgac
193621 ataaaaacca tccgttgtta gtttgagtcc attttgttct tttatatcaa ccgttttaac
193681 tttataagga aacatatccc tcagtttgtt ggtacgtagt tcttcaaaat atatcatatc
```

FIG. 19A3

193741 tttatcttct tccttttttag ctatgactat ttcatgtact atttcttgaa ctagtatgta
193801 tattttatta ttaatggatg agtatttcat aggaaagtaa acgatatcat tagctatgag
193861 agttacattt tccgtgttaa caaactggat aatatcattt ttagttcgta tacgtttcaa
193921 tgtataatgg caattatgta gacaactcct gattacatga tatcctttcg tactttttaa
193981 ccgcttatta tccgactcca atgaaatgct taaatcgctg ttaaagaaat cattaaatat
194041 gggaggtaga aatgctattt tagaatctgt aactactttg ccataattta gtatatacgg
194101 actaattata ttcttgtccg tttgcttatt atgaacacac gccataaaag tatccgtatg
194161 actttggttc tttagaaaac agcacggtat acatatcttt tgtaatttat agaatatagc
194221 aagaaaccct atattattat attttccggt cttatcatca caagtaaaca ttacctcgtt
194281 attattgacg aatacttctt tggtaggaga tttataaaag ttatcgctta cttttaacat
194341 atcaggttct agggaagata ttattacggg tttcctattt ttatctttcg tgttttgaca
194401 aatacgtgac caatagatag tttctatctt agtaaaatcc atagactgtt ttaccgtatt
194461 acacaggcgg tttataaaaa caactaagaa agtaaagtat ttttctatat tgggtatgtg
194521 atttttaacc tttatagaga tatggttctt cgctaaaatg attgatattt ttttatctac
194581 ggaaagcaat atattgttgg tagctgtttc aataaatata aaactagttt caatatctaa
194641 ttttactttt gatgtaatcg gagtagatag tttcacctta tacgtaatat cacttttgat
194701 acgttccatc tgtacgttgt tattcggtat catatctgta aaaagtttta cattattaac
194761 agtaatagta tttccgtcgc tggatatagc tagagaacca tcatcgtccc atatagacaa
194821 attaagagat tcgtcgttaa taacaaaatg gtttcctgat aaattgataa aatactcatc
194881 agatttgata aatagtatct tcttatcggt attactgaga actatattct ttaatccggt
194941 cattttgaga ttagtcctaa aaacgttatt aaatttttgat tctaccgtga agtctaaatc
195001 aagatcagga aacatttcta taagacgaga ttcaaattta aggacattag catctacttc
195061 ttcgtaagat cctaattctt ttaccatagt atcggctgct tttgctaccc atatcactaa
195121 aaagttacac gcgtccacat agacattgta taagaaactt tctgacttaa gtaacgtttt
195181 tcgttgtgtc atagtgaatg gattaaaagt agtattatct acatagctat attccaaatt
195241 atttttgtgg gaatatataa ttatttcctc atcgatattc agaagatcgc atatataacc
195301 ctttacctgg gatatcttca aggttagtat tatatgcttt tttagaaccc ttactctatc
195361 cataggaact ctcaagtgat tctttatgaa gtaatacata gaagatcttt catctattcc
195421 atcgtatagc gtaagatata gaacgtccaa tatttcctga tctttatcaa ccaatacaac
195481 taactgagga tttactacgt acatttatag ataataacta tagagtaaac gtaaaaaata
195541 attagtatat aaaattttac gaatacaata tgtacgagat agtaccagat ttagacacta
195601 gtatgagcct cgaactagga gactttaaac tatctacaac tcgtacaaaa cctagagaag
195661 aagacaacca atattacctt tcgaagaaca gacgtatgta cgtatgcagt tctaaaggaa
195721 gcgaaagagc taaaagccta ggattcttct tatccaaaat ccctttcctc aattacaaag
195781 aaaaaaacta catgtttcag aagatggata atatcaataa tattcaacta accaagaaaa
195841 ataacgttat atcagctccg tatgttatac tgattaatct ttcagcgaat ggttttaaat
195901 tcacagaaag ttttctagag atatactttc ctgagattta taaggaaagc agtaagaagt
195961 ttaaatttaa tactcaaatt caattgatac aggaaaaatt aggatatgaa cattctagtt
196021 attataatat agaatttgaa cactattata ctaccgtatg tttgatacta caaagtaaaa
196081 gaaacatgga aaaggaagat cctgaactat ttgacatacg agaaatgtct cctatactaa
196141 aatcattgtc tgagattact tataagctgt atgttttata tataaaatct aaatttgttc
196201 aatggagtat aagttcttca gcagttgtaa ctcaattagt taatactgta ttgattaccg
196261 tatataatct tgttactaaa tttataactg agaataagac cttcaaatgc aaactagctc
196321 ataataacga actacctata gatatgttag tatcctatta cgaagaattt tctgaaatta
196381 taacaaattt gatgaaactt aatagatata ggataaataa acacatacaa gaaactttac
196441 tcagcttctg taccattttt ggcgaggtag aataagccta gacctatcat gaagtagatt
196501 accatagtta ttaaaatttt aagtatgaca aacgctagcg tgttacaacg tattcgtgtt
196561 tcacaaaaat gcattataca atgcctcact agttctatta cattgctagc tacttgtagg
196621 aatgctaaag tacttataga atttagtata gaactgtaac acgacattta ttcgttatca
196681 aaaaccacag cattggcatc ttcgggattc attattcttt taatgttttc aaaataggat
196741 ttagtcattt cagtataata gttagttagt ttcaaaattt ttggtctggc gatattataa
196801 gctttctgga tatcctcctg tgtgatagga ttatcatcta tattcctccc ggttctatga
196861 actatactga gaacggattt aatttggtct atacctatca agtccttata cagcgattta
196921 gataattcta taaaatctcg atatttctct aatatagata tttttacatc gtctgaaatc
196981 ttagctttga aatacctttc tgtaaaatag atatgcatag caagttcttt aaacatcata
197041 gtaccgtgac aagttatctt cttgatacca tccatttgct tttcagaaat ctgtgtgatc
197101 gaatttagaa tattcgtggc tataaagttg gaatctttca tgttcctatc tttaagagca
197161 ttagtaatta attctattac ttcgttagta gcgttttcat caggtactct ttcatccaga
197221 ttttcaagta gttctcctac cgatacacct cccgccgata ctattaaacg atctattgtg
197281 ttgagaggaa ttatatgcgc tattgatttt ccatcgatag tatcttcttt taaaagttgt
197341 ttaagatttt ctttaaaatt tgcattttct gggagaaaca catctgtatc cataatttca

FIG. 19B3

```
197401 tttaacgcat tagcagatag tattccttta acattaattc gatctaatat gtttacgggt
197461 gaaataaatt gtactaatgt agcgtcttct tcagacgctg attctttaaa accaccgaag
197521 aaggacctat taatacgtcg ataactatcc ctattactgc tattattgac ggataacata
197581 aaacttacta gatcatgcgc agatgataag agtttttcag cttcagattg agaacacgac
197641 gccttttgta acatatttgt tagatacctt ttgcttactc tgggactaac gtagtaagat
197701 gtataactat gactagatat ggtagtccta ttaacacgta cgttaaaccc cattgcttta
197761 aaaagcataa agatgaaagt cctataactt tcaggtgtaa tatagtatgg cgaacccttg
197821 tcatcaatct taataccggt atacgccata agaatttctt ttacagcaat atggggttct
197881 ttattttcca ttaatctcaa gaactgaaag aacaacataa atccagcatc tgaaaggcct
197941 atatgtttga catcatgggt atcgtatttt ggaaaatctc ttactgatat attgtttata
198001 ttttctaata tctcgcgtat caaagtcgga atagttttac ctttaagaat tctcgggaac
198061 acgcatatac gaataggtgt ttcttctgct ctcaatacat cgtttaacat agaacaatat
198121 gttatcccat ttttattata caaagcgaat agataacagg tagtccctag aaacatcata
198181 tctataaatt tcatattctt atactcatcg tacgacatac catcccagaa aagagatatt
198241 tctttaggaa cattacgatg tcttactaaa ctcttagata caatgttcaa taaattaatg
198301 atataaggtc tgttggacgt catatttaag atacgtattc ctaattgctg agcggttact
198361 gtaatattta agttgctatt atctggccta aatacaaact gatcaatata gtctaacgaa
198421 aataacttgt tatcttctat atactttatc tctttactaa aataaattga tacaacataa
198481 gacgctaaca tagaattatc aacacgtatt cgtactcctc ccaaatatat atcccttaac
198541 gtaaaaccag aaaaatgctg gaaatacata actagatact ttagtgtctg catcgttata
198601 agatccgtgt ctatattagg attttgtaca agtacaatgt tattagcgtt acaatgaaat
198661 tgtattttaa atatagcgtc gaatatagct ctagacatag gttctaatag cgctcttaca
198721 ttcaacagat tagctaaatc cttcttttcc ataataccat taatcaacaa tggtctgtaa
198781 gtagaataat cagctcttcc ctctatatat ggataagtaa gactatgtat gtaagaattt
198841 gcaaaactga tattaggatt tatttttggg gatagaatat taggcgacga aggatgttct
198901 acgtatccac cgaagtatct agcgtgagcc tcacaaccca tggttcttat ctgtatcaat
198961 atttttgtaa atggaggaag atcgttgaaa gatatagtac atggtatagg attcgtatac
199021 ccaccggtat ttttattcca cgtagatact atttctccgt tttctctgat atttatagga
199081 aaataaatac ctaaatcatt ttttctggaa agaatgtaat taatacccag tgtatctaac
199141 tgttgtgatc tttcaccgtc tgtaagtata ctaattaatt ctggactgta tatagtatct
199201 aacgcatgta cgtatccatt cgctagtttt ggatctattt tgtaatctag acataacgaa
199261 ggtaaaacac tagaaatcaa tttatagaga taatctgaag attctaactg atctagagtt
199321 acaatattct ttattaacat catttattat atgataataa atgactggat tgatggtaac
199381 agatataaca aatatagcca aagaatataa cttaacagcc ttttcagaag acgtatatcc
199441 gtgtaataaa aactatgaac ttactaacgg acagttatca gcactcaaga ctataaatgt
199501 tgtattaaca accaggtcag ataattatga gaaggatgta acttataatg acgacgatga
199561 tcatgatcgt tgcatagtat ctgaaatagg tagccatcat tcattcaacg atgaaaaaga
199621 taattatatt caaagtaaca atatacaaca gactccttct ttatcagctg tatttgatga
199681 taataaacgg gttcatttac tcgaacaaga aattgccgaa cttcgtaaaa agaaaactaa
199741 aagcaaaaac ttgttagatt ttacaaacac ccttttttaat aagaaccctc ttagaatcgg
199801 aattctcaat aaacgcgcta taatactaaa ctatgcatct atgaacaatt ctccgctgac
199861 gatggaagat ctcgaagctt gcgaagacga agagatagaa aatatgtata tttctataaa
199921 acaatatcac gaagttcata aaaaaaagtt aatcgttact aatatcattt ctattttgat
199981 ttctgtgata gaacaattat tggtaagaat tggatttgat gaaataaaag gattaagcaa
200041 agaagtaacg tctaccataa ttgatttaga aataggcgaa gattgtgaac aattggctac
200101 taaaatgggt gtagcaaata atccagttat caatatttcg ttatttatac taaaaatatt
200161 tattaggcgc ataaacatac tctaattatg ccatgccacc gtctattgaa ttatcattac
200221 tcatacgttt tttacgggaa gttctttttg ttctagtttt tctaccaccg ttaactatat
200281 caagatctat acccaaaaga tcttcattta cttcaccgac gtgtcccttt acctccagtt
200341 gaccatctcc cgtaattaca ccgtatacta tcttttccaga attagtgaca gcttgaactt
200401 cttgttcgtt agaagccatt gctcctcctc tacgtctaga acatggtttt ctagtacttg
200461 tagttcctgt acaacgggat gatttacgag gagcaccagc tgttacatct tttggcgttg
200521 ggctattgtt gctagcaggt ggcgtagatg gcaaggaacc ttcagaaaaa ttaggaggtg
200581 tatttgccgt aatagcatta atatgattta gcagcgactt taactgcggg ttaagtttgt
200641 gcatagcttc aacatattcg ttaaagctgc tatgttgttg agatcctctt tttcccgtca
200701 tttaaaatac agaaaatgag tattataatc attattttct ttgtacttat atgttatttt
200761 gctttgtttt tctatacatc atccggcgtg atattcggac ccgattataa acgctataaa
200821 gacggtgata taatagctga cagaattaat gaagagaaag ttaaaataaa aaagattgcg
200881 aaaaatatag acgttgttaa ccgtgaatta cttaaatact agaagtaacc aagcgatgaa
200941 gagcttttac ctgatcagga gtaagagttt gattgaataa agtatcgtcg ttcaaagtac
201001 tttttagtac cttatctctg tcatcaggag aaggtataca cttgtatctt ttatacgcag
```

FIG. 19C3

201061 cgtatattaa caaacagaat attattactg ttaccgctgt aataacaaaa gtatctataa
201121 ttcccattta ttgataatta acttttgaca atatttataa tagtttaact agtaatcttt
201181 aaaaaatagt aatttactgt atttcagttc caggtgatgt agcgtatcta gattcatcta
201241 ctacgttgcc tgtacagtat ctgttatatc cagagaataa tataatacca agaagtagta
201301 atatcgctag tataaaagat ataatactaa tggatctcaa tgcgctatct gcaggtttcc
201361 ctgatttgct cagttctatg taagcacaga tacatgctac tattagcaat attataccga
201421 atactactac gtaagatggt ctgtttctga aaaagccgag aggatccatt tagatacctg
201481 aaaaactaca ataccgaata taaaaagtgg aatagaaacc acataaaaat cgcagaatgt
201541 ataaagaata taatactaaa ctttgctcta gtagacatac tgatattcat tatacacgat
201601 aatatgaata tagtgactat tataatgggt tcatagtttg aaatcattta tcataataag
201661 attatacgtt aaatagtaaa taaaaattac cgccccactt ataatttttt aaaaaattaa
201721 atactttaat tatatcatga ttgcgcggat taacaagata taggtttttg aaagatctaa
201781 aatacatatg tatgttatct atataagata tttgaacatt ttcctttttta ctaggtatta
201841 aggaatatct agagcataca catataggtt tattatcatg tatagtaaac aactgaggtg
201901 ttatagaatt agtttctgga ataattaaaa ccaatgaatt attttcgata tacatttatt
201961 gtgttagaat ttattacttt agcatcatat atcctaagga aataaaataa cacgaataga
202021 cataagagaa ctatacatac cggtattata gaaaaaaatg aaggtaattt agcttcttta
202081 ttataagaat catctcctag tacagtatct tcagctatac ttcctccaca tttagctatc
202141 aattctgcta ctgaatttct tagtcttaaa gtatctacgt taatattaca tcctatatat
202201 ttacaattgg ttctttgaac atcttggtcg aaaagtaggt attttctatc ttttgattta
202261 tccgtacact cgtgtagcca gcatacttta ggaccaagag ctaactccaa actaaaaagc
202321 ttatcgtttt tgggtgttgt aacacaccaa caatttgggt tattcctgtg cttagaacag
202381 taagataata tagcggcgtc tgaatatcca aagttatcag gtctagtgta atctacaaaa
202441 tcagaacagt aattggcatc taaatgatca ctacaaactt tcatgtacgt atcaaaagct
202501 acttctcttt tcttctctag ccattctcta caaggtaaag acccgggagt ctgtaagcat
202561 atagatgaca taatggtatc acaatgatcc gtttcataat tattagaaaa tatttccgga
202621 cagtctttat cggattcttt attgcaacat cttttaatat caggatctgt atataagtag
202681 tctatattaa taaatctaca tctagttccg tctaaaacat aactttctgt accatagggt
202741 atcttttgta aatcaagaat agaacccggt ctaaacgata atgatttgca aggttctcct
202801 ggtactatta cgaatttttt tttagcttcg ggtgatagaa aagacgcaca ttgtttttacc
202861 gtggtatctc tagttagaca aaaaggtggg gatatttcac taccgatatc acctgagtgt
202921 atgtttttctg cttcgaaaaa tctaatatat tcatcatcat aaccaccagt atattctact
202981 cttaaatatt tagtttctgg tgcttgggga gtagctatta ccgttatgtt actgacgtgt
203041 tgacccattt attttatatc aaatcagtaa tttgaatgtg tctgaaacgc attaagattt
203101 tctaacgaag aaggcccact catctgcctg caatatctac gagaaggtat agatatttgc
203161 ctatctatac cgtatatttt tactatataa aatccaagaa ttacaagtag tactacatct
203221 atagcccttt taaatccttt agaaatctta gaagtactcg tcagataaat cgtaactgcg
203281 gacgccagca ttaagagtat agagattcct acgtgcgtgg catccgatcc attctttaag
203341 tgcaaagcta tacagtaagc tattattaat gccggtaccg gtacaaaaat cgcagaaaga
203401 ataataaata tcaatgccac caaagagttt gtattaatag cgaataccaa cataataagc
203461 gccaacaaag atttatatc attgttgtta attatattcg agtatagtcg ttctactcca
203521 tcaaatcctc cattaccgag tcctttcttt ggtaaaaacg ataattgttg ttctttctgtg
203581 aaaagttcct tttctttgat accagctccc gcgtcgaact cttcgaaaac attatagtaa
203641 tttaaataat tgttatccat ttatatagat aaaaatgtcg tatattacgg ttatagatga
203701 taaactatat tcttccttga ggaagttagt aggttattca cctttatact tgtttaacga
203761 taaaggcgat tttgttgaag taatgaagaa ttctgaattt agattcttga taccatcagg
203821 ttacttttca aatagtaacg taccgttata cggattgacg ttttcttatg gaagaaactg
203881 gatgaaagat agacaaaaaa ttattcttcc ggaattatat cccatacagc gtagagttat
203941 agaagaaatt atattacagt tttctagaaa gtgtaaagaa aaaaggcctt tgtatacaac
204001 gctgcattta gcgtgtgggt ttggaaaaac agtaaccgct agctatctaa taggtactca
204061 taaaaagaac gccgtagtta gtgtaccaaa taaacttata ttaaaacaat gggaaaactc
204121 aatatcatca ttaaaagtga gctactacgt atcttatgaa ggtgtttcta aactttgaa
204181 agtactaact tctaaaagtt ttagtatatt agttgtagtt gataaacatt tttcgaataa
204241 agagttctgt gaattagtat acgaaaacta cgatgtcttt atactcgatg aagccccatat
204301 atataatctt atgaacgaat ctattatgac aagttttcta tgttactacc ccccctagaat
204361 atgttacttt ctaacggcga ctcctagaca acaaaatgca gtttattgta actctataat
204421 aaactttata aagttttcac cgttacaaaa aatcctttac gtaataagag aattgtacaa
204481 tgaatataca aaccctagta tacgagcaca cgtatctcag ttacaaacaa ctgctaataa
204541 gtatcatctt tatacagaaa aggcattagc agaggatatt cataggaata aaactatagt
204601 agataagata atagaaacat ttaaaactaa tcaaggtaat agaatcttag ttataacaaa
204661 actacgcaat cacatgataa taatatataa tgatttaaga aaagtattat ccgataaggt

FIG. 19D3

```
204721 ttacttaggt gatgcacaga aaaaatctac taccgacatg attaaagaat taaggacgat
204781 agataatttt atattagtat ctactttaca ttacgcgggt acaggattag atatcccaaa
204841 cttagatagc ctgttcatat gtaatactgt tatgaacagt atgcagagtg aacaagtaat
204901 gggtaggata tgtagagaca ctggttcaag tcctactaga tcaatatatt tatttattaa
204961 tacatcgata aaggaaataa aatcattggt aggtgtattt actcaacgtt ttgcacaaca
205021 ggctacaaag ttaggattta gagaggtctc tcaaatggca taatgaagat ccgcacgctt
205081 tacatcggat attgctatta gtgaatactt ttcctgtatt tagataatcg cttaatttat
205141 atttactaac cccagaaaac ataaccaact ttgactggca tatagaacac gttgtacatt
205201 catcttctgg tataacggta ggcggttctt tacgtgtgga tgtagcggat gtagatcttt
205261 tcttcctctt cttagcacct gctgtagagt ctgccattta agagctataa aaataattct
205321 gtatacgctc tttcgcatat gttgcgatgt ttgataaatt tagaagcatc atcacaagta
205381 actgctatta atgaatttat atttttata tcattgcata tcgctggcat tttcgtattt
205441 ttatttacta aataatttgc ttttacacca aatggtgtaa agctataatt tatcaagtta
205501 tctcctatac accgaaattt gtttccgtat atttgcctgt acttagtaaa tgcctcatgt
205561 tctaatctta atttatctgc tattttagga actattatat taaaaatgag aataaaataa
205621 caaactatta aaaataggac gaacatgtca aagtctaaag atctagataa actaagagaa
205681 ttattaaagt taaaaaagaa tatacattta ttgggtaaaa ataataccgt aagatacaac
205741 gaattgttag attggactac caaaagttat tggtctgtag gatctataca tatagaagaa
205801 catgtatgtg tcgacgaata ctatcagagt ataaaaaata attcgtatct attacaggga
205861 aggtattatt ttttgcataa atatttcggt acaaaatatg tttatcttca tgaatctttt
205921 tacgaactgt cgggtggtac tacagaagca actattgaaa aaagcttaaa ggataaaatt
205981 aaactagtaa ctaataaata tcctgatata cgatttatac tattcgtaga atataaaaat
206041 acattcgcta tagaagatat agtatcaaaa gataactaca agctatacga tattttaaaa
206101 ttttctaagt cagtaggatt aaaagttaac ggctgtttgt cattacaaat agataaaaaa
206161 acacaattca ccaaagaata ttatgagtta attcatacaa atatcgaaaa gataaaagga
206221 ttttatataa acggtttaat atgtattaga gaagatacgt tagtaagaga ggtatctgat
206281 gcaaaatcta acgagttttg ttgtgttcaa tctataaaac tagaaaagat agatgataac
206341 ttgtggttac cgtacgcgat tacttttaat aaccaagtat taaaaatatc aggatttaag
206401 agtttagtta gagctagact ctatgtagga tcttttgtat ccgttataaa atatagaaac
206461 attttgttat tgccggatag tacggttccg gataaacaga ttccaaaaaa cgaatatatt
206521 agaaaaatct tagagtattt taataatgaa tatttttcaa taggtaacta tatggtaaaa
206581 actggaacta tagaaataaa caaaataggc aattcagtaa ctggtatatt attacccttc
206641 agtaattcag aggaattaaa acaaaaacta gaagacgttg agtttgtgaa taaactgaag
206701 tctagatcgt tattcgatct atcgtgtgat tatttcttac aggataggga aaaagtaata
206761 aagttaataa atgaaatgga ttttaaatta gacgataata ataaaatagt agaatttgat
206821 cttaattcag aatctgttat taaaggggat agaattttag aagacatata tatgaaattt
206881 caccagtttg ttattgtgtt taattcttta tcgacggcta agtctatgtt acccgataac
206941 caataatgat tatatgctcc gtagatatag gtattaaaaa tcccgcctat gccatattta
207001 attacgataa cactagtaat actattaaac taatagccat tgaaaaatct gattggacca
207061 agaactggga gcgtagtgta gcgagagatc ttactagata taatccagac gtggttatct
207121 tagagaaaca ggggttcaaa tctccaaact caaaaataat atatttatc aaaggttttt
207181 tttataatag taatacgaag gtgatcgtga gaaatcctac ttttaaaggg ggtagttaca
207241 gaaacagaaa aaaacaatct attgacgtat ttatacagaa aatttctgaa tatacagatt
207301 ataaaaatga tatattaaac aagtatacaa aattagacga tattgcagac agttttaatt
207361 taggattatc ttacatggaa tcattactaa aaaagtgtaa aataagtaaa gattgatagg
207421 agtaagatgt atgaattgtt ttcatacctt cacgaaatag aagatgaata tataaggaca
207481 atatttaact tccatattaa gaaatgtgac gaaatatcta atatatataa tataataatg
207541 acaaaaataa aggatgcaaa aactttaat gatgttatcg atgaaagatt taacaaaact
207601 atcaaaaaat taatttattg tgatataaaa acaacaaaac acatcataaa ccaatcatgt
207661 tatccgacaa agaacaaaca gataaaaaag ataagtaaga taaatcaata ctttgatata
207721 aatattatat cagatacacc tgcatctaaa cgcacaaagg aaatatttct ttctgataga
207781 tcgtctttgg tttcctatat taagactagc aacaaaaaat gtaagataga ttacggtgaa
207841 ttaaagaaaa cgataaattc tcataataga tctatatatt attctggaag aagatccgac
207901 gaatacatgt ctacagaagt tcataaagat caaaagaatc cgtggattaa atctatctcc
207961 aagaaactga ctcttgatat agaaaatcaa tctattacaa ctagaggaaa aagttctata
208021 ttgcagacga ttgaaataat ttatgttaat cgtacgtgca taaaaatatt taaagattct
208081 actattcatg ttattctatc aaaggataag tcagaaacaa attgtgtaga tacaataaat
208141 aaactatttg atacatatag catactcttc gatcttataa cagatattac aggtaatgaa
208201 aaatttttag aatataaagc ggttgcctct gatatagtat ctacagataa ctttaatgaa
208261 aaaattctaa ttataaaaaa acatcctaat atgtatggta tacataattt taaaataggt
208321 atgtttaata ttacgtacaa gttatctata gatatgatta tatttccttc attaatggaa
```

FIG. 19E3

208381 ttcaacagta aaattaaatt ctttaaaggt aaaaaactaa atatagtcgc gttaagttca
208441 ttgcaagatt gcattaaata cgttaaagag gcaaaaggaa tattgtgtat gatgaaaaaa
208501 aaatctgaag aattagaaga aatagatata attacagcat ccgtggatag actaaaaaac
208561 gtaattataa atatctaaaa tagaaaaatt aatacatatc taaaatggat cagaaactag
208621 gaaacaagtt tttggaacct gatcctaagc agaatgtttt ttataggccg ctacatttcc
208681 aatatgtctc ctatgaaaat ttcatttctt acagacttaa agaaattttg tctgtgaata
208741 gaacgttgtt atcttttaag aatgatacag aaaagatagt tctaagaatt aataatatta
208801 aaattatacc tcctgattac tctcctatta ttgcaagcat taaaggaaaa agttacgacg
208861 ccttagtgac ttttacggta gatattagaa aagaggtaat gactaaagat ggactccatg
208921 taagcacgat tagtagctac gaaggaaatg attcccagtt gataaagata cctcttctta
208981 taggttacgg aaataaaaac cctcttgata attctaaatt tgtatctcct aatattatag
209041 gaggagtctt tattaataag caatctatcg agaaagtagg tattaatata gtagagaaaa
209101 caactacttg gccgaaattt aaaattgtta aacccaatgc ttatactttt tcctttttcat
209161 ctatttcacc cgttaatata ttacctacaa agtatagaca ttataaaatt acaatggatt
209221 tatcacagtt agaaaactgt tctatatcct cggcgaagac tttcattacc gttaacgtta
209281 tcgttcttat taaattcttg attaatcagg acttgaatta tatcaagaat aacttgactt
209341 atggcatgcc cttggaaacg atttatctta ttaacgctat tatagaaagt tctaaaacaa
209401 tattagaagc agaagatttc aacatcaatg attatataga gagtttaata gaatcagaat
209461 ttcagaaaca acgctctata acgtctatag acgattttag atacgatctt atgtataatt
209521 ttttaccaca tatggtcaat agttctgatc agctaaaagg attctatcta ttaggattat
209581 taagaaaatt catatattgt atctatcata ctagtaggta tccagacaga gattctatgg
209641 tatgtcacag agtattaaca tacgggaggt atttgaaat actggccaat gatgaattag
209701 aaaattatat aactaatatt aaaaatgata taactaacag tcacaaaaac aaaggcgtct
209761 gcaacgttag tatccatgta cttactactc ctggattcaa ccatgcgttc tcgggacttc
209821 taagtggaaa gtttaaaaag acggatggga gttatagaac tcatcctcat tattcttgga
209881 tgcagaatat atccattcca aggagtgtag gttattatcc ggaccaggta aaaatatcaa
209941 aaatgtttttc tgtaagaaaa taccatccga gccaatatgc tttcttctgt ccttccgacg
210001 tacctgaaag aggtccccaa gtaggtctta tttcacaact ctctgttcta acatccgttt
210061 ctaatatcag aacaacagag tatatagatc tgaagaatgc tattatgaaa tatatatata
210121 cttacgataa aaacgatatt agttattttc aaacaggaca tattattacc atagagaatg
210181 acttagtcgc ggctattaat ccggaattag tagataaatt tgtagatgat tttaaattca
210241 gaaaacgagt aaactatttt gataacctag aaataggtat ttcaaacgtt aaagatcaca
210301 tgaatgaaat acgtattaac ataggaagcg gtagattgat acgacctttc ctcgtggttt
210361 ataaaggaga attagtgatg gataccatag gtgaagaatt agaaaagcgt atagatacta
210421 ttacgttctc agacatccaa aaagagtatc cacacgttat agaaatgttg gatctggaac
210481 agtttgtttt tagcaacgta tgtgaatccg ttagtaagtt cagagaatta agcgatgaag
210541 ataaaaaact atacgattat tgtgattttc caaacgagtt tagagacgga tacgtagcat
210601 ctacattagt aggtattaat cataattctg gacctagagc catattgggc tgcgcgcaag
210661 ccaaacaagc catatcttgt ttgagttcag atcttagaaa taaaatagac aacggaatac
210721 acctgctata tccggaacgc cctattgtat taagtaaggc cactgaaaca tccaaaatag
210781 ctattaattg cttcggacag cacgtcttag ttgctctcat gtcctataaa ggaatgaatc
210841 aagaagatgg tatagtagtc aagagagaat ttatagaacg cggtggactg gatattgtaa
210901 cggctaaaaa acatcaagta gaaattccta tagaaaattt taaaaataga gaacgtataa
210961 actctaccgc ttattcaaaa ctcgatatca acgggttagt gagattgaat gcattcttag
211021 aacccggaga tgccatcgct aaaaacattt catctagaac gctagacgat gatttcgtgg
211081 cagataatca aattagtttt gacatatctg aaaagtacac cgatatgtat atgtctagag
211141 tagaacgagt acaagtagat ttaacagaca aagtaaaagt aagagttcta accatgaaag
211201 aaaggcgtcc tattatggga gataaattca ctagtagaac tagccaaaaa ggtaccattg
211261 cctatatagc ctcagaatct gaactacctt atgataagaa tggagtaaca ccggatataa
211321 tcataaactc tacatcaata tattctagaa aaactatctc gatgttgata gagatgattc
211381 tgacatcagc ttattctgta aaaccgtata ataataacgg taaaaaccgt cctatatgtt
211441 ttcctagtag caacgaaaca gatatcgaat actacattga atttgctaga aaatgttacc
211501 agtctgctat acctgatcta gataaagatg aattggaaaa cgaagtatat tgcgaaagta
211561 ttttatacga tccagaaact gataaaccat ataaaacaaa agtgtttatg ggacctctct
211621 actatcttag gcttagacat cttactcaag acaaagctac tgttagatgc cgtggtaaga
211681 aaactaaact tattcgtcaa gctaatgaag gtagaaagag aggaggtggt atcaaatttg
211741 gtgagatgga aagagattgt cttatcgctc atggggctgc aaatacgatt acagaaatcc
211801 ttaaagattc tgaagaggat taccaagatg tttatgtctg tgaaaactgt ggcgatatag
211861 ctactaaaaa gaacaataat gtttattgta ttagatgtac caaattaaat ttgtatacag
211921 ttctgacaaa aattgatact actcatgtat ctaaagtgtt ccttacccaa atgaatgcta
211981 gaggaataaa aatcaattta acttttaacg aacaaaatcc tttattctat aaaccgatga

FIG. 19F3

212041 agcaaatcga tctctcacca acaatattaa aaccatgatc tgtcataatc acgatcggat
212101 tgattatcta gtttcttcgg taattctata gcgtgtttac gcaagtgatc ataatcttcc
212161 tcaagtcgtt ccatttttga tttaattttg cgataactat ctccgaagct atcagcttct
212221 aatttacgca ttgctctatc gacatcatta agtctatctt catcagactt gtctttttct
212281 ctgggatatt ctctatcttt atccggatga ggcctgtata catctttttc aacgcccaag
212341 ttgcgatgcc ctctcgtaat aatacctatc ttcgtctttt agaagatacc cattcctacg
212401 atttctcaaa gacttgggtg tataatcatc gttatgtatg gcatccatca tttcatcttc
212461 gaagtctttg gcactttcaa gattgttggc tctcttagga acaatgtgtt catcatctga
212521 attaccacga tcatcatatt ttttgtgttt ataattatag tcatcgtaga tatcgtattt
212581 gtttctacga tgatggcgtt tattatatac atcttccata ctattatgcc tccttagtat
212641 aggagcttca tccttgatag atcatcttcg ttgttattat tataatcgtc gtagtcttct
212701 tctcgaggaa actcgtcctc attacgattt agggtaccgt ttgtactagg acagttcttt
212761 ctacgatcac attcaaaatt gtctatataa tattcttgat aatctttagg cctacgttct
212821 ctatcgttac tataatcata ggaaggatat ttatcatcat ctagatacca tttccatctt
212881 ctacaatcat cagggaaaaa tagcatatgt ctattttgat agaaatcgtt atctttgtcc
212941 ttgaagatac gaatagcgct acaatcgtga atacaattag gactaaaaga catctttgta
213001 gtcggaaatt cgtcggtcaa tctaatatat tcataactat caccaatatg gcatttagta
213061 tatagctgta caaaatcata atgattcttc ttaatggtaa cttcatcggt aaaacaataa
213121 catagaccat ccatgacctg ttcggaaatg gaatagtcag tctcaaaagg aataccacag
213181 agagatatct ttagcccttt agtctttgct tttttggatg ccataatgaa gttaagaaaa
213241 tcttggtatg cgcacatttc ctttatatgg atagtagtat ttctttcgta ttcttcagga
213301 ccagtacgcg gctttctgcc taccgattcc atagccgtga taatatcgtc tggtgacata
213361 agatgaatat agtaaacggg taaccctata aacatgcatt tgcatttaaa tctataatgg
213421 acgctagaca ctaatcttag ataatctgta acgatactag aaactttttt agatactgta
213481 cgtccggaat ctgaatagct aaatttggta tcattatttc ccatgtacag tagatacatt
213541 acgaaataaa gcacatatct acctttggta gaaatatcag gcatacgatc gttagacata
213601 tcgattttat tatatagttt tttgatgcca ttattattat attttataaa ttctcctagg
213661 aaataatttt ctaagttttt aggatacaac agttgtgctt gtactccatg gatacggtca
213721 ttatcacaac tataatgaat aaaacaccta aagatgttac gaacgacttt tctatccctt
213781 ctagttagga aacttctttc gttcaaatca tgatcccaag ttcttacaat tagagtttcg
213841 aacttcctta tgcacttttc gataccacat ttgtcccaac ccatttatat attgaaataa
213901 ttatggaata taatgtaaat tattccatgt atagatggcc atatcctgtc tggtaatcta
213961 tcttcttagc gagatttacc atagagtgtc tcagagtatc agcgtggcgt tctagacggt
214021 ctatagcttc cgctaagatg ctgcaggatt tagctacttc tacgtgatct tgttctattc
214081 tacccaacct tctttctagt cttctgagtg ctttttgttt aagggagccc aaatcacccc
214141 gctttttatt ttcatcgtat atatcaacct tcccatttc aggaatattt ttatctattc
214201 tatcatcatc atcatcatcg tcatcatcat cgtcatcaat cggatcttca tctataagta
214261 agccatcaga agctttaccg tcctcgggag gaacaagatc atctgaatct aatttaacac
214321 caccagcgga tttaacttcg cctattgtat agaatggatg ttcgtaagta gttatcagat
214381 cgtctggcct attaccttct tcttcaggat ttccgataga aatagcaaat gtatcaaatt
214441 tcacgcttac tggggatggg aacttaactt ggggagttct cgtattaacc tcatgatata
214501 catatttttt gctgtctggc aagaatctta gatagaatct taccttatca ttcgtttccg
214561 tggctattag atcgtcgtgc ctataacaca atcctttcaa tacgtattcc ggtacagaat
214621 tattaaaata ccaagtacta gcggtagtag ccaacataac aactttccta ttaccgggat
214681 ttataacatt atttttgaga tattctatat attttttatg cataatcata tacggtctcg
214741 agaacatgtt actaccccat tctagaattt ctccaaaagc cgaatcatct ggaaacagat
214801 aacacggaat acctataaac atagatttac atctgaatct catatggata ctagcgattc
214861 tattaaagta gcgatgtctt atacggcgta tagtttcgta aattttatcc gtttcgtctt
214921 gcgttaagct gatacgttct ttggcggtgg ttataaaaaa cattactata aaagcaatat
214981 acttgcctac tgtgtctacc gagttaaaac tatgaatttg ttgcaacatt tctgcgaact
215041 ctccgtgatt gtatgacatt agactagtat aggctcttcc tttaatcaac gtttcataat
215101 tgagtatttt gccataaaat tcgtaaactg atatatgatc tttgaaactc tccatatgat
215161 aacgtattat atttcttata cagtttgcat agtaatagtt gatatacgta tcttgcctta
215221 attgcgtatt ccatgattct tttactatac tcacgaataa tgtaactgga tcgttagtgg
215281 atacgggttt aggtattact acatcatctt cttcttcacc ggctccagga acaacatcca
215341 tttatagatg tgattttaaa gtgctgcact ctgcagaccc ttctccgtat tcagcacaag
215401 gattccatat ggtacctatt tctcctcgag tataattata gtacacacaa tctttccaggt
215461 tagtaaaaag tacaggattt ctacttgatg tagctaaata tccaaatttt gatgcagatg
215521 cgtattggtt attattataa ttcacgcatc tccatttagc tttaggatcg gtttccgagt
215581 cattaggatc aaataccctt ttgtcgatgt ataaacctcc aggagatcta gaatattcta
215641 acccgccata tttttcatta aattctatta tgttatgata gttatcgtat atggtatagg

FIG. 19G3

215701 cttgaaaaag aaaaagacaa attaccgcgg ttgctaatat aattatgaat acgaagagag
215761 catccattga tttataccaa attaattaat agctttatat atttcactta tagttttgtt
215821 aacagctttg tgaaaagttt tcgtgttaat ggatgaaata ttgaacttat gatacgtacc
215881 taattggcat tcacatccga agaagttaat aatgcacata gtcgttatat cgttaacaaa
215941 tacgatgtta gacttaggat cgtacgctga tgatgttggt gtatcttttt ccatatctag
216001 ttttgttata ttaaattccg ctatttgatc cgatataact tcttttagat aagataacat
216061 gcttttaaag tatacagaag aattaaacca cgtatatttt tccatgaata tacttatatt
216121 accttcgggt gcaataatgc taaaaggaaa atatgtttca taattttgtg agtgaattat
216181 tttaacgttt ttatattctc tattaaataa ttcggtatct aaaaatgata atctgtttac
216241 taactcgtca ttaattttag ttccgctact aaaagcggct aattctatag ttttagtatt
216301 tgttgctcta tattcggaga atgaatgtaa taacgtttct tttaattctt ttatgggatc
216361 taattttatt acctcttctg gtttgataat atagtagtct atatctgcca aagaaatata
216421 actgtcgttt tctttctgtg ttttcttcaa gtgaatacaa aagttacatt gcatagcaat
216481 aatatcgtat acataatcat aaaatatttt atgcgttggt aacgattcta tggatgttag
216541 ccattcttcg ttaatagcgg tagtagtatt tatcataaca actcctacgt tgagtctagg
216601 aattactaga tgcttcttac acatatgctt tataaaggtc gcaatactgg gattagcgct
216661 aacatcaata cgatactctt gacgatgcat tgttcatgct attaatattt ctattgttct
216721 ttttatattt tttatctatt tctattatcc tagaatttat tattttaaga acttcttgca
216781 ttaatgagat agtagcagag aattcaggat ctctaacatt tgctaaagtt gacagcatgt
216841 ggtttatact gtcttcattt atatcatcta tataatctat atcatccatt cctactatta
216901 aactagtata taaaaaggga aaaaaaaata aaaagtgttt aatcacaact tctgatagat
216961 tgccgagtat ttatatactg tttttaatat tcgtgatata gtagatatat atataagttt
217021 agtgtatata gttaatagat ttacaatctg ataatacatt taataaagat ggaaatcttt
217081 gaactaatat ccgaaaacga aaagtatttt aatggaatac ccataatatt accaaagaag
217141 aaaaaaacat acgtttacaa aaatattaca tttatatttt atataccttc tgataacaag
217201 atagaacaat atatacaacg aagtgaatta cactattcag attttatagt ttatggaaag
217261 gttataatag acgatgttga aatgcttctt ctttatgtaa actttgaata ttatggtata
217321 tctatagatg gtaaaacaaa atacttagga aaaagtataa aagacctaaa gataagagga
217381 actaagcggt ggaaagactt tactcattaa atggatatac taacgatcat gaaaagaatt
217441 aaaagcggta aagatattac tccttccatg gttactaggt tcgtagaatt ggtaggtaat
217501 aaagaattat tttatgatcc actaccgata aaactgagtt ctagcactct aacaggaaga
217561 aatattaatt attcagaaga acacgttaaa agtatgatcg tcattatcta tggttattta
217621 cccagtataa taaagaaaaa gatttttgtt aacaagataa gtaaattatt atctatacct
217681 cccgacgatg cattaaaaag aatatttggg gacacatcag aaataggtgt taatacattt
217741 attaagaaat tccttgctga gttaacaagc taattcttgt aaagattctt gcttagaata
217801 gcttttaagt agtttcatat tactagacgc ttctttttcg ggtgaatata tacaatcttt
217861 tttatcacga tcatcattta tagaatttag attactaaga tctttaaaat aatctgtatc
217921 cttgttatca tcgcttaata tggtatgaag ctgatctttc atatgagaga attggcttaa
217981 caatatagcg gtatcaggtt tttgttcgat aacggattta tctgctgtat catagcatat
218041 acgtatatcc ttatttgcaa atacagtatt ttctataata tagacctttt tacctctaga
218101 tgcagcacgc atgacagata gtgcttttat tatctgctta gtagcgacca gtgacataga
218161 cctagtaata ttttcgatat cggcatcaga tacattgcaa caacatagat gtgtaatgct
218221 tgatctacaa ttagacggta cgtgtctata tgtttgacat aacataacaa tagacatcct
218281 tatgtgtcta cccgtgttta ccaaccaaga taatatctta gattttaact gcatatcacc
218341 taaatcatct aatattacca aaaatttgtg attaatagaa ccgcgttttc caagatttac
218401 taaatcttgt ttcatttttg atagtgaata ttctaactcc tcggcagtag ttattttata
218461 tatatggtcg ggccatacat aataattata cgatggattg agtataggag taaacaagaa
218521 aatatgttta tatttcgtta taaatgtttt aaataaagat aggagaaatg ttgttttacc
218581 tgatccgcta cctcctaata taaccattct aaaataatca ttcaacaagc tattcctatt
218641 aaacttaact tcccttacga tatccattta agttgtttgt gatatttata tatctccgaa
218701 attgattata actatagtgc ttcagtatga aagattattt gtattaaaat atatatatgg
218761 aataaaatgt atctatatat ctatttcgat atctatgtcg tgtaataggt tatttattaa
218821 cgacatatgt cttagtgttt acgtatctta aatatgaata gacaaagcag tgagaaacta
218881 aaaaaaacat gcgcttggtt tatacattta atagcttcaa tgtgcggaac tggattattg
218941 ggactatttg ttacaaacgt tacgttatac agacagataa aaatatgtgg gaatagagaa
219001 ggcatgtcag gatgggtaca gattaataac aactgctata ctatggtaga aaatataaca
219061 tttgatgaac ttatagggca ttgtacaaaa cacgattcaa taattcccaa tgctttagac
219121 caaagcgaag tattaatcgt ttcttctgta ttgggtgtta aagaccattg gatgccgttt
219181 accaagaaaa gtagaaactg gtttcacgga aagttacctg tgaacattaa aggagatggt
219241 gataaacgtg aagagttagg aaaacctaga aaacctgata aatcagaaaa atgtactata
219301 tactatgata acggtatcat agaagaaaac tgtaacaaaa agcatacggg aatttgcttt

FIG. 19H3

219361 agtccatttt tctaaaaagt tataattggt aatttttttaa aataaatata tttacaataa
219421 atatacaaga tgcatatcag tagcttttac atattatcta ttatttgttg tactagtagc
219481 gctaatatca tagcagatat cggatcttct gtagtagtag attgcaaaat acccaacaat
219541 tatagcgtag ataccgttat attaaagcaa acttccagcg gtaagacaaa taaaataacc
219601 gtacctaacg aatacataac tggaaataca tgcaatacgg gatatagaac atacggattt
219661 actattaata atgtgactaa aaatgatgaa ggtagatata gatgtagttt ttatctaagt
219721 agcgtacaga tatacgaaac aaaactgact atgtatgtta ttcctgctat cgacgcgtat
219781 actctagatg ctagggataa taaaatgatg tacgcgtgta atagatcaag atctcgatta
219841 tatgatgacg atattaacat ggatattata ataggaggag tatatatatc tggtgaagaa
219901 aatgtacata cttttgatac ggatcacagt ttacatatat atacatttgg agataagaat
219961 tatcctgata tatcaaaaca aatgacatgt ttactaacgt ttaaaggagt aaaaaaaact
220021 aaacgtataa cgatttacga ctactcgtgg gaatctctaa taaatgataa tgaaatatac
220081 gtcgtctaaa ttcatatttt ctcttcttaa aatacactat aacatgaaat tcataattat
220141 actattatct attttacaat acgtctattc taaagacgat tattacgatg tggtatctca
220201 cgtaggagat tccgtaatcc taaattgtaa tgattatcca aatactagta atgtagattc
220261 ggttatttgg tttaaatatt ctgatcctgt taataaatac ttaagtatat ctactattaa
220321 cggaacacaa tactataaaa acgatcacaa gatatttaca agaacatcag tagacctaaa
220381 attaagttct ttaactatta ctagcgcatc tatagaaaat catggatgtt acggttgtaa
220441 atttaaatca ggaatttgta atagggaacg taagacgtgt ctaggtatac tagattcagt
220501 gtacctttcg tggatatctt tcatgtatac tactaggtta agatgttata tagtatctgc
220561 aaaaaaagat ttgagcatta actggatggt aaacggtgtt attactgaag ggatgtcatt
220621 taatgaaatt agttatgacg atagttattt gtccgggtgt tttatgatag agttaaagat
220681 aattaatagc tttagtgata aggtaatttc tcctatatgt agggttaatt tcggctctaa
220741 aggatacaaa gaatatagaa taaatctaac aaatacactt cctgatacct tatacgataa
220801 atattctaat cctataagat attataatcc atcgaattca cgtattacaa aaatgaaata
220861 ataaaactag tttgtaatgt gatggcaacg gttgctagaa tgtataaaac tataaatacc
220921 accggtatat catgcgtctt gaaaagtttg ataccagata gctataatga agaatacaac
220981 atagatgacc tagatctatt aaagataaaa gagtttatag agatatccat gcaaagatgc
221041 ttttctataa aatccgtcac agattccaca gtattataca tagagaacag gactaacaga
221101 tattctatat ctactagtca cgataagaat gaaccgtatg aagaaaatgg tattataatg
221161 aacaatatag agtgttattt tgttgcgtgt ctagaaggat cgtgtacagt aaatgtaaat
221221 cttggagaca gacaaatatc agacaatata tctgaatcat caggattcct aatggatgta
221281 aacaccgatc acgttataga tacaaaatat gtaggattat ttattacaaa aatcaaagta
221341 gatgcgcatg tattttacgg gcaaaatgtg ataatgtttc cagaaaaaaa cttgtttctt
221401 caaactaatg gtcctaattt cattttatat gatataacag ttcaagatcg taatgtactt
221461 ttgcttataa cgagcaagta tatttacaat ttgtgcgacg ataaatacta cgatattttc
221521 gaattaaaat atctagttga taactgtaaa ctacctatgc ctcttattcc actatcgaag
221581 tacgatttta catttactga tttgagtgtt atcaaatcag agaatgttaa aacggtactc
221641 tctaaagttc atacgagtat gaaatcgtac tacaacaatg atacgtctct tcctgtcgcc
221701 gttaaggtga tttacggaac agtaacaata taaaaagtgt ggagggagct ccggggggaa
221761 tagcgctggc tcgctaactg ccatattagc ttctgtaatc atgcttgctt gccttagccg
221821 ccattgtact tgatatattt cgctgatatc atttctcgga atcggcatca agagcaggct
221881 cataaaccat aaaaggaaat gtttgttgaa ggcaagcatc agaccacttg cacactaggt
221941 ggggcagcag gggtccggac tgaatcgtcg tagttcggta caacagtatt attgtataat
222001 attatatttt gtaatatata aaaaaataga aaataaataa tatattattt ttataatgga
222061 tattataact aatacaacta tgtttgatat acaatttaac gatataccga atataccta
222121 tgtagatata gaaaagccct tattggtata ttcgtgtgat tcttataggt tatataacgc
222181 taaatatgac aacaatcccg tcagtttgaa gactttaca tgcccatcta aaaatagtat
222241 aagacagttc ataaaagaac tagatctgtt acgttctcta caatcttctg aacacgttat
222301 taaactttac gggtacatat tggatatatc cgttccttta tgtagcctgg tggttgaaaa
222361 taactacctt acgttaagaa actttttaga tatggaaaaa gatatagatt acgccaagaa
222421 aacaagaatt atcatagatg ccgcaaaagg tctaaatgct atgcatacta gctactcgac
222481 tcccatacta cataaaaatt taaccagtga atctttttac atgactaata atggtgtttt
222541 aaaaataggt agcggggcat attataatat atacaaaaga gtaaatttta tggcatattt
222601 tgattatgac atgttaaaag atatcttttc aaattatact ataaaatccg aaatttatag
222661 attcggtatt gttatatggg aaattattac ccgtaaaata ccttttgaaa atatggacta
222721 ccaaggaata tacaatatgc taataaagga aaataaaggc gaatatatgc ctctagactg
222781 tcctctggaa ttacagtgta ttgttatcgc gtgtagaaat acaaattcta tatttagacc
222841 ttctataagt gcaataattg attttctgga aactttttat tctaatataa ttaaaaacag
222901 aaacttaaaa tagactaagt agagtatata cacatattac acggtaacat gtttgctatt
222961 tcagtgttaa aggaattata tgattccgga gagcctttat tattttcacc tagagggcta

FIG. 19I3

```
223021 cataaaatat tatgtaatat caggcacggg tgcaacggaa atactaaaaa tcaattagat
223081 aatttattag aagaaaccat atatgattac ggagaagacc aggcgcttaa acatataata
223141 actaacattt ctgttctact aataaaaaga tgttataata taaacgagaa atttattaaa
223201 gatagtaata cgatatataa taccgatgta ttagaatttt ataatgtaag acaaatacct
223261 agaataatga ataaatggat tagatcaaga tctaataata aaataacaga tataggatgt
223321 catatctacg ataatactaa gtctataata gccgaagcaa tgtttttttac tatgaaacac
223381 gaatctatat tcggttcaac aagaaaagat actataacct tctataagta cgatggaact
223441 tcgttacccg tagaagctat tcacgcggat ccatactact atccttatag atatttttgat
223501 gatataaagt gtagcgtatt gcaattatgg aaactaggat acgcttttaa catgtttatt
223561 atattaccag atgatgaaaa aggtttagat aacttagtag ataatattac tggagatgta
223621 ttcagtaaaa tcatgaccga acaaatggat tataagagat tagaattacg gatgccagta
223681 tttagtatta gtcaagagac taacttttgt atgcctatat ttaatctggg atgccatagc
223741 atgtttatag acggagattt tagtggaata tctgaagtgt cagatttcca actttcaggc
223801 ataattcaga aaaatatcat agaagtacag tatgacaagg ttaaaacaac taaacccttta
223861 aatgtaagat gttcaagctt ttatgttaat aaaccttttta tatttatagt tactgatgta
223921 ggcaattacg atactatccc tatactgtta ggtatatacc agggaagtag taaatagttt
223981 taattatcgt ctgattcgta ttcgctttcg tctatatggg taattaaggg ttctctatct
224041 ggatgaacgt taatcaatat aaacttttct gaattactaa tagtttttat tttttattg
224101 atatatttgt gtttgtatga aatataacat actattataa ttattataac aacacatata
224161 ctacttaaaa ctagcgtata tagctgataa ttattcaaga aatgtactaa cacaatgttt
224221 gttgtattgt tgtaaagttc cgtagagtta tagttatcgc gtcttgttat atagctatcg
224281 tctacgaata tactttctat aacagaaccc atacatttct tctttattcc tatggataca
224341 tggtatacat cacccgtact ccatctttc agtgtaattt tgtctaacgt taggttagat
224401 aagtagttag gttcttttat gtgataagag tcgggaaaaa ccattatacc taaggtttta
224461 taaatctgac ttttaggttc cttcttttct acatacatcc atttaacgca ttttatagaa
224521 gtagacgggc ataatattat attagcctct gactgttcta tagatacgct tcttttacac
224581 ggatatacat gaacaacgtt agataaaatt actaatatcc taataacacg attcatgttt
224641 aaatatatag tgatttatag tatattataa tattattata taagaaaatg taatataaat
224701 aatatacatg atacataaaa ttgaaattta attaagacta gcttacaaag atgaatttca
224761 caggtgattg tcttttatac gcaggatatg aaaaatttc actatctttg gccgttgtta
224821 ctatactcat atttcttca agcttgatat taaatatatc ggcattagtg attggatttt
224881 atactacagc gcctgggcct atgaagatgt atcttattaa cttgatagtc tctgatatac
224941 tattcacagt aactttgcct cttaaaatag attattacta ctatttcttc aattggagat
225001 ggggagaaat ggcgtgtaga ataatgtcat tcttgtctta catcaataca tacgtaagta
225061 tcaatttcat gacgtggatc agcgtaaaca ggtactacgc ggtaactagg ccccataagt
225121 acaattcgcg tgacaatatc atgagaacaa agattgcatg cgcgtgcact tgggtgatta
225181 tattagtccc tatgtcatcc atactttcg ttagtacaac gagttcggat cacgaaacta
225241 agattagatg tatggaatac aataaagtag gagattctat gtatttacct ccgtgggtaa
225301 ctatcgttat gtgctttata ggatttgtaa taccgtttgc tatgatggct ataagctatt
225361 cagctgtatg ttataccgtg ttatctggta tatctaaatc tactagatct tatagaacct
225421 gtaaactggt agcttgtata ctaacagaat ttgtcatttg tttttttacct tatcacgcat
225481 ctgttatatc ttatatgatt catataataa cttcaaaaac agtattatgt gaaaatgtat
225541 cttactacca aatgttacta catgccacac agtgtttgat gaagctgaat tgttgtatgg
225601 atcctataat atacttattt gtatctagtt ataaatctaa agctaaaagt aattctataa
225661 aattgatgtt taagtagatt tttgaaatga tatctttacc atcatcctgt caaaatatta
225721 tcaacactgt cataaacgga aagtgcttct ttggtagatg ttctaataaa cgattaaaaa
225781 tgactgttcc tatgacgtct tcggaactag cctacataca agaatggatg ttagaaaaac
225841 atgatttatt tatagaattt ccaatagatt tgattaccgt ggaacatata atgatgcatt
225901 tggctgttga cgttactatt attaaaagaa aaaaaaagtg atattactgc gtatagaact
225961 cgattgaaag atgtacccga agccgagtaa tctattctta atgtttattt caatataaat
226021 tactattctg gcgatacatc aggattttat gtaccctgtt tttatatctc tatttatagc
226081 ataacactat aaatgaggat cccaagtact tacttaatga aatgtagatg gtaaagtggt
226141 tgtttttagt agatccctcg aataaaagaa gttatagaag tgacaaactt aacggattcg
226201 gccccatttg tatatctgtc actaactgga aactgataca catattattt ctagacaaga
226261 tcctttatcg tcgatgctgt taggttctgt taaaacgtaa cagtttacaa gcaatgtgtt
226321 aaagaaaata agccgttggg atataacaat agctctaaat tcttgggtac agacaatcat
226381 cttgttatgt aatgtagtac ttataaagac gtaggaaact atggtataac atctttaaag
226441 gtatactctg gttgtagtta agtggtaaaa gaaaaatatc aagtaataga gctaatatta
226501 tagggaataa acaataacta gagaaattta catatagtta tttttgattc ttataataat
226561 ctaaatactt gattataact tccagacata gttccattta ttgtatattc tagtttatgc
226621 tttctatcat cctgtatcaa caccttattt gtacattcaa aactattatt ggttttagat
```

FIG. 19J3

226681 ataatcaaat atcttatata tttgtttaac ctatattttt attgtagttt tcatctagat
226741 attttaagag tcatggtgtt tatttttaat acatattata atataatgaa atatataact
226801 taacacatga aagaccgcaa taaaaaacta aaaagtttac ttctttagaa aatatgatat
226861 aacctattcc aattaatgaa aaggagtatc aaaagtcctg atttcataat atggataaac
226921 ggacaaagaa atatagttaa tacgcttaga ttcgaggaac caaatgtatg tataaaaaat
226981 actttacagc ttgtttcttc aagattttat aaaaatatca gataccgcac gatggggaga
227041 tgttttaccc aaatatttac atattcaaat cttccatgaa tgaaataact cttacagaaa
227101 gaattattat ataaccgtag ttctgttcta cggaattaac aactcgtgaa tataaagata
227161 caacattcag tataagaaaa taagaagcac agttatatca ttgcgtagca acaggcaagt
227221 agtaatgtaa tacagatttt ggttgcttac ttgcagttcc tttctaaagg ttattacagt
227281 tacaccggaa tactaaaatt agaatagacg attcatatta cacacctgtt tgtagattta
227341 caatttaaac ataatacttt agtttttgt attttctaat cactaaactt ctaatttctt
227401 ttggattcat agtttttata ggcattatct taatcataaa tatattatcg atattatacg
227461 aattaaatcc gtgtacgtaa tctacttctc taatataaca ttcaaaaatg taactttttc
227521 cagacgaata agtacctact tggaatcgtt gatctgggct acaaaaccta tgctttgtaa
227581 ttctatgaaa ttctgaaaat acacgtttta aatcctcctt ttcgtttata aaaaacgttt
227641 ttatagtgtc gagtcctctg tgtttccaga agaactcctc tttcgaaata ttttctgata
227701 gaaatctacc cgtgatatca tctttggtag acgccatgat attaccgcta tttactttaa
227761 acgtatatat ttaatttcat tttaaacata tattcataga tatgtaatgt aatggtatac
227821 agacaataat ataaatattt caaaacctct tttactaata atatatcatc atattttatt
227881 agaatctaaa gttattcgtt ggtctaagta ttctagaaat ataattaata taaaaaccat
227941 aggtaggtat tgtgggatac tctagttgta attgtaacaa taataggcgt aaagaatcac
228001 attcgttcct aaagataaca ccctatataa aacctgtaat gaattattat atgaacataa
228061 gatgattatc ttgaggatgt gagggagttg tagtaagtag tttctttcta gaaagagata
228121 tacatccttt taaaaaaatg tatatataca ccagtaatta tttcaaaaga tatattaatc
228181 actatacact aattcaaata ttacacatac tacggtaatc aatagtcata ggagacgtgt
228241 atgtatacac taaataaatc gaaaaataca ataaaagaat ataaaatgtc accatcggtt
228301 tacattgata tgttatatct aaaaatacat ttaaactata ataatacaac aacacaaagt
228361 actcttaaaa atatacaaga tgaaagaacc attaatagaa gtaaagagag aatacaactt
228421 aataaaaaca ttaacgggta agaagtttgt tgtttctact tccatcgtag tagtattgtt
228481 aataattaat atgatatttt atggtattag aatacacgaa ctagctgtta taagaagaaa
228541 ctctgaaact catatttctt cttttaacta taaaggacaa gcacaagcac aaaataaacg
228601 cgtgaaaaat actagatat ttgaaaaatg taaaagtaaa tttaataact tttgtatcta
228661 tggtgaatgt atgaatatta ttaatttaga taaaaaattt tgtatttgta ataaaggtta
228721 caccggtaat aggtgcgaca tagtaagtat acgttaacaa tgccccaaaa caaggtttta
228781 tcatttcctc ttcccgaagg tactttacta gaagatataa caaaaaataa atggatacta
228841 ggaaagcaat taggttctgg aggatttgga ttagtatatc aagtttcttg taagagtaaa
228901 gaaatagatt gtgtagctaa aatagaatta aaagagagtg gtgggttgtt ttgtgaaatt
228961 aatttctata atagagttat gaagaataaa acatctcttg atacatggat gaaggaacaa
229021 aaaatagatt atataggtat accttctttc catggatttg gtattactat ctacaagaac
229081 gtagaatata gatttgcgat aatacaaaga ctgggtagag atctggaaaa tatactctca
229141 gaaaaagaaa aatttaatat tactgttatt aaaaaattag ctattaagat actggatata
229201 ttaaaattta tacatagtaa agagttttct cacggtgata ttaaagctgg aaacatacta
229261 ttcggtaagg atgatgacaa agtatactta gtagactacg gattagcgac gaaatattca
229321 tcgaatggta aacacaaaga atatactatt aatcccaaaa acagacataa cggtactatg
229381 gctttcacaa gtatagacgc tcataaagga gttacggtat ctaggagagg cgatttagaa
229441 tctcttggat tttgtatgct aaaatggtac tctgggaaat taccgtggga gaaatacgaa
229501 aaagaacctg aaaatgttca aggcatgaaa gaagcatttg tcaataatat atctaaaaaa
229561 actataccct tcaaaaacgc gggtataatt tacaattata taaaggtagt cactaagtta
229621 gaatacgaag aagcccctaa ctacgaatca ctgaaacaaa tgtttttata agataaatat
229681 attaatgaaa aaacaagttc atagtaacag aggtttacac catggaacga gtaaaaaaat
229741 gttttagtaa tataatattc ttttctaaag atgtagatac tagtatgttt tctccaaaca
229801 tagtttatag cggattatta gatagttaca attttagctt tgtagatgca ttattggcgg
229861 ttaatctgtc tataggtata gtacgtcgta gagagacttt atgcagcaaa tgtactaata
229921 tatgtatttt gaataatcaa gtaaaactat tattagaatt cggatataga gacgataagg
229981 atataattaa aaaaggtagt gtatcaatag gtcttttaaa catggattct agagtaaaca
230041 taactactct atttccaccc tgttgtaatt ttatggatgc taaagtacta aatttcaatc
230101 tattattccc agaatgtgat tgtttcttcg tcgatgtaaa gatgaatata gctgaagaaa
230161 gtaactttat acccaggtac ttgtttgtat ctctttacag gatagctaat ttaaataatg
230221 acatatagtt atatttttct cgtgttcatt ataaacataa atatgaagat actttacatt
230281 gattatgtac ttttgatata acatgtgtaa tgctattaga atacggtgaa aaacggctaa

FIG. 19K3

230341 ctaatgctat cgtatcgata agtatctgag atagtaatgc cgctatgtgg taaatttatc
230401 ccacgaaata gaaattatat ttgtctatgt agataagaat ctctaatgtc aaatgatagg
230461 ctctaactaa ccttctaata tttaccgctg tagcattgaa acagtattga aaaaataact
230521 tattacgatg aagacgaggg tacaataatg ttgtatatat atattatatc aacatctata
230581 ctattagtaa aaggatacgt gatagaaaat aataattgcg gatgcggtaa tatcacggct
230641 tccaaagatg taactacttc taattccaca tttgatagat tattgtgtac tgtatacatg
230701 agttctgaag atggttacat ttattggata ggccctaata gtacttttat agaaaattta
230761 gaaggagcta atgaaggttc tgacaatact tttgaggtag gtaatgaatg ttacaaacat
230821 actagagaac ttaatataac atctagggat tatgtaggca agaactttac gtgtacgtct
230881 atgacagagt acggaaccac attcttcaat gtaatactgt aggtatacta taaaaaaagt
230941 ataaacgtag tatttgtata tttctttata tgtataaaaa cttccattct aaatatagtt
231001 actatgttgt tagtattaaa acacatatag taacatgcaa ttctttactc ctatacttat
231061 gctagttact tcgctagcga taattacggc tgtaactatg atatcgttgt tgataacggc
231121 tactataata ttacccatat ctttgatatt accatctact agctcatcta cgtttttggt
231181 aacggtaata tcacttatct cttctgtatc tatagtcgct atagctataa atacagttat
231241 gataatacga tctcattaat ccgtatgtaa aaaaaataat actaaatgaa aatataataa
231301 aatcggttac ttacgaattt agacttctat atagaaaaat attatggtag aagtctatct
231361 ataaacaaga agatgtgact tattatacgc gtacataact tcatgatatc tttcttacct
231421 gattattgtt taaagattaa aagtgaaata tattggaagg taatattact taactacttt
231481 acagcgttag gtgttatagt cttaatattt gtagtaccta tattactata attgtttaaa
231541 tagattaact attgttacgg gtatatgata tatctactat aattagtatg ttataaaaaa
231601 taaaaacaag tacaagtaaa agcaatatga gcattactag tataataaac aacctaatag
231661 atatcataac gctatatatt aggatttttt atgtaatata ctatattgct ataaaatcta
231721 aaaatcagat atgtatagcg aatatacttt atacatccat aaaattttat tatacagaca
231781 ttatagatgc cgtgcttaaa agaggtatcg accctaatat tccatttcct ttgtcagaaa
231841 atagctatgt gaatcctctt atatacgcga tagaatgtga taatcatgac gcaatattat
231901 ctttaatacg atacggcgct gatgtaaata catatagtaa ttatctagtg ataacgccat
231961 tatatatctc tgtattacac gggtgcccta aatgtgtaga aatattacta tattatggtg
232021 ctaatattaa tatagttacc tataaaatgg taactcctat agaactagcc tctagaatat
232081 gttacaataa cttagcattt atggtttgcg atagaactat aactaacata ccgaagaaga
232141 taacctataa ttttgaaata atgaaaatac tggtatctca ttttatacta caagcatcga
232201 atgatagatt aaacaatcgt cacaataaat atttttcaga gggctataat aaaaataaga
232261 tgctagtatc tacgtctatt attttgactt atttcaaaaa acagtgtata gaagatatag
232321 atatcatgaa aaatataaaa ctgggagatg attcattttt agatatctta gtagaaagaa
232381 atactatgaa actatctaca tatatatcta atcaagacat attggatatt ccaaaaactg
232441 taaaagtata caacacgaga ataaatatgt tactagatga agctataata tataataata
232501 taaatataat attataaata ataaaagcat ttatcaggat gggagagtat agcaattcca
232561 gataaaaagt tatgttcgat aatattattt taatagaatg aaatagttat ggcgtgccca
232621 tttttgtaga cactaatagt agaaaagaaa ttacattaat catttatctg taacattctg
232681 atcagaagta tattctataa aacctgccgt cgttactgta aataatataa gcacacatgt
232741 gtcagaactg ttaagcagcg tgcctctgta gtttattctg ttacggttga catagatgag
232801 cgcttataca gagatatttt catatgaagt taatacttac ttcaaaatat catacgttaa
232861 tgatatgtat gaagagaaat acgtattccg ttatagataa taagaaaaaa tgaatactta
232921 atagactata taaattaata cagttatgaa gttagtttac gtatggtatc acgatagcgt
232981 gtttgtacca gatagtttat attatccatt tctcagtaat tttagattta attccaagta
233041 tagatcttgt catgtttttt actatataaa caatacagat aacttacgta taccggaaaa
233101 tgaatataat caagatttta tcgattttaa aactgtattt ccagaagata tggccacact
233161 aacggttttg ccaaataaag cgcaaaagat agactttatg aaactatcta ttttgtttaa
233221 aggacaccgc atactaaata ctaaaagcga tatcttgtta ttagattttg actgtcacat
233281 aaaaactata ggtaagatga tatacaacgt agaacctttt tactgtaaaa aaactaaata
233341 cttatatgtt ggaggacaga atgatgaaca agattcatat atagaaaatt atgctactag
233401 aatcgacgaa gtcggttcta gaagacttta cgatatattt actcgtttag attttcatcc
233461 aggaaaatct aaaactaatt cttacgtata tatgatttat gtttctatga tcatagagta
233521 ctttaaagta tatcataact acatatttcc tacactttgt gagaacgtgt atttagaatc
233581 tagcgtagat atgtcttact ctagaggatc tacttggaag atagatattt caaatttaga
233641 tgacgattca ttatggatta taaagtacag taaaccgttt aataaagcta ttaaagatga
233701 aatacaggat tgtatacaca acaaaaactt ttctgtgttt tataccatcg tgttaaaaga
233761 acttaatctt ccttttgata aagacatatt ttggttaaac gataaacaac gaaatggtac
233821 tttgaaagaa tacgttcatg aaaacataaa agatagtagt ggtaatacat tcattagtat
233881 catagataga gctatcaatt tccagaaatc ttacataaaa taccaaatat aataaaattt
233941 aaaaacaata tttttttaaa tattattaac aatgctatca ctatattacg ccatcaacta

FIG. 19L3

```
234001 taaaaataga aaaatggtag aaaggttact tagagaagga gtccatcctg atagcactat
234061 taaaggattt tacagaccgc ttgtaaaatc aatactctta agagacgtag acctggtaag
234121 tatattatta caaaacggtg caaatcctaa taatattaac gatgaaacgg ttagtccgct
234181 ggctatagcg attaaagtca attctcctac aatagtgtct ctcttactgg attataatgc
234241 cgatacttcc ttatttccat tatacgttag ttttccgatt ataaaagtat tggtatatca
234301 tggtatagat gtaaacgtta tagacagaga atctagatct tttttacatt acgcggctaa
234361 aaacgatgat gttgatacag tgatatcatt aatattacac ggtgctaatg ttaacgtaca
234421 agattctaaa ggattatccc ctttacatca tgccgttagt aagaaaacaa cattaacagc
234481 taagatacta ttagaaaacg gtgccagagt aaatattaga gattcgttag gtaggcttcc
234541 tttacactta ggagctaata catatgaaat ggtaaaactg ttaatagatt acgggagtcc
234601 tatagatatt aaagatgtta acggttctac gcctctacat tacgctatat ggaaaagttc
234661 gttagataca atacgattac tagtaaacgt gtctactatt aacgcattag ataataactg
234721 taatagtccg ttacattata ttatattatc agaaacagaa atcctagtag aacttttatt
234781 aagaggagcg gatatcacta tcaaggatat atgtggtaat acaccattag atattctttg
234841 taaattaaga ataaaaaaac tagataatat taaagcgata atatctaatg cgtttcttat
234901 gcgagaagta gttcctgact tattaaagct atgcggattt gaaagcaata gaaaaattat
234961 ctctaatatt agcgatttaa aacagcacga ggttagttgt attaaagaaa tacatttaat
235021 gaaagagcat agtttagaa aaaacggccc aactatatta gacgtatgta cagataaagt
235081 acattttctt catcgattag ttaatgctcg tgataacgta cagtataaag attttcctat
235141 atactgtaaa tatataaaat ttagaataga gaaagcgata tacaaaaaaa caattatcga
235201 gaaaactata ttactgttag acgatatatt aattaaacac gaatatactt cttggcatga
235261 tttaccatat gaattaaaac actatataat agaatatata aacatagaat ttattaaatc
235321 gctgctagaa catacaaatc tgaaaaataa agaataactg aaatatgtga ttgtacgaat
235381 atcaaaatga aattaatcga ggcaatcgat aataataatc ttaaagaagt tataaggata
235441 atcagatcag acaatataaa cctagaatct ataaacgatg aagatgatct atctccgtta
235501 catcacgctg tttcacgtgg ttataaagaa atagttattt ctatgttaga gcatggagct
235561 gatgtaaatc tatgtaacga tgaagtatgt agtcctttgc acatagctat aaaaaatgat
235621 aacgtcgaaa tggtacaatt actaatagat aacggcgcgg acacagactg ttgtaacaat
235681 actatacacg gaactccttt acaatgtgct atactaaacg agaattatag gattacagat
235741 gctctactcg aatcgggagc tgatacacat gaaatttata ctaaaaacca ccccattatc
235801 gaggctatta aactagataa cctaccgcta gttagattat tactaagaca tggcgcggat
235861 gtaaatacat ttgatccttt atacggatat cctattcatt tagcaataag atatggaaat
235921 atagatatca tcaaagaact gctatatcac ggtgttattg aatcgtattc tttgtatcct
235981 tctcttttgc atcaatctat aatgtgtaat aataaagaag ttgtcttatt attgatatct
236041 atgggttttg atgttaatgc taaagataac gagggaaata cacctatgca tttagccgta
236101 cagaaaaatt tagtaggtat agtaaaaata ttattagata aaggtgccga taccagtatc
236161 attaataatt tatcagttac atgcttaagg agttgttatg tttatggtaa taattctaca
236221 gaaatactcc agctgctaat atctagaata gttatcaaca aatacgctaa tataccgtgt
236281 agaagtatag caggtatgaa ttataattgg agtttaatag aatcaaatcc atacatgtaa
236341 actttctagc taggtacgca atgcagcttt caactataga tctacgcgaa gtaccaatat
236401 acagaaagta cttagaaata cttattaatc cagctattaa aagacataaa atattaaatg
236461 ctgctaaaga cactatgaat aatatattgc acaggaaaga aaaattttat tggaatctat
236521 taccggtaga aataaaattt aatattttag aatacttgaa ttctaaagac ctgatttcat
236581 taatacacag taataccgta aatgaaatag atttatctca tatttttatt tgatattata
236641 tataaaacat aaattaaata acgtgtatat aataagctaa ttacaataca atatgtaccc
236701 aaggggtttt tagtaaatgt gaatactgtt atcgctttcg gctataagga aatagtaaat
236761 attctgttag aaagaggcca agatgttaac tttatagacg atgttggttt agcgccggta
236821 tactatgcta cgatatttga acggatgaat gtattaaagc tgctatgtaa ataccatgta
236881 gatataaata ttagctctca tagttctgga cgtacatctc tacattatgc cgtattgttt
236941 aatcataaaa gagcattaag ttttctgtta gctagaggtg ctgacgtgtt taaaaaggat
237001 gcgtgtatgt gcacgcctct atactacgct atgttatctg accaaagaga tatggtaacg
237061 atgttattac actctaagaa gtatatagtt aaattcagaa ataagctaga cttacacaat
237121 gctatagaaa ccggtaatat aaaggtaata aaaactttat tagataacgg agtaaatgag
237181 aatagtgttg acaaagatgg acttactcca ttacattatg ccgtaaaata tggtaatatt
237241 agcatagtaa agatgtttgt tattagatag tggaatgaac ataaacgcta ctgataattc
237301 gttatctaca cctctacatc acgctataaa cttacttaaa accgatatag tttcccttct
237361 aatgcaatac aaagccgatg cctctatacg tgacagtaaa ggaattactc cattctgtta
237421 tgccatgtat ctaggatatt acggcgttaa taaggatatt cttaatatta taacacggta
237481 taattctatt aacggaacta ctagagatat taacgatgta tataccatac tactaaataa
237541 taaaaagaag aattatgtat tcgtaaacct acacgatgcc gctagactag gatatgtata
237601 tattttaaaa aagataatat ataatggtaa gaacataaac cgcattgatg aatattacta
```

FIG. 19M3

237661 ttctgcgtta cactatgctg tcaaatccag taatttgaaa gcagttaatt tttgatacaa
237721 aaaggtatag atataaagtt aaaagatagt aatatagaac cgcgctacat tacgcggtta
237781 aattgggtaa cttagatata attaacagta ttatagaaag tggtgctgac attactacca
237841 gagatatatt taaccaatct cctcttacca tagctttaca agaaatagat aacatatatt
237901 ttttacgata aagtatttta caaaataaat gataaccaaa aaactaagat agctaatgta
237961 ttaatttcga atttagttac ctctgaaatt aaaaaaatga aacaattacg tataaagaac
238021 tatgcaatat attaggtgat aagacctata taactatatt tgtgagtaat tgctttaggg
238081 aaatacataa aatgaagtat gttaatttta taaatgcgta tagtgtctat gatatttata
238141 taaataaaaa caagatagat ataaatatac cattacatat taactatgac ctaaaataca
238201 aagaaattaa aaatgaattt cctatttaca gagatatgat agaaaagaaa atacgatata
238261 tactagataa acctaatcta gtatataaag ttattaattg tatgtccgaa tatatggatt
238321 ctacttattg gatgtttcta cccacagaaa taaaatttaa ggtgttaagt tacttaagta
238381 gcaaagattt atatttttata atataaacat ggaaggaata ccactcatag atatatatgg
238441 taaacaatgg aaaatagata aacttatagg atgtggtgga tttgggtgtg tatactctac
238501 tcaatgtgct agtaatacaa ggcaagccgt gattaaagta gagagcctaa ataacactac
238561 catggtatca gaagtattag tttataacaa catatatgat aaaaatagaa tagcgttatg
238621 gaaaaactac aagaacatag atcatttagg aatacctatg tactacgggt gtggaagttt
238681 caaacgcaat accatgtatt acagatttat tttattagag agattagtag aaaatactaa
238741 agagttatta aagagagtaa aaaaacctaa accgttaata aaaaatataa tgaaagatat
238801 gttatatacc ttagaatata tacatgagca tggaatttca cacggggata taaaaccaga
238861 aaacataatg gtagatggaa gatacagatc gtacctaata gattatggta tagtatccta
238921 tttcattgtt aatggaaagc atgtaaaata ctacaaagaa tctaagaact ggcacagggg
238981 aacattgtat tacgctagtc tagatgcgca taacggcacg tgcgttacta gaagaggaga
239041 cttagaatca ttgggatatt gtatgttaaa atgggcgggt ataccactac cgtggaaggt
239101 atttggaaat aatgggaata tggtacatgt ggcgaaatgt gattttataa aacgggtaca
239161 taaaaataaa gttaatatta agtcagcgaa taaaggcata tatgattata ttaagtgtgt
239221 tacaaaacta tcgtacgaag aaaaacctga ttatgatcta ttaaggcaat tagttaatag
239281 cttataaatt attttcagaa cataaataaa atataacata tttgtacaag cctgttatca
239341 tgtcggataa tacattatta ctgcacacta taatgatact agatctagaa cctaactaca
239401 acgaatgcag atattgtgtt agaatgctgt ttaatgctgt aaaatttaac aacataaggt
239461 tagttatgca tctactacgt aacggagtag atcctaactt ttacgatgaa tacatgaggt
239521 ctcctattca ttatgctgta gaaaaaggta atacagaaat ggtaaaggcc ttattggaac
239581 ataaggcaga tcctaatata ttcgatgata acttcgacta tccgattaca aattctataa
239641 tagaaaacaa agtagaaatc gtaaagatac ttttacaata tggagctgac aaaacaatga
239701 ttaacgaatt tgatttatta cacgacgcta tcaaaaataa gcatatagat atggctaaaa
239761 tcctaataga taatggaatt agtttaacca tgaaagacac agatgactat acgcctttac
239821 attatgctat gttagacaat gatacatctg tgatatataa tctattagac tatatattta
239881 aagtaaaagg atacgatgta ttaggcaata ttgtgcatga tatattgtgt aactatgatt
239941 tatataagga aacgacgtta gaattattaa tctcttatta cataattata tcctacctct
240001 atagaggtat agacctttca gatatttaca atagtaatat agaaatatta cttaattcta
240061 aacatctttc tgatattaaa gagaaatgtg aaaacgaaat agatgttatg aagaacgctg
240121 taatatgcga cggtatagcc atcatagatt tgtgtacagg ctacgatgca aattctatag
240181 ctagaaattc cgttaatttg aaaagattct cagatactaa actaaagatc tacagatatt
240241 atatagaacc gattgtagaa ataggaaagt atagacgcga gctattgtat aatgcgatta
240301 attctatgaa tgaatattgt aaatccgaaa gtaacgatat agcaaattgg tcttgtctac
240361 cattcgaaat aaaatacaaa atacttgaaa atataaaaga tgacgaaact ttaagaaaaa
240421 tataagtatt tacaatagta agtaataaca aggttttgag tgtatgcttt taatcataat
240481 ttttatttaa aaaaatagaa tagtgaaaat aaaatatgtt aataatgagt agtataaaag
240541 aactatatca tgcggtttct atcaatgata ggtttagtgt agttaatatt ctagagaaaa
240601 aaaatattcc tatagattat ataaattttc atcctgataa cccgttatta gaagccgtaa
240661 agttaactaa cactgatatg ataaaaacat tgctagatta tggtatttgt ataaatacta
240721 gagatatttt aggaaatacg gctttacact tgatagctat ggattattac gttccacata
240781 acgatataaa acacggccat cacaacgact atgtatttaa aatggtgcct ataattaatc
240841 tttttttaag aaagaaagct aacataaatg cgtgtaataa tctaaatcaa acaccccttgc
240901 atttggctgc cgaaagcaat aatacaacat tattaaaaat attattatat aataacgcaa
240961 aggtaaatat tctagatatt tacggaaata cttgtctgca ctatgcggtt agaggaagga
241021 acatagaatc tataaaacta ttactatcct ataatgtcga tgttaatata agaaatttta
241081 cttattggta ttctgctttg cacgaagcag tacagatagg cgattcaaaa atatctagat
241141 gtattgtatc attattactt tgtaataagg ctaacgttaa tactagatgt agacttaata
241201 caacacccat attttacgct ataaactgta tagacactct gaaactatta ttagaaaatg
241261 gtgcggatat aaacgcgacc tcggataatg ataatgccgt aatacatcta gctactgaaa

FIG. 19N3

241321 atagacgtta tgatataata aaaacgttat tggattatgg cgcggatgtg aacatgatag
241381 gatatagagg taagacacca ttatattatg ctacagaaaa ttatagttac agaaatatga
241441 aattattact agaccatgga agtaatccta atatagcaga tcatattatg aatacgcctt
241501 tatttatttc tataaagtgc acgtgcatcg aaaacactaa gatgttacta gatagcggtg
241561 ccgatattaa ccacgtaaac gataatggcg aaacacctat ttcttaccta gctcctaatt
241621 taatccccaac ccccgttgct atattagtaa tatctcatat agttctttta aaaaccaaat
241681 ataatcatat aaagtactta cccggtttta taaaaaatat ttctgttata cagaatttta
241741 ctaaattcaa taacataaaa aaggtgtgtg aagacgaatt tagatttatg agatccgtat
241801 cattatcggc taatcataat ttatcgtctt atatatgtaa tgataacttg cgtactttag
241861 taaggttcat aaaaaatcca aaaatatatt attcgataaa taaaatacgt atttatagga
241921 accgattata ttctataata gaaagattat taaatagaaa aaaattacat gatttagttt
241981 tagaattaat taaagatata ggcgtattta ataaactacc gttagatatt atatcaatga
242041 tattagattt tttatcggat gacgacttgg cgcttatggc tatatttaat tgatttatag
242101 tcctaactac cgtatatcaa taaatatata atgaaagtaa aaggtgattc atcgaatact
242161 gattactaaa ctatcagaag ccgaacaagg atgcaacttc ttcaactagt tattctccat
242221 aaaagaaata taatattatt gagattatat taaattaggg tatggatatt gacgcgcttt
242281 actattatgg ttctgtacta ctggtgggta caacgagtga atagaaacta taaacatcat
242341 aataaaacac ggagctatat taacatatta gattaacaag gattcaccga gttgtataga
242401 acttctatag agaatcttcc taaagttata gaattttgtt agtaaacggt gctaacccga
242461 atatcaataa cgagctagta tgcacgtcgt tatattatag aagaaactta ataatgttga
242521 attattgtta agatatggta ttaatattaa cgctatagat cttaacagac actcctttat
242581 ctttatcca ggccgatgat cgtgaaccac ctacattact tgtggctcat ataactttta
242641 accaattatg ctgatgatag gtcctatcta gaaaggttat cattctaaca tgtctatgat
242701 atattatagt aaaaatctaa atagttttaa gttagaacgt gaaaaagaat ctctatgctg
242761 aaatctataa taatatgtag agaaatttct ttatttatgt caacaaccct gaagaatttt
242821 agaaaatctt ttgactcgaa gtgttaatga catacatata tactttaatg cgttaataca
242881 aataatatcc taagtaaata tagacacgtt aaataaagaa gctttacaac atattgataa
242941 aatgtttctta gattgagatt attaaccaca ggtgagttaa aaatctatta gaaatatgtt
243001 aatacaaaac ttatttacca tctaatccat aacaaccatg tattattata tacaaaatat
243061 ttattttagt agatgaaaaa atccattgtt atacatcaga tacagaggta taaaattcct
243121 tatttggtgt tatatcgaac tagtgagttc aggaatctta tctaatagaa tactattaaa
243181 ttagagaaga aagactttat gagtaagtat taaacaaaat atatactcac atttataata
243241 tagtatgtaa tttatcatat atttatcat atatttctt ttctgtaact gattatttct
243301 tttaatagag atttcgtttt ttctcttaga gatatatcgc tgtcttgttc tgctaacatt
243361 tttaaaaaca aataagatct ataatcacct ttttttttta aactggttag ctttgtattc
243421 taatttatcc tcctgaattt cattattaca aaaatctgtt atttcttttt ctacgataga
243481 tattttatct tttatattct taaaaccatc tagtattaca ggatactcgt cgatttcttt
243541 atttctattt tcatacacta ttttagtggt gtctaccagt ctatctttaa cccgtttagt
243601 catatcaata tcttgtaaag aagataaaaa taattgaagt tcataattcc atgatttaag
243661 aagatgaaca gccgctgcat ctatcatgtc tatttttcca tcatctgaca taacagaaaa
243721 cacatctaat aacgtattat cactagaact attaagttta tgataaggat tgttattcac
243781 agtatgtatc atagaactag catttcccat gttaatacaa acgaccttat ttatttttat
243841 aattagtaaa tttattttaa tgtagatatt aaaattgata taaatgaaat ataaaactat
243901 tgacgataat aggaatacta ttatttcctt attatagtac tatggaaaat gaattaaaat
243961 tatactatgc tgtaagctcc caaaatgaaa acttggtaat acagttacta aacaaaggtt
244021 acaaccccaa tgctataaac aggtttaagt atatgatacc gttacacaaa gctgtagaat
244081 gcaggaacgt agatataact aaacatttat tatctaacgg cgcagacgct aacgttaggg
244141 actttctagg attaggtgta tttcacatac tgagcatgtt ttctagttta ccagaactaa
244201 aagatatatt acataataca gaaggcactt ttgtcttgtg caaatataat tacgctcctt
244261 tagaagaaga ctatgaagtt aaaacactag agatagctag aatgcttttt ataagtaaag
244321 ctaatattaa tatgacgagc aaacttggta gtacacctct tcatatagct agtaaataca
244381 ataataaaac gatggtgaaa ttctttttgg aaagaggagc cgatatcaat attctggatt
244441 ctaacaataa tactcctctc atctatgcgg tatgttcggt aatacgacta tatctaaaat
244501 gttattagac tacggagcaa gaatagattc tcgtaataaa gaggaatgtt tgcctttaaa
244561 tcatgcgata gctacaaata acaaagagct tacgagtcta tttcttgcaa gaggagccga
244621 tactaatatc gtagataaat ataatagatc ggttctacat aaagctatag gtaataataa
244681 tataacgtcg gtaaaattat tattaaatca cggtattgat tacaatttac gagataatca
244741 cgggtatacg gcactgcact acgctataac attacaaaat agagagatta cagacatgtt
244801 attatcttcg ggagccgacc ctaatataat gaataatgaa aaacatactc ctctatatca
244861 cgctctattg tatagatcgt ctaacgttga atcgctgata ttacacggag cggatataaa
244921 tattgtagat gatacaggga aaacaccatt atctaatacg tatatagata taatagataa

FIG. 1903

```
244981 taaaaatatc gaagtcatag tatctcaatt cactatttg gaatatatag caccagatga
245041 tataaaaaat caattaggtt acaaaataaa tactgaccta ataaacaaca ataaaagata
245101 ttctactata aaacagaaat gtgttcatga aataaatcta ttaaaagcaa ttaaatttca
245161 ttccggatat tcagcggaaa tatttctaat taaaagcaaa tcgaatatct ttcataattc
245221 acagggtatc caaatattat aaatataatt gaaacaagat ttcccatata ttactcgttg
245281 ataaaaaaat ctatagacat aggtaattat agaagaaagt tacttgacgg tgctgtaaat
245341 actattagtg aaatccgact gttaaacgta ttacctataa acataaaata tgttatattg
245401 gagatgctag ataataaaga tctaataaca ttgaataata atacataatt gaaaatgtat
245461 ataatactat ttttatagat atatagcaca tcataatata ttataaaaat gttaaaactc
245521 tatatatcga tgtttttaga tagtacagaa catatattga aagaaattaa cagactacaa
245581 cataaagagc aacgcaccaa cggtatatct tgtatacctc ttattccttt acaccaagct
245641 gtagaagcta gaaatctaga agtagtagaa gctttactag aaagaggcca caatgtaaac
245701 gaaacagacc atagatatct aacaccttta catattatat gttcacatcc taataagatt
245761 gggatgaagg aagtaatcgc ggaaaaaaca aaaagagatt tatcatctta cgaagaaaga
245821 gctatatcag aagcgtgtta caataatgat ataaatatct ttaaaatgtt attacttaat
245881 gatggtaata gaacgattga tgacgtccaa ctatgtacga tagattatga tgattccata
245941 gatacaaaaa taataaaact gttactggcg tatggggcag atacaaaaat aaaaacagaa
246001 gataagttaa aaacagcttt acattatgct tctacaaata aaaattataa attagctgaa
246061 tatttgttga tatacggagc ggaagtaaat tccccagata taggtaataa ttctcccatg
246121 catgaagctg tacgacatag aaacgaagat gtagtaaaaa ttctattaca atatggatct
246181 aatactgatc acatgaattc atgcggtact actccattgc atatttctgt aggaagggta
246241 cttaatagaa ataattattc tatattaaag atattactag aacacggtac gtctgtgaat
246301 atacagagca gtatactagg ttttaccgct ttgcatctat ctattcatag tgaagataaa
246361 cttaatctat tattagaata cggtgcagat cctaatattc tcaattttga gaaagaaacg
246421 cctttaagta tggctgtaaa agtaactagg tatgatataa atatttataa tcgtcttata
246481 tataatatat gcttgagagc gtttaagtat cctttcataa aaactacaga aggttatatt
246541 aagaacatga cgtgcataaa cggttatcct aaatgtaaat ccataaaaga tgcatgtgaa
246601 tacgagatta aaaacttgga atctataaaa ttaagtccta gattttctat ggccgatttc
246661 ctaaaagacg ataactcgct aatgatggat aaaataataa ataacgacct tatagattat
246721 tattactcgt ttatggattc gtttcccata tacggaaata tagttaagaa aagtatagac
246781 acagcaaaag acaggtattt attaattcag ggagctatac gcagtatgga taatataact
246841 tttccttcac aacgtgtatc ttggtataat atgcctttag agataaaaca tgatataatg
246901 tacttattag atgataaaag tctgtgtaat ttaatagtag ccgaatatga tagttaaata
246961 actgaaacaa aaattttatt tttattagta tatgaaataa tgcaaggtaa tgttatacac
247021 gtagacaagt tatataaaat gatgtacacg gataactacg aaactataaa aaaatattta
247081 gaatatactg tcatagataa aacagaaaat tatagtacta gtgctaattt aatacccttt
247141 atacctctac atcaagcgat agaagcaaga aacatagata ttataaaatc aataataacg
247201 gtagataacg ttaatcaacc ggggcacgat gatacatatc ctatacatat catatgtaag
247261 gaacccaata tgctagcaat atctttatatg ctaagatcta taaatcagtg cagcgtgttt
247321 aacacgcttg taaaaattaa agatatgttt aattacagaa acgtagaaat agctaaaata
247381 attttgacaa atagatacaa aaatatacag gatatagatt taaagtatat agataagaaa
247441 agtaaggacg atattataga aataaccaaa ttgttatttt cttacggtgc tgatattaat
247501 atggtagaca gacacggaaa ttctcctcta cattacgcta ctgaaaatcc agatcagaga
247561 ttaacccgat tattgcttag taaaggagct aacccaaata tattaaataa aactaataag
247621 tcacctctct attattctat agaatccgac aatccagata taactatgtt gctaatagat
247681 aaattcatat ttaataatac ggatccaata ttatcacacg ctattaaaca ctaccgtaaa
247741 cctatattac acgcgttaat agaaaatggt gcttctatta acgcacgaga caaatacggt
247801 aatacaccgt tacactacgc ggtaagttac tgtaaagata tagatgtgat aaaattactt
247861 ttagaaagag gtgtagatgt taacgcaaaa tcttatatta ggaatttaac tcctctgcat
247921 agttcatatc ttaaatcgcc tcgtgttcta aaactacttt tacaatacgg tgctgatatt
247981 aatagtttag attcatatag tttgactcct ttaacgtccg tagtacttca gtacttgtgt
248041 atagaatgtg ggagaatagt agtttcgcat atctgctgct taaagcgtat taaaccagat
248101 atcgaaaatt ctttgggttt tatagataat atagatgcta ttactagtaa taaaaggctt
248161 aatcaaatac gtttaaaatg tgaggatgaa ttgaatagaa tggcaagtat taaaattact
248221 aatacatatt ctttcgatgt atttgtcctt tgcgataata ttactttatt atgtaaactg
248281 gtaaataata gtattataga cgatatatta attaatagtt ttaacatata taaaggcatc
248341 attttaaaga atatatacag atctagaaaa cgactttatc taatagaaaa tacattatac
248401 gttttaaata atactttttaa acctaattat atgtggaata ggttacctgt agagttacaa
248461 aattatataa tggagtacat agatgatgca tcattaaagg taatgcacga atacgaaaaa
248521 cataaattaa agtattaagt gattacaggt ttgattttaa tcggtataat gcaggtacgt
248581 aataaagatg atatactaat atgcgaagcc atagaaaatt atgatagcga atctttacgc
```

FIG. 19P3

248641 aatattcttg aaaatggagc agatcctaat gttagagtac cttatcagta cagccatttg
248701 cataacgcta tagaaaagaa gaatggaagt gcagtatctc ttctactaaa gcatggagcg
248761 gatcctaaca tttctgggtt ctttacacca ccattacata aggctataaa aaaaggttgt
248821 gtagatatag ctagatcgct attagaatac ggagctattg ttaatttaga acattattgt
248881 ttgaaaccta tacatatagc tgctaataga acagaaagta aaatagtaaa attgcttata
248941 gaatacggcg ctgacattaa ttcagaagac ggcgcgaatg gtaaataccc tatacattac
249001 gctatgaaag tatacgatcc gtttagatta aaaataataa aagtattatt agaccacggc
249061 gccgatatta acaaacaaag cgttttaact aatacatccc ccttatacga aactaggttt
249121 attaccgacg acctattaga ttacatcata tctagaggag ctaatataaa tataaaagga
249181 agaatgggta gaaatatatt acacgaaata atattaagaa acggatataa tgattttagt
249241 aatatattgg tattaataga ccacggtgct gatataaacg ctttagatga tgaggggaat
249301 acacctttta tgttacatac tattaacaat aatgctatta ttcttgctaa ctatatagta
249361 tcattgtatt acttatctta caaagctaga atttctaacg gaatggaaaa gaatatgaaa
249421 ataattaata agtgtgaata cttaagttcc tgcataaata ttataaaaga agaaatagaa
249481 cgtatgaaaa cgttcaagat atacgacgga aattcttttc aagatttaag tcttttcgat
249541 ttattatcta acgaagataa catcgctata gtgtatagac tgtccgatac attattagaa
249601 aaaatgaata taatcaaaac aatatttccc aactgttttc gtataataca aaatatatta
249661 aaaatgttga caaaaagata tgaaatgtta ttagagataa acaatataat gaatgcaaac
249721 ctagtaaata caaaatggta tactttaccc atagaaatta gatggatgat actgacaaaa
249781 ttagatgaca tgatcttacg aaatctacta ctacaaaatg agacaaataa tattaaaaat
249841 tgtaaaaaac agtaatataa atatgataag aaaatgtgta aaaaagctag gaaacgcggt
249901 ctattaacga tagctttcac tatattgtta tttgttatta ttttagtaga tatagacaga
249961 gatagatatt tagtaaggtg tggtaaagac tggttagaat tcgataattt atgttatttt
250021 atttccgaaa ataagttaag ttgggatgat agcatgatgg tatgtgataa tcttggcggt
250081 gggaataata ttaacataaa tacgaatagt ggcttattaa atacatctaa ggactattgg
250141 ataaaaatag tagacgaact agattgtaca aatattaata tgtgtaattt cttatatagt
250201 aatatagtag gatgtgatat atgcaccata gaaaaatttt atatttgtat aaaaccgata
250261 aataaaataa acttatttag ttactttgta gagtatacta aataataatg aaatttaagg
250321 aagttagaaa tactatcaag aagatgaata taacagatat aaaaatatgc ggcattaatg
250381 agtattttat gtctatgaaa ttattagatg tagaagtagt aattatgaga agtaacgggt
250441 tcgtaaatat tactagatta tgcaacttag aaggcaaaga ttttaatgat tggaagcaat
250501 tagaatcgtc taggagattg ctcaatacat taaaagataa caacaagtta cacgatccga
250561 taataaatat taggcatact agaataaaaa taaacggaga atacgtttca caattactac
250621 tggactatgt aattccatgg atttctccat atgtagcgac tagagtatct attctcatga
250681 gatactatag acgatgcgta gcgctaaaca tagaaactga aaaagatata gaccatagcc
250741 aagaactaca gaatcagatt tccaaaatag acgaagttta tgatagatct ataaaggata
250801 taagtaatcg ctttaaagaa atagaaacat cttattacag taaattgagt acttatttac
250861 taacaaaagc tgaaagagta ttagaaaaag actattctat ggaacaggat atagataata
250921 acgaagatat ccgtacagat gaaatgatag ctgctataga agctgaaatt gaagaaaata
250981 atcgtcgcta tttgtcaata attagcggca taagaaaaca acacgcagaa gatcgtatta
251041 atatatctaa aattatgctt agtggtgatt catttaatga aataatagta aaaataagag
251101 actatataga aacaacggca aaaccagcgg tagcgaataa ttacgaatag taacggtttt
251161 aaataatatt atataaaaaa cataaaaata aatataatat acttacgaag gcccaaggct
251221 ttatataata caaatcaaaa tggaatctgt tattcgcaaa atggatactt gattctgata
251281 aactatcatc ttccaagact ttcggtgtta ttatcaccat cttaatagtt atatctgtat
251341 ttgcatattt taaactgctc atgtatacct atgatcaaag tatacaagac atcttgcaat
251401 atcatacttt tggttataat tatgcatatc aatttccatt ttttcataaa aatattatac
251461 attattagct agcatttcta taaaagtatt attctgcata tccacttctt cggtaaaaaa
251521 caaaatgacg acattataga tctatcgctt aaatatgcac aatcacctat tcctttgata
251581 ggaactatat tatcataaga tgacccatct tctaatttct aagttccatt aaaatcaact
251641 ttttctattc caatccagtg atttcccgga cctttgtatc ttaggataaa tttaaattct
251701 tctttgctag aaattgaagt cagatgcccg tccatatcct tacatctttc tacagctaat
251761 gatttattat ttttttcctc agagaaaaaa tagcagtttt tattatatcc tacccatcct
251821 tctttacagt aaagtatttt aatatctgga ggtacaggag gtcttgtgga taaaataatc
251881 acaaatacag atagcacgat aataatactt ccgcatggaa tcaacatcca taatactgcg
251941 ctactacgtc gcggtttacc ctcctccatt ttttaaatat actttatcaa gatttattaa
252001 acttaaaaat gcattcaaac tacttataat aaaattgaaa aaacaaataa tgatatatcg
252061 agaggtgttg aacacctata ttatacaatg gatcgtgtag aactttgcaa tgctattctc
252121 tttggagaac tggatgtggc tagacgcctg ttggattctt acatcaatcc gaattttact
252181 atcaacggat actcgcctat aaagatggcc gtcagactta gagatgttga aatgattaaa
252241 ttactgatga gttacaacac ttatcccgat tataactatc cggatataga atctgaattg

FIG. 19Q3

252301 catgaggccg tggaagaagg agacgttgtt aaagtggaag aattattaga ttctggaaag
252361 ttcataaatg atgttatcta caagaaagga aacactccct tacatttggc cacaattagt
252421 aaaaatcttg acatgatgag gctccttata gctagaggag ccgacactga tgtgcccaac
252481 actgatcgtt ttacgcctct ccatttagct gttatgtcaa aagatattaa aggtatagaa
252541 ttgctattag atcacagagc ctgtaccaac atagaagatt gctacggatg tactcccctt
252601 atcatcgcca tgagcaaagg agacacagaa gtatgcagga tgttgctaga ttccggagca
252661 aacattgact atttcagcaa aaggccctgt gtgacagcga tgtgctacgc tatacaaaac
252721 aacaaaatag atatggtaag catgtttctc aagagaggcg ctgatagtaa cattgtgttt
252781 accgtgatga atgaagaaca cacaacttta gagatgatct gtaatatgga tacaaatcca
252841 gaatctgaat ccgtggatat gctgatagcg gacatagcat taagacaata tacaaataca
252901 atatcatcgg ataaaggatt ttccagaaac atgacagtca ttaacagcaa aagtcgttta
252961 aaagatgtat ttgaaaaatg taaaattgaa ttaaggagaa taaacagcga aagcatcaga
253021 acctacaaca ttctggacct gtgtttaaaa ccatccaaaa atcttgatga gaacatattg
253081 gcaagacatt ctagaaaaat attaggtctg tatgataatg ccatattcta caaatatcta
253141 ttaaaagaat tggcagacac ggcatcgcaa agagcggaag ctattgaatc agcgatgcga
253201 gttatagatg aaaaaattac tggtgatgaa acaaaatgga attggttacc ccacgaaata
253261 aaatacaaca tacttgaata tataggcaat aaagagcttg acatcgcatc tatgaaataa
253321 aatacaacat acttgaatat ataggcaata aagagcttga catcacatct atgaaataaa
253381 attatttta taactaaata tatatttga tatagaaaaa tctagtcatg aatatggtac
253441 aaacagaaat attgaaggtg ataagtctta tatagcaata tagaagtaaa cataggcaaa
253501 acaagtattc taatagatat tttgctaact atgtagtaca atataagtat attaattttg
253561 ttaccgtgtc gtcttaatca ataaaacgta aaagccgtta ttaaacatat ataaatatcc
253621 tgattatcgt gatatatgat aaatattgcc ttatgatgta aagaaagata gagcgtgtac
253681 taaaaaaata aacaaataag tgactaaatt ataatataat gggcaattct acatctttat
253741 ttcaacgact agtaaatact tttatcatag cgattgtccg aatcttcgca agaagaaagc
253801 ggttatgttg tggaaggtga ttatgttgaa ttcgaggcca gatttacttg ctttataaca
253861 cttgcttgta ccgatcccaa aaataccata atctattgtc tggaataata atgtaaatag
253921 tttttgtatg tggtttttat agagaaatac aaatatttag gttattaaca aattatgaaa
253981 attaagtatt tgtattccag cttataacaa ttattcaata tggaaatcaa agtagaatcg
254041 atcaataata acttttgtaa gctaagttac gaagatatag aaattattat gatgaaagaa
254101 aatgaataca taaatgctac aaggttatgt agttctagag gaagagatat attagattgg
254161 atgagtaagg agtcctccgt agaattaata aatgaattag acaggataaa tagatcatgc
254221 aatgactact acgattatag gggaatagta ttaaatgtgg tatcggacag cgaaacaagt
254281 gaattgtacg tccaccgcga ccttatatta catatttcac attggatttc tcctctattt
254341 tctttgaagg tagtaaagtt tataaatagt tacatacaag attcttatca attagaatat
254401 gagctaatac ataaaaaaag tttaatggat cagttaaaag aaataatact gttaaacgat
254461 gataacaata tgtagttaca tgagatagct aataaaccat aaagttacgt atagatgagc
254521 tagcaatata aacgaaaatg gtaaaaatgc tattatcact aggtacaata tacatgtttt
254581 agatcatata gaacgctata cttaatgata tcttctggta gagcttaaaa ctccattgtt
254641 ttaatattat atactatcaa cacaataatc gggtgtgaat aaagattcta aatctacgca
254701 cgtaataaac caatatact aaaatataaa attatgccgc gggatgataa gatacttcag
254761 atgatcgtga tgaactatat ttattaattg gcaatactta aaaataatgt ttataacata
254821 tgtaaatata ataaacaata atttagattt ttaaaatgat aatacgtagg aataataaag
254881 ctcttggaag tgtaatgagt gatttcataa aaacaataaa tgaagaatat gatagtaaca
254941 taaaagaaat aaaatcagaa attgatataa agtgtaatag tattctaaaa gaactcgatg
255001 aaaaatatcg ccaagagata aaagaattat gtatgatagt agatcaactt aagaaccaat
255061 ataaaattat agataatatt tatagtaggt atataaccga aattagaata caacttttag
255121 ctctcaaaga ggaaaataaa tgtttaaaag aagagttaac aaaattaaag taataatttt
255181 acggatgaaa atctgagagg aagatgtttt tatgaatata tattcgtggg tatgactaac
255241 ttaataatag agataaaagt agtttaatag attactaaag taaataaccg cggcggatac
255301 agaagctact ccgctattct ctagcgtatc gattttaatc caaataaaaa aatacataag
255361 cgtacacgga catacgtatt ttgctacctt atattatata cctaaattga tacatgttta
255421 ttctccaaag aatctagaat ggcctcaaaa tctttttgtg aattatctat aagctgcctg
255481 gctttttccc ttatcttcat tatatactca tccttatccc tatcctcttc gggaagaggt
255541 tttatatcct ctctacaatg ataaacttca tttcctagat taataagtcc tatttcagag
255601 aactcttcca tagtatccgc tactttgtat agagcttcat cgtcgtacac ataaatctta
255661 ccatcttccg acattagaat gatgagattt tcattccaag aaatatcgct atcattcata
255721 acaccgatta tatccattct cgtcggctgg ggtaaataaa gaacttcgca acattctttt
255781 atatatttaa gctcttcttc gggtaaatta atgtttctat ccattttaat taagtatcta
255841 aggtgtatat ctatatgtct attttatttc ctaataaacg taaattaaga gaactatatt
255901 tctttacgat ataagtttat atactaaaca aataaaaaga tgttaaaact aatatgttta

FIG. 19R3

```
255961 cgtaatttta atacttttc tattttagga gtagttgatt ctctcaataa cggtaagaat
256021 atcaataaaa taatatctaa aaaagatatg actttgaaag aaatagttct ttatttacct
256081 aaattcgaat tagaagatga cgtagacttg aaagacgcgc taatccatat gggatgtaat
256141 gatctattca agtcaggtga attagtaggt atatccgata caaaaacttt gaggataggt
256201 aatatcaggc aaaaatctgt gataaaagta gatgaatacg gaactgaagc agctagtgtt
256261 accgaattat gcactacaga cggaataaag aaaattccta tcgtaaaagc gaacgtacct
256321 ttcatgttcc tagtagccga cgtacaaaca aaaattccgc tatttttagg aatattccag
256381 ggatagttac ttaaacaaag acattatacg tagacttatg cgcgtaaaaa gcgattaact
256441 aaattatata gaattgtatg tataccgata cctccgagta aatagttaac tcttaaaaga
256501 ggaacgtggt agtattattt tattttttt ccttagagct ttgtaaattg gaggaaagtc
256561 gcgttagtag ataactatat tcacatatct aaatacgaaa atcacaatat ctcgcagatg
256621 cgggcatacc tctttgtacg gaagtgttaa gatcggttag tatataatta ctatataatg
256681 ttaaagtaag cagataactt ataatataat cacgtaattt aactaacata tacatctaag
256741 aaaaatattt tcgggaatat aaatctgatt tagacattac gtcctatttc ttcattaaaa
256801 gaaataatac cttatacact tattgattta cgttttatca aaacatatta tttttatgta
256861 ctcgagaggt atataaatat acagatgtgc tattattatg ttgttatacg actactaata
256921 acctttttaat cccgtgatat atcgttagca caccttaaag attagaagaa atacaggtta
256981 gtgtaataat aacgtattat tatctagcac aaaaatgttt caaagggcgt gttattagat
257041 ttaaacgaag atagcgagta ctactgtgct gaaataataa caacgaatca ataattttac
257101 ttcgtttaac tttgtagtgg ttgtatagac tacggtataa taaaatagca aagtatcatc
257161 tcagggaatg caaatgacgt acgttgagaa tttaatatct agaatctgcg tttatacgtg
257221 acatcgagat attcgttatt actttgatta aaaatataaa ctatacggat tttctgttta
257281 caagaacgta caaaatacta ttgtataaaa aagaggtagt aaatctaacg catgtattcg
257341 gtataccaat gggtgtatct atcttcttta acacatatcg ttctttcgtg aaatatacaa
257401 gacatttcga taatgttact cgtgtcaaat aatagacaaa tatcattaac gccttgttca
257461 taatatagtg agaaattaat acccggaatt tttctatttt gatttatgtc tatccagtaa
257521 ctacccttac cgtatcgcga cacgaaattt agagtttcta tgttatcgaa ccttatcaat
257581 gaagaatcca taacatcgca tagtttttg ctatcattcc aattagtttc attgatagta
257641 aagtagtagc atttactatt atatcctatc cactcatcag gacatacctt gctaaagtac
257701 ggaaacgcgt aataccattt gcatgttacg actactagta tcgtaaataa tattaagcat
257761 agtattccta gtaccgttat cgcgtaacaa gatacttccg atacctgttt ttttaacaat
257821 ataggcattg cggtcgtata ttgccagaat catttctgtt ttattatttt tccgtatttt
257881 gtatatacgc gtaaaaacac tgtatagcat ctatataaaa aacctaagaa aatagttatt
257941 cgtaatatat aaaatcagtc tgttgtttgt tatacgtaga aataaagttt aagagatatt
258001 ttcatgtaga ttttaatccg ttaacacgcg cagatttttt ggaaatagac gtccgttgta
258061 tactttaaac acgatttatc agcgcactaa ataaaataca aattttctta tgtataataa
258121 gtagagcaga tgtataatat tatactacga tcaaagtctt tcgaaagatg taacgtatta
258181 ataaatatat ccttacctca tgttacagca taatttcgat tgtagaacta acagtaaagg
258241 tattattttg ctaaaactat tacttcagtc gcttgtaaac aatacttgag attagttttt
258301 agaaaagtat taccattaat gttaatcaca gccatattca ttgtcttctt caagagctat
258361 attacctctt actatattaa ataactcttc gtaagacata ttacctagga tagtttgttt
258421 aacttctata ggcagagtat accagtcggg tgtacccact gacttagtat cataatcgat
258481 agaattaatc acctcgtgta ttaaatctgt ttttgtaggt aagtcgaaat agtacttaga
258541 taccgaacaa caaatatact ccgttctgct attacaaaac cctctcaaat ctttgtattc
258601 tttatgctct ttagaagaaa tagcttttaa cttttcgtaa agtacaggat ctataggtat
258661 aaaagacgtt cctgtttttt tatcaatagt agaccatata atatgtttct tatcaccagt
258721 ccaaatttca tccacttcat tcatgttata tatacataga gcatcgaaag atccatattc
258781 ttctttacgg tatctaacaa tactaccgtt atgatgagat tttatacatc tacctgatct
258841 atcagatatc attcctaggc tatattcttt atcttctgtc attctttcta ttaccatatc
258901 acaataacac aactgaagat cattttctct gtcatataaa tttatttttt tacctaagta
258961 ttctatgcta cctattacgt ttgttgacgc ggataacttt ttttctagta agacatcgaa
259021 taacgccacg cattttctac cgctttcaac ggtaatactt tcatgttcta tagtttttatc
259081 aaatagatga tctgttttta atttcactga cgtattatta tcgatatata taaccgtttc
259141 acctcccgtt tctggttgtt ccaaatatag aagcaggtga acgcatatta tgtttttaga
259201 aaagacggta ctaaaatctc tatgcctggc aaagtaatct cctttttcat acataatcaa
259261 tgtaacggta ttctctacgg taacggaatc tactaccgta cttaattcat catagatcaa
259321 ggcgtgtaat tttttaagca agtcatcgtt tagggagttt tcgaaaacta tttgtttaga
259381 tttacgatct ttaatactta agagctccgt tctctttcc ggaaagaata ttttagaatc
259441 ctcgcatatg ttttttatat catttaagtc acttattcct aaattaacta aaagttcttt
259501 tttgaaagat gtaaaacgcg tttctgtaaa tctgtgaacg gccaactggt tattagttcc
259561 cgtacaaccg aactccatcg cgtaaatttg ttaaatgacc gccgtagcat cataataaat
```

FIG. 19S3

```
259621 acgatttagt ttttatattt tttatatatg aataacgctt ataaaactag aatatattta
259681 acaactgaaa agataattaa ttattatttt aacgtttatt tctattatct attataataa
259741 cgtaacacgc gcataaaaac gtcatcagat attttattat ttgaacggca tctacctaac
259801 gtatatcaga agagataaaa taattctata taaggatatt gagtacatat aaattaattt
259861 tttaaaactg aaaatataat caatttatta ccgagggcgt cctcgactat acgtcagcca
259921 tggctttaaa tctccgcgtt cgtccagtag aacaagagtc gggtataaag gtcttggcag
259981 ccgcgtcgga tcccttgaat tatgaaaatg atcacacggg cgacggaggc ttcgtcgcgc
260041 gagctatcag gaatatggaa ttctgtaggg ccagatacct atgcgccgct gccggcgata
260101 cagtgaaaat ctacttttg gaaggagaag gagaacttat ctactcggtg agccgagtgg
260161 gatctcccac agcggatagt ggatacgtga cgaggggcaa ctgcgtagag tttgaaaccg
260221 attcttcgtg ttttataaca ctgatgtgca ctagttccta taacacggtg gtttattgga
260281 tggaataaaa ggatacccgt cttccctctc ctccttcccc cctccccacg aacatatttt
260341 ttatttttac aataaaacaa agtaaatatc gtgtcattat tcatgatact ttagtaaaaa
260401 taaaatttct taatctttta taacgtaatt atcgtcttac gaaaagtaaa agctgttttg
260461 gtatataacc gtcgtcagaa cttaaagaag aattaataaa actaacgagg taacgtcgtc
260521 gacagagaat cacatggcaa ctcctctaga tttttattat gtataattga aaattaatcg
260581 cgtaactatt ggtggggtat atctctatag actattaaaa ttgatccgtg tatcaaaatg
260641 aaatcattaa tcttgatagc gatgttgtta atgttggatt gcgctaactc tctaaattgc
260701 agaggaccgt acacctctta caacaataag tgtatctggg taaaccgatt agataaaatg
260761 catcacaaaa aaacttacag cgaagcgtcg actacgtgtt tgataacgtt tcccatgggt
260821 acgttagcta gacgtagtct aatagacaat gaaaaagaca tgaaattcat aagcaaattc
260881 ggtatggggc agagtttgtg gataagggat gacaagaaac cagaagtggg taagtgtgcc
260941 tatacggacg ggaaaacgtt cggattctcc ccgtgtaacg cgacgtacgg tttcgtatgc
261001 atagattaat aatattcaaa acccgataac ttttaattta ttaacgatag attttttttt
261061 agcattagtt tttagtagga cgaacagcga ctttcttcat gagatataga aaagcgaacc
261121 tccaaaaatt tttcctcgcg taataaaacg ggactatatc cctaacgata ggaagcctat
261181 aggtcaccag tctgtgaaag agcatgagag cggctttagc gtaaagtttt tctccgatag
261241 ttttgataaa ggtccttaag aatcttaacc tatcccttac tctgatgaaa aagattgcgg
261301 tagacgccgt tttagaaatc gtattacgta gaatcgacag tttgttttta tcttgtattt
261361 ccttactcgc gttctcttta tcatcttcga ggcacgacga cgagcgcgat tcgtaataat
261421 acgagcgtat acctttggc gtccaatctc tttcatctac acgtcgcgat gcttcacgac
261481 gaaaagacct ttctcgatag cggagaaggt tcctcgggca ttctcggcga tcctgcgggg
261541 gcgatgaacc agtagaaaat tttttagtg aaggtgtcgc acatcgtgcg aatacatctc
261601 ttgacgtaac aacacggaga ccatatccat acgcagagat cttcgcacca gtcgttgacc
261661 caggttcccc gtctggcggg atctcttgaa tctctaaacg ctcccggttc tcttactccg
261721 gtcagtctgc ctctatgcat tcttctcaac atcatgcaag gaaagaggag acacctcaag
261781 aaaacctcgc aagggcaaca gaaacaacga caccaagatt tagctaacgg gcagatggtt
261841 cttttacaga atcttctggt gagaacgcac ggtagcctaa tacagtcgca agtcgctttt
261901 agagtaggta atatcacgcg tctccagaac tctctgataa tcaatagagg aagcacgcaa
261961 cagtaacaac aactgtgttc cagagagtct aacgtctcgc tcatgcattc gcaacatact
262021 tcgaagggat acaagagaca gtggacgcat ttgcaagtgg cgggccttac cgagttacag
262081 aggaaacatc gtagaaggca tagcggatac aataaccacg ccgctatttt ctctacgatc
262141 atatcggcgt ctcgatttaa cttctcgagc tctcgataaa aaaaagcttt tcgaaatctc
262201 gataaaaaag tttttctata actcgagctc tcgataaaaa agtttttcta taactcgagc
262261 tctcgataaa aaagtttttc tataactcga gctctcgata aaaaactttt tctataactc
262321 gagctctcga taaaaaaagc ttttcgaaat ctcgataaaa acttttttcta taactcgagc
262381 tctcgataaa aaagtttttc tataactcga gctctcgata aaaaagcttt tcgaaatctc
262441 gataaaaaact ttttctataa ctcgagctct cgataaaaaa gtttttctat aactcgagct
262501 ctcgataaaa aagcttttcg aaatctcgat aaaaactttt tctataactc gagctctcga
262561 taaaaaagtt tttctataac tcgagctctc gataaaaagt ttttctataa ctcgagctct
262621 cgataaaaaa aagcttttcg aaatctcgat aaaaaagttt ttctataact cgagctctcg
262681 ataaaaaagt ttttctataa ctcgagctct cgataaaaaa gcttttcgaa atctcgataa
262741 aaactttttc tataactcta gctctcgata aaaaagtttt tctataactc gagctctcga
262801 taaaaaagtt tttctataac tcgagctctc gataaaaaag tttttctata actcgagctc
262861 tcgataaaaa actttttcta taactcgagc tctcgataaa aaactttttc tataactcga
262921 gctctcgata aaaaaagctt ttcgaaatct cgataaaaac tttttctata actcgagctc
262981 tcgataaaaa agtttttcta taactcgagc tctcgataaa aaagcttttc gaaatctcga
263041 taaaaacttt ttctataact cgagctctcg ataaaaaagt ttttctataa ctcgagctct
263101 cgataaaaaa gcttttcgaa atctcgataa aaactttttc tataactcga gctctcgata
263161 aaaaagtttt tctataactc gagctctcga taaaaagttt ttctataact cgagctctcg
263221 ataaaaaaaa gcttttcgaa atctcgataa aaaagttttt ctataactcg agctctcgat
```

FIG. 19T3

```
263281 aaaaaagttt ttctataact cgagctctcg ataaaaaagc ttttcgaaat ctcgataaaa
263341 actttttcta taactctagc tctcgataaa aaagttttc tataactcga gctctcgata
263401 aaaaagtttt tctataactc gagctctcga taaaaaagtt tttctataac tcgagctctc
263461 gataaaaaag tttttctata actcgagctc tcgataaaaa actttttcta taactcgagc
263521 tctcgataaa aaaagctttt cgaaatctcg ataaaaactt tttctataac tcgagctctc
263581 gataaaaaag tttttctata actcgagctc tcgataaaaa agcttttcga aatctcgata
263641 aaaacttttt ctataactcg agctctcgat aaaaaagttt ttctataact cgagctctcg
263701 ataaaaaagc ttttcgaaat ctcgataaaa actttttcta taactcgagc tctcgataaa
263761 aaagttttc tataactcga gctctcgata aaaaagcttt tcgaaatctc gataaaaact
263821 ttttctataa ctcgagctct cgataaaaaa gtttttctat aactcgagct ctcgataaaa
263881 agtttttcta taactcgagc tctcgataaa aaaaagcttt tcgaaatctc gataaaaaag
263941 tttttctata actcgagctc tcgataaaaa agtttttcta taactcgagc tctcgataaa
264001 aaagcttttc gaaatctcga taaaaacttt ttctataact ctagctctcg ataaaaaagt
264061 ttttctataa ctcgagctct cgataaaaaa gtttttctat aactcgagct ctcgataaaa
264121 aagtttttct ataactcgag ctctcgataa aaaagttttt ctataactcg agctctcgat
264181 aaaaaacttt ttctataact cgagctctcg ataaaaaaag cttttcgaaa tctcgataaa
264241 aactttttct ataactcgag ctctcgataa aaaagttttt ctataactcg agctctcgat
264301 aaaaaagctt ttcgaaatct cgataaaaac tttttctata actcgagctc tcgataaaaa
264361 agtttttcta taactcgagc tctcgataaa aaagcttttc gaaatctcga taaaaacttt
264421 ttctataact cgagctctcg ataaaaaagt tttttctataa ctcgagctct cgataaaaag
264481 tttttctata actcgagctc tcgataaaaa aaagcttttc gaaatctcga taaaaaagtt
264541 tttctataac tcgagctctc gataaaaaag tttttctata actcgagctc tcgataaaaa
264601 agcttttcga aatctcgata aaaacttttt ctataactcg agctctcgat aaaaaagttt
264661 ttctataact cgagctctcg ataaaaagtt tttctataac tcgagctctc gataaaaaaa
264721 agcttttcga aatctcgata aaaaagtttt tctataactc gagctctcga taaaaaagtt
264781 tttctataac tcgagctctc gataaaaaag cttttcgaaa tctcgataaa aactttttct
264841 ataactctag ctctcgataa aaaagttttt ctataactcg agctctcgat aaaaaagttt
264901 ttctataact cgagctctcg ataaaaaagt tttctataa ctcgagctct cgataaaaaa
264961 gtttttctat aactcgagct ctcgataaaa aactttttct ataactcgag ctctcgataa
265021 aaaaagcttt tcgaaatctc gataaaaact ttttctataa ctcgagctct cgataaaaaa
265081 aagcttttcg aaatctcgat aaaaaagttt ttctataact cgagctctcg ataaaaaagt
265141 ttttctataa ctcgagctct cgataaaaaa gcttttcgaa atctcgataa aaactttttc
265201 tataactcta gctctcgata aaaaagtttt tctataactc gagctctcga taaaaaagtt
265261 tttctataac tcgagctctc gataaaaaag tttttctata actcgagctc tcgataaaaa
265321 agtttttcta taactcgagc tctcgataaa aaactttttc tataactcga gctctcgata
265381 aaaaaagctt ttcgaaatct cgataaaaac tttttctata actcgagctc tcgataaaaa
265441 agtttttcta taactcgagc tctcgataaa aaagcttttc gaaatctcga taaaaacttt
265501 ttctataact cgagctctcg ataaaaaagt tttctataa ctcgagctct cgataaaaaa
265561 gcttttcgaa atctcgataa aaactttttc tataactcga gctctcgata aaaaagtttt
265621 tctataactc gagctctcga taaaaagttt ttctataact cgagctctcg ataaaaaaaa
265681 gcttttcgaa atctcgataa aaaagttttt ctataactcg agctctcgat aaaaaagttt
265741 ttctataact cgagctctcg ataaaaaagc ttttcgaaat ctcgataaaa actttttcta
265801 taactctagc tctcgataaa aaagttttc tataactcga gctctcgata aaaaagcttt
265861 tcgaaatctc gataaaaact ttttctataa ctcgagctct cgataaaaaa gtttttcgct
265921 aacgttgggt agctttataa aatattttcc ggaaggaaat tagatatagt attattttat
265981 gtaaaaccgt atggtttttt ttattaaaac aataatatat attttaatag gggtattttt
266041 acaccttaac aaattaaggg gtaaaagaat gtgtatatta gggttttgga aggtactgtt
266101 tatacatttt ttttactata taaatactca tcgtaagatg agggt
```

FIG. 19U3

SEQUENCE LISTING

<160> NUMBER OF SEQ ID NOS: 41

<210> SEQ ID NO 1
<211> LENGTH: 266145
<212> TYPE: DNA
<213> ORGANISM: Artificial Sequence
<220> FEATURE:
<223> OTHER INFORMATION: Fowlpox virus genome

<400> SEQUENCE: 1
accctcatct tacgatgagt atttatatag taaaaaaaat gtataaacag taccttccaa 60
aaccctaata tacacattct tttacccctt aatttgttaa ggtgtaaaat acccccctatt 120 aaaatatata ttattgtttt aataaaaaaa accatacggt tttacataaa ataatactat 180
atctaatttc cttccggaaa atattttata aagctaccca acgttagcga aaaacttttt 240
tatcgagagc tcgagttata gaaaaagttt ttatcgagat ttcgaaaagc tttttttatcg 300 agagctcgag ttatagaaaa actttttat cgagagctag agttatagaa aaagttttta 360
tcgagatttc gaaaagcttt tttatcgaga gctcgagtta tagaaaaact tttttatcga 420
gagctcgagt tatagaaaaa cttttttatc gagatttcga aaagcttttt tttatcgaga 480
gctcgagtta tagaaaaact ttttatcgag agctcgagtt atagaaaaac ttttttatcg 540
agagctcgag ttatagaaaa agtttttatc gagatttcga aaagcttttt tatcgagagc 600
tcgagttata gaaaaacttt tttatcgaga gctcgagtta tagaaaaagt ttttatcgag 660
atttcgaaaa gctttttat cgagagctcg agttatagaa aaactttttt atcgagagct 720
cgagttatag aaaaagtttt tatcgagatt tcgaaaagct ttttttatcg agagctcgag 780
ttatagaaaa agtttttat cgagagctcg agttatagaa aaactttttt atcgagagct 840
cgagttatag aaaaactttt ttatcgagag ctcgagttat agaaaaactt ttttatcgag 900
agctcgagtt atagaaaaac ttttttatcg agagctagag ttatagaaaa agtttttatc 960
gagatttcga aaagcttttt tatcgagagc tcgagttata gaaaaacttt tttatcgaga 1020
gctcgagtta tagaaaaact tttttatcga gatttcgaaa agcttttttt tatcgagagc 1080
tcgagttata gaaaaagttt ttatcgagat ttcgaaaagc tttttttatc gagagctcga 1140
gttatagaaa aagtttttta tcgagagctc gagttataga aaaacttttt tatcgagagc 1200
tcgagttata gaaaaacttt tttatcgaga gctcgagtta tagaaaaact tttttatcga 1260
gagctcgagt tatagaaaaa cttttttatc gagagctaga gttatagaaa aagtttttat 1320
cgagatttcg aaaagctttt ttatcgagag ctcgagttat agaaaaactt ttttatcgag 1380

-continued

```
agctcgagtt atagaaaaac ttttttatcg agatttcgaa aagctttttt ttatcgagag   1440
ctcgagttat agaaaaactt tttatcgaga gctcgagtta tagaaaaact tttttatcga   1500
gagctcgagt tatagaaaaa gtttttatcg agatttcgaa aagctttttt atcgagagct   1560
cgagttatag aaaaactttt ttatcgagag ctcgagttat agaaaaactt ttttatcgag   1620
atttcgaaaa gctttttttt atcgagagct cgagttatag aaaaactttt tatcgagagc   1680
tcgagttata gaaaaacttt tttatcgaga gctcgagtta tagaaaaagt ttttatcgag   1740
atttcgaaaa gctttttat cgagagctcg agttatagaa aaactttttt atcgagagct   1800
cgagttatag aaaaagtttt tatcgagatt tcgaaaagct tttttatcga gagctcgagt   1860
tatagaaaaa cttttttatc gagagctcga gttatagaaa aagtttttat cgagatttcg   1920
aaaagctttt tttatcgaga gctcgagtta tagaaaaagt tttttatcga gagctcgagt   1980
tatagaaaaa cttttttatc gagagctcga gttatagaaa aacttttttta tcgagagctc   2040
gagttataga aaaacttttt tatcgagagc tcgagttata gaaaaacttt tttatcgaga   2100
gctagagtta tagaaaaagt ttttatcgag atttcgaaaa gctttttat cgagagctcg   2160
agttatagaa aaactttttt atcgagagct cgagttatag aaaaactttt ttatcgagat   2220
ttcgaaaagc ttttttttat cgagagctcg agttatagaa aaactttttta tcgagagctc   2280
gagttataga aaaacttttt tatcgagagc tcgagttata gaaaaagttt ttatcgagat   2340
ttcgaaaagc tttttatcg agagctcgag ttatagaaaa acttttttat cgagagctcg   2400
agttatagaa aaagttttta tcgagatttc gaaaagcttt tttatcgaga gctcgagtta   2460
tagaaaaact tttttatcga gagctcgagt tatagaaaaa gtttttatcg agatttcgaa   2520
aagcttttttt atcgagagct cgagttatag aaaaactttt ttatcgagag ctcgagttat   2580
agaaaaagtt tttatcgaga tttcgaaaag cttttttat cgagagctcg agttatagaa   2640
aaagtttttt atcgagagct cgagttatag aaaaactttt ttatcgagag ctcgagttat   2700
agaaaaactt ttttatcgag agctcgagtt atagaaaaac ttttttatcg agagctcgag   2760
ttatagaaaa acttttttat cgagagctag agttatagaa aaagttttta tcgagatttc   2820
gaaaagcttt tttatcgaga gctcgagtta tagaaaaact tttttatcga gagctcgagt   2880
tatagaaaaa cttttttatc gagatttcga aaagcttttt tttatcgaga gctcgagtta   2940
tagaaaaact ttttatcgag agctcgagtt atagaaaaac ttttttatcg agagctcgag   3000
ttatagaaaa agtttttatc gagatttcga aaagcttttt tatcgagagc tcgagttata   3060
gaaaaacttt tttatcgaga gctcgagtta tagaaaaagt ttttatcgag atttcgaaaa   3120
gctttttat cgagagctcg agttatagaa aaactttttt atcgagagct cgagttatag   3180
aaaaagtttt tatcgagatt tcgaaaagct ttttttatcg agagctcgag ttatagaaaa   3240
agttttttat cgagagctcg agttatagaa aaagtttttt atcgagagct cgagttatag   3300
aaaaactttt ttatcgagag ctcgagttat agaaaaactt ttttatcgag agctcgagtt   3360
atagaaaaac ttttttatcg agagctagag ttatagaaaa agtttttatc gagatttcga   3420
aaagcttttt tatcgagagc tcgagttata gaaaaacttt tttatcgaga gctcgagtta   3480
tagaaaaact tttttatcga gatttcgaaa agcttttttt tatcgagagc tcgagttata   3540
gaaaaacttt ttatcgagag ctcgagttat agaaaaactt ttttatcgag agctcgagtt   3600
atagaaaaag tttttatcga gatttcgaaa agcttttttta tcgagagctc gagttataga   3660
aaaacttttt tatcgagagc tcgagttata gaaaaagttt ttatcgagat ttcgaaaagc   3720
```

-continued

```
tttttttatcg agagctcgag ttatagaaaa actttttttat cgagagctcg agttatagaa   3780
aaagtttttta tcgagatttc gaaaagcttt ttttatcgag agctcgagtt atagaaaaag   3840
tttttttatcg agagctcgag ttatagaaaa actttttttat cgagagctcg agttatagaa   3900
aaactttttt atcgagagct cgagttatag aaaaactttt ttatcgagat ttcgaaaagc   3960
ttttttttat cgagagctcg agaagttaaa tcgagacgcc gatatgatcg tagagaaaat   4020
agcggcgtgg ttattgtatc cgctatgcct tctacgatgt ttcctctgta actcggtaag   4080
gcccgccact tgcaaatgcg tccactgtct cttgtatccc ttcgaagtat gttgcgaatg   4140
catgagcgag acgttagact ctctggaaca cagttgttgt tactgttgcg tgcttcctct   4200
attgattatc agagagttct ggagacgcgt gatattacct actctaaaag cgacttgcga   4260
ctgtattagg ctaccgtgcg ttctcaccag aagattctgt aaaagaacca tctgcccgtt   4320
agctaaatct tggtgtcgtt gtttctgttg cccttgcgag gttttcttga ggtgtctcct   4380
ctttccttgc atgatgttga gaagaatgca tagaggcaga ctgaccggag taagagaacc   4440
gggagcgttt agagattcaa gagatcccgc cagacgggga acctgggtca acgactggtg   4500
cgaagatctc tgcgtatgga tatggtctcc gtgttgttac gtcaagagat gtattcgcac   4560
gatgtgcgac accttcacta aaaaaatttt ctactggttc atcgcccccg caggatcgcc   4620
gagaatgccc gaggaacctt ctccgctatc gagaaaggtc ttttcgtcgt gaagcatcgc   4680
gacgtgtaga tgaaagagat tggacgccaa aaggtatacg ctcgtattat tacgaatcgc   4740
gctcgtcgtc gtgcctcgaa gatgataaag agaacgcgag taaggaaata caagataaaa   4800
acaaactgtc gattctacgt aatacgattt ctaaaacggc gtctaccgca atctttttca   4860
tcagagtaag ggataggtta agattcttaa ggacctttat caaaactatc ggagaaaaac   4920
tttacgctaa agccgctctc atgctctttc acagactggt gacctatagg cttcctatcg   4980
ttagggatat agtcccgttt tattacgcga ggaaaaattt ttggaggttc gcttttctat   5040
atctcatgaa gaaagtcgct gttcgtccta ctaaaaacta atgctaaaaa aaaatctatc   5100
gttaataaat taaaagttat cgggttttga atattattaa tctatgcata cgaaaccgta   5160
cgtcgcgtta cacggggaga atccgaacgt tttcccgtcc gtataggcac acttacccac   5220
ttctggtttc ttgtcatccc ttatccacaa actctgcccc ataccgaatt tgcttatgaa   5280
tttcatgtct ttttcattgt ctattagact acgtctagct aacgtaccca tgggaaacgt   5340
tatcaaacac gtagtcgacg cttcgctgta agttttttttg tgatgcattt tatctaatcg   5400
gtttacccag atacacttat tgttgtaaga ggtgtacggt cctctgcaat ttagagagtt   5460
agcgcaatcc aacattaaca acatcgctat caagattaat gatttcattt tgatacacgg   5520
atcaatttta atagtctata gagatatacc ccaccaatag ttacgcgatt aattttcaat   5580
tatacataat aaaaatctag aggagttgcc atgtgattct ctgtcgacga cgttacctcg   5640
ttagttttat taattcttct ttaagttctg acgacggtta tataccaaaa cagcttttac   5700
ttttcgtaag acgataatta cgttataaaa gattaagaaa ttttattttt actaaagtat   5760
catgaataat gacacgatat ttactttgtt ttattgtaaa aataaaaaat atgttcgtgg   5820
ggaggggggga aggaggagag ggaagacggg tatcctttta ttccatccaa taaaccaccg   5880
tgttatagga actagtgcac atcagtgtta taaaacacga agaatcggtt tcaaactcta   5940
cgcagttgcc cctcgtcacg tatccactat ccgctgtggg agatcccact cggctcaccg   6000
agtagataag ttctccttct ccttccaaaa agtagatttt cactgtatcg ccggcagcgg   6060
cgcataggta tctggcccta cagaattcca tattcctgat agctcgcgcg acgaagcctc   6120
```

-continued

```
cgtcgcccgt gtgatcattt tcataattca agggatccga cgcggctgcc aagaccttta   6180
tacccgactc ttgttctact ggacgaacgc ggagatttaa agccatggct gacgtatagt   6240
cgaggacgcc ctcggtaata aattgattat attttcagtt ttaaaaaatt aatttatatg   6300
tactcaatat ccttatatag aattatttta tctcttctga tatacgttag gtagatgccg   6360
ttcaaataat aaaatatctg atgacgtttt tatgcgcgtg ttacgttatt ataatagata   6420
atagaaataa acgttaaaat aataattaat tatcttttca gttgttaaat atattctagt   6480
tttataagcg ttattcatat ataaaaaata taaaaactaa atcgtattta ttatgatgct   6540
acggcggtca tttaacaaat ttacgcgatg gagttcggtt gtacgggaac taataaccag   6600
ttggccgttc acagatttac agaaacgcgt tttacatctt tcaaaaaaga acttttagtt   6660
aatttaggaa taagtgactt aaatgatata aaaaacatat gcgaggattc taaaatattc   6720
tttccggaaa agagaacgga gctcttaagt attaaagatc gtaaatctaa acaaatagtt   6780
ttcgaaaact ccctaaacga tgacttgctt aaaaaattac acgccttgat ctatgatgaa   6840
ttaagtacgg tagtagattc cgttaccgta gagaataccg ttacattgat tatgtatgaa   6900
aaaggagatt actttgccag gcatagagat tttagtaccg tcttttctaa aaacataata   6960
tgcgttcacc tgcttctata tttggaacaa ccagaaacgg gaggtgaaac ggttatatat   7020
atcgataata atacgtcagt gaaattaaaa acagatcatc tatttgataa aactatagaa   7080
catgaaagta ttaccgttga aagcggtaga aaatgcgtgg cgttattcga tgtcttacta   7140
gaaaaaaagt tatccgcgtc aacaaacgta ataggtagca tagaatactt aggtaaaaaa   7200
ataaatttat atgacagaga aaatgatctt cagttgtgtt attgtgatat ggtaatagaa   7260
agaatgacag aagataaaga atatagccta ggaatgatat ctgatagatc aggtagatgt   7320
ataaaatctc atcataacgg tagtattgtt agataccgta aagaagaata tggatctttc   7380
gatgctctat gtatatataa catgaatgaa gtggatgaaa tttggactgg tgataagaaa   7440
catattatat ggtctactat tgataaaaaa acaggaacgt cttttatacc tatagatcct   7500
gtactttacg aaaagttaaa agctatttct tctaaagagc ataaagaata caaagatttg   7560
agagggtttt gtaatagcag aacggagtat atttgttgtt cggtatctaa gtactatttc   7620
gacttaccta caaaaacaga tttaatacac gaggtgatta attctatcga ttatgatact   7680
aagtcagtgg gtacacccga ctggtatact ctgcctatag aagttaaaca aactatccta   7740
ggtaatatgt cttacgaaga gttatttaat atagtaagag gtaatatagc tcttgaagaa   7800
gacaatgaat atggctgtga ttaacattaa tggtaatact tttctaaaaa ctaatctcaa   7860
gtattgttta caagcgactg aagtaatagt tttagcaaaa taatacettt actgttagtt   7920
ctacaatcga aattatgctg taacatgagg taaggatata tttattaata cgttacatct   7980
ttcgaaagac tttgatcgta gtataatatt atacatctgc tctacttatt atacataaga   8040
aaatttgtat tttatttagt gcgctgataa atcgtgttta aagtatacaa cggacgtcta   8100
tttccaaaaa atctgcgcgt gttaacggat taaaatctac atgaaaatat ctcttaaact   8160
ttatttctac gtataacaaa caacagactg attttatata ttacgaataa ctattttctt   8220
aggtttttta tatagatgct atacagtgtt tttacgcgta tatacaaaat acggaaaaat   8280
aataaaacag aaatgattct ggcaatatac gaccgcaatg cctatattgt taaaaaaaca   8340
ggtatcggaa gtatcttgtt acgcgataac ggtactagga atactatgct taatattatt   8400
tacgatacta gtagtcgtaa catgcaaatg gtattacgcg tttccgtact ttagcaaggt   8460
```

-continued

```
atgtcctgat gagtggatag gatataatag taaatgctac tactttacta tcaatgaaac   8520
taattggaat gatagcaaaa aactatgcga tgttatggat tcttcattga taaggttcga   8580
taacatagaa actctaaatt tcgtgtcgcg atacggtaag ggtagttact ggatagacat   8640
aaatcaaaat agaaaaattc cgggtattaa tttctcacta tattatgaac aaggcgttaa   8700
tgatatttgt ctattatttg acacgagtaa cattatcgaa atgtcttgta tatttcacga   8760
aagaacgata tgtgttaaag aagatagata cacccattgg tataccgaat acatgcgtta   8820
gatttactac ctctttttta tacaatagta ttttgtacgt tcttgtaaac agaaaatccg   8880
tatagtttat atttttaatc aaagtaataa cgaatatctc gatgtcacgt ataaacgcag   8940
attctagata ttaaattctc aacgtacgtc atttgcattc cctgagatga tactttgcta   9000
ttttattata ccgtagtcta tacaaccact acaaagttaa acgaagtaaa attattgatt   9060
cgttgttatt atttcagcac agtagtactc gctatcttcg tttaaatcta ataacacgcc   9120
ctttgaaaca tttttgtgct agataataat acgttattat tacactaacc tgtatttctt   9180
ctaatcttta aggtgtgcta acgatatatc acgggattaa aaggttatta gtagtcgtat   9240
aacaacataa taatagcaca tctgtatatt tatatacctc tcgagtacat aaaaataata   9300
tgttttgata aaacgtaaat caataagtgt ataaggtatt atttctttta atgaagaaat   9360
aggacgtaat gtctaaatca gatttatatt cccgaaaata tttttcttag atgtatatgt   9420
tagttaaatt acgtgattat attataagtt atctgcttac tttaacatta tatagtaatt   9480
atatactaac cgatcttaac acttccgtac aaagaggtat gcccgcatct gcgagatatt   9540
gtgattttcg tatttagata tgtgaatata gttatctact aacgcgactt tcctccaatt   9600
tacaaagctc taaggaaaaa aaataaaata atactaccac gttcctcttt taagagttaa   9660
ctatttactc ggaggtatcg gtatacatac aattctatat aatttagtta atcgcttttt   9720
acgcgcataa gtctacgtat aatgtctttg tttaagtaac tatccctgga atattcctaa   9780
aaatagcgga atttttgttt gtacgtcggc tactaggaac atgaaaggta cgttcgcttt   9840
tacgatagga attttcttta ttccgtctgt agtgcataat tcggtaacac tagctgcttc   9900
agttccgtat tcatctactt ttatcacaga tttttgcctg atattaccta tcctcaaagt   9960
ttttgtatcg gatataccta ctaattcacc tgacttgaat agatcattac atcccatatg  10020
gattagcgcg tctttcaagt ctacgtcatc ttctaattcg aatttaggta aataaagaac  10080
tatttctttc aaagtcatat cttttttaga tattatttta ttgatattct taccgttatt  10140
gagagaatca actactccat ctatacctgt aactgaatca ggtatgatta taaacataac  10200
aaatctataa tcttcgtatt ctaacataac tacctgactt cttatatctt catcatgctt  10260
atagtaaaac gcaacgtctt gtatcatcat cgtatctatc ataacatctg tcccgttata  10320
ttttttgaaa ggatgtttag aagttaattc tgtatcgaaa ggatatttcc atttagattt  10380
aaagtataat acgtttatga ttgccagtct tatatcatct gctagtgaaa tgctaaaatc  10440
tttaataagt cctctcgtag atagttctac ccatttattt atagtttccg atatagtatc  10500
atctgtaaaa ctgactacct ttgcgttgaa tatatcgtaa ctagagttta taaaatctct  10560
ttttataggg tatccttctt ctattaacat aatactctta tttatgagtt cgtccttgtc  10620
gtcgtaatac tctacgtaat attctgactt atcaggtata ggaacgtagt taccaaatat  10680
tcctaataga tcttttattt tatccctcgt ctctttttta catcctatca tgatgttcat  10740
tagtatagta tatacccctc taggggaaat acatatgtct tttccaggga catatagttc  10800
ttttaataat cttactaagg aacccatcgt caactaatta tttaacaaac atatacttat  10860
```

-continued

```
atttccattt ctatgtaata tgtatatacg aagagtcaat aaaaacatta ttttactcta  10920
cctcatcttc aaatgtagct tttcttattg ttaacaacat agacattagt gcttcatcta  10980
tagtatttcc gtgatcatac tcctcgatag cacttgtaaa agtttcaatg tttttagttt  11040
cgcacgctgc taatatcttc tctatgaact tacattcctt aaaatctttg aacgcgggaa  11100
aaatatcttt atatttatct agagaacgtt tagcacgtga tacgtcagaa cacagataac  11160
acatgatagc ataaagtaat tgatgtctgg attcgtattt tgacaacata gtgttcattc  11220
tattatatcc cacttgttca aaaattttac cagccctgtc aaaatcttct ttttgtatag  11280
ataacctagc aattagcaac atacaatcat ccgatagttt attatatcct tcaccgccat  11340
aatatccaga tgcattctca tagtgaaata ttgctttatc tagttctaat atatcattct  11400
cataaatcgc ggctatattc atgtgacatc tcgcaactgt ataaaacttt cctaaacaag  11460
tatatacctc tatagcttta gatagacagt ttatagcttc ataactatct atcttcttaa  11520
atgcgtttgc ggcatctaca aaactcgaag ccgcggcaat agaattttta ttcttttgca  11580
atagcatatc acctgattta aaaaatgctt tacccgcaca ctcccataac tgtacggacg  11640
caaaaagatt agcagcgtga cttaccatgc cggcggcttc ttctatttct ataggtggcc  11700
caaatagatt cttaaaaaag gacttacctt taattttatt ttctgcatct tctaaaatct  11760
tggttgcttt ttgttctact tctttgcgat ccatctatac taactactat aacctcattt  11820
atatttacat attatacata tgcgataatc tgtataaaaa taaatctctg ttatcgagta  11880
ctgtatttct ataggaaaaa atctccaata actgagtcga aggacatcgt gtaattaatt  11940
tatttaggga tatttctatg gaatttagta tctcgtctat acctgatatt acttttatct  12000
tctctatata ttttaaaatc tgccgtgtct agtctcgtta ttacaggatt cctcgcagtt  12060
tagaatttaa aatctccatt accgaacatt agtaaaccat agcttgaatt aagttttatt  12120
tcgtatatag ttttcagttc tttctcacag gtgtgtcata aatgttctta gcagtgcaga  12180
agaatttatc ttattcatat taagttcaaa accttgtact tattttcttc cgaacctacc  12240
ttttcttata gtaattatta atattggtaa taggaacatc gtatccagaa catacgtatc  12300
acatatgttc gttattttat aaagcatgta catatcgttg tttctatgtc tagtggaata  12360
catggtggat tacatactat taataccata tactttatca acaatttatc tagagtgtga  12420
caaccgcaag gtcattttat tattcctgta atattagata acaagaaagt atctagatca  12480
tgacctctct tttaccttat cgaatatatc gtataagttc taagtaaact cggcattaat  12540
gactctataa tgttggcaag aaacctcgaa cgggtattaa tatgaaatgc agtcatatta  12600
acgcgataat aaaaattaca ttctcaaact atcatccatc gcttactata ttatttctac  12660
tttataaaat cggttaacca gtcttattat taactttaat agcgtcattc aagatcaatt  12720
tttttatatt atcgttatta agtttactta atatattcaa tttacccttt aatggaagta  12780
aacaccattc tgtatttaac gatgataaat tacaactatt aacacgtacc gcggaacaca  12840
gcaactcttt cctatatctg cccatttcta taatcttatt catcgtataa ccgtaaatac  12900
gtaagttgct ttgagattct ataagcttat ctagaaaggc gacaaaactg ttatggtcta  12960
tgtctttaat atcttccaag atacatattt caaaaaggct tttatcacct atccctctag  13020
tagtcatgaa agctatttcg gatttacatt tcagcgcaac ttctagtaat ctactatttt  13080
ttgcaatagc cgctatattc ctattaaaac cttctatatt aaccgttata gatgctttaa  13140
attttgaaat aattatataa ggtacaagat taaggatagg tatcttgtat tcgtcaaata  13200
```

-continued

```
agttaataaa atattccatg attgtataag ttacctgacc tatgttaata atctggttac  13260
agttagcccc tctatccatc aataacttaa gaatagtagg tctatagtaa ctaattattc  13320
ttacaagagg agtaataccg tatttgttaa catagttagg attagcaccc tcatctaaca  13380
aaacattaca cgttttaata tctccagtac atatcgctat taatagagcc gtataaccat  13440
cattagtctc tttatctaca ttagctccgt atcttatcaa tcgtcttatt atttttatat  13500
tgcccgtttt agcggcaata tgtaacggag tgtaggaatc tacgttcggt gtattaggat  13560
ttacaccttt atacaataac tcaaccacct tttttatatt acctttagca gtttccttat  13620
ataaagaagt atatccatcg ttattgacac cgtccatttc tgtatccatg aatacaatag  13680
attagttata ttctatgtaa taataacgat tacatgtata taacatatac tatttctatt  13740
ttcttatgtt atataaaaaa gttatttatt tacataataa gacttttcat atcagtattt  13800
tctagtcttg agaatatata gtgttttatt ttagagtaat ctattaccca tacacggcct  13860
tccgaatctt aaatatttat ctgttaaggg tattgcattt tgtagtttca tttttcttgt  13920
tgacgctatt ttaataatac gaggcatggt gtatttatat gattttgcgt tttactatcc  13980
tattatagga tcttgcgaac gcatttttac cgtattgtag ttttagtgta tagatattat  14040
acagatttga tttatctatt atatcgcttt ccatgtgtat aagctattta ctattattcc  14100
acggctattc tcagaagtgg ttcacgccct ttctttaaca ggaccttgca catttccggg  14160
tttaataact aatactaaag acgtattaac ttttccatct tctatattag gattagttgt  14220
tttatacttt cttctattat aattgagttg ttgtttttac gtcaagaagg agctagtata  14280
tccatggtga gaatatcgga gtctgcaccg ctttgtagta atagtcttat tattttagcg  14340
ccgttaaagt ttacatctaa gtggggtagt attattatct agagttatag cattgtgtaa  14400
ttctttttc cgccgtgatt tatcctgatc cgggtaggaa ttgagcaact ctatagcttc  14460
attgcttttg attataacca aatccatatg agaaggatac cagtcagtcg taactcttgt  14520
tttcattttt catggataat ataaaaatat tctaacaata agggagatct tcttcatcta  14580
ttttttctaa gatatcatac ttaatcccta atggaagatc tgaccaatct ttcaatccat  14640
tatcctttac attccgattt ttttcaaacg ccttttccat gacatcaaga gccttgtcca  14700
gagattcgtg tctcagcaat cctctttcga tggtatattc tattagttgc ctgtaaatga  14760
agaatccttc acaagatata caatttaagc attttgctat ggcattgtca tcgcaattga  14820
gacataagtc taatagggaa cgtctatcag aacctaaagt agtttttctc attttctcta  14880
cttcttctat acaggaatct ttccaatctt tcatttcatt gttagattct attatctcga  14940
gatcatttct tctagcttct tcgttaatca ctttgtggta cttatattct gtgtttataa  15000
ccattgttga tattatttgt ttagctattt ctattcctgt gtcggagttt aaatcacaaa  15060
ctgaaagagg tgtatttctc cctgatgaaa cagaagtatc tgcccagaag tccaacaaaa  15120
cttttacgat atcgagttca gatgcgttag ctgcgaggaa taaaggtgtt cttccgcaaa  15180
agtcttgaac ttctacgcta gcgccgtgtt ccaacagcgt aagtaccata tctgcagaac  15240
cttccattac cgcgtgatga agggaactaa atgaaagttc atcttcgaca tcaggtaacg  15300
cacccctgga gagcaattca actactaatt cataattgcc agatcttata gcatgatgga  15360
tggtgtaaac agatcccata ctccttgaat taatcctggc tccggcatct attagaagct  15420
tacagatttc aagatttcca ttagcggctg cgtcgtttat agggcaatta aacctataga  15480
tatcttctgc atcagcgcca taatctaata acgttttagt catctttaca tcattgagct  15540
taacagcata ttccagggga gtacgacttt cgtggttttc ataattatca ggatcaacat  15600
```

-continued

```
tgaattccat taacaggtta actatatcat aatgtcttaa tataacagct ctatgtaatg  15660
ctgtaggcgt agactcggtg tacagatcag gatttgcacc ttcgagtaac agaattctag  15720
ctatttcagt atttccattt tctacggcgc agtgcaaaag ggaacatcca tattcattaa  15780
ccatattcgg gtccgagtca ttgcctttta aagctttaat aacatcagaa acacagccag  15840
attcgatagc ctcaaatacc tccatgttgt ataatattgg tagtatccgt gtagatacac  15900
cggatgtacc aagcgatata aaaataatta aaatttcaat ttatttaaca ttagtatgtt  15960
tatttcataa tgtcattatt agtatttagt agttagcaag tgccatatta caactaataa  16020
gatcaaaaat aaaactgctg atgtataatt tatacccata aagaaattat ttataaaatc  16080
ctccgccata gaaataataa aatgacataa ccaattcatt tacaatgttt atttattcat  16140
ttatttatag gtatctatta ataagttaaa tatttttaca agagtaaaca cgatttaata  16200
aaatctaata taatataaat atatttcaaa taatataaaa tgtatatagt tagtaattgt  16260
cttttaattt ataacaaaat aaaatctaat agagtaatat ctttttagtt tcatatacat  16320
cattaggatt tacacattta actaggtttt caggttcata acttctataa tctctatagt  16380
ctctataatt atcataagta ggcttaaaca tttcttcttt attgacattc ttacatttgt  16440
tggtatcggt catgttggat ttcaaatctt cattatatac taaaggtgcc attgccaaac  16500
agaactctga cataggagac agtttttcta cataaaattt accttcaccg tctaccatat  16560
taaggatttc atctcttgta gtatattgag tacatccaga aacatattcg gtatcaggat  16620
gtagacatcc tatgaatata ttgaatatta tacatgatgt cataaactta catttagtat  16680
cgtaatcgaa agcctttaat atcgattctg gagtaggtct agttccattt acctgcatga  16740
ataccatgct attagtaatc ggagttactt cattaaagca tgatttgatt tcactactta  16800
tttcgcgtag tataaccatt attgtaaatt ttagtagtta tatattactc aaaagaaatt  16860
accatttact agttaattta taaaacagag agtattaata attcacttat atattactca  16920
aaagaaatta ctatggttca atgtatagac atatagaagg aataattaat tcaaaatatt  16980
tataaaatag tattctacca tcttccgtaa acatctttgt attctgttac tatgtattcc  17040
tttccttgtt cttttccgac gtaatgtact ggaaattctc tagcgtgtgt attattaatc  17100
caatatctgc aatatggcgt ttcaacatga ccgactacac tttcgtttac ctttatactc  17160
gtgtatctgt aatactctac attttgtgta aaaccccgag gtatctcgta tgacataaca  17220
cctcccgtta ctataccggt tactatccat ctaggatcgc cgtgtttact tcctacaaaa  17280
caagttattg ttgtttcatt tctatgcttt tctactacat acgttatatc ttctttttga  17340
atttcggtac atctttgata cgtttcctct tttccagaag ccgtacgtag tacacaggta  17400
aagcacaaac tttgaggatc tggttttttg accgtaaaag tagaagtact tccactaaca  17460
gttacttcat acatatcttt ataaggacca ggaacataat tgaaagcgtt caacccgtaa  17520
ccgcctactt gttcttgagc taccatgata ttatcatcgc ctctccaagt agctctcgat  17580
atttcgtctc catctttggt tctacattgc aattttacag ggctatccgg taaatcttct  17640
tccccgtaga tattttttaa gataaatgat attataatag cgattgctat aaccatatag  17700
ttcattttca tattgattgt ttttatatca aacgctgaac aatatacgag gatgacatac  17760
tagatactat acttattcac ttttattaaa aatatgttaa tcttaaaaaa atcaaaaatt  17820
attccaacca cctcttataa cgggatttct ctccgtattc caaaaatgat cccgaaatca  17880
gaaccacgga aaggtcttga cgaggttctt tatcatcaca agatataata gatgctatat  17940
```

-continued aatctctact tagacccttg taacttacgg tgaatatcac ttcggtagtg aaatcagtat 18000
aatttttatt ggcgactact ttttcacatt catgatattt cttgtattct actaattgag 18060
tatcttcgct taacaccaca ccacccgctc tagcatccac ttttacttcg ctatcttcca 18120
tagttctagt cctgtttatt ataaaatcaa tcaaacctct acccacatca tctaccgcat 18180
aagcgtctac tcgaggcatt actctaagtt ctataatgtg tctgtaactc tctgtcttgt 18240
tgtaatagaa gatacatcta tagcgacctt cgtcatttct ggatgatctt ctcggaagct 18300
cgacgttata ttctttatct ggatcgttac aatagcagat actatcttct ccggcattat 18360
gtatgtcaat agttacctta aatgtgttgt ttttcaggtt tccttttata actaccagtt 18420
tagtcgcgtg tatgtcaggg ggtagaatac aagtcaaatt aactcttaca tcgttatgta 18480
ctaccattgt ataggaatta cattgtataa acgtagtcaa taagaataga gaaaatgagt 18540
atatctttcc gtacatgatt atctccagta atttttttac caagcactag tgattcaaca 18600
atagtgttag tgttatactt tatgtttttt tctaataata tccggaaatc gttttaagat 18660
cttccataga taaattcgat acaattactc tatgtatctc aggagataaa agccaccatc 18720
tactaagatg atctttacta gtgtattcat tgatgatcga taataccgac tctatagccg 18780
aatttctttt ttccatgtat tttatatgtt ttttaataaa acgacgaaat attattatct 18840
gtttaagatc tatccgtcgt atacgtttta tagtgttagc cagatcatcc agtttatcta 18900
atatcagaac atcgtacaag gatattttct tatcacccgt ataaaataca ttgtctttca 18960
taatagacaa ttcgttctct atttcgtctt ttaatgattt ggtttcttta tgattgttta 19020
cgaatctcat attacgtaca aaccccttgtt tattccttat agaagaatcg tttattacag 19080
aaaagtatag gtatatcgca gctaggaata cagcaggatt atcatgagtt ttatgaatgg 19140
taatgggagt atgaaatcta ttcataaaac acatatccgc tccgtgttct agaagtactc 19200
gagtacactc tttactctta ttgcgtatag cgtatgttaa tgcggtattt ttatcataat 19260
ctgtttgatt aacgtcggca ccattagcta ataagtattc catattactt actttaccct 19320
ctctagaaca aatcattaaa ggtgttatac cgtaattatc cctttcgtta acattagctc 19380
cgttcttgat taatactttt atattaccga tcttagaata catacaggct aaatgtattg 19440
gtgttttacc gtatctattt cttacgttta catcggcacc tttattaata agtagtctag 19500
taagccttga ggtatttata gaaacagccg cgtgtatagg atacatatta caagcatcgc 19560
acgatacgtt tatatcattt atcttttttta atagttttct tgtaattggc aaattcctta 19620
attcgtatat acacatacaa agtatagaaa taggtagata attaacaggc aaactaagta 19680
tgtatgagat aatgctataa taccgtttac atattgcttc tattagtata tcgttacaac 19740
accttattcg agctccgttc ttaaccagaa tattgaataa ttttacaccg tgtttactag 19800
acattatagc gtattttaac atcgaatata tatctcctat atccggatct gcaccatgat 19860
ttaataatag cattaccagg gtaacgtttt cttgttctac agcatgatat agtgcagtat 19920
gcgagttttc acatattgta gaattaatat caataccaga atcaaggaat agtttcacca 19980
ttttagggct attggtttta acagcttcta gaaaataatc ttctaacgct gtatccgtgt 20040
ccgctaataa gttattagat ataaagtgtt tcaccagttc tatatttact tctctaatag 20100
cacacttaat agtaattctt ctcatataat ataaactggg atgtttagtt tcttcccata 20160
gaatttggca tagaggtata gtactaaaat atgaatatcc tatagcgtaa ccggttttaa 20220
tgcaatacga accacccttg taaaaatcta atacgtaaga tctacatacc attttcaagt 20280
ctgctccgtg ttttatcaga agttttacta ttttggtgta tttttctgta ttattaaccg 20340

-continued

```
ttaatagacg tcttattctt ttactaggtt ttacgggctt gttatcatta tataacatca  20400
ttctacctcc cgctaatatc atagctatgt tgatgggatg tgtttttatt gtttctcctc  20460
cgttgataac ggcattgttg tctagtagca tttctactat ttctatgtct gaatgttcta  20520
tagcgatgtg taaaggaagt agtctattgc tgtcgtacat gtttattaca tctttatctg  20580
attctatcaa ttctcgaagt ctgtctacat tattttcttt taagatgtta tgtaatgata  20640
acaaacgatc catagtgctg tatttgtacg ttaacgtcat tattttttct tgcgttatgc  20700
aaagataaca gtgattttta atatatgaat tcatttattt tagaactaag ctattataat  20760
aatatatttt aagaataaat tacttattat ataataaaac acaattctca ttactttatt  20820
tatctgttaa tttttgttta taaggatttt gaataaaaga cgtcataccc gtattaataa  20880
cactcttgac gatcatatgt gtaatttttt gcattatgtt tgtaaggcat tttccgttta  20940
tatgcgatct atatttgcaa attgatgttt tacatttagt taaataataa aatattgtat  21000
ccttgttatt ttcataagca ttatatatat gtaaacctat aatatttagg tactttataa  21060
aaattttgca acatgtattt ctccttttc ttcttttata tgtccttttt ccttttatag  21120
agtattccat ttttattcat aaaaaacatt tgtagcgtgg gtgatggtaa gtatataacg  21180
agttacttat agatatattt aatatcttat cgacggaagg acgaagatcc atggtatgtg  21240
ttatgatgtt tctgtccata aagggtaatg atcaatacta taatgttttt acgatcccta  21300
aaatctaaat atacgaatct agatattgat ataaaagcgt attggataaa tacggttatt  21360
catataaaga taatatgact gttactaaat ctggtgttat agaagagtta gaaaactaat  21420
ataaaataac taattgatgc aatacactac tttgacaata gcactgaaga cttctacaaa  21480
ataagcgata cgtataaaat aagatttata tctgaatagt agctttatgg taaaccggta  21540
aatacgaatc catctactta tgaaatacgc ggaaaaatat ttcatagcta aaggtattta  21600
taacgattat accaagtcat aaaaatctat actatagaga gaacgaatct tctttttta  21660
tacactaatc gttatcgatt gtaatgtcgc tatcgctttc gtcagactga aggtcatact  21720
cttgtttact taaaactatt ttgaatagtt gatcgcgttc ataactagaa agcaaatcac  21780
gctttttgga atcttctagt tctttccaat ctgtagaaat agcttcaaga gaatcacctt  21840
gttttataat atagttaata atactttctt tatccggtaa tttaaaatag tatttgctta  21900
ccatacaata cgcgtaatac ggttctgcat cttcattact ttcatcaata tattctattt  21960
catagcattt agcgtgttct ttactagata ttttcattaa tttgtcaaat agttctttat  22020
cgttaggcaa gtagttgtcg ttttcgttac tatctatact agaccaagct atatcgttaa  22080
ttgtattttt ctctagatac gctactgtat attctctatt aaatttagaa acgctaacat  22140
cctgaaaaga agaaaataca ataggatgtt ctatgctatg tattttgttg tttatatgcg  22200
ttaatagaca ttttcccttt ctatttatca aaataccagc acgcacaagt tttttattac  22260
agggcggtgc tatatatata acttcacaat aacataatgt attattgttt tcgcggtcgt  22320
ataaattaat agaaacatcc aagtattcta ttgtatctac tatacctttt tctgctttta  22380
atttcatcgt gacgtcaagt aacgctacgt acgttacacc ggattcaact atagttgttt  22440
catgatatac ggatttatca aacagaacat cggatgaaat atctaatgaa tttattcctt  22500
taagatagaa ttttgttttt cctccttctg tagctttctg aagtagtaat aatatgtaca  22560
tgcatagtgt attttttgat tttttttac agggtttatt atttgttttt tttaaatagt  22620
cccctacacc gtaaacaaca aaagttacct tgttttctac gcgtacttcg ctaactatgt  22680
```

-continued

```
attttaactg cgatactata agattctcga gtttagtagt taagtcttta cagagggatt  22740
cataaacaat ttgcttagat ttacaatgtt ctaagtcgag tatctcgtat ccagtatgtt  22800
catctaaaat tcttgactcg ctaaagtcat agtccatata gttagtttct atttcttcta  22860
ttaacaattt cttgaaatca gaaaagtaat catctgaaaa tatatgcatt tttggaatac  22920
catctcttat atacgtgaat gacatattta caaaaaaata tattatttat gttttatatg  22980
aatctatata agtaataaat gaaattaaag ttatcaacta ttatagtata caaaaatgga  23040
taccgattac gggacggttc atacacagca gtctgtaaag ggaaatactt tgattctctt  23100
aatatatttt atatcgttta tagtaggatt tcctggtaat tgtacggtta tatggtttac  23160
gggatataga tggaaaaaat ctgttacgac tatatggttt cttaatctgg caatagctga  23220
tacattgttt gtaatattta ttcctttcga gattacttat atattaatgg gacactactg  23280
gccgtttggt ttattcgtgt gtagaatagg atctcttatg tttaatacag gcatgtacgc  23340
tagtatattt ttccttacat ttataagcat agacagatat tgtctcgcat ttcgtaggga  23400
tatatgcaac aaatataggt atagaattaa cataatggtt atgataatca ttagttggat  23460
aatatctata ctgctatcta ctccttacat gtattttaaa aacactaacg aaaaataccg  23520
taataacaga gactgcttgg aagattacca ttcggataat aatacttatt tactgcgtcg  23580
tgtagtattt tgtatatcgt tagtaatgag atatttagta ccctccgtag tcatgttatt  23640
ctgttattgc ttattacttt tcaaacacag tttatttcta tctaagggac agacttacac  23700
catagtgatt atgataactt catttatggt tttatggacg ccttacaata tattatattt  23760
tatagatgtt ataggtagtc attactacaa cgcagatacg ataatagatg ctgctcctat  23820
atctatctct ttgatatttt taagtagttc aatcaatccc atgatttaca tgctggttgg  23880
tagatatgta tcttttgaaa attattctat gcgcgaatcg ctaaaattaa tattatctga  23940
agaaagagac aatcaaacaa atcatgaaaa cgagattaaa atggaaaata ttaattaata  24000
aaaataatat aagtatatca taatttttct agttcattat ttgataaaaa acaacatata  24060
attgatctta tttctaaagg cagcatatgc agatatggtt ctgtagtcag tacagccctt  24120
tctagtagag tatatctagt tagtgacatg cctatgtttt tatcagctag ttctttgtac  24180
acgttagctg tttgttttag tacctttaat tttggatgat tcacaaatct ggctattacg  24240
ttataatctt tttctattac aaaatcgaat aaactatatc ccctaactag tttttggtta  24300
atcagttcgt ttagttcatt ttcacattgt aacattatat ttttataata ttcaattccg  24360
ttaatgaaag acacgcttct tatcactaat ggatctttta ttaactcttt attcttctta  24420
atcataataa ttaggtgaga tattaatgtt cttatagttt ttttacacgg acacgcttct  24480
tctataggag ttcttccatt tgtattaacg ctattgatat ccgatcctaa atctaatacg  24540
agttttattt tcttatattt acaacacgct gctaaagtgt gtaatatagt attcccgtca  24600
gagtttttag cgtttacatc cgctcctttt tgtaataaata aattaaacac gttatcagtt  24660
tggtaaatga tagccgtttg taacggtatg ttaccgtaaa ggtcgcgctt gtttatattc  24720
gctcctagac cgaggatgag tgatacaatt tcaggattat ttgtttttat agattcatac  24780
agtaactccg ataagtaatc ttctgataat gcaatatctt ttattccgtg cattaaattc  24840
tttaactcgt ctatactgca atagtacatg gctaaaggta atgttctttt atccatgtta  24900
accataaact ctacggtata aaattttata agttcatcta atataatttt attctttctc  24960
ttaatagcgt aatacaaagg agatacagag tgttcgtcta atactttagg atcgcatcct  25020
atatccagta agtatcttac agcttccaac ctttctgctt ctacggcgta gtgtaaagcg  25080
```

-continued

```
gtggttcctt cggtacctaa tatatctctg tctaacgata atatctttag tacttctata  25140
ttgtaatgag ttactataca tctccgcaat atttttattc tttctatatt atccgtaatt  25200
gctttgtttt ctaccaataa tttgattaat gataagttac ctttcttaac cgcataatat  25260
aaggcagtat gtccgtagcg atcaggtata tctaatctaa tattattctt tattagtaac  25320
gaacatgatt ctaatgttag tttgtcatat atcatatcat gaccaggata tggaccgcta  25380
ggttctaaag acagtaaata atctataatt tctatataac ccgtctttat agccgttaat  25440
aggggtgttt ctcctttgta acaaacatct acagaagcac cgtaagaaac caatattttt  25500
gccatcgtaa gatctttgtt tctaacagat attattagag gaggtacttt acaagcggac  25560
atttttgatc cgttactaag aagaaattca gctactttat gggatttcat acttaccgcc  25620
ctacataata tagtgcggtt tttactacct ggtttattaa gatctatagg tttgtaagaa  25680
agtaatttcc ttattatatc tacatcatct tcatctatag cgcgtttaaa cgcgcttttt  25740
cttctatagg ccattatgtg tggtataatt agcctatgca cataaattta cgctatatat  25800
tttcaataat tgttagttaa atatagttat tcattcaact aatagaacaa gatgtggatc  25860
tccacccatc taaatcgtat tcttcatcca acaattccga cgatattcta tcaggaacta  25920
tatccttact ctttttattc tttataagtt tttcacatct tttagccatg ttcatgagat  25980
tttcatgaga ttctatacat tcgagatttt ttattaaacc ggccggataa tacattttat  26040
cattaaacag ttttctaatt aacattatct gtaatattat tatagagttc agcttttcgt  26100
tgtcgtaaga cattagatta gtaaaaggag tatttccttg gttatcaatt atatttatgt  26160
cagcgccgta cataaaaagt aatttaactc tattgtagtt atgcattgct tggaatagag  26220
gagttgttcc attagaacat ttgatattcg gatctgctcc attatccaat aatagttcta  26280
atagcgcgta gctgtcttca tctatagccg ctacgtgtaa cggcgtaaca cccgctttat  26340
cgcctatatt aggatcggct cccgattcta ttagttcctt agctatatta aagtttccgg  26400
agcctaccgc cgtatggagt actttggtgc ctatagaaga agacgatgaa gaatttggat  26460
cagcgccgct atctaatagt atacttacta attctatatt acgagtacta acggcacatg  26520
ctaaaggcgt agttccataa tcgttttcta tatttatatc cgctccgttt ttaattaaat  26580
gtcttaccat atttaatccg ttcctgtaat cacaggcata gtgtaatgcg gtattaccta  26640
tatcgtcttt gaaattaata tctatccctt tagacaacag tatatccatg atctgaattt  26700
cttctatttg cctgctaggt tccattcgcg atatagttaa gcatttacta atttcatcgt  26760
ctttacaata atccattatc attctcataa gttcaactct ttgaaatgaa taactagttt  26820
ttgatttatt caatctattg ataacttcta gcaattctgt atatgtattt gagcaccaat  26880
tatcgagttc gataaatgat gaattcggag gcatagttaa agtatgaagt gaggtaatac  26940
cgtgtgtatc tatagctaca ggatctacat cgttattcag taatagtctt actgcctcta  27000
tatttcttag ttcaatagcc ttatgaagga gaatctttaa tctgtaagtt gtaggtctta  27060
gatctataca gttctctatt agtttataca gtatactatc tattccagtt gtatatctag  27120
ttattttagt atagtccatt atacaggtaa ataataattt aagtttaata tcgtaattga  27180
ataagatata aaaattggtt atatttattt gttaactgaa tcaattatag attttaaatc  27240
tttattatct aacatttcca ttatcatata ttttacgtta ataggtactg aatttatcat  27300
acttatatta ttactgtatt ctatagcatc gtgaatcagt ttatatcgta tacttgaaga  27360
taatttagtt ttttgaatgt attttttata tatactaata caagaagata atttctcgac  27420
```

-continued

```
cttggggtgg ttcaagaatc taattagaat attattgtta ttatccgaat gaagaaatat  27480
cgatagcgaa tatcggtgat tcaactttat attccttata ctttttaatt catcctcaca  27540
atttttcta ataactttaa atctatcatt ttggtctata cattctatat ttgctttgaa  27600
tccatccaat aaaaatagat tactatcttt ttctaaatct aatactatct tagagattat  27660
gattgtagct attttatcgg atatgtaatt aatacaggat agaggcgtgt gacctaattt  27720
gttaatagag tgtacatcga cgttgtaaga catgagtaat tctacgctat ctagtctatt  27780
cgataagata gcgccatgga gaggtgtatt ttcattgctt tcatttttca tattagggtt  27840
agatccgtac cgtaatagta acttagcaaa ttttatttgc ataaacgtaa taatggctat  27900
gtataaagga gtgtaacctt ctctgttata tatatttact tccgccccat gattcagaat  27960
ttcagaaagt atatttatgt ctttggtttc taaagcttta tgtatcaaag gatttctact  28020
ttttaggcga gtgtttgcgc cgtacattag gagtaagttt attaaaatct tgttcctgtt  28080
acctacagct atattaagaa cggtatctat agtatcgtta tgtatattta cgtttgcacc  28140
tttttctata agtaatgtag tagcgattat atcgttcctc gatacagcgt aatgtaaagg  28200
agtgcctaga cacgaatctg ttatattagg atctgcgtca taatctagta atagtttaag  28260
tatgtcgtgt tttccagcac taacacaata atgtaacgaa gtcctttcta agtcatcttg  28320
ttcgtttacg ggtacgccat attttatcaa taaacgtaaa atagaaatat cacagttatg  28380
tttcacagcc gtaattaaat aatgattatt atatccttcc ggtattgtta aagaagcgtt  28440
attttccaaa agaagcttaa taagtggata atttgtgcat tttatagcat aatatatagg  28500
ggttttaaaa tgactatttt gaatatttag acttacttta tactttatca gtattttgaa  28560
aatatctata ggtattttat tatatatagc atcacaatag tttatgaata aagtattagg  28620
atcagcgcct ctttccaaaa gatatttagt aatatttgta ttacgtttac acaaagctag  28680
atataaagga ctattaccta aatatacttg ttcgatatcg gcaccgtgat ctactaatag  28740
ttttaccatt tctacattac ctaagttaat agccttatga aggggaggag atttacattt  28800
atttatatct gcgccgttat ctagtaaaaa tttaacaata tctatatcgg aattacttac  28860
cgctaaatat aagggtgtcg ataacgcatt tttgttagaa aatgtatact tcttaaggat  28920
aatatgtttt accgcgttta aatctctagt tctaatagtt ctatgtaaat cttttctaag  28980
tttttcattg cccatgttat ataatcatta tttactctaa tataatatgt ggtcgtatga  29040
acgttaataa atataagttt tcctcttttt tgttatatta cctatattga taaaaaatca  29100
ctcgtaccaa ccagttactt taatttttga acccctgaat gcttccgcca attcgatgaa  29160
acgattttta ttgtcttcat catccgcgct cacgtagcct atggtaacgt gcggacacca  29220
tacaggatct gataacacag agccgaaaat ttctctaggt gtcggcacaa cgttaaatag  29280
tacgtttctc aaggctttca catcatcaga tgcctccagc ttcataacca ctgctctacc  29340
gttcgctcct aattctttag acgcacgact ttgaggaaag caaatcactt ccttgcacgt  29400
gaaggaaagc gatgtcaaat ctatattttt tgttaactct ttaaatcttt tgaagtttga  29460
ttcttggtct ttgtttgcta ttcccaacgt tacgtgggga ggtatatcac atcccgtcat  29520
gtatttgact gctatgcttt ccaggtctga tattcccttt tctaatctaa tatcgtagaa  29580
tgaaatggag gcccaattac agtaatccca aggaacttct acttctaatc ccattaatat  29640
agcatccttt ttattttgct tttcttttac cacgattttc tctaactcct tctgtatagt  29700
agtagccatt ttggttagag taccaatggc tctccaataa taaaaagatt aaaatttcac  29760
ttattttgaa cacgctgcta taaataatat aatttttaag tagttcgaat atatattttt  29820
```

-continued

```
attaatttta aagtaatata cggaaaaaag tatcctttat atttaccagt ttgatgtttt  29880
taatgtatag aatgtttttg tctctgtctt ctgagtaggt gacatataat tgatatattt  29940
ttgattatcg ctgtataaga tagaaatctg cgtttgtaaa tagtatcgat atcgtatgag  30000
aacatcaggt tatatccaat atatttatgt ttagttctat acagtaatat atgtaatact  30060
ccattaagta ttatttatcg aagttattat cttatttcgc ataattcttt attagtcatc  30120
ttttctacaa taatatatat aacttcataa ggtaggttag tgatggtact cgtcaagcta  30180
ttaacaacac gatctaattg ttcttttcta tataaaccaa tctttatata ctgatctata  30240
atatcaccgt atatctgaaa ttcgttttta ttaactccta cgagtaatag ttctatacat  30300
cttgctagcg tgttatgatc atcttgtttt ccagctttta taaaatcaaa taccgtcaat  30360
ttatatccag ctctgcgaat tttcatattt ctaatttctt cctcgcataa atttttataa  30420
tagttaaacc ggtagatact attagtaaag tcttcgttta ttttgaatcc tggtgttaat  30480
ttaactttat cacgaatatg agatatcata acagccgatg atataagatc cttgacggtc  30540
atggatagag aatttccatg gcagtaacaa taccatgtta gcggtatgtg attgagtttt  30600
atattcaaga agaaaggatt agcgcctcta tggagtagca tttttattat aaaggggtcc  30660
gttctgttta cactagatag aagaatggta tacccttcta tacattttga atccactaga  30720
gctccgttct ctagcaatag tgatacgatg tttatatttt tgtctaaaac agcattatgt  30780
agtaccgtac gtccgttata atcagctatc tcgagatttg gagaatattg gagtaaaatc  30840
tttaccatct tttcatcgtt atatgttaca gctatctgaa tcgggatatt accgttttcg  30900
ttagtaatat tttgatcagc accggaatct agtaacagtt ttgcaatatc agtatttttt  30960
tgttgaatcg ctaaatgtag aggagtatta cgtaaataac atctggtatt gttaacgtcg  31020
gctcccgcgt acaatagtat acttacaata tctttgttac ctatatctac agcaaagtgc  31080
aataccgaat aacatgttaa ttcttcttca tagtattcat tttcattaac attcaccccg  31140
tattccagta atatttttat gatatctatt ctttcgaact ttatagccat tcttagtacc  31200
cgtattcctt catctttcgt attaccttcc attaatcttc ttactaagtt tatactataa  31260
ggttgtactg tagattcttc atgcggtgta tcatcatcta aaaacatagt tgtaatagtc  31320
aaataacatt ctatgtaaaa actaattaat agattttcat ttttcaaata atatacccgt  31380
tctggaaata gccacataac tgaaaataaa atacttaagt atatattata ggataacaat  31440
gtctatgaat aatattacga gtaaaatgaa tcaagatagt tatggatatt ttcaattaca  31500
tatgagcgat tttacacgtg tgtcgctatc gattgtattt acactagtat ttttggtagg  31560
tataataggt aatgctgtta tcatttggtt tataggattc aaatggacaa aaactatttc  31620
tacgctatta tttatcaacc tagctttagc agactcgtta tttttaatat tcattccagt  31680
atatactgtt tatgtattat ctaactttca ttggtatctc ggagaattct tatgtagggt  31740
tagttctttc ttctttacta ctaatatgta cgccagtatg tttttactta cgtttatatc  31800
tatagataaa tacttaacac taaccagtca ccgtttagtg tataaatacc gaaaatatag  31860
aaactactac gtgtgtatag gtgctatttg gtgtatttct atagctttag gtgttccaac  31920
tttatattat aagagggtta tattatcatc atctagaaac gagacacggt gtattagtta  31980
ttacggcgat gataaacaca cggctattac tatttataga attattgtgt gtattagatt  32040
tattatagga tacgtgtttc caatgacagt aatattgcta tcttatgcat taatagtata  32100
taaggtaaaa ttcataaata aaccaccgaa tagaagtttc atgataacaa cggcatctat  32160
```

-continued atttgtattt ctcgcttgtt ggacccctca tcatgtatta aatattatat cgttgtatgg 32220
attaaaatcg acatctatgt ataattatat aaaagaatct attccgttcg taaatgctat 32280
tgcgtttgtt tatagcgcta taaatcctat tatctatata tttgttatta ggttaacgag 32340
tacttacgat tccgatacca tggatgaact aagaagtgcg ttattagatg aagaaactac 32400
gtctacagaa gattgtagcg atatatctag atagatttaa tttttgtaaa cataaaaaaa 32460
agtatatagt atcaaaaaac taccatggaa gaaaatattt tagtaaaaac ctttgacgaa 32520
ttatacaaaa atagattcgt agatgagatc tatcataacg ataaactcat tacgtttaat 32580
aaaaagaagg gtaaaggaaa caacttgtgt tattctataa ttgaatacat taatcccatt 32640
tatgattctt gttattctgt ggctaaagtt gtatatataa ctaacggagt tatgtatgct 32700
actttaaact atatgggaaa acctgtagaa aatcgtgagc tcgttcctat taataaatta 32760
ctatcggatt cagaaatctt atctatggga gtaaacgcta aagatctatc tactaaacat 32820
tacgaatata aatataaggt atctactaac cacgataaaa aaagggactc gtcattagtt 32880
aatataatta aagatgatag tttgttagaa aaattagatt attttcttga aggttacggt 32940
gattggaaga ttaccactat aagacccagg cagtttccta ataagttttg taaatacagg 33000
atatctaaat actacttttc attgtaatgt ttattatatt tttatagtag atgccgcata 33060
gtgaatcatt atcataaact tagtttagac taactataca agatagattc aaaccgattg 33120
attagctagt atcgaagaat caatcatctc tctatgctcc tgaaatttat tatagcatta 33180
tgattatcga atttatatgt tagctcgtga ttagtagtga tattgtagtt tagtaaatcc 33240
taatagatta ttacgtttat ctttaactat ataataaata tctgtttctt ctataattaa 33300
gcctatggct tctgatcata ttacatagta ttatctacta ctataggcct ttatttagta 33360
taagtatagt ctaacaactg ttacatccga atgtataata aaaataatac taatggcgtg 33420
ttcacgaggg taaataaatt tcggccatag ttacctctat ataataaaaa ttttattaat 33480
tttttattct tgtttttttac agaatgttta aatctcgaat gtataccaac gagatttttc 33540
actctgtttt agtagtaact agcgtattat atagcatgta tgtggatatt ttctggtata 33600
tacaataatt cataattcta taaagtatca aggttatttt ataaaaatat taataatggt 33660
tttaaagatc tcgtcaaaga ttcaaacata taattaggag caggacctta actaaaacag 33720
tattacattt ttgtctttta tcgttttgta caatataata gttaacgcct atagctgtag 33780
cgttttctct aatatccatc atttcatttt cgttatctac tttgacagtt tctttaacct 33840
ggccattttt taaccatctt ttaagataat caggagaata ttttttagat ttctcgtagg 33900
cacttatagc accatggcag cattgagaaa ctatttcacc tttagtcatt tttaaatcat 33960
ctctaataac gaataccatt tttaacatat ctctgtaaga agagttatca aaaacattag 34020
ccattattag cacaatatga taatctgtat tatttattta tgttttcagt atttacttaa 34080
tacaagttac ataaaatata tccttctttt tacaggtaca tatactacat gtaagttttt 34140
aagtaagcta cattagaaga tgttttgtaa acattacgat agaaactcat actcgttact 34200
gtttctatat cttttattct tactctatga agactgaata ttttcctcac ataacttacg 34260
gaagttatat tctctctaga acacgattcg ttataatagg tatcgctatt gggtactaca 34320
aatgactctg ttttaatatt agagtaacaa tcatttaagg aagaatcttt atccttacag 34380
tatgttagta taacgaaata atccgaaggt atataaactt tgttattata accgcttgac 34440
atagatatta accaatcact atctcttata ccgttgctgt tgctatcgaa tacagggcct 34500
accataacgt taacgacatg atgtttttgt acatattcga taagaataga tgacataaat 34560

-continued

```
actteccata tctttttgaa attacgatac ataggtacag tatttgtctc caataggctt  34620
tgaaagtcag ttgcccttgc ggggtaaaga tatccataag taacatcttt ttgagtacta  34680
tagtatctac atggttcttt ataatacata actctcatat cctgaagata gcaggtcttg  34740
ttatatatat ttgtactatt atatgtaata tcgatactaa aagacgtcca aaggggaagt  34800
ctatttacct tactgtaggc agtaacgtaa ttatcatttt taataataca atgatggtgg  34860
cgattgagta gaacagcggg tttaccaaac ggtagattat atatgtaaga tgatgaacgt  34920
gttctggaac tgtcttcttt atttccttta gaagagaatc tgtctatgtt cttacaagta  34980
caacctttca gatgatctcc aacatacgcg tgtctatcgc actcagattc tattgttatt  35040
atatctagag aagaaacgtg agtatatcta ctatttctaa gaatattatt caaagatcct  35100
acagtaccgt tgttgttagc gggatttatg cctaatattt cacacatcat attatagagt  35160
tcgatgttat cgaagatcgg gactcttaca tcatcgagaa aagcaggtcc ataacctaag  35220
aataccgcgg tcatatcttg gaaactatta tcagatccgt ggaatccacc cgatcgatgt  35280
tttaagttgc cgttttcatc ggttgactgc catccttctt ctagatatac tcccagtatc  35340
tccgttctga accctgatcc gtaatgcaat cttttaggta gcctgctcct ataacttacg  35400
atgaaaggtt gatcgtccat cacacaacta gtagaagata taattccgtc ataatcgaat  35460
aatcttatat ggtttaaatt ttgaggcttt attactggag tagctcctgg ttttataact  35520
acgtcattat ttgttatgta atctttcaga tttactatct ttttgggatc tacattagac  35580
ataccatgat ccgatactag tattaggtta gcgcatccta ttaattgcaa atcttttaaa  35640
cctttcatca gtaaagcgat tgctttgtca actttttcta aagcttttcc tactctttca  35700
tcatctgtac cgtattcata cccagaagac ccgggttctt caaggtatag cgcatagaag  35760
tagggtctat atcccgtatc catttttaac cacctcaata cggtatttat tctttcttca  35820
taaggaaccg atttattata gcttctatac atggtagggc gttttctagg aacaactttg  35880
tcagatcctg gccaaaagaa ggttgctgat ttaaatccgt tcttcatgat agtagtccat  35940
atgggttcac ctccaaacca ttctacttct tcagtttctt ccgaagctat cgtaaactcg  36000
atatcggttc ccctatctat gaattcatta tccgttatac cgtgagatat gggatacaat  36060
ccggtaacta tactgtacaa gtttgggaat gtattcgtag gatatacggg cctcataggt  36120
gccgtaactc cgtgttccat taaatctttt atcgtaggaa tatacttctc ccatttatta  36180
agataatcat atctaaatcc attcatcgct attagtatga gaggcggcct ttcaaattca  36240
ggaggacagg ttacctggaa tgatatacaa cccccctaacc tcgaatctct atatccgaat  36300
aacaaacaca aaggtatcat tattacggat attgcagcga tagtagctag tgaatacaat  36360
aagatatctc tagtttcaca cttacgcttt tttattggta tagtgtaaaa tatatccacc  36420
ttttttttctt tgtcgataat agaactatta tcttcatcgc ttatgcattc tttagattct  36480
tcttttacag gatacaatgt ataattatca ctgtgtatag acatatcttc atcggactga  36540
tatccatgat ccatagtggt actatttttc atagacattc gtataaacta attacttaat  36600
ccatcatttt tattatatat tattgtttga aagaaaaaaa tacgcgataa aataacaatt  36660
attatacttg atacgagttt gaattcttat ttttcaacaa tatcacgttt tacttcctgt  36720
catgatcttt aattcatcat tatttatata ggtaaagata tgatccttaa tttcattagg  36780
taaattgttc caagaggatg tattactgtc attatctaga aataaatctt ctaatacttt  36840
acttgcttta ttaagaagta cgtgtcttga cataaaagta tctataaaat ctgtatataa  36900
```

-continued

```
aatattaaac acggtaagtt ttttatcaaa atttactata aatctattat ccttatttat  36960
gcatcttagt aataaatcaa cattattatt aacgaataaa tcaaaaagtg taaatctcga  37020
gtttatactt acctgtttca ttttctcaat atcttttaaa caatgtatcg ctatacgttg  37080
taatctttta ttatctttaa ctagtttctt attatggtcg aatcctttag ttttattact  37140
catacaagta gaataatcta atctaataac gtgtgacact aataatgata ttatttcgta  37200
gttattacaa ctcatggcga tatctaaagg agttaaccct gtattttctt cttcgttatc  37260
tcttatatta acatctgctt tataacgtaa tagttttttt atgatatcta tactagcgtt  37320
ataaattact gctttatgta atggtgtaaa tccatcatta ttagtaatat tagtattagc  37380
accgtgaaat agtaatatat caactgttat gcggttatcg ttttttacag ctaaatgaag  37440
agctgtattt ccacatgtaa gactacgttg atttatgatc gctccgttat ttaatagtaa  37500
ttctaccaat tggtggctat taaatctaga tgctatcatt aaaggtgtaa gattatctct  37560
tatagtttcc tgaaagttaa tatcaacgcc ttttttaaca agatatctta caacatctat  37620
ataattacgt ttagtagcta ctaatagtaa actgtttcta tcaagtctat attttggaca  37680
taaagttact attccagtaa tgcgtaataa ctctattaga aaaggcatag ttttagttat  37740
ataatcaaaa ttataaaact ttaaaatcaa tttagatttt tattaaacta catgtttata  37800
acacaacctt cgtactcaat gactgtttct tttagtaatt taaacagata tccattccta  37860
gtacaggcgt atccacctcc tctatgacgt tgagtaggac tcctattaat atcacctata  37920
catacccatc ctttttttatc gtaaagtgaa acaatccatt tagaatgatc ataataatta  37980
ataaacgatg ttccatttac gtttatcgat tttatgttat gtacatggta ttttgacgag  38040
caattggtta tcatactctc tcctctacgt tgccatgttt ctgatagtag gtcagattcc  38100
aaagtcggac ctatccatgc actcattata tcatggcgaa aatattttga cttagcaaat  38160
gttaaaaact tttctccttt tctagattcc atccacctag aaacattttt atataaagtc  38220
gtatagtttt tatcgttaca tagatggtat agattattca gattcttatt tgttactgaa  38280
cagttataca cgtttgggtt attaacaggt agtgtattgt ctaaggccgt aagacctcct  38340
ttgtaatcca agttaataca taacatagat tgcccgtata cataaccaga gtaaggataa  38400
ttgtatccca acacaggaga aggtggaaat ctaggtacag aatgtatcaa ccaaaatcct  38460
gttacgctat cactattcca tgccataaca cctttagtat gacctacctt cgatgaataa  38520
tttttgcttc ctgggatgcc atcattataa aaaatgtatt ctatatattt actatcatat  38580
aggtcataaa taggatatag tgttttccct attatactgt atctagagtt tataggtact  38640
ttacctcgtt tccatttagg attattacta tctatgtata aatattcatt acctttagtg  38700
cctaattttt ggagcttagg gagcttgtat acgaaatacc agtctactac ttcgccttct  38760
tcatttacac aatttacttt acctttatca tattcgttaa agtttgaacc gatggaattc  38820
agtatcttag agatatttga gatatctata ttattaccga tataatatgt aatacatatg  38880
catacggaca atgtaattgc cgtaggtgat atcattttat tgtatttatt atacttatta  38940
tacttatcta tatttcatta ataaacaact tgtatttata gtattatata gtgatatctt  39000
tctactataa acatataaag taataattga aaggtagtag tcttagttac gtactataaa  39060
aagtatatca tatggatttt attccctaac aactagaatt agttttaata ttattgtatt  39120
ttggaactaa caagataata ggaatagtcg ctaccatagc aataaaatatt acgaccatta  39180
ttaaaacata tggatctatg aatttattaa tttctttttt tataatttct aaaattagta  39240
ccatcttaat attaatttaa ttatatcacc atattctaat attgtattat ttttatgtta  39300
```

-continued

```
tttattatat cattgtgttt gtatattctt cttaatttct aataacatga tcgttaagat  39360
ataatccaat ctagtaaccg aaccgtattc tcttaatgca tctactaata tatctaaatt  39420
gcatgtatca caagattcta cgactttcat tattaacgtg tactctctat aatcaataaa  39480
ttgagcataa agttctgtat agtatcccac tatcaatctc atatctttat ctcctataca  39540
gaaatggcaa agtatagctt tgagaaattg atctttaata cgatgtttaa gaataggtag  39600
tctcatgcat atgataccta tttgttcgta tacagacgcg gctttatcga attgtttcat  39660
tcgtgtaaaa cagtcagcta cttttatcat acaatcgtta gctgatttta tggatccttc  39720
ttctctatag tattcggtag catattcgta atgcatacat gctttttcta aatccataat  39780
acacgattca tatatttcag ctaccgtcat ttggtgtttt gccgccgtgg tgaaattatt  39840
tatcgattta tagacttcta tcgcttgtaa caggcattct atagattttt taggatctat  39900
ctttctatac atattactcg catttacaaa atttatagca gtatctaata cgaaatcaga  39960
ttcctgagat tgtaacacag cagctttaag aaatgaatat ccagctaact cccagttctt  40020
gaccgcttta aaaagtatag ctgaacgaat caataagttt ccaacttctt taacgttatt  40080
tacgtttctt aagaacttcc aagaaaataa aaatcccaca tcctttagtc tacgattggc  40140
ttccgatatt agtctatacg cttcttgttc catgtcaaaa taatatcgta tcttaattgg  40200
taatattgta tatttattga atgagtgtat tattataatt ataacgtttc ttatacggaa  40260
gaaatctgga ctcgttatga gatactttgg attgtatttt actataattt ataggcttat  40320
catcggttaa aacggagtat ggtagatgcc attcatagat gtctcctatg tattccataa  40380
agagcctcgg cgatccataa tttatcctat gtattagatt catattttgt ttatacgcac  40440
aaaagtcatt tagtacgatg ttgtcaactt ttagtgaaat cagatatgat acagtatatt  40500
gtgtaacttc tttcgaacca cctgttataa ccatattaac gggtgtttca ccaaatacat  40560
ttctgacatt tatatccgcg ccgttgtcta ataataattt cataaatctt acatcttgta  40620
aactggctgc aataaagata ggagtattac ctacatcgtc aaagctatcg acattagctc  40680
cattattaat taatacaaaa gcggcttcat aattacgttc ttttatggct aaatgtaacg  40740
atgttctacc accgtgtaat tctttaatgt ttacgtctgc gtttctgttt ataagtaaca  40800
tggtgccgta aatattatta cgttcgacag ctacgtgaat aggcgctttt acatgattta  40860
ttatatttac gtctattcct ttatctaata gaactgccat aacattatgg tatttattgg  40920
aagtagatag aaaatgcaac atactatact tgtttactat ggatatatca gcattttttt  40980
ctaaaagaaa gcataccata tcgtaattat tgttacaaat tgtatagtat aatgctgtat  41040
atcctttatc gtcttttaca tttatgttaa ttccgtgtaa gcatagtagt tctatcattt  41100
ttttattttc atgtgttata gcactatgta gtaacctata atcattttta tttattatag  41160
atccagcatc taataatatc ttagctatgt tgacgtcatc tacttctacg gcgtatctta  41220
ataaagtata tcctacggaa tcagctatat ttatgttaaa atttttatct ataaagatgt  41280
ttactaaatt gtgatcgtgg tttaaaaccg ccttccttaa catgttaaaa tgtttataag  41340
tattaatatt ttcttgttga tttaaaatca tacgtactac gatatagtct tttaattcta  41400
tagcctgttc taatagcttt atacagatag gttcgtgtaa tccaaacatt ttagttttca  41460
tatttgtatg ctaaatatat ctatatagta aaaatagtcc attaaatttc tattttaatc  41520
aataatttac ctcgcattcg tagcttatta gacaaaaagt acatacctac caccagtcta  41580
acaaattaaa tagcacctct agtattactt ccccgaagat aagacattga tatgttaata  41640
```

-continued

```
tccttcatat aatcttacgt attccgaata taaccacttc aaaatcattg ttagttatgc  41700
attctataag gtagtctgta ttacatttta tagctataat agacagcatg tcaatgtatg  41760
taaatttagt actagtggat gtagatactc ttatagtaag tccactagaa tctatataag  41820
atccatagat tattatttca tctccagatt ttatatgatg aatacaatta tttattttat  41880
ttagtctaaa cattcctata atgttactag tatctcttaa gtttaatagt tttctcatta  41940
taaaatttat agaatttggg aacatggtat gacaagaaca taaatctttt atcttgttta  42000
tatagttaat cacatcctta tcatgttcta attcttttat gtttatatcc attgtgctta  42060
tataagattt taaattgtat tttcattaat tacgtacgag aaataaaaaa tacgataata  42120
ttatacttgc tatctgtagc aatactattt tttatatcta tactgttata cggataagat  42180
acaaatctta ccatattatt tggatataac actatacatt ttccatcgtt atgtaataat  42240
aatccacagt cttccgaatc tatacataat attataaaat ttgaatagtt tcccacttct  42300
aaagtataat cattaatatc cattacaagc atgacgtgag ctaaatattc attattaaga  42360
agatactgag atagaatgtt agttaatgtt tccgatacaa atatattaat aactttagta  42420
ttattgatta atctgtaaaa atctgttatc cttgaacatt ccgtatatag atctatatca  42480
tcaataaaag atatcatgtg ataattcata ctgtatatat acgtataata tttattatat  42540
ttcattttca tgccattatt gtgacttttc agacttttta ctcaagctta ttacgttata  42600
gttaagcaat aagtgtagag aagaaacgac cataaagggc gatatacaag cacctattac  42660
agcgctcata ctattccaag ttagaaagtt atacacggat aacaagacat taagcgcgga  42720
aatgatagca cttgtcctta acatactcat gatgtagaat actaaaaacc atgacatatc  42780
cagaaataat tgcaagaaat aaaaaataat gatatgtcga ctgatctttt cgccagaggt  42840
catcaaatac atcgcatgcc ccatacaagc ataacttata gctgatagca cacatctaaa  42900
gtagtattct tttactacgt ggtatttatt atatcctatg taattgtaaa aactgtattt  42960
ttctattatc tttacgacta ttaaccataa cgtaagagat attagagaat aagaatgatc  43020
gcatatatat tcgaatagcg tcattttaat cctgtagatc caaatcctga attgcctcta  43080
tccgttatat tgatttcctc taaagtagtt acttctatta tttttgggta tgctattttt  43140
tcgaatataa tttgagctat cctatcaccc ttacatacat taaattgagt tgatccgaag  43200
ttaaataata aaacgcccac gtttcctcta tagtctgagt caattacgcc agcacctacg  43260
tctataaaat aattataagc aagccccgat ctaggagcta ttctaccgta gtatccgtta  43320
ggtattttta gaattatatc tgtttttatc agttctttat tcataggctc tattacataa  43380
tcatacgcgc tatataagtc ataacccgct gaataactag tctgtttata tggtaacttg  43440
gccctatcag aaattttata tactgttact tcctccattt acgccgataa cttatacttt  43500
caatttcgta ataaagtata aaaagttatt acatataaaa ggaacatatt ttaaaaactg  43560
ctagtgaagc aatgatcaac gaggctgtaa aaatacaata tgaagctgta ttgaaaatat  43620
acgaatagtt tttatatata cgaattccat tccaataatc ttggtctatg aaccaagatc  43680
tatatttaga tagtatggca tcagttatcg cttctgatat tattccatcg tagtactgag  43740
gtgaagtatc ttgtttaact tttttagaat agtatgcaca aaaggcaata atagttatta  43800
ttctacccca attaatttta tcttctaata cttgcgttac tataacgtta aaatcaatat  43860
tcctagatat aattatatca aattcattat aattggtttt tattactgat ttacacgctg  43920
cctttagaac atcataggat atagaatcta ttacaaaact ttttcttggt ttatttgtgt  43980
tatattctat gatatagttc tgtatcatat tcaaagcgat ataataagtt tcgtctttca  44040
```

-continued

```
tattactact agccattatg tatattatga ttgatactat cttgttatag cttcaatttt  44100
ttagaatgaa tctctaagta ccccaaagta tatacaattt cctgtcactc tgcattgtaa  44160
tatgaaaata aatggttttc caactacagt ttcgctacat gaagaacagt ttattttttgg  44220
gtattcgtta ttagtaaatt caagttctat atctgtattt aaactaatgg attcagcctt  44280
aatttccata atagaagatt gtgctattct ttcaacaaat aaagtagttt ctgggaatac  44340
atttgaaaac ttaatttcca taaggttcag gcctaaggat ttaagtaatt ctacgatatc  44400
ataagacgat gacatcttta ttttaggaat tttaagcctg tgttgagctt ttttcatctt  44460
actattatct atccaatcta ataagctatc tacgttgata ctattttcca ataaattgaa  44520
tatctcttct ttatcttcat taggagatat cgtagtaagg atatatctgt tgctagctaa  44580
tgaagttctt acgacgctac atcctatatt gtccaatctt cttaacatat gaagacgcct  44640
cttagcgtcg acgagaatgg atacaatttc caccgagtta tgccgtttcc ttatttgttc  44700
ttcggtagga gcggtaaacg gtctattcca tagagcttca aattctaaca cgttcttgaa  44760
tttaatactg caaccttctg tttcatctac ggtacatgtt ttatagcagt tgtagagtat  44820
gttttttgta cgttgattga tacatacatt atttaatcct agtttacaga aataatctat  44880
atcggaacta ttcatattat catttatttt tttcatgtat agatctatgt ttgggcattc  44940
tatgtttaat atatcatata ttttatcagc tgttgagtga tcagttagtt tactcaacgc  45000
gcataaagaa gaaattatac tacaaggtgc tattattata ttttcagtac ctgtagattt  45060
tatataattg tatatcttga tagctacatc taactgtatt tttatgatat ccataccgat  45120
aataatttgt attaatagat attatttcag tttatatatc tataatatag atgtatatat  45180
aaaataccgt aatttttatg aattttcctc atccaaagag tcatagtctt caatatctcc  45240
cattttaaaa agattatata gtataatcaa aggcataagc gatataaata ttactagtag  45300
tgctaatata taaattatca tatgacctat cgtaaatgcc cacgtatgtt ctttttctat  45360
taaacacact actacaccgg tagtatatac cgtctttaca ccgtatgtta tatcgtagta  45420
tactgaattg ggatatataa ctttttttatg tgagttctta gtagattttc tacataccat  45480
aacttttaac gagttatata tatcgctatg agtaacatta tggccagcgt atttgcaatt  45540
atttagataa ggtaagtttt ctttatgttt atttatatca catatatagc acttataatt  45600
atcggtgtct aataatgtaa cagatacgtc ttttcctagc ctgatcactt tccatgcttt  45660
attactgggt atcatatatt cagatctttg atatcccaaa gtatactcgt ctatgtcagt  45720
tatcctacca aaacgacata caatattcgg agaaataggt ttagcatcga catggtacaa  45780
tacataaagt ataacattaa taattattat acgcatgatg gtcgcgggta attaactacg  45840
tatagtattc tacggtttta tgaaattatt tttctattta ttaattgtgt ataaaaagta  45900
ttattcttca ggaggagata tagaaaccgc gtataactgc ttaatatcat ttagattatt  45960
agccgtttca tacgttttgt cttctcttat cctagaacat ctaggaaacc gtatagatat  46020
attagaagcc gtatgggtag aagatctggt gaattcagat ccaattattt cccatacagg  46080
tgctaatgaa atatctgaga ttatcacgtc ggggtagtgt attttattaa tagataacca  46140
atcgggaatt gcatttctat cgaaaggaac tacagaaaga ttatcgttaa tttcctgaag  46200
ctctagatca gtatgcccac cagaacactt tgtaacagtg caccattttt cagattttgt  46260
atcgtagcat cccataagaa aactggataa aataccagac ttgttaccct ttccgtaata  46320
agcacccaaa actactagat cagctttatc cgccataaca catccatcta agtagtcttt  46380
```

-continued

```
ttttattttc agccatctac gcataccagg ttcgtataca ccttttgcat ctttgagtac  46440
aaacccttct atatttttac ttaatactat gtgtaataat ttagataatt cttcatcggt  46500
actaatattc tttacttctg aaagtaaaat tctattaggt atttccttta tattagcatg  46560
aataatattt cgtctttcaa ttagtggttt atctataagt acggtatcgt taaaatacag  46620
acagtcgaat atgaagatac atacacaagc gttatggtac atactttttt tgttaatacc  46680
tagagtaccg aacggtagag gttgattagt ttctgtatct attagtataa tttcaccatc  46740
tagaatcatg ttcttagcgg aaggaaaagc tctatcgagt aattcttcaa agtcagtaac  46800
cttatgaggt gtaataggtt taagacttct actaaaatat ttaaaatttt tatcatgttt  46860
atgtatttgt attctttctc catcgtactt aaactctaca attataccat tagggcattt  46920
ttttaccgct tccgaaaatg tcttacacgc ggatgctaac atcggctgta aaggcaccat  46980
taattctatt agtggtttaa tattatcttc caaagatcgt tgtactacct gttctaaatt  47040
attacataat ttgaatattc cataagcgtc tttatggagc cctgataaca catgttttgg  47100
accaatgttc attcgtaaat catgttttat taatcttatg atatgtcgaa gatcattagg  47160
tgtacatctg ggtattattt tttttatttc tttgatttga tcatttttctc tagttactgt  47220
agataatctt gttagaaaac aatcaacttc atgtaacgtt aatgtacttt ctgtggcata  47280
atctaccaca gatttactct ttttaagaaa tgaacctatc acataagcta catctcctat  47340
attaattaca tatttataca tttcatcagc atcatgacaa aatattttac taaataactt  47400
tactaactgt ttatcgttta tattataaat tagtttaccc gttcccggta gtaataactt  47460
tgtaataata tatacatcat tataatcacg accgcgatgt ataaattctg atattagttt  47520
tgttttcttt acatagcttg attctgtgga tatagatgta catagttctc taaattcttt  47580
caatgttact tccatgtctt tataataagc caggtatttt ttacgttttt attcagggtc  47640
ttttattttg cccatgaaaa ccacagaacc tgttttatta tattttatta cgaatataaa  47700
aggtctattt atatggtagt tgttattaga tattttttcc catttctttt ggtcacctag  47760
tacaatctta ttatttataa aatctacttg tgatttaaca aacaaactgg taatagaaaa  47820
cttgtctgga ctaactgatt tcatggaaca attttcatca aaaatatcag ttatacctag  47880
ttctacaaag acagacttga tgttatgttg tgtttgtata gaaaattttg ggatactaac  47940
tgatatttct gaatatttca tgttacttac tcctatctta gacgataata aaattcgagg  48000
cgtaatatgt ttttccaaat atttgaaatt cttatacgta tcggcgaaga aaagtaacat  48060
actataagtg ttatgcaagt aaggtatgtt aatgatattg gatttaattt catgacaata  48120
catatgtcca aacattccac tcgtaattat gtacggaacg actttagtta aatacttagt  48180
cacaaaaaac ttatgactgt cattatctga aaacggtgat tcccataaat cagaatactt  48240
aatattaaat agaatgctcg cttctggagg tttccggata ctagataaca tatcttctgt  48300
attatagttt aattcactca ttttattaca taatacagta acatctcccg aaaccaatga  48360
tgttatatta gatttactta catacttctt gtaactatca tgaatacgtt tgttatgatc  48420
tataaagaag atggatgtat attctgttct agatagcagt tctttaagta tcttgtctgt  48480
attactatca tcgtcttcat catcgtctaa aggtagcata tataataaat ctaatagttg  48540
atttctcgat ctatcagtac tcgctttcaa taacattttt actataagca taatagaagg  48600
cggtgatatc actatatttt tatcgggtat tcttttagta attagttcgt agaatttcgt  48660
agagataaaa gccaatttgt tgttgatact gcttacgtta ctcatgtttc ttgtttctgt  48720
taattaacag gtataccctt acaataagtt taattaactt ttaggttttt gtgaagaact  48780
```

-continued

```
tttagcttct agttccctta tccataattg ggtcttagat ctagattctt cccatgtata  48840
aagggggaca tacccaaaat ctttaaatgc tttgtccgtt tctatagtaa atgtcgtaca  48900
ttccttaatc aaagtataag gatttagtaa aggcgtgtaa gaacaaatag gtgatagtaa  48960
tactcttaaa cctttattaa tattagcgat aaaccttaaa caccataaag gaagacatgt  49020
attccgtaga tccatcccta attgattaaa gaaatgcatg ttaaaatcat gataatgttc  49080
agtaggagag gtatcgtaac agtaatacac gttcttgcag agaggactat gttgaccatt  49140
ttctatcata tttcttgctg ctaaaatatg catccaagct acgtttcctg catagactct  49200
gctatgaaat actttatcat ccgcatattt atacattttc ctgcttttat acgatcttct  49260
gtataaagtt tctagtactg gacagtattc tccgaaaaca cctaatgggc gtagcgcaca  49320
agtgcataat ctaagtccta tattagacat agtaccgtta gcttctagta tatatttctc  49380
agataactgt ttactaagag gataagcctc tttatggtta gattgataat acgtattctc  49440
gtttcctctt atcatcgcat ctccgagaaa gttaggacct accgcagaat aactactcgt  49500
atatactaag actcttacgc cgttatacag acaagaatct actacgttct tcgttccgtt  49560
gatattaacg tccattatag agtcgttagt aaacttaccc gctacatcat ttatcgaagc  49620
aatatgaatg accacatctg ctgatctaag cgcttcgtcc aaagtacttt tatttctaac  49680
atctccaatc acgggaacta tctttattat attacatttt tctacaagat ctagtaacca  49740
ttggtcgatt ctaatatcgt aaacacgaac ttcttttaaa gaggattcga acaagataag  49800
attatttata atgtgtctac ctaaaaatcc acaccctccg gttaccacgt atactagtgt  49860
acgcattttg agtattaact atataagacc aaaattatat tttcattttc tgttatatta  49920
tactataata aaaacaaata aatatacgaa tattataaga aatttagaac acgttattaa  49980
agtattgcct tttttattaa cggcgtgttc ttgtaattgc cgtttagaat agtctttatt  50040
tactttagat aactcttcta tcataaccgt ctccttattc caaccttctt cagaagtaca  50100
tgtgtactta ccgaagttat catcatagag attatatatg aagaaatagc acatatcatt  50160
attatcaggt ccacaatcga cgatagtttt gttatgttta tttacccaga cgtaattggc  50220
ttgatgagat tctatgggac aacttaaaac atgataggat gatgaactta aatacacctt  50280
tctactaaaa ggttctctct ttattaaact accggaacat atatttttag gaacatcgta  50340
tatatctttt tgtaggagtt tcttttctcc accgtaaacg cagtcaatat ttgtccatcc  50400
gcaatgaggg tctctactca ggagacaact atcgcacgta ccgccgtata aatggcaaaa  50460
tgctaaaggt agttcgatag tactatcgtt gtaagataca aataattttt ccgaacgttc  50520
gtccgacact agagcgagca caggagatgg atattgtttt agagttaatt ctatgacatt  50580
tataactcca tcttcgtaaa ctactacttt gtgtatttta ccatcggacg tagaaagata  50640
gaacgtggta accctgtagt ctttatgttg gtagtttata acagctgtat taattactat  50700
atgtgtatac gtatattttg ttttaaatat aaaatctcct tttacaccat ataatgtttc  50760
aggatataaa tcgattactt caaaagtatc tctgggagtt gatgtgttta aacaagtacc  50820
tggcctaacc gacagaactt taccaccgct ataccctttc agtggagaag tattaaagtt  50880
attctgtatt ttatcgaact taaacataca tacggcagaa tagttccatt cattaaagaa  50940
tagtccatat ataatagttt catttggact tttacctttg attacgacaa catcttttag  51000
ataattaaat cgtacattca gatcttcgca gatcattatc gatttcagga aggtagacca  51060
ttttgaaccc gataatgacc ccgatcctcc ctgatcgtgt ttacatactc tagatacttt  51120
```

-continued

```
tgccattcct tcttcctgga agaatatata tattgtatca tttatactgt ttgtttcttg  51180
tagcgatact aaatgtacaa atttaggatt tttcattgta gaactagatg tatataatac  51240
aggcttacct acgattctac taaatcctgt acttagatga ctatattttt ttatagttga  51300
gtatatttct ttaccatcta ttaataccag tcctgtcata tcataactct ccggagagag  51360
tcctctaccg taaggcgtgg gttcttttat ggtaccgttg atataccagc atgtgggtga  51420
actagaattc gttccacaca ctagaatttt gtcatcatat ccacctataa atgtaatata  51480
attagcgcct gattgtgtcg atacattatc gggtgaaaag tccaccgtaa tattgctttt  51540
atcggttgta tttaccacgt atacagtatt tgttactcct ataattagtc gggtattaca  51600
atccgtgcga tatataacca catcttccat ataagtttta tacctaaact cgatattatt  51660
ttcagtcaac ttgctcttaa cacgggggaga tattatttta gcgatattac acggtattac  51720
caaaagtata acgatgatga tacttatata aaacattatg gttggtatac tgttatattt  51780
tataatacta ttgatatttt gtgtatcgta tagattatat attcatatat tacgtcatat  51840
taatacatat ctatttttta tgttttacga tatagataaa aatgaatata ataatttaat  51900
tacttattag tatcttgggt tttgtaagga cattctggct cacaacaacc cccatcagaa  51960
ggtttaggtc cggtatttac gcctttatca tcggtagatg gaggttgtac attcccttct  52020
gggggagaat cgattgttgg tttttcagct ggagattcca tggctttagg gttcaataat  52080
attaatgttt ctttttcatt tttaatgtac gttattttgt aataatgttt atataaatta  52140
ccatacttta gatattataa atattgaagt aaaagaatag tctaaattac ctaacataga  52200
acatcatgtc cacgagttta atagaattct ataattggtc tcttaccata cgtgataagc  52260
gtgtagacaa ttggctgtta atgaattctc ctattcccac aatatgtata agtactttat  52320
atctaattat agtctggtta ggacctaaat ggataaaaac tagaaacgcg tttaacatta  52380
gatggttact agttttgtat aatttttcta tggtatttct taatttctat attctgaaag  52440
aattatttgt atcgtcggca gcaaaaggtt atagttatgt ttgccagcct atagattatt  52500
cagataacgt tcacgaggtt aggatagcca gagcattatg gttgtactat atatccaaag  52560
ggatagaata cttggatacg gtatttttca tacttaggaa aaaatttaat caggttagtt  52620
ttctacacgt atatcatcat tttactatgt ttactctagg atggataggt attaaatggt  52680
ttgctggagg tcaggcattt tttggagctc agctaaattc ttttatccat gttattatgt  52740
acacttatta tggtatggcc gcttgtggtc ctatgttcag aaagtatcta tggtggaaac  52800
gttatcttac tataatgcag ttggtacagt tccatatagc tataggacat actgctatgt  52860
ccatttacat agattgcccg tttccaaaat ggatacagtg gtcagttatt atctattcta  52920
ttagtttcat attactgttt ggtaacttct attttagaac atacaagaat tctagtaaga  52980
aggttaaata agcatatatc taaaatgaca tacggttatc acaaatagaa atttatataa  53040
atagcaaatt ggtaatataa ataataatgt ataaaaaagt caacctttct ggtatagtta  53100
tatcagaacc aaaatcggta aaaaaattta agacaaaaga ttctatagtt aatgtattgc  53160
cagaatacta ccatactatt gctgacaaaa gactcgaaat acgtaaagat aaagataatt  53220
gctggttctg taaacaagat atgaatacat ataatcccta ttttatagag actctatacg  53280
gtgatcatat aggggtattt tgttccaaaa tttgtaggga ttctttcgct aacatgataa  53340
aaagtgtaat agctttacga gaagaaccta aaatatctct tctgccgttg gaactatatg  53400
aaaagccgga agaagtatta gaagtaatca acgatctaag acacaaagaa ggaatatatg  53460
gaagctgtat acttgaatcc gacaaaaata tcattaaatt aacactaaga tgccattgta  53520
```

-continued

```
atactaatta aataattttc acttactata aatgaataat tctataataa gttcggtaat  53580
taactctata gattctagca gcaagcgaac taacatattt agcttcgatg tacaacagcc  53640
cacggcttat atgccacaat atatatccgt taacggatat cataataaaa aagacaatga  53700
cgctaatcaa gtatgcagcg tgtcattcga tattagggat cagcatatag cagctataaa  53760
ttatttcttt atatcaatac aattgccaga agtatcggga gaaggtaagt ttgcttacgt  53820
accatacgta ggctataaat gcattcaaca cgtagctatt acctgcgggg atattactat  53880
atgggaaaca gatggagaag aacttttcga taagtgtgta gatgataaga tagcgagttt  53940
atccggttat tctccagagt taaacgatat ctccacagga tatactccta acgatacgat  54000
aaaagatcct actactctat atgtatatat aaaatctcct tttgatgcgg ataaaactat  54060
tagtagtttg aaactagtta ataataagat aaccgttaca ataacattca gaagtattaa  54120
tgatgtaata gtttatgatt ctaagtttca agtagagagg tttgttaaag actttgttta  54180
ttctactgaa ttacatctaa tcgcttacgc ggttagtgat ataaaaccta agtctgctta  54240
tatagagttg gatcgtagag tagtctcgtg ttctagtacg cctaccccta tacccgttat  54300
ttcagatgta tacgcgtgta ctgctatgtc tgtttatgtt aagccctatt acggaatgat  54360
ggaaaacaaa tttatatctt accccggata taaacaaacc gaatctgact atgtaagatg  54420
tatggtaaat cgcttgctag acgatcttgt tgttgtggca gatacagtac caaaaggttt  54480
tccgagcacg gcaacatttg taaaagttcc tgttgatgga cagataaatc tacaagatgt  54540
tgatataata gttaaaatag acaacgtacc cgatgataaa gatatatact accatactaa  54600
tctattaata ttcggaacaa ggaaaaactc tttcgtttat aatatatcca agaagttttc  54660
atctataata ggtatgtatt ctcctaatac agatagtatc aacttttcta aagtaaacca  54720
taccatcagt attacggatg cttctatacc tgttagcttc tgggtatcac aaaagaacgt  54780
ctatcaggga gataacagat ctaactattc taaatctaaa gacttagtag taaacgatcc  54840
cttcaggaaa ggaatagata tggttaataa aacggatgta atttctagac tagaagtacg  54900
ttttggaaat gatcctatat attcagaaat ctctcctatt acaaaagtat ttaacatgct  54960
acttactggg agtagcataa atatgaggaa gattattttt aatatgaatc cggctaatat  55020
atttagacct accactctca atgctaatac taagagaggg aaagataaac tcacagttag  55080
gatatcttat atcgatacag atcctaataa tcctatacat tatgtagcta aacaactagt  55140
agttatatgt acagatctat acaggataga ttatgatggg aatattaata taactaaaat  55200
tactgaataa aaaatgattt tataaataag gtattaataa aatgaatacg gacaggataa  55260
ccgctttcat taaaaatggc atttcagcaa gaatgccttt ttatgatact ttgccagata  55320
tggatcttgt ttttggtaaa aaccatttgc ctagtctaga atacggtgct aattattttc  55380
ttcagctttc aaaaattaac gatattaatc gtttatctac tgaaatgtta tctctatata  55440
cacacgatct taacaaagaa tctgatatta gtaaactttt tgaaccttat aacataaaga  55500
ccataaaatc ttacggaaga tctattcaag cagatgctgt agttgtagac ctgagaccta  55560
gcaactcgct ttataagaac gaacatcctt actataaatc taataactac ttaaaagaaa  55620
ataatctata tatatgcgat tatactatga taacttttga gatatatcgt ccgatatttg  55680
aattatccac agagaaaaca tgtattatta aggtaccaac tctttttgga aaaacaatcg  55740
taaacgcagt gcgcgtttac tgcagtctat ttagatatgt caagctttac aaactatcgg  55800
ccgatagttg gttaaaagat agtgctatta tagtgtgtca acaaccccat gccgcaaaca  55860
```

-continued

```
taaataaatt tataacttat attagaaaag ttactaaatc acaaacttgg ctagacagca  55920
acaatgtaaa ttttatatta atccacgatt ctgtagaaag agtatttata gaaaaattct  55980
tatcattttc atataaaata tatgaatctt tatattacgt tcattcgtta ctctacagta  56040
gcatgacatc tgatctccaa tctctagata acgaatatca aaaaaagttg attaagttgt  56100
tacgcggtta atcgtattaa taatatcata gctgttacca atactttact aatgataatt  56160
tgttcaacaa attacatata gttaaatgaa cacgtacgct gcgtatattg attatgcgct  56220
taagaaatta gataccttc  ctgtagatat gactggcggg aacgataata cggttttatt  56280
gaaggattac caattatttg tagcaaaagt ttttttagga ctcaatagta tgaactctat  56340
actattattc caggaaacag gtgttggaaa aacaattact acggtatata tgctcaagaa  56400
ccttaaaaaa atatatagtg aatggactat tatcatcttg gtaaaaaagg cattaataga  56460
tgatccatgg acgcatacta tcttagatta tgcaccagaa gtaatgaaag attgtattat  56520
catgaattat gatgatcaaa attttcataa taagtttttt acaaatataa aatctataaa  56580
cgtaaaaagt agaattttca tcatcataga cgaatgccac aactttatat ctaaatcact  56640
gaccaaagaa gataataaaa aacgtaatac taaacttgtt tataactaca tagcgaaaaa  56700
tcttatgcaa aaaaacaata aacttatatg tttgtcggct acacctattg taaacgatgt  56760
tagggaattt cagatgcttg ttaatcttct tagacctggt atattaactc ctgataagtc  56820
tttgttttat aataaaaagc taatagatga aaaagagatc atttcaaaac tgggatgtat  56880
atgttcctat atcgttaaca atgaagcatc tatattcgag gacgtagaaa atactactct  56940
ttttgctaaa aaaactgtac atattaagca cgtgtttatg tctaaaaaac aagaagaact  57000
atatctaaaa gccagatatt tagaacgtaa actcggcata tcggtattca aaatatatca  57060
acgtatggcg tctacttttg tatttgatga tattccagat aagaaaaagt taaccgaaga  57120
agaatatgaa aaatttgtag attcgttatc tatagatttt aaaaatacct tatacggtaa  57180
aaaaatatct aaacagtcgt tagatatatt atcagctgga ggtacaatta atgatatcaa  57240
agacgttaaa gatatagaat tatataacta tttgtacgag catagttgta aattcacatt  57300
cgtatgtgtt tcaataatac aatctaaagg aaaatgtctc gtatttgaac cttttataag  57360
atcgtcagga atagaaatat tgctacaata ctttaacgta tttggtataa catatataga  57420
gttctcttct aggacgaagg atattagatc taaaagcgta tccgatttca ataaagtaga  57480
taataccgat ggtgaaataa cgaaagtatg cgtattttcc caaagtggaa acgaaggtat  57540
aagttttctt tctataaacg atatttttat actggatatg acgtggaacg aagcatcttt  57600
aaaacaaatt ataggacgtg ctatacgcct taacagtcac gttaataacc cgccagaacg  57660
tagatacgta aacgtgtatt tcgtggtagc taaactatcg tctggtagat ctagcgtgga  57720
cgatattttg ttagatatta ttcaatctaa gtctaaagaa ttttcacagc tctataaggt  57780
atttaaacat tcgtctatag aatggatcta ttctaactat acagattttc agacagtgga  57840
cgatgaaaag gggtttaaaa aattaatttc taggaatatc atactagatg aaaatacaat  57900
aacaaataaa aaaaagttaa ctatgggtga aaatatatgg tattcatttt cttcttcttt  57960
agtatccatt cacagaggtt tcaaatccat ggataataaa atttacgact ctgaaggatt  58020
tttcatcaca gtattacccg ataagcctac tataaaaata tatgaaggaa aattaattta  58080
tatattaaca gttagataga tgttaactat tgctagcgga tgttcttaca gcgtttatta  58140
tatatttaat tacattagta tacaaataat ctttgttaat atctcttgcg tctataaatg  58200
atattccttt aatttctcta ttagggatga atctattcaa tatttgtcta ctcgtaagat  58260
```

-continued

```
ctgtttctac gtaaagggct ataacttcaa aatctttatc tatcaatctg tcgtatatag  58320
aaccgtatac aaaacagttc ttacagatag cgagataaga ggaatcgata tttaattctt  58380
cttttatttc tcttactaga caattagtta tactttccaa gtcttttatt ttaccacctg  58440
ggaagattat atctatatgg tttgtattat agttattagg aagcgatagc ttataactta  58500
atatatcacg ttcgatgtta ctcatatact ttgaatattt cttaaagagt cttattttcc  58560
gtcgtttatc ttttgtaaat gctatttctg aaaacaagaa actattgtat ctatggcata  58620
aaacaaactt gtcatctatt gttttcatta tacctattac ggatagtgga tatttagcat  58680
gtagtttgcc atattcatat gctaccagtt tgattttttg tatattatca gaatatacag  58740
acggcctaag gagcaattta tttttataat actcccccat atttatatgt taataaggta  58800
ttataaataa aatgcaagta ttcgtatttt tcattacttg atcgatcaaa taatgatcct  58860
aattctttga tttctatgtt atataaaggt ttaatgattt ctgaatagag ttggtctata  58920
aaacacacta tacaataccc ataaaatgtt ctacgaagta tcttatcttc tatggtaagt  58980
tttaatattt tattaccaaa tgtttttata gtaagtattc catcgctttc ttccgatagt  59040
tctctactca ggcattgata tattgattct ttatttttaa ctcttcctcc taataatact  59100
aactcttcaa agttgttgaa tccgctatat gtgaatggta ctattgatct aatgatattt  59160
ctttaatttc gttattatac atatacttta gatggtttat atcgacggct aatatttctg  59220
aaaagcttct tctttttgat ataaccgatt gatacataaa agacgttctt cttataccga  59280
ttataggtat attatctgat gtaatacata acgcgaatat gtgaattcgt ctatcgctaa  59340
gtatatcttt tatgttagtg ttttctatag ttattcttta tttgtttcga aagtaataac  59400
acaatcttta tttttttcta atatattttg ttgttctctg gatatatcga acatgatctt  59460
agtttttata gttgtttatt tttcacttat gtttgataaa ctatatatag tgaaatagca  59520
tatcgtaaac tatataaaaa aatactagtg tatcccattt atgaatatat ttttttaatt  59580
aagatataaa ggaatatatg atataattaa actaataagt taacgattat atcgttaaag  59640
tagaaaaatg tattgagaaa ttattttact ttatagcaat atataccgcg tccctgagat  59700
gatctattct actatccatc caccgtacgg actttttttg actttgcatc tttccataaa  59760
atgtgatcct tcctctgaag tataactatg atcagattct gtatctgata aaggagataa  59820
tgattttacc agtctaaatc caacatttcc aatatctcca caggtaacta cgcacatata  59880
cttacctgtt gattctcctg ttgtaggatt tgggatactt agcgatccta tccctccata  59940
agtatgtaac agtaagttaa ctcccgaagt ctgttgttcc cattttcgtg taataccgtc  60000
aatcttccac cattttatgt tgacttggct tctaccatat attcgtcggg tactaaaagc  60060
acattcaatt tttagcggcc gaccatccga catatctact ctcgatcttc gaggggttat  60120
acttacttcg ttatgcatgt aggttttttt tgaaacagta aacactccta gattcatttt  60180
tttataatca gcgtcgccgt ttatccatac aacacacata tatgaacctt ctgcttcttt  60240
agataccttg gatatatgta gcatggtttg gcccacttgt cgtgtcgtat cccaagttgt  60300
ttttattcct tgagtaactt ctccgtcacc ctgttgccac gctacaatta ctttatcttc  60360
tccagcaccc tgatcatctt taataaaaca agtaagattt atatcactac cttccggtac  60420
gagtacatag ggaggtgctt ttacttctac aaaagttttt gatagatata taaagcagag  60480
aaatattatc aacgtcaatt ctttatgtcg aatactattt ttacatatca ttgtgtgtat  60540
aactaatatc tttctacatg ataaagaatt caatatacta ttaaaatatt tatagttatt  60600
```

-continued tttgatttta caaatattac taaatgctat ccatgtttaa taagctatac gttacatgat 60660
gtaggtatta tgtaaattaa tctttattaa agtattattt ttcaattatg ttacctaaga 60720
aaacaaaaga tgattccatt ccagattggg cttcttttaa cataacagta actgtacttt 60780
cattagcgta gactttaccg ttctttatga aacagtattt tgaattatca tatgaaacag 60840
taccggagtc gcttctgatt ttacaaatta gatcactaca aactaccgaa atatcagatt 60900
cgtctgtaat agttagtata ccagaaacta tatcacctac cttatagtat ttataatcta 60960
tgttacatgt cacatgaaca actatttcat tattaactaa ctccgctaat ggcatggggg 61020
tatcttctac tatctgtatc tttttggcca taaacccaga tgtttccttg tgtaaatact 61080
tatttataac tgcctttttt atattatcca ttagatctaa atttaattca tggggttgta 61140
taactacggg taaatacgcg tttgtattaa acaacgacat ttagttcctt tctaaaatta 61200
atcatccaag aatattctgt aaacaataga ttgaaaggta ctactataat atcattttta 61260
tgtttatata acaatgattt ttcaaatact ttattagtaa cgaagaaatg gtcgtctgtt 61320
atcttctcta tatattttg tgttttttct ttggatttaa aaatactatt taccatttta 61380
aaaagtttag catcgtttat acttactcta gaattgtggt aaaaaaattg tctaaccagc 61440
tcgcctaata caacatccgt tatataagga tggggtgatg atctatagtt tatagatata 61500
tcttttagta tggaataaat tcgttttgtt tctttcgttt taaactttag ataaagtagt 61560
tttttgatat cgaatggtaa agtatttata tcatctatac tataatcatc tagagaagtt 61620
attgtatcgt taaaatctga ataaaccgta gctaataggt atacgttaac aggtttcgaa 61680
acatctttat acgagaactt tctaatagat ctacccaaaa tctgattgta ttgtgaaaaa 61740
gtatcaggta tagtcataaa ccagatgttt cttacttcct tcaaagtata tgattctgac 61800
ataatattgg aggaaaataa aaacataatc ttttctccgt tatcattccc tggggaatta 61860
tacacttcca ataaatcttc taaggatgac ttcattttac tcgtgactat agcaaatgtt 61920
ttaagatgtc cgtttatcat ttttggattg gtaccttgcg aaccggcgta ttcagaatat 61980
ccgttgttaa gcatgatata cttgatgact aatccaccgt atgtagaatt agaaaaatag 62040
ataaaatttt tacccgtaag attcccgata gtatctataa aatatttaaa ttttgagctt 62100
atattaagtt tagttaattc gtctccgtat aagacaccgt cgtttatttt caaattagga 62160
taaagttctt tatcctgttc tacgaataac agttctaaac tattagccaa attcaaaggt 62220
cctaatacag ctaaagaaac atttgtcatg tttttttcaa acatttcatt attgcacaat 62280
ttccgtacgt ttatgtagtc agtttcctgt agtttagaca ttttacaata aactactttc 62340
gtatctaaaa actctttacc gtgaaagatg atactcggta gttccgtatc acataattca 62400
tagtaggata tcttattctt cagaatattt tttaatacgc ttacaccttt ttcgtttaat 62460
attatctgaa atactttctt tccctggatt ataatatcgt taaagtttat accttcatcc 62520
gacataatac taataatatt agatagtgta ataggtgtat tagtgatagg agaccctgat 62580
agtaaaagaa aaggtacctt attcttattt ttaataatag tcattaattc acctgtattg 62640
tttccgaata tgttatgagc ctcgtctatg atgaaaatag agtcgttgta cttagataaa 62700
gcattgtagt tcactacatt atcgttgtag ttaagactat agaaattaat cgtcgaataa 62760
atatgaatat tttcaataac atattctgta ttgatgagat tagttgccaa atctaaatta 62820
tacgtaaata tattaagtat attaatatta ggtaccaata tgtaaacctt tttaaacttt 62880
gacacgataa gtgcaaatag cagtgctata atagttttcc ctgaccccat aatatgaaac 62940
aacaaaacac tttcattatg atctagtata gtccttaaaa gataatccaa ggtagctaat 63000

-continued tgatgaggta agatattagg aatgttatct atgtgcccat taaagagttc aagtatttct 63060
aggttcattt atagtattca aatcttctat gaatataaaa gacatgtatt catcggccaa 63120
gttcatatat tttttattct tcatgataaa actgtcaatg tcttgcccgt atagttttac 63180
attaaaatgg agacttaatt tctgttgaaa tatgtttaat tgtagtacag gtattccatc 63240
atcgtctgtt atatatccta atttcattaa tttatctaca tatttcacat gcgtagaatt 63300
actaggaata atgagagatt ctacttttaa tctgaactta aagtctggta ttttatctgg 63360
tgttggtaat attcttaagt taggaacatg atatttacta aaccatccta aaagtatttt 63420
cagaaacgcg tatctaaaat aattagattg aatttttgaa tcaagacttt cgtttaacgg 63480
tttaataaaa tcatactttg agttatgcac cttctttttt gtattagtaa agtgagtttt 63540
aaaattaact agagctatcc ttctcattat agcgttatct actttatcga atacgggttt 63600
atagttggta tctattatga tagtagcatg attcctgtta ttgattttat tagaataaca 63660
agatcttcct actacacagg gttctgttaa cttcttgata ttgtcggatc ttattttttt 63720
ggacgtatta caactaaaat caggaagttc gctacaaaat actactctct tcaagtgcat 63780
gttagcgata aagggattag gacctttatc catttgttct gttagaataa cctgaccggt 63840
ttctagaaac atattatgca tgacagattt tagtaatttt ttagtcgtcg attttccagt 63900
agctgtttct ccataaaaga agaatatgca ttgttttgta gtacccatga gacaactcga 63960
aagtatctgt tcgtagagtt ctctattttc aaaattttcc tttgtctttg gttggatatc 64020
gtctagtata gacattagtt ctgtagttat atcatcaaca tttatacctt cttcgtattt 64080
atacccagtt gatacagtac aaacaaattt ctttgcgtca ttaccttgat agaatataga 64140
atcttttata tcatacacac cgttaagaaa ttgtaatttt tctggataag tgtcggtttc 64200
tatcgtatct atcaacatat ctttaaggtt atgttctatg actttccgat ttctaggaca 64260
tagtaacaaa tcggtacagt cggatgataa gtgatctctc atatatagta ttaatttggt 64320
tatattatta tcatcttcac acattctcca cacgttttc aaccaaacta gatattctcc 64380
tctatctgaa acattaatta cattaagatc tattatttgc tgtgaaatac tgaataattt 64440
attaccttct aaggaaatag ttttaatctt acagctattg ggatttccgg atttatatat 64500
tcttatacaa tcgttactaa tcagtaagtg atgaggatgt ttatgagata ctttttttaca 64560
tagattacaa ggcgtggcat agtaaatatc taaaggagtt actgtaaagt tttcagctgt 64620
aatatccttt agattaatta tgctattacc tatagcttta gatatttttt tgatagcgtc 64680
gtgaaaaggt atatattcct ctttccagtt taagagatct ggagattgat gttgttgctc 64740
gctgacgaaa taataacagt cttcttcatt ataatctaca taggtgaata gataattttt 64800
aaaatgaata ttttgtttag tctttttatg aacgtgaatg ttaatcgaat ctttcttagt 64860
tcccactatc ctaagagatg gcttatgtct gtaaactgat gtatctatag cttttactaa 64920
acggttattt gattcttttg tcaatacaat taatttttta cgcatattta tgagagtatc 64980
cagggtagta tagcaattga aaaatataag atgaaaactt gttttttctt tatcggtaga 65040
ctcggttatt gaaaaattcg atttcatatc agttatcatt ttatctttat ctctatgatt 65100
acttatcatc ttacaatcgt tataggcgta atctgctaca aactttgtaa tgatgtttac 65160
aaaattatga gtagcctgat atttatcatc taacctccca tccatatcca catcaaaaaa 65220
caccctgaca tttgaataat actcttcatc ttttagcgtt tcgaataacg tacaatctgg 65280
attgctatag atatatcttt ccagttcatc gcatgtaaat gattctacat atttgctgtt 65340

-continued

```
attattttct ctatgttttg tacgtacacc tatctgctta agtacaaaaa taatgtgatt  65400
gtttcttatc acagaaaggg ccatttaaat cattaattaa aatttcacta aaaggatata  65460
gtttcttcta taagtattta ctatttttaa agttagatat aatgtaaata ttgtttgata  65520
atgataacgt ggttacaaac acaaacatac agtataaaca aatatgactc tttgtattaa  65580
tataaattga ttttctattt taaatctcgt tatcgttata cgatttaaat attatgtaac  65640
tctgtattta ttcgacacta ttaatctagt acatacagaa tttctttcgt atcttttaaa  65700
caatataaac ttcaatactc gtcgccgaag taaggcaatc ctagtacact tctactattt  65760
gaaatatcac aaaatgtatt attggaagca atagcgggaa tactttggtt tttacacgaa  65820
tgtagaatgt tctatagttt ataacagcat aagctgatat actatttata ttaagatctc  65880
tatgattatg acaagattta ttgtctgtat ctacgttgaa ttatatttct ttgataaaga  65940
tattatttat aaaaagtatt attattttta ggaatacaca gtagagatat ataagactat  66000
gattagatat ctcttaaccc caatactcat ctccttcaat gaaattatag ctacgtctat  66060
ctacagacgc acgaattaca taacttaaac ggaaagatag tgcggttact agatatcccc  66120
atctctccag aacagcagca tagtgttagg acaatcatct aatgcaatat catatatgaa  66180
tctcactccg ataggatact ttaccacagc tattataatc ttaatgtatg ttctatcata  66240
ttttaaaaac agaaacaaac ggctataagt ttatatgatg tctatattat agtgagtata  66300
ttataagtat gcgggaatat ctttgattta acagcgtacg attcgtgata agtaaatata  66360
ggcaatggat agcataaatg aattcacatc taaaaaacta tccatagaag gaaatatatc  66420
ttctggaaag acagacgtcc taaatatact aagaaatatt aataacgttg tttctttcca  66480
cgacgtagaa gatagatata ctcctataga aaaagaatta ataagaaaat tccatgaaaa  66540
tccttcaaga tggagttacg cgttacaaac gcattactgt atgaagagag tcagaatgca  66600
cttagaatgt tttgtaccta gccgcgtaaa tatattagaa agatctatat ttagcgatag  66660
gtatgttttt gccgaagcag ccacagccct aggatatatg gatgacccag aatgggcact  66720
ctactgtaaa cagcacgatt ggtatacgga taaattagag atccagtttg atggtattat  66780
ttatttaaga actataccgg agtcgtgtaa agaacgtatt aatgaaaaat ctataacgga  66840
gaaaaactat ccaaatataa gtatagacta tttaaagaca cttcatgaaa aacacgaatt  66900
atggctgacg caatgtaaaa aagttccggt attaataatc gatggagaag aagattttat  66960
attcgatcca tgtgcaaaaa aaaaattaat aaacgaggtt acggaattca taaattctat  67020
ataaactatt atattaaata aaattgtcag ttaacggtac aaataccgtt aacctttttct  67080
ggataaatct gaacattcac taccaaaata gaatcctata ttatcgtttt tactgttttc  67140
tggtatgcaa accgccgaac cgttatttct caccagtaag tatcctctat cttcacagga  67200
agcatctgat ttcctgcagt ctataacatc atcttcgttg agtgaactag atgaaacttt  67260
tgtatagtca ttgcagcatc ctagcggatt gttggctcta agactatcta cattttctct  67320
taaatcacag cactctccgg tacatcctcg atccggcaga ggcgggcatt tagcgatgca  67380
attacggagg tcttctcttg tttttgaagt atagttactg gataggcaac actgtaaaat  67440
ttcacctata ccttcattgc tgcttgccag atattgaaga ttacatagta acacgcatag  67500
gtctctatca atagcagcat catcgtattt tttacccgcc atacagcact ctgtttcgca  67560
tgataacggc atacagagta tattatagaa atttattaca aaaaataata tacttaattt  67620
gtaacgcgta tacattttgt aatcctttta tttatattta aaaaaaatta ttttagaata  67680
atcttgaaat tggtatatac ttaagagata gaggatagct ctgcgcagct ataccccact  67740
```

-continued taataaatta taccgcgcag agtataaaag attatattat ccattactat ttataataga 67800
gataacagaa cagtataata tttcatatac taactcatta gtacgagaga tgtttttaac 67860
catctatcgt attattaaat tattagtact accgacgtac aagtattatc cattttacct 67920
atttttaaat gtatcgtacg tagtatacga tactcgtata gcaaaactta ccatactata 67980
gcatataatg tcgttattat atgttatttt agcaacttat ttttatgtta ttaatactgt 68040
tattactagg tgatttacca cgcggatatt cttccaacat cctagttata agtctgccgg 68100
caccaacgtt cataccgcta caatttggaa atatggcacc aattgtttgt ggataattac 68160
ctttatccgt ctcattccct gttatgcaat aagttttatt ttcactagtt gttaataggt 68220
agccactgtc cgggcatccg ggcccagttt tggtacaatt taaaactttc caaggagcgg 68280
gaactggtcc gtatctgcca ttacagcaat catctctaca ctcgtacgtt agtataaaag 68340
gattgtaaaa acaggatcct attacagtta acacgtatat agaaatatta ctctgcatat 68400
ctgcgttaat taagatactt gtaaacactt aatagtaatt catctgttaa tggctatatt 68460
atttttaaat ttttttaacc ttttataaaa acattatatt tcaaatcctt gtacccaatt 68520
tattctgggt tcgttcttga gttctaataa cgtgttaaca atttcgaaag tttcgtctgt 68580
atcgaattga cgattcctag ccgctggatg atagcctact actacagtag ttggagagtt 68640
taatatagat ctaaaattcg agaaatcgct tttacctaaa aagtaaaaca cggatacgta 68700
ggccgctata tggttgatga aaacatccgc taacctttcc cagaaaatct tgtgactttt 68760
tgtttcgcct tctctgcaac ttaagtaata gttccacgct aatacacctt ctacaaacaa 68820
aaaattgtag ttcttgaaga gtctgacgtt atatcttcta gaaatatttt ctgctatagc 68880
cttaatagtt ttttttgaaa aatccggaga ttcgaaaggc acgccggtag catccgtggg 68940
gtaaggatct ataccgacta tacatactct tttatctttt agtgattgtt taagttgttt 69000
aaaaatattt tcatgagacg gtgatgtatt ttcttctagc agccaaggtc ctgtctcttc 69060
tataacatca gatatatggt taataatatt ttcccaatcc tcgtggtatt ctataggata 69120
cggccaatta tttaacttta acgtcttcat tatagattac aattattcat atttattttg 69180
ttttcaattt cgctgtatca tgcacgtgat agaacaggcc agtcattata ccacttattt 69240
ttatctagta aattcaattt taaatcatcc cacagttcga cttctttact gatatctaac 69300
atccaaggat taaatggaag atatttatat tgattattat caggtgatat tactttatta 69360
ttttgtttat ttttattatc catagaagat ttatacttat tatacctaat aagttgtatc 69420
gatgctactt ctttccaaaa atttctaaat gtaatacgtt tacaatctaa tcctagttta 69480
ttagcttgtt ttcttactat accaaaagcg tatattagta tatctcctaa accgcaatta 69540
ttagttattt ttctacccgt cattcgtttt agaatacgta cgatggtgtc caaattaatg 69600
ttatgtgtac cgtattctcc tataatccat agtctaaaaa acgttatact gggctttccg 69660
aggggccatc ttaaagcttg tattaaactt ttatttttac tttttagaat atctgaaatc 69720
ttgtatttat aatgatatat aggattacaa atccagtaag cgtttataga actaatatca 69780
gtaactttta tattagttct atccaggtaa tattcactcg taatacattt cttagttatt 69840
ctagatatac tgtgttttac aacacgtgtt ttcttttttt ctatatacca tttaccgatg 69900
ataaatccac aaccaactag taatgctttt ttattattct gttctataga tttatatctt 69960
aacatgttag agtcgtagta acatattaat atcttatatt ttttaccaag agttaattta 70020
tattgttctt cttcgttgtt atttatttta acagttgtaa taactatatg gttagtatgt 70080

-continued

```
tctgaagaat ttatcaccat atggtatcta gcggacagtc ttttcaagaa cagctttaac  70140
ctatctattc ctaccttcag tttaatatta tcgggtaaat ccaaaaccag tattaataaa  70200
tgggaattat gtaattttaa tgatattgtt gtgtatttgt taactattat tccgttaagc  70260
attctaatat taataatatt accaaatttt gatagaaacc tatcgaatct aaatctattt  70320
acgcttatat tcttttcatc tatcataaat ctatccaatg aataattatt gcttaatata  70380
ttagtgtatg tagagatcat gattgtatat attatagaca agtaaatttt tatttttttt  70440
tcaatatttg atgcgataac atattttata ggagattaaa taaagtacaa ttattgccta  70500
tagttgataa caattaatat attattacgt gcttttaaca gttaaataac atacgtttta  70560
taataaatta aatgaatgat gattggatat tgcatcatac catttataat tttaacctca  70620
atctattaaa tggggagagt tttgacttta aaacatataa agataagata tgtatatttg  70680
taaacgtagc atcggaatga cgactagctg acaggaatta taaggaactt acaaaattat  70740
acgacaggta tttttgtgat ggattacgta taatggcatt tccttgtaac cagtttggtg  70800
gacaagaacc aggtggtgtc aaagaaataa tggaaaccat aaagaaatat tcggtattat  70860
ttgatgtgtc cgaaaaggta atagtaaata ccatatacgc gcatccttta tggaagtggt  70920
tacaaacaag gcctatactg ggagatgtgc ccggtcctat aaaatggaat ttttgtaagt  70980
ttctaataag tccttttggt tacgttatta agagattcga tcctgaagtc aaccctatgt  71040
cgatacaaaa agatatagaa catgttatag aacaacgtgc taatgaagaa atgactataa  71100
atagatgggt catgcctgac acgcattgtt ctgaggaaga atctctttct aaagatgtgt  71160
taaatgacgt ataataaatg gtatctaact actgtgttgt attcatgtta aataattatt  71220
catcggatga ttataaaaaa ataaaatctc tagattatca ctatctaata cttgataaac  71280
attcagatag ttctcataaa acaatatctg gatacgtaga gttaaaagat ggtatatctt  71340
gctcgataat agaaaacata aattctcgaa tattatataa aaaactacaa ggaaacaagg  71400
attttttaag aattaataaa aagaatatag tagacagttt taaatctaaa ggttgttacg  71460
aagaatacag atcgagaaga ttagatctta gtatttttga ttactataag taaattcatt  71520
tctaagttta cggcttttag ttttttttata catgtctttg tttaatattc ttttacatat  71580
tgtctttcta cttaataccg tattttttag catagatagg tattccgtaa agtgatacat  71640
tatatggtct aatgaattat cgtctagttt aaaagtatct atggaatcga gataattatc  71700
ctttaaaaac cgagtatata attattttat ttcgtatatg ttgtaaaggt tatattcaga  71760
aacatctagg tttaatatat cttctctgca ttctccgaag taacacggac ttataccatc  71820
gtgtttaaga atatcattta cttcatctat actcatttct tgatattctt gcacgctatc  71880
acatctgcag gccttgcttt taatgtataa ttatatttat gttttttgtt tttttccttt  71940
attatattaa atctaaaaag caaataagtt gttatgtttc ttcaggctga atagttatct  72000
tgtaaacagt aaatcctctt atccttttta tcaattcctt gattttaggt tctatagtgt  72060
ttctaaatgt aacggttttg tgatatttac ccattctgct acattgtagt ctataacaga  72120
aacgttgata aaccgattta aatgcataat tagtcatttc atgaaatcga cataatatta  72180
catctatgtc ctttcttgaa ttcatcacaa acactatttt taccatgatt ggtgatataa  72240
acatatagta tggtatttat ttttatatat tacagatcac gatattattt ttgggtgcgg  72300
gtaatcctta atacatgtat tgtatatcac agaagtaatt aaatcctgct gtgatactat  72360
ttactatcat tacaaaaagt aatgataaaa acatccataa ctacctacca cgtacgataa  72420
cgtgataaag aacggatgtg acaataaata ttttataaat taattattaa gttaaaacat  72480
```

-continued taatatataa taatcattat tttttgctaa tttcctattt cggactagag caaaatatat 72540
gtaaaaagtt attacattaa ctcaattgat ttaaattaaa taataatatt ggataaatgc 72600
tccaacagtt ctttcaaaaa ttaatttctt tattacgtaa accactaaag atatctgtac 72660
ggggtttgct agaagagcct ttttcgggtt cgggagtagg ttgatctgat ggtttactag 72720
aagagtcttt ttcgggttcg ggagagggtt gctcgggtgg tttactttcg ctaggttggg 72780
gctgtggctc agaaccagca tcattagaag gaggcatcgt atcaatatcc gacttctcgg 72840
tgggtgcttt gctactacct ccagccaatg ttctaaatac gtcactaatt aacttagtca 72900
tgttgtccat tctgccacgc atatcttcgt ggcagataag tagctgcctg gtaaagacat 72960
ctttggcctc ttggcctttg agtttttcat actcttgaat cagtttcttt tccatgattt 73020
ataggctata aaaaatagta ttttctactc attattttac tgttacttaa actaaaatac 73080
aggattattt atattctttt ttctatcatt tcataaacgg ttttgatagt ttcgttttct 73140
tctttacaat tacttagttg tccgctatac caagctctaa caaatgcatg aaacttatct 73200
ctatcgtaat cgaattttac taatttttct atatcactac tatcgaataa ttcatcagaa 73260
ataattactt tccaaatgtc agtatcgctt aatgatacta tatgtttatt taatatacag 73320
taaaggttag atgattcctg ttttcttatc aagcaattta tctcttttct caataaaatg 73380
tttttataaa acaaatctga tttatccata tttatttgtt ttataagatt gggagatgta 73440
taaaaaaatg aactgtcgtt gacttgataa ccatctataa ctatctcttt ttcgggtttt 73500
aataattgat gacatttgat catcgttata gttttgatat ctccgttaca tctgtaacat 73560
aatacataaa catggagttt atccggttga gaatacatct ttatatttcc ctcgttgttg 73620
attacacatg aacctattac ttttttatat tctttatata acattaaatt gattctttgt 73680
ttgataggac agacaacgtt ggatgtaata aaagaatggt ataactcatc ttcatcgtta 73740
acacttattt cataaacata ataaagttct atgttgttca tcaataatat tattctttta 73800
tttataaatt catccgtatc tcctagtaaa atgtatacat tattactact attacataaa 73860
tagtctactg atgtataact atttaaccta tgtatttcca tctaaatatg atatttaatt 73920
tatatataaa atatagataa aatatcacat ataaaagagg tttttttataa tattataata 73980
gtagtatata attttttata ttatatatga ttcaaatatt tatataatgt gtatattgtt 74040
tttattcttc gatccccata atatatatgg gagatttaaa tatataatag cgtctaatag 74100
agatgaaatt tattctcgtg aagcaatacc tgctaaattt tggaattcta acggctatga 74160
tgtactcagc ggtatagacg taaaatccgg ggtacctggt taggcataaa tactgacggc 74220
aagttttccg tagtcactaa ttacttacaa ccttacgaag atcctaattt tataagtagg 74280
ggaaatttag tatctgatta tttaacatct aatatatctt ctcgtgaata tctatgctat 74340
ttatcaaaga gagggcattt atacaacgga tttaatctta ttacggcgtc tttttctaaa 74400
gaatccgatg atttatatta ctactctaat agatcaggta ctgcaccaga aaggctagga 74460
accgggatat acggattatc taattctttg ttagatatat catggcctaa agtttgtgtc 74520
ggtaagaaag tattcacaga tataattcat gcccataaga atgatttaaa ccaagaatca 74580
ttaatcacgg aattactaga aatgttaaac gataccagtc cgctaccgat agatcctaga 74640
atacaggaac agggccaaga tttcataaga ccgatgataa aagaattttc atctatatgc 74700
gttagagccg atggttacgg tacaagaaca aatacgatag taactataga tagtcattat 74760
agtgttaatt ttattgaaaa aaccataacg gatatggaca caaaagagtt taaaatatcg 74820

-continued

```
agatatacat ttagtttatt atcttagaaa aagtaagtgt atcaaagttc tttatttata  74880
taataacata ctgtaacttt atttaatata tgtataatct tataggttaa aataacacta  74940
actatcagat ttatcattaa tattattatt actattatac ttaacctctc catctacatc  75000
ctcctttcaa gagaataacc aattacgtag tggattcttt ctgtattata atcagataga  75060
gttctataca gtccttgtta gtcgggaggt attcctttct tattttgggt ctttaatttt  75120
aaattttcaa ccgtattact aggttcagct aaataaatga ttatctttac aaatatctgc  75180
attactgtat ttttatacta aacgcgtatt atatacgaga aataattata tttttatatt  75240
ctagatattt attaactact tttatctata tgttcatcat gcatttcctt tatagattta  75300
attatcttat cttctattac tattccttct ttgctatctt tatcgctaag tactatattt  75360
gattaagaat gattagtaat tagtaatacg ttagttcttc tggtatctag agaattagct  75420
attacaacat ggtgattata tttatatagc gcttgcctag ctttagttac taacatgttt  75480
ttatcggtct ctaatttgaa tgacactaca aaagcatttg gacaccattc gtctactaaa  75540
tgaaataaca tcttagggac ggtttttaac tctaaagtaa tatctgtaga cgaatctatt  75600
ttatgttcat acatttcgtc ttctggaata tagaaatcag aaacggccgc tgcaagatat  75660
acaacggcat gactaccgag tatagataaa gatttagaaa tcatttctaa gaaatttaga  75720
tactgatgta tacaagtata actaatagcg agtaatttat tttgttctat agcttcatta  75780
tatttttta aagcagatac aagttgtgta tttagagcgt cgttaaagta aacagtattt  75840
ccttctacat ttaatgaact caataacata tttcccgaag gtaataatct tgaccaaggg  75900
aaaatagatt attcacggta taagaaacat acagaataac cattttctat taactttca  75960
acagaaatag ctcctctcat acccgtacta aaattctcta aaaatctgac tggtttttt  76020
tctaaagata ctctagtccc tccagatgtg actaaagcta cacgcctgtt tttctcttt  76080
tgtaatttta cccaattatt aatgttagta gtcgtgtcca tttttttaat ataagaattt  76140
atattaggtt aatttataag aaaccaatac tttaaatctc taattcgttg ttctaaacaa  76200
cagttatggt ttcttaaatt gttgattcat gataatatta tcgtaataat tctattattg  76260
aaatatctag tctcgttttt gagataaata ttacgaataa agcatattca tatcaaagca  76320
acattagctt tacatttaag ttgtactacg catacgcacg aagtacctat tcttatatat  76380
tcccaggaag gcattccatt tttaataact atagagttaa caaaagaatg agacgtagaa  76440
caataagagg accaaaatcg tgtatctatt cctaaacagc cactaatagc cggatattcc  76500
ttacacttgg tttcgaatag gtactgatag taaacttgtt tattatgtac tatttgatcc  76560
aatagttcta gtttattacc tctgtgatca aagactgtag ttttgttagc gacccatgta  76620
gaactacttt cacaagataa gtatattcct tcactggtat tacctacaga caataattca  76680
tctatgcttc gtttaccacg atgttctata ttcggagtac gagtactaaa aacaacttta  76740
gatgtatcta atttatcgtt tataagataa ggattagtaa attggagtaa cgatcccttg  76800
catactatac ctaatacaca tataaagatt agccttctaa aattacaggg gtgcgtatgg  76860
tatgccattc ttatttatat atgaacttac taattaagta atagaatatg tctcagtaat  76920
aattgacggt acactgtagt atttgattcc actagtaaac acataaattc cttaccatta  76980
tgtttattat ccactaatag ttctctaata aaaaatgtag agttttgtaa cggaattgtt  77040
acaggacttt tatgaattac cgattccatt tcgctaatgg gtttaccacc gggaccggcc  77100
caaaacattc tcgctgacga acctttccta ccacacccta cacatattaa gctagtagta  77160
tttatatctt caggcagtct agtaatatta acgtaggtac aatcttcgcg tgttacagga  77220
```

-continued

```
cagcattctc gcacaccgtc ggaatttttt cttgcgtttt ccggaagata tccttctagg  77280
tctagaaaaa tagtttcgtc actatcatct tcctcataac taactgtact gtaatctcct  77340
tcatcgccat agtctatcgg attcaagagt acgggtatta tcaaacatag aataaaaata  77400
gttctataca tcatgttaat ttagatattt cttctggaca cgatatctat cctactaagt  77460
atgtatggta tttatttatc aattaatctg cgtatgtagt aactactaca gcgtttctaa  77520
gatcatcatg tcctacaatt ttatttcttt gacgtcgtgt ttatatcatt ttctgttttg  77580
ggataataat tttctctaat ataaaattat atattaattc tttttctata ttgaagtgat  77640
ttaattaaag aaaatatgta atctttatct aattaggttt ttccttatct aataatagaa  77700
ctgtatacct ggtgatcttc ctacttgatt tacgtgacct aatataatta tttagatatt  77760
tacctgtttt tcgcataaat ataattccta aaaatattat tattaagata ttaatatcta  77820
ttatccatga taatatatag agaaacatta tattaatcgc caatcgaata tgaataacat  77880
acatagtaat aataaagata gcagttaatg gcaaactaat attattcatg ataactgcta  77940
taaaagaaga taatatagca agatatattg aagtgtctat catatcttat tttatggata  78000
aacctttaac ggcaacttct aagttactta ttttttggtt tattaaacta ttggtttttt  78060
cgtacttttc ttccaatttt tttgtatttt tctttaattt taatatctca ttatcatgaa  78120
tgtcgtatag tattttactt ataccctcag agaagaagcc gcttcgtatc tgatcttcat  78180
tatcagaacc ttttttaagc ctcgtgcaat aggagttaga aagataggag ttaagtatct  78240
tggaaaaatt aagtgcaata ctaggaaaaa cccaacagat aatatgaggc acgagatcga  78300
tatgcacata tgttcctaca agttcgtatt tataggcact atttgatgct aatccgattt  78360
ctaaaacggc tttattatag ataccgtttt tatagttcaa tgtttttatg agtttttttag  78420
atgactctag tctacaccac tgcctaaagt tcttatttcc aagatcacat attttagtag  78480
catttatata tccgttgtat tttaacatga ttacttctat gttcgcatag ttgataaagc  78540
aaaagttctc atctatatgt ttaacggtgt taggtacaaa ctccatattg taatactttc  78600
attcagaata gtattgtttt tacatttttt attataagga aaaaactggt ttattcattt  78660
tcttttaacc atgcatacac aatttacagg aactgataca tgtttagtca ttacagcatt  78720
attttcacca agatacatta ttttttttaat ttctgtgacc gtagaacagt aagattccca  78780
tcttgactca tcaatgccct tacaaggaga tgtagaatta gggaatccca tgcagctaat  78840
catttgaatg tattgtgtgt atccatctcc tttctcagaa tatctgccca aaaattctat  78900
tttactgaca ccagttccat taacagggct tacttctcta atatctaccc atgtagttac  78960
taattcacaa gcgggttcgt ataaataaac agtagtatta tcattactag atgtctgggt  79020
atcgtataat acagctgcat gatagtactg aaaacatgtt agtaacacaa gtatatgtgt  79080
aacgtacata atagaaaaaa gtataattta tgccttattt ttacattata gttaaaacca  79140
taaaactatc ttaattacaa ataaaatact atgtagttcc attatttttg atcgcattaa  79200
atgaaaggaa ctattatatt gtttggtaaa ccaaattgcc cgttatgtaa attttcaaac  79260
gaaatacttt cgaataaaaa gatagctagt aaatatgaaa tcgttagaat aaatatagct  79320
acattcttcg ataaatcaaa ggtcgtagaa atactcggta tggataagtc ttacgatcta  79380
ttaaattcta ttggagaaaa attaggaaac gaatatgttc ttgtatttag gtatgatgat  79440
actagtaagc aaatggcgta tattccattt aagaaataca tagtaatagg acaaatatca  79500
caagattcta tagatttcga taagctgctt aatgaattag aaacaacacc ttacaatata  79560
```

-continued cttcttaagg ataagtagat atcgtttagt gtactggata taatattatt aggtttattg 79620
ctaaagaccg tatctaacat atcagtattg gattcattca aaagatggtc tatacattgg 79680
tctgttactt ttatttttat atccttgtta gataacactt ttttagctaa catgtaagta 79740
aagtagtcta agtaatcttt accaaaaatc agaacaatag attctttggg tatatcttct 79800
gttttaatac catctgggta ttctgtatat ctatatatag atggaatata cttgagttta 79860
gagtaagcta tagtattatt atcggcgttg tattttattt catttccatt aataactatt 79920
atacctatac cttcgttagg aagtttataa ctacgtttaa ttgttttagt aaatttgcct 79980
aactttatgg ttacgagttc cttaagtatg ttgtctggat aagataattc tatttctttt 80040
aaatacgtat cacagtttaa tgctttactt ataagctttg tatttttaga attataatac 80100
ttagttaata cctttactct gtctacgttg aaagaattac ataacgatat aaatttttcc 80160
atatatgctt catcaccact gtctaaatac tttaatagat tataagatat aagggttcta 80220
aatgacatta ttcttagtta tattctttat actattcttg ttattatgtt atttttttag 80280
ttttaaacga actaataaaa tggaaattgg gataaatcct attaagaaaa ttccatggag 80340
tgataacgag catatatttg tatcatcttt atttactaat aaggacaaat atctcaccgg 80400
tcctatgagg ttaacctata gacccgatag taaaacagca gttttagatt ttaaaggtac 80460
caactatacc tattatctag acaattttga tgatgttagg aaattagtac ctacgttgct 80520
actgagtaaa tagtatattt aataatactt gatttatttt caaatacatt tacagctttt 80580
tacagaaacc ttacgaagaa tcgcggtttt aggtgtcctt cctaacctat aatgcactac 80640
taaatcatcc atactctgaa tgctacaaca ctgttttaat tctataccat ctatatagtg 80700
gaatgctagt aaactatata aaaaactatc agtatataca aacgactggc attcgcccat 80760
gcaatagcca taatctatac ccggaggatg taatatccat ttaagaccta tactcctgaa 80820
atttatatac tttctatata ctttacaatt atcggacgga gatgagtagt ctacccact 80880 atcagattca acatattttt tagaacctac actcatttta ttagttgact cggtagggcg 80940
gtccgtgctt ttaatacttc tttttcttat atcgaatgaa taatctacgt gatcatccga 81000
gtagagttct tcttcatcgg taatacttaa aagcttcttt attaacccct caacagatat 81060
atatctatgt ctgttattag tagagactgt atagtatcta tcatctttag gttctgtttc 81120
atttacgtag tattctagaa aaacatgcct ggttctgtta ataataccat caggagctaa 81180
tagagtataa ttacaatgtc tattatagat agattgttta gccatattct cagtaagtaa 81240
gatacaatac catttatcag caggtagtac atgataatca ccagttccgc atattttatt 81300
aatgctacaa ttacaaatga ctttcaaaac tacttcttcg tgttgagtat taagatatat 81360
acaaatacta acgtttagta ttctgttaac aaaatataca tcatgagtat taaaatatgc 81420
agtattcatg tatttaccac ttccgtacat accgtgtaaa tctatggatg gtttgttctt 81480
atggttttca ggaacttcta ctatggtatc atagtattcg tcttgcaagt tttcttcatt 81540
ctctcctatc atagaaagta ttaaatcttt tatagacggc aagttaccat atcctattac 81600
acagtatact aaacatgaac tgataaaaat tattatatta cgacatacca ttttaacgct 81660
tgacgcatat acaaaattcg aacgaatgaa agaaaactac ttcttatttt aactgtactt 81720
aaatgattca actaaataat ggtatacgta tatttgttaa tcattctatg aaaaaagata 81780
tatatatagg tatttcagat tttgggttcg aaaaagatat aaacgatgga attctaggga 81840
tagcgcattt actagaacac atattaatat cattcgataa caagtatttt aatgctaacg 81900
ccagtacttc gcgtacgtat atgagtttct ggtgtgttgc tttacaaaag cgtcattatg 81960

-continued

```
aagatgctat tagaacagct ataagctggt tttttgataa aaagtatata ctaaaaacag  82020
atttttctag aattgtatta gaaaattata ttaccgaact agaaaatgaa tactattatc  82080
gtacagaaat gtatcattgt atggatgtat tggcgtatct atatggagga gatctttata  82140
acggaggccg tataactatg ttagaaaggt tgccagaaat acgtaatatg ttaagtaacc  82200
gaatgaaatt tctatccggt aagaacatag ttatctttgt taaaagacta actaataaca  82260
tactaacgtt actaacaaac acattcggta gtataccaaa gtatcctatt ataatacctc  82320
tagatcctca gattcaggat gctaggagaa agattatcat gatgccttgc ccgttttata  82380
ctcttcttat ccaagtagat aatacaatga ataatttact agctattatc tgtttagtag  82440
aaaactataa ccttatagac tatgaaacaa taagcgataa attatatgtg tgtatttcat  82500
tcgctaacga ggatcaatac gaatatcttt tgtataacat aaaggatatg gattttaaca  82560
taaatagaat agaactagat ctcggagagg attatattat gaatctatat atcaactttc  82620
cttggctgaa gaatgatata ttcgaatata tacataccat gaataccaaa agcgcgatgc  82680
tgttagccga tttaaagaaa aatatgcata acagtatact agaacataag tttatgatta  82740
tatatcctag ttttacgaag ctattatata atataaccga taaacaaaat cacggtatat  82800
tagttgtagg agatgttagt tttacaccag aaaaagatcc aagtatgcat cattctaaca  82860
aagaaaataa taacaattat tctaaaactg taaccaaacg caagagtaaa tatgttatgt  82920
atagaaagac accgacgact aataatatag ttattgatta tacagacagt agtttttttg  82980
attacgcgac tttttaccat gttatgaaat caaaatatga aaagacaaat ttattttcta  83040
ggcttaagac ttcaacaggc atgtgttata aacattgttt tgataatgat gatcttaatg  83100
aattaataaa ttcagatacg tttatacggt ataatagttc taaaccagct gtattatacc  83160
aatatatact tttagcatat tttgttaccg aacgagatat aaaagagtta gtagattata  83220
aagacgctat agaattagac atgaaatatt atagtaaaaa taaaatactc tttggaaaga  83280
atactagata tgatatacgt accaaatcaa tgtttgtatg tggattaatc aaaggacgta  83340
aattaagtga aaaagtcatt accgattata tgtggaagct aaaaagttta ggattaatat  83400
attatcttac ttctattaaa ctaggaatat caaatacttt ttatattttt gcatttacta  83460
tatttccaga aaaagtatat aatttttttg ttgggttaaa agagataacc aatcgttgtc  83520
tcatagtttc aaataaaaat acaaaaatag aagaagatga ctattcctct ttaaacaagc  83580
agatagttat cggtataaag taaaacttct ttctgttaac atataaacat aatttctata  83640
tagttgttta ctagataatc ttataactgt attcatgtag ggaccgaaca aaatttctcc  83700
tttgtaacaa tacatctttt tgcgtctagt agttgtattg attttaacta aaagctgaag  83760
attctttatg tccttaagag tttctccggt tagaatatca ttcctttcaa acatgtctag  83820
gttttcggct ttcttaccac ccttgttata aattttgacg tattctacca tattaacgaa  83880
ataattaaca taaatttcga ataatctatc aaacgatata ttaaaagact tgatatactc  83940
ttctgatttt tttaacatat ccttatcact aggaattact aataaatcgt taggtagtga  84000
taatttgaat ttttttgcat atactatgta ttcgtataaa aattcatggt ctatgctttt  84060
aatcggtttt aaaagacaca tatcataaaa gtatacgtaa atacctttttg ataccctacc  84120
tacacggcct tttctttgcg tcatcataga cttggatata aacagttgat cacctccgaa  84180
gggttttggg acgtatacac gtcccgtgtc gtatacgtga gtagccgtac gaatagtaat  84240
actggattca aggtaaggag tagaaaccaa gatacatgga cgttctctac caggtctctg  84300
```

-continued aacggcgtta agaacctctg taatatcagg tattttaccg tgtattatta taaagtccat 84360
atcggagtta cttttctcta ggtatttttt ataacttata cactgagaaa cggatgctaa 84420
aaatagtatt ccacacatgc cgtttctagg tctacaccag ttaagagtgg tcgatatatt 84480 cttttttttct tcctctgtat acgctttgga atcgtaagag tacttgtttt tgacatatat 84540
ctctttaatg gagtagagta cgggaccttc tatatggtaa aattctacat ctggtaagaa 84600
ttcttgtaat ctgtccctat cgtcttctaa agtagccgac attaatacca gagaatgtat 84660
agtatcgata ttttttctta gaacggatat aataatatct gctattctat catgctcgtg 84720
gatttcatca actataataa tattataatt agataaagaa taactagtaa gcttgttcgt 84780
agataatact ataccatcgt gttgtcgtgt agtatgttct gtttttcctc cgtatcttag 84840
ttctacaggc gaaccttcaa aatctgaaaa ccctaatgac tgtaaaaaat taataccgtt 84900
acttttaact aaagctactc taggtaatga taaaactatt ggtctagata tgtaatcaaa 84960
tcttacacga tctaaattat cccatcctcc gaataaatag ttataccaca taatcacttt 85020
tggtaactga gatgttttcc ctattcctgt acttcctgta acgactattt gtttgcgctt 85080
tctaagtagt tcgaagattt gtaattgtgt aattaagctt aaagacttaa atttaattac 85140
agtaaatggt tttggatttt tgagtatgcc tattgaagat ttttcaggca tctgtttatt 85200
ggaagaaaaa atagataata tatttcctgc agataataga cctcttttat catctagagt 85260
tatatcgtaa atactgttat accccttaca ctttagatag ctgtaacatt cgaacgtaat 85320
aaatgtttta tctgaaatct tgtatatttc ttttttata tcggtactta taggacgtat 85380
atcgataaga tgttggatag gtactctatc gtaaggtttt gaagtatcta attcgatatt 85440
tagcatatag acattattct gaaaacatat ataagctttg gaccatcggt gctttataac 85500
cggaaatata gtatacgaga aaaataaagg attttttcgg tgatattctt ctagttcttt 85560
ttgactatac ttcctaggaa atatatcata catattagaa aatgcataaa tagaaaatag 85620
atcgtttgtt gtcatgtcac agatgttata tatttagtta gtaataaatg gacaagtata 85680
cagaactcgt tatcaataaa ataccagaat tgggattcgt taatttactt tctcatattt 85740
atcaaacagt gggattatgt tcatctatag atatatcaaa atttaaaaca aactgtaatg 85800
gttatgtagt agaaagattt gataaatcag aaactgcggg aaaagtatca tgcgttccaa 85860
tatccatact aatggaatta gtagaaaggg gaatgttatc caagcccgat aatagtaaat 85920
cacaattaga agttaaaaca gacttagtaa acgaactaat cagtaagaat aacggatttg 85980
aagatataat gactattcct actagtatcc cgatgaaata tttttttaaa cctgttctta 86040
aagaaaaggt atctaaagct atcgattttt cagttatgga tattaaagga gacgatgtta 86100
gtcgaatggg tatacgctac ggagaaaatg ataaagttgt taaaattaaa attgctccag 86160
agagggatgc ctggatgacc aatactagca ttcaccagtt tcttatcccc atgtgttacg 86220
gtacggaagt aatttatata ggacagttta attttaactt catgaataga cacgctattt 86280
acgaaaaatc atccgtgttt aacaaaaaata cggaagtgtt taaattaaaa gataggataa 86340
gggataacag atcctcaaga tttattatgt ttggattctg ctatttacat cattggaaat 86400
gtgctatata cgataagaat agagacttta tctgttttta tgattccgga ggtaataatc 86460
ctaacgagtt taaccattat agaaacttct tcttttatag taattcagac ggactaaaca 86520
gaaattcata tttatctagt ttagcgaatg aaaatgccga tatagatata ttatttaact 86580
tctttataga taattacggt gtaaccgctg gttgtataaa cgtagaagtc aatcagttac 86640
tggaatcaga atgcggtatg ttcacgtgtt tatttatggc cgtatgttgt ctaaacccac 86700

-continued

```
caaagggatt caaaggaata cgaaaaatat acacctactt taaattctta gctgataaga  86760
aagtaacgat gttaaaatct atattattta atgttggaaa aatggagttc actataaaag  86820
aagtagatgg agaaggtatg caacagtata aaaaaatgga gaaatggtgc gccaacacta  86880
taaatatatt ggctaataag ataacctcaa gagtagaaga tattataaat tgataatgga  86940
taactttta aagcaaattt cttctaacgt gaaaaaacct atagcagaac ttgaagatcc  87000
ggatgccgtg ataaaattcc attacatgaa tatatctttt aatttcccgg atctgtatta  87060
ttgtaataat aatttgtttg ataaacccga aaacaactta ttagatatat caaaatcgct  87120
actgatgctt aactcatttt cacacgaatg ttttatatta caagatatat tgagagtcat  87180
tcgccgttac ggccatgtat acgatgttta ctttttacct attggttggt tggtaggaca  87240
tggtgaagcg cctaaatatc atgcatcgat aaaattaata aggagcaata cacaagaaat  87300
aatagacggg atcatacgca gacagttatc ccaatacggt atacaaggag acaatttatc  87360
aatttttgta gattcttcca atgaagttgc tataaacagg cactctatta taggagctag  87420
acagttgaat cctatatgcg tagtatcttt ttatcccttt gatccagaac ataaagtttt  87480
tttcgttata tatgttggta gatataaaga taagtattgt ggaatttcct acgtagctga  87540
tagagaagat atgtacaaag ttatcaacag gatatacccg tacgttagtt gtttttacct  87600
cgtatcagat ggtataataa attttcatac tactcccgta gctaatcaca ctagaaatat  87660
taaacccctt ccagttaatt attgtaatac tttatgtgaa atagtatatg attttgaata  87720
tttaaagttt gaacaaggtg ttatgtctat tccggtgttc atgccttttg taccaaaaca  87780
gtttgtatct attatcaatt taccagatga tattctcata acatgtacag cgtccagtaa  87840
catagaatac ataacacata tagataataa aaagctaaaa agaatactta taataataaa  87900
agataaattt ctaaagggta ctatcatgca aggtactttt aaaaaagtaa atatcataag  87960
acacaagaag tatacatata ctataacgta ttcttctttt gattgcccta aactagaaga  88020
tactaagtca tcgctgccaa gtacgtgcaa taaagccata ttagatgggc gtagatatgt  88080
tacaaaaact tttaatgata caatataaat ggaaatagct agagaaacgc taataacgat  88140
aggccttact atattagtag tgttattgat aataactgga ttctcgctag tgctaagatt  88200
aataccgggt gtttatagtt cagtatcgag gtcatcattt acagcaggaa gaatacttcg  88260
ttttatggaa atattttcta ctattatgtt tattcctgga ataattatat tgtacgctgc  88320
ttatataaga aaaattaaaa tgaaaaataa ttagaatctg aaaatgtctt ctggaagcat  88380
ccatgttatt acaggcccta tgttttccgg taaaacatcg gagctagtaa gaagaataaa  88440
aagatttatg ctatctaact ttaaatgtat tattattaaa cattgtggag ataatagata  88500
taatgaggat gatataaaca aagtatatac tcatgatcta ttgtttatgg aggctacggc  88560
atcttctaat ctatctgtat tagtacctac gctattaaat gatggagttc aggtaatagg  88620
tatagacgag gctcaattct ttctagacat agtagaattt agtgaatcca tggctaattt  88680
aggtaaaaca gttattgtgg ccgcgcttaa cggtgatttt aaacgcgaat tattcggtaa  88740
cgtatataag ttattatcat tagctgaaac agtgtccagt ttgacagcta tttgcgtgaa  88800
atgctattgc gacgcttcgt tttctaaacg agttacagaa aataaagaag taatggatat  88860
aggtggtaaa gataaataca tagccgtgtg taggaaatgt ttttttagta attaaggggt  88920
ttagtgtaat aaatttaata aaatattgac aaaatagtta aatgaatata tgaaagtaca  88980
ttatacacgg aatggagttc gatattagtt cttgcagaat gatatattct gttctcgaac  89040
```

-continued

```
aatatcactt tgttactgat aatcgttata acaaccataa tcaaaaattt agaattatat  89100
tatactgttt aaaagattct acgataaaga aatatccgta caggtttgtt tctgaaattc  89160
actttgtaag atacataatt aacaaattca gggggaaaaa tctttacaaa attagtatag  89220
aagctataga tatatcaaaa ggtagacaac aaataatcag aacctaattt ttttatcaaa  89280
aaattaaaat ataaataaaa tgaaaaataa cttgtatgaa gaaaaaatga acatgagtaa  89340
gaaacaagta aaaactcaaa gtaaatgtaa taataacgca tctagattta catgcctgga  89400
tgcggtgcaa tacgctaaag ctttgtgtac taaagatact aaaatagtta aatcagtgaa  89460
attaactcct tctcatcata atctatgcag taatatttct gtgacattag aacctaaata  89520
taatgaaaaa cttgtatctc cgtttatttt ggtggaagga gaaggaaaaa tatatcaaac  89580
tagaagtgac aatttcagtc gtgaggaatc atacttccta aaaatacgcc cgagtgtaat  89640
tagtcctatt ttacatcaga tgatggaatg catttatagt gacttgggtt atctggatcc  89700
ggaaaatact atggatgaaa aaacatttaa agatggttat atatacatta ataaaaataa  89760
aatgtcatct actataatag aatatacgag aaacaacaag gaagtagctg gtagaaaaac  89820
tctatccagc gaagtagaac atctatcgaa gaaagatcct cagatggtta aagctgtact  89880
agttgcttct atatttttcg aaaatgcggt aatgtgtaaa ataagcttta gcttgaaaaa  89940
gcttattatg gaaaaagttt gtaggaaaac tctgatagat actaacggag aagtaatcag  90000
cgtcgtaacc tccggagacg atgatataga ggatgaatcg ggagagtttg aatatgaatc  90060
agacggtgta tctggaattt tagaagaaag atctgatggt aacaggagag gtggttacaa  90120
aataaaagaa acagatgaat atgatgaacg atcattattt aacgtaaact aaatggaaaa  90180
gctatttaca ggtacatacg gtgtttttct ggaatcaaat gattctgatt ttgaggattt  90240
tatcaataca ataatgacag tgctaactgg taaaaaagaa agcaaacaat tatcatggct  90300
aacaattttt attatatttg tagtatgcat agtggtcttt acgtttcttt atttaaagtt  90360
aatgtgttaa gattaaatgg agcaatttga tcaacttgtt cttaatagta ttagcgctaa  90420
agctttaaag tcatatctga ctacgaaaat agctgaagct atagatgaac tagccgctaa  90480
aaagaattct cctaaaaaga aggcacaaac taaaaaaccc gagaatagaa ttcctctaga  90540
tctcataaat aagaactttg tgtctaagtt tgggctaaag ggatataaag atggtgtact  90600
gaatagtttg atatgtagtt tagtagaaaa taattacttt gaaaatggca aacttaaaag  90660
gggtaaacac gatgaactag ttcttctaga tatagaaaaa gaaatattgg ccagaataga  90720
tgaaaattct agtctcaata tagacgtact agacgttaag gttttagcaa atagattgag  90780
aacaaatgcc gatagatttg agtttaaagg tcatacttat tacttagaac aaaataaaac  90840
agaggatatt atcaatcagc ttattaagaa ttcagctata tctatggata tgaaaaatac  90900
tattaaagat acattttata tgatatccga tgaacttctg gatgtattta aaaatagact  90960
atttaaatgt cctcaagtta aagataatat tatatcacgt gctcgattgt acgaatattt  91020
tattaaagct acgaaacccg acgattcaaa aatatacgtt attctaaaag atgataatat  91080
cgctaaaata ctgaacatag aaactatagt tatagaccat tttatctata cgaaacacag  91140
tcttttggta tcgtcgattt ctaatcaaat agataagtat tctaaaaagt ttaacgacca  91200
gttttatagc tccatatcag agtatatcaa agataacgag aaaattaatt tatctaaggt  91260
aatagaatac ctaactatat ctactgtgaa aatagaaaat actgtagaat aaatgatagt  91320
aacagtactt tttttaatta tgttcttcat ttgcacgtta tacagctatc actatttgaa  91380
accatggatc ttctatgtcg aacgtgaagt cacgtagata cgaaatggaa atataaattt  91440
```

-continued

```
ataattatat aatcactact tgtcatcttg tctgagatgg cgaatctcta ttctaagaaa  91500
gttagaaaat ccatacgcaa atttattcgt tcaggtttaa acttcgactt attacatgag  91560
aaacacggac gccgattaat aattaacaat atattcgtta aattaccccc aaaatattat  91620
aactttgcta aaggtctgga tttaaacaat atactagcgt ttgatagcga aataatacaa  91680
cttaatgact taaaaaaact gattatgaga ctacctcttt taccagactg ttttaccgat  91740
gtaatatcgt gtcataaaaa atacttatta tcggatgctg ctattgtgaa taaacttatt  91800
aactctaata tggtatctct ttcagatata cgtaatataa tagataacag aataaaaaca  91860
cctgttgaaa tagcattgct taacagctct ttagttatac cgggtactcc attttctcta  91920
gatgaagtaa aatatatttt tgaaaacact agtgcagaaa acgtgaaaga gctatacaag  91980
agaatagaaa cacctattca cagcgttctc tatatggaag aaaaattttc tatatcaccg  92040
gttcattcat ccctatatca agtaactgat gttgataaaa ttatatattt gataaagaag  92100
tatcccgatg atgatattat tgattatgtc aatggaatag taaaatcaaa aaaagatttt  92160
atagaatcaa taattactat cattaaggat agattacccg atatatcacc ttgcttgaat  92220
aaatggatat caacacaatt accacccgat aaacttagag atgaatttgg tatatacttt  92280
tatgcgttgt ttgaatggat agatatacct ctatacatag ataagtactt gtttctaaac  92340
ataacggagg atgaaactaa atttatctgc cgttatatag atatatacaa aaaaaagtca  92400
gagttgtttg taaatgcgtt tagatggcat ctatattatt gtaatagtat gtatcctcaa  92460
aaagtatttc ccgttattac ttataaacaa gattctaaag aaaaatatgt tgtaaaagaa  92520
tcattcaagt atttagataa taaacaaact atgaaagtac tattaaatga ttttaaatat  92580
aactatgcta tagggaaata catacttgac tcgtcatcgt ccaatgaggt aaagatggat  92640
gctctaaaca tgttacagaa acaagtagtt tgtttagaaa atgctaagtg ttttgatcta  92700
ggtaatttat attctgtatt aataaagttt caatatcacc cggtagatta tgtaatgtat  92760
agcgataaac tgttagatta tatgtctaaa aatagtactt tcgataataa tgatatagga  92820
ttattgactc tagcaagttt cttattttct accgccaaga aaggtattat agatatcaat  92880
tttctgaata ctaactcgct atggagtcct ttgatgtatc ttatagatga ttcgtgtaaa  92940
gtagatttca cgaggtttat gatggctaca aagaatataa aagccgataa cataaattat  93000
ctcaaaaaca aggacgaaaa tattaataat aattttgaac atatagataa tatagatata  93060
tataaactat tagactatag tcgaataaaa ctttatggaa taaacttcat taaaaaagta  93120
atactagcta atgttatttt cgaatatatt tttactttga taattatcag atatcaaaaa  93180
acaagctata atttaagatc gtttttagaa atgttattat atagatgctt aaaaggattt  93240
ggtatatcac caaaactgta taaaaatgta tacgttaatg aaatgaatat ttgttgtgaa  93300
ttagaaaacc taatcaataa ctatgttgta cctttcaaaa cctacggaat attaatgaaa  93360
ctattaataa ccatttttaa taacttaaat ggaattagta aacattcttt tagaatcaga  93420
gtcagaaaga gtaaaactct attatgatat tccaccaaaa aaatctttaa gaaccaagtg  93480
tgaggtagat agagcggtta aatatttcat atcggttata aagaaatata taaaactaaa  93540
agaatctacg ttctatgtag tagttaagga tacaacatta tttacatata aatacgataa  93600
aggagaacta actccagtag ataatactta ttatacattc agtaaagaac tagctagcac  93660
ggactatact tcctcagaaa taacttctat ttgttttact attactgacg atatgagtat  93720
ttctgtaaag ccaaaaacgg gttacattgt taaagttaga tctgataatt ctaggtatta  93780
```

-continued

```
ctaaattagt ttttttactt tttttatatc tatacatctt tctggattaa acactagatt  93840
gttgtaaaga cttatgaaaa agaagtatat ataattaata tcgttgcttg acataatatt  93900
attcttctgt attgcctgta gagcatggtc cttacattca gcacacggta atgctttaca  93960
tatgttatac aagtgacgtt tgcaagtttc tatatcgtgt ttaaacttgg taattataat  94020
aaatataact atccaaaagc tgcgtcccca gtatctagga tccataactg aaatttaacg  94080
tatctaaaaa aatggatata aggtgcgtaa actggtttga gaataaagga gaaacaaaat  94140
atatttactt aaaagctatt aaccgagaat cgaatgttat atttataaga ttcaattatt  94200
actatcacta tgtatacgat gcttccaaag aactagaata taaacctaat gagtgtatag  94260
atttaggacc gttcaaaatt attaatatag acgaaaagct aagtaccgat ataaggtatg  94320
tcgaacctcg aaattactat acttcggaat tggtactcgt aaaggatcta aaaagaaata  94380
gggaaaaaca atatctgcaa gaatatttag atataacttg gttttatcta cttaataata  94440
taacaccgga cgggtgttat aaaatagata tagaacatct aactcctata aaaaaagatt  94500
gttaccattg tgatgatgtt agcaaagtat tcattcaaga aatacctatc ttcgaagtta  94560
aatttactta cttactgttt gacatagaat gtcaatttga taaaaagttt ccttctgtat  94620
ttgtaaaccc tatttcacat atcagttgtt ggattataga caaggtcacc gaatataagt  94680
ttactttaat taatacagat atcttacccg ataaagaacc tagtatatta catcacaaag  94740
acttctctcc aaaagatagg ataacctatt gtacagaaat tgtgatgttg cttataatga  94800
aaaaaattct agaacataga ttcgattttg taataacttt taacggaaat aattttgata  94860
tcaggtatat atctggaagg ctagaaattc tcgagaaatc ttttatatat ttctctcttc  94920
ctgatgcgac ggaaacagtt aaacttaaaa tatttgaaag attcgttaca ggaggaacat  94980
tcactaataa aacataccac ataaacaata ataatggtgt tatgtttttt gatttgtatg  95040
cgttcataca aaaaacagaa cgattagatt cttacaaact agatagcata tcaaaaaata  95100
tatttaattg taacgttgct ataaaagaaa tagatgatac aattttaaca ttggaagcca  95160
cggtaaaaga taattctaaa gataaattat ctatattttc tagagtatta gaaaccggta  95220
attatatcac tataggagat aacaatgtaa gcaaaaatagt atacaaagat ataaaccaag  95280
atagtttcat aattaaagtc atatctaaca gggattacga aataggatcg gtacataata  95340
taagttttgg aaaggacgat gtagacttaa aagacatgta taaaaactat aatctggaaa  95400
tagcgttaga tatggaaaga tattgtattc acgacgcttg tctctgtaaa tatatatggg  95460
attattacag ggtgcccagt aagattaacg ccgcatcatc tacttatctt ttaccacaaa  95520
gcttagcgct agaatatagg gccagtactc ttattaaagg accattactg aagttactat  95580
tagaagaacg agtaatctat actagaaaaa tcacaaaagt aagatatccg tatataggtg  95640
ggaaggtatt tcttccttct cagaaaactt tcgagaataa tgtaatgata tttgattata  95700
atagtctgta tccaaatgta tgcatctacg gtaatctatc accagaaaaa ctagtatgta  95760
tattattaaa tagtaataag ctagaatcag aaataaatat gagaactatc aaaagtaagt  95820
atccatatcc tgaatatgtt tgtgtttctt gtgaatctag actttcagat tattatagcg  95880
aaattattgt ttacgataga agagaaaaag gtataatacc taaacttttg gagatgttta  95940
tagggaagag aaaagaatat aaaaaccttt taaagacagc atcgacgact atagaaagta  96000
ctttgtatga ctctttgcaa tatatctata agataatagc aaactctgtt tacggtttaa  96060
tgggattcag taatagtact ctatattctt attcgtcagc aaagacgtgt actactatag  96120
gtagaaatat gattacctat ctagattcta taatgaatgg cgctgtgtgg gaaaacgata  96180
```

-continued agcttattct agcagatttt cctagaaaca tattttcagg agaaacaatg ttcaacaaag 96240
aactagaagt tcctaacatg aatgaatctt ttaagtttag gagcgtatac ggcgatacag 96300
attctatatt ttcagagata tctaccaaag atatagagaa aacagccaag atagcaaaac 96360
acctagaaca tataataaac acaaaaatat tacacgctaa ctttaaaata gaatttgaag 96420
caatttatac gcaattgata ttacagtcaa agaagaaata tactacaata aagtatttag 96480
cgaactacaa accaggggac aaacctataa gagtaaacaa aggaaccagc gaaacacgta 96540
gagacgtggc attgttccat aaacacatga tacaaagata taaagatatg ttaatgaagc 96600
tgttaatgca aagcaaagga cagcaagaga taaccagatt aattcttcaa agtttagaaa 96660
cagatatgat atccgaattt acacacaaca gagaatttga aaagtatttg ttgagtagga 96720
aacatcacaa taattacaaa tcagcgactc actcaaattt tgaacttgtt aaaagataca 96780
atttagagaa tacagaaaaa atagaaatag gagaaagata ctattatatc tatatatgtg 96840
atattagttt gccatggcaa aaaaagctat gcaatatatt atcctatgaa gtaatcgccg 96900
atagcaagtt ttatctgcct aaagacaaaa gaatattcta cgaaatatac tttaaaagaa 96960
tagcatctga agtagtaaat ctgctaacgg ataaaacaca gtgtatgtta tttttcagta 97020
gacttttcgg tactaagcct gtattttcat cagactaata tcacattttc tttttttagt 97080
cctaatttat tcattagata ttctacagcg ggtgtaattt ttgtagttac tgataaacct 97140
ggaaggtaga atatcaaaaa aatcaataca ggatcctgct ttgtattaga aataataaca 97200
gacaagtttt ccaatgtttc aatattcaat agatacagat ttggagatgt tgcaggaatt 97260
tgtaacgtgg ccatattaac aggaaataaa gttccatcgt atagaccctg ccggtccagt 97320
ttaccaaaga taggtttgta atcaccgcct cgtataagat atttagctag ttctatatgc 97380
ttagcatcat ctatatagaa actacccgta aggctgtgga ttctaggatt aaaagttgta 97440
tttttaaaga agaataatat attatatatt ggaatgctcg taagcaataa gaaacttatt 97500
aactgatcaa cgggtaatat agaaaatttc ttaaagtaat cgtttagatt aacagtagaa 97560
atctggttca aatactgtat atttatttta ggagtatatt gcggaggcgg accttgatga 97620
agacctagca tgaactcaaa tttgtttaat agacctaatg ttataggata atagcttctt 97680
atatctagtt tttcatactg ggtgttccat aatgctgttt caggtatcca tccataagca 97740
taatcgtgat acaaaaacgt attattaagt ataggggta aattcatacg attaaacgtc 97800
ttttgatcat ctgtgcgttc atgagcgttt cctataaatat ctcttatacc acgattagcg 97860
ttagtcataa ttgccgttga ttatttgtaa tataaatttt ttatcatttt tagataaatg 97920
tttagtattg tctagatatt cattaacata atatatgttt tcttgtagaa actgtttaaa 97980
taatataata atagctactt taaaatgatt aataattgta cgcacaactg atttaagtat 98040
agatttatca ttacaggttg cataaactat aaaagaagta aagttttgta aacaactaga 98100
tcccgttatg attttaagga ttatatcatc cttatagttt tctattatta accctaacga 98160
tgctaattta gaatcaagat agtatttcaa aagactttta ctaaataaag aaaaaacaat 98220
agagggtgaa ttaagatcta aatcagatag tttttttagc tctcctttat aaatgactat 98280
gggattatcc tcatttaagt ataaataagt attatactct tttatagcat attctgtatc 98340
tttattatat atctgacaaa gttttttatt ttctaacgct agcaagtcta cattttgtgt 98400
ttggtatatc atttgagaaa catatgtaga atttattttc atatcatcaa atctctttac 98460
taaagtagcg tctgttctga atatagattc tatgtctctt cttatatcaa acttttccgg 98520

-continued

```
gtctatttta gcaatcacgt taaacaaatc gtcgtagaat ctattagcgg atgtaaatgt  98580
tttatcatct ataaagttat catgataaaa atcaacaaaa tatgatttcc aggtttcatc  98640
cctttcgtct ataatagaaa ggatatcacc tggtatacca tatattaatt ccaacataaa  98700
tttcttaatt tcgctatcgc tatccaacat atatacaact tttaacatat tcttattaac  98760
acgagcttgt ttaatttctg agtagatata acttaatacc ttttcgtaaa tcgtgatcgc  98820
gggttcattc gtatatactt tctcatcatt atagattctt tctttcataa acaaccaata  98880
actcgtagta ctattttttg gaaatacaaa ttctttaaat gtttctgtca ttatactgct  98940
gactacaggt cccgttttct gtaatatagt atacagatcg tgactatcat tatcatcaaa  99000
tttcatccct gtatccattt ttagcgaata ggcccatatt agaagtcgta acacacttat  99060
cctgtctact ttgataaatc tagtttcctt aaagagtttg gaatatatta tctctaagtc  99120
tttaataggc tcattcaagt gaaataaagg atttaactca gtactaaagt taacgcttat  99180
aatatcttga aagtaaggtg aaagttttgt tacgaataag aaacgtttgt catccaggag  99240
tgtattagac tgttgtttat aaatatcaat aaaatctgta aaagatgtat agttttttac  99300
taactggttt aggtataaaa gagttacatc gaaagacgac ttaagaacta tatcgtatgt  99360
ttcacagtct cttatgaaat gcaaaaatat ataaaaattg gtattattaa aaatgtcctt  99420
agtcagcact gatttatgat actttttaat aatatagtta atagctacga cgtgattaag  99480
acaaaagttt gatatcttat ccgctagttc ttgcgtaaag aaattaatat tgttttctac  99540
agtatatata agatatttcc ttcttataaa atccatacta atactatctt atattaatcg  99600
atatttataa aatgtttaaa tgatatatat tataacgata aacaacagta acttaatgac  99660
atattttact atatctttat atttatattt aattattact gttatgaaag tgatgtaata  99720
ttattttttta ttaacgaagt actaattgta gcgtccaaat catatattag atcttgcata  99780
gcatcttcta tggcatgtaa cagtaaattc ttttctatgt ctttgatcac actttgtttt  99840
aacggtacta tagtaggata gaaacaagtt aatataggta taccagtaac acctactaga  99900
tcataatcta cgaaacttcc gttcactaac aaccatgtat tttcatcatc tgtatacatg  99960
aaatctttca atacaccaca tgtataatgt tcatcaggat ataacttaat agatgaatta 100020
tttactacgt ctaacagaca gcatttttca tcactctctt tatagaatat ttcctctacg 100080
tcttcgtctg ataatgtgtt gatgagaaca tctctagtag tctgtactat agattcttct 100140
agttctaata ttttttcttt atctgcttcg taagctattt ctagaacttc actatccact 100200
actacgtcag atatgcttct tccatcattc gttaacgcac tagctaatct atttatagca 100260
ttaggtaaag acccgtctct atattccata agccttgtat aatctttata tagcttttcg 100320
agtttatccg aaagttcttt atccacatat tcgttagtac ttttcttatc atatttaaaa 100380
tcaaatacat aaggcggttt atctaatacc tcagattcta tccacgtatc cctataatgt 100440
attaatatat tagctctgca agcttcatat ttaggatggg tataaggaac atgatttagg 100500
ttactaatat atccgcaata gtgtccagga tctcgttcat ctggccatac gtgcgaaccg 100560
cagtatctaa ccttatcagc ggttgtctta ggataaccgt atttcttata atcatcagat 100620
tgtatagcgc agtgatctct agaagtgatt gttacaaaac atagaccctc atacttattt 100680
atagttctag gtattgtaaa catgggacat ttcaacctca ttaatttagt ctttagatct 100740
agttctgcca tacattctcc tccttcaata tgtttaaaag tatatttctt accgtctcca 100800
taatcgttag tcattgactg tatatatcct aaaacagata ttatctcttc cgctttataa 100860
gtaagaatat tagctctcga cgtacacggt aatacaacca gtaagatact actgtacgtt 100920
```

-continued

```
ctaaattgtt tctccgcatc caaccaaaat ctatcagggt cgtcgtatgc catacctaga 100980
tttcctacag aaaattcaac atccaattcg taagggaatt ttaaattcgc tttttctata 101040
ttatagatat ccacagtatt aggatcgtac ttttctgtaa ctagtaattc actacctaca 101100
tctacctgta acaagaaatc aggagtccaa acttctactt tcccgtaata tcctatacag 101160
gtcctacctt gcttccatgt aacgcacgtt cttgatctcc aaggcattct atgattacca 101220
gttagatcat caaatattct atttttacct tcgtacgtat caatcagtac tgattcatta 101280
tcgtattttg gatttatgaa acttaccatt atcatatcag atttatatct tttatcgtaa 101340
ttattaacac agaatacacc tatagtacgc ggtttaatag aagaaaacat tttaaccgta 101400
tagaagtcgg ccaaaggtaa ttctattatg ccatctttat cacctacggc tacaggagtg 101460
gacccagaag gacacgttaa tacgaaacta gtgaaacctc ttccatttcc aaaagtgtag 101520
agctctaaat atatagttct agatctagaa gcacaggaag gtgatgtatc gtctagtacc 101580
attaattctg cccaataaca ttctgtggcg tgtctattgg tacagaattt agaatgaccg 101640
ggtatttcat taggttttat aacagtttcg ttaaaatcgt atttctgaaa cgtaaacaat 101700
tgacgtaatc taccattctg ttcaaaagga ttttcgagta cccatctctg atataaaggt 101760
tcccaagtag ccagtctcaa gagaacacta caagtagtat aaactacaga taccatagaa 101820
ttgtcaaacg ggcatcctct taccgtaagg taaaacctct ttaaaggaaa tatatcacat 101880
acgttactag gaatactctt agtttcttca ggctccccgg gcgtagacat ttttagtaac 101940
tgcatttcgt ttaatgctat ttcaaaaggc cgtagagtta gtgtaatatc tcttccacaa 102000
gttaagagca ctacaggaaa ctttgaaagc atagcaccga gtctagtaaa tgtatagaat 102060
ctagcaccgt cttcgctagt aaatttaaga acagtatacg cgttaatatc caatgtaggc 102120
gatcttaaat agccaatagg acacgctacc gtcaatgaaa agtcgagtat aatattactg 102180
gtattaagat agtaaagaac actgtctata gaatcgacga aaaacaatga caatttttct 102240
aaagacggta taactataga atcgttcctg tatgacatgt aaactatagt ctcagtaccc 102300
ggcatcatac attttcggac gccagatttt gaagtatcgg taacataatc cctataagca 102360
ttaaaagtct taagtacagg atcttgaggt cgttgttttc ctgataatat ataataaata 102420
tctctcccag catccaataa tccagatatc gcggataaac ccattccagc aaaagcaacc 102480
tgcggagacg cgataatacc cgatgctgta acgacgcttc ctatagtacc tatagctgta 102540
ctaactacat caaatacaac ctccgcgtca tctctatcat cgtcttgtat cataaatgat 102600
cgtagatttc tgtccattaa tccctgagta ataaattggg cggctaggcc tactgctaaa 102660
gtcttgtcaa aagatcttga tattcttctc attctagctc cgtagtcatt gtcactagca 102720
tgattattat taccatcacc actagaatac ccacttgaac ttatactgtt accacctcct 102780
ccaccaccac cactacctcc acttctcctt ccgttattcc tactgctact actgctacta 102840
cttacatgta acgaactatc atctctagaa cttagtcttt ggctgctagg acccgctccg 102900
gcattaacat cagactctgt atcgctagaa gataaccaat aagatgtaag atccacggaa 102960
ccaataaggc tactactgga cgaatctaaa gcaaaactac ccattggaga aacactaact 103020
agactatccg acgaagaact gtcgctttgt acaggaggaa ccggccttct agtacgcggt 103080
aaaggagtga gcattagtaa tccacacatc gcactcgtta aacctctttt acatcgtcga 103140
ttagagtgtg taacgggttt agtattatga tataatatac tattaggtaa cgaagacggt 103200
aaactagggc gggtgctact agaatgcata gattgttctg gttggaaaat agatttaccg 103260
```

-continued ggtttagtaa taacgcttcc tatatttata cccactactg gatttttgta tactatcgaa 103320
gataatactt tactaccacc tgatttacta tatttatcta tactatcttt atagtgttct 103380
actacttttc tagttttcgt attcttatgg tttaacatat ctttatctcc taattgtttt 103440
tctcttaact ctagatgagt aaggcgtctt tttatgtcgt ctaactcttc ttctatagat 103500
gtactaagac tttgtgttgt tagtgcctct ttaatagatt gttgtttttg gtaactaata 103560
gatgatatta atcctggtgt aaaaccaccg tcagaattta ttatattttt acttattgta 103620
gacattatgc tatttggtgg tgtttcaaca ggaactaaag taaccatttt ttctaactta 103680
gatttcatag aatcttttaa tgtagatatt atatcgtcgt ctcctaatac attatcttca 103740
ctaccgctta tacctacttg gatataagat gccttacgag gtattacttc ttccaaccca 103800
aagtattctt ttaaattgtt catcttgtgt tcatctaatg atcttttagg tctgttttta 103860
taagactgtt tacgcaattt attagtatcg tggtactttc tattaggctt tctttttta 103920 tactttttat tcttatcagg attttttatg cagttatcgt atctatcatc gttgtcattg 103980
tcgttatcgt aagacaaata catacattct aagtcggtat catctatatt tgttgtttca 104040
tcagtatctt ctgaatcacc cgcgtttctt ctaggccttg attttcttcg ctttctacta 104100
gatcccgtat acgcacttaa cactttaaat gaactatcct ttatttttatc agtaagcggt 104160 atataattta tacaattatc gccaccagtt acttcgcaaa ggtaaaacaa attaactaaa 104220
tcgctatacc ctataccacc acattctttt aaagaaatat taaattcatt aggtacttca 104280
gtaacttcag ccattaaacc catgcggcaa tcactgcaat gcccagttag tattttcttt 104340
actcttactt tatccttttg atcgttatat tcttcacagg ttgttatcat ctctgttaca 104400
cactcttcaa aaatatctga agattcgtac ggtggactgg atgaaatacc gtcaaacgta 104460
atgaatatat cggtatgtgc attctcgtta ttattgtcag taagaacact ataattccca 104520
acagtaactt tgtctactgt aatattccta catttattac ctgtatatgt aatactagac 104580
acgctgggta aagaacaagt aagtttatta tccgatgttt tacatattag atactgaaca 104640
tcttcttttg ataatgatag tgcactagct actatacacg atgtaacttt tcttctcgcg 104700
ctagtattat cgcctctttt aggcttttta ggagcataaa tcgatacatc taatacatat 104760
gtataattat actgatatct agtatgatct ttatctgtcg ataattcaca ctgttttaca 104820
aatctgtttt ttacagtttg ttgaatgtta gtccagttaa aacattccga gaatctctgt 104880
tcttcctttt ttcttacgga actaaggtac ttaactgtcg cagaagcttt atgatcggat 104940
aattctttcg gacttattgt tttagaaaga ctatggtact ttgcatgttt ccttaaacac 105000
gtgttttcgt cttcatcttc atcttcataa tctgaataaa ctaatgaaaa caataacaca 105060
attaacataa atattatgtt tttcatatta ctagtggcta tgatggttat aataatagta 105120
cattacttaa tatccgtaag tctttttagt tcatttttaa tcaactaacc aagtaataaa 105180
aatgtcatta atgctcgcgt atatgaatga aatgtattgg acaacgttag ttttatacta 105240
actatagtaa atactatgca tattcttgta tttcgtagtt aaactattag taaaatacct 105300
acatcttagg gttaatctac agtaatttaa ctagaaaagc tagaataaga ttcattgtct 105360
agttcgatat gttcctgcat ataaaatctt tttaggatat tatatttctt tgctctttta 105420
agccagaaac agatacaaat tattatcaac aatacggata ctgaacttat agctacgggt 105480
actaaagacg cgattagaat gttgcttgaa gaagattcta tgtagtcatt ttcggaggct 105540
attagagcta gactgatatt agcgtccatc tcatcaaata catcatttaa cgcgtctgat 105600
acggcattat atattatagc atcctctact atcttccttg attcttttgt gtctaacggt 105660

-continued ataatactaa cgttataaca agtagttact accgctcccg atcgatttaa atactcgtat 105720
gttatataag tgtcattaat cagtacgtac ttcgtttctt cttcatccgt gtacacgtag 105780
tcactaactt ctccacatat atatttatct atcggataat acttcactgt aagattgttg 105840
cgaacgtcta taatacaaca cctatcattt tctgcagctt ccataatctc ttttaaatct 105900
tgatctgtta gagtatgaat gaatatgtca ttggttattt cagatatttt atcttgaatt 105960
tccattatct tttctttatc agcctgataa gccagctcca agatatttcc gtctacgttc 106020
acgctcgtaa tttctctacc ttctttggtc aatgccgttg ctaatctgtt aatggactta 106080
ggaagtgttc catccgtata ttctattagt tttttgtatt cttcatatag ttcgttcatt 106140
ctatcgctta gttccttgct gacatactcg ttattcctat cgtgtgtgaa ctcaaaggta 106200
taaggaggtg actgtattac ttcggattct atccaaagat ccttgtattc tatgtggata 106260
taggatttgc acgagtcata atctgggaag taatcatata tatctccgtt atatccgcag 106320
taatagtctg taggtgtata gtaaaacgcg gttcgtttta tacatgttct agaatgacta 106380
gaatatttag aggtataccc gtgattcttc atccattctt tttcagtagc gcaatgatct 106440
tttgatgtta ctacagcaaa gcataatcct tcataattta ctacattggc tctaggaata 106500
ctaaatggat cacaacttac agttatatct cgagaattaa ggtctaattc agcacggcaa 106560
ttgccttcgg aagtatctat tttcttgaaa taatagtgtt taccatcgcc ataatcttca 106620
gtctctgatt gcagatatcc catggttgac actatatacc cgagttttat gtctttattt 106680
cttgaagtgc aaggtactaa actaattaat atggcactat aagtacgttt cttattaatg 106740
gcatcttccc aaaatctgga aggattctta tacgcgttac ctaaattgtt tacggtaaat 106800
gttactttta tagacgtggg aaagcttgtt ttgcttttct tgacaatatc cggatctata 106860
ctttccattt cataactttc ctttagcata atttcttgac tactgtgatg tatgtctagt 106920
tctacatcgg gattagtgaa atcaacatct ccaaagtaac attcttgtct cctgttgtcg 106980
caatatcgcg atctgaaagg cattccagat gatagaccag taaacaattt atccctatcg 107040
ttatagttgg atttatgtat tcccctagga tttgaatttt tatcgaataa tattactata 107100
atgtctgatt tgtacctagt atcgtaatta tgcatacaga acactcctat tcttttcttt 107160
tctgtggagg cgaataattt ggacgtccca taatcaccta caggcaattc tattatttta 107220
tcgtttccat ctatagatac cggagtagaa ccgctagggc acgtaagtac aaaactatca 107280
aatcctctat ctccgaacag agcaattttt acgtatatct ttctaactct agtctggcac 107340
gatgttacat cttctaacat catcgattcg gtccaataac attgactact ctgtttgtta 107400
gtgcagaaat ctgaatgccc cggaactcca tttggatcta ttattgtgtc gttaaaatcg 107460
tacttagaaa aggtgaatag ttgtttaaat tcaccttctt gcctgaaagg atttttaagt 107520
acccatctgt tcctgaaagg atcccaggta gacattttaa gcaagatact gcaagtggtg 107580
tgtactatca tagtttgaga agtatcgtat ggacaaccgt ccgccaataa gtagaacttc 107640
tttagaggat atttatcaca cacgtctgat ggaatagatc tcgtcgattt aggttctcca 107700
ggagtagcca tttttagcaa ctgcatacta ctcataggaa cttcataagg cctgatggtt 107760
aatgtagtaa ctctgccaca tgttaaacgt actaccggtg ttctagatag taatatccct 107820
aagcgtgtaa atacatattt cttgacttct ccatcatcgt acataatcgt gtatgctgta 107880
atgtctgtat ctggggatct caagactcct ataggacagg caactcgtag ctgataatcc 107940
aggataatat ctgaagtatt catgtaaagt aattcagaat tgatagtatc tagaaaatat 108000

-continued

```
agttctgtat tttccttttc gggtttaaat gactttgtat cattctggta agccatgtat 108060
atcatcatac tatctccagg aaccatacat ttcctcactc ctgatttttc gcggtcgttt 108120
ataagtccag aatatgtatc caataactta attaaaggat ctttaggcct ttcgataccg 108180
gaaaacaagt agaatacatc tttaacagta tctataattc cagttatagc agtaacggcc 108240
attccagcta tcataagttt tggacctccc gccaaacccg ctgatgtcag agtagttcct 108300
agagttgata agctcatcgt aactgcctcg aataccttttt cttctttagt catagaatct 108360
tttctttgta taaccgattg cctggcttga tgttgagccg cttgctgtcc ggccattaac 108420
atggcacctc caaaaataag agatttatca agagatgaag atattttttt cattgatcct 108480
ttataaccac cagaagattt tgaatttcca gatgggtctg ttccacgagt tatcgtagac 108540
ttgtcaacta cattgacttt atctttaggt atacctccta tttcttcgta gatcggagat 108600
tctggttttc cggctagaga ataagatgat tctggtgatc cggctagcga ataagtacct 108660
tctagttttg gcttgctctg taacatgccg catattactc cgtctagact tcttctacat 108720
cttctatgta gattcttagg tatagcaccg ctttttggat ttgcttcttc cggaatagca 108780
tgcaaaggtc ttctagaccc atcacgagga gatagtggag gtggaccgtg tgtaacagaa 108840
ggcgatggtc tattaggagg aaacaagtta ctaggttttc catctgtagg tccttccgtg 108900
tatatttcat tgtctagttg cggtgttcta gcgggtgaaa attgtatacc gttacttaaa 108960
tgtgtagtac cactatcggg ccgctttcta atagctgctc ttctagtaag aggagtagtt 109020
attacagttc ctgtatcaac acctttgatc atactgggtg aataaggaga cggtggttgt 109080
tttataatgt ctacaccttt aagtactttg gctgtatttt ctaatttttt tgttatagcg 109140
ttacccgctg gatctaaacc ttcagttcct ttcttcattt ttatgatatc ttttggtgga 109200
ggtggatatt caaaatcact actatcgctg cttagtcgtc tacgaggagg tggtggatat 109260
tcaaaatcgc tactggtact agatctacga ggaggtggat attcgaaatc actactatcg 109320
ctacttagtc gtctacgagg aggtggtgga tattcaaaat cgccgctact gctactactg 109380
tgccttcgtg actgctgcac gttacctagt ctcatctctt gtagttgcct tttaacatct 109440
tcaatatcca cgaaatcggg ttcagaatct atgctgctaa cagattcttt cctagaaaat 109500
tcgattctag tataaaccgg caaaccatgt ttacttttag acggtagatt attactaatc 109560
tctaattccg tgaacaatac ctccgatatt gatttttgtt tttgacctat agtttcgcgt 109620
accgcttctg tgaaaacatc agattttaat tttggaggta gtttaggtgg ttttcttact 109680
ttggtgtata ggtcttcggg ttttccggta gatggtaaac taggagctat actagataca 109740
agatctttag ctcttttttt tacgtcgttg tagatagccc catcacccgt aacaccagat 109800
tcccttttct gttggatgcc tacctgaagg tgcgatgctt ttggaggaag tactggttta 109860
tttcctaaat gttttctagc attagctgta aatcctgtat ctttttcctt ttttggttct 109920
ttatcagatc tcctatttct gatttttgct tcacaaccat ccatgttact tacatcagga 109980
tagtacaagt atctgcaatc aaattcttct atactggagg attctgtttt taatgcaata 110040
ctccttctat gtctagaatg ggaggtgttg tttaaattgc tatgttttaa catttctgct 110100
gttttaccaa ccgttatcga actaagatct ataaattcca tacaatcgtc gtcatctatc 110160
aaattacaca aatagaaact atcagtagaa ttatccatct ctattcctaa ttctttcatg 110220
gtgttattaa aatcttcagg aacagatgtt acactcgcca taaatttcat ggaacatttc 110280
tcacatccac taattacttc atgggtataa acggtatcat tattaatgtt tatggaaatg 110340
cattttatca gttcgtcaga atttacgtta ctaccgtcgt cggtattaat attcgataga 110400
```

-continued

```
gatactctga ctttcacccc atttgtagta ttaattatag aaaagtttac cttattagct 110460
gtcacattat tacaattact gtattgtaat atttttgtgc ttccttttag tatattaggg 110520
tcattttctt cggatgtatt tttcgtagag ttgatatttc ctgccatgat taacgattcg 110580
tttgaataca taaatgcttc aacagttgtt tcgttaacgt ctagtactga tatcaagaat 110640
ttcatagcgt tatcgtaatc agaagaacca tcatttatag gaatggaagt agtttctacg 110700
gatgattgaa ttgtagttgg gatgatggtg gtaaaagttc cattatctgt aacggtataa 110760
taactgttag tagttaagac tacagtagta gttatttctt gtgttgtaga ttctatagtg 110820
ctatttttac ctatagttgc ctcaaatacg atagtatagt tatacgcgta tgtatcgtta 110880
ccgagattac aagatctatt aaactccgat ctaatatctt cctttatttt tgtccaatta 110940
aacgaactaa gaagacgaga ttgttctttc ttttcagcaa tttgtaaata tctgaaagta 111000
gccgatgatt tacggtcgat ggtatcatcc tgtacaagca taccggtgtc gtggtataaa 111060
gaggattttc tcgcgcatgt tttgtatcct tcagaaacgg aaattaaaat taatataggg 111120
gtaatatacc acgagaatat tttgatattc attgttacat aaccgcgtac aggcatcgcg 111180
ataattatac taattattca ctttatctgt acgctattaa atagtaacat tataattata 111240
taatggatat gatgaagatc ataaaaaaat acataaattc ggaagaagaa gcgcaaaaat 111300
tgctaaaatg ggctatagat aatgcaaata tatattactt aagaaatatc gttaatacaa 111360
aagttaatat tgaagaaact aagtttaaaa cagtccataa tataggaata gagtattcta 111420
aagataataa gtataagcta tcttatagaa acaagccgtc tatcgctact aacgagaaat 111480
acaaagaact atgtaatctt atcaggtcca ccaatggtat agaaaaggaa acccttaggt 111540
atcttttatt cggtataaag tgtgttcacg ccaaagtaga atatgatata gaaaaagtac 111600
ccgattacga ttatagtaac tactttgatg tacttaaaga aaaatctact ataagatgcg 111660
tagcgtgtaa gtctaataat acgattccta tgatactcca aactagatca tctgacgaag 111720
aacctactgt acgcgtagta tgcaaagatt gtggcaaaaa cttcgcacct cctaggttga 111780
agtttaatta aatagcgtat ggttgtaatt atttactaat aaataattga tatactataa 111840
atcatgtttg atatcactaa tctgatagaa ttatacgagt ctaacgatta tgtatccggc 111900
gactacaagc attctcagct tcagaaagct tttttaaaac taccgataac agaagttgta 111960
atgttagtta aatctggatt ctatccatct aaattatcta aaaagttcta caagccaata 112020
gctaaattct gtgttgataa gatatattta tttaaacctg aatacgtatc gttaaaagac 112080
ttatttacag taatttatac attcgatgac ttaagcaaat ataaagaaat tataagatat 112140
tattattacg agctatctgt ttctaacagc tatcaagtat ataaaaaatg taaaaacatc 112200
ttaggataca aggatgaata cgataatgat attatagaag aactttctga aaatgattta 112260
gtagaaaaaa tggtaaactt tccaggtttt agaaaaatag tatataaaaa gaaaatttta 112320
tctataagaa tactaaaaga gatgtattac aaacataagg tattacctat caacaagggt 112380
ataactccta tcagagaaga agatatatgc ttttttatag acgcgttgta tgatgcacac 112440
gatgatgacg acgttctata tttgttacta gagattaacg agcaaatact agattctgac 112500
gaggttaaag aaacaataat aagaaaaata tgtaaaggcg aaaatataga tgtattgcgt 112560
tattatgtat ctcattacct aatagatcat gcaaagttgg gcgtatacta taatatcttt 112620
ttctcagaac gcgatattat ttcagagtat ggtttaaccg acgaatcatt aaaagtaatt 112680
tgtaagtata tagacagata ttccagttct attccttcta ataataaatt actattggat 112740
```

-continued aattctaatt atacattatt agcatcagta atagactata taccagaaga aagactcaat 112800
gaaaatctat atatgcaaat agttagacat tcaaacgata acaaacctaa aatcaagagc 112860
ttcaaagcag aatttttatc agaatgtttg atggtaatgt gttatctgag aggatacgaa 112920
gatattgtag atttccttat cgctttagat gtagaaacta ttgtacgaaa tagaataaat 112980
ccttttaacg attatacgtt tacaacggat tggtttaata aaaacactga attagtacgt 113040
ctttatatat ccttttattg tatagatcct gttatgatgc gtaagctact attcgaatat 113100
cccctttgtg agacttctac tacagtagcg atagaagaac ttaagaaata cagatcgtca 113160
ataaataata actataatat agactatcac gaagaattca aaattgtaga tttgcctaga 113220
tcatttaaca taccgataag cgaggtagtt tcaactaaag aatataattc tattatttca 113280
tttatttcag acaaaagtta taaatttaag ataacttcac agttactaaa atataacata 113340
ttacaaacta taaaagtaga aaacttatgt tactctcata tcaataacct acattccttt 113400
tattttaata ttactaaacc aagtggtata atcgataata tatctagact tatatatcag 113460
ataggtgatt taggcagact acttagacac gggtttttat cgtttactga taactatttt 113520
ggaaaatgga taccctcatt aaattattct aaaatactgg atcattatca gtataatgga 113580
cctgattatg tattatcttg gcaaataggt aaactagatc taaaggcgtt cgtaaagtat 113640
aaagattttc ctaaattctt tttaacaaaa tataatatcg atttcctgtt agaaaaagag 113700
gtactattat actactgtat atattcttat ttattgctgt atatactagt gggttcggta 113760
acgtacgtag aacaggaaaa catatattat tttattacaa atataataaa ttcgttcatt 113820
caaggattgg gtatacgtaa ttctatagat tcactatcag aagaggtagt aaaagagtta 113880
ataattatac aaaaattacc agaaaataaa cgtaaactat catctatcag acccgtaagt 113940
ctgttaaact tatgtaaaag agtttgtgct tttatatcta gagatggaaa gaagtagaca 114000
agtatactat attattaacg agtatttagg tagacatcca tcatctaccg aataccaagt 114060
attaaaacac caagtagaga agatttcaaa aattaataat tttaataaag aaactttctt 114120
ttttctgcta aaaaaaaata aaaacaaatt ttttaaggat ctagaactat cagatgattt 114180
gctcaaaaag agaatagacg aatatttttc aaaacagaaa cacgcgaaaa ggttaggcaa 114240
cttattcgct atcatggaat tacagaagat attaatttct agttttacta agactatagg 114300
tatcctaaca accaaagtac cagaatatta tcattccact ataaaactgg aatattcgtc 114360
tatggaaaaa atagcggatg atattttaga ttcttataat gttgttgaac ctagtaaaga 114420
agtaaaaggt agacacaagg tatccgatct agtaggtcat gtttataaaa taatggaaga 114480
ataccttaga agacatagca acagttgttt atgttacgga tcttattctt tacacttctt 114540
aaacaataaa atagaatacg gggatataga tgttttacaa acaaatgcta gaacattttt 114600
gattaatata gcctttctaa taaaatttat aactggaaga cgtatagtcc ttctaaaagt 114660 tcccttttttg aagaactacg taataatgca cgatgaagaa actaatcacg ttatggatac 114720
attcaatata cgtgaaaaaa ccatgaatat gatacctaag ataatgatcg ataatatgta 114780
tatagtggat ccgtgtatac aattacttaa tatgattaaa atgttatctc agattgatag 114840
attggaggaa cttcaagcca aattcgaaaa attgagcgta cgactaggaa cgttgttaga 114900
atatacgagg tatagatatt ctataccact ggatagcgaa agtatattag aggtacgcgc 114960
taaacttgat aaagataaaa gaaaaataac agttgacttc aagaaataca aactcaatta 115020
tataaaatgt tatttctatt tagatgaagt cgaactaaag aaatttataa gtaaaaattc 115080
tggtttagac gaatacgaag attttgaggc ggtaacaaat tcagagtacg ctatacgtaa 115140

-continued

```
taaaacgatg tacacgtact tttcaaatac cgcccttatg agatcggaaa acgaaataca 115200
tcccataacg ataaacgcgt taactagtca cgcactttta tatcatgtta tcacaaggaa 115260
gttttacgat gatttattag gcgatctagt tagatctctt atgatcgtgg aaaaagttcc 115320
tgtatttaaa atcataccta gagataaaaa acaaggtagg cacacgatca ttgatattga 115380
aaaggatatc atatttcact gatttattac tctcgctgct ttatctgttg tattggcaaa 115440
caaattagat aatgcacctg tattaataaa tctcaattgc ggagcttgac gttgctgctg 115500
aggcgatgtt tgttgcatat aacattttgg tgctgaatcc gaagaactaa tagggcaagg 115560
tgattggggc ttatctactt tcagtacgca actcgtttct tgtttcatgc aatctatagt 115620
tctcacattg catagtttta tagcttttag aactaaatat cttccttcat ccgtgtttag 115680
aatgaaagga ctaacaaagt attttggatc gtgaaatggg gttccagcac tttcttccat 115740
ttatagtatg aatatttctt cttcttgtat tggcaaaaac gtataagtca gatacaaaaa 115800
taaaataatt atataaatgt ttaaaaatta caagtatact ctgttatctg aagatactaa 115860
taatatgaaa ctacttattc cgggattgga agatgatatg gaagcaggaa caatagaaaa 115920
ttccggatac agaaatatat ctacgaagat gtttaaagat caagtaaaag acatagttaa 115980
gaaaacttac aatcagactt acttacagtt attacaactt cttgaaaggt ctaatgtaga 116040
ctgtaacgaa ttagaattgt tatatagaat aatcaatatt aatccaagaa tttgtcatag 116100
attctatata aatagatacg atagtatatt tgggtctttt aataaattac atgaatttat 116160
aagcaacgtt atgattaaaa tatttaaaat aggtaattct atatatatat tacgtttatc 116220
agtgataata ctagtctaga aattaatgta gataacgata cagaaggaag actaatgaat 116280
atagattaca ctattaaatt tggtgatgta attatactac aattaggtag aatatctata 116340
aaatttagcg gtaattttgt gataatgaaa gacatacttt tcttagtcac ggattctaac 116400
aaaatagtat ataacgaaga tgagttttta ttagagatat ataatacata aaattgataa 116460
aataatcaga tatcgtagat tgggatatct gtcgcgcaca tatgttagtc aattattttt 116520
aaatataaaa tatacgaata caatctattt attgctattt ttaaataaga taacaatgaa 116580
cgtatcaaga ttagaagagt taatttctat gaatccattt agcgatatgg aaaatatagt 116640
catcaacgaa aaagaaaaat gtatattagg aaacaggtgt tttgtcaaac tttcagaggt 116700
atataatatg cctatgtgtt gtatagatac caatcaatgt ttaactatga atagatttaa 116760
atttagctta aatgaactac tctacacacc tttttactat aaacaactac aatatcagta 116820
tctaacaccc cagttcatat ttagatgtat acaagaagct aatgaaaaca atatgagttg 116880
ctattactgt tatactaaga aaaaggaaca taacggatta aatattgata ttttcattcc 116940
aactgcaaat tcaaagtctt atatagttat aggactacgt ataaaagatt tttggaaaca 117000
atcttttaaa gtaaataagt aaataaacat taacatggta aaaatctata tatttatgtg 117060
catttataac ttatgtacgt tagtacacaa tggtgttata aatcactttt tgttattaac 117120
ttaatcaata aaattatatt tttatataca tatttcccaa aactgaaaaa aaataaaatc 117180
ttgaagataa acaggtgttt attgataaat tatatatatc aataaatatt ttattatacc 117240
atggcgatat ttaaaaggct aagaagattt ctaggaatcg aaaaaaaata gacttaagaa 117300
aagaatacct agcatgtatg tatcagaact agacttatct aaaggcttta tggtcatatc 117360
cgacataaaa accaacgaga taataaatat agatctatac aatcaaaaag gtttttcaac 117420
tataaacaac aatcatgaac aaaatcatct gaatagatta tctaaaagct gttttgatat 117480
```

-continued acataacaag ataatgtgca aggcagagat gagaaaatta tgctactaag acactaactt 117540
tttttaggaa aaacactaca tatttatttt aacaaatcag tctatatatg taatattgtt 117600
actcaacatt atgctactaa tattataatc taattcttcc attaatgagc ccaaaccaag 117660
ttctattgaa tataataata tatttttttc tacttcggat ctcgcggatc ctatagacag 117720
aggtatcacg ttatcgtcta agcaggttac gacgctagct tctgataccg aaaacatgtc 117780
gtagtccata tgagttccgt taataagtac agtgatttct gttgtgttgc cggtgtcttc 117840
ttcgtatata aaatcatcta gagtaccgca tgtataatta caattaggat acaccttagt 117900
actggtgttg agtttaaaat ctaaaaggca acacatgccg tattgctctt tcattattat 117960
ctcataaaga tcattatctg ataacgtgct tatcaatact tctttagata aatcttttat 118020
tttttcctct aattgagcca tcttttccat atcagctaaa tacgctactt ctaatacact 118080
gctatctatg ttaacacttg ctatatctct acctttatca gataacgcac cggctaatct 118140
attaatagac tttggtagag tcccgtcggt gtattcgtac aactctttgt aagcttgata 118200
taagccgcgt aacttacctg atatggtact atctatatat tcgtttttgc tagtatcgta 118260
tttgaaatta aaagcgtaag gaggttcgtc taatatttct ttttctatcc atgtatcact 118320
gtagtatatg tgtatgtatg acttacacgc ttcatactgt ggaggataat aagttccgta 118380
cagagaaccg taaccgcaat agttatctgg aacgtacatg ctgatactag gatatttata 118440
catgtcacat cttcgtggag tattagcatg cgaagaagaa tagcctctat actttgaaga 118500
atctaaagta gtaccacaat gatccttaga cgatatagtg atagaacata taccttcata 118560
ctgaggcaga gtagacctag gcaaagaaaa ctcttcgcac tgtaaggata ataatttagt 118620
agtcaagtct aactcggcgg tgcatttgct cccgcttagc gtagtaaaca catacttttt 118680
accatctcca tatttattag taagggcttg ctgatattgt aatatagata ttctctgact 118740
atgatatttt atgatattct gtatcatatt gcaaggtact aatacaataa gcatagaact 118800
gaaagttctg aatttctttt tcgcgtcttg ccaaaatcta tccgctgtat catacacttt 118860
tcctagaccc gataatgaat acttaagttg taacttgtaa ggaaaataat ggctggattt 118920
actgatactg gataacgtag caatatcggg gtcatacttt tcagttatca taatctcgct 118980
acctatttct gtatctacta catagttagg attccatata tctattcttc cgtgaaagct 119040
aatacacgac ttactaccca ctatattaga acacgtccta gaacgccacg gcatgtgatt 119100
gtataccaat tcgttaaata gtttattttg tccatcgtag gtatctagag gcaatacatc 119160
ctttggaaaa ttaggttcta caaattttag tattatcatg tctgatctat atcttgtatc 119220
gtaatcgttt acacaaaata ctcctatgtt tgttttctta accgaggcaa acatctttac 119280
agtaaaaaga tcagagaatg gtaattctat aatcccatct ttattaccta cagcaacagg 119340
agtagatcca gaaggacacg tcaacacaaa actagtaaat cctctactcc cggaaaacaa 119400
gtatatttct acgtatattt ttctaacacg attttcacag gatgaaatat catccagcac 119460
catgacgtcg aaccagtgac aatggttgga ctgtctattg gcgcaaaact tcgcatggcc 119520
tgatatttcg ttaggtttta tgaccgtatc attaaaatta aatctattaa aagtaaataa 119580
ttgtttaaat ctgtttttat tatcaaatgg attttctaat aaccatcgtc tattttcttc 119640
ctcccaaatg gacattctta ataatacact gcacgtagta taagctatag ctactttaga 119700
attatcaaag ggacatcctt ttactagtag gtaaaagttc ttgagaggga aaagatcaca 119760
aacgttagaa ggcatcgact tggactcttc gggttcaccc ggagtagcca ttttcagtaa 119820
ttgcatatta gatagaggta tctcaaatgg ttttaaagtt agagtaactt ctctcccaca 119880

-continued tgtaaaccgt actataggtg acttagaaag catcgcccct agcctagtca cttgataaaa 119940
tctaacttct tcagtaacat cttttaaagt aacaaacgca tttacatcta aatcaggaga 120000
tcttaaatat cctataggac acgcgatagt caaggaataa tccattatta tattactagt 120060
attgaggtag taaactatac tttcaggtac atctataaaa tgtaaattaa gtttctccaa 120120
tgatggttta aatgaggaat catttctata agctaaataa ataactagat cagatcccgg 120180
cataagacag gttcttacac ccattctggt agaatcagaa actagttcgt tatactgatt 120240
aaattttttt actagtggat cctcgggttt tggtttaccc gtgattaact gataaagatg 120300
atttcctaga tctaataatc cagatatgaa tgataatccc atgcccgcaa aagctacagt 120360
aggagatgct ataattcctg cagaaagcat agcgttacct acactactaa aagaagcact 120420
aactgcttcg aatatagtct cggcttcgtt aaagtcaacg tttttaaaat tttcattcct 120480
aattctggca ctaatcatac cttgaactat caactgtgta gcagatgtca gagcagccgt 120540
cttatcgaac tttttagcag tttctatcat tttctctctg tatactttct tgcttttaat 120600
atctagctct ttaattgatg gttgatatac agatccttcc atatcagatc tggatgtatc 120660
tccttgatat ccgctttccg accgtaaacg attactacga gttccacctg aataagttct 120720
agatcttcca tataagctgc tatcgatatc atctatatca ctgttcgata tccaacttac 120780
cctactacga gtcgatcctt gtcttacgta ctgtctactt ctttcatggt tatctatctt 120840
agattcatcc gagaatgtta catgggatac cgtatgtttt atacccgatc tgcctaatat 120900
actagtactt atgggaattt ttggtactct taatggtgtc ttagaatttc ttaatttatc 120960
aatcaagata ttaacagccg tgttatgttt tacgttatta ttattatttt tacccatatc 121020
aggcacgcgt cctaatagtg cacaagccgc ggtattgccg aactttccgc aatcttcaat 121080
actatttgtg ctcttagtcc ttctcaatga atcgaaatta ttttcttgta ttgtttccat 121140
agttaggcta tctatacgac gaccaaattc cttcattgaa ctctcgatgc tatgacgtct 121200
aggttttacg atactcgtac tagtgtctac attaaacatc aaactgctct gtctttgatt 121260
gtacttagta agtaatactt caccgcctgt gtccctaaag tctctaattt tttctttcat 121320
agtgtcaaat attgaactag atacaatctt tttggaacta taactagttt tgacatctcc 121380
gtgtaaggct tttgattgtt ttgttattcc atctccttcc gtgagatatt cttttatcac 121440
cgttttatgt ctgttatcgt cggataaagc agataatacg ctattcactt tattggtagc 121500
cacgctgtat actccagcaa taacgggatt tttactagga ggaggaaggt ttgaagtcga 121560
tgtccttaag acatcccgaa tactataggg gtctgtatcc agaggtactg aaggcatata 121620
aggcgcgaaa gcttgtctag cttgtaaaga tagtctggat atgagctgac cgtcgcctat 121680
tattccatca ttttcactcc ctccatggat tcctgtttgt atatgcgata ctcgatccgg 121740
tattacctgg ccatctacac ctagataacg agccatcatt ttagtttcat catctgtatc 121800
tgtatttata gagggtacta ttgtcctttt ctttctggat ttagcaattt ctgctttctt 121860
actattaaca cattcggtat attcagttcc ttctctgtaa ggttcgtaag cttcatacat 121920
acattcaaga tcttcgctgt ctaaaggtat ctcgcccgta tctcttttat gtctgttacc 121980
ctttgtatac atataagagg ataaaatttt tgttgcttgt gcagcggtat ccgctgctaa 122040
cgaaacgtag ttcgagcaat cgggattatt ttccaacata cactcataaa acaaacgggt 122100
attaacatca tccttaatgg agaaatttcc aataatatta agatatgaat taggaggggt 122160
tacaacttct gccatcaaag acatactagc atgatcgcaa ttaccagtta gtgtttttct 122220

-continued aatagtactt ataaaagaat tagatgtttt acatgattct actatcttat taatacagtc 122280
aggaaactta tcagaatcca tatacggatg ttggacagat acaccgttaa aatttataat 122340
aatatcttcg gcagcgctgc gtgaatcggt aacagagaaa ttacctattg ataccgtact 122400
tatagtaacg ttattacact taggattttc atattttacg tagtctatat ccggtatttt 122460
gaaactgtat ccggatccgc tggttgttac gtactcgtct atactattag cagtagttaa 122520
ttgttgaatt aaagacataa gtgtcttttt cttgctgtct ccgatcttgg ttcccttagt 122580
tacttgtacc attaccctta agacatattt gtaagagtag tcatacttat agtgcgtact 122640
cccgttggat tttttaatac acttagtctt gtaggcatct tttacttctt ttcttatttt 122700
ttcccagtca aactttccca tgaacaacga tttttctttt tcttcagcga gttctagata 122760
tttatgtaac gcttctgctt tagtatccgt tgattgtttg ttctcgactg agttttgtgc 122820
agaatgatac ataggtaaat ttttcataca tgtttttgaa tccgttttat gtatatatat 122880
gaatgcatat atcattatgt atttgtacat tattgtaatt tataacatac tatattaaag 122940
ctataaagtt tttagttcaa ttttgatttt ttgtatattt atatacataa cttaaagaag 123000
taagttatta acatttttgc acattaaaaa tagcattcat catattttac agtaataaaa 123060
taacatacat tactcttaat tcgtttcaaa aatgggaaat atttttaagc ctattccaaa 123120
ggccgattat cagattgtgg aaacagtacc acaaagctta acagctatta attctactaa 123180
tctttctact tatgaatgtt ttaaacgttt aatagatcta gcaaaaaaag agatctacat 123240
agctacgttt tgttgtaacc taagtactaa tcctgagggt actgacatac taaacagatt 123300
aatcgatgtt tcgagtaaag tttctgtata tattttagta gatgagagca gtcctcataa 123360
agattatgaa aagattaagt cttcccatat tagttatatt aaagtagata taggtgtgct 123420
taataatgaa tcagtaggaa acttgttagg taatttctgg gtagtggata agcttcactt 123480
ttatataggt agtgcgtctc ttatgggaaa tgcgctaaca actattaaaa atatgggcat 123540
atattccgaa aataattctt tagcaatgga tttatatttc agatcgttgg actataaaat 123600
tataagcaag aaaaaatgtt tattctttac cagaatggcc acaaagtacc atttcttcaa 123660
aaaccataac ggtatattct tttcagattc tccagaacat atggtaggta gaaaaagaac 123720
ttttgacttg gattgtgtta ttcattatat agacgcggcg aagtctacta tagatctagc 123780
gatagtatct cttcttccta caaagagaac aaaagattct atcgtctatt ggcctataat 123840
aaaagatgca ttaatacggg ccgtattaga acgaggtgtc aaactacgag tgctattagg 123900
attttggaaa aaaacggatg ttatatcaaa agcatctata aaaagcctta acgaactagg 123960
agttgaccat atagatatct ctactaaagt atttaggttt cccgttaatt ctaaagtaga 124020
tgatattaat aattctaaaa tgatgattat agatggaagg tatgctcatg ttatgactgc 124080
taacctagac gggtctcatt ttaatcacca tgcttttgtt agctttaact gtatggatca 124140
acaatttaca aagaaaatag ctgaagtgtt tgaaagggac tggatatctc cttacgcaaa 124200
agaaatagat atgtctcaaa tatagtatat atgataaaaa gatcctaata aataaatata 124260
gcatggcact aatagaacag ttacaatctt ctgaacaatc aatactttca ccgtttagat 124320
attatggttt taaagatttt cataatgtaa tttttaccac aatagatgac gaaacattaa 124380
tagtaattac agtcaacaat gtaccattag taactaggtt aataacgttt gaaaaaataa 124440 catttttag atcgtttaat agtacttgta ttataacttc caacaataat tcggatattg 124500
atacagatac ttattttata ccaaattcgt tatcactact agatattttg aagaaaagag 124560
catatgatgt agaactaaga gatctatcat ttgctataat gtcggaaatg aataacgatg 124620

-continued

```
aattgagaaa tagtgatatt gtatctctaa acaaatggct acataagcat aatttactag 124680
actacaaatt agtactaata agtgatatcg atagaagata taaattatac aataaaaaaa 124740
atacaataat tgatgttata tccgtaaatg gtagaaatta taatatatgg gttaaagatg 124800
ttatagaata ttattcaccg gaatacttaa gatggtctat agatattaaa agagccacag 124860
aaagtaataa ctggttaccg tatagccagt ctataaaccc tttgaatgaa aatatatacg 124920
cttttgaatt tatagctact ttagaaagat ccaatgagcg cttaaatatc ggagcgatat 124980
tcctgtatcc ggatataata attacaggta gaaacaacga agatataata gaaaagtttt 125040
tagatcagtt agaagaagta atatataaaa aaaattctga tagtattgtt ttaacaggtt 125100
atcatctaac atttttagag aatactattt tagagagata tatcagtaag tataaagact 125160
ggatttttac atgtaatcgt ctagtacatt gtaaaaccgg cactgaagta ttcttatttg 125220
atgccgctat attttttcca tcctctaata agaaaggata tgtaaaacat tggacaggta 125280
aaaaattaaa ttttaaaaac tttttccaaa aagatagtca gctagaaaaa tacataaata 125340
ataacagtgt agcagaacgt atatattatt tacagtcttc tttacacaag catatatcct 125400
gtctaataga aattttcgag ttaaatggat ttgattttaa tttttctggg ttgttagata 125460
tacttatttt cagtattcgt gttaagaata ataatggtaa ttactattac cctaaacatt 125520
cttcagctgt gaatttgatg ttgtcatcta tttacacgga ctattatgct attgatgata 125580
tagataaaga tagtaagaaa cttgttttta actctatttt tcctttaata atggaaggat 125640
attaccctga aggaaaacct tattatacga aaacacccaa agaagggtat ttgtcaatat 125700
gtttatgtga tgtagaaata tctaatgata taaagaatcc tatattgtat tgtaaagaaa 125760
acaagtcagc taggaagttt acaggagtat tcacatctgt agatatagat accgctgtaa 125820
aactaagagg atataaaatt aaaatattag aatgtattga atggcctaat aaaataaaat 125880
tattcgacaa tatatgttat ctgaataaat tatttataga acatcaggat tacacacacg 125940
atgaaaaatc tttacaaggc tatctttttt cttatttact taaaggcaac gttaccgaag 126000
atgttttagc tatgaaaagt tgtagaaata atctttctat aatatcattt ataataagtt 126060
actgcagaaa ctatacttac aaactattag aatgtccagt atacgaatca agtaatatag 126120
ttaaatgtaa atataatcaa gttatatata agtaaacaat ataattgaaa ataaaaaatat 126180
aatataccag cagcatggat actaatagaa aaagatcact agatgaacat gacaccggtg 126240
aagaatcacc cggtaaatta caaatagttg aaattaacga tgaagaagat atcacattta 126300
cagataaccc atattataaa ctagtgaaat ctcgcgataa tagtattaat ctcgtacctt 126360
tagtcggatg tgttatgatt aagataaatg atattaaggg tgtaacagat aaagtaaata 126420
aactattacc taaaacatct agtaagacaa attctactag ttgtataaat attcctatag 126480
atagtattcc tttgaatttt ctggatgatg gtaataaata tttcaatgtt tccgaagtga 126540
gtatacttca ggtaagtcat ggaaatgata tgatgaacat agataaatat gtcgatggta 126600
gctttgatta catagccgta ttatgtttaa aaaattctgg tagatctgtg attatgttaa 126660
atcattgcaa caaacaacac gtaatgcaag ataatttctg cttaatattc agatctttct 126720
atggtataaa catattgact caaataattg gagaatctgt atatttatta gttaaattat 126780
cacctagtga tttatttaaa ataagatggt cgtctgttat cgactctaat agattcatgg 126840
ggaagaaatt ctatatccga aatttacaag aagacgcgtg tatagaaaaa atgaaaaata 126900
tggaaaaaga tatctacaaa aacatagagt ttataataat taatagcgtt ttattggaag 126960
```

-continued

```
atttaaaatc tcgtcttgat ataacaagag agttaaatca caccatagat aaaatgttta 127020
atcataataa taatacactg tttagtgata taataaaatt atcagaagaa attatagata 127080
aagactttaa aaacatggaa aaaatgtctg atagtgtatt agcagatgta aaacaaatat 127140
ctaaaacgaa gaataaatta cgtgaaagac ttttaaaagc agcgatttcc tctaaagaag 127200
tagaagaaat attatccgat atacccgtta tagaagaagg tacaataaaa caattttctt 127260
taaatcaacg agctgtatac gatcactaca aaaaagtaat ctacaaaaat aacagtagct 127320
tggacttagg atgtatgaat atagaaaaga gttatatgtt caacctatac aaggtatacg 127380
gacaaaacga gtacatgatt acatatatac taaacttaat aaatagagta aaaaagggta 127440
tggatgctat aaaaagtaac ctaggtgata tatacaaata taatattgat aatattaatt 127500
tagttgtatc agaaagaata aacaaagtta tatcagggga atctctgtaa atattagata 127560
tataaaaata ctgttagtta cgtatataaa atcactttcc gtatagttgt atttgcttct 127620
acattaaatg gaatttccgg acatacatgc ttataattct accaagtatt tagaagatgg 127680
agacactacg atattaggag atactattca gtttcagttt atatacgaaa atatagacaa 127740
taaggagcat atctccttac caaaaataaa gattttcaag tattttagag ataagatatc 127800
ttttgaaaca ctagatagaa ttattaaaaa tgattacata aatccttcct attttcagtt 127860
aaaagataaa aagttttgtg cgcacaatag ggatttttac catctatcta ccgggggata 127920
tggtattatt tttaggatgg aaaaatatgt agttaaattt gttttcgaag acgggagtaa 127980
aaaatataaa cctatggaag taacatctga atttacaatt cctagatttt tatataataa 128040
tcttaaaggt gatgaaagga agtttatagt ttgtgcaatc gcgatgggga ttaattttaa 128100
gatagatttc ttacgtacaa tctattataa cacgatgagt ttaatgtctg cgttatttaa 128160
catcatggaa ggagaacctc tagaaaacaa atattctcat agaaaagtat tacgttattt 128220
cgctaagtac aaacaatcta atgattttgt aaaattgata tcacagtttt atccgtatgt 128280
tgttaactct aatatcaatg taattaataa ctttaattat ctaattaatt tttttgaacg 128340
tagtaggaga tcaaacggtt attttaacag aggtaacata ataatattcc ctttagcaaa 128400
atgttccgca gaaaaaataa ctccggataa ctatgcacaa tatggatttt ctagtatagt 128460
agaatatact aaatttatgt ttttacaaat agctttattg tacataaaaa tttatgaatt 128520
gccatgcagt aactttgttc atttagactt gaaaccggat aacatattaa tttttgattc 128580
caaagaacct ataaatatat acgtaggtga tatgcattat gtgtttaaag aacctataag 128640
atgtacatta aacgactttg acttttcaca gatatcggaa attattccta ataagaaagc 128700
tgtaaccgct attaacaaag aacagaattg gtattacgac ttccactttt tctcgcatgt 128760
actatttaaa gtatatccag aaatatctaa agacgaagat tttacttctt tgcttaacga 128820
atttactatc tgtgataaat atatctgtga aaactttaga ctacaagtaa ataaattacc 128880
ttctatatcg tttttaataa atatagtttc tagagatatt ttttcaaagt ggatagatgg 128940
aaaatcaaca agtcatcagt aatctatact atttattttc tgaaaagtac ctagagaaat 129000
tgaatcaaca cccagacact agtaacgtta gatgcggaat acatataggt tatttaagcg 129060
gtgaagcaaa aaactgtata gttagtataa taaacgcgtg taacagtaat gaacaaaaaa 129120
gctttcaact tctgatagaa tcattaattg aaacaataga aaatcttcca gaaaaacaac 129180
aaaaagaaat agctaaaagt ataggaatca acatagatga ttacaaagcg ggtaaaaaga 129240
cagaattaca gcagcattgt gaagcctatg ctaatctgac gcagcacata gatatacaac 129300
acttcaacat aggtacgtgc tattctccta acgataaata cactgatata aaaattataa 129360
```

-continued atacaggatc tgctttatca aactgcggag tagaaattat tctaaataaa attaaaacaa 129420
ataatcctat agtacctata gataataaac tatccatgga gtctttttca ataaaatggt 129480
ttattatata tatagtttta tgtgtgttaa tattattatt gctgggttat atatatagaa 129540
ctgtcaggat aaaatatacc tacggtgtat atatttaaat ctaaaataat aagaaaataa 129600
caaaaataaa atagaaaatt aagtccaaga atatcttatt caatcagtat tcgggtacgt 129660
gcagtacaat ggctgatagg aatgttaagt cttctaataa tcttacaaag aagcgtatca 129720
agaaagttag aataaagcag cctgatccta ctaccgaaga aatagatact tacggcgccg 129780
atataaatgt taaacttatt caacctaata taagtataga acaagatgac ggtgaaatac 129840
aaactattca tatagatgac tttaattagt tgataataat tacaaaaatg tccggagaca 129900
tttcattgat ataaatttaa attctatcaa gtcatgatat gaaggataca tactgtgaat 129960
aagttatact actggttatg ggttatacta cgataaactg acaatatcca taatgtgtaa 130020
atggtataga aaggaataac ttcactagat gttgttctac atggcgattg ttataccaca 130080
tattacatat ttgtattcta aacttgttat gtatatccta cctacttttg gatattttca 130140
tgcgttatta tatattatac tataccttaa cagtattatt acttatttta ttaagatagt 130200
aaaataacgt catctttttt ttctaataaa tagtaattat gtctagaata aaaatactaa 130260
taggtataac aggtagcgta gctgcggtta agttacctga cctgataaaa gaattaacgc 130320
gtttggaaaa catagaatta agaatagtcg ctacagaaaa ttctatgaag ttcacagacc 130380
aaaaaactat aggtattcct atttatacag ataaagacga gtggactacg tggaaaaaaa 130440
tacccgatcc tgttttgcat atagaactta ggagatgggc ggatgttttt attatagcgc 130500
ccttaacggc aaatacgtta gcaaaaatag ctaatggtat atgcgataat ttactgacgt 130560
ctattgtaag agcctgggat acaaacaaac cactcatttt ctgtcctgca atgaatactc 130620
ttatgtggga acatcctatt acagaaaaac atatagatac gttaaaatat atgggtttca 130680
tagaaataga atgcatagaa aaaaaactag catgtggaga cgtaggaaat ggtgctatgg 130740
cagaagttgc agaaatctat agggttgtta gagatataat gagagtttaa atatataaaa 130800
aatattatgt ataactaaag catacttcct ttaattaagg gcatgtacaa gtttacaaag 130860
acggatgaaa agatagagtt tagtagagaa atttcttccc gtaagataaa actacggtaa 130920
tatctaaaca tttcgttttg acgtaacatg aatacgtcaa aacatataga gattatcagt 130980
atccaagaca ctaataaaca cgtagcttgt ataactatta ctataagata aaatacttct 131040
atcttacgta taacaaaaat gctaatagat aacggcacta atattaactt atctaaaggg 131100
ctaacacctt tacatatagc gcccaaatcg ttataatata taattaatta acaaagtact 131160
caaagtaaac actttgtaaa gaaacataac agagatataa tactagactc ttttattatg 131220
cacgatgaga caggtttact ttagatagcg gtactgatgt ccacacgcgt tagataaata 131280
taataaatct catctacatt atgctgtgtt tacgtaatat ctataaaata gcagagatat 131340
aaatataaga gatgaatcaa cgatacgccg atattctacg tttttcattc ttctagaaac 131400
atttgaacta ttattagaca atggagaaaa gtgaatatac gtaataaaaa taaaactata 131460
ctattgatta aatatgtcaa taccttaggt gcctatactt catacttgct atataatcaa 131520
tctacatata atgctataat tagactattg gtaaaatata tacgttgatt tagatgagtt 131580
atcatataat aaaaatattg aatacataaa cagaaaaaag aaataacaaa atataaaatc 131640
tggtactcta gttattgcct ggaccgtttc tttcatttta taaacggtta atttgttaac 131700

-continued caagttaata gcttttgtaa ataatataga tatagaggaa tattccctac gtataaaaac 131760
aaaactagcg gtgaacagag caaatctata caatatatgt ttaaataaga ttaacggact 131820
cttatcacgt aacgataact gtgttcattg cctgtagaaa ttaggtgtta tatagtatct 131880
ttttctaggt actatgaatt acttgtaata ttgaaataaa agactacatt aagtacttgt 131940
ataataattt tacattatgg acggacgatg tctccataat attatgtata cgggtactta 132000
tgatgaaatc atgagagcta taaatatata cgaacaccgt aactattctt ctttcagaaa 132060
tctaccgtta cactacgcga tttattctag aaggaaagat atagtagaaa ccttgctaaa 132120
gtcgggttat gatcctaatt ctgtagatat cacggataat aattgtcttc aattattatc 132180
aatgcctttt gatataacta tgcttcccgt tgatgaagaa gtacaagact atgctatttc 132240
gttctattta tctaaaaata tgaaacacac atccatgtta atacctatta ctaaagaagc 132300
tttacgcggg aataggtatc cttcagagcc ttattttagt agcatgtgta gaaaatttaa 132360
agataatgag ttatgtataa tggatctttt attacggtac ggggctttac ctaattctag 132420
aaaggatgga ttattacccc tatatcatgc cgcggcggct ggtaatacag agatggtaga 132480
attactttta agttacggcg ctaagactaa tctacatacg cgttatgaag attctatttt 132540
catgtgcgct ataaagtcta acaatgtaaa aactgctaaa attattagcg atctatataa 132600
ttacaaaaac gatataaaca atatattaaa aacaatacag ttatataatg ctgatagaga 132660
taggcttaga tataaacact aaagacaaaa aaggaaaaac agctttacac tatgcttgta 132720
attcgattaa ctgtatagaa actgttaaag aaattatgaa atacggtgcg gatataaatg 132780
taaaagatcg tgaaggacta acaccgttac attcggcgtg taaatacggt gatctaaaat 132840
tatccaaatt attaatcgag tatggtgctg atgttaaagt aaaaacaaca tctaccgtac 132900
taaacttagc ggtagaatcg ggtaatgtag aactagtaaa atttcttata gagaagaatc 132960
ccgaatttat tacatcagac tacttatcgt tgtcactggc gattagatgt aaagatatta 133020
atatagtctt acttcttttg gacgctggaa tggatgtaaa ctctagtaag tgtatatcga 133080
cacccctca tttaggagtt attttaggca attcaaatat cgtcaagttg cttttagatc 133140
atggtgctaa tattaacgct atagataagt acggcgaaac acctttagag gcagctaata 133200
aacgcataaa tatagattat gcggaattat ataaatctaa tagatttatt ataaagtatc 133260
tagtattcct atcacgatat gactataaaa taaagaataa tataggtttc attaaaaata 133320
tgtatataat agataaagat gaaacgctaa gttgttttag aaatatgtgt gagacagaat 133380
tagataagat atcatctata aaaataggtc agtattctct atatagtctg ttagcatcag 133440
ataatgatgt aaaagaatat atatgtaaaa acagacagga aataacacaa aaaattattg 133500
ataatctaaa agatattatt atatatcgtt cttttataga gaaatatatt tctagaataa 133560
atatataaaa cttttttaa catattagta tggaaaaatt aattatatat agttttatac 133620
tagttgtatt aaaccacgtt tacggacaat atctatactt aggaggacta tttagttcac 133680
cgcgtaaaac tattatcatg aagttatgtt gtccatccgt agatggagat atgttaccag 133740
cggataaaat cggtagtaat ataagagcta cagattgccg atgtaaaagt aaaccgtcta 133800
taatagtatc taccaccaaa gaagaagaga agtgttttcc tcctaatact ccgtggttgg 133860
aacaagctat aaaagaaaaa aatttaaaaa taccgaagtg cgtatactat cctaacaaga 133920
taggcgctcc taaaggattt ggttataagt agtttttaaa acactcgaaa ttcttcgaat 133980
acagattaca agtaatgtta tgcttttaat agttttgaaa tatctatgta ataaagcaaa 134040
attaaaccta ttatctaata atacattact cgcgttacat aattactcta gctttaccta 134100

-continued tgtcaagact gtagctatcg gtattaattt catgatccgt tatagaatta gtgtatctcc 134160
atgagatacg ttatatagtt catacctata gcacatccaa aacatatgtg tatgaactta 134220
tctcctgcct tatcagttat cgtataagat gagaaattgt aacaaagact tcttccttga 134280
caacagtgga agttctaaac ttgtaacgtt aattaaaccg gaggaaacta taaatataga 134340
ccagcatata cttatatagt aatacccaca tatttataaa aatcgttttc gcgataaaac 134400
acatacagtt atatttatac taactagtag ttagttgctt tatcaaaaaa aatcataaaa 134460
ataaatctat acacattaat ttaatcaggt atctataatg ggtattaaaa acctaaaatc 134520
cgtattgcta ttaaagcaca gcttgaaagt acttgattcc gctgtaaaaa gtaaagaaat 134580
atacgttgat tttctaggat tatttatggc aatcgcatac tcggttacat ctacagcaat 134640
gttacatcat attataaaag aaaaatttaa gtttatacat tctatagctg ataatgttac 134700
tgtgtttgta gatagaggaa gtatttctct aaaaacatca ttaagagaga agagaaaaca 134760
atcgttaaag aatcaatata aaaggaagca agaagaactg aaaaacttgg aaatagcgat 134820
agacaatctc tctgtagacg atgaaatgta tgaagaacaa aaagagagct tgttttctaa 134880
aatagataaa aatagctatt atatgttctt ggcggataag aaaaatatgg aagctattat 134940
aacagatgta ctagcttctc taaaaaatac agaaatctat tactgtgatc atatagatgc 135000
ggaatttatg atgtgttgta gagcaaggga atattatact aataacggta catggccttc 135060
tatactaagt agtgatcagg atactatttg tctagtatgc gttgacacgc aagaaaaaat 135120
attatacgat actaaaagcg tatacaaatt atctcccaac aagtacacat cttatcttac 135180
aaaattaata gtattaacta acggttgtga tttctttaga ggactttacg gaatttctat 135240
aaataaagat aattatatga gatacgaatt atttacagaa tttaatagag agaatgcatt 135300
cagaagcata gctcataaaa actatagctt aaataattct aataccgatg aaaatataga 135360
tgaaatttct actaacatag atgtgatttt tgattttata aaccactata catcgttaaa 135420
tgaagatgct tacaaatttg aagatttgcc ggatatacgt gttaaggatt tcttggacgt 135480
tatggtccgt agtaaatggt acgaagctaa aaacaagtac gatcttggat cggatatatt 135540
acaaaacatt tacaacgttt ataaagtaca tagacgtaat tatgaaaagg aaaaagaaac 135600
gaatatacta aaaatgatag aatcttataa atatagaaac ataaaaaataa atactataac 135660 tacatttata aaacttctag gaatagaaac ttctgattct atatgcgtat tgggtatatt 135720
ggcgccttca gaattatata taggtttcga aggaagattc tattttaata aaacatctat 135780
tattaaaagt tctccgaaat taattaatat aaatatctag aatggtattc ccgttagtat 135840
gttctacttg cggtagggat ctcagcgaag ctagatatag attattagtc gaacaaatgg 135900
aattaaaaaa agtagtaatt acttattctc gtaaatgttg tagattaaaa ttgtctactc 135960
aaatagaacc ttatcgaaat ctaacagttc aaccttccct agatatcaac taatggatat 136020
ctcattattt gattatgtag cgccaggagc tgttatatta agtcaatcta atcactctat 136080
cgtaaatttt ttcaatccat cagaagaaaa acattcttct ttatatttcg gttatggtat 136140
agtagatttc atcattaaaa atgatatcaa cttttctatt aacggattaa ataattttac 136200
aaattatatt atagaattca acacatctgg ttttgctata atacctttaa gggaattcat 136260
gttagatagg aagtatgcaa aagtatacta ctatatggaa ggaatatttc caaattatag 136320
attgatggaa gatactgtaa aacaagcatt tttacacgct aacaaagaat atggtttcgg 136380
gaaagataaa acttactgtt tcaagatgat agccgactgt tatctagata taggtataaa 136440

-continued

```
tgttaaatcg tataaaattt taggtaaata tatttatctt agtcaatctt tttgtaccga 136500
tgatagatgg actaaagtat tagatacttt aacgggagaa aatctaatta ctaggaacag 136560
ttactatttt ataaggtgaa ttaatggtta acgtagttcc tggctttttt gttttaaatg 136620
atttcttctt tttaatgcaa ttagctagta ctctaatggt atatagataa tccagtatag 136680
caaattttct taagtcatta ttagtaagtc ttattctatc ttctgtgata ggactgatga 136740
cagcaccgtc aagatcatgt cctttagaat atttgtaagc catgtctaaa actttattgt 136800
tgttggctat gtaggtagcc aattgattct tgacggtatt ttcagcttct tcaccaactt 136860
cttctatttt taatccagct atatattctg gataagtatc cttacacagc cctatctcgc 136920
atatggtctt atacatttta tctagttttg gagactttaa gggtaaatcg ataattatat 136980
ctatttcttc cgaaaaagac atcactttac ctccggctat agtctctatg tcttgctggc 137040
cagtgagtat aggaaatatc ttatactgcg cgaatttaag tatggcatac ttcatatcta 137100
gtagatcgga tacctcactt gacggtcgtt tttttgaatc gaataggtaa ttttctatct 137160
ccatgactat cttcgccgca tgaatgagtt gattggcaag aattaaggtt aaaagtgtag 137220
cagctgtagt atttatgaga tagttacaag ttataaaaaa agacttatta tgagtcaatc 137280
tagtaagaat gtttcttaac tcattaaatt ctatttcgtc ttgcacgtgt ctttcataat 137340
ttctagtttt atcaactagg gattttacac ccgctatagt aggaatagat atatcggact 137400
cgcatttttg atatatgcta tttataatgc tatctctatt agaggagtta tatatatatt 137460
tagctctagc tactataccg gctattgctt tatcgtctaa gtagtctttt aacagtgttt 137520
ctattaaaga tttagacacc atgttaaaaa tcctcgattg tttctggtct tccatttaaa 137580
tcaaatattt ttaaaaatat aaaagtaatt tattacaact agttaatatc actaaaaaga 137640
catatagtag taggttacct attatcctta aggctcatca tgtatgacct acgtttatta 137700
taatctcgcc gagtgtgtag ttaatatttt tcttctttcg acatagaaga agctaatacc 137760
atcgtagtgg actttcgctt tgaagagtta atgttaatat atttactcca tagattcgat 137820
ataatttatt acgggaagct aaagaattaa gaaaacagta tcgcgatacg caagaactat 137880
taccatttta atcggagagc tttctatgga tatagggtta gcgtctcaag aaatacataa 137940
aaataagtat tatattacgt atatattata tatacagcat ggatacaact aaaagaatgt 138000
ggcctctaca actttgtgcg ttaattgcta tctgctttac atctactact gtatctgctg 138060
ctagtggtga tggatgttgt ccatacggat tttctccaga tggtactgac gtgcctgtat 138120
ggaatctgtt aaactgtacc aaaataccgg ataattgtga gaaaaaggga tttttattcc 138180
attacaaaag cggtggtgga acatgcggaa ccggcgatga agactggttt agtcctcata 138240
gtcttatgaa tgatctctgt aataatggac taaccgcgat tgttaaacgt actatgtccg 138300
gagactgtaa ttgcaaatgt acttgcgata tggaggataa gtagcgtgta taaaaaataa 138360
atttttgcta gtctcgtata gtacttaact gtagatgtag atttgatgac actcactact 138420
agtcgttttg aaataggtga tttagaatat tggatttttc tactctatac tagataatag 138480
agttgcatac aatattttag ctatcgtatg gataaatata ttctagaata caaaaatatg 138540
gtctaatctc gctactggat aaatcgaaaa atacttttta ttatatacat atagtctatt 138600
aaacaaaatg atagctcgta acctataaaa ggaagcagtg tgtctgcatc gcttgctctg 138660
aagatgtcaa atattataaa ctgctacatt tctgctgggg acaatactaa aattggcgac 138720
attgttatgc aggtttaaca atgggatata gatgacacta aagaatacta ttgtgaacaa 138780
catggtatga attatctaac tccgttagac gtgtgggata gaaaccaagt taaggttaaa 138840
```

-continued gaaattggag aactcaagag atatcccggc attatttttt cctaaaagtt atatacccaa 138900
cagaaatgtg cgttatttca cgagtaacga tatcgaagaa gtcaataatg ttattactag 138960
ttacttaagt gaagcctatt attgttcata aaaatgcata atgagataaa gtgattaacc 139020
cggtgatatt gtaaaagaag attgatccta ttcttaagac tttacgatta caagcaaagg 139080
taaaggagag actttaaact agaacgcgta aaaatcaatt acagagattt tacgttatgc 139140
aatatagaat agccactatt taatacggca ataatggttt tgggaatata ttaatagtaa 139200
agtcgaatac cggtttatta taacatgctt ttcaagtatc caaatctact gagtataaga 139260
taactcacta gttaataatg ctatactaat attataatcc agttcgtata ataattcctg 139320
gataccctct tctatcgcgt gtagtattat agcatcttct acttcttttt ttgtagctga 139380
aactaatggt acgataattg gatagataca agtcaatact ggcattccga taacattaac 139440
tagttcgtaa tccataaagg tgtcattaac taataataaa atttgatcat tgtgttcata 139500
aacgaaatct tctagtaaac cacatgagta attctcttct ggatatacct ttatagataa 139560
tttcttttct agatccagta aacagcactt ctcgtaatcg tttttgtaaa atatttcttc 139620
taagtcttcg tctgataaag tgctcgttag tacttcttga gtagtttctt taatcttttc 139680
ttctagttct aatatctttt cttgatcagc cgcataagat atttctataa gatcagtatc 139740
taccaataca tcagtaatac tccgcgcctc tttcgtaagt gcttcagata atctattaat 139800
agacttagct aaagatccgt ctctatattc gattagtttt atgttatcgt cgtataatgt 139860
tttaagctta tccgaaagtt ctttatccac atattcgtta gtacttttct tatcatattt 139920
aaaatcaaat acataaggcg gtttatctaa tacctcagat tctatccacg tatccctata 139980
atgtattaat atattagctt tacacgcttc gtattcagga tgggtataag gaacatgatt 140040
taggttacta atatatccgc aatagtgtcc aggatcttct tcatttggcc aagtatacac 140100
tccacagtgc ctaacttcat ttgccttatt actgggatag ccgtatttct tatattcgtc 140160
tcccttaatg gcacaatgat cttttgatgt aatagtaacg aagcaaagtc cttcgtattt 140220
acttatattc ctaggtatag taaacatggg acatttcata gatatagatt ttaacgtaag 140280
atctaacgta gcggtgcatt cgcccccctc catatgtcta aaagtatatt ttttgccgtc 140340
cccgtaatcg tttatctgtg attgcatgta tcctaaaaca gatataacaa cattagcgtc 140400
gtatattaat atatttgctc tggaagtaca cggtaataac aaaagtaaaa tactactata 140460
agtccttaat tgttttttag catcatccca aaaccgatta ggatcatcat acgctctacc 140520
taactcgctt acagaaaatt caatatcgag ttcataagga aatctagtaa ttgccttttt 140580
tagattcatc gcatcaaccg tactaggatc atatttttca gtaattaaca gttcagtacc 140640
aatatctata tttagtatat aatccggtgg ccatacagcg acttttccat aatatcctat 140700
acacgttcta ccctgcctcc aagtaacgca cgttctggac cgccaaggca tcctcaccgc 140760
ttttaccaaa tcgtcgaata gttttttttt acctttgtaa gtatctacta agacagcgtc 140820
ttccggatat acgggtttga cgaaagatac cattagtata tcggatttat atcggctatc 140880
ttcgttgtga acacaaaaca ccgctacact acgctcttct gtagaaccga acattttaac 140940
gctaaagaaa tctgacaacg gtagttctat cagtcctaaa gtattaccta cggctacagg 141000
agtagaccct gagggacaag ataatacaaa actattaaaa cccgcgttgc tattaaacgt 141060
ataaacttct acgtataaga ttctaactct actattgcaa gaagttatat catctaatat 141120
cataacatca ttccagaaac attcttttat atgtctattt gtacaatact tcgcatgtcc 141180

-continued

```
tggaatagta ttaggtttta taatagtatc gttaaaatcg tacttatcga aagtaaataa 141240
ctgacgatgt ttattactat cttcaaaagg attttccagt atccaacgtt gggttttatc 141300
atcccatatc gtcattttca ttagtatact acacgtcgtc cgcgttatag aagtttgtga 141360
agcgtcgtac ggacaccctt tcaataaaag ataaaagttc ttcatgggga atagatcgca 141420
tacattagat ggaaatgttt tagtatcggg tggttcaccg gacgtagaca tctttaaaag 141480
ttgcatgtct gtcattttaa cttcgaacgg tttcagagtg agcgttatat ctttcccaca 141540
tgtaagttct acgatcggaa actttgaaag catcgccgcc agcccaacaa actgataaaa 141600
cttaactccc tcatccgtgg tgaattttaa tgtggtgtac gccgtaatat ctaaagtggt 141660
agatcttaga tgtcctattg ggcatgcgac ggttaaccca aaatctacta taataccgct 141720
agtgttaaga tagtataaaa cactatcgat ggtatctatg aaatgcgtcg ctaacttttc 141780
tgactgcggc ataaaactag tatcagatct gtaacttaag aatatagtca aatctgaacc 141840
aggcattaaa catttcctaa caccggtgtg ctcggtatct gcaactatct ctctatacat 141900
gttaaatttt agaactaatg gatctgaagg tttttaata ccggagagtg aatagtatat 141960
atcttttccg atatctatta agccggtaat taatgttaac cccattccag ctagggcaag 142020
atgaggagat ataactatac ccgctgtcga catagatgtt cctatactac ttaaagcggt 142080
actaacagat tcaataacgg cttccgcatc atctctaaat ccttcatgta ttcgttgtaa 142140
cctagactgt ctattgatca tattcataga cattgtttgt atggctagac taaataccat 142200
ggctttgtct gtagaagatg atagtttctt catcttttca ctatacttag agatagcagt 142260
agatttataa ctatcatcat cattagccga taaccgagaa cttacgctaa ctacgctacc 142320
tcttctacca ccactactac tgccaccgac atcgcctatc actgaatata tgtcatcgat 142380
atctaaatta ctgtataacg aatcgtaata agacgatgaa tgcgatcttg aacttcctgg 142440
aattcttggg agaggacggc gggcgagatt ataagaatcc ctcatacggt catagtcatt 142500
atagctagtc agtctcgccg aatttactac atcataatat gcgtaaggtg ttactaggtt 142560
cacaaaaggt ctggcagccc gctgttgcgt attttctaaa aaccccatat tagggctaga 142620
catatagata agttcttgtg attgtgcggt agagggatgc ctacgtcttc cttgtaaaga 142680
gtgcttttcg ggtactatta ttcccatagc tcttgcggcc tctatatgtc gttggtacgg 142740
atcttgaaaa gattcctgat gtacttgtgc gtgaccttgt cttcctgtcg ctattcccat 142800
agctcttgcg gcctctatat gtctttggta cggatcctgt gaaaaacctc ttgctgatga 142860
actacgcgcg gagttcatag cgcttgaagc cgtatgagcg tccacataaa catcgttagg 142920
attaccttcc ggtctagatc gttgacctaa catcgcacac actacatcgt tagtacctcg 142980
cttacatctt ctgcgcgacg tcgatgaatt ttctggttca tttcttgaaa agagttctga 143040
caccgatgtc actggtgaac ctactaattc tcgtacgttt ttatatttac ccatcgtgtt 143100
cctgatgata gtggttcctt ttcttgttaa cggacttacc actaccgtag atgtatcgac 143160
gtcgaataaa ccggtaggtg tatctgatac agtagatact acgtgtattc ctttgccgcc 143220
tttttttctg tacgctgcga tgttttctac gagattatct cctgttctgt accgcgcacg 143280
tcctcgtctt atatggttct ctactattcg gatatcctct tcctcagatt cgtacctcga 143340
caccataaat tgtaattctg cgtaaccagc atcttcagta ctactactat acccgattct 143400
agactctagt actcccctaa cagattctat ttttctagct gttatcgccg ctaatcttct 143460
agaaagtata ttttgtgaat cttcagggac tttatttata ggcctaggcc tatttatctt 143520
atcgtatatc tcgtcagtgc gtgtatcagc cgggatattt ggtaagaaac tttgtaacgt 143580
```

-continued

```
tttcttagct ctatctttta cttttgcacg tatatcgata tcaccggcta cttgtgtagt 143640
agatccttta gaataagaag tacttgttcc taattgtaaa tgggtggctt ctttaggaat 143700
aatgtctctt attttcatga tcttcttcaa gtattgtgcc atgtctatat taccatgacc 143760
atcctctgaa gtttctctct tagatctact tttagatgta atcatacact gtgtaaaatc 143820
atcttttta cgagtatcgt acatattata aatacattta atatcttcca tagatatctc 143880
gccgtgggta tcgatatcgc gttttactcg atgtttatat tgttttatat aactagatag 143940
agataacaag gtatcagatt gaaacttttc agtaggcgcg acgtaatcta tacaatcttt 144000
accgtttgtc atcatacaag cgtataataa ttcggataac gtatcagatg tagctccgtt 144060
ctttttaaa gtagtgtaaa attcttccgg aatatctgtt acttccacca ttaaacctac 144120
cgtacacgtc tcgcaattat taattaccga tttatctatt ttcgccttgc ctttagggga 144180
caggcatcct tcgttgactt tcttcgtgat gcattctata aattgatctg aatcggtata 144240
aggttcatgc gtagagactc ctttaaagat tatcggtata atagatttag attgtggtaa 144300
ccttgcttta tctccgtcta ttacactaaa tttagatatt atcactttat ctatggttac 144360
attgttacag ccgctatcgg agtaggaaat gtgttccata actggtaatt cgaaatacgt 144420
tctatcattt gtctcgttta taaattgatc cgtaacacta ttgttgtgca atagtagagt 144480
attgattata tttttattta tatccttata ttgcttataa ctcgttcctc gaactccgtc 144540
ttcagtatcg gcggatacgg taatattcat catgacggta taattatatt ttataactcc 144600
tctatcatta gaacatttat ctagaaacat tttcttaacg gacgccaaaa tgctatccca 144660
attaaaagat tctatgaaag tctctttgtg aattctttcc gcgattgaca gataaccgta 144720
tgttgcggta gcggcataat cggtcttttc tttgggattt aaatcttttc tagtatcatg 144780
atatattggt aactttcttc tacaaaattc tgatcgcgtt atcgcaacaa aaataataag 144840
tatagtaatt atatccataa taactatgtt aataaccttt tagttcattt attctaagtt 144900
tgttaacgaa ctgacgttat gtctcattaa tatagtactt atattcatgt cgaattcata 144960
catcaattct tctaaccctt ctttaaaagc gcgtaataac attatctctt ctacctcgtg 145020
tctaatactt tttgttctaa gaggtattac ggtggcttct atacaggtaa ctactggttc 145080
tcctattagg tataataact cgaagtcttg taacgtcccg tttataagta tcataggtct 145140
gatctgatcg ttagacatat tactatattc tataaaatca tcatacatat aatcggttaa 145200
ctcaccgcag taataactgg ataaatcatc tacctttgta atactattgt ctctgaaatt 145260
aattagacaa catttatctt tattcccaat tatatcgttg atatcttcag ccgacaaaga 145320
attcgctata acttcttgag aagttatact aatagcatgt tctaattcgg ttaaacgttc 145380
agaatcggct ttataagccg tttcaagtat tctaccgttt acaatgattt cagtaatgct 145440
acgtccgtta gaagtaagac tttccgataa cctgtttata gcagatggta gcgacccttg 145500
cttatattct gatatcgaac ggtactcttc gtataatctt ttcaacgaat ttgataattt 145560
tggattaaca tattcattat ttttatcgta tgtgaacttg aacgcgtacg gaggtttaga 145620
aagtacttcc ttctctatcc aagtatcttt atagtaaacg tgaatataag acctacaagc 145680
ctcgtattta ggatagcgat atcctatatg cctaaactta ctaaaataac cacagtaatg 145740
atcaggatct tcccaaacag ccggaacaat atacgtctcg cagtatctag cagtattagc 145800
ttgctcttta gagtatccgc tcgttttaat atcgtcttct aaggtagcac aatgatctct 145860
agacgtaacg gttatcgaac atatgccttc atatttgtgt atcgtcctcg gaatagaaaa 145920
```

-continued tggatcgcaa gtaactttca tcattcttga ggttaattct aattctgcaa aacaattact 145980
accagacact ctagtcagta tatacttttt accgttaccg taatcttgag tcatagactg 146040
gtggtacgct aaactagaaa tagtatcgct agtattatat attagcatgt tagctctcat 146100
cgtacacggt attaaaatta aaacgataga actatacgtt ctatacatat ttttagcatc 146160
tgaccaaaat ctattagaat cgtcgtatgc ttttcctaga tctttgatgt agtaatgtat 146220
ttttaggtcg caaggaaacc ataccttaga tttttctacg ctattaatat ctatggtacc 146280
agcgtcgtat ttttctgtga tcattatttc atctcctata tctgtttcta tgatatagtc 146340
ctccgtccat atatctatct ttccgtgata actaacgcac gatctcttgt gtttccaggt 146400
tacacatttc ctagaccgcc aaggcatagt ccctagtttt gccatgtctt caaatactcg 146460
ttctctaccc gtgaactcgt ctatgaatat aacagactcg ttgtacgctt gggatacaaa 146520
gttaatatgg atgagatcgg atttaaaatc actatcataa ttatctatac aaaacacgcc 146580
tattttattt tcttctgtag aagcaaacat tttactcgtc gcaaaatcac ctataggtag 146640
ttctattact ccatctttat tacctacggc tacgggagta gatcctgaag gacacgataa 146700
tacaaaactc gtaaaccccc taccatatcc aaaagtatat atttctacat atatatttct 146760
agatctggat tcgcaggaag aagtgtcgtc caataacatt gtgtctttcc aataacattc 146820
agtagtatgt ttattagcgc aaaatttaga atgtccttga acagtattag gttttattac 146880
tatatcactg aaattacggt tttgaaacac aaataattgt ttgagttcag gatctttacc 146940
gaacggattt tctaatatcc atcgcttacc tgcaggatcc caacttgaaa tccttaatag 147000
aatactacat gtagtatgaa tgatgtaagt tatggaacta tcaaacggac aaccccgtac 147060
caacagatta aaacttttta gaggaaatat atcgcacacg ttagaaggca tagtcttagt 147120
ttcttctggt tctcctggtg tagccatttt aagtagctgc atgtttctta gctctacttc 147180
gaaaggtttt aaagtaagag ttatatcttt tccacatgtt aatctaaccg taggaaaact 147240
agaaagcata gttcctagat ttaaaaactt ataaaaccgt actccgtctt cattagtata 147300
tttaagagta gtatatgctg ttatatcaac atctatggat ctgagatatc ctagaggaca 147360
ggctactgtc aacgaaaaat ctagtataac gttactcgta ttaaggtaca tgaggacact 147420
atctatagta tctataaaat gtaacgataa tttatccaat ggttgtttaa agctagtatc 147480
gtttctgtag gacatataaa cgagagtttc tgttcctggt atcatacact ttctaacgcc 147540
agttctttca gtatcagata tatattcttc atacgtatta aacatcttga taacaggatc 147600
tggagatcta ggttttcctg ttagtatatg atatatatct acaccagcat ctattaatcc 147660
ggctatagtg gataaaccca ttcctgaaaa ggctagtcta gtagacataa acgacccggc 147720
tatagacatg actcctccca tgctttccaa acaagtactt actgtttcag caacagcggt 147780
agccacagaa ttatcatcgt tatatcttag ctgtaaatct attaacctat gtacgagcaa 147840
ttgtgaagct aagttaaaat ttactgcttt atctaattgt ttggctatct tgtccatatt 147900
agacccataa tcggtcatcg gataaccgct gcctataatg taattactac tttctgtagt 147960
ataactggtt ccgctaatac ttcctgtact gtatccactg agtatgctat taacgctctc 148020
gctatacatg ccgtaaacac tatgcgtatc acctctaccg gatgtgtgta tgctattatc 148080
gctatatcta ccgctagaat cataataccc gtataaatct tgcgacgtgt ctagactacc 148140
tcccgtactt aaactcggcg tcgatcgtct acgtgaagaa tcactatggc gagtaagaga 148200
taacaatcca caaacagcgc ctattcctcg cttacaccgg atagatggtt tatgattttg 148260
ggacgtatag atttctgtat caagaactcg ctttacgtcg cgcgatgagt ccacggagcg 148320

-continued

```
aactcttctt tgaaggacgt cctgactctc atccgaggtg gttggtttag aaatgatact 148380
ccttacttct acgcctaata ctgatttact cggagtagcc acgacagaaa cagtacgtcc 148440
tccatattct ttataagcgt ttattccgtc tttaaaacac gatattatgt ttttatgttg 148500
tttgttattt aactcgatat gatttaaccg tctctctaat ttatccaaat cttcttcgaa 148560
tatatggtaa ctatgtttat tatttgttat cacgctcttt atggattcta tttttgtaaa 148620
agctatgtaa tatagactcg ctgaaacgat attcctacca tctaatctag gcacaggaat 148680
atcgagtata tttaatacat ctttaggtaa tatatttgat gaaatttctg gcatgtatgt 148740
tctgaacgtt gactttacca tgtcctttaa cgtattcact aactcgccgt ctccactaat 148800
accttttttgc ttcttataca tacctatctg cagatgagta atatcttcta atattacgct 148860
atctatacct agatagtttt taagaagagt cctaatatcc ttcgaagaag agttcgttcc 148920
gattacgtcc tctacactat catcttctaa gatagatctt ttacgtctgt gtctataact 148980
acgatacgcg ttatttagtt tacgtttatt tttatagtcg ccagaatgtt ctatgcactt 149040
ttcgtattct tcgccgtcgt ctaagtcgta catattatac atacaattta aatgctcgtg 149100
gttaatcgac gaatctttca gttcttcttt aaaggacatc tgtggagtga gcgtatctct 149160
tttagttttt gttcttctct ttttacctgt ataagcacgt aaagttttta tggaattgga 149220
ttttatctta tcatttatat agatatagtt ggtacaatct gtacctcccg taacttcaca 149280
agtataataa agactagcca ttttatcata aggtaatcct ccgcaagtcg ctagagatgt 149340
cttaaattca tcaggtacgc ttaccacatc taccattaaa ctcatctgac agtcgtgaca 149400
attactagtt agttttgtgt ctataataac ttgacctata cgtccaaagg ttggtgcctt 149460
ttggcaatta gataatatat gttttacgca ttcagcaaat acgttagacg gctcataagg 149520
aggactagac gatacaccgt taaaagtaac ggttatagta ctattatttt tacttttatt 149580
catagtaaag tttttaacaa tcaccgtatc ggctgtaatg tttttacatt tatcattatt 149640
gtaggtaacg gcatacatgg gtggtacact acacgttagt acgttatcgt gagtttcaca 149700
gttagtatat tcaatatctt ctttagataa agataaagca gcggctgata tacacgagaa 149760
tagtttcaaa ccttcacgca aataattatg tctatttctt gctttattat gaatatataa 149820
tgatacgcta taagtatagt tatatctata aactgcgtca agacgatctt ggttactacg 149880
tgtatcgcac atactaataa aactgcgctt gatttcttct ctaatacttt tccagtcgaa 149940
gcaattatga agacgttctc tttctcgagt tctaattatc gacaagtatc tcatagcggc 150000
gatagcttta tggtctgtca gttctttggg ttttatgttg ttaacgatgc gatgatatct 150060
agactctttt cttaagcatg attcattttc agagtcatct gcataatatg cgaatgttaa 150120
tgaatagaat aaaatactta taataattcc cttcaaagaa gaactctctc cgcgtacgtc 150180
cttcgacatc ctttcatcct atggtgtata tagtattata ataatatata gctagtttgc 150240
cttttagttc atttttaata catggaaaac atgaagcata attacctact gtaggtgata 150300
tatatcaaat cctacttgta tgattagtga gaaaacattt agttattggg tattctagat 150360
atcacgacct tgaaaaatgc gataaatacg ataaagatat tttggagctt gagatttacc 150420
gagaacaacg taaagagaaa gaagaatata aaaaagcaaa gtaaatgggt agctaaagac 150480
gggtcgtggg atgctgcgtc agttaatgta tacattacag aggaagacat tgatggttca 150540
acgtaaaaca agatcgctat aaactagtaa attctattat atcgttatct tggatttgct 150600
tgtacggtaa aggtattgtt ggtctatggc atgggataat gcttttgtgc tacaatgtgt 150660
```

-continued attttatatt actaatgtga gtgatgttat agcaagactt tagttgttac tagaaaacta 150720
atgcgtttgc ttgcatacaa agtgtataaa taacttctaa tagaactaac ccgcttatac 150780
atgcatagct aagtcacata tctctgtata ctgtgaaaac agactctggg gactagtgtt 150840
tcctatctca aggaacttaa atgaagagtt gtagacaaac ttagtaatct tatagaaagt 150900
ttatgaagat ttataagata cgtgaaataa tataccatat caagtttaaa taacaaatga 150960
aaaataaatg agtttgcgta taaaaatcga taagcttcgt caacttgtaa cctatttttc 151020
agaatttagt gaagaagtat ctataaatat agatgtaaaa agcaacgttt tatatatatt 151080
tgccactcta ggtggatcta taaatatatg gaccattgtc cctctaaatt ccaacgtttt 151140
ttataacggt gtggaaaaca ccgtgttcaa tctacccgtt ttaaaagtaa agaactgtct 151200
atgtagtttt cataatgatg cagttgtatc aataacagcg gatcatgata ataataccgt 151260
cacgctatct agtcattata ccgtaagcat agactgtaac aacgaacaaa taccccatag 151320
tacaggaacg agtatttctt taggtataga tcagaagaag tcctatatct ttaactttca 151380
taaatatgaa gaaaagtgct gcggaagaac ggtgtttcat cttgatatgc tacttggatt 151440
tattaaatgt attagccagt atcaatacct caatatatgt tttgatgata aaaaattgtt 151500
gcttaaaaca ccgggtacta gggatacgtt tgtaagaagt tattctatga ctgaatggtc 151560
tcctactctt cagaattatt ctttcaaaat agcaattttc tcgttgaata agctaagagg 151620
gtttaagaaa agagtattag tattcgagtc aaagatagtt atggatacgg aagggaacat 151680
actaggattg ctgtttagag atagaatagg tacttataaa gtcaatgttt ttatggcgtt 151740
tcaggattaa tcagtaaaat aaatgggggg tggtttagtt ctacctacta gggatccgcc 151800
caaagaacaa gatacttcgg agacagctac taatattcct aaactattaa aatctattcc 151860
tggtgtaaag ttaggacaac agataagaat aggttacaaa cctggtcctg aaactgccaa 151920
ggcatttcca gaatttgata tcaaagaagt aagtaatgga ttatacgaac ttagcagaaa 151980
atcgtatctc ggtgatacta aaacgtgttg tataaatcct tctctaagtt actattggga 152040
agactccaaa aataaaatat ttgacgagta cgctacaggt agaagtctta aaacatgcga 152100
tcctttaaca aaaactatat ctggttctac attatgtgat aatatattaa cgagcttatg 152160
tctggacgaa aaatctggag tagatagaac tatgtgtaac gaatggatgg gatatgctct 152220
taatagaccc gatctttcca ttccgaaatc aattaacgat agatatacga agctatgctc 152280
caagggagcc aataaatatag tatgtgaaga ttggttgcat catttaagaa ttataggagg 152340
aaaagaaaat gatgaagtta tagacaacgt attaatgcaa caaacgcctg aatttaaaga 152400
aaaatatatg aagtgtagtt ttcctagcca taatacagta tttctggcat atagagtaat 152460
agaacctaga gaatgctggg accaagaatg tattacgtct aacgtccatt ttcttctaag 152520
taaaaactat cataatttaa cattatgtca catctataga tgtaacatta gtatcaataa 152580
ccttttgata gatggtaaat catctgttaa aatatcttgt catgacgaga atataagtaa 152640
taaagataag ccaaaagcac gtaataaagc aaaatttata gacgatatac tagggtcctc 152700
gtttaatata aattttggat tctttttgt gatttttatt atgatagcgt taatattaat 152760
tgttttactt taaatggggg cagcggctag tatccaaact acagttacaa ccattaataa 152820
aaaaatatct gaaaaactag aacaaactgc ttccgcgtca gctactgcta attgtgatat 152880
taatatagga aatataattt ttaaaaagaa taaaggatgc aatgttttag taaaaaatat 152940
gtgttctgcg aatgcgtctg cacaattaga cgctatagta tccgctgtga gagaagtata 153000
tgatcaacta acagaacaac agaaggctta cgcacctagc cttcttaccg cggcgcttaa 153060

-continued

```
cattcaaact aacgtgagta cgataacgca agactttgaa acctatataa agcaaaaatg 153120
taattcggat gctgttatca ataatatcat taacgtacag agtttagaag tggatgaatg 153180
ctcggcgccg cctgggcaga ttatgacgtt tgaattcatt aatactggta cagctactgg 153240
aaattgcgct atgaaatcag tattggacgt tcttacaaaa agcagtgata gagtatcagg 153300
taatcaatca acgggtaacg atttctctaa atatctatat ataataggag gcataatatg 153360
ttttttgatt ttactatatt atgctaaaaa gttatttttt atgtccacca atgataaagt 153420
aaaagttcta ttggctaaaa aaccagacgt gcattggacg acgtatatag atacatactt 153480
tagatcgtca ccggtgttgg tttagagaat taaattcaac ttaacataat atacattaaa 153540
tgcatacctt tttaacagct cgtctacaag caatagaaga tgtatcaaat aggaatttga 153600
gtatgttgga actaatattg acgagagcta tagttactca ttggataata ctagacttgg 153660
tactaaatct aattttcgat agtctaataa catcattcgt cattatatat tctttatatt 153720
catttgtagc cagaaataat aaggtattat tatttttact gatgtcttat gctatattcc 153780
gatttatcgt catgtattta ttgtatatag tatccgagtc tatagattga tattagttga 153840
tcgtgttatt aattctttcg ctgtaaatac atcattagta gaaaaatcat ctatttcaaa 153900
aatatttccc ccatcgatag aataaattac acgaactatg ttattcagcg atacatcgga 153960
taaagttata cccataatta aagcatcgtt atacattaca taaaccaatg atccgggttc 154020
tgtgagcctg tgtatttggg gtgtattaat atagttcttt tttatcttaa atatatccaa 154080
atactgccta gatatgtttt caaagtgatt tcttataaac cattcaaaaa aatagtttgt 154140
agatttcaag tttcttctag tcatcaagtc ttgatgggca gtcatataat ctaaatagca 154200
cgattgtgat aattcagact tatagagatg agtatttgta gacaatagta ttaaagattc 154260
tgtattaaac aataatacta gatggttaat cgacatagat atagtactcc taggtataga 154320
aactaaatcg aatttaaaat catctgagaa tatgttgttt ttataaagag aatataatat 154380
agcgactatt tgcagtatta tgtctttagt taggcataca gtatttatat tcagattagt 154440
acgtttcata ttcttgaaat actcgaagta gatagttctt ccgtatgtat gatctttaac 154500
actatatact agtggaaatc ctagagcttt accggctttt actaaagcag ataatgttac 154560
ccaataatta gcttcgtcta tacatacttg cttacgaata ttaaaatatt ctcctatata 154620
acaagaaatt tcgtatctct ttctttcttg gtagtaatcg cataatctct gttctgtaaa 154680
aggtatttgc ctattagact ctgtagttgc attattttta ctcatttaat cttaaaaaaa 154740
acttatctaa atgaacgatc ttctattaga aaatctgttt ggagaaaaag cattatgcgc 154800
gcaagtaacg agagatcaac tgttagaaat aatagcggcg ggagcgagat caaagtttcc 154860
taaatcttta ctatctatgt acagagtaac tcctagagta atgactcgct atcctctgaa 154920
acttataact aacgaatcta ttaccggagt ggttatcact acagtatata atcttaaaaa 154980
gaatttgaat attcctcaga ataataaact tacaacacaa gatatcgaac gttattattt 155040
agataaaagt gtagaagtta ttaatcttat ggttggtaat acgtctctcg gagatttggc 155100
atgtgggaga cccaggagaa caaaatcttc aaagaagaaa gatcccgtta tattcttggg 155160
tatatcagca cctcttatat tggttatgaa ttctaagaag tcgataaata catacataca 155220
agataagaag tctgatccca gtagcgatta tgttaatata aatccaggca tcggagtact 155280
agagaactat ggaaatacgt atctactaga catccataat ccgtcatcgg tattaactat 155340
ttctactata tacgggctcg ataataatat ggaactgaaa aaattaagta cagccagtga 155400
```

-continued aatagatgct taccaagatg taaacatagg taaatcagta gatctaaaaa agtttaatga 155460
aatatttaat acgatgaaaa aacatttgtc tttgtcaaat tttagtatct aaatggatag 155520
aaatatcaat tttagtcctg tatttataga acctaggttt aaacacgagt ttctattatc 155580
tcctcaaagg tatttttata tattagtttt tgaagtaata gtagctttga ttatattgaa 155640
ttttttcttt aaggaagaaa tattatatac attttttccg ttagctaagc cttctaaaaa 155700
ttcaataaat agtctgctgg atagaactat gttaaaatgt gaagaagatg gatctttgat 155760
gatttcgaga ccttccggta tctattcggc cttgagttta gatggttcac cggtaaggat 155820
ttccgattgt agtttgcttt tatcgtcaat aaatggcgca tcctcatcaa catctcctta 155880
ctctattttt aacagacgat aacggatttt attcttatct atccgaaaaa agtgatgatg 155940
aagctcttga agacataaat actattaaga aatatatgga ctttattcta agcgttctta 156000
tacgttctaa agagaaacta gaaaatatag gatgttctta cgagcctatg agtgaatcgt 156060
ttaaggctct tattaaagta aaggatgatg gtactttagt aaaagcattt accaagccat 156120
tgttaaatcc tcattccgaa aagatagttt tagatagagg ttatacttcg gattttgcta 156180
taagcgtaat aagactatct agtaaaagca gttatatact tcccgcaaat acaaaataca 156240
taaatccaaa cgagaatatg tatataaaca acctaatatc attgttaaaa aggaattgaa 156300
agaaaatatt ttatatcgta ataaattaaa tatgcatgaa ggacatcagg agtcttttaa 156360
agaacttgaa atgacaaaac cttatatgtt cttcaatgaa ctagtaggtg aagaagacta 156420
taacaaagag ttagaaaatt ctaatactaa gtttcaagga cagggccagc ttaagctgtt 156480
attaggagaa ctttatttct taaatacatt aatcaagaat aaaacgttat gttcagatac 156540
agttatcgtg tatatagggt cagcaccagg aagccatata aatttttttat atcattatat 156600 ggatgatctt aaaatagatt taaaatggat attaatagat ggtagagatc atgatcgatc 156660
tctagaaagt cttaaaaatg tgtctataat acataggttt gtagatgaac aatacttgtt 156720
taagctacgt aatatgatta ggaaaaacca taaaattgta ctgatatcag atattagatc 156780
gctaagagga aaagaaccta ctagcgagga cctattacac gattacgcgt tgcagaatca 156840
aatggtaagc attcttaaac caatagcatc gagcctgaaa tggagatgtc cgtttccgga 156900
tcagtggata agagactttt acattccttg tggagatgag tttctgcagc cgttcgcgcc 156960
tcctttttca gcggaaatga gattgctaag ttgttactca cgggcaccca ttcgtctaat 157020
acgtatagat aagaatgcag ctatagaata tgaaaaaaaa atgttttatt taaataccaa 157080
aatcagacct aaaatagttc ttgattttga ttatccaaac caaaaatacg attactttta 157140
tatgttttat atccttaaag acatcgtgtt gcctacttat aaagagtttt caacatataa 157200
acaaaaggtt atatttctac aggaggcaat ctttaacgcg ttaaatataa aaccatgatg 157260
aaccaatata atgtcacata tttatcaaaa atattgtgtc taaaaacaga aatactatac 157320
aagccttttt ccataattaa taggagtata gttaatcagt ataatataga tgttaagtac 157380
gacgatatta caagtatcgt aaagattaga cataaaacag aaaatactat tttagtattc 157440
caaatattta acgaatctaa tgtaaaatat tctcctatag aatatgatta tggtgatccc 157500
atcattataa cgtctaactt acaacacggt cataatagaa tccctattaa catgttgtat 157560
atagatgtcg tagaatcaga catgtttcca acgttttcca ggttagacag tgaaacaatt 157620
aaaattataa ctagtatatt acaatctgat aataaaaagg aacaatctat taagctacct 157680
aaagtttcag aaaacgaact atctgtaaaa atattatatc ataaagacta tccgctgaaa 157740
tacgttagat attataaaaa caatatggta actggtatag aagtcataga tagatcggtg 157800

-continued

```
gcgattacca gttaataaga acgattaacg ctaatatcgc taaacctaat attaaatatt 157860
ttggatcgat aataggaagg tgtatctcct gttcaagagg tttaactgaa taacccgcgt 157920
atatagcatg actagataaa caatcattat ttacttttaa aataccatct aataagttga 157980
tctcgcccaa agatacgcta caatctataa gattacatct tttcatgtta tcccttaaag 158040
cggtaggtat tttagcggtt ttccttttac atggttcata ccaacaataa taaggcaata 158100
ataggtcttc tccaattttt tctatagtag gttctggatg aatacataga cagtctctat 158160
ctttagggtt agattcacaa tacttaaata ttgcttcatc gtttataacg ttgtccatat 158220
taaaatttaa aatctaaaaa taatagttat aatcaaaaat gtctgtgata tctaaagtaa 158280
gttatagttt atattctcaa aacgaaataa atgctacaga tattaatatc aattatgtta 158340
agaacgacga cgaagtcggc accgtcaagg acagtaggct aggagcaacc gatggagtat 158400
tatgtagaac gtgcaaccgt actgaattag aatgtttcgg tcactggggg aaagttagga 158460
tatacgaaaa tattattatt aaaccagaat atataagcga agtaatacgc attctaggcc 158520
atatttgttt aacgtgcggt cttctcagat ctcgagaacc ttatactgtt aatatttctt 158580
ctcttactag cggtgaatta aaaaaactaa aggacaaaat atcgtccaaa aagaaatctt 158640
gttggaatag tcgttgtatg caaccttacc aaaaagtaaa cttctcaaaa aagaaagtat 158700
gcttggttaa taaaacagat gaattctgtg tgcctaatgc tttagtatac gaaaaaataa 158760
catctattca ccataaattt tggccggtat tagatattca tcaagatcca gctactttat 158820
tttatagagg ctatttttcg atacctccat tattgattag acccgtaatc agcttttgga 158880
tagataacgt acctaaagat accaacgaac ttacctacct tctaggagtt attgttaaac 158940
attgtaacgc aaatgcggat gaaccaacta ttcaaaaagc tattatcgaa tatgataata 159000
ttaagttaat atctactaat agtactacta ataatctttc ttatattact tctggtaaaa 159060
ctaatatgtt gagaagtttc gtagttgcta ggagaaaaga tcaaacagct agatccgtct 159120
taggactcga ttcttcatta gatattacag aagtaggtat acctgactac gtaagaaata 159180
ctctaacaga aaaaatattt ataaacgcat ttacaataga taaagtcaaa gatatgtttc 159240
agcgcggtga gattaagtat tactttaaca aacaattaca ccaattgacg aaaataaaac 159300
aaaataaatt tattaagaat aagatacatc ttcttcccgg agattgggta gaaactaaca 159360
ttcaagaatt tactaatatc attttcggta gacaaccttc tttgcatagg tataacgtta 159420
tatcgtcttc tgtaagaaaa acagaagaag ataccattaa aataccacca ggtatcgcta 159480
attcacaaaa tgcggatttt gatggagatg aagaatggac tatagtcgaa caaaatccaa 159540
aaagcgtgat agaacaaagt attctaatgt atccaactac tctattaaaa cacgatgtac 159600
acggaatgcc cgtatacggt tctatacaag acgagatctt agctgcttac aatctatttc 159660
gtgaatacga tctaacccaa gacgaagtac ttaatatctt aggaaagtac ggattggaat 159720
tcctaaccga ttatgaaagg aaagataaat ataccggtaa agatattttt aaatttttga 159780
tcaacgaacc agaaattaat tatcccggta taatatgtaa tggagaaatt atagccgaaa 159840
acatagatag taattttata gtatcgatga aacacatgtc catatccggt cttataacgg 159900
attataaatc tagcgtagaa ggtataaaat ttataaacaa agcatcctat gtgtttaaaa 159960
gatatttaaa gatatatgga tttagtatca ctttcagaaa tttatgcccg gattttgagt 160020
ttacaaaaaa actcagagaa caaaatataa aaaagattaa cgatattaaa cattcttatg 160080
ttaagtattt gtacgacgtt gctaacggtg atattatacc attatctaga tccgatgaga 160140
```

-continued tggatgctgt cgattctatt ctttccggcc ttaccaactt taatattcag gagattgaga 160200
aatacatgaa agaagttata tcaaaggacc cagataatag cttgatgaaa atgtcttgcg 160260
cgggatataa ggtaaatcca acagaactca tgtatatctt aggtacatac ggacaacaac 160320
gtatagatgg agaacctatt gatacaaaaa tatatggaag agtactaccc tatttcttac 160380
ccgattctaa ggaccctgaa ggaaagggtt acatactcaa ttctctcata caaggattga 160440
cgggttccca atattattat gccatgttaa tagctagatc tcaatctact gatatagttt 160500
gtgagacatc aaggacgggt actctagcta gaaagattat caaaaagatg gaagatatgg 160560
tggtggacag ttacggacag attgtgtacg gtaatactct agtcaaatac gccgctaatt 160620
acacaaagat acaaggatct gtttgtaaat ctgtagagtt aatatatccc gatgaatctt 160680
taacctggtt tctagaaata agcgctttgt gggataagct aaaaaatggc tttatatata 160740
atcaaggtca gaaaatagct aaatatattt tagctccttt taacttcaaa gtatttatga 160800
agttggacga aactaatccc atgaagtcta aagacttata tgacaagata caactagtaa 160860
ttaaagatgt aagagaaaat tatttcttcg atgtcactag tatagacttc atagaatacg 160920
tatttctaac tcatttaaac ccgtctagag taaaagtttc tgaagataca gcaaatttaa 160980
ttttcgaaaa actgtatgaa aaattaaatt acacgttagg aggaggaact cccatcggca 161040
ttatatctgc acaagtgcta agtgaaaagt tcactcaaca ggctttatct agttttcata 161100
ccactgagaa aagcggtggt ataaaacgca aactcggatt taacgaattc aaccagttaa 161160
caaatcttag caaaaacaaa acagagatta tcactctcat atctgatgat atcacaaaac 161220
tacaaactat taagatgaat tttgagtttg tatatttagg agaactattt ccagagatta 161280
caatagaaga agacaaaaac tattaccgta tagatataaa tgttaataga ctttacataa 161340
aacgtaatca actaacagaa ctgatcgtcg aatacatgtt agaaaagttt gtttcctata 161400
gtgtgttggt taaaaactgg ggaatggaaa cgaacataat taacgaacat atcattagat 161460
ttagcttatt cattgtattt acagagccgg taaatctcaa taaaaataaa tttatgatga 161520
tgttaccagg agcggcaaat aaaggcaaaa ttagtaaata caagatacct atatctgaat 161580
atcagtcata taccgattat aacaaaacag taaagttata taggcttact gtagaattaa 161640
tgggccttaa agagcttgga acctttgatc tagttaatgt caatgttata cctggtgtat 161700
ggaatactta cgagatattc ggtatagaat ctgcaaagag ttatctttgt gaagctctgc 161760
tcagtactta tggagaaggg ttggattact tatatcaacc gtgtgattta ctagctagct 161820
tgatatgttt aaactatgaa ccggaatcta taaacaagtt taaatttggt cctgtaagtg 161880
ctttaaagcg cgctacattt ggcgataaca aagccatcat taacgcagca ttatacaaga 161940
aaacagaacc cgtaaatgat aacagtagtt gccacttttt tagtaaagta ccgaaaatag 162000
gtacaggata ttacaaatat ttcatagatt tggaaaagtt tcttcgcatt aaaaagacta 162060
tctcagagaa acttatagat aaaaagttag tagatatagg tgataatatt actgattttt 162120
agtacatcag tcatatatac ttatctatta tttggttcaa gaatgattta ttttctataa 162180
aagctcccct tatagatttt agttcatgat atatatacaa aaagtatatt acaaatggta 162240
tatttttgtc tctaatctcc ataagataac ccataatcat agccgaactt ctgttaatac 162300
ctgccataca gtgtaccaat acgggaatct ttaaagattc acattttttta agtacatatg 162360 taaccgcgtc gatatgtttt gatatactaa cagtgtcatt gtcttctaat ggaaagtgta 162420
ataccgttat atctgttctc ttgagtttat attttaacat cgatacgttt actatatatt 162480
tgaagaatgt tttattaggt aattcgatta catttctata atttcctaga tatacataat 162540

-continued

```
cggtaatttt agttatatct ctaggcgtaa attttacaca tgtgttagta gatttagtaa 162600
taatatgctt atatagttgt ttttcatcca tttatatagg ttacaaatgg gaaacgaagt 162660
agagttatcg gttcatggaa tagaacttaa ctatgctaga aataatatta ctaaaaatat 162720
acgatatgct agagtatcta ctttaatatt tttcttttta cttttagtaa ttagcgttgt 162780
tttattcttt ttccagatat ccaataatag tatattctca acactgagta aatatactcg 162840
tataaaaaac aatttaagct cctggaaacc actagtaata caaaaatcta aaataaatag 162900
cgagttagga aagcacgcgg ctcttaacag acaggattta atgagattta aatgtgttga 162960
ctttggtagt tactttctac ctgtaagatt gaataataat aacttcttac cggaagcggt 163020
tagaagagga gatggagatg gatggatgat aaaaaaggcg gggaagtacg atcctgctgc 163080
tgagcagtat tgtgatttta tactggacag atataaagat acaatcacat gcggtgacca 163140
aatgtttaat agcctagggt atagcggtta tttcgaatct gggcactggt gtcagacctt 163200
tctagattta gttaaataac tatgatgtta ataagcattc taacttcaat aacagtttta 163260
tagtaaacat cactcaagat tacttacttc tattttaatg tatagattaa aaggttattt 163320
cgtatgatta tgttatatta aacaattaat ttagcactat tatagttctg aatgtattac 163380
atagaatacg ctaaaaatac tccagatagt aaccataata gcttgttatt gatatcgaat 163440
atagcgagtc ctatgataat aactattgcg attaaaaaca tcatagtgat atcgtatttc 163500
ccaaatacgg aaaatagagg atagtacatg cgatgataaa atgacggcca gttatccata 163560
atccagccat ctatacgaga tttaatagac aatctatttt tcttgttctt catgaattcg 163620
tttgctagtt tatagtcgtg ataaacgtat ctatcgttat ccacgacgta tctagttata 163680
cccagagtat tctcaattct aagaatttct aaagatatat caaagctcgg tttattattc 163740
gtaaaatagc tatataattt ccttaccgct tcctgtctaa taatataagc agataacgat 163800
acatcaaaac tacctttaaa agcttctaaa tctggaagta gcataaggtg ttgagagttt 163860
ctatctttta gcaatttggt atgtgttact aattgcagta tatctacgtt gttatcgtta 163920
agtaccttgg ttatgttatc taaatttgta ataaaacctt ccccggttat tgtattatcg 163980
tcttccataa tgacaacata attcggtaat ttttctgcat tatccataat atacctccat 164040
agacttatgt ggtccgcgat gaagatttta gtatcttccg tacatgttag tctacagacg 164100
tcagaataat aaccatctct aacagaaacc atttcatcgt attctatgtc acctacctta 164160
tcgtccgcat ttggttcttg tttgcttttt ggaagtggtt taggagacgg cgggtctctg 164220
taatcatcgt atccattttt aataccettt ttataactcc attcggatac ctccaaattc 164280
ttaaagggta ctacggtaga tgaaggtcta cctatcgtag ttattacaaa tataatttgt 164340
ttcttgtcgc ccggcgccat ttaattgtta aaattaatta tgtatagttc cttgatcttt 164400
ttgctatttt cttctatcca ttctgttaca ttgacgtagc tagccaaaaa catgtaaaaa 164460
ctaaattcaa gttcttgtct attcaaacta tcgctaaaat acgtaaacac gttactatta 164520
ggtaataatt cctgcctaag catattatat ccggtgattt tatggttagt atgttcttga 164580
ctaatcaagt cataatgaaa tggaaatgga tcaccaaatt tgaaaacata aaaatctaca 164640
ttagatgaat aatacttgag aacattatat acaaaaagac tagtcaatgg aataattatt 164700
tttttctttt ccacttctaa tttgatatga gttgtaaaaa atgaggcgtt gtacgcgttt 164760
gtatcattca cccttataag aactttagta gttttcttca ttatatcttc aaaaatttct 164820
ttatcttcat cagtgccttc ttttattctt acaggatgtt ttatcgttat gatttctgta 164880
```

-continued ttctcggcta ctaccttttc gtaagtaatg aacaacttag tacttgttat acaactagga 164940
aaaaaagcta tttcatctgt tctctgtatc tgcctataga tactaatatc atagttaggt 165000
gtttttctat ctttcttaat ggctattaaa cgttccattt cgagttttat tctattatag 165060
tggactataa gttcttcggt tgctattttc atgtatgttt ccgtaaatag ttctatagta 165120
ttgaactgct tggagtcaac tgtcctggtt ttcttcagaa aatcaaatac gataactgat 165180
ataatatgat ttagatccga atagttagtt tcttcctttt tgttagtcat ataatacata 165240
ataaagtccg caccactgtt aagtactata actagggcta ctataaaatg gatattcaat 165300
atcttagcag aatagaataa ctccatagaa gacatctgaa tgtcaaaaag attagcggaa 165360
agccttagga agaatatacc tttcttaatt tctgtagcaa actgtttttc gtattcgtgt 165420
cttttgctgt taatgtctat taggaaattc agaataagac gatttatatt atacttcata 165480
ttccacattt gagacttcat aatagtatcg aacgacataa tcgtattaaa tataaacctt 165540
tggctatgtg agaaataatt ataggggttcc gacataaata tagatttatt ataagtaacg 165600
ttaataagag atattttcgt gacatcggta gcatccaagt ttagttcctg tatgtttatt 165660
ccgcatagat tacagtacgc tagtccatct tcataatata tatatttagc tataaactta 165720
ttaatgttct cgtagtattc tagactaact tttttagcat cgataaatatc tatctcatgt 165780
tcacagggta caaaatctac gctacctcct tcttcccaga atttcaattc ggatacgtat 165840
atgtactcta taggattctt cctaggttcg aaggtgactt gttttatatt aattaactcc 165900
ataaacaaat cacacaaacc atagttagac aaaaagaagt aactatataa acgaggattt 165960
ttaaacttag gtataataac cttaccccat tcgtaaaagt acttattgtc atcatcaaaa 166020
ttattcctgt aggctttatt agtttcttcc aagtatacgt attttacatc gaggtagtct 166080
ttaataacta taggtatagt tagttcgtct ataacgtagt taaaaatgta cctaacgtta 166140
tattttcgtt tagatatttt tatacctatg tttctacaca aatatgcaaa gtctaaatac 166200
tttttagaaa aacgtaactg atctaaattc tttgatacgt acgataataa ctccttcatg 166260
ttaaaaggga tttcgtttac tacctgttca tatttatctt ctttgtatga taaactcgta 166320
gtaaaacttc tgtaattgat attaaagtcg ttattacctt cgtcattcac gagaatgttg 166380
acatgttttt gccttattat gaaatctaaa gtagaaaaga aggtatcata catattataa 166440
ttcatatcac ctgtcatcct atcacctaaa tcgatactag aattgtcatc gtggatgttc 166500
ttttcaaaat tatatcctat ataagaaaat atagctacca aagatttatc atctatatct 166560
atgttttgtt ctatagtaat gtaaagtagt tttatatctt catccgtaat catattaacg 166620
ttatatagat tacagataaa taattctttg ttttttgcta taaaatcttg ataagatttt 166680
tcctttaccg tatcatcttt tatatacgcc tttatcttag gcactaactc taataataca 166740
gattccttgt tctccattta atgtatagaa ctaatttata ataaacatag taaatatggg 166800
taacttctta atagccataa ttaaaattga aaaaaaaata tcattataaa acgtaaacga 166860
acaaaaaaca ttaatttaaa tttgccaata acaaaccaat atgtcttgga caaattctga 166920
agataaatcg tttaaaacaa tagatgagct taaagccaag gtaaaggcgg atagcagtca 166980
tcatgtttcc aactctgctt ctgatacaga accggaaatg attccggaag tagtaaaaaa 167040
gcctaccaaa aaaactgcta aaaaaacaaa aaaacaagaa cttgcatctt gtaattctag 167100
taatccaaat acagatccat ttactaagga tctagatctt tacgatcttg atgttcttag 167160
cgatggaaag tgtgcggaag aaaacaaacc gtcgtctata gatcttgtag agactagatt 167220
ggtaataaag actatctcta aatcaataaa agatatagca catagaatag cggcattgag 167280

-continued gtcagtaata catgatttgg accttactga tatcccgaag aatacgggtc aagctatcaa 167340
ggaagtagac aaattaaaag aagcgttatg taatctaggt gttagcgtac caccacctaa 167400
acaacaaagg aaaaaagcta agtaaatggt aaagaaagtt ttttttcatt ataaagatga 167460
taaactatat tacgatgccg catataaaaa tctagttcct gctagtaata aaacatacga 167520
aataattaaa gcgtatagag ttcctcctca tttgaaagaa gtaatcgtat acgagcaatc 167580
tctagaagag gcgtctaaca gcttaatatt tatcggagta gattctaaag gacgaaagca 167640
atatttttat ggcaaaaatc atgtaatatt aagaaataag aatcgagata aagttttcat 167700
taaagtacat aaaataataa aaaaaattaa taattatata gacaagaata tatgttccga 167760
atcaaatact ctagaatttc aactagcagt attcatgtta atggaaacta gcttttatat 167820
acggatagga aaagtaaaat actataaaca aaacgatact gttgggttat tgacgctaca 167880
aaataagcac ctgactgtta cggacgagaa tattactata aaattcacag gtaaagataa 167940
agttgttcac gcgtttaacg tcaagaaaga aaacagatta tatgagcctt tattaagaat 168000
acatgacttt tcgaaaccag attccgtatt attttcttta ttatcagaaa agaaagttta 168060
ttcatttatt aagcaatatt caataaaaat aaaagacttg cgtacttacg gtgtaaatat 168120
cacattttta tataatatat ggaataacgt aatttctatg ttgaaattac ctagtatcaa 168180
aaaactaata gtattatcta taaaacaaac tgcggatact ataggccaca cccctaatat 168240
ttctaagcaa gcgtatatgg ctattactat actagaacta atgaaagaag aaaatataac 168300
agaaactatt aaacaaaaga cattcgacga gtttcttaat tttgtgatta attatgtaaa 168360
taaaaaaaag atataattaa atggaccata aatctagaat gcttttagat accatattta 168420
aagatatgct aaatacgaaa gacgtatatg cattaataaa atatattttt aaaaaagatc 168480
ctgtagaaac tatattttct aaaaaagacg atgatatatt tatagatttt gtctataacg 168540
ataatgttct agcatctgat tacctgggta tgaaaactac taaagtagag gattgttgca 168600
gttgtagaaa agtagtagct gtagaatata tgaatacatc tattatagat aatgacttag 168660
aaggatatat aaagcaatcc gataaactaa aaagatttat taaactatat aataaaaata 168720
atgctattaa aaaagcgaga aacataaaat cacgccagaa aatgctaaaa gatgctggta 168780
tagatgatat aggatatgaa tttataaaag acgccattgg tctaataagt cgtaagtaaa 168840
tttcatagcc gtgtatgggt ccatacgctt tatatcttta tgtttattca attcattaga 168900
tgatgttaaa tcgtaccaag cactataatt agtctttttc tcagataact cttcttgtaa 168960
tttcactagt gtattttgag cggttatttt atctttgtat aatccactta gtatcatatt 169020
atctttatct aaccgaacag atgttgcttt cttagttaac ataaatagaa aaaaaacgat 169080
aactataata taaataacca atataactat catttaataa atggataaat atatatcaaa 169140
aaccccactt agctgttatt ttgaagaact agtagataca tttatttctg tagttaacag 169200
tataaacaaa gtagatgaat ctaagcatca tgaagtcgaa cttatcttat ttaaaccacc 169260
tattattacc ctcactaacc tatataacat ggcaactacc acagaatctt atatagagtt 169320
taccatgtta cccgtagata aaccaaacac taagtttaga aacagaatac ccttatctaa 169380
gattcatgga ctagatgtaa aaaataatca actagtagaa agtttggatg gttttatttg 169440
ggaagaaaaa tctcttttgt taaaaaaaga catatcggat aattcttccg cgattataaa 169500
atattctatt gaagaaaaaa ctttattcgt ggattacaaa agacgtaacg cgtctattaa 169560
actagaactt gtaagtgtag tacgagctaa acttagaaac atagttatag attttaaaat 169620

-continued gaaatacttt ctaggttcag gcgcacaatc agcaaattct agttctctat tatgtgcttt 169680
aaaccatcct aaaaataaac ccagtctgta tatagagttc gagatcatga tgcaagacaa 169740
aaacatatct aaaaagaagc tactcgaaga actaaatatg tcagctagtg ctttatttct 169800
aagtcatcca aagtacatta gactgtgtcc tagtataaac cctatactta gaactcactt 169860
actcaaaaaa caggatatta ttaatataaa tacagacgac ttatatatta caagcaagac 169920
ggatggtata ttttcacacg tctatataga aaagaagtct atattctgct attttagcca 169980
tctagggtat ataaaagagt atacagcgtc tagggaaata gaagaaacta tatatctata 170040
tgctgaaatg cgtaaagaag aatctatatt atatcttaca gttattaaag tattaaaacc 170100
gtgtatggaa gatcggttgt cagaactagc attcgtaaaa aatcacctta ccggtatcca 170160
tgatagattg gtatttgtta caaaatgtta cgatggacct tttgaatcta gttctgatct 170220
tgtggtgtct atagaagaaa tgttaaaaac agaacaagaa ggtattatac ttttttactc 170280
caagggagaa gattctacaa cagattataa agttaagaaa gataatacta tagatcagtg 170340
cgttaatgtt atatatagat atatgtctag tgaacccata gtatttaacg ataaaggttc 170400
gttcttggaa tataaaagat acagtaatga taagggtttt cctaaagaat tctctacagg 170460
gaaattagat ctcaacggaa gcgttgaata tataaataac atatattgta tagaaattaa 170520
acaccttaat ccatgtaccg gtattactaa tcttgtatta cctataaaat tcatagcaga 170580
attctctcat aacgatgaat taatacaacc cagaatagat aaaactatga aatatctata 170640
tgaaagcgga tactacggga atcaactatc cgttattatg gatcatttga acgatcaaaa 170700
actgagaata ggagatgttt ttgaggaaga aaaattagca gatatagcag cacacatgaa 170760
attaaaagat tctatgcgtc taaatccgga cggtaactac ttcctatcga acagagtgag 170820
aggagcgtta ggtattttat ctaattttgt taagacgtta cttatatcgt tatattgttc 170880
gaaaacatac ctagataatc attccaagag aaaagttcta gccatagact ttggtaacgg 170940
agctgactta gaaaaatact tttatggtga gatagcattg atggtagcta cagatccaga 171000
cgataatgct atcgaaacgg gtaaaaaaag gtataacgaa cgtaacgcag gtgataaatc 171060
caagtactat aagtttaatt atataaaaga aactattcga tctgaaactt acgtttctag 171120
tatcagacaa gtgttatatt ttgaaaagtt cagtttggta gattggcagt tcgcgataca 171180
ttattcgttt catcccaaac attatagtac catcatgact aacctacagg aattaacaga 171240
atcaggatgt aaagtcctta ttactactat ggatggggat tatctggata ctcttaagga 171300
aaaaaagaaa tttattattc gcaaattatt acccgaaacc gaaaactatt tatcgataga 171360
aaaaatagac gatgataaag tgcttgtgta taatccttcg agtatgtcta aacccatggc 171420
ggaatacata gttagacgcg acacgctgat acgtgtattc agggagtaca agtttaagtt 171480
aatagattca tgtaatttta aaactatcat tgatagaaac ataagtttta ttaacggggt 171540
ttcgaggttg gaatctaggg gatcgacaaa aaatttcttc gagttaaaca ggaaagcttt 171600
agaagaatgc aacgacactg atgttcttga attattgagt cattatatgg tatatgtgtt 171660
ttctaaagag gtatagtgta ttacattgtt tttatatata gtttctagtt atttaaatta 171720
tatcagggtt aaatatggga cccgaattat atcataccga tgctatgaca ttttcattaa 171780
gcgataagta cgatatatat ggcatattca gaacgtttca tattaacact gacggtaagt 171840
attctaaacc cggatcatta tacgattatt acataactta taatactgac ggagtagaaa 171900
gttattttct cttcgaacgt gctacagaag aacaattata taaaatatta aaatcatata 171960
actatttact tataaccaag gtaactgttt atcctaatga taattcctac gatagaaggt 172020

-continued

```
ataaacatag aagagatcgt aggtactaag gacgtgtata ataataacaa catcctaata 172080
ctttatttgt tttaaagcta ttaaagagtt ctaacaatat catttttgga tgtttatttg 172140
cggacggtat acgtagggta ctactttcct ttctaatagg aaattcttca ttaaatgatt 172200
ctaatatatt ttgactggga aatataacag gaaggtaatc atgtctatct ttgtatacgt 172260
tttttatttg ttgatatata attccattat caaatctggc tactttatca aagttatata 172320
tttcaaacag tttaccatta tcacaaaacg atacaattat ataatctgat tttaatatat 172380
tatttatatc ttgttggaac ctgatgactt tattaaacaa cgtatgtatg tttattaatc 172440
ctatactctt caattctagt tccattttga ttgaacgtta tatttatagc tagctacagg 172500
tttacctatt ttatcacgat tgatatctga ttatattgtg tacaagtaaa ataattacta 172560
cctttgtaac tatcgagtat aatctatgcc ttgtagatgg tgtgacgaat tataaaaaaa 172620
tctcaatatg ttgtattact atattagaaa attagaatat tattgtgaaa attggtgata 172680
tactttttat attaatgaaa aataataatt aaaagtttgg acaatataaa aaatgaatat 172740
ttgtattaac cccgagagta ctaattgcgt tcactcgact aatgatgtta aagcccggac 172800
tcccataaaa aataaatatt tacctgatta cgcgttaata agatttatga ttaaaaagtt 172860
taataaacta ttcatcgaaa aaggtttacc tataacagct gtatatagtt ggaccgtgtt 172920
tcgtgaagct gctatatgta gaggtcaata cagaagttgg ataatgtcat ttatacatac 172980
tatttctggt aataatattg ctaattttag attagataga gcttactcag attccagata 173040
taattctata ataatagact ccacatcagg aaagattata tgtgaaggaa ttggcatcat 173100
ggagaagttg agattacacg gggtagattt tattaacgac aagttattca ccgaagaaga 173160
aataataaca catgtatacg gagttcaacc gcttcaggat atatgtatta ggatgatacg 173220
taatacggta agtagagacg attatgataa gctagaactt ccaagatcat tactaaaaga 173280
aattaagaaa taaggcagta aatatttatg tcaaaattga agtataatag caaataatac 173340
gctataaatg taggtgatta tgtcacatct tcatcttaat aatggagata cagagtatag 173400
agttattgaa gataatggat tttccattat attgcttaaa catacagaat atataaatgt 173460
tacaaaatta tgcaagatac ataacaaaga gttctataga tggaaaagac tgatctctgc 173520
gggacgtatt atcgaaactg tttcacgaga tatatcgaat caaggttttg aatctcctct 173580
agtatacgta aataggaaag gcaataaaga attttatgga ttttatgccc atcctcaatt 173640
agcgttgtat atagctaaat ggatatctga agatatattt aacaagatta agcatttaat 173700
aaactcctat acgatatcag ataaaaccgt agtaataaaa gatttttcat attgtgacga 173760
actatgtccc gacgctataa taggaaagtg ttgtaaaacc aaatcatcat gcgagtacgt 173820
ccatggagat atatgcgata tatgtgggtt tgaggcttta catccaaccg atattgataa 173880
aagattgact cacgaaaagg tatgtatgca actactatgc aaagaagata taaaatacga 173940
taaatgcggt atttgtttgg atgctataaa aggaaataag aaaccttatg gtattttatc 174000
agactgtaat catatgtttt gtattaactg tattaaaaca tggatgacta ctattaattc 174060
taagaagcaa tgccctgaat gcagagtacc ttctaagtat atcatacaaa gtcctatctg 174120
gacagtggat aaggttagta agaatcagtt aagtgtttcg tacaagactg tatatataaa 174180
atcatgttaa cgttttgtag aagttgaaaa aataatatac tgatacaaaa tggcttttca 174240
agaactttgt tgtagtaatt tgttaaaatt cgagaactgt tcactactcg aaacgcataa 174300
aaagatatct atagaaggaa atatttctgc cggaaagtct acgttgataa atatattatc 174360
```

-continued tgataatggg tataacgttg ttcaagaacc tttagaacaa tggagaggta ataatttact 174420
ggacaaatta tacaaagatc catctagatg ggcatatact ttccaatctc acgctttttg 174480
gactcgaact aaaacttata tagatgctct aaacaaaaat aaaggtaata taattttaga 174540
aagatctgta tttagtgata agtatatatt tgcgacagcg ttacacgata taggatatat 174600
agatgataca gaatggaata tttataacga atacagtaag tggatgaccg aatttatgga 174660
tataaagata gatggaatta tatatttaaa gacatcaccg gatatatgtt ataaacgaat 174720
gttaaataga gcccgtcatg aagaaaatac cgttaaaata gattatttga atctgctcca 174780
tgataagcac gaaaagtggt tgtccgagaa taacgagcac gaatttaaag ttccggtatt 174840
agaaataaac ggagacggcg acttcatcga cgatagtaac agacaatcaa gcatacttag 174900
taacatttat gattttatat cggaattata catataagta aaacttttat aggttataga 174960
atttgtcttc tatttcctta ttcgttaatt ctcttatagg cattatgctt atcttatata 175020
agtcacataa tgatgcatta tttacaagtt cagcatattc tgattccgta gtataataag 175080
tatattcata ttttttattc ttagaatata atcctatttg gaaatgttga tcttgatttc 175140
tatatttatc gtcagtgatt acatgatagc attcgaaaat tctaggtata tcgcacgtat 175200
tacttatttg tagtgaaata agatctccta ctgcaaattc tttccaaaaa aattgctcgt 175260
cgtaagatac ggtatttaca tcgttatcgt gaacagttaa gattaatgat ttacaattgc 175320
cattctccat aattttggtt ttaatatatt tataacacaa tttataataa taaatcttat 175380
agattaaata gaggtttaat aaacgcgtag ttatatatca ttataaaaat gatacttgct 175440
tggaaaatta tatatctagc tattcttttg tatataccga cagaaagact agttttaagt 175500
cataccgtga ttacgcgtag taagctttcc acagaagata acgaaataga tgacgttcca 175560
acatgtccgt acagaatgtt caataaaaag aagattatgg gtcctatcgt gtctgtaaag 175620
tcacctgata atccgacggg ccctatcatg gctttggatg cttatcataa ctatacgtcg 175680
tgtaagtata atcaatattg tacttttttt gatttctgta tggcgggtaa cactactatt 175740
cggtttggaa ggcagaaaat aaacttaata tactttgtat ttatagaagc tgtaaccaga 175800
gatgattata caaaaattac acaagaagtt accttgaagc atctagatga tgttagattt 175860
aaaccagtat ccgttacttt tgcagcatta tataaacaat ttgtgaaaat gtctgcatat 175920
cacgaatgta ataaaacagg ttttaaaaaa ccagttagag attcatgtag aaaagatagt 175980
aactctgcta tacaatatag taatgaacaa aaatcacatt acaatttctt gttaaaaagt 176040
agtaaaaaaa tataaaatga aaataaaaca atattttata atagcttaga taatatagat 176100
tttgattcac tcataaacat tattaaatta gaaaataaga ctataatatt tggaaaaaga 176160
ttgcagatat atatcaggtt gctgcttatg tattgactta tacatcatag ggtagcgtta 176220
aaatacacaa gttgttcaga cactacatga aaatataata gtacgggacc tgtaatgata 176280
tgtccggtaa taaaaatata atatttagtg aaatattgga aattcttaat agtaagtaca 176340
agaaggatat gaagctttta aatatagtct atgaaaaata tagagctatt atattctggg 176400
aattagacga cattaaatca gagagcaaaa aattgagaac acaatatcaa gaagaactta 176460
gtaaaaactt aatgccggat ttactaaaaa ataaatatca aagggatatt aggtatttca 176520
ggagtaaatt aatagagtta aaaactagac tagatgatat tgaaagaaag ttaatagata 176580
ggtctaatag tcttatgctt aaatacgtat cagatctaca aaaaatacaa tcatacctat 176640
cgagtaaaac aagcgactct gtaatcatcg atcttgttac tcagttaata gcttatagga 176700
tagtagatgg atataaagaa gctgaaaaat aatctatttt ttattacaaa ctaaacaagt 176760

-continued

```
atgatgttta atagtatgat aaccggttat atagatgaag aattttgcta tatacaatat 176820
tctggatttc atcttgttat gatgatttcc aattgttata ttaacgctag taagttatgc 176880
gatacaaagg attttaaaaa atggttgcgt ttagatagtt cgttatcgct tttacaagaa 176940
atagaaaaca caaactttcc atcggagaaa aagttttcta tcaaaaattc aaaatcggtt 177000
attattctag aaaagtatta tcacgaagaa gtagaaggat attacattca tcctgatata 177060
ctaccgcata ttgtaggatg gttatctcct acattcgcta ttagtatgtc taaattcatt 177120
aatgggtata tatctaatag ttttacaatt accgaaaaag atgacaaaaa atacaacacg 177180
ttaccaccat cttcatcata caaacaagga gatagaaatt gtttcataga tatgcttaac 177240
gaaatgacaa ataaacatct caatgatata acagaactaa aaactcatta tagagagcag 177300
aaaagagaac taaaatatca aaataccgta cttagctcaa aaataacaga attaaagaac 177360
gtcaatgacg aatttagata caggataaaa cattttgatg atagtattaa agaaataaaa 177420
gatgaaaata acactttaaa atcaaatatc aaaattacag aaaaacataa caaagaatta 177480
caaagagata acaatagatt aaagacttta ttgagagaac tatacgaaaa gaatacttct 177540
ttgcaaaaca atataacaga acttagagaa acaatagcca gagaaacaaa agaattacat 177600
aatcaagtaa ttgaactttc caaagacaag gggatagaac ctatagaaga ataccgcgtt 177660
gacagatgct ttgtaaggaa tagattacac cgatctaata aaaataatta tataattatc 177720
tttcaacata aaaaggactt gtttactttc aaatacttta aactacatat aagaaaagta 177780
tgcatagaac tatttaatta tagagagagc cataatttat ttttaattat ttacgaacct 177840
actaataaat ctataatccg attcaagaat atgcttgaaa ataacgaaca tatagaacta 177900
aaagataaca actttaaaat aacagatact agatataccg ttataaatat attaaaggat 177960
ataaataaaa tattttcaga taactaatat aacttttcgt accgtgtaaa ttgcataatt 178020
ttttatacta taaatatgga tggtaacacc aataaccaac agaagaaagt ccctgacggg 178080
gtgattcccc agggccaaca aaagcttcct ccaaaagcac cgccgactaa cggcggtagt 178140
acaggagatg taaaaagtag tgatcaaaat acagaaccat cacagaaaag tgtataatat 178200
aaaattacgt cttatatcag taatactgat ataagtgaag ttatgtgttt taaggacgtt 178260
aggacccttt acaagaataa aagaagaaac aactgtgaaa tagtttataa atgtaattcg 178320
tatgcagaaa acgataatat attttggtat gagaaatcta aaggagacat agtttgtata 178380
gacatgcgct cttccgatga gatattcgat gcttttctaa tgtatcatat agctacaaga 178440
tatgcctatc atgatgatga tatatatcta caaatagtgt tatattattc taataataaa 178500
aatgttatat cttatattac gaaaaataaa tacgttaagt atataagaaa taaaactaga 178560
gacgatattc ataaagtaaa aatattagct ctagaagact ttacaacgga agaaatatat 178620
tgttggatta gtaatatata acagcgtagc tgcacggttt tgatcatttt ccaacaatat 178680
aaaccaatga aggaggacga ctcatcaaac ataaataaca ttcacggaaa atattcagta 178740
tcagatttat cacaagatga ttatgttatt gaatgtatag acggatcttt tgattcgatc 178800
aagtatagag atataaaggt tataataatg aagaataacg gttacgttaa ttgtagtaaa 178860
ttatgtaaaa tgcggaataa atacttttct agatggttgc gtctttctac ttctaaagca 178920
ttattagaca tttacaataa taagtcagta gataatgcta ttgttaaagt ctatggtaaa 178980
ggtaagaaac ttattataac aggattttat ctcaaacaaa atatgatacg ttatgttatt 179040
gagtggatag ggatgatttt tacaaacgat atatacaaaa tgattaattt ctataatgcg 179100
```

-continued ttattcggta acgatgaatt aaaaatagta tcctgtgaaa acactctatg cccgtttata 179160
gaacttggta gatgctatta tggtaaaaaa tgtaagtata tacacggaga tcaatgtgat 179220
atctgtggtc tatatatact acaccctacc gatattaacc aacgagtttc tcacaagaaa 179280
acttgtttag tagatagaga ttctttgatt gtgtttaaaa gaagtaccag taaaaagtgt 179340
ggcatatgca tagaagaaat aaacaaaaaa catatttccg aacagtattt tggaattctc 179400
ccaagttgta aacatatttt ttgcctatca tgtataagac gttgggcaga tactaccaga 179460
aatacagata ctgaaaatac gtgtcctgaa tgtagaatag tttttccttt cataatacc 179520
agtaggtatt ggatagataa taaatatgat aaaaaaatat tatataatag atataagaaa 179580
atgattttta caaaaatacc tataagaaca ataaaaatat aattacattt acggaaaata 179640
gctggtttta gtttaccaac ttagagtaat tatcatattg aatctatatt gtttttttagt 179700
tatataaaaa catgattagc ccccaatcgg atgaaaatat aaaagatgtt gagaatttcg 179760
aatacaacaa aaagaggaat cgtacgttgt ccatatccaa acatataaat aaaaattcaa 179820
aagtagtatt atactggatg tttagagatc aacgtgtaca agataattgg gctttaattt 179880
acgcacaacg attagcgtta aaactcaaaa tacctctaag aatatgcttt tgtgtcgtgc 179940
caaaatttca cactactact tctagacact ttatgttttt aatatccggt cttaaagaag 180000
tcgcggaaga atgtaaaaga ctatgtatag ggttttcatt gatatatggc gtaccaaaag 180060
taataattcc gtgtatagta aaaaaataca gagtcggagt aatcataacg gatttctttc 180120
cattacgtgt tcccgaaaga ttaatgaaac agactgtaat atctcttcca gataacatac 180180
cttttataca agtagacgct cataatatag taccttgttg ggaagcttct gataaagaag 180240
aatacggtgc acgaacaaag acaaacgtgg ttataaacaa aagccattac ccggattgga 180300
aactaaaata ctagatagta ttataagatt ttaaaaacat aaaattaata ggtttttata 180360
gattgactta ttatatacaa tatggataaa agatatatat caactagaaa gttgaatgac 180420
ggattcttaa ttttatatta tgattcaata gaaattattg tcatgtcgtg taatcatttt 180480
ataaatatat cagcgttact agctaagaaa aacaaggact ttaatgaatg gctaaagata 180540
gaatcattta gagaaataat agatacttta gataaaatta attacgatct aggacaacga 180600
tattgtgaag aaccttacgg cgcatcacat tccagtgtaa ttattgaggt caaagctagt 180660
aacttaatag atgacaggac agctggattt tatgtacata aagatttgat accttatata 180720
ctgacatgca tatctatacc ttttagtctt aaagttgtcc gtgtattaga tacttatata 180780
ggtgaaaaac tagaaaacag aattaagcta agtcagagta tggatttgga aacgaacaat 180840
tcatacaaca tgtagaaaag aaaaaataat gttcttataa taatactata actccatatt 180900
gttatgtaaa cctagtagta acagctatga gagagattct aattatatta atgctaaaaa 180960
atatgtagta tcatcgataa taaaaaattt ataaatggca tagattagaa tattctaaag 181020
aactaatagc ttacaataga tacgatcgtt aatacaaaaa atctaagata aaaataagta 181080
gtaccataat taatagtgct cctagtaata tagatatact aggttattac gtccatccgc 181140
tgctagtacc tcataccata taccatcttg gaggtcagcg gaataagaat taaaaatttc 181200
aaagatagta aaggttatct attctaagat gtatcataac aatggaaaaa tctaaaaatt 181260
aaaaaaacaa ctaatataat tataactata atgcatgatt atatataaca gaatggtaat 181320
aacagtaaga tataccattt ttaacaatat aaagttattt gtaattacta taggattgtt 181380
atgtagtgta ttattattac gtaatatagt gtacttgtac aatagaatat tacagttaat 181440
aattgattaa ataaaagaaa ttaccatgat tttaaatgta taagttctaa acatattaat 181500

-continued agtaaattct gttatataca gcataattat ttagaactaa taaagatgag agataattct 181560
tttataaatg ccatacattt atgtttatca ggaggaaagg atttttctac gtggttatca 181620
ttatatacac ctaggtgtct actagatacg ttagctaaaa caatcttcaa tggaacgtcg 181680
atgttgacta gtcagaagga ataattaaag aaaagtctta tgatactgat gaagagtata 181740
aatgttacta tattctcact atgaccatat agccgtgggt atttagttat tttgctgtaa 181800
acttatacga gctcgttagt aacatctata tcatatgcaa aaacagatga catgttttaa 181860
actatatttt gcgttcatat tagactacaa acctaatgat aataacaaaa atcatttata 181920
ttttacaagt tttaacaata ttgaacgcgt aattagataa accaaaatgg ttttatatta 181980
gtgtaaatat aatatcgagt ttatgtaatt aaatatcatg gttatagtgt aataaagtta 182040
aggataatta tgctaaatag cccgtattat aatacacgat aaattaataa attgaagcta 182100
tttatatcac aaggagatat aataccgtcg taaagtaaat ataaaatatt atcagaatac 182160
acgtatttat ctaaaatcat taaatggact tgtatgataa taattgaaaa acaattatct 182220
caatacattt gaatggtgat atattgtaac ctacatacag taattatgaa tatattctat 182280
aacaatattc atcgatgttt taaagacacg cctttacata aagccgtaat gttacctgat 182340
gcggtagaaa gaataagaat gtttgtatct aaaggcgcgg acataaacgt aatatcagat 182400
tttaaaaaga cggcattgca ttatgcggca aagaaattgg ctactccaga agtacttaaa 182460
acactcatat atttaggtac taacgtaaac gtcaccgaca tgtttgaatc aactcctttg 182520
cattacgccg tacaagaaaa tggattagaa gcaacaaaaa agttattaga cctaggtgca 182580
gatcccaaca ccaaatacat gaacggtcag actccgttac attgcgcagc gatggttata 182640
cccgatggtc ctgaactggt aagaattctg gtcgagtacg gtgctaatgt taatgcgcta 182700
gacaataaac ataatacacc gctagctcta gccgcagaat tatctaatac aaacaaaaca 182760
atagaaacgc ttatcgagct cggcgcggac gtaaaaataa aaaataatga cggtataaca 182820
cccttacatt tagccgctaa atcatcgtct gattccaaaa cagtggaaac acttatcctt 182880
cacggagctg atgtcaacgc tacatgctcg gaagggaaca cgcctttaca tgatgcggct 182940
acttcatacg agttatctaa tacaatagaa atgctgatag aatacggagc tgaagtaaac 183000
gccgcgaatt cggtaggtga tacaccttta cattgcgctg ctcgttctcg taatcctgtt 183060
cataagctga aaacactcat agcacacggt tctaacgtaa acgctgttaa cgggatatcg 183120
gtaactcctt tacatcttgc gacttattca gataatgcaa cggaagcatt aaaggtatta 183180
atagagcacg gcgctgaagt aaactccgta gatatctacg gaagaacacc catgcattat 183240
atctctaggt cttattcttc acaatcatta aaaaccgctg ttgagttact ggtagaacac 183300
ggtgccgata tagaagctaa aaatgtaata ggtggtacac ctttatccag cgcgtgtaat 183360
aatatagagt atgatctaag acttatagaa tgttttatag aatacggagc ggatataaat 183420
actagagata tacgtgatga aacacccttta tattcggcaa taaagtatcc ggagatagtt 183480
aatttattaa tgaattatag cgctagtaca aacataacaa ataaaagtaa tattactcct 183540
ctggaatcag ctatcgccaa ttgtatagt tctgcagaaa ttatagtaac tcaaattata 183600
ttagacgcgt ttagatttcc tgatataaaa aatgatgcga tatttatcag aaacatgaaa 183660
accatagaag aatgtaccat gcttatcgat gtaaaagaat cctgtgaata tgacataaat 183720
aaaatgcgat ctattaaatt taataatatg tacggactgg atatattcat tcgctcaaat 183780
aatataaatt tgttgtcaag tttggtatct aatgtagaag atatatactt agaaccaggt 183840

-continued tgttttttag tatatggaaa taaattaaga aaatctgtat atgccgctag gaagcgatta 183900
tcgttactaa aaaactctat atctattctg agtaatatca ctacagatgg ttactggaat 183960
gctttaccta tagaacttaa atataatata ttagctatgt taggagataa tgatttgttt 184020
aatattgtaa gaaactgttc gtaaagaacg tgataagata cagccacgtt tactagcggg 184080
acttataagt gaaatcattt tattgttcta tattagatta cgtaaatgta gatttttttc 184140
attatgttgg aaggaaatat tataatattt taatggcttg ttaatagtta ttatcttaaa 184200
aacatacatc atataaataa actcagttaa aaagttaaaa ataatctcat agtttcgagt 184260
aaagactatt acaatcatga ataccttacc gtatattatt caggatattg attcgcattt 184320
ctgttatata aaatacgatg gaattacact tactatgatg aaagacaacg gctacataaa 184380
tgctacacaa ctgtgtatgc ttggaaataa agactttaaa gaatggataa agttagatca 184440
cagtatagaa ctaataaaag aaatagaaaa aaatatcaat aaagaaacta ccaaatatgt 184500
aaaagctgtt atatcagtta gatcagatta ttataattca gagacctcca atgacataaa 184560
aggattttat atacacggta atataatgcc acatatctgt gcctggatat catctaagtt 184620
tgctataaaa gtatctaata ttgttcataa ctatctaaac gatagatatg tacaaaatga 184680
taaagaggaa atacaccaag aacccgataa ggatattaaa tatataaaga aacaatgtaa 184740
gttaatgcga gaaataagaa ttctatttaa aaaaaactat actcgcgagt tagacgaact 184800
caaaaaagta agggagcttt attacgaaaa aaataaagga cttgaagaat atattgataa 184860
attagaatat agttacactc agagaatgaa agaattaacc ctatctatag atgaattaaa 184920
aaatagtaac aagcaattaa agaacaagtt agaaaatata gagaaacgta taaaatgtat 184980
taatccacct actgaaagta gtaaaaatgt gatctatgat aggttcaaaa agttatatca 185040
cattctaaca ttcagaaaat ctaaataatc aattaattat tataaccatt aatagctatt 185100
attttgaata tattcaaaaa cagacataca tcatgtaata taacactata taataccttt 185160
acaccacgca actacatata ttgctttgta tatgttgtat gaaaggtaat tacgtaaaca 185220
taataggtcg ccttactaac gatcctaaaa gaagttatag cttcacatga tatagatata 185280
aaactaggta atctatacac actaaaaagt ttttatacat tacgatagat attatggata 185340
aaagtagaga aactcgcatt tgcgattatg cttctaggac tatactgtaa agtgtctcga 185400
tcttagcata tagataaatg tttgaactaa tatcctaaag gctgtatgta acagttggtg 185460
actattgaaa gatactgatt atcaaggaga agaataatat aaatcgtaaa aataatactt 185520
attatataat ataatgtata ataatataca aaaacagcca tgatacgtat tataatatta 185580
tcgttattat ttattaacgt aacaacagat agtcaagaat cttcaaaaaa tatacaaaat 185640
gtattgcacg ttacagaata tagtagaact ggtgtaacag cttgctcgtt acattgtttt 185700
gatcgttcca aaggtttaga tcaaccaaaa acatttatcc tgcctggtaa atatagcaat 185760
aacagtataa aactagaagt agctattgat acatataaaa aagatagcga cttcagttat 185820
tctcacccat gtcaaatatt ccagttctgt gtgtctggta attttagtgg taaacggttc 185880
gatcattatc tatatgggta tacaatttcc ggatttatag atattgctcc aaaatattat 185940
agcggtatgt ctataagtac tattactgtt atgccattac aagaaggatc attaaagcat 186000
gatgatgccg atgactatga ctacgatgat gattgtgttc cttataaaga aacccagcct 186060
cgacatatgc cagaatcggt aataaaagaa ggatgtaaac ccattccact accaaggtat 186120
gatgaaaatg acgatcctac ttgtattatg tattgggatc actcgtggga taattactgt 186180
aatgttggat tttttaattc tctacagagt gatcacaatc ctctggtttt tccgttaaca 186240

-continued agttattctg atataaacaa tgcatttcat gcttttcaat catcttattg tagatcacta 186300
ggctttaacc aatcatacag tgtatgcgta tctataggtg atacaccatt tgaggttacg 186360
tatcatagtt atgaaagtgt tactgttgat cagttattac aagaaattaa aacactatat 186420
ggagaagatg ctgtatatgg attaccgttt agaaatataa ctataatggc gcgtacacgg 186480
attcaaagtt tacctcttac taacaatacc tgtatcccta aacaagacga tgctgatgat 186540
gttgacgatg ctgatgatgt tgacgatgct gatgatgttg acgatgctga tgatgctgac 186600
gatgatgatg attacgagtt atatgtagaa actacaccaa gagtgccaac agcgagaaaa 186660
aaacccgtta cagaagaata taatgatata tttagtagtt ttgataattt tgacatgaaa 186720
aagaaataag acatatttta ttaaatcaaa aagtctgtcg aacttttagt gtttaaccta 186780
tatcgattta tgattttcca tgatgatcca ggctatgact gactatggca aatgtataaa 186840
aagcagtaat ctgtatacga cttaatagat tctaaaaatc aagaaaacct taatttctat 186900
ctcacgttct tgagaatttt tgatgtatag ttgactacga cctagtagaa agattttgaa 186960
aagaagtttc tatgtttttc aaataggtat agaaaaataa tcattctgaa gcacgtgctc 187020
caataaaatg aaactatttt tgctactgag gtagactttt aatgtaataa caataagcat 187080
gactacctat tatctgcttt aaaatatact atgttgatgt gatagatcct tggttattat 187140
attccttata ctagtagaat agttacttag ttaatgatgt aattctaaca agaaatctgt 187200
gatacgtgat tatgatgatt cataaaaaag aataatatat agcgttattt agaaaatgta 187260
tctaaaataa tcatatcatc tggctctgtt attgtacccg atataacggt aatactaatt 187320
tatctaaata tgatgtataa gagttagata atggtttaat tccttagtat catattctcc 187380
agagactgta agattgttac cagattattg ttctaatact accgttatag ataaactaga 187440
cttcactttt tatggaatta taacattagt agaggtgaaa tattatagac gatatagaac 187500
attatactat ctgaagaata tataataact gatatagtat tatcagctat atcatacaag 187560
gattgttata tattttctaa aaatgtatac ctatacacaa taattgatac attaaaagaa 187620
acaacgaata actatgaatt aacattagct aactcattga ttattaataa gaacacagag 187680
cgataaaagt aatagaaaac actataccat gtctaccgat aatatgaaga ttatattcat 187740
aaagtcgtag ataattaaag agaagtttaa atttattata aattatccta cgttactaca 187800
cttctaaaga acatgttgta aaaccataat ctacaaatac gtattcgtgt ccgtaatcgt 187860
atacagatgt attaattttt ttctttttca tgtaatctag aaagttttcc catactagtt 187920
gattactatt gttcttcgtg tagtttttaa ccgtttgggg tttaaggtta ttcgttacag 187980
atgtaagact aaatatttta tccaaaaaaa acgaataatt aatagttttc gaaggggtat 188040
tttcttgaca gaaaaatact aagtgtttaa aaatttctat aacttcgttt attttacttg 188100
tatctaaatt taatttttct tcttttatat gatttattat ttcgaatact agtttataat 188160
ctttttttatt tattttttca ttcgctttta aaaacgatga tacaaaatta gcgtctatat 188220
ctgtagaaga tatattattt tttgtcatta cagactttaa ttcgacaatg acgtctgaag 188280
aacattgatt agaaagtaat ctacgtagaa cgtttctcaa gtgtatcaat ttattagata 188340
catgaaaatt tgatttttta gatactttgt tagaaagttg gaatatagat tgacagaaaa 188400
tacagaattc atgattagat tctgttatca atccgttatg cttacaatta ctacaatgtt 188460
ttagattact catgttaaaa ctcttcttat ttccggatct agtattttag ttaacagagt 188520
tttatttcta ctaaatatta gaaattgttt taatatattt ttcttatatt cgttattatt 188580

-continued

```
taacattaat tttatcaatt gtctatctga ttttagatat tcaactaaat tattactaca 188640
gttactacac ctaactggag gatctatact atatttatac tccgacattt actttacgta 188700
aattaaacaa atatttctgt tatgctttta gttgctaagt aaggtagata gtcttgagca 188760
tacactaaaa tacaacaatt tctagaaata aggttcatag cttcttcgtg ggacaataaa 188820
tcatcttcaa acataacagt atgatgcatc agttgctgtt gctttatatc gcatagtttc 188880
ttagtggatt cttctttcaa ccaatcgtag aacattccgt cgtcatttcc atgttcttta 188940
taatattgat tcttcatcac tctcattaat cttgactctc ttgactgttt gctataaata 189000
gatagaggat cgtacatcca aggacccatt tccgtgaata gaatagtata gtatcctttg 189060
agaaatacat ctccgccgtc gcaacttccg gacatggtag ataacaaatc gtgtgtcttg 189120
taacaaactg ctgattttag tagatatgta ataccgttga tatttagttc attagctata 189180
tccattggac gatcgttaat tactgatcta aagcctgtaa aacactcacc tgatactata 189240
tttttatttt gtcgacgttc tatgtagtag ataagagtcc cgtttactat tactggggaa 189300
tttataatcc tatcatgaga aatagaattc aatacaggta gagcgtctac agtcctacaa 189360
gaaatagtac cttggtatct catattagca ggcatgaaca ttactctacc cgtagtatta 189420
tcgaaactta gagaataaat tgaattagag ttaatggata taggattgtt tatagtggta 189480
atcattttg aagggcttac aactatataa gatacgggtt taagaactac gttaagcggt 189540
tggtaaggat ctgtgataga tactagcgcc ggtctgaatc ctacaataga tagaatcgaa 189600
gctagcattt gttcttcgtc ggccatcatc tgagagctgt ttatgtgaat aatcttcata 189660
agatggttgt cgacaagatc acaatccttg ctgtagaata tacctaatct caaattcaat 189720
attgttttc tcagcatagt atgaatactg gctctatgta tttcactaga tacagaatca 189780
ttaataccccg taaagataat aggagaatct tcagtaagcc tattaatcaa caacatatag 189840
ttttctggct ttactttctt cgagttatac aattgtttca taagactata actatcacct 189900
aataccatag cgttttctag agccggtagc ttaacgccga ataaagcaac taatatagga 189960
tgaacgtagc ctatggaatc ctggtctttg aatctaaata acatatcact agatgttgac 190020
atgtcaacaa agtttgttga ttgaaaccta gtcgtatcta tcaacgcttg atatctggat 190080
ggatcatatg tattttctag tagttttaac tgttctccta tcttattatc tgagtgcgaa 190140
taaataacca ttagaggatg actcgttttt accgaaacgc tattactaga aagtgatcct 190200
ttgacatgag atagtaactc gaataactct tgtctttcat ttctaataat atttaattcc 190260
ctcataacgc gaataaggtc ttgtatcgta aagttattta tatcacattt tctatccatg 190320
agatatctta ctatagcatc tgcgtctttt ctaagattat attgccagtc atgagtagat 190380
gtaatttcat ctatgttgat aattgtgttt ttttgtttta cagaatctga aactccttta 190440
catatatcag gttttggttt actacgaaga cgcataggtc gttgttgttt agcacctgct 190500
gatataacat cttcttcagt aattttattc aagacatcac atacgttaca taaattattt 190560
ttatccggtt tatgtaaatg agatcctatt acttctaggt tattatagta aacaggttct 190620
aataaaatat taggatattt aacttcttca atcgctatat tagaatcaga ttccatttat 190680
atttgatagt tttttacttg taacgtatca aaataagtac ctaaagagac gtaactagtt 190740
aaggaataat agcatctctg agttctctta tatcatctgg taacataata cccttttcct 190800
gaagatatat atttatccac gtaataactt catcaaaaaa catttgttta tctatcttat 190860
tgctattaga taatggtact ttaataggtg gtaggatatc aatatattta tcatgcagat 190920
ttcttatcca aagtggagta ctactaggca atgttaatac ttgtgactgc tgaatattag 190980
```

-continued aagacggtac taaagtacta ctactgctag atgaagaagg tgtttgaggg ccaaaactac 191040
taccactaga tgaggttgtt tgaggtccaa aactactatt gctagacaat gacgatggtc 191100
cttgtaaacc aatattgcta gacaatgacg atagtccttg tggggctaat ccactaacgg 191160
aagacgaagt tccttgtggg gctaatccac taacggaaga cgaagttcct tgtggggcta 191220
atccactaac ggaagacgaa gttccttgtg gggctaatcc actaacggaa gacgaagttc 191280
cttgtggggc taatccacta acggaagacg aagttccttg tggggctaat ccactaacgg 191340
aagacgaagt tccttgtggg gctaatccac taacggaaga cgaagttcct tgattgccgc 191400
tagtcgaggg tagagtagta cttgaattat aggaaggagg tcctaaattt tgtggataag 191460
gcaaattact gctttgttga ttgttaaatc tattaagaaa actggtaaaa ataccagcag 191520
tatcgttact acgtaatata gatatcattc tatcctgaat agacctacta tcgtctgtat 191580
tgtattcgtc tactatagat tccttctcat ttctactatc atcttcatct agcttttctg 191640
aaaatatctc tggattatta ctaacattac gtttgattct agaaataaaa tctttgtgga 191700
agttctcagc catttagtat cctaaaattg aattgtaatt atcgataata aatggacaat 191760
tctatggata ttaacgatat actactgtca gatgataacg attataagag ttacgatgaa 191820
gatgatgact ctatatccga tataggagaa acaagtgatg attgttgtac gactaaacaa 191880
tcggattcca ggatagaatc tttcaagttc gatgaaacta ctcaatcacc tcatccaaaa 191940
caattgagcg aaaggataaa ggctataaaa caacgataca ctagacgtat aagcctattt 192000
gaaataactg gaattttatc cgaaagttat aatttattac aacgtggaag aattccatta 192060
cttaatgacc tgacagaaga aacgtttaaa gattcaatta ttaatattat gtttaaagaa 192120
atagaacaag gaaattgtcc tatagttata caaaagaatg gagaactttt atccttaacc 192180
gactttgata aaaaaggagt acagtatcat ctggactaca ttaaaactat atggcgtaac 192240
caacgtaaat tataatttag atatataatg ttcttgaata aaatcgaata tgaattctat 192300
atctacagca ttttctttat agttaatgtt gtaattatcg gttatacatt gaacaattga 192360
tataagtgtt gttttgtgct tttcatattc ttccacaaat atgtttttat acatttcacg 192420
gttatttgat atctcactta tcaatccctg aatgttatta acctttcttt tctttaaatc 192480
ttctacggaa actttagtct taaatgatgc cattatttca ctaaaaagaa cgtgtaagcg 192540
ttcgttagta agtatttcag aatacactat actagagagt ttagaaaata tgttaacaaa 192600
ttgtgttgtt ttgacacagc tagtttgaaa taaaataata ttaggtaata ccttttttaaa 192660
gaagcttacg tatttattat ttatctggtc tataccgtct atcgttatat cgcagaaaca 192720
cttaatacca aatattacgt tttctttaga gaaagaaaat acatctttat attcttcaag 192780
ttttatctta tcagatacta catctgtatt aaaaagtgca attatcttta tgatataatt 192840
gctatccgct aggactttat ttattgttct gataatgaaa ctattgtttt ccattaatat 192900
tttgtaagct tgatgttcgt tattagcact tttaattaac gacacaattc ctagtatctt 192960
ttttaaatcc tgcactattt catttgtatc ttttttcata ttagagtaca tattgtttat 193020
agatgtaata actttttgcat atactaacat atctttaaat attctgataa actgttcttt 193080
tgtttcttta tctgttattt tgttgagcat agattttacg tttgccgctg atcgcatata 193140
ccaaaatgta aacatcttga attctacttg ctgcatggct agaataacag tctcgtcaga 193200
cattgcgcag ttaatatcac cgcctatctt actttctaga ataggaaaaa ccgttaaaaa 193260
tgaatcgata tcattatcat aatttacttc atacactttt tgacctgtac tattctctaa 193320

-continued atacttctta cttaattcat aaaattcaat aaatgcattc ctgaactttt ccatgattta 193380
tagcttgtag tatttttcta atattgattt gatttgtata tgtgtataat ctttaccgat 193440
acctaattta agcatagtat taataaccca agtttttata aatatttctt tgttatcggt 193500
taccacatat ttaaatactg aattaaagta tttaactata ggattattct gagtagatat 193560
attatccata aatacagacc gttttgtaga tagaggttct gtaaataatt caccgtcgac 193620
ataaaaacca tccgttgtta gtttgagtcc attttgttct tttatatcaa ccgttttaac 193680
tttataagga aacatatccc tcagtttgtt ggtacgtagt tcttcaaaat atatcatatc 193740
tttatcttct tcctttttag ctatgactat ttcatgtact atttcttgaa ctagtatgta 193800
tattttatta ttaatggatg agtatttcat aggaaagtaa acgatatcat tagctatgag 193860
agttacattt tccgtgttaa caaactggat aatatcattt ttagttcgta tacgtttcaa 193920
tgtataatgg caattatgta gacaactcct gattacatga tatcctttcg tactttttaa 193980
ccgcttatta tccgactcca atgaaatgct taaatcgctg ttaaagaaat cattaaatat 194040
gggaggtaga aatgctattt tagaatctgt aactactttg ccataattta gtatatacgg 194100
actaattata ttcttgtccg tttgcttatt atgaacacac gccataaaag tatccgtatg 194160
actttggttc tttagaaaac agcacggtat acatatcttt tgtaatttat agaatatagc 194220
aagaaaccct atattattat attttccggt cttatcatca caagtaaaca ttacctcgtt 194280
attattgacg aatacttctt tggtaggaga tttataaaag ttatcgctta cttttaacat 194340
atcaggttct agggaagata ttattacggg tttcctattt ttatctttcg tgttttgaca 194400
aatacgtgac caatagatag tttctatctt agtaaaatcc atagactgtt ttaccgtatt 194460
acacaggcgg tttataaaaa caactaagaa agtaaagtat ttttctatat tgggtatgtg 194520
atttttaacc tttatagaga tatggttctt cgctaaaatg attgatattt ttttatctac 194580
ggaaagcaat atattgttgg tagctgtttc aataaatata aaactagttt caatatctaa 194640
ttttactttt gatgtaatcg gagtagatag tttcacctta tacgtaatat cacttttgat 194700
acgttccatc tgtacgttgt tattcggtat catatctgta aaaagtttta cattattaac 194760
agtaatagta tttccgtcgc tggatatagc tagagaacca tcatcgtccc atatagacaa 194820
attaagagat tcgtcgttaa taacaaaatg gtttcctgat aaattgataa aatactcatc 194880
agatttgata aatagtatct tcttatcggt attactgaga actatattct ttaatccggt 194940
cattttgaga ttagtcctaa aaacgttatt aaattttgat tctaccgtga agtctaaatc 195000
aagatcagga aacatttcta taagacgaga ttcaaattta aggacattag catctacttc 195060
ttcgtaagat cctaattctt ttaccatagt atcggctgct tttgctaccc atatcactaa 195120
aaagttacac gcgtccacat agacattgta taagaaactt tctgacttaa gtaacgtttt 195180
tcgttgtgtc atagtgaatg gattaaaagt agtattatct acatagctat attccaaatt 195240
atttttgtgg gaatatataa ttatttcctc atcgatattc agaagatcgc atatataacc 195300
ctttacctgg gatatcttca aggttagtat tatatgcttt tttagaaccc ttactctatc 195360
cataggaact ctcaagtgat tctttatgaa gtaatacata gaagatcttt catctattcc 195420
atcgtatagc gtaagatata gaacgtccaa tatttcctga tctttatcaa ccaatacaac 195480
taactgagga tttactacgt acatttatag ataataacta tagagtaaac gtaaaaaata 195540
attagtatat aaaattttac gaatacaata tgtacgagat agtaccagat ttagacacta 195600
gtatgagcct cgaactagga gactttaaac tatctacaac tcgtacaaaa cctagagaag 195660
aagacaacca atattacctt tcgaagaaca gacgtatgta cgtatgcagt tctaaaggaa 195720

-continued gcgaaagagc taaaagccta ggattcttct tatccaaaat ccctttcctc aattacaaag 195780
aaaaaaacta catgtttcag aagatggata atatcaataa tattcaacta accaagaaaa 195840
ataacgttat atcagctccg tatgttatac tgattaatct ttcagcgaat ggttttaaat 195900
tcacagaaag ttttctagag atatactttc ctgagattta taaggaaagc agtaagaagt 195960
ttaaatttaa tactcaaatt caattgatac aggaaaaatt aggatatgaa cattctagtt 196020
attataatat agaatttgaa cactattata ctaccgtatg tttgatacta caaagtaaaa 196080
gaaacatgga aaaggaagat cctgaactat ttgacatacg agaaatgtct cctatactaa 196140
aatcattgtc tgagattact tataagctgt atgttttata tataaaatct aaatttgttc 196200
aatggagtat aagttcttca gcagttgtaa ctcaattagt taatactgta ttgattaccg 196260
tatataatct tgttactaaa tttataactg agaataagac cttcaaatgc aaactagctc 196320
ataataacga actacctata gatatgttag tatcctatta cgaagaattt tctgaaatta 196380
taacaaattt gatgaaactt aatagatata ggataaataa acacatacaa gaaactttac 196440
tcagcttctg taccattttt ggcgaggtag aataagccta gacctatcat gaagtagatt 196500
accatagtta ttaaaatttt aagtatgaca aacgctagcg tgttacaacg tattcgtgtt 196560
tcacaaaaat gcattataca atgcctcact agttctatta cattgctagc tacttgtagg 196620
aatgctaaag tacttataga atttagtata gaactgtaac acgacattta ttcgttatca 196680
aaaaccacag cattggcatc ttcgggattc attattcttt taatgttttc aaaataggat 196740
ttagtcattt cagtataata gttagttagt ttcaaaattt ttggtctggc gatattataa 196800
gctttctgga tatcctcctg tgtgatagga ttatcatcta tattcctccc ggttctatga 196860
actatactga gaacggattt aatttggtct atacctatca agtccttata cagcgattta 196920
gataattcta taaaatctcg atatttctct aatatagata tttttacatc gtctgaaatc 196980
ttagctttga aatacctttc tgtaaaatag atatgcatag caagttcttt aaacatcata 197040
gtaccgtgac aagttatctt cttgatacca tccatttgct tttcagaaat ctgtgtgatc 197100
gaatttagaa tattcgtggc tataaagttg gaatctttca tgttcctatc tttaagagca 197160
ttagtaatta attctattac ttcgttagta gcgttttcat caggtactct ttcatccaga 197220
ttttcaagta gttctcctac cgatacacct cccgccgata ctattaaacg atctattgtg 197280
ttgagaggaa ttatatgcgc tattgatttt ccatcgatag tatcttcttt taaaagttgt 197340
ttaagatttt ctttaaaatt tgcattttct gggagaaaca catctgtatc cataatttca 197400
tttaacgcat tagcagatag tattccttta acattaattc gatctaatat gtttacgggt 197460
gaaataaatt gtactaatgt agcgtcttct tcagacgctg attctttaaa accaccgaag 197520
aaggacctat taatacgtcg ataactatcc ctattactgc tattattgac ggataacata 197580
aaacttacta gatcatgcgc agatgataag agtttttcag cttcagattg agaacacgac 197640
gccttttgta acatatttgt tagatacctt ttgcttactc tgggactaac gtagtaagat 197700
gtataactat gactagatat ggtagtccta ttaacacgta cgttaaaccc cattgcttta 197760
aaaagcataa agatgaaagt cctataactt tcaggtgtaa tatagtatgg cgaacccttg 197820
tcatcaatct taataccggt atacgccata agaatttctt ttacagcaat atggggttct 197880
ttattttcca ttaatctcaa gaactgaaag aacaacataa atccagcatc tgaaaggcct 197940
atatgtttga catcatgggt atcgtatttt ggaaaatctc ttactgatat attgtttata 198000
ttttctaata tctcgcgtat caaagtcgga atagttttac ctttaagaat tctcgggaac 198060

-continued

```
acgcatatac gaataggtgt ttcttctgct ctcaatacat cgtttaacat agaacaatat 198120
gttatcccat ttttattata caaagcgaat agataacagg tagtccctag aaacatcata 198180
tctataaatt tcatattctt atactcatcg tacgacatac catcccagaa aagagatatt 198240
tctttaggaa cattacgatg tcttactaaa ctcttagata caatgttcaa taaattaatg 198300
atataaggtc tgttggacgt catatttaag atacgtattc ctaattgctg agcggttact 198360
gtaatattta agttgctatt atctggccta aatacaaact gatcaatata gtctaacgaa 198420
aataacttgt tatcttctat atactttatc tctttactaa aataaattga tacaacataa 198480
gacgctaaca tagaattatc aacacgtatt cgtactcctc ccaaatatat atcccttaac 198540
gtaaaaccag aaaaatgctg gaaatacata actagatact ttagtgtctg catcgttata 198600
agatccgtgt ctatattagg attttgtaca agtacaatgt tattagcgtt acaatgaaat 198660
tgtattttaa atatagcgtc gaatatagct ctagacatag gttctaatag cgctcttaca 198720
ttcaacagat tagctaaatc cttcttttcc ataataccat taatcaacaa tggtctgtaa 198780
gtagaataat cagctcttcc ctctatatat ggataagtaa gactatgtat gtaagaattt 198840
gcaaaactga tattaggatt tatttttggg gatagaatat taggcgacga aggatgttct 198900
acgtatccac cgaagtatct agcgtgagcc tcacaaccca tggttcttat ctgtatcaat 198960
atttttgtaa atggaggaag atcgttgaaa gatatagtac atggtatagg attcgtatac 199020
ccaccggtat ttttattcca cgtagatact atttctccgt tttctctgat atttatagga 199080
aaataaatac ctaaatcatt ttttctggaa agaatgtaat taatacccag tgtatctaac 199140
tgttgtgatc tttcaccgtc tgtaagtata ctaattaatt ctggactgta tatagtatct 199200
aacgcatgta cgtatccatt cgctagtttt ggatctattt tgtaatctag acataacgaa 199260
ggtaaaacac tagaaatcaa tttatagaga taatctgaag attctaactg atctagagtt 199320
acaatattct ttattaacat catttattat atgataataa atgactggat tgatggtaac 199380
agatataaca aatatagcca aagaatataa cttaacagcc ttttcagaag acgtatatcc 199440
gtgtaataaa aactatgaac ttactaacgg acagttatca gcactcaaga ctataaatgt 199500
tgtattaaca accaggtcag ataattatga gaaggatgta acttataatg acgacgatga 199560
tcatgatcgt tgcatagtat ctgaaatagg tagccatcat tcattcaacg atgaaaaaga 199620
taattatatt caaagtaaca atatacaaca gactccttct ttatcagctg tatttgatga 199680
taataaacgg gttcatttac tcgaacaaga aattgccgaa cttcgtaaaa agaaaactaa 199740
aagcaaaaac ttgttagatt ttacaaacac ccttttttaat aagaaccctc ttagaatcgg 199800
aattctcaat aaacgcgcta taatactaaa ctatgcatct atgaacaatt ctccgctgac 199860
gatggaagat ctcgaagctt gcgaagacga agagatagaa aatatgtata tttctataaa 199920
acaatatcac gaagttcata aaaaaaagtt aatcgttact aatatcattt ctattttgat 199980
ttctgtgata gaacaattat tggtaagaat tggatttgat gaaataaaag gattaagcaa 200040
agaagtaacg tctaccataa ttgatttaga aataggcgaa gattgtgaac aattggctac 200100
taaaatgggt gtagcaaata atccagttat caatatttcg ttatttatac taaaaatatt 200160
tattaggcgc ataaacatac tctaattatg ccatgccacc gtctattgaa ttatcattac 200220
tcatacgttt tttacgggaa gttctttttg ttctagtttt tctaccaccg ttaactatat 200280
caagatctat acccaaaaga tcttcattta cttcaccgac gtgtcccttt acctccagtt 200340
gaccatctcc cgtaattaca ccgtatacta tctttccaga attagtgaca gcttgaactt 200400
cttgttcgtt agaagccatt gctcctcctc tacgtctaga acatggtttt ctagtacttg 200460
```

-continued tagttcctgt acaacgggat gatttacgag gagcaccagc tgttacatct tttggcgttg 200520
ggctattgtt gctagcaggt ggcgtagatg gcaaggaacc ttcagaaaaa ttaggaggtg 200580
tatttgccgt aatagcatta atatgattta gcagcgactt taactgcggg ttaagtttgt 200640
gcatagcttc aacatattcg ttaaagctgc tatgttgttg agatcctctt tttcccgtca 200700
tttaaaatac agaaaatgag tattataatc attattttct ttgtacttat atgttatttt 200760
gctttgtttt tctatacatc atccggcgtg atattcggac ccgattataa acgctataaa 200820
gacggtgata taatagctga cagaattaat gaagagaaag ttaaaataaa aaagattgcg 200880
aaaaatatag acgttgttaa ccgtgaatta cttaaatact agaagtaacc aagcgatgaa 200940
gagcttttac ctgatcagga gtaagagttt gattgaataa agtatcgtcg ttcaaagtac 201000
tttttagtac cttatctctg tcatcaggag aaggtataca cttgtatctt ttatacgcag 201060
cgtatattaa caaacagaat attattactg ttaccgctgt aataacaaaa gtatctataa 201120
ttcccattta ttgataatta acttttgaca atatttataa tagtttaact agtaatcttt 201180
aaaaaatagt aatttactgt atttcagttc caggtgatgt agcgtatcta gattcatcta 201240
ctacgttgcc tgtacagtat ctgttatatc cagagaataa tataatacca agaagtagta 201300
atatcgctag tataaaagat ataatactaa tggatctcaa tgcgctatct gcaggtttcc 201360
ctgatttgct cagttctatg taagcacaga tacatgctac tattagcaat attataccga 201420
atactactac gtaagatggt ctgtttctga aaaagccgag aggatccatt tagatacctg 201480
aaaaactaca ataccgaata taaaaagtgg aatagaaacc acataaaaat cgcagaatgt 201540
ataaagaata taatactaaa ctttgctcta gtagacatac tgatattcat tatacacgat 201600
aatatgaata tagtgactat tataatgggt tcatagtttg aaatcattta tcataataag 201660
attatacgtt aaatagtaaa taaaaattac cgccccactt ataatttttt aaaaaattaa 201720
atactttaat tatatcatga ttgcgcggat taacaagata taggtttttg aaagatctaa 201780
aatacatatg tatgttatct atataagata tttgaacatt ttccttttta ctaggtatta 201840
aggaatatct agagcataca catataggtt tattatcatg tatagtaaac aactgaggtg 201900
ttatagaatt agtttctgga ataattaaaa ccaatgaatt attttcgata tacatttatt 201960
gtgttagaat ttattacttt agcatcatat atcctaagga aataaaataa cacgaataga 202020
cataagagaa ctatacatac cggtattata gaaaaaaatg aaggtaattt agcttcttta 202080
ttataagaat catctcctag tacagtatct tcagctatac ttcctccaca tttagctatc 202140
aattctgcta ctgaatttct tagtcttaaa gtatctacgt taatattaca tcctatatat 202200
ttacaattgg ttctttgaac atcttggtcg aaaagtaggt attttctatc ttttgattta 202260
tccgtacact cgtgtagcca gcatacttta ggaccaagag ctaactccaa actaaaaagc 202320
ttatcgtttt tgggtgttgt aacacaccaa caatttgggt tattcctgtg cttagaacag 202380
taagataata tagcggcgtc tgaatatcca aagttatcag gtctagtgta atctacaaaa 202440
tcagaacagt aattggcatc taaatgatca ctacaaactt tcatgtacgt atcaaaagct 202500
acttctcttt tcttctctag ccattctcta caaggtaaag acccgggagt ctgtaagcat 202560
atagatgaca taatggtatc acaatgatcc gtttcataat tattagaaaa tatttccgga 202620
cagtctttat cggattcttt attgcaacat cttttaatat caggatctgt atataagtag 202680
tctatattaa taaatctaca tctagttccg tctaaaacat aactttctgt accatagggt 202740
atcttttgta aatcaagaat agaacccggt ctaaacgata atgatttgca aggttctcct 202800

-continued

```
ggtactatta cgaatttttt tttagcttcg ggtgatagaa aagacgcaca ttgttttacc 202860
gtggtatctc tagttagaca aaaaggtggg gatatttcac taccgatatc acctgagtgt 202920
atgttttctg cttcgaaaaa tctaatatat tcatcatcat aaccaccagt atattctact 202980
cttaaatatt tagtttctgg tgcttgggga gtagctatta ccgttatgtt actgacgtgt 203040
tgacccattt attttatatc aaatcagtaa tttgaatgtg tctgaaacgc attaagattt 203100
tctaacgaag aaggcccact catctgcctg caatatctac gagaaggtat agatatttgc 203160
ctatctatac cgtatatttt tactatataa aatccaagaa ttacaagtag tactacatct 203220
atagcccttt taaatccttt agaaatctta gaagtactcg tcagataaat cgtaactgcg 203280
gacgccagca ttaagagtat agagattcct acgtgcgtgg catccgatcc attctttaag 203340
tgcaaagcta tacagtaagc tattattaat gccggtaccg gtacaaaaat cgcagaaaga 203400
ataataaata tcaatgccac caaagagttt gtattaatag cgaataccaa cataataagc 203460
gccaacaaag attttatatc attgttgtta attatattcg agtatagtcg ttctactcca 203520
tcaaatcctc cattaccgag tcctttcttt ggtaaaaacg ataattgttg ttcttctgtg 203580
aaaagttcct tttctttgat accagctccc gcgtcgaact cttcgaaaac attatagtaa 203640
tttaaataat tgttatccat ttatatagat aaaaatgtcg tatattacgg ttatagatga 203700
taaactatat tcttccttga ggaagttagt aggttattca cctttatact tgtttaacga 203760
taaaggcgat tttgttgaag taatgaagaa ttctgaattt agattcttga taccatcagg 203820
ttacttttca aatagtaacg taccgttata cggattgacg ttttcttatg gaagaaactg 203880
gatgaaagat agacaaaaaa ttattcttcc ggaattatat cccatacagc gtagagttat 203940
agaagaaatt atattacagt tttctagaaa gtgtaaagaa aaaaggcctt tgtatacaac 204000
gctgcattta gcgtgtgggt ttggaaaaac agtaaccgct agctatctaa taggtactca 204060
taaaaagaac gccgtagtta gtgtaccaaa taaacttata ttaaaacaat gggaaaactc 204120
aatatcatca ttaaaagtga gctactacgt atcttatgaa ggtgtttcta aacttttgaa 204180
agtactaact tctaaaagtt ttagtatatt agttgtagtt gataaacatt tttcgaataa 204240
agagttctgt gaattagtat acgaaaacta cgatgtcttt atactcgatg aagcccatat 204300
atataatctt atgaacgaat ctattatgac aagttttcta tgttactacc cccctagaat 204360
atgttacttt ctaacggcga ctcctagaca acaaaatgca gtttattgta actctataat 204420
aaactttata aagttttcac cgttacaaaa aatcctttac gtaataagag aattgtacaa 204480
tgaatataca aaccctagta tacgagcaca cgtatctcag ttacaaacaa ctgctaataa 204540
gtatcatctt tatacagaaa aggcattagc agaggatatt cataggaata aaactatagt 204600
agataagata atagaaacat ttaaaactaa tcaaggtaat agaatcttag ttataacaaa 204660
actacgcaat cacatgataa taatatataa tgatttaaga aaagtattat ccgataaggt 204720
ttacttaggt gatgcacaga aaaaatctac taccgacatg attaaagaat taaggacgat 204780
agataatttt atattagtat ctactttaca ttacgcgggt acaggattag atatcccaaa 204840
cttagatagc ctgttcatat gtaatactgt tatgaacagt atgcagagtg aacaagtaat 204900
gggtaggata tgtagagaca ctggttcaag tcctactaga tcaatatatt tatttattaa 204960
tacatcgata aaggaaataa aatcattggt aggtgtattt actcaacgtt ttgcacaaca 205020
ggctacaaag ttaggattta gagaggtctc tcaaatggca taatgaagat ccgcacgctt 205080
tacatcggat attgctatta gtgaatactt ttcctgtatt tagataatcg cttaatttat 205140
atttactaac cccagaaaac ataaccaact ttgactggca tatagaacac gttgtacatt 205200
```

-continued catcttctgg tataacggta ggcggttctt tacgtgtgga tgtagcggat gtagatcttt 205260
tcttcctctt cttagcacct gctgtagagt ctgccattta agagctataa aaataattct 205320
gtatacgctc tttcgcatat gttgcgatgt ttgataaatt tagaagcatc atcacaagta 205380
actgctatta atgaatttat attttttata tcattgcata tcgctggcat tttcgtattt 205440
ttatttacta aataatttgc ttttacacca aatggtgtaa agctataatt tatcaagtta 205500
tctcctatac accgaaattt gtttccgtat atttgcctgt acttagtaaa tgcctcatgt 205560
tctaatctta atttatctgc tattttagga actattatat taaaaatgag aataaaaataa 205620
caaactatta aaaataggac gaacatgtca aagtctaaag atctagataa actaagagaa 205680
ttattaaagt taaaaaagaa tatacattta ttgggtaaaa ataataccgt aagatacaac 205740
gaattgttag attggactac caaaagttat tggtctgtag gatctataca tatagaagaa 205800
catgtatgtg tcgacgaata ctatcagagt ataaaaaaata attcgtatct attacaggga 205860
aggtattatt ttttgcataa atatttcggt acaaaatatg tttatcttca tgaatctttt 205920
tacgaactgt cgggtggtac tacagaagca actattgaaa aaagcttaaa ggataaaatt 205980
aaactagtaa ctaataaata tcctgatata cgatttatac tattcgtaga atataaaaat 206040
acattcgcta tagaagatat agtatcaaaa gataactaca agctatacga tattttaaaa 206100
ttttctaagt cagtaggatt aaaagttaac ggctgtttgt cattacaaat agataaaaaa 206160
acacaattca ccaaagaata ttatgagtta attcatacaa atatcgaaaa gataaaagga 206220
ttttatataa acggtttaat atgtattaga gaagatacgt tagtaagaga ggtatctgat 206280
gcaaaatcta acgagttttg ttgtgttcaa tctataaaac tagaaaagat agatgataac 206340
ttgtggttac cgtacgcgat tacttttaat aaccaagtat taaaaatatc aggatttaag 206400
agtttagtta gagctagact ctatgtagga tcttttgtat ccgttataaa atatagaaac 206460
attttgttat tgccggatag tacggttccg gataaacaga ttccaaaaaa cgaatatatt 206520
agaaaaatct tagagtattt taataatgaa tatttttcaa taggtaacta tatggtaaaa 206580
actggaacta tagaaataaa caaaataggc aattcagtaa ctggtatatt attacccttc 206640
agtaattcag aggaattaaa acaaaaacta gaagacgttg agtttgtgaa taaactgaag 206700
tctagatcgt tattcgatct atcgtgtgat tatttcttac aggataggga aaaagtaata 206760
aagttaataa atgaaatgga ttttaaatta gacgataata ataaaatagt agaatttgat 206820
cttaattcag aatctgttat taaaggggat agaattttag aagacatata tatgaaattt 206880
caccagtttg ttattgtgtt taattcttta tcgacggcta agtctatgtt acccgataac 206940
caataatgat tatatgctcc gtagatatag gtattaaaaa tcccgcctat gccatattta 207000
attacgataa cactagtaat actattaaac taatagccat tgaaaaatct gattggacca 207060
agaactggga gcgtagtgta gcgagagatc ttactagata taatccagac gtggttatct 207120
tagagaaaca ggggttcaaa tctccaaact caaaaataat atattttatc aaaggttttt 207180
tttataatag taatacgaag gtgatcgtga gaaatcctac ttttaaaggg ggtagttaca 207240
gaaacagaaa aaaacaatct attgacgtat tttatacagaa aatttctgaa tatacagatt 207300
ataaaaatga tatattaaac aagtatacaa aattagacga tattgcagac agttttaatt 207360
taggattatc ttacatggaa tcattactaa aaaagtgtaa aataagtaaa gattgatagg 207420
agtaagatgt atgaattgtt ttcatacctt cacgaaatag aagatgaata tataaggaca 207480
atatttaact tccatattaa gaaatgtgac gaaatatcta atatatataa tataataatg 207540

-continued acaaaaataa aggatgcaaa aaactttaat gatgttatcg atgaaagatt taacaaaact 207600
atcaaaaaat taatttattg tgatataaaa acaacaaaac acatcataaa ccaatcatgt 207660
tatccgacaa agaacaaaca gataaaaaag ataagtaaga taaatcaata ctttgatata 207720
aatattatat cagatacacc tgcatctaaa cgcacaaagg aaatatttct ttctgataga 207780
tcgtctttgg tttcctatat taagactagc aacaaaaaat gtaagataga ttacggtgaa 207840
ttaaagaaaa cgataaattc tcataataga tctatatatt attctggaag aagatccgac 207900
gaatacatgt ctacagaagt tcataaagat caaaagaatc cgtggattaa atctatctcc 207960
aagaaactga ctcttgatat agaaaatcaa tctattacaa ctagaggaaa aagttctata 208020
ttgcagacga ttgaaataat ttatgttaat cgtacgtgca taaaaatatt taaagattct 208080
actattcatg ttattctatc aaaggataag tcagaaacaa attgtgtaga tacaataaat 208140
aaactatttg atacatatag catactcttc gatcttataa cagatattac aggtaatgaa 208200
aaatttttag aatataaagc ggttgcctct gatatagtat ctacagataa ctttaatgaa 208260
aaaattctaa ttataaaaaa acatcctaat atgtatggta tacataattt taaaataggt 208320
atgtttaata ttacgtacaa gttatctata gatatgatta tatttccttc attaatggaa 208380
ttcaacagta aaattaaatt ctttaaaggt aaaaaactaa atatagtcgc gttaagttca 208440
ttgcaagatt gcattaaata cgttaaagag gcaaaaggaa tattgtgtat gatgaaaaaa 208500
aaatctgaag aattagaaga aatagatata attacagcat ccgtggatag actaaaaaac 208560
gtaattataa atatctaaaa tagaaaaatt aatacatatc taaaatggat cagaaactag 208620
gaaacaagtt tttggaacct gatcctaagc agaatgtttt ttataggccg ctacatttcc 208680
aatatgtctc ctatgaaaat ttcatttctt acagacttaa agaaattttg tctgtgaata 208740
gaacgttgtt atcttttaag aatgatacag aaaagatagt tctaagaatt aataatatta 208800
aaattatacc tcctgattac tctcctatta ttgcaagcat taaaggaaaa agttacgacg 208860
ccttagtgac ttttacggta gatattagaa aagaggtaat gactaaagat ggactccatg 208920
taagcacgat tagtagctac gaaggaaatg attcccagtt gataaagata cctcttctta 208980
taggttacgg aaataaaaac cctcttgata attctaaatt tgtatctcct aatattatag 209040
gaggagtctt tattaataag caatctatcg agaaagtagg tattaatata gtagagaaaa 209100
caactacttg gccgaaattt aaaattgtta aacccaatgc ttatactttt tccttttcat 209160
ctatttcacc cgttaatata ttacctacaa agtatagaca ttataaaatt acaatggatt 209220
tatcacagtt agaaaactgt tctatatcct cggcgaagac tttcattacc gttaacgtta 209280
tcgttcttat taaattcttg attaatcagg acttgaatta tatcaagaat aacttgactt 209340
atggcatgcc cttggaaacg atttatctta ttaacgctat tatagaaagt tctaaaacaa 209400
tattagaagc agaagatttc aacatcaatg attatataga gagtttaata gaatcagaat 209460
ttcagaaaca acgctctata acgtctatag acgattttag atacgatctt atgtataatt 209520
ttttaccaca tatggtcaat agttctgatc agctaaaagg attctatcta ttaggattat 209580
taagaaaatt catatattgt atctatcata ctagtaggta tccagacaga gattctatgg 209640
tatgtcacag agtattaaca tacgggaggt attttgaaat actggccaat gatgaattag 209700
aaaattatat aactaatatt aaaaatgata taactaacag tcacaaaaac aaaggcgtct 209760
gcaacgttag tatccatgta cttactactc ctggattcaa ccatgcgttc tcgggacttc 209820
taagtggaaa gtttaaaaag acggatggga gttatagaac tcatcctcat tattcttgga 209880
tgcagaatat atccattcca aggagtgtag gttattatcc ggaccaggta aaaatatcaa 209940

-continued aaatgttttc tgtaagaaaa taccatccga gccaatatgc tttcttctgt ccttccgacg 210000
tacctgaaag aggtccccaa gtaggtctta tttcacaact ctctgttcta acatccgttt 210060
ctaatatcag aacaacagag tatatagatc tgaagaatgc tattatgaaa tatatatata 210120
cttacgataa aaacgatatt agttattttc aaacaggaca tattattacc atagagaatg 210180
acttagtcgc ggctattaat ccggaattag tagataaatt tgtagatgat tttaaattca 210240
gaaaacgagt aaactatttt gataacctag aaataggtat ttcaaacgtt aaagatcaca 210300
tgaatgaaat acgtattaac ataggaagcg gtagattgat acgacctttc ctcgtggttt 210360
ataaaggaga attagtgatg gataccatag gtgaagaatt agaaaagcgt atagatacta 210420
ttacgttctc agacatccaa aaagagtatc cacacgttat agaaatgttg gatctggaac 210480
agtttgtttt tagcaacgta tgtgaatccg ttagtaagtt cagagaatta agcgatgaag 210540
ataaaaaact atacgattat tgtgattttc caaacgagtt tagagacgga tacgtagcat 210600
ctacattagt aggtattaat cataattctg gacctagagc catattgggc tgcgcgcaag 210660
ccaaacaagc catatcttgt ttgagttcag atcttagaaa taaaatagac aacggaatac 210720
acctgctata tccggaacgc cctattgtat taagtaaggc cactgaaaca tccaaaatag 210780
ctattaattg cttcggacag cacgtcttag ttgctctcat gtcctataaa ggaatgaatc 210840
aagaagatgg tatagtagtc aagagagaat ttatagaacg cggtggactg gatattgtaa 210900
cggctaaaaa acatcaagta gaaattccta tagaaaattt taaaaataga gaacgtataa 210960
actctaccgc ttattcaaaa ctcgatatca acgggttagt gagattgaat gcattcttag 211020
aacccggaga tgccatcgct aaaaacattt catctagaac gctagacgat gatttcgtgg 211080
cagataatca aattagtttt gacatatctg aaaagtacac cgatatgtat atgtctagag 211140
tagaacgagt acaagtagat ttaacagaca aagtaaaagt aagagttcta accatgaaag 211200
aaaggcgtcc tattatggga gataaattca ctagtagaac tagccaaaaa ggtaccattg 211260
cctatatagc ctcagaatct gaactacctt atgataagaa tggagtaaca ccggatataa 211320
tcataaactc tacatcaata tattctagaa aaactatctc gatgttgata gagatgattc 211380
tgacatcagc ttattctgta aaaccgtata ataataacgg taaaaaccgt cctatatgtt 211440
ttcctagtag caacgaaaca gatatcgaat actacattga atttgctaga aaatgttacc 211500
agtctgctat acctgatcta gataaagatg aattggaaaa cgaagtatat tgcgaaagta 211560
ttttatacga tccagaaact gataaaccat ataaaacaaa agtgtttatg ggacctctct 211620
actatcttag gcttagacat cttactcaag acaaagctac tgttagatgc cgtggtaaga 211680
aaactaaact tattcgtcaa gctaatgaag gtagaaagag aggaggtggt atcaaatttg 211740
gtgagatgga aagagattgt cttatcgctc atggggctgc aaatacgatt acagaaatcc 211800
ttaaagattc tgaagaggat taccaagatg tttatgtctg tgaaaactgt ggcgatatag 211860
ctactaaaaa gaacaataat gtttattgta ttagatgtac caaattaaat ttgtatacag 211920
ttctgacaaa aattgatact actcatgtat ctaaagtgtt ccttacccaa atgaatgcta 211980
gaggaataaa aatcaattta acttttaacg aacaaaatcc tttattctat aaaccgatga 212040
agcaaatcga tctctcacca acaatattaa aaccatgatc tgtcataatc acgatcggat 212100
tgattatcta gtttcttcgg taattctata gcgtgtttac gcaagtgatc ataatcttcc 212160
tcaagtcgtt ccatttttga tttaattttg cgataactat ctccgaagct atcagcttct 212220
aatttacgca ttgctctatc gacatcatta agtctatctt catcagactt gtctttttct 212280

-continued ctgggatatt ctctatcttt atccggatga ggcctgtata catctttttc aacgcccaag 212340
ttgcgatgcc ctctcgtaat aatacctatc ttcgtctttt agaagatacc cattcctacg 212400
atttctcaaa gacttgggtg tataatcatc gttatgtatg gcatccatca tttcatcttc 212460
gaagtctttg gcactttcaa gattgttggc tctcttagga acaatgtgtt catcatctga 212520
attaccacga tcatcatatt ttttgtgttt ataattatag tcatcgtaga tatcgtattt 212580
gtttctacga tgatggcgtt tattatatac atcttccata ctattatgcc tccttagtat 212640
aggagcttca tccttgatag atcatcttcg ttgttattat tataatcgtc gtagtcttct 212700
tctcgaggaa actcgtcctc attacgattt agggtaccgt ttgtactagg acagttcttt 212760
ctacgatcac attcaaaatt gtctatataa tattcttgat aatctttagg cctacgttct 212820
ctatcgttac tataatcata ggaaggatat ttatcatcat ctagatacca tttccatctt 212880
ctacaatcat cagggaaaaa tagcatatgt ctattttgat agaaatcgtt atctttgtcc 212940
ttgaagatac gaatagcgct acaatcgtga atacaattag gactaaaaga catctttgta 213000
gtcggaaatt cgtcggtcaa tctaatatat tcataactat caccaatatg gcatttagta 213060
tatagctgta caaaatcata atgattcttc ttaatggtaa cttcatcggt aaaacaataa 213120
catagaccat ccatgacctg ttcggaaatg gaatagtcag tctcaaaagg aataccacag 213180
agagatatct ttagcccttt agtctttgct tttttggatg ccataatgaa gttaagaaaa 213240
tcttggtatg cgcacatttc ctttatatgg atagtagtat ttctttcgta ttcttcagga 213300
ccagtacgcg gctttctgcc taccgattcc atagccgtga taatatcgtc tggtgacata 213360
agatgaatat agtaaacggg taaccctata aacatgcatt tgcatttaaa tctataatgg 213420
acgctagaca ctaatcttag ataatctgta acgatactag aaactttttt agatactgta 213480
cgtccggaat ctgaatagct aaatttggta tcattatttc ccatgtacag tagatacatt 213540
acgaaataaa gcacatatct acctttggta gaaatatcag gcatacgatc gttagacata 213600
tcgattttat tatatagttt tttgatgcca ttattattat attttataaa ttctcctagg 213660
aaataatttt ctaagttttt aggatacaac agttgtgctt gtactccatg gatacggtca 213720
ttatcacaac tataatgaat aaaacaccta aagatgttac gaacgacttt tctatccctt 213780
ctagttagga aacttctttc gttcaaatca tgatcccaag ttcttacaat tagagtttcg 213840
aacttcctta tgcacttttc gataccacat ttgtcccaac ccatttatat attgaaataa 213900
ttatggaata taatgtaaat tattccatgt atagatggcc atatcctgtc tggtaatcta 213960
tcttcttagc gagatttacc atagagtgtc tcagagtatc agcgtggcgt tctagacggt 214020
ctatagcttc cgctaagatg ctgcaggatt tagctacttc tacgtgatct tgttctattc 214080
tacccaacct tctttctagt cttctgagtg ctttttgttt aagggagccc aaatcacccc 214140
gctttttatt ttcatcgtat atatcaacct tcccattttc aggaatattt ttatctattc 214200
tatcatcatc atcatcatcg tcatcatcat cgtcatcaat cggatcttca tctataagta 214260
agccatcaga agctttaccg tcctcgggag gaacaagatc atctgaatct aatttaacac 214320
caccagcgga tttaacttcg cctattgtat agaatggatg ttcgtaagta gttatcagat 214380
cgtctggcct attaccttct tcttcaggat ttccgataga aatagcaaat gtatcaaatt 214440
tcacgcttac tggggatggg aacttaactt ggggagttct cgtattaacc tcatgatata 214500
catatttttt gctgtctggc aagaatctta gatagaatct taccttatca ttcgtttccg 214560
tggctattag atcgtcgtgc ctataacaca atcctttcaa tacgtattcc ggtacagaat 214620
tattaaaata ccaagtacta gcggtagtag ccaacataac aactttccta ttaccgggat 214680

-continued ttataacatt atttttgaga tattctatat attttttatg cataatcata tacggtctcg 214740
agaacatgtt actaccccat tctagaattt ctccaaaagc cgaatcatct ggaaacagat 214800
aacacggaat acctataaac atagatttac atctgaatct catatggata ctagcgattc 214860
tattaaagta gcgatgtctt atacggcgta tagtttcgta aattttatcc gtttcgtctt 214920
gcgttaagct gatacgttct ttggcggtgg ttataaaaaa cattactata aaagcaatat 214980
acttgcctac tgtgtctacc gagttaaaac tatgaatttg ttgcaacatt tctgcgaact 215040
ctccgtgatt gtatgacatt agactagtat aggctcttcc tttaatcaac gtttcataat 215100
tgagtatttt gccataaaat tcgtaaactg atatatgatc tttgaaactc tccatatgat 215160
aacgtattat atttcttata cagtttgcat agtaatagtt gatatacgta tcttgcctta 215220
attgcgtatt ccatgattct tttactatac tcacgaataa tgtaactgga tcgttagtgg 215280
atacgggttt aggtattact acatcatctt cttcttcacc ggctccagga acaacatcca 215340
tttatagatg tgattttaaa gtgctgcact ctgcagaccc ttctccgtat tcagcacaag 215400
gattccatat ggtacctatt tctcctcgag tataattata gtacacacaa tcttccaggt 215460
tagtaaaaag tacaggattt ctacttgatg tagctaaata tccaaatttt gatgcagatg 215520
cgtattggtt attattataa ttcacgcatc tccatttagc tttaggatcg gtttccgagt 215580
cattaggatc aaataccctt ttgtcgatgt ataaacctcc aggagatcta gaatattcta 215640
acccgccata tttttcatta aattctatta tgttatgata gttatcgtat atggtatagg 215700
cttgaaaaag aaaaagacaa attaccgcgg ttgctaatat aattatgaat acgaagagag 215760
catccattga tttataccaa attaattaat agctttatat atttcactta tagttttgtt 215820
aacagctttg tgaaaagttt tcgtgttaat ggatgaaata ttgaacttat gatacgtacc 215880
taattggcat tcacatccga agaagttaat aatgcacata gtcgttatat cgttaacaaa 215940
tacgatgtta gacttaggat cgtacgctga tgatgttggt gtatcttttt ccatatctag 216000
ttttgttata ttaaattccg ctatttgatc cgatataact tcttttagat aagataacat 216060
gcttttaaag tatacagaag aattaaacca cgtatatttt tccatgaata tacttatatt 216120
accttcgggt gcaataatgc taaaaggaaa atatgtttca taattttgtg agtgaattat 216180
tttaacgttt ttatattctc tattaaataa ttcggtatct aaaaatgata atctgtttac 216240
taactcgtca ttaattttag ttccgctact aaaagcggct aattctatag ttttagtatt 216300
tgttgctcta tattcggaga atgaatgtaa taacgtttct tttaattctt ttatgggatc 216360
taattttatt acctcttctg gtttgataat atagtagtct atatctgcca aagaaatata 216420
actgtcgttt tctttctgtg ttttcttcaa gtgaatacaa aagttacatt gcatagcaat 216480
aatatcgtat acataatcat aaaatatttt atgcgttggt aacgattcta tggatgttag 216540
ccattcttcg ttaatagcgg tagtagtatt tatcataaca actcctacgt tgagtctagg 216600
aattactaga tgcttcttac acatatgctt tataaaggtc gcaatactgg gattagcgct 216660
aacatcaata cgatactctt gacgatgcat tgttcatgct attaatattt ctattgttct 216720
ttttatattt tttatctatt tctattatcc tagaatttat tattttaaga acttcttgca 216780
ttaatgagat agtagcagag aattcaggat ctctaacatt tgctaaagtt gacagcatgt 216840
ggtttatact gtcttcattt atatcatcta tataatctat atcatccatt cctactatta 216900
aactagtata taaaaaggga aaaaaaaata aaaagtgttt aatcacaact tctgatagat 216960
tgccgagtat ttatatactg tttttaatat tcgtgatata gtagatatat atataagttt 217020

-continued agtgtatata gttaatagat ttacaatctg ataatacatt taataaagat ggaaatcttt 217080
gaactaatat ccgaaaacga aaagtatttt aatggaatac ccataatatt accaaagaag 217140
aaaaaaacat acgtttacaa aaatattaca tttatatttt atataccttc tgataacaag 217200
atagaacaat atatacaacg aagtgaatta cactattcag attttatagt ttatggaaag 217260
gttataatag acgatgttga aatgcttctt ctttatgtaa actttgaata ttatggtata 217320
tctatagatg gtaaaacaaa atacttagga aaaagtataa aagacctaaa gataagagga 217380
actaagcggt ggaaagactt tactcattaa atggatatac taacgatcat gaaaagaatt 217440
aaaagcggta aagatattac tccttccatg gttactaggt tcgtagaatt ggtaggtaat 217500
aaagaattat tttatgatcc actaccgata aaactgagtt ctagcactct aacaggaaga 217560
aatattaatt attcagaaga acacgttaaa agtatgatcg tcattatcta tggttattta 217620
cccagtataa taaagaaaaa gatttttgtt aacaagataa gtaaattatt atctatacct 217680
cccgacgatg cattaaaaag aatatttggg gacacatcag aaataggtgt taatacattt 217740
attaagaaat tccttgctga gttaacaagc taattcttgt aaagattctt gcttagaata 217800
gcttttaagt agtttcatat tactagacgc ttctttttcg ggtgaatata tacaatcttt 217860
tttatcacga tcatcattta tagaatttag attactaaga tctttaaaat aatctgtatc 217920
cttgttatca tcgcttaata tggtatgaag ctgatctttc atatgagaga attggcttaa 217980
caatatagcg gtatcaggtt tttgttcgat aacggattta tctgctgtat catagcatat 218040
acgtatatcc ttatttgcaa atacagtatt ttctataata tagacctttt tacctctaga 218100
tgcagcacgc atgacagata gtgcttttat tatctgctta gtagcgacca gtgacataga 218160
cctagtaata ttttcgatat cggcatcaga tacattgcaa caacatagat gtgtaatgct 218220
tgatctacaa ttagacggta cgtgtctata tgtttgacat aacataacaa tagacatcct 218280
tatgtgtcta cccgtgttta ccaaccaaga taatatctta gattttaact gcatatcacc 218340
taaatcatct aatattacca aaaatttgtg attaatagaa ccgcgttttc caagatttac 218400
taaatcttgt ttcatttttg atagtgaata ttctaactcc tcggcagtag ttattttata 218460
tatatggtcg ggccatacat aataattata cgatggattg agtataggag taaacaagaa 218520
aatatgttta tatttcgtta taaatgtttt aaataaagat aggagaaatg ttgttttacc 218580
tgatccgcta cctcctaata taaccattct aaaataatca ttcaacaagc tattcctatt 218640
aaacttaact tcccttacga tatccattta agttgtttgt gatatttata tatctccgaa 218700
attgattata actatagtgc ttcagtatga aagattattt gtattaaaat atatatatgg 218760
aataaaatgt atctatatat ctatttcgat atctatgtcg tgtaataggt tatttattaa 218820
cgacatatgt cttagtgttt acgtatctta aatatgaata gacaaagcag tgagaaacta 218880
aaaaaaacat gcgcttggtt tatacattta atagcttcaa tgtgcggaac tggattattg 218940
ggactatttg ttacaaacgt tacgttatac agacagataa aaatatgtgg gaatagagaa 219000
ggcatgtcag gatgggtaca gattaataac aactgctata ctatggtaga aaatataaca 219060
tttgatgaac ttatagggca ttgtacaaaa cacgattcaa taattcccaa tgctttagac 219120
caaagcgaag tattaatcgt ttcttctgta ttgggtgtta aagaccattg gatgccgttt 219180
accaagaaaa gtagaaactg gtttcacgga aagttacctg tgaacattaa aggagatggt 219240
gataaacgtg aagagttagg aaaacctaga aaacctgata aatcagaaaa atgtactata 219300
tactatgata acggtatcat agaagaaaac tgtaacaaaa agcatacggg aatttgcttt 219360
agtccatttt tctaaaaagt tataattggt aattttttaa aataaatata tttacaataa 219420

-continued atatacaaga tgcatatcag tagcttttac atattatcta ttatttgttg tactagtagc 219480
gctaatatca tagcagatat cggatcttct gtagtagtag attgcaaaat acccaacaat 219540
tatagcgtag ataccgttat attaaagcaa acttccagcg gtaagacaaa taaaataacc 219600
gtacctaacg aatacataac tggaaataca tgcaatacgg gatatagaac atacggattt 219660
actattaata atgtgactaa aaatgatgaa ggtagatata gatgtagttt ttatctaagt 219720
agcgtacaga tatacgaaac aaaactgact atgtatgtta ttcctgctat cgacgcgtat 219780
actctagatg ctagggataa taaaatgatg tacgcgtgta atagatcaag atctcgatta 219840
tatgatgacg atattaacat ggatattata ataggaggag tatatatatc tggtgaagaa 219900
aatgtacata cttttgatac ggatcacagt ttacatatat atacatttgg agataagaat 219960
tatcctgata tatcaaaaca aatgacatgt ttactaacgt ttaaaggagt aaaaaaaact 220020
aaacgtataa cgatttacga ctactcgtgg gaatctctaa taaatgataa tgaaatatac 220080
gtcgtctaaa ttcatatttt ctcttcttaa aatacactat aacatgaaat tcataattat 220140
actattatct attttacaat acgtctattc taaagacgat tattacgatg tggtatctca 220200
cgtaggagat tccgtaatcc taaattgtaa tgattatcca aatactagta atgtagattc 220260
ggttatttgg tttaaatatt ctgatcctgt taataaatac ttaagtatat ctactattaa 220320
cggaacacaa tactataaaa acgatcacaa gatatttaca agaacatcag tagacctaaa 220380
attaagttct ttaactatta ctagcgcatc tatagaaaat catggatgtt acggttgtaa 220440
atttaaatca ggaatttgta atagggaacg taagacgtgt ctaggtatac tagattcagt 220500
gtacctttcg tggatatctt tcatgtatac tactagggta agatgttata tagtatctgc 220560
aaaaaaagat ttgagcatta actggatggt aaacggtgtt attactgaag ggatgtcatt 220620
taatgaaatt agttatgacg atagttattt gtccgggtgt tttatgatag agttaaagat 220680
aattaatagc tttagtgata aggtaatttc tcctatatgt agggttaatt tcggctctaa 220740
aggatacaaa gaatatagaa taaatctaac aaatacactt cctgatacct tatacgataa 220800
atattctaat cctataagat attataatcc atcgaattca cgtattacaa aaatgaaata 220860
ataaaactag tttgtaatgt gatggcaacg gttgctagaa tgtataaaac tataaatacc 220920
accggtatat catgcgtctt gaaaagtttg ataccagata gctataatga agaatacaac 220980
atagatgacc tagatctatt aaagataaaa gagtttatag agatatccat gcaaagatgc 221040
ttttctataa aatccgtcac agattccaca gtattataca tagagaacag gactaacaga 221100
tattctatat ctactagtca cgataagaat gaaccgtatg aagaaaatgg tattataatg 221160
aacaatatag agtgttattt tgttgcgtgt ctagaaggat cgtgtacagt aaatgtaaat 221220
cttggagaca gacaaatatc agacaatata tctgaatcat caggattcct aatggatgta 221280
aacaccgatc acgttataga tacaaaatat gtaggattat ttattacaaa aatcaaagta 221340
gatgcgcatg tattttacgg gcaaaatgtg ataatgtttc cagaaaaaaa cttgttttct 221400
caaactaatg gtcctaattt cattttatat gatataacag ttcaagatcg taatgtactt 221460
ttgcttataa cgagcaagta tatttacaat ttgtgcgacg ataaatacta cgatattttc 221520
gaattaaaat atctagttga taactgtaaa ctacctatgc ctcttattcc actatcgaag 221580
tacgatttta catttactga tttgagtgtt atcaaatcag agaatgttaa aacggtactc 221640
tctaaagttc atacgagtat gaaatcgtac tacaacaatg atacgtctct tcctgtcgcc 221700
gttaaggtga tttacggaac agtaacaata taaaaagtgt ggagggagct ccggggggaa 221760

-continued tagcgctggc tcgctaactg ccatattagc ttctgtaatc atgcttgctt gccttagccg 221820
ccattgtact tgatatattt cgctgatatc atttctcgga atcggcatca agagcaggct 221880
cataaaccat aaaaggaaat gtttgttgaa ggcaagcatc agaccacttg cacactaggt 221940
ggggcagcag gggtccggac tgaatcgtcg tagttcggta caacagtatt attgtataat 222000
attatatttt gtaatatata aaaaaataga aaataaataa tatattattt ttataatgga 222060
tattataact aatacaacta tgtttgatat acaatttaac gatataccga atatacccta 222120
tgtagatata gaaaagccct tattggtata ttcgtgtgat tcttataggt tatataacgc 222180
taaatatgac aacaatcccg tcagtttgaa gacttttaca tgcccatcta aaaatagtat 222240
aagacagttc ataaaagaac tagatctgtt acgttctcta caatcttctg aacacgttat 222300
taaactttac gggtacatat tggatatatc cgttccttta tgtagcctgg tggttgaaaa 222360
taactacctt acgttaagaa actttttaga tatggaaaaa gatatagatt acgccaagaa 222420
aacaagaatt atcatagatg ccgcaaaagg tctaaatgct atgcatacta gctactcgac 222480
tcccatacta cataaaaatt taaccagtga atctttttac atgactaata atggtgtttt 222540
aaaaataggt agcggggcat attataatat atacaaaaga gtaaatttta tggcatattt 222600
tgattatgac atgttaaaag atatcttttc aaattatact ataaaatccg aaatttatag 222660
attcggtatt gttatatggg aaattattac ccgtaaaata ccttttgaaa atatggacta 222720
ccaaggaata tacaaatatgc taataaagga aaataaaggc gaatatatgc ctctagactg 222780
tcctctggaa ttacagtgta ttgttatcgc gtgtagaaat acaaattcta tatttagacc 222840
ttctataagt gcaataattg attttctgga aacttttat tctaatataa ttaaaaacag 222900
aaacttaaaa tagactaagt agagtatata cacatattac acggtaacat gtttgctatt 222960
tcagtgttaa aggaattata tgattccgga gagcctttat tattttcacc tagagggcta 223020
cataaaatat tatgtaatat caggcacggg tgcaacggaa atactaaaaa tcaattagat 223080
aatttattag aagaaaccat atatgattac ggagaagacc aggcgcttaa acatataata 223140
actaacattt ctgttctact aataaaaaga tgttataata taaacgagaa atttattaaa 223200
gatagtaata cgatatataa taccgatgta ttagaatttt ataatgtaag acaaatacct 223260
agaataatga ataaatggat tagatcaaga tctaataata aaataacaga tataggatgt 223320
catatctacg ataatactaa gtctataata gccgaagcaa tgtttttttac tatgaaacac 223380
gaatctatat tcggttcaac aagaaaagat actataacct tctataagta cgatggaact 223440
tcgttacccg tagaagctat tcacgcggat ccatactact atccttatag atattttgat 223500
gatataaagt gtagcgtatt gcaattatgg aaactaggat acgcttttaa catgtttatt 223560
atattaccag atgatgaaaa aggtttagat aacttagtag ataatattac tggagatgta 223620
ttcagtaaaa tcatgaccga acaaatggat tataagagat tagaattacg gatgccagta 223680
tttagtatta gtcaagagac taacttttgt atgcctatat ttaatctggg atgccatagc 223740
atgtttatag acggagattt tagtggaata tctgaagtgt cagatttcca actttcaggc 223800
ataattcaga aaaatatcat agaagtacag tatgacaagg ttaaaacaac taaaccttta 223860
aatgtaagat gttcaagctt ttatgttaat aaaccttta tatttatagt tactgatgta 223920
ggcaattacg atactatccc tatactgtta ggtatatacc agggaagtag taaatagttt 223980
taattatcgt ctgattcgta ttcgctttcg tctatatggg taattaaggg ttctctatct 224040
ggatgaacgt taatcaatat aaacttttct gaattactaa tagtttttat tttttattg 224100
atatatttgt gtttgtatga aatataacat actattataa ttattataac aacacatata 224160

-continued ctacttaaaa ctagcgtata tagctgataa ttattcaaga aatgtactaa cacaatgttt 224220
gttgtattgt tgtaaagttc cgtagagtta tagttatcgc gtcttgttat atagctatcg 224280
tctacgaata tactttctat aacagaaccc atacatttct tctttattcc tatggataca 224340
tggtatacat cacccgtact ccatcttttc agtgtaattt tgtctaacgt taggttagat 224400
aagtagttag gttcttttat gtgataagag tcgggaaaaa ccattatacc taaggtttta 224460
taaatctgac ttttaggttc cttcttttct acatacatcc atttaacgca ttttatagaa 224520
gtagacgggc ataatattat attagcctct gactgttcta tagatacgct tcttttacac 224580
ggatatacat gaacaacgtt agataaaatt actaatatcc taataacacg attcatgttt 224640
aaatatatag tgatttatag tatattataa tattattata taagaaaatg taatataaat 224700
aatatacatg atacataaaa ttgaaattta attaagacta gcttacaaag atgaatttca 224760
caggtgattg tcttttatac gcaggatatg aaaaattttc actatctttg gccgttgtta 224820
ctatactcat attttcttca agcttgatat taaatatatc ggcattagtg attggatttt 224880
atactacagc gcctgggcct atgaagatgt atcttattaa cttgatagtc tctgatatac 224940
tattcacagt aactttgcct cttaaaatag attattacta ctatttcttc aattggagat 225000
ggggagaaat ggcgtgtaga ataatgtcat tcttgtctta catcaataca tacgtaagta 225060
tcaatttcat gacgtggatc agcgtaaaca ggtactacgc ggtaactagg ccccataagt 225120
acaattcgcg tgacaatatc atgagaacaa agattgcatg cgcgtgcact tgggtgatta 225180
tattagtccc tatgtcatcc atacttttcg ttagtacaac gagttcggat cacgaaacta 225240
agattagatg tatggaatac aataaagtag gagattctat gtatttacct ccgtgggtaa 225300
ctatcgttat gtgctttata ggatttgtaa taccgtttgc tatgatggct ataagctatt 225360
cagctgtatg ttataccgtg ttatctggta tatctaaatc tactagatct tatagaacct 225420
gtaaactggt agcttgtata ctaacagaat ttgtcatttg ttttttacct tatcacgcat 225480
ctgttatatc ttatatgatt catataataa cttcaaaaac agtattatgt gaaaatgtat 225540
cttactacca aatgttacta catgccacac agtgtttgat gaagctgaat tgttgtatgg 225600
atcctataat atacttattt gtatctagtt ataaatctaa agctaaaagt aattctataa 225660
aattgatgtt taagtagatt tttgaaatga tatctttacc atcatcctgt caaaatatta 225720
tcaacactgt cataaacgga aagtgcttct ttggtagatg ttctaataaa cgattaaaaa 225780
tgactgttcc tatgacgtct tcggaactag cctacataca agaatggatg ttagaaaaac 225840
atgatttatt tatagaattt ccaatagatt tgattaccgt ggaacatata atgatgcatt 225900
tggctgttga cgttactatt attaaaagaa aaaaaaagtg atattactgc gtatagaact 225960
cgattgaaag atgtacccga agccgagtaa tctattctta atgtttattt caatataaat 226020
tactattctg gcgatacatc aggattttat gtaccctgtt tttatatctc tatttatagc 226080
ataacactat aaatgaggat cccaagtact tacttaatga aatgtagatg gtaaagtggt 226140
tgtttttagt agatccctcg aataaaagaa gttatagaag tgacaaactt aacggattcg 226200
gccccatttg tatatctgtc actaactgga aactgataca catattattt ctagacaaga 226260
tcctttatcg tcgatgctgt taggttctgt taaaacgtaa cagtttacaa gcaatgtgtt 226320
aaagaaaata agccgttggg atataacaat agctctaaat tcttgggtac agacaatcat 226380
cttgttatgt aatgtagtac ttataaagac gtaggaaact atggtataac atctttaaag 226440
gtatactctg gttgtagtta agtggtaaaa gaaaaatatc aagtaataga gctaatatta 226500

-continued tagggaataa acaataacta gagaaattta catatagtta tttttgattc ttataataat 226560
ctaaatactt gattataact tccagacata gttccattta ttgtatattc tagtttatgc 226620
tttctatcat cctgtatcaa caccttattt gtacattcaa aactattatt ggttttagat 226680
ataatcaaat atcttatata tttgtttaac ctatattttt attgtagttt tcatctagat 226740
attttaagag tcatggtgtt tatttttaat acatattata atataatgaa atatataact 226800
taacacatga aagaccgcaa taaaaaacta aaaagtttac ttctttagaa aatatgatat 226860
aacctattcc aattaatgaa aaggagtatc aaaagtcctg atttcataat atggataaac 226920
ggacaaagaa atatagttaa tacgcttaga ttcgaggaac caaatgtatg tataaaaaat 226980
actttacagc ttgtttcttc aagattttat aaaaatatca gataccgcac gatgggggaga 227040 tgttttaccc aaatatttac atattcaaat cttccatgaa tgaaataact cttacagaaa 227100
gaattattat ataaccgtag ttctgttcta cggaattaac aactcgtgaa tataaagata 227160
caacattcag tataagaaaa taagaagcac agttatatca ttgcgtagca acaggcaagt 227220
agtaatgtaa tacagatttt ggttgcttac ttgcagttcc tttctaaagg ttattacagt 227280
tacaccggaa tactaaaatt agaatagacg attcatatta cacacctgtt tgtagattta 227340
caatttaaac ataatacttt agttttttgt attttctaat cactaaactt ctaatttctt 227400
ttggattcat agtttttata ggcattatct taatcataaa tatattatcg atattatacg 227460
aattaaatcc gtgtacgtaa tctacttctc taatataaca ttcaaaaatg taactttttc 227520
cagacgaata agtacctact tggaatcgtt gatctgggct acaaaaccta tgctttgtaa 227580
ttctatgaaa ttctgaaaat acacgtttta aatcctcctt ttcgtttata aaaaacgttt 227640
ttatagtgtc gagtcctctg tgtttccaga agaactcctc tttcgaaata ttttctgata 227700
gaaatctacc cgtgatatca tctttggtag acgccatgat attaccgcta tttactttaa 227760
acgtatatat ttaatttcat tttaaacata tattcataga tatgtaatgt aatggtatac 227820
agacaataat ataaatattt caaaacctct tttactaata atatatcatc atattttatt 227880
agaatctaaa gttattcgtt ggtctaagta ttctagaaat ataattaata taaaaaccat 227940
aggtaggtat tgtgggatac tctagttgta attgtaacaa taataggcgt aaagaatcac 228000
attcgttcct aaagataaca ccctatataa aacctgtaat gaattattat atgaacataa 228060
gatgattatc ttgaggatgt gagggagttg tagtaagtag tttctttcta gaaagagata 228120
tacatccttt taaaaaaatg tatatataca ccagtaatta tttcaaaaga tatattaatc 228180
actatacact aattcaaata ttacacatac tacggtaatc aatagtcata ggagacgtgt 228240
atgtatacac taaataaatc gaaaaataca ataaaagaat ataaaatgtc accatcggtt 228300
tacattgata tgttatatct aaaaatacat ttaaactata ataatacaac aacacaaagt 228360
actcttaaaa atatacaaga tgaaagaacc attaatagaa gtaaagagag aatacaactt 228420
aataaaaaca ttaacgggta agaagtttgt tgtttctact tccatcgtag tagtattgtt 228480
aataattaat atgatatttt atggtattag aatacacgaa ctagctgtta taagaagaaa 228540
ctctgaaact catatttctt cttttaacta taaaggacaa gcacaagcac aaaataaacg 228600
cgtgaaaaat actagattat ttgaaaaatg taaaagtaaa tttaataact tttgtatcta 228660
tggtgaatgt atgaatatta ttaatttaga taaaaaattt tgtatttgta ataaaggtta 228720
caccggtaat aggtgcgaca tagtaagtat acgttaacaa tgccccaaaa caaggtttta 228780
tcatttcctc ttcccgaagg tactttacta gaagatataa caaaaaataa atggatacta 228840
ggaaagcaat taggttctgg aggatttgga ttagtatatc aagtttcttg taagagtaaa 228900

-continued

```
gaaatagatt gtgtagctaa aatagaatta aaagagagtg gtgggttgtt ttgtgaaatt 228960
aatttctata atagagttat gaagaataaa acatctcttg atacatggat gaaggaacaa 229020
aaaatagatt atataggtat accttctttc catggatttg gtattactat ctacaagaac 229080
gtagaatata gatttgcgat aatacaaaga ctgggtagag atctggaaaa tatactctca 229140
gaaaaagaaa aatttaatat tactgttatt aaaaaattag ctattaagat actggatata 229200
ttaaaattta tacatagtaa agagttttct cacggtgata ttaaagctgg aaacatacta 229260
ttcggtaagg atgatgacaa agtatactta gtagactacg gattagcgac gaaatattca 229320
tcgaatggta aacacaaaga atatactatt aatcccaaaa acagacataa cggtactatg 229380
gctttcacaa gtatagacgc tcataaagga gttacggtat ctaggagagg cgatttagaa 229440
tctcttggat tttgtatgct aaaatggtac tctgggaaat taccgtggga gaaatacgaa 229500
aaagaacctg aaaatgttca aggcatgaaa gaagcatttg tcaataatat atctaaaaaa 229560
actataccct tcaaaaacgc gggtataatt tacaattata taaaggtagt cactaagtta 229620
gaatacgaag aagcccctaa ctacgaatca ctgaaacaaa tgtttttata agataaatat 229680
attaatgaaa aaacaagttc atagtaacag aggtttacac catggaacga gtaaaaaaat 229740
gttttagtaa tataatattc ttttctaaag atgtagatac tagtatgttt tctccaaaca 229800
tagtttatag cggattatta gatagttaca attttagctt tgtagatgca ttattggcgg 229860
ttaatctgtc tataggtata gtacgtcgta gagagacttt atgcagcaaa tgtactaata 229920
tatgtatttt gaataatcaa gtaaaactat tattagaatt cggatataga gacgataagg 229980
atataattaa aaaaggtagt gtatcaatag gtcttttaaa catggattct agagtaaaca 230040
taactactct atttccaccc tgttgtaatt ttatggatgc taaagtacta aatttcaatc 230100
tattattccc agaatgtgat tgtttcttcg tcgatgtaaa gatgaatata gctgaagaaa 230160
gtaactttat acccaggtac ttgtttgtat ctctttacag gatagctaat ttaaataatg 230220
acatatagtt atatttttct cgtgttcatt ataaacataa atatgaagat actttacatt 230280
gattatgtac ttttgatata acatgtgtaa tgctattaga atacggtgaa aaacggctaa 230340
ctaatgctat cgtatcgata agtatctgag atagtaatgc cgctatgtgg taaatttatc 230400
ccacgaaata gaaattatat ttgtctatgt agataagaat ctctaatgtc aaatgatagg 230460
ctctaactaa ccttctaata tttaccgctg tagcattgaa acagtattga aaaaataact 230520
tattacgatg aagacgaggg tacaataatg ttgtatatat atattatatc aacatctata 230580
ctattagtaa aaggatacgt gatagaaaat aataattgcg gatgcggtaa tatcacggct 230640
tccaaagatg taactacttc taattccaca tttgatagat tattgtgtac tgtatacatg 230700
agttctgaag atggttacat ttattggata ggccctaata gtacttttat agaaaattta 230760
gaaggagcta atgaaggttc tgacaatact tttgaggtag gtaatgaatg ttacaaacat 230820
actagagaac ttaatataac atctagggat tatgtaggca agaactttac gtgtacgtct 230880
atgacagagt acggaaccac attcttcaat gtaatactgt aggtatacta taaaaaaagt 230940
ataaacgtag tatttgtata tttctttata tgtataaaaa cttccattct aaatatagtt 231000
actatgttgt tagtattaaa acacatatag taacatgcaa ttctttactc ctatacttat 231060
gctagttact tcgctagcga taattacggc tgtaactatg atatcgttgt tgataacggc 231120
tactataata ttacccatat ctttgatatt accatctact agctcatcta cgtttttggt 231180
aacggtaata tcacttatct cttctgtatc tatagtcgct atagctataa atacagttat 231240
```

-continued gataatacga tctcattaat ccgtatgtaa aaaaaataat actaaatgaa aatataataa 231300
aatcggttac ttacgaattt agacttctat atagaaaaat attatggtag aagtctatct 231360
ataaacaaga agatgtgact tattatacgc gtacataact tcatgatatc tttcttacct 231420
gattattgtt taaagattaa aagtgaaata tattggaagg taatattact taactacttt 231480
acagcgttag gtgttatagt cttaatattt gtagtaccta tattactata attgtttaaa 231540
tagattaact attgttacgg gtatatgata tatctactat aattagtatg ttataaaaaa 231600
taaaaacaag tacaagtaaa agcaatatga gcattactag tataataaac aacctaatag 231660
atatcataac gctatatatt aggatttttt atgtaatata ctatattgct ataaaatcta 231720
aaaatcagat atgtatagcg aatatacttt atacatccat aaaattttat tatacagaca 231780
ttatagatgc cgtgcttaaa agaggtatcg accctaatat tccatttcct ttgtcagaaa 231840
atagctatgt gaatcctctt atatacgcga tagaatgtga taatcatgac gcaatattat 231900
ctttaatacg atacggcgct gatgtaaata catatagtaa ttatctagtg ataacgccat 231960
tatatatctc tgtattacac gggtgcccta aatgtgtaga aatattacta tattatggtg 232020
ctaatattaa tatagttacc tataaaatgg taactcctat agaactagcc tctagaatat 232080
gttacaataa cttagcattt atggtttgcg atagaactat aactaacata ccgaagaaga 232140
taacctataa ttttgaaata atgaaaatac tggtatctca ttttatacta caagcatcga 232200
atgatagatt aaacaatcgt cacaataaat atttttcaga gggctataat aaaaataaga 232260
tgctagtatc tacgtctatt attttgactt atttcaaaaa acagtgtata gaagatatag 232320
atatcatgaa aaatataaaa ctgggagatg attcattttt agatatctta gtagaaagaa 232380
atactatgaa actatctaca tatatatcta atcaagacat attggatatt ccaaaaactg 232440
taaaagtata caacacgaga ataaatatgt tactagatga agctataata tataataata 232500
taaatataat attataaata ataaaagcat ttatcaggat gggagagtat agcaattcca 232560
gataaaaagt tatgttcgat aatattattt taatagaatg aaatagttat ggcgtgccca 232620
tttttgtaga cactaatagt agaaaagaaa ttacattaat catttatctg taacattctg 232680
atcagaagta tattctataa aacctgccgt cgttactgta aataatataa gcacacatgt 232740
gtcagaactg ttaagcagcg tgcctctgta gtttattctg ttacggttga catagatgag 232800
cgcttataca gagatatttt catatgaagt taatacttac ttcaaaatat catacgttaa 232860
tgatatgtat gaagagaaat acgtattccg ttatagataa taagaaaaaa tgaatactta 232920
atagactata taaattaata cagttatgaa gttagtttac gtatggtatc acgatagcgt 232980
gtttgtacca gatagtttat attatccatt tctcagtaat tttagattta attccaagta 233040
tagatcttgt catgtttttt actatataaa caatacagat aacttacgta taccggaaaa 233100
tgaatataat caagatttta tcgattttaa aactgtattt ccagaagata tggccacact 233160
aacggttttg ccaaataaag cgcaaaagat agactttatg aaactatcta ttttgtttaa 233220
aggacaccgc atactaaata ctaaaagcga tatcttgtta ttagattttg actgtcacat 233280
aaaaactata ggtaagatga tatacaacgt agaacctttt tactgtaaaa aaactaaata 233340
cttatatgtt ggaggacaga atgatgaaca agattcatat atagaaaatt atgctactag 233400
aatcgacgaa gtcggttcta gaagacttta cgatatattt actcgtttag attttcatcc 233460
aggaaaatct aaaactaatt cttacgtata tatgatttat gtttctatga tcatagagta 233520
ctttaaagta tatcataact acatatttcc tacactttgt gagaacgtgt atttagaatc 233580
tagcgtagat atgtcttact ctagaggatc tacttggaag atagatattt caaatttaga 233640

-continued

```
tgacgattca ttatggatta taaagtacag taaaccgttt aataaagcta ttaaagatga 233700
aatacaggat tgtatacaca acaaaaactt ttctgtgttt tataccatcg tgttaaaaga 233760
acttaatctt ccttttgata aagacatatt ttggttaaac gataaacaac gaaatggtac 233820
tttgaaagaa tacgttcatg aaaacataaa agatagtagt ggtaatacat tcattagtat 233880
catagataga gctatcaatt tccagaaatc ttacataaaa taccaaatat aataaaattt 233940
aaaaacaata ttttttaaa tattattaac aatgctatca ctatattacg ccatcaacta 234000
taaaaataga aaaatggtag aaaggttact tagagaagga gtccatcctg atagcactat 234060
taaaggattt tacagaccgc ttgtaaaatc aatactctta agagacgtag acctggtaag 234120
tatattatta caaaacggtg caaatcctaa taatattaac gatgaaacgg ttagtccgct 234180
ggctatagcg attaaagtca attctcctac aatagtgtct ctcttactgg attataatgc 234240
cgatacttcc ttatttccat tatacgttag ttttccgatt ataaaagtat tggtatatca 234300
tggtatagat gtaaacgtta tagacagaga atctagatct tttttacatt acgcggctaa 234360
aaacgatgat gttgatacag tgatatcatt aatattacac ggtgctaatg ttaacgtaca 234420
agattctaaa ggattatccc ctttacatca tgccgttagt aagaaaacaa cattaacagc 234480
taagatacta ttagaaaacg gtgccagagt aaatattaga gattcgttag gtaggcttcc 234540
tttacactta ggagctaata catatgaaat ggtaaaactg ttaatagatt acgggagtcc 234600
tatagatatt aaagatgtta acggttctac gcctctacat tacgctatat ggaaaagttc 234660
gttagataca atacgattac tagtaaacgt gtctactatt aacgcattag ataataactg 234720
taatagtccg ttacattata ttatattatc agaaacagaa atcctagtag aacttttatt 234780
aagaggagcg gatatcacta tcaaggatat atgtggtaat acaccattag atattctttg 234840
taaattaaga ataaaaaaac tagataatat taaagcgata atatctaatg cgtttcttat 234900
gcgagaagta gttcctgact tattaaagct atgcggattt gaaagcaata gaaaaattat 234960
ctctaatatt agcgatttaa aacagcacga ggttagttgt attaaagaaa tacatttaat 235020
gaaagagcat agttttagaa aaaacggccc aactatatta gacgtatgta cagataaagt 235080
acattttctt catcgattag ttaatgctcg tgataacgta cagtataaag attttcctat 235140
atactgtaaa tatataaaat ttagaataga gaaagcgata tacaaaaaaa caattatcga 235200
gaaaactata ttactgttag acgatatatt aattaaacac gaatatactt cttggcatga 235260
tttaccatat gaattaaaac actatataat agaatatata aacatagaat ttattaaatc 235320
gctgctagaa catacaaatc tgaaaaataa agaataactg aaatatgtga ttgtacgaat 235380
atcaaaatga aattaatcga ggcaatcgat aataataatc ttaaagaagt tataaggata 235440
atcagatcag acaatataaa cctagaatct ataaacgatg aagatgatct atctccgtta 235500
catcacgctg tttcacgtgg ttataaagaa atagttattt ctatgttaga gcatggagct 235560
gatgtaaatc tatgtaacga tgaagtatgt agtcctttgc acatagctat aaaaaaatgat 235620
aacgtcgaaa tggtacaatt actaatagat aacggcgcgg acacagactg ttgtaacaat 235680
actatacacg gaactccttt acaatgtgct atactaaacg agaattatag gattacagat 235740
gctctactcg aatcgggagc tgatacacat gaaatttata ctaaaaacca ccccattatc 235800
gaggctatta aactagataa cctaccgcta gttagattat tactaagaca tggcgcggat 235860
gtaaatacat ttgatccttt atacggatat cctattcatt tagcaataag atatggaaat 235920
atagatatca tcaaagaact gctatatcac ggtgttattg aatcgtattc tttgtatcct 235980
```

-continued

```
tctcttttgc atcaatctat aatgtgtaat aataaagaag ttgtcttatt attgatatct 236040
atgggttttg atgttaatgc taaagataac gagggaaata cacctatgca tttagccgta 236100
cagaaaaatt tagtaggtat agtaaaaata ttattagata aaggtgccga taccagtatc 236160
attaataatt tatcagttac atgcttaagg agttgttatg tttatggtaa taattctaca 236220
gaaatactcc agctgctaat atctagaata gttatcaaca aatacgctaa tataccgtgt 236280
agaagtatag caggtatgaa ttataattgg agtttaatag aatcaaatcc atacatgtaa 236340
actttctagc taggtacgca atgcagcttt caactataga tctacgcgaa gtaccaatat 236400
acagaaagta cttagaaata cttattaatc cagctattaa aagacataaa atattaaatg 236460
ctgctaaaga cactatgaat aatatattgc acaggaaaga aaaattttat tggaatctat 236520
taccggtaga aataaaattt aatattttag aatacttgaa ttctaaagac ctgatttcat 236580
taatacacag taataccgta aatgaaatag atttatctca tatttttatt tgatattata 236640
tataaaacat aaattaaata acgtgtatat aataagctaa ttacaataca atatgtaccc 236700
aaggggggttt tagtaaatgt gaatactgtt atcgctttcg gctataagga aatagtaaat 236760
attctgttag aaagaggcca agatgttaac tttatagacg atgttggttt agcgccggta 236820
tactatgcta cgatatttga acggatgaat gtattaaagc tgctatgtaa ataccatgta 236880
gatataaata ttagctctca tagttctgga cgtacatctc tacattatgc cgtattgttt 236940
aatcataaaa gagcattaag ttttctgtta gctagaggtg ctgacgtgtt taaaaaggat 237000
gcgtgtatgt gcacgcctct atactacgct atgttatctg accaaagaga tatggtaacg 237060
atgttattac actctaagaa gtatatagtt aaattcagaa ataagctaga cttacacaat 237120
gctatagaaa ccggtaatat aaaggtaata aaaactttat tagataacgg agtaaatgag 237180
aatagtgttg acaaagatgg acttactcca ttacattatg ccgtaaaata tggtaatatt 237240
agcatagtaa agatgtttgt tattagatag tggaatgaac ataaacgcta ctgataattc 237300
gttatctaca cctctacatc acgctataaa cttacttaaa accgatatag tttcccttct 237360
aatgcaatac aaagccgatg cctctatacg tgacagtaaa ggaattactc cattctgtta 237420
tgccatgtat ctaggatatt acggcgttaa taaggatatt cttaatatta taacacggta 237480
taattctatt aacggaacta ctagagatat taacgatgta tataccatac tactaaataa 237540
taaaaagaag aattatgtat tcgtaaacct acacgatgcc gctagactag gatatgtata 237600
tattttaaaa aagataatat ataatggtaa gaacataaac cgcattgatg aatattacta 237660
ttctgcgtta cactatgctg tcaaatccag taatttgaaa gcagttaatt tttgatacaa 237720
aaaggtatag atataaagtt aaaagatagt aatatagaac cgcgctacat tacgcggtta 237780
aattgggtaa cttagatata attaacagta ttatagaaag tggtgctgac attactacca 237840
gagatatatt taaccaatct cctcttacca tagctttaca agaaatagat aacatatatt 237900
ttttacgata aagtatttta caaaataaat gataaccaaa aaactaagat agctaatgta 237960
ttaatttcga atttagttac ctctgaaatt aaaaaaatga aacaattacg tataaagaac 238020
tatgcaatat attaggtgat aagacctata taactatatt tgtgagtaat tgctttaggg 238080
aaatacataa aatgaagtat gttaatttta taaatgcgta tagtgtctat gatatttata 238140
taaataaaaa caagatagat ataaatatac cattacatat taactatgac ctaaaataca 238200
aagaaattaa aaatgaattt cctatttaca gagatatgat agaaaagaaa atacgatata 238260
tactagataa acctaatcta gtatataaag ttattaattg tatgtccgaa tatatggatt 238320
ctacttattg gatgtttcta cccacagaaa taaaatttaa ggtgttaagt tacttaagta 238380
```

-continued gcaaagattt atattttata atataaacat ggaaggaata ccactcatag atatatatgg 238440
taaacaatgg aaaatagata aacttatagg atgtggtgga tttgggtgtg tatactctac 238500
tcaatgtgct agtaatacaa ggcaagccgt gattaaagta gagagcctaa ataacactac 238560
catggtatca gaagtattag tttataacaa catatatgat aaaaatagaa tagcgttatg 238620
gaaaaactac aagaacatag atcatttagg aatacctatg tactacgggt gtggaagttt 238680
caaacgcaat accatgtatt acagatttat tttattagag agattagtag aaaatactaa 238740
agagttatta aagagagtaa aaaaacctaa accgttaata aaaaatataa tgaaagatat 238800
gttatatacc ttagaatata tacatgagca tggaatttca cacggggata taaaaccaga 238860
aaacataatg gtagatggaa gatacagatc gtacctaata gattatggta tagtatccta 238920
tttcattgtt aatggaaagc atgtaaaata ctacaaagaa tctaagaact ggcacagggg 238980
aacattgtat tacgctagtc tagatgcgca taacggcacg tgcgttacta gaagaggaga 239040
cttagaatca ttgggatatt gtatgttaaa atgggcgggt ataccactac cgtggaaggt 239100
atttggaaat aatgggaata tggtacatgt ggcgaaatgt gattttataa aacgggtaca 239160
taaaaataaa gttaatatta agtcagcgaa taaaggcata tatgattata ttaagtgtgt 239220
tacaaaacta tcgtacgaag aaaaacctga ttatgatcta ttaaggcaat tagttaatag 239280
cttataaatt attttcagaa cataaataaa atataacata tttgtacaag cctgttatca 239340
tgtcggataa tacattatta ctgcacacta taatgatact agatctagaa cctaactaca 239400
acgaatgcag atattgtgtt agaatgctgt ttaatgctgt aaaatttaac aacataaggt 239460
tagttatgca tctactacgt aacggagtag atcctaactt ttacgatgaa tacatgaggt 239520
ctcctattca ttatgctgta gaaaaaggta atacagaaat ggtaaaggcc ttattggaac 239580
ataaggcaga tcctaatata ttcgatgata acttcgacta tccgattaca aattctataa 239640
tagaaaacaa agtagaaatc gtaaagatac ttttacaata tggagctgac aaaacaatga 239700
ttaacgaatt tgatttatta cacgacgcta tcaaaaataa gcatatagat atggctaaaa 239760
tcctaataga taatggaatt agtttaacca tgaaagacac agatgactat acgcctttac 239820
attatgctat gttagacaat gatacatctg tgatatataa tctattagac tatatattta 239880
aagtaaaagg atacgatgta ttaggcaata ttgtgcatga tatattgtgt aactatgatt 239940
tatataagga aacgacgtta gaattattaa tctcttatta cataattata tcctacctct 240000
atagaggtat agacctttca gatatttaca atagtaatat agaaatatta cttaattcta 240060
aacatctttc tgatattaaa gagaaatgtg aaaacgaaat agatgttatg aagaacgctg 240120
taatatgcga cggtatagcc atcatagatt tgtgtacagg ctacgatgca aattctatag 240180
ctagaaattc cgttaatttg aaaagattct cagatactaa actaaagatc tacagatatt 240240
atatagaacc gattgtagaa ataggaaagt atagacgcga gctattgtat aatgcgatta 240300
attctatgaa tgaatattgt aaatccgaaa gtaacgatat agcaaattgg tcttgtctac 240360
cattcgaaat aaaatacaaa atacttgaaa atataaaaga tgacgaaact ttaagaaaaa 240420
tataagtatt tacaatagta agtaataaca aggttttgag tgtatgcttt taatcataat 240480
ttttatttaa aaaaatagaa tagtgaaaat aaaatatgtt aataatgagt agtataaaag 240540
aactatatca tgcggtttct atcaatgata ggtttagtgt agttaatatt ctagagaaaa 240600
aaaatattcc tatagattat ataaattttc atcctgataa cccgttatta gaagccgtaa 240660
agttaactaa cactgatatg ataaaaacat tgctagatta tggtatttgt ataaatacta 240720

-continued gagatatttt aggaaatacg gctttacact tgatagctat ggattattac gttccacata 240780
acgatataaa acacggccat cacaacgact atgtatttaa aatggtgcct ataattaatc 240840
tttttttaag aaagaaagct aacataaatg cgtgtaataa tctaaatcaa acacccttgc 240900
atttggctgc cgaaagcaat aatacaacat tattaaaaat attattatat aataacgcaa 240960
aggtaaatat tctagatatt tacggaaata cttgtctgca ctatgcggtt agaggaagga 241020
acatagaatc tataaaacta ttactatcct ataatgtcga tgttaatata agaaatttta 241080
cttattggta ttctgctttg cacgaagcag tacagatagg cgattcaaaa atatctagat 241140
gtattgtatc attattactt tgtaataagg ctaacgttaa tactagatgt agacttaata 241200
caacacccat attttacgct ataaactgta tagacactct gaaactatta ttagaaaatg 241260
gtgcggatat aaacgcgacc tcggataatg ataatgccgt aatacatcta gctactgaaa 241320
atagacgtta tgatataata aaaacgttat tggattatgg cgcggatgtg aacatgatag 241380
gatatagagg taagacacca ttatattatg ctacagaaaa ttatagttac agaaatatga 241440
aattattact agaccatgga agtaatccta atatagcaga tcatattatg aatacgcctt 241500
tatttatttc tataaagtgc acgtgcatcg aaaacactaa gatgttacta gatagcggtg 241560
ccgatattaa ccacgtaaac gataatggcg aaacacctat ttcttaccta gctcctaatt 241620
taatcccaac ccccgttgct atattagtaa tatctcatat agttctttta aaaaccaaat 241680
ataatcatat aaagtactta cccggtttta taaaaaatat ttctgttata cagaatttta 241740
ctaaattcaa taacataaaa aaggtgtgtg aagacgaatt tagatttatg agatccgtat 241800
cattatcggc taatcataat ttatcgtctt atatatgtaa tgataacttg cgtactttag 241860
taaggttcat aaaaaatcca aaaatatatt attcgataaa taaaatacgt atttatagga 241920
accgattata ttctataata gaaagattat taaatagaaa aaaattacat gatttagttt 241980
tagaattaat taaagatata ggcgtattta ataaactacc gttagatatt atatcaatga 242040
tattagattt tttatcggat gacgacttgg cgcttatggc tatatttaat tgatttatag 242100
tcctaactac cgtatatcaa taaatatata atgaaagtaa aaggtgattc atcgaatact 242160
gattactaaa ctatcagaag ccgaacaagg atgcaacttc ttcaactagt tattctccat 242220
aaaagaaata taatattatt gagattatat taaattaggg tatggatatt gacgcgcttt 242280
actattatgg ttctgtacta ctggtgggta caacgagtga atagaaacta taaacatcat 242340
aataaaacac ggagctatat taacatatta gattaacaag gattcaccga gttgtataga 242400
acttctatag agaatcttcc taaagttata gaattttgtt agtaaacggt gctaacccga 242460
atatcaataa cgagctagta tgcacgtcgt tatattatag aagaaactta ataatgttga 242520
attattgtta agatatggta ttaatattaa cgctatagat cttaacagac actcctttat 242580
cttttatcca ggccgatgat cgtgaaccac ctacattact tgtggctcat ataactttta 242640
accaattatg ctgatgatag gtcctatcta gaaaggttat cattctaaca tgtctatgat 242700
atattatagt aaaaatctaa atagttttaa gttagaacgt gaaaaagaat ctctatgctg 242760
aaatctataa taatatgtag agaaatttct ttatttatgt caacaaccct gaagaatttt 242820
agaaaatctt ttgactcgaa gtgttaatga catacatata tactttaatg cgttaataca 242880
aataatatct taagtaaata tagacacgtt aaataaagaa gctttacaac atattgataa 242940
aatgttttta gattgagatt attaaccaca ggtgagttaa aaatctatta gaaatatgtt 243000
aatacaaaac ttatttacca tctaatccat aacaaccatg tattattata tacaaaatat 243060
ttattttagt agatgaaaaa atccattgtt atacatcaga tacagaggta taaaattcct 243120

-continued

```
tatttggtgt tatatcgaac tagtgagttc aggaatctta tctaatagaa tactattaaa 243180
ttagagaaga aagactttat gagtaagtat taaacaaaat atatactcac atttataata 243240
tagtatgtaa tttatcatat attttatcat atattttctt ttctgtaact gattatttct 243300
tttaatagag atttcgtttt ttctcttaga gatatatcgc tgtcttgttc tgctaacatt 243360
tttaaaaaca aataagatct ataatcacct ttttttttta aactggttag ctttgtattc 243420
taatttatcc tcctgaattt cattattaca aaaatctgtt atttcttttt ctacgataga 243480
tattttatct tttatattct taaaaccatc tagtattaca ggatactcgt cgatttcttt 243540
atttctattt tcatacacta ttttagtggt gtctaccagt ctatctttaa cccgtttagt 243600
catatcaata tcttgtaaag aagataaaaa taattgaagt tcataattcc atgatttaag 243660
aagatgaaca gccgctgcat ctatcatgtc tatttttcca tcatctgaca taacagaaaa 243720
cacatctaat aacgtattat cactagaact attaagttta tgataaggat tgttattcac 243780
agtatgtatc atagaactag catttcccat gttaatacaa acgaccttat ttattttat 243840
aattagtaaa tttattttaa tgtagatatt aaaattgata taaatgaaat ataaaactat 243900
tgacgataat aggaatacta ttatttcctt attatagtac tatggaaaat gaattaaaat 243960
tatactatgc tgtaagctcc caaaatgaaa acttggtaat acagttacta aacaaaggtt 244020
acaaccccaa tgctataaac aggtttaagt atatgatacc gttacacaaa gctgtagaat 244080
gcaggaacgt agatataact aaacatttat tatctaacgg cgcagacgct aacgttaggg 244140
actttctagg attaggtgta tttcacatac tgagcatgtt ttctagttta ccagaactaa 244200
aagatatatt acataataca gaaggcactt ttgtcttgtg caaatataat tacgctcctt 244260
tagaagaaga ctatgaagtt aaaacactag agatagctag aatgcttttt ataagtaaag 244320
ctaatattaa tatgacgagc aaacttggta gtacacctct tcatatagct agtaaataca 244380
ataataaaac gatggtgaaa ttctttttgg aaagaggagc cgatatcaat attctggatt 244440
ctaacaataa tactcctctc atctatgcgg tatgttcggt aatacgacta tatctaaaat 244500
gttattagac tacggagcaa gaatagattc tcgtaataaa gaggaatgtt tgcctttaaa 244560
tcatgcgata gctacaaata acaaagagct tacgagtcta tttcttgcaa gaggagccga 244620
tactaatatc gtagataaat ataatagatc ggttctacat aaagctatag gtaataataa 244680
tataacgtcg gtaaaattat tattaaatca cggtattgat tacaatttac gagataatca 244740
cgggtatacg gcactgcact acgctataac attacaaaat agagagatta cagacatgtt 244800
attatcttcg ggagccgacc ctaatataat gaataatgaa aaacatactc ctctatatca 244860
cgctctattg tatagatcgt ctaacgttga atcgctgata ttacacggag cggatataaa 244920
tattgtagat gatacaggga aaacaccatt atctaatacg tatatagata taatagataa 244980
taaaaatatc gaagtcatag tatctcaatt cactattttg gaatatatag caccagatga 245040
tataaaaaat caattaggtt acaaaataaa tactgaccta ataaacaaca ataaaagata 245100
ttctactata aaacagaaat gtgttcatga aataaatcta ttaaaagcaa ttaaatttca 245160
ttccggatat tcagcggaaa tatttctaat taaaagcaaa tcgaatatct ttcataattc 245220
acagggtatc caaatattat aaatataatt gaaacaagat ttcccatata ttactcgttg 245280
ataaaaaaat ctatagacat aggtaattat agaagaaagt tacttgacgg tgctgtaaat 245340
actattagtg aaatccgact gttaaacgta ttacctataa acataaaata tgttatattg 245400
gagatgctag ataataaaga tctaataaca ttgaataata atacataatt gaaaatgtat 245460
```

-continued ataatactat ttttatagat atatagcaca tcataatata ttataaaaat gttaaaactc 245520
tatatatcga tgtttttaga tagtacagaa catatattga aagaaattaa cagactacaa 245580
cataaagagc aacgcaccaa cggtatatct tgtatacctc ttattccttt acaccaagct 245640
gtagaagcta gaaatctaga agtagtagaa gctttactag aaagaggcca caatgtaaac 245700
gaaacagacc atagatatct aacaccttta catattatat gttcacatcc taataagatt 245760
gggatgaagg aagtaatcgc ggaaaaaaca aaaagagatt tatcatctta cgaagaaaga 245820
gctatatcag aagcgtgtta caataatgat ataaatatct ttaaaatgtt attacttaat 245880
gatggtaata gaacgattga tgacgtccaa ctatgtacga tagattatga tgattccata 245940
gatacaaaaa taataaaact gttactggcg tatggggcag atacaaaaat aaaaacagaa 246000
gataagttaa aaacagcttt acattatgct tctacaaata aaaattataa attagctgaa 246060
tatttgttga tatacggagc ggaagtaaat tccccagata taggtaataa ttctcccatg 246120
catgaagctg tacgacatag aaacgaagat gtagtaaaaa ttctattaca atatggatct 246180
aatactgatc acatgaattc atgcggtact actccattgc atatttctgt aggaagggta 246240
cttaatagaa ataattattc tatattaaag atattactag aacacggtac gtctgtgaat 246300
atacagagca gtatactagg ttttaccgct ttgcatctat ctattcatag tgaagataaa 246360
cttaatctat tattagaata cggtgcagat cctaatattc tcaattttga gaaagaaacg 246420
cctttaagta tggctgtaaa agtaactagg tatgatataa atatttataa tcgtcttata 246480
tataatatat gcttgagagc gtttaagtat cctttcataa aaactacaga aggttatatt 246540
aagaacatga cgtgcataaa cggttatcct aaatgtaaat ccataaaaga tgcatgtgaa 246600
tacgagatta aaaacttgga atctataaaa ttaagtccta gattttctat ggccgatttc 246660
ctaaaagacg ataactcgct aatgatggat aaaataataa ataacgacct tatagattat 246720
tattactcgt ttatggattc gtttcccata tacggaaata tagttaagaa aagtatagac 246780
acagcaaaag acaggtattt attaattcag ggagctatac gcagtatgga taatataact 246840
tttccttcac aacgtgtatc ttggtataat atgcctttag agataaaaca tgatataatg 246900
tacttattag atgataaaag tctgtgtaat ttaatagtag ccgaatatga tagttaaata 246960
actgaaacaa aaattttatt tttattagta tatgaaataa tgcaaggtaa tgttatacac 247020
gtagacaagt tatataaaat gatgtacacg gataactacg aaactataaa aaaatattta 247080
gaatatactg tcatagataa aacagaaaat tatagtacta gtgctaattt aatacccttt 247140
atacctctac atcaagcgat agaagcaaga aacatagata ttataaaatc aataataacg 247200
gtagataacg ttaatcaacc ggggcacgat gatacatatc ctatacatat catatgtaag 247260
gaacccaata tgctagcaat atcttatatg ctaagatcta taaatcagtg cagcgtgttt 247320
aacacgcttg taaaaattaa agatatgttt aattacagaa acgtagaaat agctaaaata 247380
attttgacaa atagatacaa aaatatacag gatatagatt taaagtatat agataagaaa 247440
agtaaggacg atattataga aataaccaaa ttgttatttt cttacggtgc tgatattaat 247500
atggtagaca gacacggaaa ttctcctcta cattacgcta ctgaaaatcc agatcagaga 247560
ttaacccgat tattgcttag taaaggagct aacccaaata tattaaataa aactaataag 247620
tcacctctct attattctat agaatccgac aatccagata taactatgtt gctaatagat 247680
aaattcatat ttaataatac ggatccaata ttatcacacg ctattaaaca ctaccgtaaa 247740
cctatattac acgcgttaat agaaaatggt gcttctatta acgcacgaga caaatacggt 247800
aatacaccgt tacactacgc ggtaagttac tgtaaagata tagatgtgat aaaattactt 247860

-continued ttagaaagag gtgtagatgt taacgcaaaa tcttatatta ggaatttaac tcctctgcat 247920
agttcatatc ttaaatcgcc tcgtgttcta aaactacttt tacaatacgg tgctgatatt 247980
aatagtttag attcatatag tttgactcct ttaacgtccg tagtacttca gtacttgtgt 248040
atagaatgtg ggagaatagt agtttcgcat atctgctgct taaagcgtat taaaccagat 248100
atcgaaaatt ctttgggttt tatagataat atagatgcta ttactagtaa taaaaggctt 248160
aatcaaatac gtttaaaatg tgaggatgaa ttgaatagaa tggcaagtat taaaattact 248220
aatacatatt ctttcgatgt atttgtcctt tgcgataata ttactttatt atgtaaactg 248280
gtaaataata gtattataga cgatatatta attaatagtt ttaacatata taaaggcatc 248340
attttaaaga atatatacag atctagaaaa cgactttatc taatagaaaa tacattatac 248400
gttttaaata atacttttaa acctaattat atgtggaata ggttacctgt agagttacaa 248460
aattatataa tggagtacat agatgatgca tcattaaagg taatgcacga atacgaaaaa 248520
cataaattaa agtattaagt gattacaggt ttgattttaa tcggtataat gcaggtacgt 248580
aataaagatg atatactaat atgcgaagcc atagaaaatt atgatagcga atctttacgc 248640
aatattcttg aaaatggagc agatcctaat gttagagtac cttatcagta cagccatttg 248700
cataacgcta tagaaaagaa gaatggaagt gcagtatctc ttctactaaa gcatggagcg 248760
gatcctaaca tttctgggtt ctttacacca ccattacata aggctataaa aaaaggttgt 248820
gtagatatag ctagatcgct attagaatac ggagctattg ttaatttaga acattattgt 248880
ttgaaaccta tacatatagc tgctaataga acagaaagta aaatagtaaa attgcttata 248940
gaatacggcg ctgacattaa ttcagaagac ggcgcgaatg gtaaataccc tatacattac 249000
gctatgaaag tatacgatcc gtttagatta aaaataataa aagtattatt agaccacggc 249060
gccgatatta acaaacaaag cgttttaact aatacatccc ccttatacga aactaggttt 249120
attaccgacg acctattaga ttacatcata tctagaggag ctaatataaa tataaaagga 249180
agaatgggta gaaatatatt acacgaaata atattaagaa acggatataa tgattttagt 249240
aatatattgg tattaataga ccacggtgct gatataaacg ctttagatga tgaggggaat 249300
acacctttta tgttacatac tattaacaat aatgctatta ttcttgctaa ctatatagta 249360
tcattgtatt acttatctta caaagctaga atttctaacg gaatggaaaa gaatatgaaa 249420
ataattaata agtgtgaata cttaagttcc tgcataaata ttataaaaga agaaatagaa 249480
cgtatgaaaa cgttcaagat atacgacgga aattcttttc aagatttaag tcttttcgat 249540
ttattatcta acgaagataa catcgctata gtgtatagac tgtccgatac attattagaa 249600
aaaatgaata taatcaaaac aatatttccc aactgttttc gtataataca aaatatatta 249660
aaaatgttga caaaaagata tgaaatgtta ttagagataa acaatataat gaatgcaaac 249720
ctagtaaata caaaatggta tactttaccc atagaaatta gatggatgat actgacaaaa 249780
ttagatgaca tgatcttacg aaatctacta ctacaaaatg agacaaataa tattaaaaat 249840
tgtaaaaaac agtaatataa atatgataag aaaatgtgta aaaaagctag gaaacgcggt 249900
ctattaacga tagctttcac tatattgtta tttgttatta ttttagtaga tatagacaga 249960
gatagatatt tagtaaggtg tggtaaagac tggttagaat tcgataattt atgttatttt 250020
atttccgaaa ataagttaag ttgggatgat agcatgatgg tatgtgataa tcttggcggt 250080
gggaataata ttaacataaa tacgaatagt ggcttattaa atacatctaa ggactattgg 250140
ataaaaatag tagacgaact agattgtaca aatattaata tgtgtaattt cttatatagt 250200

-continued aatatagtag gatgtgatat atgcaccata gaaaaatttt atatttgtat aaaaccgata 250260
aataaaataa acttatttag ttactttgta gagtatacta aataataatg aaatttaagg 250320
aagttagaaa tactatcaag aagatgaata taacagatat aaaaatatgc ggcattaatg 250380
agtattttat gtctatgaaa ttattagatg tagaagtagt aattatgaga agtaacgggt 250440
tcgtaaatat tactagatta tgcaacttag aaggcaaaga ttttaatgat tggaagcaat 250500
tagaatcgtc taggagattg ctcaatacat taaaagataa caacaagtta cacgatccga 250560
taataaatat taggcatact agaataaaaa taaacggaga atacgtttca caattactac 250620
tggactatgt aattccatgg atttctccat atgtagcgac tagagtatct attctcatga 250680
gatactatag acgatgcgta gcgctaaaca tagaaactga aaaagatata gaccatagcc 250740
aagaactaca gaatcagatt tccaaaatag acgaagttta tgatagatct ataaaggata 250800
taagtaatcg ctttaaagaa atagaaacat cttattacag taaattgagt acttatttac 250860
taacaaaagc tgaaagagta ttagaaaaag actattctat ggaacaggat atagataata 250920
acgaagatat ccgtacagat gaaatgatag ctgctataga agctgaaatt gaagaaaata 250980
atcgtcgcta tttgtcaata attagcggca taagaaaaca acacgcagaa gatcgtatta 251040
atatatctaa aattatgctt agtggtgatt catttaatga aataatagta aaaataagag 251100
actatataga aacaacggca aaaccagcgg tagcgaataa ttacgaatag taacggtttt 251160
aaataatatt atataaaaaa cataaaaata aatataatat acttacgaag gcccaaggct 251220
ttatataata caaatcaaaa tggaatctgt tattcgcaaa atggatactt gattctgata 251280
aactatcatc ttccaagact ttcggtgtta ttatcaccat cttaatagtt atatctgtat 251340
ttgcatattt taaactgctc atgtatacct atgatcaaag tatacaagac atcttgcaat 251400
atcatacttt tggttataat tatgcatatc aatttccatt ttttcataaa aatattatac 251460
attattagct agcatttcta taaaagtatt attctgcata tccacttctt cggtaaaaaa 251520
caaaatgacg acattataga tctatcgctt aaatatgcac aatcacctat tcctttgata 251580
ggaactatat tatcataaga tgacccatct tctaatttct aagttccatt aaaatcaact 251640
ttttctattc caatccagtg atttcccgga cctttgtatc ttaggataaa tttaaattct 251700
tctttgctag aaattgaagt cagatgcccg tccatatcct tacatctttc tacagctaat 251760
gatttattat ttttttcctc agagaaaaaa tagcagtttt tattatatcc tacccatcct 251820
tctttacagt aaagtatttt aatatctgga ggtacaggag gtcttgtgga taaaataatc 251880
acaaatacag atagcacgat aataatactt ccgcatggaa tcaacatcca taatactgcg 251940
ctactacgtc gcggtttacc ctcctccatt ttttaaatat actttatcaa gatttattaa 252000
acttaaaaat gcattcaaac tacttataat aaaattgaaa aaacaaataa tgatatatcg 252060
agaggtgttg aacacctata ttatacaatg gatcgtgtag aactttgcaa tgctattctc 252120
tttggagaac tggatgtggc tagacgcctg ttggattctt acatcaatcc gaattttact 252180
atcaacggat actcgcctat aaagatggcc gtcagactta gagatgttga aatgattaaa 252240
ttactgatga gttacaacac ttatcccgat tataactatc cggatataga atctgaattg 252300
catgaggccg tggaagaagg agacgttgtt aaagtggaag aattattaga ttctggaaag 252360
ttcataaatg atgttatcta caagaaagga aacactccct tacatttggc cacaattagt 252420
aaaaatcttg acatgatgag gctccttata gctagaggag ccgacactga tgtgcccaac 252480
actgatcgtt ttacgcctct ccatttagct gttatgtcaa aagatattaa aggtatagaa 252540
ttgctattag atcacagagc ctgtaccaac atagaagatt gctacggatg tactcccctt 252600

-continued atcatcgcca tgagcaaagg agacacagaa gtatgcagga tgttgctaga ttccggagca 252660
aacattgact atttcagcaa aaggccctgt gtgacagcga tgtgctacgc tatacaaaac 252720
aacaaaatag atatggtaag catgtttctc aagagaggcg ctgatagtaa cattgtgttt 252780
accgtgatga atgaagaaca cacaacttta gagatgatct gtaatatgga tacaaatcca 252840
gaatctgaat ccgtggatat gctgatagcg gacatagcat taagacaata tacaaataca 252900
atatcatcgg ataaaggatt ttccagaaac atgacagtca ttaacagcaa aagtcgttta 252960
aaagatgtat ttgaaaaatg taaaattgaa ttaaggagaa taaacagcga aagcatcaga 253020
acctacaaca ttctggacct gtgtttaaaa ccatccaaaa atcttgatga gaacatattg 253080
gcaagacatt ctagaaaaat attaggtctg tatgataatg ccatattcta caaatatcta 253140
ttaaaagaat tggcagacac ggcatcgcaa agagcggaag ctattgaatc agcgatgcga 253200
gttatagatg aaaaaattac tggtgatgaa acaaaatgga attggttacc ccacgaaata 253260
aaatacaaca tacttgaata tataggcaat aaagagcttg acatcgcatc tatgaaataa 253320
aatacaacat acttgaatat ataggcaata aagagcttga catcacatct atgaaataaa 253380
attattttta taactaaata tatattttga tatagaaaaa tctagtcatg aatatggtac 253440
aaacagaaat attgaaggtg ataagtctta tatagcaata tagaagtaaa cataggcaaa 253500
acaagtattc taatagatat tttgctaact atgtagtaca atataagtat attaattttg 253560
ttaccgtgtc gtcttaatca ataaaacgta aaagccgtta ttaaacatat ataaatatcc 253620
tgattatcgt gatatatgat aaatattgcc ttatgatgta aagaaagata gagcgtgtac 253680
taaaaaaata aacaaataag tgactaaatt ataatataat gggcaattct acatctttat 253740
ttcaacgact agtaaatact tttatcatag cgattgtccg aatcttcgga agaagaaagc 253800
ggttatgttg tggaaggtga ttatgttgaa ttcgaggcca gatttacttg ctttataaca 253860
cttgcttgta ccgatcccaa aaataccata atctattgtc tggaataata atgtaaatag 253920
tttttgtatg tggtttttat agagaaatac aaatatttag gttattaaca aattatgaaa 253980
attaagtatt tgtattccag cttataacaa ttattcaata tggaaatcaa agtagaatcg 254040
atcaataata acttttgtaa gctaagttac gaagatatag aaattattat gatgaaagaa 254100
aatgaataca taaatgctac aaggttatgt agttctagag gaagagatat attagattgg 254160
atgagtaagg agtcctccgt agaattaata aatgaattag acaggataaa tagatcatgc 254220
aatgactact acgattatag gggaatagta ttaaatgtgg tatcggacag cgaaacaagt 254280
gaattgtacg tccaccgcga ccttatatta catatttcac attggatttc tcctctattt 254340
tctttgaagg tagtaaagtt tataaatagt tacatacaag attcttatca attagaatat 254400
gagctaatac ataaaaaaag tttaatggat cagttaaaag aaataatact gttaaacgat 254460
gataacaata tgtagttaca tgagatagct aataaaccat aaagttacgt atagatgagc 254520
tagcaatata aacgaaaatg gtaaaaatgc tattatcact aggtacaata tacatgtttt 254580
agatcatata gaacgctata cttaatgata tcttctggta gagcttaaaa ctccattgtt 254640
ttaatattat atactatcaa cacaataatc gggtgtgaat aaagattcta aatctacgca 254700
cgtaataaac caaatatact aaaatataaa attatgccgc gggatgataa gatacttcag 254760
atgatcgtga tgaactatat ttattaattg gcaatactta aaaataatgt ttataacata 254820
tgtaaatata ataaacaata atttagattt ttaaaatgat aatacgtagg aataataaag 254880
ctcttggaag tgtaatgagt gatttcataa aaacaataaa tgaagaatat gatagtaaca 254940

-continued taaaagaaat aaaatcagaa attgatataa agtgtaatag tattctaaaa gaactcgatg 255000
aaaaatatcg ccaagagata aaagaattat gtatgatagt agatcaactt aagaaccaat 255060
ataaaattat agataatatt tatagtaggt atataaccga aattagaata caacttttag 255120
ctctcaaaga ggaaaataaa tgtttaaaag aagagttaac aaaattaaag taataatttt 255180
acggatgaaa atctgagagg aagatgtttt tatgaatata tattcgtggg tatgactaac 255240
ttaataatag agataaaagt agtttaatag attactaaag taaataaccg cggcggatac 255300
agaagctact ccgctattct ctagcgtatc gattttaatc caaataaaaa aatacataag 255360
cgtacacgga catacgtatt ttgctacctt atattatata cctaaattga tacatgttta 255420
ttctccaaag aatctagaat ggcctcaaaa tctttttgtg aattatctat aagctgcctg 255480
gctttttccc ttatcttcat tatatactca tccttatccc tatcctcttc gggaagaggt 255540
tttatatcct ctctacaatg ataaacttca tttcctagat taataagtcc tatttcagag 255600
aactcttcca tagtatccgc tactttgtat agagcttcat cgtcgtacac ataaatctta 255660
ccatcttccg acattagaat gatgagattt tcattccaag aaatatcgct atcattcata 255720
acaccgatta tatccattct cgtcggctgg ggtaaataaa gaacttcgca acattctttt 255780
atatatttaa gctcttcttc gggtaaatta atgtttctat ccattttaat taagtatcta 255840
aggtgtatat ctatatgtct attttatttc ctaataaacg taaattaaga gaactatatt 255900
tctttacgat ataagtttat atactaaaca aataaaaaga tgttaaaact aatatgttta 255960
cgtaatttta atactttttc tattttagga gtagttgatt ctctcaataa cggtaagaat 256020
atcaataaaa taatatctaa aaaagatatg actttgaaag aaatagttct ttatttacct 256080
aaattcgaat tagaagatga cgtagacttg aaagacgcgc taatccatat gggatgtaat 256140
gatctattca agtcaggtga attagtaggt atatccgata caaaaacttt gaggataggt 256200
aatatcaggc aaaaatctgt gataaaagta gatgaatacg gaactgaagc agctagtgtt 256260
accgaattat gcactacaga cggaataaag aaaattccta tcgtaaaagc gaacgtacct 256320
ttcatgttcc tagtagccga cgtacaaaca aaaattccgc tatttttagg aatattccag 256380
ggatagttac ttaaacaaag acattatacg tagacttatg cgcgtaaaaa gcgattaact 256440
aaattatata gaattgtatg tataccgata cctccgagta aatagttaac tcttaaaaga 256500
ggaacgtggt agtattattt tattttttt ccttagagct ttgtaaattg gaggaaagtc 256560
gcgttagtag ataactatat tcacatatct aaatacgaaa atcacaatat ctcgcagatg 256620
cgggcatacc tctttgtacg gaagtgttaa gatcggttag tatataatta ctatataatg 256680
ttaaagtaag cagataactt ataatataat cacgtaattt aactaacata tacatctaag 256740
aaaaatattt tcgggaatat aaatctgatt tagacattac gtcctatttc ttcattaaaa 256800
gaaataatac cttatacact tattgattta cgttttatca aaacatatta tttttatgta 256860
ctcgagaggt atataaatat acagatgtgc tattattatg ttgttatacg actactaata 256920
accttttaat cccgtgatat atcgttagca caccttaaag attagaagaa atacaggtta 256980
gtgtaataat aacgtattat tatctagcac aaaaatgttt caaagggcgt gttattagat 257040
ttaaacgaag atagcgagta ctactgtgct gaaataataa caacgaatca ataattttac 257100
ttcgtttaac tttgtagtgg ttgtatagac tacggtataa taaaatagca aagtatcatc 257160
tcagggaatg caaatgacgt acgttgagaa tttaatatct agaatctgcg tttatacgtg 257220
acatcgagat attcgttatt actttgatta aaaatataaa ctatacggat tttctgttta 257280
caagaacgta caaaatacta ttgtataaaa aagaggtagt aaatctaacg catgtattcg 257340

-continued

```
gtataccaat gggtgtatct atcttcttta acacatatcg ttctttcgtg aaatatacaa 257400
gacatttcga taatgttact cgtgtcaaat aatagacaaa tatcattaac gccttgttca 257460
taatatagtg agaaattaat acccggaatt tttctatttt gatttatgtc tatccagtaa 257520
ctacccttac cgtatcgcga cacgaaattt agagtttcta tgttatcgaa ccttatcaat 257580
gaagaatcca taacatcgca tagttttttg ctatcattcc aattagtttc attgatagta 257640
aagtagtagc atttactatt atatcctatc cactcatcag gacataccct gctaaagtac 257700
ggaaacgcgt aataccattt gcatgttacg actactagta tcgtaaataa tattaagcat 257760
agtattccta gtaccgttat cgcgtaacaa gatacttccg atacctgttt ttttaacaat 257820
ataggcattg cggtcgtata ttgccagaat catttctgtt ttattatttt tccgtatttt 257880
gtatatacgc gtaaaaacac tgtatagcat ctatataaaa aacctaagaa aatagttatt 257940
cgtaatatat aaaatcagtc tgttgtttgt tatacgtaga aataaagttt aagagatatt 258000
ttcatgtaga ttttaatccg ttaacacgcg cagatttttt ggaaatagac gtccgttgta 258060
tactttaaac acgatttatc agcgcactaa ataaaataca aattttctta tgtataataa 258120
gtagagcaga tgtataatat tatactacga tcaaagtctt tcgaaagatg taacgtatta 258180
ataaatatat ccttacctca tgttacagca taatttcgat tgtagaacta acagtaaagg 258240
tattattttg ctaaaactat tacttcagtc gcttgtaaac aatacttgag attagttttt 258300
agaaaagtat taccattaat gttaatcaca gccatattca ttgtcttctt caagagctat 258360
attacctctt actatattaa ataactcttc gtaagacata ttacctagga tagtttgttt 258420
aacttctata ggcagagtat accagtcggg tgtacccact gacttagtat cataatcgat 258480
agaattaatc acctcgtgta ttaaatctgt ttttgtaggt aagtcgaaat agtacttaga 258540
taccgaacaa caaatatact ccgttctgct attacaaaac cctctcaaat ctttgtattc 258600
tttatgctct ttagaagaaa tagcttttaa cttttcgtaa agtacaggat ctataggtat 258660
aaaagacgtt cctgtttttt tatcaatagt agaccatata atatgtttct tatcaccagt 258720
ccaaatttca tccacttcat tcatgttata tatacataga gcatcgaaag atccatattc 258780
ttctttacgg tatctaacaa tactaccgtt atgatgagat tttatacatc tacctgatct 258840
atcagatatc attcctaggc tatattcttt atcttctgtc attctttcta ttaccatatc 258900
acaataacac aactgaagat cattttctct gtcatataaa tttatttttt tacctaagta 258960
ttctatgcta cctattacgt ttgttgacgc ggataacttt ttttctagta agacatcgaa 259020
taacgccacg cattttctac cgctttcaac ggtaatactt tcatgttcta tagttttatc 259080
aaatagatga tctgttttta atttcactga cgtattatta tcgatatata taaccgtttc 259140
acctcccgtt tctggttgtt ccaaatatag aagcaggtga acgcatatta tgtttttaga 259200
aaagacggta ctaaaatctc tatgcctggc aaagtaatct ccttttttcat acataatcaa 259260
tgtaacggta ttctctacgg taacggaatc tactaccgta cttaattcat catagatcaa 259320
ggcgtgtaat tttttaagca agtcatcgtt tagggagttt tcgaaaacta tttgtttaga 259380
tttacgatct ttaatactta agagctccgt tctcttttcc ggaaagaata ttttagaatc 259440
ctcgcatatg ttttttatat catttaagtc acttattcct aaattaacta aaagttcttt 259500
tttgaaagat gtaaaacgcg tttctgtaaa tctgtgaacg gccaactggt tattagttcc 259560
cgtacaaccg aactccatcg cgtaaatttg ttaaatgacc gccgtagcat cataataaat 259620
acgatttagt ttttatattt tttatatatg aataacgctt ataaaactag aatatattta 259680
```

-continued acaactgaaa agataattaa ttattatttt aacgtttatt tctattatct attataataa 259740
cgtaacacgc gcataaaaac gtcatcagat attttattat ttgaacggca tctacctaac 259800
gtatatcaga agagataaaa taattctata taaggatatt gagtacatat aaattaattt 259860
tttaaaactg aaaatataat caatttatta ccgagggcgt cctcgactat acgtcagcca 259920
tggctttaaa tctccgcgtt cgtccagtag aacaagagtc gggtataaag gtcttggcag 259980
ccgcgtcgga tcccttgaat tatgaaaatg atcacacggg cgacggaggc ttcgtcgcgc 260040
gagctatcag gaatatggaa ttctgtaggg ccagatacct atgcgccgct gccggcgata 260100
cagtgaaaat ctacttttg gaaggagaag gagaacttat ctactcggtg agccgagtgg 260160
gatctcccac agcggatagt ggatacgtga cgaggggcaa ctgcgtagag tttgaaaccg 260220
attcttcgtg ttttataaca ctgatgtgca ctagttccta taacacggtg gtttattgga 260280
tggaataaaa ggatacccgt cttccctctc ctccttcccc cctccccacg aacatatttt 260340
ttatttttac aataaaacaa agtaaatatc gtgtcattat tcatgatact ttagtaaaaa 260400
taaaatttct taatctttta taacgtaatt atcgtcttac gaaaagtaaa agctgttttg 260460
gtatataacc gtcgtcagaa cttaaagaag aattaataaa actaacgagg taacgtcgtc 260520
gacagagaat cacatggcaa ctcctctaga tttttattat gtataattga aaattaatcg 260580
cgtaactatt ggtggggtat atctctatag actattaaaa ttgatccgtg tatcaaaatg 260640
aaatcattaa tcttgatagc gatgttgtta atgttggatt gcgctaactc tctaaattgc 260700
agaggaccgt acacctctta caacaataag tgtatctggg taaaccgatt agataaaatg 260760
catcacaaaa aaacttacag cgaagcgtcg actacgtgtt tgataacgtt tcccatgggt 260820
acgttagcta gacgtagtct aatagacaat gaaaaagaca tgaaattcat aagcaaattc 260880
ggtatggggc agagtttgtg gataagggat gacaagaaac cagaagtggg taagtgtgcc 260940
tatacggacg ggaaaacgtt cggattctcc ccgtgtaacg cgacgtacgg tttcgtatgc 261000
atagattaat aatattcaaa acccgataac ttttaattta ttaacgatag attttttttt 261060
agcattagtt tttagtagga cgaacagcga ctttcttcat gagatataga aaagcgaacc 261120
tccaaaaatt tttcctcgcg taataaaacg ggactatatc cctaacgata ggaagcctat 261180
aggtcaccag tctgtgaaag agcatgagag cggctttagc gtaaagtttt tctccgatag 261240
ttttgataaa ggtccttaag aatcttaacc tatcccttac tctgatgaaa aagattgcgg 261300
tagacgccgt tttagaaatc gtattacgta gaatcgacag tttgttttta tcttgtattt 261360
ccttactcgc gttctcttta tcatcttcga ggcacgacga cgagcgcgat tcgtaataat 261420
acgagcgtat accttttggc gtccaatctc tttcatctac acgtcgcgat gcttcacgac 261480
gaaaagacct ttctcgatag cggagaaggt tcctcgggca ttctcggcga tcctgcgggg 261540
gcgatgaacc agtagaaaat ttttttagtg aaggtgtcgc acatcgtgcg aatacatctc 261600
ttgacgtaac aacacggaga ccatatccat acgcagagat cttcgcacca gtcgttgacc 261660
caggttcccc gtctggcggg atctcttgaa tctctaaacg ctcccggttc tcttactccg 261720
gtcagtctgc ctctatgcat tcttctcaac atcatgcaag gaaagaggag acacctcaag 261780
aaaacctcgc aagggcaaca gaaacaacga caccaagatt tagctaacgg gcagatggtt 261840
cttttacaga atcttctggt gagaacgcac ggtagcctaa tacagtcgca agtcgctttt 261900
agagtaggta atatcacgcg tctccagaac tctctgataa tcaatagagg aagcacgcaa 261960
cagtaacaac aactgtgttc cagagagtct aacgtctcgc tcatgcattc gcaacatact 262020
tcgaagggat acaagagaca gtggacgcat ttgcaagtgg cgggccttac cgagttacag 262080

-continued aggaaacatc gtagaaggca tagcggatac aataaccacg ccgctatttt ctctacgatc 262140
atatcggcgt ctcgatttaa cttctcgagc tctcgataaa aaaaagcttt tcgaaatctc 262200
gataaaaaag tttttctata actcgagctc tcgataaaaa agtttttcta taactcgagc 262260
tctcgataaa aaagtttttc tataactcga gctctcgata aaaaactttt tctataactc 262320
gagctctcga taaaaaaagc ttttcgaaat ctcgataaaa actttttcta taactcgagc 262380
tctcgataaa aaagtttttc tataactcga gctctcgata aaaaagcttt tcgaaatctc 262440
gataaaaact ttttctataa ctcgagctct cgataaaaaa gtttttctat aactcgagct 262500
ctcgataaaa aagcttttcg aaatctcgat aaaaactttt tctataactc gagctctcga 262560
taaaaaagtt tttctataac tcgagctctc gataaaaagt ttttctataa ctcgagctct 262620
cgataaaaaa aagcttttcg aaatctcgat aaaaaagttt ttctataact cgagctctcg 262680
ataaaaaagt ttttctataa ctcgagctct cgataaaaaa gcttttcgaa atctcgataa 262740
aaactttttc tataactcta gctctcgata aaaaagtttt tctataactc gagctctcga 262800
taaaaaagtt tttctataac tcgagctctc gataaaaaag tttttctata actcgagctc 262860
tcgataaaaa actttttcta taactcgagc tctcgataaa aaactttttc tataactcga 262920
gctctcgata aaaaaagctt ttcgaaatct cgataaaaac tttttctata actcgagctc 262980
tcgataaaaa agtttttcta taactcgagc tctcgataaa aaagcttttc gaaatctcga 263040
taaaaacttt ttctataact cgagctctcg ataaaaaagt ttttctataa ctcgagctct 263100
cgataaaaaa gcttttcgaa atctcgataa aaactttttc tataactcga gctctcgata 263160
aaaaagtttt tctataactc gagctctcga taaaaagttt ttctataact cgagctctcg 263220
ataaaaaaaa gcttttcgaa atctcgataa aaaagttttt ctataactcg agctctcgat 263280
aaaaaagttt ttctataact cgagctctcg ataaaaaagc ttttcgaaat ctcgataaaa 263340
actttttcta taactctagc tctcgataaa aaagtttttc tataactcga gctctcgata 263400
aaaaagtttt tctataactc gagctctcga taaaaaagtt tttctataac tcgagctctc 263460
gataaaaaag tttttctata actcgagctc tcgataaaaa actttttcta taactcgagc 263520
tctcgataaa aaaagctttt cgaaatctcg ataaaaactt tttctataac tcgagctctc 263580
gataaaaaag tttttctata actcgagctc tcgataaaaa agcttttcga aatctcgata 263640
aaaacttttt ctataactcg agctctcgat aaaaaagttt ttctataact cgagctctcg 263700
ataaaaaagc ttttcgaaat ctcgataaaa actttttcta taactcgagc tctcgataaa 263760
aaagtttttc tataactcga gctctcgata aaaaagcttt tcgaaatctc gataaaaact 263820
ttttctataa ctcgagctct cgataaaaaa gtttttctat aactcgagct ctcgataaaa 263880
agtttttcta taactcgagc tctcgataaa aaaaagcttt tcgaaatctc gataaaaaag 263940
tttttctata actcgagctc tcgataaaaa agtttttcta taactcgagc tctcgataaa 264000
aaagcttttc gaaatctcga taaaaacttt ttctataact ctagctctcg ataaaaaagt 264060
ttttctataa ctcgagctct cgataaaaaa gtttttctat aactcgagct ctcgataaaa 264120
aagtttttct ataactcgag ctctcgataa aaaagttttt ctataactcg agctctcgat 264180
aaaaaacttt ttctataact cgagctctcg ataaaaaaag cttttcgaaa tctcgataaa 264240
aactttttct ataactcgag ctctcgataa aaaagttttt ctataactcg agctctcgat 264300
aaaaaagctt ttcgaaatct cgataaaaac tttttctata actcgagctc tcgataaaaa 264360
agtttttcta taactcgagc tctcgataaa aaagcttttc gaaatctcga taaaaacttt 264420

-continued

```
ttctataact cgagctctcg ataaaaaagt ttttctataa ctcgagctct cgataaaaag 264480

tttttctata actcgagctc tcgataaaaa aaagcttttc gaaatctcga taaaaaagtt 264540

tttctataac tcgagctctc gataaaaaag tttttctata actcgagctc tcgataaaaa 264600

agcttttcga aatctcgata aaaacttttt ctataactcg agctctcgat aaaaaagttt 264660

ttctataact cgagctctcg ataaaaagtt tttctataac tcgagctctc gataaaaaaa 264720

agcttttcga aatctcgata aaaaagtttt tctataactc gagctctcga taaaaaagtt 264780

tttctataac tcgagctctc gataaaaaag cttttcgaaa tctcgataaa aactttttct 264840

ataactctag ctctcgataa aaaagttttt ctataactcg agctctcgat aaaaaagttt 264900

ttctataact cgagctctcg ataaaaaagt ttttctataa ctcgagctct cgataaaaaa 264960

gtttttctat aactcgagct ctcgataaaa aacttttttct ataactcgag ctctcgataa 265020

aaaaagcttt tcgaaatctc gataaaaact ttttctataa ctcgagctct cgataaaaaa 265080

aagcttttcg aaatctcgat aaaaaagttt ttctataact cgagctctcg ataaaaaagt 265140

ttttctataa ctcgagctct cgataaaaaa gcttttcgaa atctcgataa aaactttttc 265200

tataactcta gctctcgata aaaaagtttt tctataactc gagctctcga taaaaaagtt 265260

tttctataac tcgagctctc gataaaaaag tttttctata actcgagctc tcgataaaaa 265320

agtttttcta taactcgagc tctcgataaa aaactttttc tataactcga gctctcgata 265380

aaaaaagctt ttcgaaatct cgataaaaac tttttctata actcgagctc tcgataaaaa 265440

agtttttcta taactcgagc tctcgataaa aaagcttttc gaaatctcga taaaaacttt 265500

ttctataact cgagctctcg ataaaaaagt ttttctataa ctcgagctct cgataaaaaa 265560

gcttttcgaa atctcgataa aaactttttc tataactcga gctctcgata aaaaagtttt 265620

tctataactc gagctctcga taaaaagttt ttctataact cgagctctcg ataaaaaaaa 265680

gcttttcgaa atctcgataa aaaagttttt ctataactcg agctctcgat aaaaaagttt 265740

ttctataact cgagctctcg ataaaaaagc ttttcgaaat ctcgataaaa actttttcta 265800

taactctagc tctcgataaa aaagtttttc tataactcga gctctcgata aaaaagcttt 265860

tcgaaatctc gataaaaact ttttctataa ctcgagctct cgataaaaaa gtttttcgct 265920

aacgttgggt agctttataa aatattttcc ggaaggaaat tagatatagt attattttat 265980

gtaaaaccgt atggtttttt ttattaaaac aataatatat attttaatag ggggtatttt 266040

acaccttaac aaattaaggg gtaaaagaat gtgtatatta gggttttgga aggtactgtt 266100

tatacatttt ttttactata taaatactca tcgtaagatg agggt                266145
```

<210> SEQ ID NO 2
<211> LENGTH: 98
<212> TYPE: DNA
<213> ORGANISM: Unknown
<220> FEATURE:
<223> OTHER INFORMATION: Fowlpox Orf1 gene bases deleted from pEFL29

<400> SEQUENCE: 2

```
agagatcccg ccagacgggg aacctgggtc aacgactggt gcgaagatct ctgcgtatgg     60

atatggtctc cgtgttgtta cgtcaagaga tgtattcg                             98
```

<210> SEQ ID NO 3
<211> LENGTH: 17
<212> TYPE: DNA
<213> ORGANISM: Unknown
<220> FEATURE:
<223> OTHER INFORMATION: Deletion in fowlpox virus genome -continued

<400> SEQUENCE: 3
actggtgcga agatctc 17

<210> SEQ ID NO 4
<211> LENGTH: 9
<212> TYPE: PRT
<213> ORGANISM: Artificial Sequence
<220> FEATURE:
<223> OTHER INFORMATION: P1A epitope

<400> SEQUENCE: 4

Leu Pro Tyr Leu Gly Trp Leu Val Phe
1 5

<210> SEQ ID NO 5
<211> LENGTH: 10
<212> TYPE: PRT
<213> ORGANISM: Artificial Sequence
<220> FEATURE:
<223> OTHER INFORMATION: MSR epitope

<400> SEQUENCE: 5

Gly Tyr Cys Gly Leu Arg Gly Thr Gly Val
1 5 10

<210> SEQ ID NO 6
<211> LENGTH: 9
<212> TYPE: PRT
<213> ORGANISM: Artificial Sequence
<220> FEATURE:
<223> OTHER INFORMATION: CT26 epitope

<400> SEQUENCE: 6

Ser Pro Ser Tyr Ala Tyr His Gln Phe
1 5

<210> SEQ ID NO 7
<211> LENGTH: 11
<212> TYPE: PRT
<213> ORGANISM: Artificial Sequence
<220> FEATURE:
<223> OTHER INFORMATION: LMCV1 epitope

<400> SEQUENCE: 7

Lys Ala Val Tyr Asn Phe Ala Thr Cys Gly Ile
1 5 10

<210> SEQ ID NO 8
<211> LENGTH: 9
<212> TYPE: PRT
<213> ORGANISM: Artificial Sequence
<220> FEATURE:
<223> OTHER INFORMATION: LMCV2 epitope

<400> SEQUENCE: 8

Phe Gln Pro Gln Asn Gly Gln Phe Ile
1 5

<210> SEQ ID NO 9
<211> LENGTH: 11
<212> TYPE: PRT
<213> ORGANISM: Artificial Sequence
<220> FEATURE:
<223> OTHER INFORMATION: LMCV3 epitope

<400> SEQUENCE: 9

-continued

Ser Gly Val Glu Asn Pro Gly Gly Tyr Cys Leu
 1               5                   10

<210> SEQ ID NO 10
<211> LENGTH: 8
<212> TYPE: PRT
<213> ORGANISM: Artificial Sequence
<220> FEATURE:
<223> OTHER INFORMATION: LMCV4 epitope

<400> SEQUENCE: 10

Tyr Thr Val Lys Tyr Pro Asn Leu
 1               5

<210> SEQ ID NO 11
<211> LENGTH: 10
<212> TYPE: PRT
<213> ORGANISM: Artificial Sequence
<220> FEATURE:
<223> OTHER INFORMATION: LMCV5 epitope

<400> SEQUENCE: 11

Cys Ser Ala Asn Asn Ser His His Tyr Ile
 1               5                   10

<210> SEQ ID NO 12
<211> LENGTH: 20
<212> TYPE: PRT
<213> ORGANISM: Artificial Sequence
<220> FEATURE:
<223> OTHER INFORMATION: LMCV6 epitope

<400> SEQUENCE: 12

Gly Leu Asn Gly Pro Asp Ile Tyr Lys Gly Val Tyr Gln Phe Lys Ser
 1               5                   10                  15

Val Glu Phe Asp
            20

<210> SEQ ID NO 13
<211> LENGTH: 20
<212> TYPE: PRT
<213> ORGANISM: Artificial Sequence
<220> FEATURE:
<223> OTHER INFORMATION: LMCV7 epitope

<400> SEQUENCE: 13

Ser Gly Glu Gly Trp Pro Tyr Ile Ala Cys Arg Thr Ser Ile Val Gly
 1               5                   10                  15

Arg Ala Trp Glu
            20

<210> SEQ ID NO 14
<211> LENGTH: 8
<212> TYPE: PRT
<213> ORGANISM: Artificial Sequence
<220> FEATURE:
<223> OTHER INFORMATION: 8 B-gal epitope

<400> SEQUENCE: 14

Asp Ala Pro Ile Tyr Thr Asn Val
 1               5

<210> SEQ ID NO 15
<211> LENGTH: 9
<212> TYPE: PRT

-continued

```
<213> ORGANISM: Artificial Sequence
<220> FEATURE:
<223> OTHER INFORMATION: B-gal Model epitope

<400> SEQUENCE: 15

Thr Pro His Pro Ala Arg Ile Gly Leu
 1               5


<210> SEQ ID NO 16
<211> LENGTH: 9
<212> TYPE: PRT
<213> ORGANISM: Artificial Sequence
<220> FEATURE:
<223> OTHER INFORMATION: HA tag epitope

<400> SEQUENCE: 16

Tyr Pro Tyr Asp Val Pro Asp Tyr Ala
 1               5


<210> SEQ ID NO 17
<211> LENGTH: 20
<212> TYPE: PRT
<213> ORGANISM: Artificial Sequence
<220> FEATURE:
<223> OTHER INFORMATION: epitope

<400> SEQUENCE: 17

Gly Leu Asn Gly Pro Asp Ile Tyr Lys Gly Val Tyr Gln Phe Lys Ser
 1               5                  10                  15

Val Glu Phe Asp
            20


<210> SEQ ID NO 18
<211> LENGTH: 11
<212> TYPE: PRT
<213> ORGANISM: Artificial Sequence
<220> FEATURE:
<223> OTHER INFORMATION: epitope

<400> SEQUENCE: 18

Lys Ala Val Tyr Asn Phe Ala Thr Cys Gly Ile
 1               5                  10


<210> SEQ ID NO 19
<211> LENGTH: 9
<212> TYPE: PRT
<213> ORGANISM: Artificial Sequence
<220> FEATURE:
<223> OTHER INFORMATION: epitope

<400> SEQUENCE: 19

Leu Pro Tyr Leu Gly Trp Leu Val Phe
 1               5


<210> SEQ ID NO 20
<211> LENGTH: 9
<212> TYPE: PRT
<213> ORGANISM: Artificial Sequence
<220> FEATURE:
<223> OTHER INFORMATION: epitope

<400> SEQUENCE: 20

Phe Gln Pro Gln Asn Gly Gln Phe Ile
 1               5


<210> SEQ ID NO 21
```

-continued

<211> LENGTH: 10
<212> TYPE: PRT
<213> ORGANISM: Artificial Sequence
<220> FEATURE:
<223> OTHER INFORMATION: epitope

<400> SEQUENCE: 21

Gly Tyr Cys Gly Leu Arg Gly Thr Gly Val
1 5 10

<210> SEQ ID NO 22
<211> LENGTH: 11
<212> TYPE: PRT
<213> ORGANISM: Artificial Sequence
<220> FEATURE:
<223> OTHER INFORMATION: epitope

<400> SEQUENCE: 22

Ser Gly Val Glu Asn Pro Gly Gly Tyr Cys Leu
1 5 10

<210> SEQ ID NO 23
<211> LENGTH: 9
<212> TYPE: PRT
<213> ORGANISM: Artificial Sequence
<220> FEATURE:
<223> OTHER INFORMATION: epitope

<400> SEQUENCE: 23

Ser Pro Ser Tyr Ala Tyr His Gln Phe
1 5

<210> SEQ ID NO 24
<211> LENGTH: 9
<212> TYPE: PRT
<213> ORGANISM: Artificial Sequence
<220> FEATURE:
<223> OTHER INFORMATION: epitope

<400> SEQUENCE: 24

Thr Pro His Pro Ala Arg Ile Gly Leu
1 5

<210> SEQ ID NO 25
<211> LENGTH: 10
<212> TYPE: PRT
<213> ORGANISM: Artificial Sequence
<220> FEATURE:
<223> OTHER INFORMATION: epitope

<400> SEQUENCE: 25

Cys Ser Ala Asn Asn Ser His His Tyr Ile
1 5 10

<210> SEQ ID NO 26
<211> LENGTH: 20
<212> TYPE: PRT
<213> ORGANISM: Artificial Sequence
<220> FEATURE:
<223> OTHER INFORMATION: epitope

<400> SEQUENCE: 26

Ser Gly Glu Gly Trp Pro Tyr Ile Ala Cys Arg Thr Ser Ile Val Gly
1 5 10 15

Arg Ala Trp Glu
20

-continued

<210> SEQ ID NO 27
<211> LENGTH: 8
<212> TYPE: PRT
<213> ORGANISM: Artificial Sequence
<220> FEATURE:
<223> OTHER INFORMATION: epitope

<400> SEQUENCE: 27

Asp Ala Pro Ile Tyr Thr Asn Val
1 5

<210> SEQ ID NO 28
<211> LENGTH: 9
<212> TYPE: PRT
<213> ORGANISM: Artificial Sequence
<220> FEATURE:
<223> OTHER INFORMATION: epitope

<400> SEQUENCE: 28

Tyr Pro Tyr Asp Val Pro Asp Tyr Ala
1 5

<210> SEQ ID NO 29
<211> LENGTH: 146
<212> TYPE: PRT
<213> ORGANISM: Artificial Sequence
<220> FEATURE:
<223> OTHER INFORMATION: Amino acid string sequence

<400> SEQUENCE: 29

Met Gly Leu Asn Gly Pro Asp Ile Tyr Lys Gly Val Tyr Gln Phe Lys
1 5 10 15

Ser Val Glu Phe Asp Lys Ala Val Tyr Asn Phe Ala Thr Cys Gly Ile
20 25 30

Leu Pro Tyr Leu Gly Trp Leu Val Phe Phe Gln Pro Gln Asn Gly Gln
35 40 45

Phe Ile Gly Tyr Cys Gly Leu Arg Gly Thr Gly Val Ser Gly Val Glu
50 55 60

Asn Pro Gly Gly Tyr Cys Leu Ser Pro Ser Tyr Ala Tyr His Gln Phe
65 70 75 80

Tyr Thr Val Lys Tyr Pro Asn Leu Thr Pro His Pro Ala Arg Ile Gly
85 90 95

Leu Cys Ser Ala Asn Asn Ser His His Tyr Ile Ser Gly Glu Gly Trp
100 105 110

Pro Tyr Ile Ala Cys Arg Thr Ser Ile Val Gly Arg Ala Trp Glu Asp
115 120 125

Ala Pro Ile Tyr Thr Asn Val Tyr Pro Tyr Asp Val Pro Asp Tyr Ala
130 135 140

Ala Ala
145

<210> SEQ ID NO 30
<211> LENGTH: 19
<212> TYPE: DNA
<213> ORGANISM: Artificial Sequence
<220> FEATURE:
<223> OTHER INFORMATION: Flanking sequence

<400> SEQUENCE: 30
gggcccgccg ccaccatgg 19

-continued

<210> SEQ ID NO 31
<211> LENGTH: 33
<212> TYPE: PRT
<213> ORGANISM: Artificial Sequence
<220> FEATURE:
<223> OTHER INFORMATION: String sequence

<400> SEQUENCE: 31

```
Met Gly Leu Asn Gly Pro Asp Ile Tyr Lys Gly Val Tyr Gln Phe Lys
 1               5                  10                  15

Ser Val Glu Phe Asp Lys Ala Val Tyr Asn Phe Ala Thr Cys Gly Ile
            20                  25                  30

Leu
```

<210> SEQ ID NO 32
<211> LENGTH: 57
<212> TYPE: PRT
<213> ORGANISM: Artificial Sequence
<220> FEATURE:
<223> OTHER INFORMATION: String sequence

<400> SEQUENCE: 32

```
Pro Tyr Leu Gly Trp Leu Val Phe Phe Gln Pro Gln Asn Gly Gln Phe
 1               5                  10                  15

Ile Gly Tyr Cys Gly Leu Arg Gly Thr Gly Val Ser Gly Val Glu Asn
            20                  25                  30

Pro Gly Gly Tyr Cys Leu Ser Pro Ser Tyr Ala Tyr His Gln Phe Tyr
        35                  40                  45

Thr Val Lys Tyr Pro Asn Leu Thr Pro
    50                  55
```

<210> SEQ ID NO 33
<211> LENGTH: 41
<212> TYPE: PRT
<213> ORGANISM: Artificial Sequence
<220> FEATURE:
<223> OTHER INFORMATION: String sequence

<400> SEQUENCE: 33

```
His Pro Ala Arg Ile Gly Leu Cys Ser Ala Asn Asn Ser His His Tyr
 1               5                  10                  15

Ile Ser Gly Glu Gly Trp Pro Tyr Ile Ala Cys Arg Thr Ser Ile Val
            20                  25                  30

Gly Arg Ala Trp Glu Asp Ala Pro Ile
        35                  40
```

<210> SEQ ID NO 34
<211> LENGTH: 15
<212> TYPE: PRT
<213> ORGANISM: Artificial Sequence
<220> FEATURE:
<223> OTHER INFORMATION: Flanking sequence

<400> SEQUENCE: 34

```
Tyr Thr Asn Val Tyr Pro Tyr Asp Val Pro Asp Tyr Ala Ala Ala
 1               5                  10                  15
```

<210> SEQ ID NO 35
<211> LENGTH: 7
<212> TYPE: DNA
<213> ORGANISM: Artificial Sequence
<220> FEATURE:
<223> OTHER INFORMATION: Pox virus early gene transcription termination
      sequence -continued <220> FEATURE:
<221> NAME/KEY: misc_feature
<222> LOCATION: (6)...(6)
<223> OTHER INFORMATION: n is any base

<400> SEQUENCE: 35 tttttnt 7

<210> SEQ ID NO 36
<211> LENGTH: 19
<212> TYPE: DNA
<213> ORGANISM: Artificial Sequence
<220> FEATURE:
<223> OTHER INFORMATION: Del 10.17bp deleted in FP9

<400> SEQUENCE: 36
atgttattat tcctgatag 19

<210> SEQ ID NO 37
<211> LENGTH: 25
<212> TYPE: DNA
<213> ORGANISM: Artificial Sequence
<220> FEATURE:
<223> OTHER INFORMATION: Del 12.23bp in FPV

<400> SEQUENCE: 37
attagatagt atctgtttaa aagat 25

<210> SEQ ID NO 38
<211> LENGTH: 5
<212> TYPE: DNA
<213> ORGANISM: Artificial Sequence
<220> FEATURE:
<223> OTHER INFORMATION: Del 14.3bp in FPV

<400> SEQUENCE: 38 taacg 5

<210> SEQ ID NO 39
<211> LENGTH: 4
<212> TYPE: DNA
<213> ORGANISM: Artificial Sequence
<220> FEATURE:
<223> OTHER INFORMATION: Del 16.2bp in FPV

<400> SEQUENCE: 39 tatc 4

<210> SEQ ID NO 40
<211> LENGTH: 11
<212> TYPE: DNA
<213> ORGANISM: Artificial Sequence
<220> FEATURE:
<223> OTHER INFORMATION: Flanking sequence

<400> SEQUENCE: 40
taaggcgcgc c 11

<210> SEQ ID NO 41
<211> LENGTH: 8
<212> TYPE: PRT
<213> ORGANISM: Unknown
<220> FEATURE:
<223> OTHER INFORMATION: epitope -continued

```
<400> SEQUENCE: 41

Tyr Thr Val Lys Tyr Pro Asn Leu
 1               5
```

VACCINE

RELATED APPLICATION(S)

This is a continuation of International Application No. PCT/GB02/05411, which designated the United States and was filed on Dec. 2, 2002, published in English, which claims the benefit of U.S. Provisional Application No. 60/334,649, filed on Nov. 30, 2001, and claims priority under 35 U.S.C. § 119 or 365 to Great Britain, Application No. 0128733.3, filed Nov. 30, 2001. The entire teachings of the above application(s) are incorporated herein by reference.

BACKGROUND OF THE INVENTION

Poxviruses

Poxviruses have been previously exploited as recombinant vectors for the heterologous expression of foreign proteins. In particular, recombinant vaccinia virus has been studied as a tool for transient expression of genes in mammalian cells and an experimental recombinant vaccine vector (reviewed by Moss, 1991*, Proc. Natl. Acad. Sci., USA* 93, 11341-8; and Moss, 1996*, Proc. Natl. Acad. Sci., USA* 93, 11341-8).

In common with the other poxviruses, vaccinia virus resides within the cell cytoplasm where it expresses the proteins needed for viral replication. Recombinant vaccinia can, therefore, deliver foreign antigens to the cytoplasm of mammalian cells, thereby allowing them direct access to antigen processing pathways which leads to presentation of antigen derived peptides in association with MHC Class I and Class II molecules on the cell surface (Moss, 1991*, Proc. Natl. Acad. Sci., USA* 93, 11341-8). This property makes vaccinia useful as recombinant vaccines, particularly for stimulating CD8+ and CD4+ T-cell immune responses.

Concern about the capacity of vaccinia virus to replicate in mammalian cells has limited its clinical use and led to the search for safer alternatives. These include attenuated vaccinia viruses, such as modified vaccinia Ankara (MVA) (Meyer et al, 1991*, J. Gen. Virol*. 72, 1031-8; Sutter and Moss, 1992*, Proc. Natl. Acad. Sci., USA* 89, 10847-51; Sutter et al, 1994*, Vaccine* 12, 1032-40), which undergoes limited replication in human cells (Blanchard et al, 1998*, J. Gen. Virol*. 79, 1159-67), and the avipox viruses, such as fowlpox, which do not proliferate in mammalian cells (Somogyi et al, 1993*, Virology* 197, 439-44).

Wild-type fowlpox viruses, which cause proliferative skin lesions that are rarely lethal in birds, are of commercial concern in the poultry industry. Live attenuated vaccines against fowlpox virus have been produced by multiple passage of the virus in avian cells. Such attenuated fowlpox viruses expressing antigens from poultry pathogens have been extensively exploited as recombinant vaccines for avian use (reviewed by Boyle and Heine, 1993*, Immunol Cell Biol* 71, 391-7; Paoletti, 1996*, Proc. Natl. Acad. Sci., USA* 93, 11349-53). In fact, two recombinant fowlpox viruses expressing antigens from Newcastle's disease virus are commercially available for veterinary use in the USA (Paoletti, 1996*, Proc. Natl. Acad. Sci., USA* 93, 11349-53).

The observation that avipox viruses can express antigens in mammalian cells and can induce a protective immune response against mammalian pathogens (Taylor and Paoletti, 1998*, Vaccine* 6, 466-8; Taylor et al, 1998*a, Vaccine* 6, 504-8; Taylor et al, 1988*b, Vaccine* 6, 497-503), led to the development of recombinant fowlpox viruses as vaccines for use in mammals. Most significantly, recombinant fowlpox expressing antigens from HIV have shown promise as vaccines in non-human primates (Dale et al, 2000*, J Med Primatol* 29, 240-7; Kent et al, 1988*, J Virol* 72, 10180-8; Kent et al, 2000*, Vaccine* 18, 2250-6). In addition, recombinant fowlpox vaccines encoding tumour-associated antigens have been evaluated in animals (Grosenbach et al, 2001*, Cancer Res* 61, 4497-505; Irvine et al, 1997*, J Natl Cancer Inst* 89, 1595-601; Wang et al, 1995*, J Immunol* 154, 4685-92) and are presently undergoing human clinical trials.

The majority of attenuated fowlpox vaccine strains are not fully defined in terms of their genome organisation and exact sequence. In fact, the genomes of some have recently been found to carry an infectious copy of the provirus of avian reticuloendotheliosis virus (REV) (Hertig et al, 1997*, Virology* 235, 367-76) which may limit their use as recombinant vectors.

There is an upper limit on genome size for vectors derived from pox viruses. For vaccinia, it is thought that the maximum size of heterologous sequence that can be effectively packaged and delivered is 10% of the size of the genome.

Thus there is a need for an improved vector system, which lacks the capacity to replicate in mammalian cells, but which is better characterised, is better at eliciting T-cell immune responses, has an improved capacity to accommodate and deliver heterologous DNA and/or has improved safety over known attenuated fowlpox vaccine strains.

Vaccination Strategies

There are numerous methods known in the art to stimulate an immune response in a subject in order to prevent and/or treat a disease. Examples of antigenic preparations used as vaccines are shown in the following table (Table 1).

TABLE 1

| Type of antigen | | Vaccine examples |
|---|---|---|
| Living organisms | Natural | Vaccinia (for small pox)<br>Vole bacillus (for TB) |
| | attenuated | Polio (Sabin; oral polio vaccine)<br>Measles, mumps, rubella, yellow fever 17d<br>Varicella-zoster (human herpes virus 3)<br>BCG (for TB) |
| Intact but non-living organisms | viruses | Polio (Salk), rabies, influenza, hepatitis A,<br>typhus |
| | bacteria | Pertussis, typhoid, cholera, plague |
| Subcellular fragments | Capsular polysaccharides | Pneumococcus, meningococcus, *Haemophilus influenzae* |
| | Surface antigen | Hepatitis B |
| Toxoids | | Tetanus, diphtheria |
| Recombinant DNA-Based | Gene cloned and expressed | Hepatitis B (yeast derived) |
| | Gene expressed in vectors | |
| | Naked DNA | |
| Anti-idiotype | | |

There are also other types of non-antigen based immunisation, which include passive immunisation (the direct administration of antibodies) and non-specific immunisation (such ad by the administration or cytokines or cytokine inhibitors).

A problem with many of these approaches is that the immune response wanes over time, such that it is no longer effective, for example in controlling or eradicating an infection.

It is important that a vaccine induces the right sort of immune response for the disease. Many known vaccines are useful for generating antibodies, but do not induce significant cell-mediated immune responses. A number of diseases are particularly susceptible to prevention and/or treatment by a T cell immune response. For example, cytolytic CD8+ T cells may protect against or help to clear viral infections. Also, in the case of diseases such as tuberculosis, malaria and *H. pylori* infection there is evidence for a protective role for CD4+ T cells which can secrete IFNγ.

Some known viral vaccination strategies are associates with a number of complications and side effects. For example smallpox vaccination can cause generalised vaccinia, eczema vaccinatum, progressive vaccinia, and neurological and cardiac complications (Feery (1977) *Med J. Aust* 6 180-183; Goldstein et al (1975) *Pediatrics*, 55, 342-7).

There is thus need for improved vaccination strategies, particularly those capable of stimulating or boosting the T-cell arm of the immune system which cause a minimum of adverse reactions.

SUMMARY OF THE INVENTION

The present inventors have obtained the full genomic sequence of an attenuated fowlpox virus strain (FP9).

FP9 lacks (or has modifications in) a number of genes present in wild-type fowlpox virus (FPV). The genome of FP9 is 266 kbp, which is smaller than the genome for FPV-M, a fowlpox vaccine strain which has previously been described as a vector system (Coupar et al (1990) *Virology*, 179, 159-167). The present inventors have shown that FP9 is superior to FPV-M is its capacity to elicit CD8+ T-cell immune responses.

Thus the present invention provides an attenuated Fowlpox virus genome which has a modified form of one or more of the following wild-type FPV genes (gene nomenclature according to Afonso et al (2000) *J. Virol*., 74, 3815-3831):

FPV001, FPV018, FPV054, FPV063, FPV066, FPV070, FPV071, FPV093, FPV097/098, FPV115, FPV 124, FPV125, FPV127, FPV158, FPV159, FPV160, FPV190, FPV191, FPV207, FPV219, FPV220, FPV221, FPV222, FPV239, FPV241, FPV242, FPV243, FPV244, FPV245, FPV246, FPV247, FPV260.

The present invention also provides a method for attenuating fowlpox comprising modifying one or more of said genes. Preferably said genes are modified as described in more detail below.

The present invention also provides an attenuated fowlpox virus genome which is less than 275 kbp in size. There is an upper limit on the total size of genome which can be efficiently packaged by the virus. If the genome itself is small, the larger the amount of heterologous sequence it can carry.

In a preferred embodiment, the attenuated Fowlpox virus genome comprises the sequence shown in SEQ ID No.: 1.

The attenuated Fowlpox genome of the present invention may also comprise a nucleotide of interest "NOI". The "NOI" may be a therapeutic gene.

The present invention also provides a viral particle which comprises such a genome. Where the genome comprises an NOI, preferably the viral particle is capable of delivering the NOI to a target cell. Alternatively (or in addition) the viral particle may be capable of delivering a pre-expressed protein to a target cell.

The present invention also provides a vaccine, priming or boosting agent comprising such a genome or viral particle.

The present invention also provides a boosting composition comprising a non-replicating viral vector. In a preferred embodiment, the composition is capable of boosting the immune response primed by *M. bovis* BCG in primates.

For vaccination (and treatment) purposes, multiple-dose procedures are often more effective at generating an immune response than a single administration of vaccine. Prime-boost regimes may be homologous (where the same composition is administered two or more times) or heterologous.

The present invention also provides a vaccination kit which comprises:

(i) a first composition which comprises an FP9 fowlpox viral particle; and (ii) a second composition for simultaneous, separate or sequential administration.

The use of viral vectors in heterologous vaccination regimes where either the priming or boosting agent is a DNA-vaccine has previously been recognised (Schneider et al (1998) *Nature Medicine* 4(4) 397-402; Kent et al (1998) *J. Gen. Virol* 72(12) 10180-8; Robinson et al (1999) *Nature Medicine* 5(5): 526-534).

However, the present inventors have shown for the first time that heterologous prime boost regimes using two different non-replicating viral vectors are surprisingly effective at inducing a T cell immune response in primates. The use of non-replicating vectors avoids the adverse reactions associated with replicating virus (such as smallpox, see above).

Thus the present invention also provides a vaccination kit which comprises:

(i) a first composition which comprises a first non-replicating viral vector;

(ii) a second composition which comprises a second non-replicating viral vector for sequential administration in either order.

In a preferred embodiment the vaccination kit comprises:

(i) a first composition which comprises a first non-replicating poxvirus vector;

(ii) a second composition which comprises a second non-replicating poxvirus vector for sequential administration in either order.

The kit may be suitable for administration to a primate subject in order to treat and/or prevent a disease.

In the kits of the present invention, preferably the first and second compositions are capable of expressing the same antigen.

The present invention also provides a vaccination method which comprises the step of administering such a vaccine, priming or boosting composition or kit to a subject. Such administration should elicit a T-cell immune response in the subject.

The vaccination method may be used to treat or prevent, for example, diseases caused by or due to a chronic infection such as HIV, malaria, tuberculosis and East Coast Fever.

When one or more of the genome, viral particle, vaccine, priming agent/composition, boosting agent/composition, construct or kit (s) of the present invention involve or are at least in part derived from HIV, then said genome, viral particle, vaccine, priming agent/composition, boosting agent/composition, construct or kit (s) are not those disclosed in WO 02/068654 (corresponding to PCT/CU02/00001). In particular, the present invention does not involve the recombinant CR3 gene as described in WO 02/068654 such as in Example 1 of WO 02/068654.

BRIEF DESCRIPTION OF THE DRAWINGS

FIGS. 1A-1E: Annotated genome of FP9.

FIG. 2: A table showing the genes modified in FP9 during its passage in CEF tissue culture from HP1.

FIG. 13 shows two bar charts.

FIG. 16A depicts the summed epitope-specific responses and the response elicited against phytohemagglutinin (PHA) for each group, whereas FIG. 16B depicts the response against individual epitopes.

FIG. 17A depicts the summed epitope-specific responses and the response elicited against phytohemagglutinin (PHA) as a positive control for each group, whereas FIG. 17B depicts the response against individual epitopes. The legend of FIG. 17B indicates immunodominant (DOM) and subdominant (SUB) epitopes that are recognised by CD8+ T cells, as well as those recognised by CD4+ T cells (CD4).

FIGS. 19A-19Z, 19A2-19Z2, 19A3-19U3 show the annotated Fowlpox virus genome (SEQ ID NO.: 1).

DETAILED DESCRIPTION OF THE INVENTION

Figure 3:
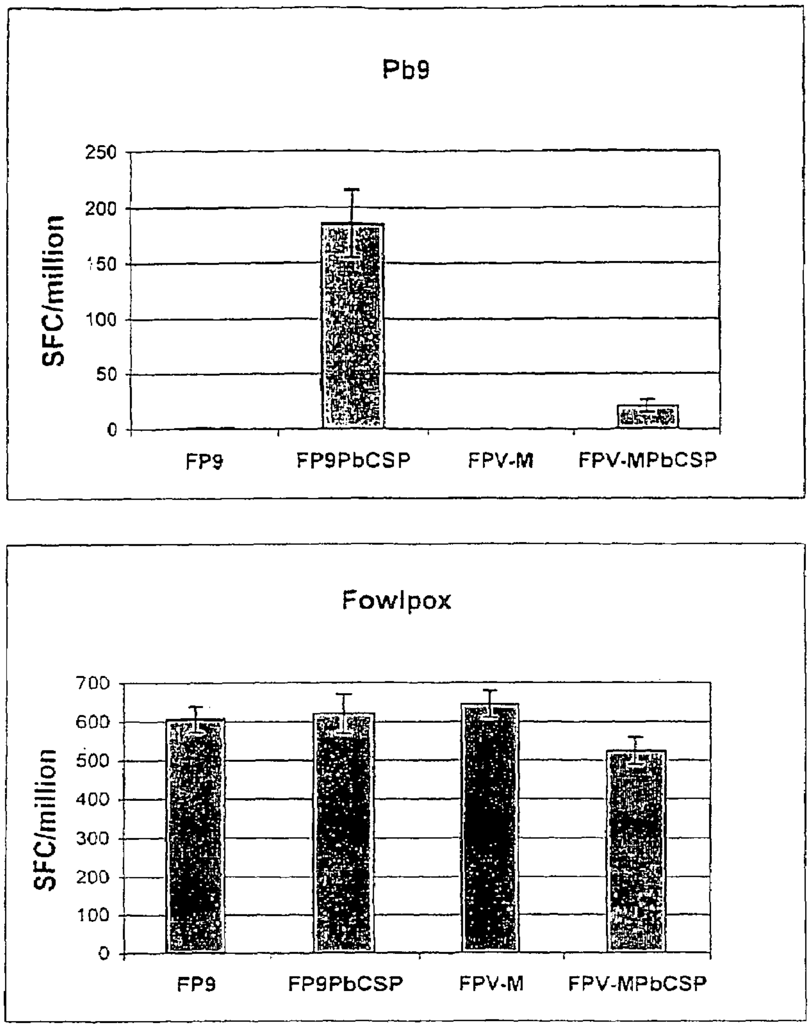
FIG. 3: Comparison of the T-cell immune response elicited by recombinant FP9 and FPV-M.

The present invention relates to pox viruses. In particular, the present invention relates to a fowlpox virus genome which has a modification in one or more wild-type FPV genes, a viral particle comprising such a genome, and its use to deliver a nucleotide of interest ("NOT") to a target cell.

The present invention also relates to vaccination methods using viral vectors, in particular heterologous prime-boost vaccination regimes employing two different nonreplicating viral vector compositions.

Viruses and Viral Vectors

The present invention relates to vaccination regimes using non-replicating viral vectors.

Many viral vectors are known in the art which are capable of delivering an NOI via infection of a target cell. Suitable recombinant viral vectors include but are not limited to adenovirus vectors, adeno-associated viral (AAV) vectors, herpes-virus vectors, retroviral vectors, lentiviral vectors, baculoviral vectors, poxviral vectors or parvovirus vectors (see Kestler et al., 999 *Human Gene Ther*. 10(10):1619-32).

Examples of retroviruses include but are not limited to: murine leukemia virus (MLV), human immunodeficiency virus (HIV), equine infectious anaemia virus (EIAV), mouse mammary tumour virus (MMTV), Rous sarcoma virus (RSV), Fujinami sarcoma virus (FuSV), Moloney murine leukemia virus (Mo-MLV), FBR murine osteosarcoma virus (FBR MSV), Moloney murine sarcoma virus (Mo-MSV), Abelson murine leukemia virus (A-MLV), Avian myelocytomatosis virus-29 (MC29), and Avian erythroblastosis virus (AEV).

A detailed list of retroviruses may be found in Coffin et al., ("*Retroviruses*" 1997 Cold Spring Harbour Laboratory Press Eds: J M Coffin, S M Hughes, H E Varrnus pp 758763).

Poxviruses

In a preferred embodiment the present invention provides a vaccine, priming or boosting composition which comprises a non-replicating pox virus vector.

The family of poxviruses can be split into two subfamilies, the *Chordopoxvirinae* and the *Entomopoxviriniae*. The *Chordopoxvirinae* (poxviruses of vertebrates) include orthopoxviruses, parapoxviruses, avipoxviruses, caripoxviruses, leporipoxviruses, suipoxviruses, molluscipoxviruses and yatapoxviruses. A review of poxviruses, their structure and organisation, biological and antigenic properties is given in Murphy et al., (1995) *Virus Taxonomy* Springer Verlag, Vienna pp79-87. The following table (Table 2) gives some examples of species within each genus of the pox virus family.

TABLE 2

| Genus | Species |
| --- | --- |
| Orthopoxvirus | buffalopox virus, camelpox virus, cowpox virus, ectromelia virus, monkeypox virus, rabbitpox virus, raccoonpox virus, teterapox virus, vaccinia virus, variola virus, voleopox virus, skunkpox virus, Uasin Gishu disease virus |
| Parapoxvirus | bovine papular stomatis virus, orf virus, parapoxvirus of red deer in New Zealand, pseudocowpox virus, Auzduk disease virus, chamois contagious ecthyma, sealpox virus |

TABLE 2-continued

| Genus | Species |
|---|---|
| Avipoxvirus | canarypox virus, fowlpox virus, juncopox virus, mynahpox virus, pigeonpox virus, psittacinepox virus, quailpox virus, sparrowpox virus, starlingpox virus, turkeypox virus, peacockpox virus and penguinpox virus |
| Capripoxvirus | goatpox virus, lumpy skin disease virus, sheeppox virus |
| Leporipoxvirus | hare fibroma virus, myxoma virus, rabbit fibroma virus, squirrel fibroma virus |
| Suipoxvirus | swinepox virus |
| Molluscipoxvirus | Molluscum contagiosum virus |
| Yatapoxvirus | Yaba monkey tumor virus |

The present invention provides a vaccination kit which comprises:

(i) a first composition which comprises a first non-replicating viral vector;

(ii) a second composition which comprises a second non-replicating viral vector for sequential administration in either order.

The first and/or the second viral vector may be a pox virus vector.

In a preferred embodiment the present invention provides a vaccination kit which comprises:

(i) a first composition which comprises a first non-replicating poxvirus vector;

(ii) a second composition which comprises a second non-replicating poxvirus vector for sequential administration in either order.

One of the compositions may act as a "priming" composition, to be administered first, and the other composition may act as a "boosting" composition, to be administered after an appropriate time interval (such as three weeks).

The first and second non-replicating viral vectors should be sufficiently different that no significant cross-reaction occurs.

The two viral vectors may be derived from viruses belonging to different familes, for example, a poxviral vector and an adenoviral vector. Alternatively the two viral vectors maybe derived from viruses belonging to the same family (such as pox viruses) but different geni. For example, the first non-replicating poxvirus vector may be an avipox virus vector and the second non-replicating poxvirus vector may be an orthopox virus vector.

The two non-replicating viral vectors may even be derived from different species within the same genus, as long as the species are sufficiently different.

Distinguishing features of each pox virus genus are known in the art, for example see Murphy et al. (1995-as above).

In a preferred embodiment, one of the two non-replicating poxvirus vectors is a fowlpox virus vector (i.e. derived from a fowlpox). For example, the fowlpox virus vector may comprise a genome according to the present invention.

Non-replicating

The virus vectors used in the present invention should be non-replicating in the cells of the subject (for example in human cells). The term "non-replicating" or "replication-impaired" as used herein means not capable of replication to any significant extent in the majority of normal subject cells. Viruses which are non-replicating or replication-impaired may have become so naturally (i.e. they may be isolated as such from nature) or artificially e.g. by breeding in vitro or by genetic manipulation, for example deletion of a gene which is critical for replication. There will generally be one or a few cell types in which the viruses can be grown, such as CEF cells.

Replication of a virus is generally measured in two ways: 1) DNA synthesis and 2) viral titre. More precisely, the term "non-replicating or replication-impaired" as used herein and as it applies to poxviruses means viruses which satisfy either or both of the following criteria:

1) exhibit a 1 log (10 fold) reduction in DNA synthesis compared to the Copenhagen strain of vaccinia virus in MRC-5 cells (a human cell line);

2) exhibit a 2 log reduction in viral titre in HELA cells (a human cell line) compared to the Copenhagen strain of vaccinia virus.

Fowlpox Viruses

As mentioned above, wild-type fowlpox viruses cause proliferative skin lesions in birds. It is possible to obtain field isolates of FPV from scab material collected from poultry infections (Boyle et al., (1997) *Arch. Virol.* 142:737-748). The genomic sequence of a pathogenic fowlpox virus is available (Afonso et al (2000) *J. Gen. Virol.* 74(8) 3815-3831).

Live attenuated virus strains may be produced by multiple passage of the virus in avian cells. Various attenuated virus strains of fowlpox virus are known such as FPV M (mild vaccine strain) and FPV S (standard vaccine strain) obtainable from Cyanamid-Websters PtY, Ltd Australia.

Pox viruses have evolved strategies for evasion of the host immune response that include the production of secreted proteins that function as soluble receptors for tumour necrosis factor, IL-I p, interferon (IFN)-oc/ and IFN-γ, which normally have sequence similarity to the extracellular domain of cellular cytokine receptors (such as chemokine receptors). These viral receptors generally inhibit or subvert an appropriate host immune response, and their presence is associated with increased pathogenicity.

FPV genes

The genome of a fowlpox virus is composed of a single double-stranded DNA molecule with covelently linked terminal hairpins. Basic information about the sites for restriction endonuclease cleavage is available (Coupar et al., (1990) as above).

The genome of US Dept. Agric. Standard Challenge (virulent) fowlpox strain has been sequenced and the nomenclature used for this strain is followed herein (Afonso et al (2000) *J. Virol.* 74 3815-1831). This review also lists the 260 ORFs of this fowlpox strain (Table 1) together with their predicted structure and/or function and Accession number.

The present inventors have sequenced the virulent precursor of FP9 (HP1) at all positions where the sequence of FP9 differed from this sequence. This method reveals differences which are attributable to lineage variations and those which have accored during tissue culture passage, adaptation and concomittant attenuation. The genes modified in FP1 during its passage in CEF tissue culture from HP1 is shown in FIG. 2.

The fowlpox virus genome of the present invention may have a modification in one or more of the following wild-type genes:

FPV001, FPV018, FPV054, FPV063, FPV066, FPV070, FPV071, FPV093, FPV097/098, FPV115, FPV124, FPV125, FPV127, FPV158, FPV159, FPV160, FPV190, FPV191, FPV207, FPV219, FPV220, FPV221, FPV222, FPV239, FPV241, FPV242, FPV243, FPV244, FPV245, FPV246, FPV247, FPV260.

The term "modification" is intended to mean a variation (such as a deletion, substitution or addition) from the wild type sequence.

Where the gene encodes a protein, the modified gene sequence may encode a protein with a different amino acid sequence. For example, the amino acid sequence may have one or more amino acid deletions, additions or substitutions when compared to the wild-type sequence.

In a preferred embodiment the fowlpox virus genome of the present invention has a modification which results in a non-conservative amino acid substitution in one or more of the following genes:

FPV018, FPV063, FPV066, FPV093, FPV127, FPV191, FPV207.

Alternatively (or in addition) the genome may have a substantial modification in one or more of the wild-type genes. The term "substantial modification" is intended to mean that the gene is modified in such a way that it no longer functions as the wild-type gene. For example, if the wild-type gene encodes a protein, the substantially modified gene may be incapable of encoding a protein, or it may encode a protein which is incapable of or has a greatly reduced capacity to function as the wild-type protein.

The modification may be a deletion. For example, the entire gene may be deleted. Alternatively, the modified gene may comprise one or more partial deletions sufficient to remove or greatly reduce the function of the gene.

Alternatively the modification may be a substitution or an addition. For example, a recombination event may have occurred, with the effect that portion of sequence from elsewhere in the genome is incorporated into the gene (with optionally a corresponding loss of wild-type sequence).

A partial deletion, substitution or addition may cause a "frame-shift" mutation, resulting in incorrect reading of the downstream sequence. Alternatively (or in addition) the mutation may result in the creation of a stop codon (a "terminating mutation") such that the downstream sequence is ignored.

The mutation may result in the removal of a stop codon, which may result in two genes becoming fused to form a chimaeric gene.

In a preferred embodiment, the genome has a partial deletion in one or more of the following genes:

FPV158, FPV219, FPV222.

In another preferred embodiment, the genome entirely lacks one or more of the following genes:

FPV001, FPV124, FPV125, FPV159, FPV160, FPV220, FPV221, FPV241, FPV242, FPV243, FPV244, FPV245, FPV246, FPV247, FPV260

In another preferred embodiment, the genome has a frame-shift mutation in one or more of the following genes:

FPV054, FPV070, FPV071, FPV115, FPV190, FPV207.

In another preferred embodiment, the genome has a termination mutation in one or more of the following genes:

FPV071, FPV239

In another preferred embodiment, the genome has a chimaeric gene caused by fusion (by deletion) of genes FPV097 and FPV098.

Genome Size

The genome of FPV-M has been estimated to be in the region of 308 kb (Coupar et al., (1990) as above). The smaller the viral genome, the more heterologous DNA can be included.

The fowlpox virus genome of the present invention is preferably less than 275 kb in size. More preferably the genome is about 266 kbp. The size of the genome is considered without any heterologous sequences (for example a "nucleotide of interest" (NOI) see below). In order to use the fowlpox virus as a vector system, a heterologous sequence for delivery may be incorporated into the fowlpox genome by homologous recombination. For the purposes of size determination, the genome size is considered before such a recombination event.

Preferably the fowlpox virus genome according to claim 1 comprises the sequence shown in SEQ ID NO. 1. This "sequence" is intended to encompass homologues of the sequence, provided that the fowlox genome as a whole is capable of acting as a vector system (i.e. receiving a heterologous gene by homologous recombination and, when incorporated into a viral particle delivering the heterologous gene to a target cell).

Homologues

Here, the term "homologue" means a nucleic acid sequence having a degree of homology with the sequence shown in SEQ ID NO 1. Here, the term "homology" can be equated with "identity".

In the present context, a homologous sequence is taken to include a nucleotide sequence which may be at least 75, 85 or 90% identical, preferably at least 95 or 98% identical to the subject sequence. Typically, a homologue will comprise sequences that code for functional portions of an encoded protein (active sites etc.) which are the same as the subject sequence but may differ in other areas. Although homology can also be considered in terms of similarity (i.e. amino acid residues having similar chemical properties/functions), in the context of the present invention it is preferred to express homology in terms of sequence identity.

Homology comparisons can be conducted by eye, or more usually, with the aid of readily available sequence comparison programs. These commercially available computer programs can calculate % homology between two or more sequences.

% homology may be calculated over contiguous sequences, i.e. one sequence is aligned with the other sequence and each base in one sequence is directly compared with the corresponding base in the other sequence, one residue at a time. This is called an "ungapped" alignment. Typically, such ungapped alignments are performed only over a relatively short number of residues.

Although this is a very simple and consistent method, it fails to take into consideration that, for example, in an otherwise identical pair of sequences, one insertion or deletion will cause the following nucleic acid residues to be put out of alignment, thus potentially resulting in a large reduction in % homology when a global alignment is performed. Consequently, most sequence comparison methods are designed to produce optimal alignments that take into consideration possible insertions and deletions without penalising unduly the overall homology score. This is achieved by inserting "gaps" in the sequence alignment to try to maximise local homology.

However, these more complex methods assign "gap penalties" to each gap that occurs in the alignment so that, for the same number of identical bases, a sequence alignment with as few gaps as possible—reflecting higher relatedness between the two compared sequences—will achieve a higher score than one with many gaps. "Affine gap costs" are typically used that charge a relatively high cost for the existence of a gap and a smaller penalty for each subsequent residue in the gap. This is the most commonly used gap scoring system. High gap penalties will of course produce optimised alignments with fewer gaps. Most alignment programs allow the gap penalties to be modified. However, it is preferred to use the default values when using such software for sequence comparisons. For example when using the GCG Wisconsin Bestfit package the default gap penalty for nucleic acid sequences is −12 for a gap and −4 for each extension.

Calculation of maximum % homology therefore firstly requires the production of an optimal alignment, taking into consideration gap penalties. A suitable computer program for carrying out such an alignment is the GCG Wisconsin Bestfit package (University of Wisconsin, U.S.A.; Devereux et al., 1984, *Nucleic Acids Research* 12:387). Examples of other software than can perform sequence comparisons include, but are not limited to, the BLAST package (see Ausubel et al., 1999 ibid—Chapter 18), FASTA (Atschul et al., 1990, *J. Mol. Biol*., 403-410) and the GENEWORKS suite of comparison tools. Both BLAST and FASTA are available for offline and online searching (see Ausubel et al., 1999 ibid, pages 7-58 to 7-60). However, for some applications, it is preferred to use the GCG Bestfit program. A new tool, called BLAST 2 Sequences is also available for comparing protein and nucleotide sequence (see *FEMS Microbiol Lett* 1999 174(2): 247-50*; FEMS Microbiol Lett* 1999 177(1): 187-8 and tatiana@ncbi.nlm.nih. gov).

Although the final % homology can be measured in terms of identity, the alignment process itself is typically not based on an all-or-nothing pair comparison. Instead, a scaled similarity score matrix is generally used that assigns scores to each pairwise comparison based on chemical similarity or evolutionary distance. An example of such a matrix commonly used is the BLOSUM62 matrix—the default matrix for the BLAST suite of programs. GCG Wisconsin programs generally use either the public default values or a custom symbol comparison table if supplied (see user manual for further details). For some applications, it is preferred to use the public default values for the GCG package, or in the case of other software, the default matrix, such as BLOSUM62.

Once the software has produced an optimal alignment, it is possible to calculate % homology, preferably % sequence identity. The software typically does this as part of the sequence comparison and generates a numerical result.

The sequences may also have deletions, insertions or substitutions of nucleic acid residues which produce a silent change and result in a functionally equivalent substance. If the gene encodes a protein, the protein encoded by a homologue may be identical (due to the degeneracy of the genetic code) or functionally equivalent (for example a conservative mutation may appear in the sequence). Preferably the homolog encodes a protein having at least 90%, preferably at least 95%, more preferably at least 98% homology to the protein encoded by the SEQ ID NO.: 1 gene.

Conservative substitutions may be made, for example according to the Table below. Amino acids in the same block in the second column and preferably in the same line in the third column may be substituted for each other:

| | | |
|---|---|---|
| ALIPHATIC | Non-polar | GAP |
| | | ILV |
| | Polar - uncharged | CSTM |
| | | NQ |
| | Polar - charged | DE |
| | | KR |
| AROMATIC | | HFWY |

Fowlpox Virus Vectors

The present invention also relates to a viral particle comprising such a fowlpox virus genome.

The viral particle (or part therof) may be used as a vector system for delivering a nucleotide of interest (NOI) to a target cell. In this sense, the term “viral particle” as used herein includes a viral vector comprising such a particle (or part thereof) capable of delivering an NOI or a pre-expressed protein to a target cell, The NOI may be inserted into the viral genome by homologous recombination using methods known in the art (see for example Schneider et al., (1998) *Nature Medicine* 4(4) 397-402).

The construction of recombinant poxviruses which express an NOI requires that the insertion of the NOI is made at a site which is nonessential for the replication of the viral genome. Suitable insertion sites for FP9 have been described (Pollitt et al., (1998) 17: 5-9; Laidlaw et al., 1998 *J. Virol.* 72, pp6742).

Pre-expressed Protein

The fowlpox viral particle of the present invention (or part thereof) may be used to deliver a pre-expressed protein to a target cell. A “pre-expressed protein” is a protein translated before it reaches the target cell. For example, the cell in which the viral particle is grown may express a protein which is then incorporated into the viral particle.

The cell in which the viral particle is grown may be engineered to express one or more proteins of interest (POI). If the cell is a primary cell (such as a CEF cell) it may be transiently transfected with a nucleotide encoding such a POI. Alternatively, a stably tranfected cell line may be used for growth, such as the quail cell line QT35.

Preferably the pre-expressed protein is targetted to be incorporated into the viral particle.

NOI

In the present invention, the term NOI includes any suitable nucleotide sequence, for example, a synthetic RNA/DNA sequence, a recombinant RNA/DNA sequence (i.e. prepared by use of recombinant DNA techniques), a cDNA sequence or a partial genomic DNA sequence, including combinations thereof. The sequence need not be a coding region. If it is a coding region, it need not be an entire coding region. In addition, the RNA/DNA sequence can be in a sense orientation or in an anti-sense orientation. Preferably, it is in a sense orientation. Preferably, the sequence is, comprises, or is transcribed from cDNA.

The NOI may encode a protein of interest (“POI”). In this way, the vector system could be used to examine the effect of expression of a foreign gene on the target cell. For example, the fowlpox virus delivery system could be used to screen a cDNA library for a particular effect on the target cell.

The NOI may be capable of blocking or inhibiting the expression of a gene in the target cell. For example, the NOI may be an antisense sequence. The inhibition of gene expression using antisense technology is well known.

The NOI or a sequence derived from the NOI may be capable of “knocking out” the expression of a particular gene in the target cell. There are several “knock out” strategies known in the art. For example, the NOI may be capable of integrating in the genome of the target cell so as to disrupt expression of the particular gene. The NOI may disrupt expression by, for example, introducing a premature stop codon, by rendering the downstream coding sequence out of frame, or by affecting the capacity of the encoded protein to fold (thereby affecting its function).

Alternatively, the NOI may be capable of enhancing or inducing ectopic expression of a gene in the target cell. The NOT or a sequence derived therefrom may be capable of "knocking in" the expression of a particular gene.

An NOI delivered by the vector delivery system may be capable of immortalising the target cell. A number of immortalisation techniques are known in the art (see for example Katakura Y et al., (1998) *Methods Cell Biol.* 57:69-91).

An NOI delivered by the vector delivery system may be used for selection or marker purposes. For example, the NOI may be a selection gene, or a marker gene. Many different selectable markers have been used successfully in retroviral vectors. These are reviewed in "Retroviruses" (1997 Cold Spring Harbour Laboratory Press Eds: J M Coffin, S M Hughes, H E Varmus, pp. 444) and include, but are not limited to, the bacterial neomycin and hygromycin phosphotransferase genes which confer resistance to G418 and hygromycin respectively; a mutant mouse dihydrofolate reductase gene which confers resistance to methotrexate; the bacterial gpt gene which allows cells to grow in medium containing mycophenolic acid, xanthine; the bacterial hisD gene which allows cells to grow in medium without histidine but containing histidinol; the multidrug resistance gene (mdr) which confers resistance to a variety of drugs; and the bacterial genes which confer resistance to puromycin or phleomycin. All of these markers are dominant selectable and allow chemical selection of most cells expressing these genes.

In a preferred embodiment, however, the NOI may have or encode a protein which has a therapeutic effect. For example, an NOI delivered by the vector delivery system may be a therapeutic gene—in the sense that the gene itself may be capable of eliciting a therapeutic effect or it may code for a product that is capable of eliciting a therapeutic effect.

The NOI may, for example, be or encode one of the following: cytokines, chemokines, hormones, antibodies, anti-oxidant molecules, engineered immunoglobulin-like molecules, a single chain antibody, fusion proteins, enzymes, immune co-stimulatory molecules, immunomodulatory molecules, anti-sense RNA, a transdominant negative mutant of a target protein, a toxin, a conditional toxin, an antigen, a tumour suppresser protein and growth factors, membrane proteins, vasoactive proteins and peptides, anti-viral proteins and ribozymes, and derivatives thereof (such as with an associated reporter group).

In one preferred embodiment, the NOI is capable of encoding a disease associated antigen. Exposure to an antigen in the context of a fowlpox vector may provoke or boost an immune responses to the antigen such that an existing or subsequent challenge is dealt with more effectively.

The nature of the antigen will depend on the disease. If the disease is caused by an organism or infectious agent (bacteria, virus, protozoa, prion) the antigen may be derivable from this organism or agent. If the disease is caused by tumour(s) the antigen is preferably a tumour associated antigen such as HER-2/neu, MUC01, cancer testis antigens or oncogene(s) or product(s) thereof.

Preferably the disease-associated antigen comprises one or more T cell epitopes. The antigen may comprise a complete protein from a disease causing organism (such as Antigen 85A from *M. tuberculosis*). Alternatively, the antigen may comprise a string of T cell epitopes from one or more proteins from disease-causing organism(s). An example of this is the MEPfTrap polypeptide from *P. falciparum* which comprises a string of T-cell epitopes from *P. falcipraum* CSP and the Pb9 epitope fused to the *P. falciparum* TRAP gene.

Preferably the plasmid pEFL or derivatives thereof is used in the making of fowlpox constructs according to the present invention, preferably the plasmid pEFL29. PEFL 29 has regions of homology which allow it to integrate into FP9 at ORF1. This disrupts ORF-1 but does not delete it. The plasmid adds three genes lac A, lac Y and lac Z to the genome. This disruption is an insertion, and some nucleotides are deleted. The Fowlpox Orfl gene bases deleted from pEFL29 are (capital letters):

```
Agagatcccgccagacggggaacctgggtcaacg

ACTGGTGCGAAGATCTCtgcgtatggatatggtc

tccg

Tgttgttacgtcaagagatgtattcg          (SEQ ID NO.: 2)
```

Vaccines

The genome and/or particle of the present invention may be used in a method to treat and/or prevent a disease in a subject.

For example, the genome and/or particle may be employed in a vaccine which is administered to a subject for prophylactic or therapeutic purposes. The vaccine may also comprise an adjuvant (see below).

It has been found that multiple dose vaccination (for therapy or disease prevention) is often more effective than single doses. A multiple dose vaccination program may involve repeat doses of the same composition or one or more doses of two or more different compositions.

For homologous vaccination programs, the present invention provides a vaccine pack which comprises a vaccine provided in a manner which facilitates repeat administration. For example, the pack may contain a plurality of vials comprising the correct dose of vaccine ready to be injected into the patient. If the vaccine is to be taken orally, the doses may be present as pills or capsules.

In heterologous vaccination programs, there is usually a "priming" composition which is administered to the patient first and a "boosting" composition which is administered some time later. The genome and/or viral particle of the present invention may be used in a priming composition and/or a boosting composition.

A number of other compositions may be employed in heterologous vaccination programs. If the genome/particle of the present invention comprises an NOI (optionally capable of encoding a POI), then preferably the other composition comprises the same NOI or POI. Other compositions include "naked DNA", non-viral vector systems and other viral vector systems.

Naked DNA (or RNA) may be linear or circular (for example, a plasmid). It may be provided in a carrier such as a liposome or in a free form.

Suitable non-viral vectors for use in the priming composition include lipid-tailed peptides known as lipopeptides, peptides fused to carrier proteins such as KLH either as fusion proteins or by chemical linkage, whole antigens with adjuvant, and other similar systems.

If a viral vector system is used, it may be an advantage if it is derived from a different virus (i.e. not fowlpox) to minimise cross-reaction. The vector may be derived from another avipox virus, such as canary pox, or from a different genus of pox viruses (as shown in Table 2). Particularly preferred is an attenuated vaccinia vector system such as MVA or NVYAC. Other suitable viral vectors are vectors based on non-pox viruses, such as adeno virus, herpes virus and Venezuelan equine encephalitis virus (VEE). Suitable bacterial vectors include recombinant BCG and recombinant *Salmonella* and *Salmonella* transformed with plasmid DNA (Darji A et al., 1997 *Cell* 91: 765-775).

For heterologous vaccine programs, the present invention provides a vaccination kit which comprises:

(i) a first composition which comprises a fowlpox viral particle; and (ii) a second composition for simultaneous, separate or sequential administration.

Heterologous Vaccination Regimes

The present invention also relates generally to heterologous vaccination regimes using two different non-replicating viral vectors.

The present inventors have shown for the first time that heterlogous prime-boost regimes using two different non-replicating viral vectors is efficient in generating an immune response in a primate subject.

In particular, the present invention provides a method for treating and/or preventing a disease in a subject which comprises the step of administering (i) a first composition which comprises a first non-replicating viral vector;

(ii) a second composition which comprises a second non-replicating viral vector to the subject in either order.

Preferably the subject is a mammal, more preferably the subject is a primate, most preferably the subject is a human.

In a preferred embodiment the first and/or the second composition is a poxvirus vector.

Thus in a preferred embodiment, the present invention provides a method for treating and/or preventing a disease in a subject which comprises the step of administering (i) a first composition which comprises a first non-replicating pox viral vector;

(ii) a second composition which comprises a second non-replicating pox viral vector to the subject in either order.

In another aspect, the invention relates to a method for treating and/or preventing a disease in a subject which comprises the step of administering (i) a first composition which comprises a first non-replicating viral vector;

(ii) a second composition which comprises a second non-replicating viral vector to the subject in either order.

In another aspect, the invention relates to a method for treating and/or preventing a disease in a subject which comprises the step of administering (i) a first composition which comprises a DNA vaccine;

(ii) a second composition which comprises a first non-replicating viral vector (iii) a third composition which comprises a second non-replicating viral vector;

to the subject.

In another aspect, the invention relates to a method for treating and/or preventing a disease in a subject which comprises the step of administering (i) a first composition which comprises a first non-replicating viral vector;

(ii) a second composition which comprises a second non-replicating viral vector;

(iii) a third composition which comprises a third non-replicating viral vector;

to the subject.

In another aspect, the invention relates to a method as described above wherein at least one of the composition(s) comprises a poxvirus vector.

In another aspect, the invention relates to a method as described above wherein said non-replicating viral vector(s) comprise poxvirus vector(s).

In another aspect, the invention relates to a method as described above wherein at least two of the poxvirus vectors are derivable from poxviruses from different genera.

In another aspect, the invention relates to a method as described above wherein at least one poxvirus vector is derivable from an avipox virus and at least one poxvirus vector is derivable from an orthopox virus.

In another aspect, the invention relates to a method as described above wherein at least one of the vectors is derivable from a fowlpox virus.

In another aspect, the invention relates to a method as described above wherein at least one of the vectors is, or is derivable from, FP9.

In another aspect, the invention relates to a method as described above wherein one of the vectors comprises a fowlpox virus genome selected from (i) a fowlpox virus genome which has a modified form of one or more of the following wild-type FPV genes:

FPV001, FPV018, FPV054, FPV063, FPV066, FPV070, FPV071, FPV093, FPV097, FPV098, FPV115, FPV124, FPV125, FPV127, FPV158, FPV159, FPV160, FPV190, FPV191, FPV207, FPV219, FPV220, FPV221, FPV222, FPV239, FPV241, FPV242, FPV243, FPV244, FPV245, FPV246, FPV247, FPV260;

(ii) a fowlpox virus genome which has a partial deletion in one or more of the following genes:

FPV158, FPV219, FPV222;

(iii) a fowlpox virus genome which lacks one or more of the following genes:

FPV001, FPV124, FPV125, FPV159, FPV160, FPV220, FPV221, FPV241,

FPV242, FPV243, FPV244, FPV245, FPV246, FPV247, FPV260;

(iv) a fowlpox virus genome which has a frame-shift mutation in one or more of the following genes:

FPV054, FPV070, FPV071, FPV115, FPV190, FPV207;

(v) a fowlpox virus genome which has a termination mutation in one or more of the following genes:

FPV071, FPV239;

(vi) a fowlpox vines genome which has a chimaeric gene caused by fusion (by deletion) of genes FPV097 and FPV098;

(vii) a fowlpox virus genome which is less than 275 kbp in size;

(viii) a fowlpox virus genome comprising the sequence shown in SEQ ID No. 1

(ix) a fowlpox virus genome comprising the sequence shown in SEQ ID No. 1, with a deletion of ACTGGTGC-GAAGATCTC (SEQ ID NO.: 3) from ORF1.

In another aspect, the invention relates to a method as described above wherein the fowlpox virus genome also comprises a NOI.

In another aspect, the invention relates to method as described above wherein the NOI is under the control of a poxvirus promoter.

In another aspect, the invention relates to a method as described above wherein the NOI encodes an antigen from *P. berghei, P. falciparum, P. cynomolgi, P. vivax, M. tuberculosis* or *T. parva*.

In another aspect, the invention relates to a method as described above wherein the composition comprising the viral vector derivable from an avipox virus is administered as a boosting composition.

In another aspect, the invention relates to method as described above wherein the composition comprising the viral vector derivable from an avipox virus is administered as a priming composition.

In another aspect, the invention relates to method as described above wherein the subject is a primate.

In another aspect, the invention relates to method as described above wherein the subject is a human.

In another aspect, the invention relates to use of a non-replicating viral vector in a vaccine for an animal, wherein said vector is, or is derivable from, FP9.

In another aspect, the invention relates to use as described above wherein said animal is a mammal.

In another aspect, the invention relates to use as described above wherein said mammal is a primate.

In another aspect, the invention relates to use as described above wherein said primate is a human.

In another aspect, the invention relates to use of a non-replicating viral vector in medicine, wherein said vector is, or is derivable from, FP9.

In another aspect, the invention relates to a method of eliciting an immune response in a subject comprising administering a composition comprising a non-replicating viral vector to said subject wherein said vector is, or is derivable from, FP9.

In another aspect, the invention relates to a method of boosting a pre-existing immune response in a subject comprising administering a composition comprising a non-replicating viral vector to said subject wherein said vector is, or is derivable from, FP9.

Preferably the subject is a primate, in particular a human.

Preferably the vectors are derivable from poxviruses from different genera. In particular, one may be derivable from an avipox virus and the other from an orthopox virus (see Table 2).

When one of the compositions comprises a vector derivable from an avipox virus, preferably this composition is administered as a boosting composition.

In a preferred embodiment, one of the vectors is derivable from a fowlpox virus. More preferably one of the vectors is or is derivable from FP9. For example, one of the vectors may comprise a fowlpox virus genome according to the first aspect of the invention. In a highly preferred embodiment, the vector comprises a genome having the sequence shown in SEQ ID NO.: 1

When the disease is malaria, preferably the FP9 or FP9 derived vector is used as a prime.

When the disease is tuberculosis, preferably the FP9 or FP9 derived vector is used as a boost.

Preferably the first and second compositions are capable of expressing the same antigen.

The first and second compositions may be packaged together or individually for separate sale.

The kit may comprise other components for mixing with one or both of the compositions before administration (such as diluents, carriers, adjuvants etc.—see 10 below).

The kit may also comprise written instructions concerning the vaccination protocol.

Boosting Compositions

The present inventors have shown that a non-replicating viral vector according to the present invention is effective at boosting a pre-existing immune response to an antigen. In particular, the present inventors have shown for the first time that non-replicating viruses can be used to boost the immune response primed by *M. bovis* BCG in mice and in primates and melanomas in primates such as humans.

The pre-existing immune response may have been generated by a vaccine. A number of different vaccine types have been developed and are known in the art, these include living organism, intact but non-living organisms, subcellular fragments, toxoids, DNA based vaccines and anti-idiotype (see Table 1). In a highly preferred embodiment, the pre-existing response is generated by an attenuated living pathogen, such as BCG.

The present invention provides a boosting composition comprising a non-replicating viral vector capable of boosting a pre-existing immune response in a subject.

Preferably the subject is a primate.

Preferably the viral vector is a pox viral vector. For example, the viral vector may comprise a genome according to the first aspect of the invention.

Triple and Multiple Regimes

The present invention also relates generally to multiply heterologous vaccination regimes, such as triply heterologous regimes, using different non-replicating viral vectors.

The invention thus provides a triple regime comprising administering to a subject three heterologous compositions. Preferably said three compositions each differ from their neighbouring composition. For example, if the first composition comprises X then the second composition will preferably differ from X. Clearly, in this embodiment, it is possible that the third composition may be similar or identical to the first composition, Preferably all three compositions are different from one another.

In one embodiment, one of the compositions may be a DNA based composition such as a DNA vaccine. Preferably at least the second and third compositions comprise non-replicating viral vectors.

Thus the invention provides a method for treating and/or preventing a disease in a subject which comprises the step of administering (i) a first composition which comprises a DNA vaccine;

(ii) a second composition which comprises a first non-replicating viral vector;

(iii) a third composition which comprises a second non-replicating viral vector;

to the subject.

In a preferred embodiment, the invention provides a method for treating and/or preventing a disease in a subject which comprises the step of administering (i) a first composition which comprises a first non-replicating viral vector;

(ii) a second composition which comprises a second non-replicating viral vector;

(iii) a third composition which comprises a third non-replicating viral vector; to the subject.

In a preferred embodiment, the first and the second compositions are heterologous, and the second and third compositions are heterologous. More preferably the first and the second and the third compositions are heterologous. Most preferably said compositions are heterologous with respect to the viral vector component of said compositions. For example a treatment regimen may involve pDNA priming followed by recombinant MVA boosting followed by recombinant FP9 boosting followed by recombinant adenovirus boosting and so forth. These treatment/immunisation cycles may be advantageously repeated to sustain a therapeutic T cell response in a therapeutic setting.

Preferably three or more different viral vectors are used in the triply heterologous regimes of the invention.

In a highly preferred embodiment, immunisation is performed using the following vectors: DNA-FP9-MVA-adenovirus-recombinant herpes in any order. Preferably each vector expresses the same antigen(s). Preferably the vectors are administered in the order DNA-FP9-MVA-adenovirus-recombinant herpes.

Further preferred immunisation orders and regimes are: DNA-FP9-MVA and DNA-MVA-FP9.

Preferably the vectors are derivable from poxviruses from different genera. In particular, one may be derivable from an avipox virus and another from an orthopox virus (see Table 2).

In a preferred embodiment, one of the vectors is derivable form a fowlpox virus. For example, one of the vectors may comprise a fowlpox virus genome according to the first aspect of the invention. In a highly preferred embodiment, the vector comprises a genome having the sequence shown in SEQ ID No.: 1.

Preferably the first and second and third compositions are capable of expressing the same antigen.

Figure 11:
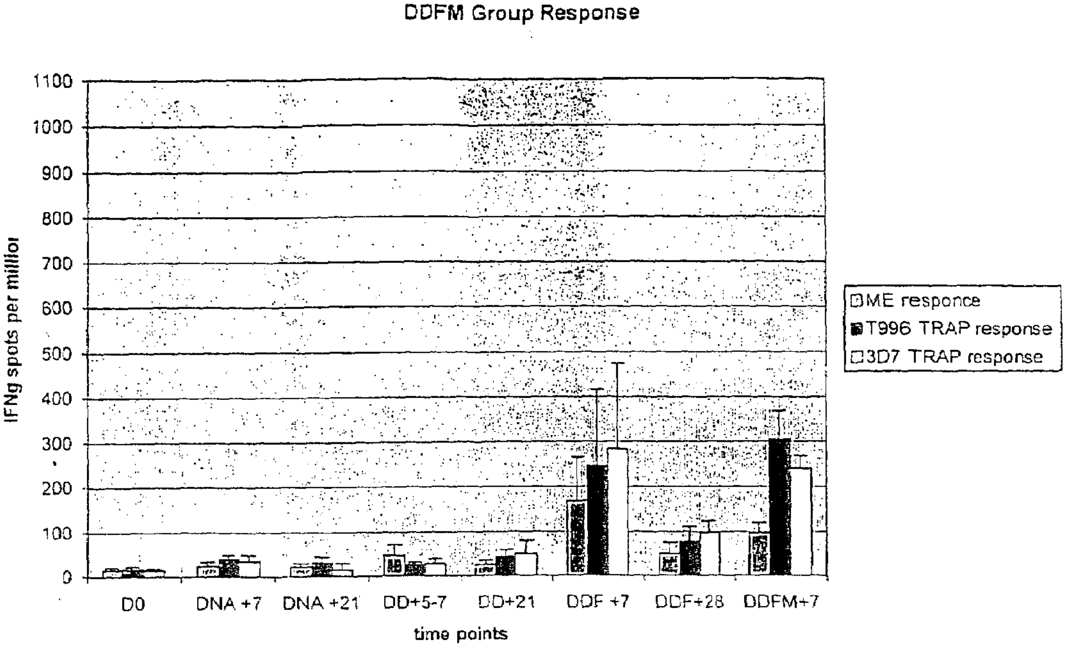
FIG. 11 shows a bar chart.

Example 12 (eg. FIG. 11-DDFM) demonstrates the effectiveness of the triple regime.

Preferably the subject is a primate, in particular a human.

The first and second and third compositions may be packaged together or individually for separate sale.

The kit may comprise other components for mixing with one or more of the compositions before administration (such as diluents, carriers, adjuvants etc.—see below).

The kit may also comprise written instructions concerning the vaccination protocol.

T Cell Responses

The vaccination method or program should elicit a T cell immune response in the subject.

The nature of a T cell immune response can be characterised by virtue of the expression of cell surface markers on the cells. T cells in general can be detected by the present of TCR, CD3, CD2, CD28, CD5 or CD7 (human only). CD4+ T cells and CD8+ T cells can be distinguished by their co-receptor expression (for example, by using anti-CD4 or anti-CD8 monoclonal antibodies).

Since CD4+ T cells recognise antigens when presented by MHC class II molecules, and CD8+ recognise antigens when presented by MHC class I molecules, CD4+ and CD8+ T cells can also be distinguished on the basis of the antigen presenting cells with which they will react.

Within a particular target antigen, there may be one or more CD4+ T cell epitopes and one or more CD8+ T cell epitopes. If the particular epitope has already been characterised, this can be used to distinguish between the two subtypes of T cell, for example on the basis of specific stimulation of the T cell subset which recognises the particular epitope.

CD4+ T cells can also be subdivided on the basis of their cytokine secretion profile. The $T_H$I subset (sometimes known as "inflammatory CD4 T cells") characteristically secretes IL-2 and IFNγ and mediates several functions associated with cytotoxicity and local inflammatory reactions. $T_H$1 cells are capable of activating macrophages leading to cell mediated immunity. The $T_H$2 subset (sometimes known as "helper CD4 T cells") characteristically secretes 1L-4, IL-5, IL-6 and IL-10, and is thought to have a role in stimulating B cells to proliferate and produce antibodies (humoral immunity).

$T_H$1 and $T_H$2 cells also have characteristic expression of effector molecules. $T_H$1 cells expressing membrane-bound TNF and $T_H$2 cells expressing CD40 ligand which binds to CD40 on the B cell.

The type of T cell immune response may thus be readily determined, for example using fluorescence activated cell scanning (FACScan).

Target Antigens

The target antigen may be characteristic of the target disease. If the disease is an infectious disease, caused by an infectious pathogen, then the target antigen may be derivable from the infectious pathogen.

The target antigen may be an antigen which is recognised by the immune system after infection with the disease. Alternatively the antigen may be normally "invisible" to the immune system such that the method induces a non-physiological T cell response. This may be helpful in diseases where the immune response triggered by the disease is not effective (for example does not succeed in clearing the infection) since it may open up another line of attack.

Preferred Breast Cancer antigens are MUC-1, HER2, CEA.

Preferred Colon cancer antigens: CEA, MUC-1, MAGE-12, mutant P53.

Preferred Cervical cancer antigens: human papiloma virus proteins E6 and E7.

Preferred EBV-induced B and T cell lymphomas antigens: EBNA1 and 2, LMP 1.

Preferred renal cancer antigens: HER-2 neu, RAGE, MUC-1.

Preferred HPV antigens are viral proteins E1-8, L1 and L2.

Preferred HSV antigens are viral proteins gM, gH, gK, GG, gD.

Preferred HBV antigens are viral proteins small, middle and large surface antigen, core antigen, polymerase.

Preferred HCV proteins are viral proteins core protein, envelope protein, NS2, NS3, NS4 and NS5 region.

The antigen may be a tumor antigen, for example HER2/neu, MUC-1, MAGE-1, MAGE-3 or NY-ESO.

The antigen may be an autoantigen, for example tyrosinase.

In a preferred embodiment of the invention, the antigen is derivable from *M. tuberculosis*. For example, the antigen may be ESAT6 or MPT63.

In another preferred embodiment of the invention, the antigen is derivable from the malaria-associated pathogen *P. Falciparum.*

The compositions of the present invention may comprise T cell epitopes from more than one antigen. For example, the composition may comprise one or more T cell epitopes from two or more antigens associated with the same disease. The two or more antigens may be derivable from the same pathogenic organism.

Alternatively, the composition may comprise epitopes from a variety of sources. For example, the ME-TRAP insert described in the examples comprises T cell epitopes from *P. falciparum*, tetanus toxoid, *M. tuberculosis* and *M. bovis.*

Target Diseases

The method of the present invention will be useful for treating and/or preventing a number of diseases, especially those which are susceptible to a T-cell mediated immune response.

In particular, the method of the present invention will be useful in the treatment and/or prevention of diseases which are or are caused by chronic infections, particularly persistent, latent infections.

A non-exhaustive list of suitable diseases includes: tuberculosis, HIV, malaria. *H. pylori*, influenza, hepatitis, CMV, human papilloma virus (HPV), herpes virus-induced diseases and other viral infections, leprosy, non-malarial protozoan parasites such as toxoplasma, and various malignancies such as tumours and/or cancers, infectious disease caused by protozoans: malaria, particularly *Plasmodium falciparum* and *P. vivax*, toxoplasma, *Theileria parva, Trypanosomas cruzi*, by mycobacteria such as tuberculosis and leprosy, bacteria such as *Chlamydia pneumoniae* and *Helicobacter pylori*, by viruses such as HIV, EBV, CMV, HBV, HCV, HPV, HSV, RSV, influenza virus and various malignacies such as renal, colorectal, lung, skin (melanoma), liver, ovary, testis, pancreas, uterus, prostate, stomach, head and neck, cervix, breast cancer and various lymphomas, as well as HIV/AIDS, heptitis B, hepatitis C, malaria, tuberculosis, HPV infection and disease, HSV infection and disease, CMV infection and disease, EBV infection and disease, leishmaniasis, listeriosis, theileria, HTLV infection and disease, pneumococcal disease, staphylococcal disease, lung cancer, breast cancer, colon cancer, melanoma, myeloma, lymphoma, renal cell carcinoma.

The method of the present invention is particularly useful in vaccination strategies to protect against tuberculosis, malaria and East Coast Fever.

The compositions described herein may be employed as therapeutic or prophylactic vaccines. Whether prophylactic or therapeutic immunisation is the more appropriate will usually depend upon the nature of the disease. For example, it is anticipated that cancer will be immunised against therapeutically rather than before it has been diagnosed, while anti-malaria vaccines will preferably, though not necessarily be used as a prophylactic.

Pharmaceutical Compositions/Vaccines

The present invention also relates to a pharmaceutical composition such as a vaccine, priming or boosting agent.

The pharmaceutical composition may also comprise, for example, a pharmaceutically acceptable carrier, diluent, excipient or adjuvant. The choice of pharmaceutical carrier, excipient or diluent can be selected with regard to the intended route of administration and standard pharmaceutical practice.

In particular, a composition comprising a DNA plasmid vector may comprise granulocyte macrophage-colony stimulating factor (GM-CSF), or a plasmid encoding it, to act as an adjuvant; beneficial effects are seen using GM-CSF in polypeptide form. Adjuvants such as QS21 or SBAS2 (Stoute J A et al., 1997 *N. Engl. J. Medicine* 226: 8691) may be used with proteins, peptides or nucleic acids to enhance the induction of T cell responses.

In the pharmaceutical compositions of the present invention, the composition may also be admixed with any suitable binder(s), lubricant(s), suspending agent(s), coating agent(s), or solubilising agent(s).

The pharmaceutical composition could be for veterinary (i.e. animal) usage or for human usage. For veterinary usage, the composition may be used to treat for example mammals (especially cattle) or birds.

Preferably the subject is a mammalian subject, in particular a primate (e.g. human) or ungulate (e.g. cow) subject.

Administration

In general, a therapeutically effective daily intradermal or intramuscular dose of the compositions of the present invention is likely to range from $10^5$–$10^{10}$ plaque-forming units (pfu).

Typically, the physician or veterinary surgeon will determine the actual dosage which will be most suitable for an individual patient and it will vary with the age, weight and response of the particular patient. The above dosages are exemplary of the average case. There can, of course, be individual instances where higher or lower dosage ranges are merited, and such are within the scope of this invention.

Transmission of members of the *Chordopoxvirinae* may occur by aerosol (Murphy et al., (1995) as above). The compositions of the present invention may also be administered by aerosol for inhalation by the subject. The compositions of the present invention may also be conveniently administered by injection, such as intradermal and/or intramuscular injection. In addition, the compositions may be administered using a suitable devine into the skin or other tissues (for example using a "gene gun" or similar).

Where appropriate, the pharmaceutical compositions can be also be administered in the form of a suppository or pessary, topically in the form of a lotion, solution, cream, ointment or dusting powder, by use of a skin patch, orally in the form of tablets containing excipients such as starch or lactose, or in capsules or ovules either alone or in admixture with excipients, or in the form of elixirs, solutions or suspensions containing flavouring or colouring agents, or they can be injected parenterally, for example intracavemosally, intravenously, or subcutaneously. For parenteral administration, the compositions may be best used in the form of a sterile aqueous solution which may contain other substances, for example enough salts or monosaccharides to make the solution isotonic with blood. For buccal or sublingual administration the compositions may be administered in the form of tablets or lozenges which can be formulated in a conventional manner.

It is also possible to administer the compositions of the present invention in sustained release formulations.

Poxvirus Growth Method

It is known to grow wild-type and recombinant poxviruses in vitro in cultured chicken embryo fibroblasts (CEFs). The present inventors have surprisingly found that substantially improved plaque formation and virus yield can be obtained for avipox viruses by using non-cultured CEFs.

The present invention provides the use of non-cultured CEF cells to grow an avipox virus.

Preferably the avipox virus is a fowlpox virus, especially one which comprises a fowlpox genome according to the first aspect of the present invention.

The term "non-cultured" is used to indicate that the cells are used before they multiply to any significant extent in culture. Preferably the cells should be in culture for insufficient time for the number of cells in the population to double.

It is routine practice to maintain primary CEF cells in culture for up to one month by regular passage and supplementation of the growth medium. The non-cultured CEF cells of the present invention should be used without being passaged.

Primary non-cultured CEFs can be obtained by loading freshly prepared CEFs into tissue culture dishes at a concentration sufficient to give a confluent monolayer without growth. The plate is then used, preferably within 24 hours of being plated out.

The invention is further described, for the purposes of illustration only, in the following examples

EXAMPLE 1

Production and Characterisation of Fowlpox Strain FP9

Fowlpox strain FP9 was derived by 438 passages through chicken embryo fibroblasts in tissue culture from the virulent wild-type fowlpox HP-1 strain (Mayr and Malicki (1966) Zentralbl Veterinarmed 13 1-3) and then plaque purified.

The genome of Fp9 has been fully sequenced (SEQ ID No 1) and annotated (FIGS. 1A-1E). FP9 does not contain the REV provirus. At 266 kbp the genome of FP9 is somewhat smaller than the estimated size of FPV-M (greater than 300 kbp).

EXAMPLE 2

Comparison of the Immune Response Elicited by Recombinant FP9 and FPV-M

To determine whether recombinant FP9 was superior to FPV-M in its capacity to elicit T-cell responses against a recombinant antigen, the *Plasmodium berghei* circumsporozoite surface protein (PbCSP) was inserted into the terminal 6.8 kbp BamHI fragment (Boursnell et al., 1990*a, J. Gen. Virol*. 71, 621-8; Boursnell et al., 1990*b, Vet. Microbiol*. 23, 305-16; Campbell et al., 1989*, J. Gen. Virol*. 70, 145-54) of the genome of both viruses by homologous recombinantion (Quingzhong et al., 1994*, Vaccine* 12, 569-73). The vaccinia p7.5 early-late promoter was used to drive the expression of the inserted genes in both recombinant viruses. The PbCSP protein contains an H-2$K^d$ restricted 9 amino acid peptide epitope that can induce a protective CD8+ T-cell response against liver stage *P. berghei* infection in Balb/c mice (Plebanski et al., 1998*, Eur. J. Immunol*. 28, 4345-55; Schneider et al., 1998*, Nat. Med*. 4, 397-402). Surprisingly, FP9 encoding the PbCSP gene (FP9PbCSP) elicited a significantly higher CD8+ mediated T-cell response in Balb/c mice than that elicited by FPV-M encoding the CSP gene (FPV-MPbCSP), although both viruses induced substantial T-cell responses against viral antigens (FIG. 3).

Method

Female Balb/c mice were immunised intravenously with $1\times10^6$ PFU of FP9 or FPVM alone or expressing *Plasmodium berghei* CSP (PbCSP). Seven days following immunisation, the T-cell immune response elicited in splenocytes was determined using the IFNγ ELSPOT assay. The response against the recombinant antigen, PbCSP was determined using the MHC-class I restricted Pb9 epitope (recognised by CD8+ Tcells). As a positive control, the T-cell response against whole virus was determined by exposing immune splenocytes to those infected with fowlpox virus. Columns in FIGS. 1A-1E represent the mean IFN-γ spot forming cells (SFC) per million splenocytes± the standard error of the mean for four mice per group.

EXAMPLE 3

Prime-boost Immunisation Regimes with FP9PbCSP and Induction of a Protective Immune Response against *P. berghei*

Figure 4:
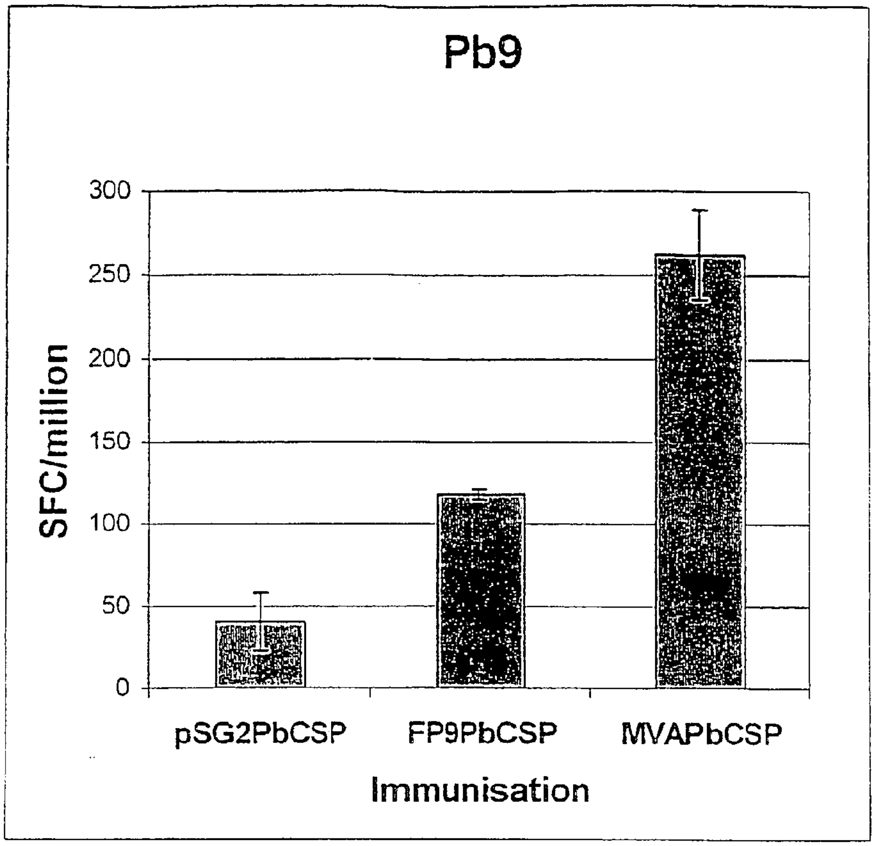
FIG. 4: Comparison of the CD8+ T-cell immune response elicited by recombinant FP9, MVA and a DNA vaccine encoding PbSCP.
Figure 5:
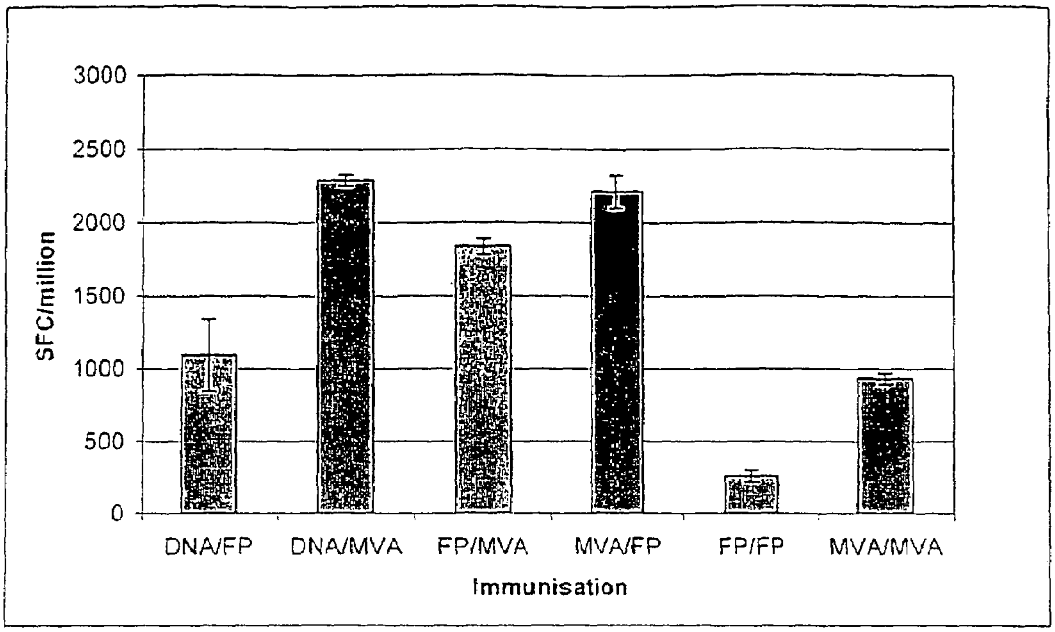
FIG. 5: Fowlpox FP9 can serve as both a priming and boosting agent in heterologous prime-boost immunisation regimes.

Comparison of the CD8+ T-cell response elicited by FP9PbCSP with a DNA-vaccine and MVA encoding the PbCSP antigen in Balb/c mice (FIG. 4) revealed that the response elicited by recombinant FP9 was significantly higher than that elicited by the DNA-vaccine, although lower than that elicited by recombinant MVA. Nevertheless, FP9PbCSP boosted the CD8+ T-cell response primed by DNA-vaccination, as well as acting as either a priming or boosting agent in combination with MVAPbCSP (FIG. 5). Significantly, priming with FP9PbCSP and subsequent boosting with MVAPbCSP induced considerably higher levels of protection against challenge with *P. berghei* sporozoites than other homologous or heterologous prime-boost immunisation regimes (Table 3).

TABLE 3

Protection against *Plasmodium berghei* challenge by prime-boost immunisation regimes using recombinant FP9PbCSP

| Prime/Boost | Animals Protected | Protection (%) |
|---|---|---|
| DNA/FP9 | 5/40 | 12.5 |
| DNA/MVA | 7/40 | 17.5 |
| FP9/MVA | 27/40 | 67.5 |
| MVA/FP9 | 15/40 | 37.5 |
| FP9/FP9 | 3/19 | 15.7 |
| MVA/MVA | 3/20 | 15.0 |

Method

Female Balb/c mice were immunised intravenously with $1\times10^6$ PFU of FP9PbCSP (FP9) or MVAPbCSP (MVA), or intramuscularly with 50 μg of pSG2PbCSP (DNA) and boosted two weeks later with either FP9PbCSP or MVAPbCSP. The CD8+ T-cell response against PbCSP was determined using the MHC-class I restricted Pb9 epitope in an IFNγ ELISPOT assay 14 days following the boost. Columns represent the mean IFNγ spot forming cells (SFC) per million splenocytes± the standard error of the mean for three mice per group (FIG. 4).

Two weeks following the booster immunisation, animals were challenged by intravenous injection with 2000 *P. berghei* sporozoites and subsequently monitored for blood stage infection 6 to 14 days after challenge (Table 2). Results are cumulative for four experiments.

EXAMPLE 4

Construction of FP9 Viruses Encoding Different Foreign Recombinant Antigens and Epitope Strings To demonstrate that FP9 can be used as a general system for delivering recombinant antigens, genes encoding whole antigens of both prokaryotic and eukaryotic origin and synthetic genes encoding poly-epitope and poly-protein fusions were inserted into the genome of FP9 by homologous recombination (Table 4). These genes encode antigens which differ widely in structure and are derived from a variety of different pathogens. Each of the recombinant FP9 derivatives listed in Table 4 have been propagated in vitro in chicken embryo fibroblasts to high concentrations, indicating that they are both viable and stable. The vaccinia p7.5 early-later promoter was used to drive expression of the encoded antigens in all of the recombinant viruses. The encoded antigens have been found to be expressed in all cases where this has been determined (Table 4). This includes the largest of these constructs, $FP9L_3SEPTL$, which harbours a 9.9 kbp synthetic gene encoding a polyprotein expressed as 6 fused malarial antigens.

TABLE 4

Recombinant FP9 viruses constructed to date

| Construct Name | Recombinant Antigen | Expression | Pathogen | Disease |
|---|---|---|---|---|
| FP9PbCSP | Circumsporozoite surface protein (CSP) | | *Plasmodium berghei* | Malaria - Rodent |
| FP9MEPfTrap | Epitope string fused to Trombospondin-related adhesive protein (TRAP) | Yes | *Plasmodium falciparuni* | Malaria - Human |
| FP9PfLSA-1 | Liver Stage Antigen 1 (LSA1) | Yes | | |
| FP9L3SEPTL | Exp 1, Pfs16, LSA1, LSA3, TRAP, STARP | Yes | | |
| FP9PcCSP | CSP | ND | *Plasmodium cynomolgi* | Malaria - Non-human primates |
| FP9PcTRAP | TRAP | | | |
| FP9PvCSP | CSP | ND | *Plasmodium vivax* | Malaria - Human and non-human primates |
| FP9PvTRAP | TRAP | | | |
| FP9Ag85A | Antigen 85A | Yes | *Mycobacterium Tuberculosis* | Tuberculosis - Human |
| FP911e | Antigen 11e | ND | *Theileria parva* | East Coast Fever - Cattle |
| FP9Pfs 16 | Pfs16 | ND | | |
| FP9Tel | Epitope string | ND | | |

[a]Expression of the recombinant virus was determined either by immunofluorescence or by the presence of an immune response.
ND, not determined.

EXAMPLE 5

Induction of T-cell Immune Responses Against *P. falcipraum* Antigens by FP9

The MEPfTrap polypeptide, which consists of a string of T-cell epitopes from *P. falciparum* CSP and the Pb9 epitope (Gilbert et al., 1997 *Nat. Biotechnol.* 15, 1280-4) fused to the *P. falcipraum* TRAP gene (Robson et al., 1988, *Nature* 335, 79-82), was developed as an antigen for vaccination against *P. falcipraum* malaria in humans. FP9 encoding MEPfTrap has been constructed (Table 4) and shown to elicit CD8+ T-cell responses in potency tests carried out in Balb/c mice (107±20 IFNγ spot forming cells/million splenocytes).

EXAMPLE 6

Induction of CDS+ and CD4+ T Cell Immune Responses against Antigen 85A of *M. tuberculosis* by FP9

Figure 6:
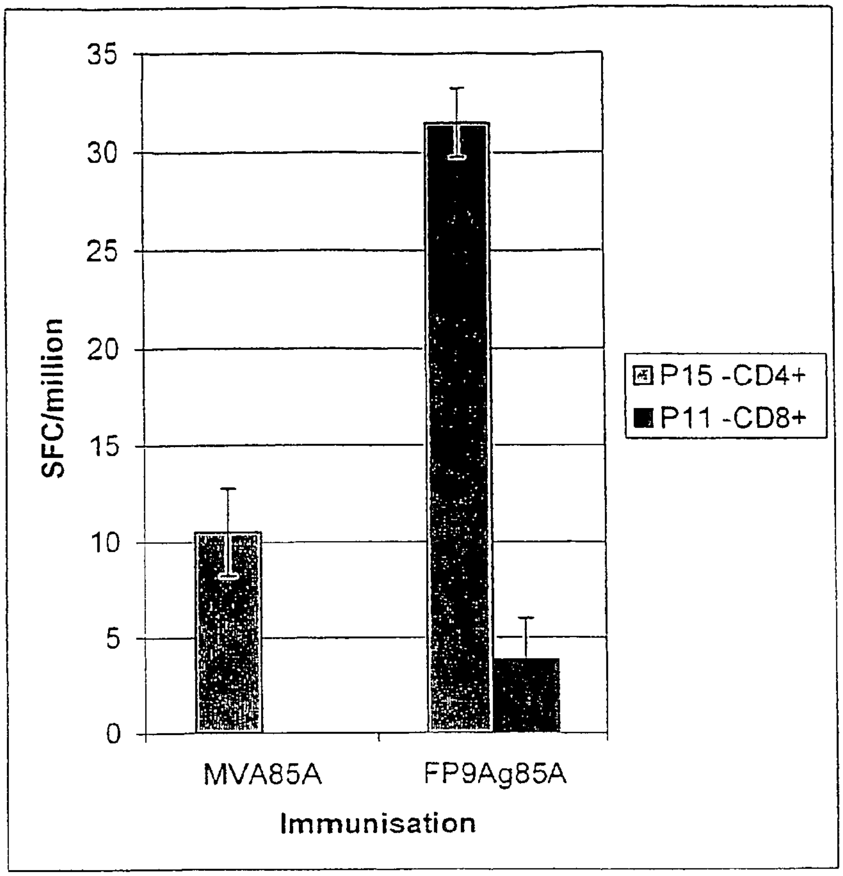
FIG. 6: Fowlpox FP9 can elicit both CD4+ and CD8+ T cell responses against *M. tuberculosis* Ag85A in Balb/c mice.

Antigen 85A (Ag85A) is a major secreted and protective antigen from *M. tuberculosis*. The immune response elicited by FP9 encoding Ag85A from *M. tuberculosis* was initially determined in Balb/c mice (FIG. 6). Antigen 85A contains a 20 amino acid $H\text{-}2^d$ MHC class II-restricted peptide epitope (recognised by CD4+ T-cells) as well as a nine amino acid $H\text{-}2^d$ MHC class I-restricted epitope (recognised by CD8+ T-cells) (Huygen et al., 1994). Immunisation with FP9Ag85A induced both CD4+ and CD8+ T-cell responses against Ag85A, indicating that FP9 will induce CD4+as well as CD8+ T-cell responses against encoded antigens in mice.

Figure 7:
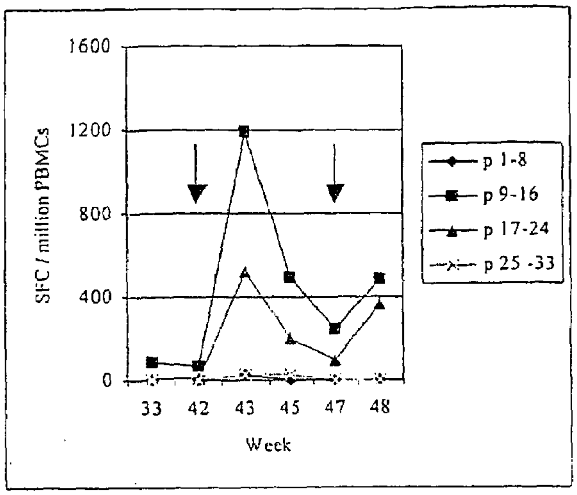
FIG. 7: Fowlpox FP9 elicits a T-cell immune response against *M. tuberculosis* Ag85A in non-human primates.

In further experiments, FP9Ag85A was found to induce significant boosting of the T-cell response induced by immunisation with MVA85A in *Rhesus macaques* (FIG. 7).

Method

Female Balb/c mice were immunised intravenously with $1\times10^7$ PFU of recombinant FP9 encoding antigen 85A (FP9Ag85A) from *mycobacterium tuberculosis* or, for comparison, $1\times10^6$ PFU of MVA encoding the same antigen. The response against 85A was determined using the MHC-class II restricted P15 epitope (recognised by CD4+ T-cells) and the MHC-class I restricted P11 epitope (recognised by CD8+ T-cells) in an IFNγ ELISPOT assay six days following immunisation. Columns represent the mean IFNγ spot forming cells (SFC) per million splenocytes± the standard error of the mean for three mice per group.

A male *Rhesus macaque* immunised twice with recombinant MVA encoding antigen 85A (MVA85A) was boosted (↓) 21 and 26 weeks later with $5\times10^8$ PFU of FP9Ag85A. The response against Ag85A was determined in peripheral blood mononucleocytes (PBMCs) using pools of overlapping peptides covering the amino acid sequence of the Ag85A.polypeptide in an IFNγ ELISPOT assay. Curves represent the IFNγ spot forming cells (SFC) per million PBMCs for 4 pools of peptides.

EXAMPLE 7

FP9 and MVA do not Elicit Cross-reactive T-cells Against Viral Antigens

Figure 8:
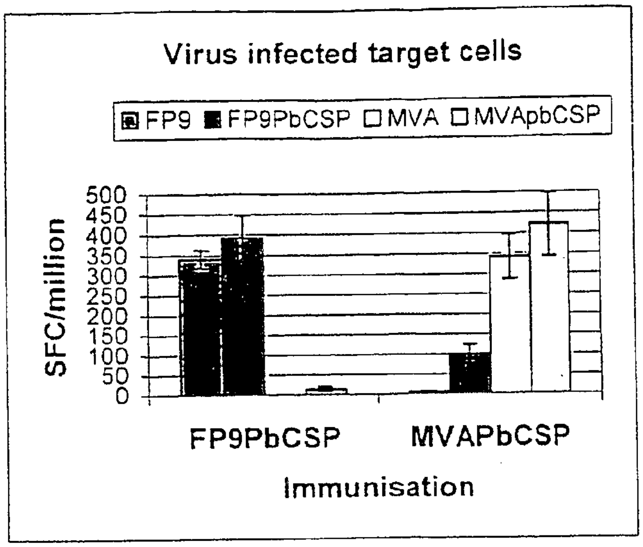
FIG. 8: Ex vivo IFNγ ELISPOT responses against FP9 and MVA viral antigens.

There is evidence to suggest that prime-boost immunization with different but not the same viral vector will elicit enhanced CD8+ T-cell responses against recombinant antigens (Gilbert et al., Vaccine In Press). Recent evidence suggests CD8+ T-cell responses against the viral vector will inhibit boosting when the same recombinant virus is used as a priming and boosting agent (unpublished observation, Eric G. Sheu). Immune splenocytes from mice immunised with FP9PbCSP do not produce IFNγ when exposed to naive cells infected with MVA but do when exposed to cells infected with FP9 (FIG. 8). Conversely, MVAPbCSP immune splenocytes recognise naive cells infected with MVA but not FP9 (FIG. 8). Despite this, an IFNγ secreting T-cell response can be observed when FP9PbCSP immune splenocytes are exposed to spleen cells infected with MVAPbCSP and vice versa (FIG. 8). Considered together, these results indicate that recombinant FP9 and recombinant MVA will elicit T-cell responses against an encoded antigen without eliciting T-cells that cross-react with antigens from both viruses.

Further preliminary results indicate that non-replicating canary poxviruses also do not cross-react with MVA. Thus, the avipoxviruses and orthopoxviruses may not elicit cross-reactive T-cells in general making them suitable as priming or boosting agents in the same vaccination regime.

Method

Ex vivo IFNγ elispot responses against PbCSP and viral antigens in splenocytes isolated from mice fourteen days after i.v. immunisation with either FP9PbCSP or MVAPbCSP. The IFNγ response was determined by exposing splenocytes isolated from immune animals to naive splenocytes pulsed with Pb9 peptide or those infected with FP9, FP9PbCSP, MVA, or MVAPbCSP. Columns (FIG. 8) represent the mean number of IFNγ spot forming cells (sfc) per million splenocytes±S.E.M. for three mice per group.

EXAMPLE 8

Growth of Avipoxviruses in Vitro

Wild-type and recombinant poxviruses are usually grown in vitro in cultured chicken embryo fibroblasts (CEFs). In initial attempts to grow recombinant FP9 by infection of cultured CEF monolayers in our laboratory, we observed erratic viral plaque formation and poor yields of virus (Table 5). In contrast, good plaque formation and consistently high yields of MVA were obtained following infection of similar cultured CEFs (Table 5). Primary "non-cultured" CEFs can be obtained by loading freshly prepared CEFs into tissue culture dishes at a concentration sufficient to give a confluent monolayer without growth. The present inventors have found that FP9 and recombinant FP9 forms visible viral plaques and give good yields of virus (Table 5) following infection of monolayers of primary "non-cultured" CEFs. Similarly, plaque formation and higher yields of attenuated canarypox virus, ALVAC have been obtained using primary "non-cultured" CEFs by the present inventors.

Together these studies indicate that the avipoxviruses are more fastidious than MVA, and possibly other orthopoxviruses, in terms of their growth requirements. Without wishing to be bound by theory, the present inventors believe that the replication of avipoxviruses within CEFs may require a specific host molecule that is lost as the CEFs are cultured in vitro. In contrast, MVA, and possibly the orthopoxviruses in general, do not require this host molecule for replication. The main consequence of this observation is that primary non-cultured CEFs are likely to be required for the production of large quantities of recombinant avipoxviruses. Accordingly, in practice, large-scale production of recombinant FF9 for Phase I clinical studies has only been achieved using "non-cultured" CEFs.

TABLE 5

Approximate yield of virus from cultured and non-cultured CEFs

| | Approximate yield of virus (viral particles per cell) | |
|---|---|---|
| Virus | Cultured CEFs[1] | Non-Cultured CEFs[2] |
| Fowlpox | <1 | 10 |
| MVA | 100 | Unknown |
| ALVAC | <1 | 10 |

[1]Cultured CEFs were passaged in culture prior to infection with virus.
[2]For "non-cultured" CEFs, primary CEFs were loaded at approximately $1.5 \times 10^5$ cells/$cm^2$ in tissue culture flasks and grown for 12–18 h prior to infection.

EXAMPLE 9

Induction of a Protective Immune Response against *P. falciparum* Malaria by FP9 in Human Volunteers Phase I clinical trials of FP9MEPfTrap (see Example 5):

Healthy adult volunteers were immunised twice with over $3\times10^7$ PFU of FP9MEPfTrap and subsequently boosted with the same dose of MVAMEPfTrap. Two of five immunised volunteers were protected against challenge with bites from five female *anopheles stephensii* mosquitoes infected with virulent *P. falcipraum* malaria.

In contrast, five out of five malaria naive volunteers succumbed to *P. falciparum* malaria in the same experiment. Thus, demonstrating for the first time that heterologous prime-boost immunisation of human volunteers with two recombinant non-replicating viruses can elicit a protective immune response against an infectious disease.

Protection was determined by the failure of volunteers to develop blood-stage malaria, demonstrating that poxvirus immunisation blocked the *P. falcipraum* infection in the liver.

Experiments also determine the mechanism of protection, although it is likely that protection is mediated by T-cell responses elicited against the MEPfTrap polypeptide.

EXAMPLE 10

Clinical Trials in a Malaria Endemic Region

Phase I Trial

To determine whether a heterologous prime-boost immunisation regime using recombinant FP9 and MVA can boost immune responses in a malaria-exposed population, a phase I clinical trial using constructs encoding the MEPfTrap molecule is conducted in the Gambia.

Adult volunteers (approximately 12) are immunised twice with the FP9MEPftrap construct and boosted with a single dose of MVAMEPfTrap. T-cell and antibody immune responses are determined in blood, the primary purpose of the study being to demonstrate whether immunisation with the recombinant non-replicating poxviruses boosts the existing anti-malaria response primed by natural infection.

Phase IIb Study

Phase IIb study is conducted in Gambian adults using the same immunisation regime.

Volunteers are monitored for enhanced immune responses and evidence of blood stage infection during the course of the trial, which runs through the malaria season (June to December).

Further Studies

Further phase I studies are also conducted in the Gambia during 2002 using appropriate recombinant FP9 and MVA to vaccinate against *Mycobacteria tuberculosis* and HIV. Both trials are conducted using volunteers who are infected with the respective pathogens and, therefore, evalute both the capacity of FP9 and a heterologous primeboost immunisation regime using two non-replicating viruses to serve as a therapeutic vaccine.

Thus it is demonstrated that vaccination according to the present invention produces and/or enhances protective response in humans.

EXAMPLE 11

Boosting the T-cell Response against Ag8SA Primed by *M. bovis* BCG Using Non-replicating Recombinant Poxviruses

*M. bovis* BCG is widely administered to children throughout the developing world as a vaccine against tuberculosis caused by *M. tuberculosis*. Although effective against severe childhood forms of tuberculosis, the protective efficacy of *M. bovis* BCG against adult forms of the disease is highly variable and thought to wane over time. Since Ag85A is a major secreted antigen of both *M. bovis* BCG and *M. tuberculosis*, boosting the immune response elicited against Ag85A by *M. bovis* BCG immunization is a credible strategy for enhancing the protective efficacy of this vaccine against adult tuberculosis. This strategy has been pursued by others in murine models by boosting with recombinant Ag85A protein (Brooks et al., 2001 *Infect. Immun.* 69, 2714-7) or a DNA-vaccine encoding this antigen (Tanghe et al., 2001 *Infect. Immun.* 69, 3041-7).

Figure 9:
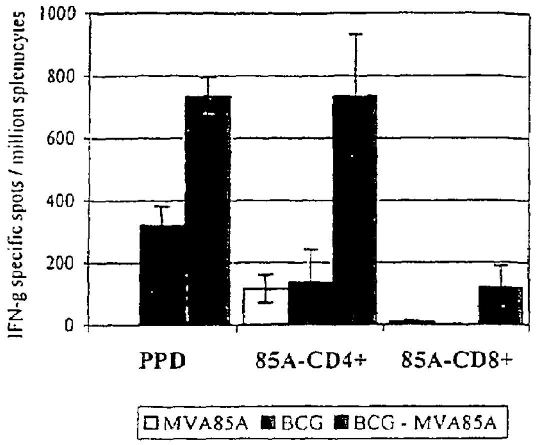
FIG. 9: Ex vivo IFNγ Elispot response in Balb/c mice following aerosol or mucosal priming with *M. bovis* BCG and boosting with MVA85A.
Figure 10:
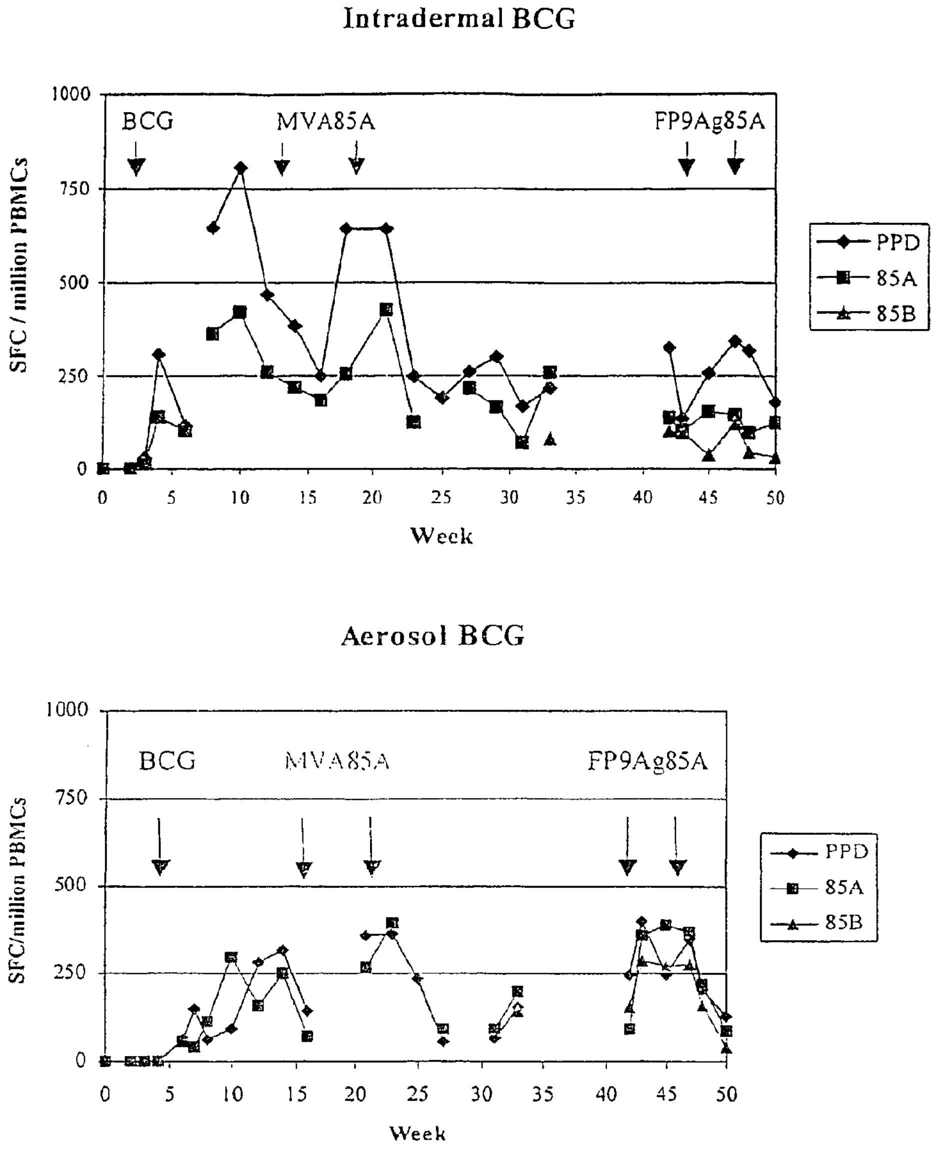
FIG. 10: Ex vivo IFNYγ Elispot response in *Rhesus macaques* following aerosol or mucosal priming with *M. bovis* BCG and boosting with MVA85A and FPAg85A.

Based on the observation that FP9Ag85A can boost an immune response primed by immunization with MVA85A, the present inventors wished to determine whether poxvirus constructs could boost the immune response primed by *M. bovis* BCG. Preliminary experiments conducted in Balb/c mice indicated that both the CD4+ and CD8+ T-cells responses Ag85A could be boosted primed by immunization with *M. bovis* BCG (FIG. 9). Further experiments conducted using *Rhesus macaques* showed that immunization with *M. bovis* BCG by either intradermal or aerosol routes will induce T-cell responses against Ag85A. Boosting with MVA85A early after administration of *M. bovis* BCG elicited a variable and short-lived enhancement of the immune response against PPD and Ag85A protein. However, subsequent boosting with FP9Ag85A significantly enhanced the T-cell immune response against these proteins (FIG. 10) as well as against peptide pools spanning the Ag85A protein sequence. Further experiments determine the nature and location of the T-cell response elicited in the immunized animals.

These experiments provide the first example that non-replicating viruses can be used to boost the immune response primed by *M. bovis* BCG in mice and in primates. In addition, they establish the concept that non-replicating poxviruses may be effective as therapeutic vaccines against persistent latent infection with *M. tuberculosis* in man.

Method

Balb/c mice were immunized intradermally (i.d.) with *M. bovis* BCG and boosted 12 weeks later id. with $1\times10^6$ PFU of MVA85A. Control animals were immunized with *M. bovis* BCG or MVA8SA alone. T-cell immune responses were determined against PPD and Ag85A using the P15 (CD4+) and P11 (CD8+) epitopes in an IFNγ ELISPOT assay 12 days following immunisation. Columns (FIG. 9) represent the mean IFN-γ spot forming cells (SFC) per million splenocytes± the standard error of the mean for three mice per group.

Male *Rhesus macaques* were immunized either intradermally or by aerosol delivery with BCG and boosted twice with $5\times10^8$ PFU of recombinant MVA85A and twice with $5\times10^8$ PFU FP9Ag85A. The response against Ag85A was determined in peripheral blood mononucleocytes (PBMCs) using purified Ag85A, recombinant Ag85B (which shares approximately 80% homology with Ag85A) or purified protein derivative from *M. tuberculosis* (PPD) in an IFNγ ELISPOT assay. Curves (FIG. 10) represent the IFN-γ spot forming cells (SFC) per million PBMCs from a single animal.

EXAMPLE 12

Fowlpox is an Effective Boost

Three healthy malaria-naive human volunteers were immunised as follows:

2 mg of DNA-ME.TRAP intramuscularly at week 0, 2 mg of the same vaccine again intramuscularly at week 3 (day 21), 1x10e8 pfu of FP9-ME.TRAP intradermally at week 7, and 1.5x10e8 pfu of MVA-ME.TRAP intradermally at week 11.

Mean responses measured by ELISPOT in PBMCs are shown in FIG. 11.

The ME response is predominantly to CD8 T cell epitopes. The T996 response is the the homologous strain of TRAP, the 3D7 response to a heterologous strain of TRAP.

It is clear that FP9-ME.TRAP boosts a DNA primed T cell response. It is also clear that a further immunisation with MVA-ME.TRAP enhances responses induced by the DDF regime.

It is therefore demonstrated that FP9 provides an effective boost to T cell responses in human primates.

The effectiveness of a triple immunisation regime with DNA then FP9 and then MVA is also demonstrated in human primates (DDFM).

EXAMPLE 13

Fowlpox is an Effective Prime

Malaria-naive human volunteers were immunised with a FP9-MVA prime-boost regime as follows:

In this Example there are two cohorts, one of five vaccinees and one of 12 vaccinees.

FFM Regime

FP9-ME.TRAP was Administered Intradermally at 1x10e8 pfu at day 0

FP9-ME.TRAP was Administered Intradermally at 1x10e8 pfu at day 21

MVA-ME.TRAP was Administered Intradermally at a Dose of 1.5×10e8 pfu at day 49.

All volunteers were challenged with 3D7 strain *P. Falciparum* sporozoites administered by the bites of five infectious mosquitoes, along with non-vaccinated controls.

In the first cohort ⅖ FFM vaccinees were fully protected from infection. This level of protection is significantly different from 24 pooled non-vaccinated controls challenged at various time points in the same way (P<0.05, chi-squared test); all the controls were infected.

Two of the protected vaccinees were re-challenged six months later and one was still fully protected.

11 volunteers in the second cohort were challenged identically and these vaccines developed patent malaria parasitaemia significantly later than control vaccines (P<0.05).

Figure 12:
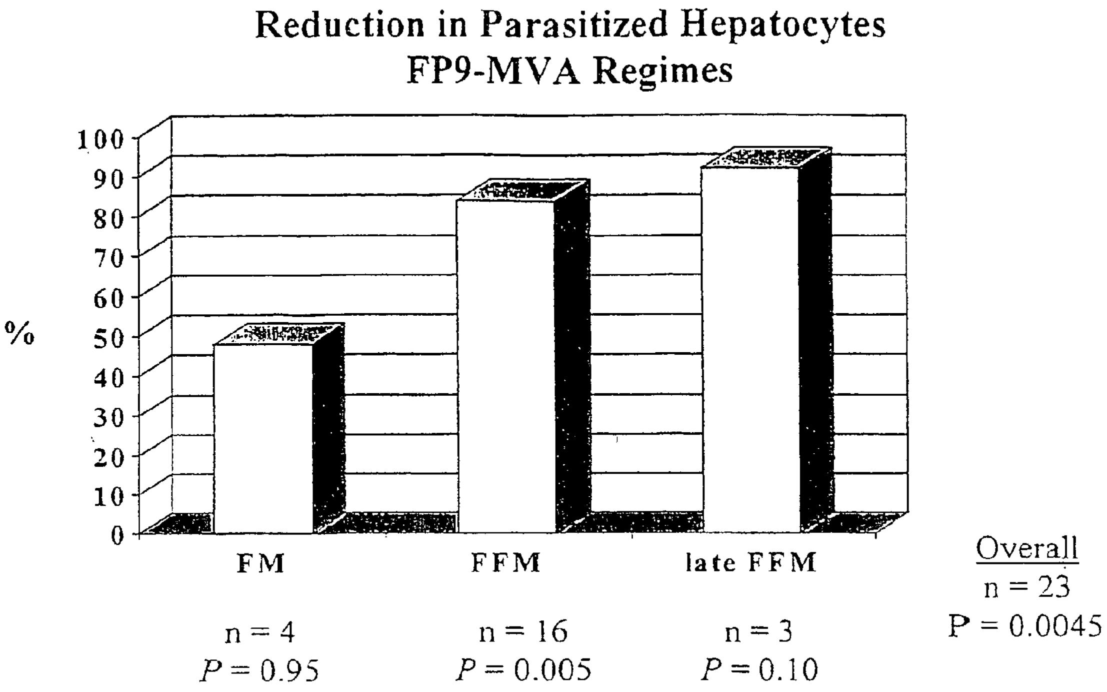
FIG. 12 shows a bar chart.

FIG. 12 shows the calculated reduction in liver stage parasites resulting from vaccination assuming that parasites multiply 8 fold every 48 hours in peripheral blood. The "late FFM" group represents the two rechallengees (see above) and a further volunteer challenged for the first time at 5 months post vaccination (the FFM group were challenged 13-50 days post the last vaccination).

Also shown are results for four vaccinees administered only a single priming immunisation with FP9 ("FM"). The significance levels are calculated from log rank test Kaplan-Meier analysis of times to parasitiaemia in vaccines and non-vaccinated challenge controls.

Overall there was highly significant protection observed in the FFM vaccines compared to controls (P<0.01).

Four individuals immunised with a DDMF regime (two DNA does of 2 mg i.m. at four week intervals followed by 1.5×10e8 MVA ME.TRAP 3-4 week later followed by 1.0×10e8 FP9-ME.TRAP 3-4 weeks later) were also significantly protected (P<0.05).

Thus it is demonstrated that fowlpox such as FP9 is an effective prime as well as an effective boost in the methods of the present invention.

EXAMPLE 14

Clinical Trials of Higher Dose Immunisation Regimes

Higher dose prime-boost regimes were studied in rural Gambian adult males who have had life-long exposure to malaria infection.

28 subjects were immunised with ME.TRAP vaccines according to one of the regimes set out below (14 subjects per group/regime):

1) DDM Regime

DNA (2 mg i.m.) administered two (DDM) or three (DDDM) times at a 3-4 week intervals followed by MVA-ME.TRAP 1.5×10e8 id (DDM group—In FIG. 13 the DDM and DDDM vaccinee subgroups are merged as there was no siginificant difference between these.)

2) FFM Regime

FP9 (1×10e8 i.d.) administered twice at 3 week intervals followed by MVA-ME.TRAP 1.5×10e8 id (FFM group).

Data are presented in FIG. 13.

Both groups showed T cell responses to the malaria ME.TRAP insert prior to vaccination. These responses were boosted more by a FP9 immunisation than by a DNA immunisation (compare DD+7 days with FF+7 days) indicating that FP9 immunisation boosts naturally primed T cell responses in human primates.

Both DDM and FFM regimes induced high level (>250/million) T cell responses in these volunteer subjects naturally exposed to malaria.

It is demonstrated that prime-boost regimes (DDM and FFM) are more immunogenic than FP9 alone and MVA alone even though T cell responses in these individuals are primed by natural malaria infection.

It is also demonstrated that the induced responses show good malaria-strain crossreactivity—the magnitude of responses to the vaccine strain (T996) and the 3D7 non-vaccine strain of TRAP are comparable.

Figure 14:
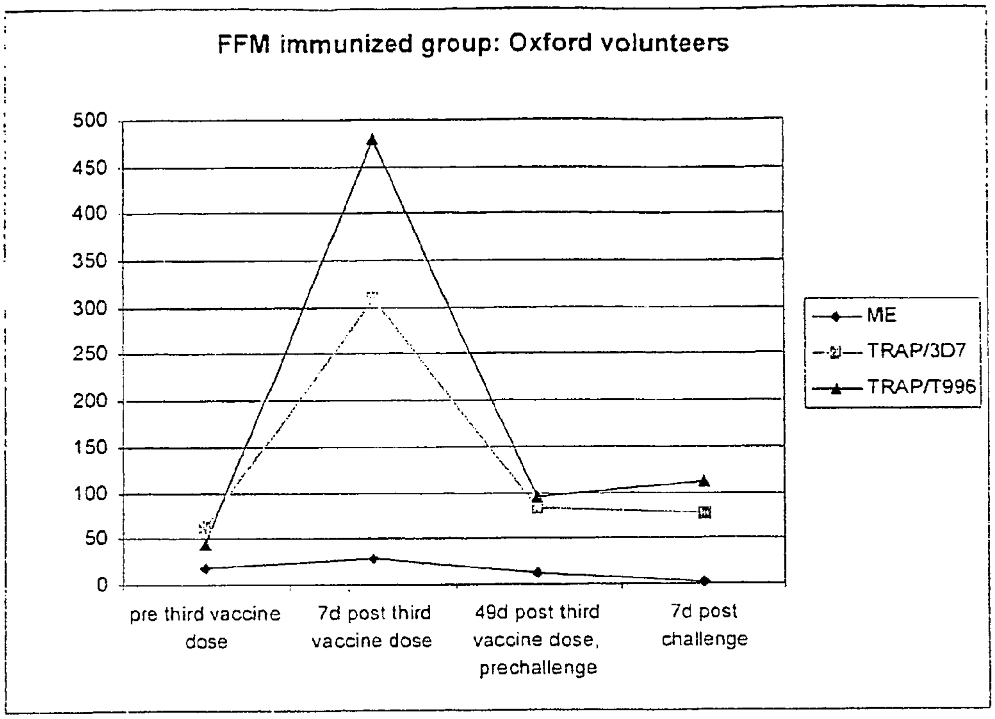
FIG. 14 shows a graph.

Comparable immunogenicity was observed in 1 human primate volunteers immunised with the same FFM regime (see FIG. 14).

Thus it is demonstrated that treatment of subjects according to the present invention produces protective immune responses in said subjects.

EXAMPLE 15

Immunisation against TB Antigens in Primates

To assess the possible protective efficacy of prime-boost immunisation against tuberculosis using recombinant FP9 as a boosting agent the following study was performed in primates.

In this example the primates are Macaques, animals naturally susceptible to *Mycobacterium tuberculosis.*

At the biomedical primate centre (BPRC) in the Netherlands three cynomolgous macaques were immunised with BCG intradermally and administered MVA-Ag85A intradermally after 8 weeks and FP9-Ag85A intradermally after a further four weeks. In parallel three other macaques were immunised with BCG alone. Four weeks after the final immunisation all these macaques along with unimmunised macaques were challenged with a large intratracheal dose (of 1000 CFU) of *M. tuberculosis*. The animals were observed for 28 weeks, immunoassays performed and the animals were sacrificed at 28 weeks post-challenge and an autopsy performed.

At autopsy all non-immunised macaques had macroscopic evidence of tuberculosis; ⅓ BCG immunised macaques had no macroscopic evidence of tuberculosis; ⅔ 15 BCG-MVA-FP9 immunised macaques had no evidence of tuberculosis.

ELISPOT assays post-challenge using PPD and ESAT-6 as mycobacterial antigens showed substantially lower responses in the BCG-MVA-FP9 immunised animals than in challenge controls.

Figure 18:
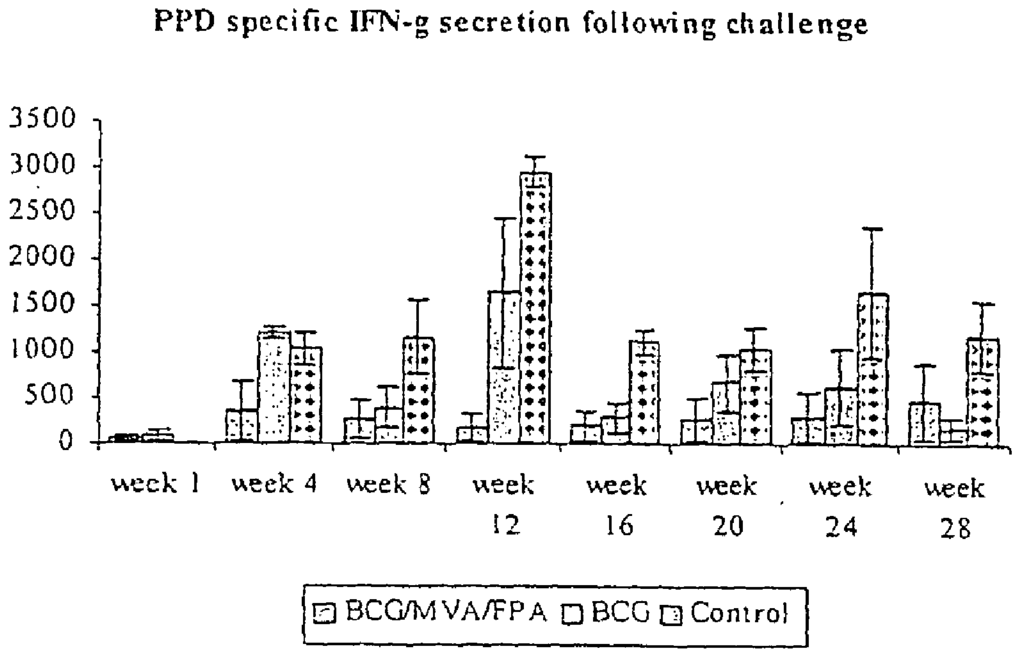
FIG. 18 shows the mean interferon gamma response to PPD at various weeks after intratracheal *M. tuberculosis* challenge of cynomolgous macaques.

Interferon gamma ELISA assays post-challenge using PPD as the mycobacterial antigen showed substantially lower responses in the BCG-MVA-FP9 immunised animals than in challenge controls immunised with BCG alone or an adjuvant alone (control animals), supporting the view that these BCG-MVA-FP9 prime-boosted macaques were very substantially protected from tuberculosis (FIG. 18). The figure shows the mean interferon gamma response to PPD at various weeks after intratracheal *M. tuberculosis* challenge of cynomolgous macaques. BCG-MVA-FP9 animals have the lowest immune responses to PPD indicating the least *M. tuberculosis* replication after challenge and thus the highest degree of protection. Similar data were obtained using ESAT6 as an antigen.

Thus it is demonstrated that primates such as macaques which are prime-boost immunised according to the present invention are very substantially protected from tuberculosis.

EXAMPLE 16

The FP9 Strain is more Potent than Webster's FPV-M in Priming and Boosting CD8 T Cell Response.

Objective: To determine whether FP9PbCSP will elicit enhanced antigen-specific T cell responses when compared to FPV-MPbCSP when administered by a clinically relevant route in prime/boost immunisation regimes with MVAPbCSP.

Method

Female BALB/c mice (6-8 weeks old) were immunised intradermally (id.) with FPPbCSP, FPV-MPbCSP or MVAPbCSP and boosted in a similar manner two weeks later. Viruses were diluted to $2\times10^7$ PFU/ml in pyrogen free PBS, characterised as described in EXAMPLES 1 and 2 of the patent application, and administered id. by bilateral injection of 25 ul into each ear of a mouse. Fourteen days after immunisation, the mice were sacrificed by cervical dislocation and the T cell response elicited against the Pb9 epitope of PbCSP and a control epitope from β-galactosidase were determined using the IFNγ assay as described below:

Murine IFNγ ELISPOT protocol

A. Materials

IFN-gamma ELISpot ALP Kit Mabtech 3321-2A

600 μg anti-IFN-gamma purified Mab AN 18

50 μg anti-IFN-gamma biotinylated Mab R46A2

50 μl Streptavidin-Alkaline Phosphatase

Complete α-MEM medium 500 ml MEM α-modification Sigma M-4526

50 ml FCS [10%] Sigma F-2442

5 ml pen/strep [I00U penicillin 100 μg strep] Sigma P-0781

10 ml L-glutamine [4 mM] Sigma G-7513

500 μl 2-Mercaptoethanol [50 μm] Gibco BRL 31350-010

ACK buffer 8.29 g $NH_4Cl$ [0.15M] (Sigma A-4514)

1 g $KHCO_3$[1 mM] (Sigma P-9144)

37.2 mg $Na_2EDTA$ (Sigma ED2SS)

800 ml milli-Q water

Adjust pH to 7.2-7.4 with HCl (Sigma S-7653)

Make up to 1000 ml with water and autoclave

Colour Development Buffer:

BioRad AP Conjugate Substrate kit (170-6432).

For one plate:

5 ml deionised water

200 μl of 25× buffer

50 μl reagent A

50 μl reagent B

Mix well and use immediately

Protocol

1. Preparation of Plates:

1.1. Coating plates: coat MAIP multiscreen plates (Millipore MAIPS4510) with 25 rat anti-mouse IFNγ (Mab AN18) antibody. Dilute to 10 μg/ml in Phosphate Buffered Saline (PBS; Sigma P-3813) and add 50 μl per well to MAIP plates. Incubate overnight at 4° C. in a humidified chamber.

1.2. Blocking plates: Flick off coating antibody and wash plates once with 150 ul of sterile PBS (Sigma P-3813) per well using a multi-channel pipette. Flick off the PBS, add 100 ul complete α-MEM medium per well, and incubate at room temperature for 1+ hour. It is important to keep the plates sterile at this stage.

2. Splenocyte preparation:

2.1. Crush individual spleens in 2 ml of PBS with the plunger of a 10 ml syringe in a 70 μm cell strainer (Falcon 352350) contained in a petri dish, add 5 ml of PBS, suspend splenocytes by pipetting, and transfer into a 50 ml tube. Rinse cell strainer and dish with a further 10 ml of PBS and add to the 50 ml tube. Centrifuge at 1500 rpm for 5 min.

2.2. Remove supernatant, re-suspend cells by tapping tube and add 5 ml ACK buffer and mix by inversion. Incubate at room temperature for no longer than 5 minutes. Add 25 ml PBS, mix by inversion and centrifuge at 1500 rpm for 5 min.

2.3. Remove supernatant re-suspend pellet by tapping the tube, add 10 ml PBS and vortex. Count using an improved Neubauer haemacytometer by diluting 1:10 in 0.4% trypan blue solution (Sigma T-8154). Aliquot amount needed for the Elispot and centrifuge at 1500 rpm for 5 min, resuspend by vortexing in an appropriate volume of complete Alpha MEM medium to give a concentration of 10 million cells/ml.

3. Plate setup:

| | 50 μl | | | | 50 μl | | | | 50 μl | | |
|---|---|---|---|---|---|---|---|---|---|---|---|
| 1 | 2 | 3 | 4 | 5 | 6 | 7 | 8 | 9 | 10 | 11 | 12 |
| | 150 | | | | 150 | | | | 150 | | |
| | 150 | | | | 150 | | | | 150 | | |
| | 150 | | | | 150 | | | | 150 | | |
| | 150 | | | | 150 | | | | 150 | | |
| | 150 | | | | 150 | | | | 150 | | |
| | 150 | | | | 150 | | | | 150 | | |
| | 150 | | | | 150 | | | | 150 | | |
| | 150 | | | | 150 | | | | 150 | | |
| C | | | | C | | | | C | | | |

Note: Plate layout may be chosen by the operator according to the needs of the particular experiment.

3.1. Flick blocking media from plate and add 50 μl of complete alpha MEM medium to columns 3, 4, 7, 8, 11 & 12.

3.2. Add 150 μl of splenocytes to columns 2, 6 and 10 in duplicate. (Up to 12 samples per plate)

3.3. Take 50 μl of splenocytes from columns 2, 6 and 10 and transfer to columns 1, 5 and 9 respectively: these are the negative control wells.

3.4. Serially dilute each sample by taking 50 μl from columns 2, 6 and 10, to columns 3, 7 and 11, mix well and transfer 50 μl to 4, 9 and 12. Discard 50 μl after mixing final columns in dilution.

3.5. Add test peptide and control peptide to twice the desired final concentration to naive splenocytes at 10 million/ml in complete α-MEM medium. Add 50 μl of control peptide and target cells to columns 1, 5 and 9. Add 50 μl test peptide and target cells to remaining columns.

3.6. Incubate plates at 37° C. for 18-20 hours.

4. Developing the Assay 4.1. Wash plates twice with PBS containing 0.05% Tween 20 (Sigma P1379), once with distilled water and twice with PBST.

4.2. Add 50 μl/well of biotinylated rat anti-mouse interferon-gamma diluted to 1 μg/ml in PBS. Incubate for 2 hours at room temperature.

4.3. Wash plates four times with PBST, then add 50 μl Streptavidin Alkaline Phosphatase (Mabtech) diluted to 1 μl in PBS. Incubate at room temperature for 1 hour.

4.4. Wash plates four times with PBST, add 50 μl/well of colour development buffer 4.5. Incubate at room temperature until spots develop (approx. 10 min). Wash plates well with tap water, peel off plastic bottom and leave, to dry overnight on paper towels.

Results

Results were calculated as the number of antigen-specific IFNγ spot forming cells/million splenocytes (sfc/million). Differences between groups were determined by the students T-test (two-sample assuming equal variances) using Microsoft Excel 2000.

Figure 15:
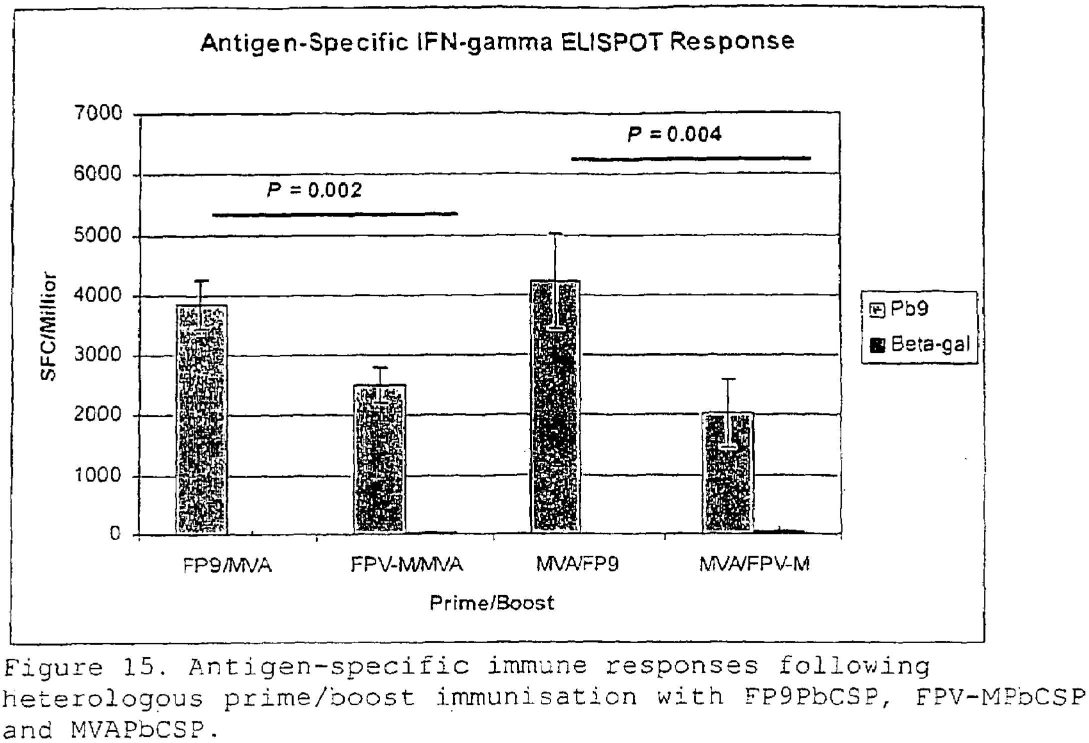
FIG. 15 shows a bar chart.

FP9PbCSP elicited a significantly enhanced antigen-specific T cell response against PbCSP compared to FPV-MPbCSP when used as a priming (P=0.002) or boosting (P=0.004) agent in combination with MVAPbCSP (FIG. 15). Interestingly, there was no significant difference between groups that had been primed with FP9PbCSP and boosted with MVAPbCSP and vice versa.

Thus, FP9PbCSP proved to be more potent than FPV-MPbCSP as a priming and/or boosting agent, and is equally potent as a priming or boosting agent in combination with recombinant MVA.

EXAMPLE 17

Recombinant FP9 Protects against Viral Diseases

Objective

To determine whether immunisation with recombinant FP9 alone, or in a prime/boost regime, will elicit T cell responses against CD4+ and CD8+ T cell epitopes from viral and tumour antigens.

Method

A synthetic gene of 440 by encoding for a novel polypeptide (ME I) consisting of characterised CD8+ and CD4+ restricted epitopes from lymphocytic choriomeningitis virus (LCMV) antigens and murine tumour (P815 and CT26) antigens was synthesized as follows:

ME1 Model Epitope String:

A T cell epitope string encoding tumour and virus epitopes relevant in murine models of chronic infection (LCMV) and cancer (P815/CT26) is generated as set out below.

| Disease | Model | Abbr. | Epitope | | MHC Restriction | CD8/4 | Antigen |
|---|---|---|---|---|---|---|---|
| Cancer | P815 in DBA/2 | P1A | LPYLGWLVF | (SEQ ID NO.: 4) | $L^d$ | CD8 | P1A |
| | P815 in DBA/2 | MSR | GYCGLRGTGV | (SEQ ID NO.: 5) | $K^d$ | CDS | MSR |
| | CT26 in BALB/c | CT26 | SPSYAYHQF | (SEQ ID NO.: 6) | $L^d$ | CD8 | gp70 (MuLV) |
| Chronic Virus | LCMV | 1 | KAVYNFATCGI | (SEQ ID NO.: 7) | $K/D^b$ | CD8 | GP33—43 |
| | LCMV | 2 | FQPQNGQFI | (SEQ ID NO.: 8) | $D^b$ | CD8 | NP396—404 |
| | LCMV | 3 | SGVENPGGYCL | (SEQ ID NO.: 9) | $D^b$ | CD8 | GP276—286 |
| | LCMV | 4 | YTVKYPNL | (SEQ ID NO.: 10) | $K^b$ | CD8 | NP205—212 |
| | LCMV | 5 | CSANNSHHYI | (SEQ ID NO.: 11) | Db | CD8 | GP92—101 |
| | LCMV | 6 | GLNGPDIYKGVYQFKSVEFD | (SEQ ID NO.: 12) | $H\text{-}2^b$ | CD4 | GP61—80 |
| | LCMV | 7 | SGEGWPYIACRTSIVGRAWE | (SEQ ID NO.: 13) | $H\text{-}2^b$ | CD4 | NP309—328 |
| Model Epitopes | Beta-gal | 8 B-gal | DAPIYTNV | (SEQ ID NO.: 14) | $K^b$ | CD8 | Beta-gal |
| | | Model | TPHPARIGL | (SEQ ID NO.: 15) | $L^d$ | CD8 | |
| | HA tag | | YPYDVPDYA | (SEQ ID NO.: 16) | Antibody Tag for detection of expression | | |

To avoid potential immune competition LCMV-derived epitopes are H-$2^b$ restricted and the cancer epitopes are H-$2^d$-restricted. The order of the epitopes alternates between H-$2^d$ and H-$2^b$.

Epitope String Sequence
Showing Epitopes:

| | |
|---|---|
| Cloning site Kozak M | |
| [GLNGPDIYKGVYQFKSVEFD] | (SEQ ID NO.: 17) |
| [KAVYNTATCGI] | (SEQ ID NO.: 18) |
| [LPYLGWLVF] | (SEQ ID NO.: 19) |
| [FQPQNGQFI] | (SEQ ID NO.: 20) |
| [GYCGLRGTGV] | (SEQ ID NO.: 21) |
| [SGVENPGGYCL] | (SEQ ID NO.: 22) |
| [SPSYAYHQF] | (SEQ ID NO.: 23) |
| [YTVKYPNL] | (SEQ ID NO.: 41) |
| [TPHPARIGL] | (SEQ ID NO.: 24) |
| [CSANNSHHYI] | (SEQ ID NO.: 25) |
| [SGEGWPYIACRTSIVGRAWE] | (SEQ ID NO.: 26) |
| [DAPIYTNY] | (SEQ ID NO.: 27) |
| [YPYDVPDYA] | (SEQ ID NO.: 28) |
| AA (stop signal) | |

Amino Acid String:

MGLNGPDIYKGVYQFKSVEFDKAVYNFATCGILP (SEQ ID NO.: 29)
YLGWLVFFQPQNGQFIGYCGLRGTGVSGVENPGG
YCLSPSYAYHQFYTVKYPNLTPHPARIGLCSANN
SHHYISGEGWPYIACRTSIVGRAWEDAPIYTNVY
PYDVPDYAAA

Flanking nucleotides and amino acids

| | |
|---|---|
| GGGCCCGCCGCCACCATGG... | (SEQ ID NO.: 30) |
| MGLNGPDIYKGVYQFKSVEFDKAVYNFATCGIL | (SEQ ID NO.: 31) |
| PYLGWLVFFQPQNGQFIGYCGLRGTGVSGVENP | (SEQ ID NO.: 32) |
| GGYCLSPSYAYHQFYTVKYPNLTP | |
| HPARIGLCSANSHHYISGEGWPYIACRTSIVGR | (SEQ ID NO.: 33) |
| AWEDAPI | |
| ...TAAGGCGCGCC | (SEQ ID NO.: 40) |
| YTNVYPYDVPDYAAA | (SEQ ID NO.: 34) |

The epitope string does not contain ApaI nor AscI target sequences.

The epitope string does not contain the pox virus early gene transcription termination sequence, TTTTTNT (SEQ ID NO.: 35).

Vector Manufacture The ME1 epitope string was ligated into a DNA vaccine vector (PSG2) and the fowlpox shuttle vector pEFL29. Plasmid pEFL29.ME1 was subsequently recombined into the chromosome of FP9 following established methods to construct FP9.ME1.

This virus was subsequently bulk-purified by propagation in chicken embryo fibroblasts (CEF) and centrifugation through a 30% sucrose cushion. The titre of the virus was confirmed by titration on CEF and X-gal staining, following established methods. Viruses were prepared for immunisation by suspension in pyrogen free PBS at $1\times10^7$ PFU/ml. Plasmid PSG2.ME1 was bulk-purified using a Qiagen Giga column and resuspended at 1 mg/ml in pyrogen free PBS.

Female BALB/c (H-$2^d$) C57BL/6(H-$2^b$) mice (6-8 weeks old) were immunised intramuscularly (im.) with PSG2.ME1 or a control plasmid pSG2.Mel3, which contains an irrelevant epitope string. Viruses FP9.ME1 and the empty control virus FP9.EFL29 were administered intravenously (iv.) into the tail vein at a dose of $1\times10^6$ PFU. Animals were boosted two weeks after immunisation. Fourteen days after boosting, the mice were sacrificed by cervical dislocation and the T cell response elicited against the LCMV, P815, CT26 and control epitopes from β-galactosidase were determined using the IFNγ assay as described in Example 16.

Results were calculated as the number of antigen-specific IFNγ spot forming cells/million splenocytes (sfc/million). Differences between groups were determined by the students T-test (two-sample assuming equal variances) and ANOVA using Microsoft Excel 2000.

Experimental Design and Results

To avoid competition between the viral and tumour epitopes, ME1 encodes epitopes from LCMV antigens characterised in H-$2^d$ haplotype mice and those from tumour antigens characterised in H-$2^d$ haplotype mice. Accordingly, the capacity of FP9.ME1 to elicit CD4+ and CD8+ T-cell epitopes was tested in both BALB/c (H-2 d) C57BL/6 (H-$2^d$) mice as described in Table 6. The results of these experiments are shown in Table 6.

TABLE 6

Experiments to determine the immunogenicity of the ME1 multiple epitope string

| Expt | Mouse Strain (haplotype) | Group | Prime | Boost | ELISPOT Response LCMV | ELISPOT Response Tumour |
|---|---|---|---|---|---|---|
| I | C57BL/6 (H-$2^b$) | A | PSG2 | FP9.EFL29 | 0 | 0 |
| | | B | FP9.ME1 | PSGZ.ME1 | >200 | 0 |
| | | C | PSG2.ME1 | FP9.ME1 | <2000 | 0 |
| | | D | FP9.ME1 | FP9.ME1 | >200 | 0 |
| | | E | PSG2.ME1 | PSG2.ME1 | >100 | 0 |
| 2 | BALB/c (H-$2^d$) | A | PSG2 | FP9.EFL29 | 0 | 0 |
| | | B | FP9.ME1 | PSG2.ME1 | 0 | >200 |
| | | C | PSG2.ME1 | FP9.ME1 | 0 | <2000 |
| | | D | FP9.ME1 | FP9.ME1 | 0 | >200 |
| | | E | PSG2.ME1 | PSG2.ME1 | 0 | >100 |

Experiments 1 and 2 were conducted in parallel. Each group contained four 6-8 week-old female mice. Vaccines were administered as described in Methods and priming and boosting were 14-16 days apart. T-cell responses were determined by the IFN-γ ELISPOT assay as in Example 16 using the LCMV, tumour and model epitopes described above. Results relate to the cumulative response against the LCMV and tumour derived epitopes, which are based on observations using the murine malaria and tuberculosis models.

EXAMPLE 18

Recombinant FP9 Protects against Cancer

Objective

To determine whether immunisation with FP9.ME1 alone, or in a prime/boost regime with pSG2.ME1, will elicit a protective immune response against CT26 tumour challenge in mice. Therefore, demonstrating in principle that recombinant FP9 can elicit antigen-specific T cell responses that will protect against cancer.

Method

Female BALB/c (H-$2^d$) mice (6-8 weeks old) will be injected with pSG2.ME1, FP9.ME1, or control constructs pSG2.Mel3 and FP9.EFL29 as described above. Animals are boosted two weeks after immunisation. Fourteen days after boosting, the mice are challenged by subcutaneous (sc.) injection in the left flank with $5\times10^5$ CT26 tumour cells as follows:

Growth of CT26 Tumours Subcutaneously

Some experimental questions are best addressed using a measurable solid tumor mass implanted subcutaneously. CT26 cells are amenable to this experimental approach. Although conventional wild-type CT26 cells grow in a laterally spreading fashion in the subcutaneous space, the highly transfectable variant, CT26, grows well as a more compact tumor mass, probably related to increased adhesion properties, making for more reproducible measurements.

Materials

CT26 cells

Complete DMEM medium with 10% (w/v) FCS

Sterile PBS

BALB/c mice, 6 to 8 weeks old 1-ml sterile disposable syringes

16-G and 25-G needles

Calipers

Additional reagents and equipment for counting cells.

1. Culture CT26 cells as in complete DMEM media with 10% FCS under
2. Harvest cells and rinse two times with PBS by centrifuging for 5 min at 200×g, room temperature.
3. Count cells and resuspend in PBS at $2\times10^7$ cells/ml. Transfer suspension to 1-ml syringe and 16-G needle then change to a 25-G needle.
4. Inoculate BALB/c mice by subcutaneous injection of 50 μl/mouse.

Ensure the cells are uniformly resuspended in the syringe just before injecting by gentle tapping and inversion.

The conditions given will result in $10^6$ tumor cells being implanted. A cell concentration of $2\times10^5$ to $1\times10^7$ cells has been used successfully.

5. The procedure can be accomplished rapidly by a single operator. The mouse is held in the left hand with the scruff of the neck between the first two fingers and the tail held against the palm with the fourth finger. With the right hand, the syringe is held and the needle inserted just through the skin on the left flank of the mouse. Using the syringe and needle as leverage, the skin should be gently lifted away from the body of the mouse to ensure that the tip of the needle is within the subcutaneous space. Only then is the 50 μl volume expelled.

Examine mice at least two times a week to examine for tumour growth and to assess general health. Once tumours appear, measure and record the longest and shortest dimensions using callipers.

The mean of these two measurements will yield the Mean Tumour Diameter for that mouse at that time point.

Tumours are first palpable 1 week after implantation. Measurements should be made to the nearest 0.5 mm.

Mice are observed for two weeks following challenge for evidence of tumour development, then sacrificed and dissected. Tumour size is determined by measuring the length and the width of the tumour, then taking the average of these measurements. Statistical analysis is performed using GraphPrism Instat, with differences in tumour incidence determined by the Fishers Exact test and differences in tumour size using the students T-test (two-sample assuming unequal variances).

Experimental Design and Expected Results

CT26 is a colonic carcinoma cell line derived from BALB/c mice. CT26 forms a solid tumour in BALB/c mice approximately 1 week after subcutanteous injection. The ME1 epitope string contains a protective CD8+restricted epitope derived from the MuLV gp70 envelope protein that is expressed by the CT26 tumour (see above). Since the prime/boost immunisation regime using pSG2.ME1 followed by FP9.ME1 elicits an enhanced CD8+ T cell immune response against this epitope (see above), we showed that this immunisation regime elicits protection against CT26 challenge in BALB/c mice. Table 7 shows the results.

TABLE 7 tumor incidence in immunised BALB/c mice following tumor challenge

| Group | Prime | Boost | Tumor Incidence |
|---|---|---|---|
| A | None | None | 12/12 |
| B | pSG2.Me13 | FP9.EFL29 | 11/12 |
| D | FP9.MEJ | pSG2.ME1 | 8/12 |
| D | pSG2.ME1 | FP9.ME1 | 0/12 |
| E | FP9.ME1 | FP9.ME1 | 5/12 |
| F | pSG2.ME1 | pSG2.ME1 | 8/12 |

Groups of 12 BALB/c mice are primed and boosted 14 days apart as shown. Fourteen days after boosting the animals are challenged by sc. injection with CT26 cells in the left flank. The animals are observed for two weeks, then dissected and tumour presence and size determined as described in Methods.

The table presents tumour incidence based on the immunogenicity data presented in 16. Differences between the average tumour size in each group would also be expected, but are not shown in the table.

EXAMPLE 19

Recombinant FP9 Protects against Lymphocytic Choriomeningitis Virus (LCMV)

Objective: To determine whether immunisation with FP9.ME1 alone, or in a prime/boost regime with PSG2.ME1, will elicit a protective immune response against LCMV challenge in mice.

This demonstrates that recombinant FP9 can elicit antigen-specific CD4+ and CD8+ T cell responses that will protect against viral infection when used in accordance with the present invention.

Method Female C57BL/6 (H-2$^b$) mice (6-8 weeks-old) were injected with PSG2.ME1, FP9.ME 1, or control constructs pSG2.Mel3 and FP9.EFL29 as described above. Animals were boosted two weeks after immunisation. Fourteen days after boosting, 6 animals per group were challenged by intraperitoneal (ip.) injection with 2×10$^5$ PFU LCMV Armstrong (mild infection) and 6 animals iv. with 2×10$^6$ PFU LCMV Clone 13 (severe infection).

Animals challenged with LCMV Armstrong were sacrificed 3 days after challenge and those challenged with LCMV Clone 13 were sacrificed 7 days after challenge.

Viral load in the spleens of challenged animals is determined as follows:

Plaque assay for the titration of LCMV
1. Aliquot 3×105 Vero cells in 3 ml of medium into each well of a six-well plate and culture overnight at 37° C. under 5% CO2 until they form a confluent monolayer.
2. Make serial dilutions of the test samples on ice, starting at 1:100 (10 µl sample+1 ml medium) and making subsequent 10-fold dilutions (100 µl+900 µl medium).
3. Remove the medium from the Vero cells (taking care not to damage the monolayer) and add 500 µl per well of the diluted test sample. Include at least one well per assay to which medium only is added as a negative control. Incubate the plates at 37° C. under 5% CO2 for one hour to allow virus infection.
4. Overlay each well with 3-4 ml of a 1:1 mixture of 1% agarose in water and 2×199 medium containing 10% FBS. Wrap the plates in foil and culture at 37° C. under 5% CO2 incubator for six days.
5. Fix and stain.

Statistical analysis was performed using Excel 2000, with differences in incidence of infection determined by the Chi-squared test and differences in viral load determined using the students T-test (two-sample assuming equal variances). Two-sided P-values are determined in all cases.

Results

LCMV is a well characterised virus that causes chronic and acute infections in mice. The Armstrong strain causes a mild, self-resolving infection, whereas the Clone 13 strain causes a severe infection that can develop into a chronic infection. The ME1 epitope string was designed to contain two CD4+ epitopes and several CD8+ restricted epitopes from LCMV (see above), some of which have been characterised as protective against LCMV infection. Since prime/boost immunisation using FP9.ME1 elicits a significantly enhanced T cell response against the LCMV epitopes in ME1 (FIGS. 17A-17B), this immunisation regime exhibits protective efficacy against challenge with both the Armstrong and Clone 13 strains of LCMV. Table 8 shows the results.

TABLE 8

LCMV challenge in C57BL/6 mice

| | | | Viral Load | |
| --- | --- | --- | --- | --- |
| Group | Prime | Boost | Armstrong Log$_{10}$ PFU/ organ | Clone 13 Log$_{10}$ PFU/ organ |
| A | None | None | 6.26 ± 0.33 | 7.53 ± 0.04 |
| B | LCMV (Arm) | None | 3.11 ± 0.05 | 3.00 ± 0.05 |
| C | pSG2.Me13 | FP9.EFL29 | 5.24 ± 0.15 | 7.32 ± 0.11 |
| D | pSG2.ME1 | FP9.ME1 | 3.00 ± 0.05 | 3.00 ± 0.05 |
| E | FP9.ME1 | FP9.ME1 | 5.00 ± 0.10 | 6.00 ± 0.10 |
| F | pSG2.ME1 | pSG2.ME1 | 4.00 ± 0.10 | 5.00 ± 0.10 |

Groups of 12 C57BL/6 mice are primed and boosted 14 days apart as shown.

Fourteen days after boosting, 6 animals per group will be challenged with LCMV Armstrong (mild infection) or LCMV Clone 13 (severe infection) as described in Methods. The limit of detection of the assay is 1000 pfu/organ (Log$_{10}$ 3.00). Viral loads for groups A, B and C are based on results using 6 animals per group. Viral loads for D, E and F are on the immunogenicity results presented in FIGS. 17A-17B).

FIG. 15 shows antigen-specific immune responses following heterologous prime/boost immunisation with FP9PbCSP, FPV-MPbCSP and MVAPbCSP. BALB/c mice were immunised id. bi-laterally in the ears with FP9PbCSP (FP9), FPV-MPbCSP (FPV-M), or MVAPbCSP and boosted heterologously 14 days later in a similar manner. Fourteen days after the booster immunisation the T cell response elicited against the Pb9 epitope of PbCSP and a control epitope from β-galactosidase were determined in splenocytes using the IFNγ ELISPOT assay. Columns represent the mean antigen specific IFNγ sfc/million splenocytes±1 SD for four mice per group. P values were determined by the student's T test assuming equal variances using Microsoft Excel 2000.

EXAMPLE 20

Websters' Attenuated Fowlpox is Disctinet from FP9

In this Example the unique character of FP9 compared to existing fowlpox vectors is demonstrated. The genetic composition of FP9 is determined as above and compared to existing pox vector 'Websters'. Data are presented in Table 9.

Deletions

Twenty-five deletions were observed in FP9 relative to the virulent US FPV sequence (FPV US; Afonso et al., 2000). Of these, 6 were differences between the US and European lineage and 19 occurred during passage (and concomitant attenuation) that eventually led to FP9.

Of those 19 passage-specific deletion loci, 15 have been examined in Websters (FPVM) and all show the same sequence as FPV US, not that of FP9.

Insertions

Similarly, 15 insertions distinguish FP9 from FPV US. Of these, only 5 occurred during passage and attenuation.

One of these 5 passage-specific insertion loci has been checked in Websters and it shows the same sequence as FPV US, not FP9.

Base Substitutions 77 single base substitutions distinguish FP9 from FPV US. Of these, 25 occurred during passage and attenuation.

11 of these 25 passage-specific substitution sites have been checked in Websters and, in all cases, they have the same sequence as FPV US, not FP9. Another FP9 mutation, which is also found in HP1 and is thus a lineage-specific mutant, is also the same as FPV US in Websters.

Thus is shown that Websters attenuated vaccine is clearly genetically distinct from FP9.

TABLE 9

Example 20

| Gel Read | PCR For | PCR Rev | Seq Prim | FP9v Mut1 | Mut Type | Comment on FP9 v. FPV US mutation | Webster Seq Result | Webster PCR Res | FPV genes affected by mutation in FP9 |
|---|---|---|---|---|---|---|---|---|---|
| SMLP CR26_ 11_02 | 947 | 217 | 217 | 3982 | Deletion | De12. 1534 bp g-FPV001-a in FPV US -> ga | | as US del 1.5 kb | 001 |
| x125_ B7 x125_ B8 | 366 | 371 | 366 | 59153 | Deletion | De16.1 bp tAC in FPV US -> tG Minor AC peaks in forward. Destroys FPV054 orthol. D9R f/s | as US | | 054 |
| | | | | 59378 | Deletion | De17.4 bp tTCTCt in FPV US -> tt, disrupting FPV054 orthol D9R | as US | | 054 |
| x125_ C1 | 928 | 223 | 928 | 74189 | Deletion | De18.1 bp G5 in FPV US -> G4. K/O FP9 FPV070 T10 | as US | | 070 |
| x125_ C11 x125_ C12 | 146 | 945 | 146 945 | 1014 31 | Deletion | De19.5831 bp Equivalent to FPVUS 100799–106676 | as US | | 097, 098 (results in 098/ 097 hybrid fusion protein) |
| x125_ D1 x125_ D2 x125_ D3 x125_ D4 | | 147 | 147 | | | | | | |
| x125_ D7 x125_ D8 | 245 | 550 | 550 | 1326 56 | Deletion | De110.17 bp deleted in FP9 aTGTTATTATTCCTGATAg (SEQ ID NO: 36), splits FPV115 into 2 FP9 orfs | as US | | 115 |
| x125_ E1 x125_ E2 | 585 | 935 | 935 | 1504 65 | Deletion | De111.3426 bp del rel FPV US(a-3426 bp/del FPV124/delFPV125 319/345aa-t) | as US | | 124, 125 |
| x125_ E1O | 602 | 696 | 604 | 1633 76 | Deletion | De112.23 by aTTAGATAGTATCTGTTTAAA AGAt (SEQ ID NO: 37) in FPV US -> at (intergenic) | as US | | Intergenic |
| SMLP CR26_ 11_02 | 626 | 250 | 626 | 1802 56 | Deletion | De113.2187 bp del rel FPV US (c-2187 bp FPV158 1–182/464 f/s k/o FPV 160-a) | | as US del 2.2 kb | 158, 159, 160 |
| x125_F4 xi63_C1 | 31 | 247 | 657 31 | 1939 28 | Del./Sub | Del 14.3 bp de I tAACg (SEQ ID NO: 38) in FPV US -> tg (1 aa sub, 1 aa del) | as US | | 171 |
| x125 F8 x125 F9 | 737 | 843 | 737 87 | 2123 54 | Deletion | Del 16.2 bp tATc (SEQ ID NO: 39) in FPV US -> tc (f/s) | as US | | 190 |
| xi63_C3 | 737 | 843 | 847 | 2126 58 | Deletion | Dell 7.1 bp. T2 in FPV US -> T (f/s) | as US | | 190 |
| x125_ H1 x125_ H2 | 758 | 823 | 760 | 2301 93 | Deletion | De120.1 bp CC in FPV US -> C (f/s) | as US | | 213 |
| SMLP CR26_ 11_02 | 766 | 816 | 766 | 2363 29 | Deletion | De122.2942 bp del rel FPV US (c FPV2191ANK 1–314/434 to FPV222/ANK 658–747/747-c) | | as US del 2.9 kb | 219, 220, 221, 222 |
| x125_ H9 x125_ H10 | 924 | 939 | 924 | 2537 74 | Deletion | De124.9334 bp del rel FPV US t-FPV241 to FPV247-t | as US | | 241, 242, 243, 244, 245, 246, 247 |
| x125_ D5 X125_ D6 | 490 | 884 | 490 | 1162 01 | Insertion | Insert6.2 bp (AT)x4 in FPV US-> x5 (f/s) | as US | | 104 |
| x125_A3 x125_A4 | 789 | 934 | 790 | 6577 | aa Sub | A in FPV US -> G (sub) | as US | | 006 |
| x125_B1 | 400 | 272 | 272 | 70103 | aa Sub | A in FPV US -> G (sub) | as US | | 063 |
| Xi63_B1 | 264 | 230 | 264 | 71724 | Nonsense | C in FPV US -> A (nonsense) | as US | | 066 |

TABLE 9-continued

Example 20

| Gel Read | PCR For | PCR Rev | Seq Prim | FP9v Mut1 | Mut Type | Comment on FP9 v. FPV US mutation | Webster Seq Result | Webster PCR Res | FPV genes affected by mutation in FP9 |
|---|---|---|---|---|---|---|---|---|---|
| x125_C4 | 928 | 223 | 409 | 75219 | | A in FPV US -> G (intergenic) | as US | | |
| | | | | 75365 | Nonsense | C in FPV US. (nonsense) | as US | | 071 |
| x125_C6 | 928 | 223 | 223 | 75909 | Nonsense | A in FPV US. (nonsense) | as US | | 071 |
| x125_E3 | 589 | 886 | 886 | 15245 | aa Sub | G in FPV US -> T (sub) | as US | | 127 |
| x125_E4 | | | | | | | | | |
| x125_E5 | 597 | 37 | 597 | 15834 | aa Sub | G in FPV US - A (sub) | as US | | 137 |
| x125_E6 | | | | | | HP1 as FP9 | | | |
| x125_E7 | 597 | 37 | 207 | 15912 | aa Sub | C in FPV US -> T (sub) | as US | | 137 |
| x125_E8 | | | | | | | | | |
| x125_F5 | 116 | 859 | 859 | 20339 | Silent | T in FPV US -> C (silent) | as US | | |
| x125_G1 | 737 | 843 | 844 | 21403 | aa Sub | C in FPV US -> A (sub) | as US | | 191 |
| x125_G2 | | | | | | | | | |
| x125_G3 | 740 | 842 | 740 | 21468 | aa Sub | C in FPV US -> A (sub) | as US | | 191 |
| x125_G4 | | | | | | | | | |
| x125_G5 | | | 843 | | | | | | |
| x125_G6 | | | | | | | | | |

Example 21

Recombinant FP9 Elicits CD4 and CD8 T Cell Responses against Epitopes from Viruses and Tumours Objective Further to Example 17, this Example further determines whether immunisation with recombinant FP9 alone, or in a prime/boost regime, will elicit T cell responses against CD4+ and CD8+ T cell epitopes from viral and tumour antigens.

Method

A synthetic gene of 440 by encoding for a novel polypeptide (ME1) consisting of characterised CD8+ and CD4+ restricted epitopes from lymphocytic choriomeningitis virus (LCMV) antigens and murine tumour (P815 and CT26) antigens was synthesized (see above). ME1 was ligated into a DNA vaccine vector (pSG2) and the fowlpox shuttle vector pEFL29. Plasmid pEFL29.ME1 was subsequently recombined into the chromosome of FP9 following established methods to construct FP9.ME1. This virus was subsequently bulk-purified by propagation in chicken embryo fibroblasts (CEF) and centrifugation through a 30% sucrose cushion. The titre of the virus was confirmed by titration on CEF and X-gal staining, following established methods. Viruses were prepared for immunisation by, suspension in pyrogen-free PBS at $1\times10^7$ PFU/ml. Plasmid pSG2.ME1 was bulk-purified using a Qiagen Giga column and resuspended at 1 mg/ml in pyrogen free PBS.

Female BALB/c (H-$2^d$) or C57BL/6 (H-$2^b$) mice (6-8 weeks old) were immunised intramuscularly (im.) with 50 μg of pSG2.ME1 or control plasmid pSG2.Me13, which contains an irrelevant epitope string. Viruses FP9.ME1 and the empty control virus FP9.EFL29 were administered intravenously (iv.) into the tail vein at a dose of $1\times10^6$ PFU. Animals were boosted 14-15 days after immunisation. Fourteen to 15 days after boosting, the mice were sacrificed by cervical dislocation and the T cell response elicited against the LCMV, P815, CT26 and control epitopes from β-galactosidase were determined using the INFγ assay as described in above. Results were calculated as the number of antigen-specific IFNγ spot forming cells/million splenocytes (sfc/million). Differences between groups were determined by the student's T-test (two-sample assuming unequal variances) using Microsoft Excel 2000. One-sided P-values are given in all cases.

Results

To avoid competition between the viral and tumour epitopes, ME1 encodes epitopes from LCMV antigens characterised in H-$2^b$ haplotype mice and those from tumour antigens characterised in H-$2^d$ haplotype mice (Appendix II). Accordingly, the capacity of FP9.ME1 to elicit immune responses was tested in both BALB/c (H-$2^d$) and C57BL/6 (H-$2^b$) mice.

Figure 16A:
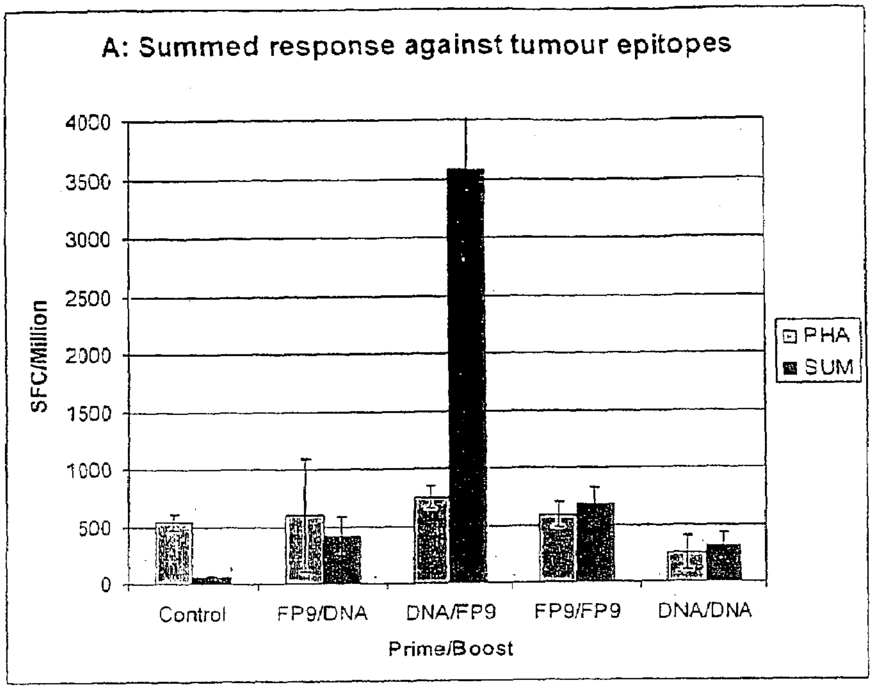
FIGS. 16A-16B show specific immune responses in BALB/c mice following prime/boost immunisation with pSG2.ME1 and FP9.ME1. BALB/c mice were immunised im. with pSG2.ME1 (DNA) or iv. with FP9.ME1 (FP9) and boosted 15 days later in a similar manner. Control animals were immunised with identical vectors encoding irrelevant antigens. Thirteen days after the booster immunisation the T cell responses elicited against the tumour epitopes were determined in splenocytes using the IFNγELISPOT assay. Columns represent the antigen-specific IFNγsfc/million splenocytes±1 SD for four mice per group.
Figure 16B:
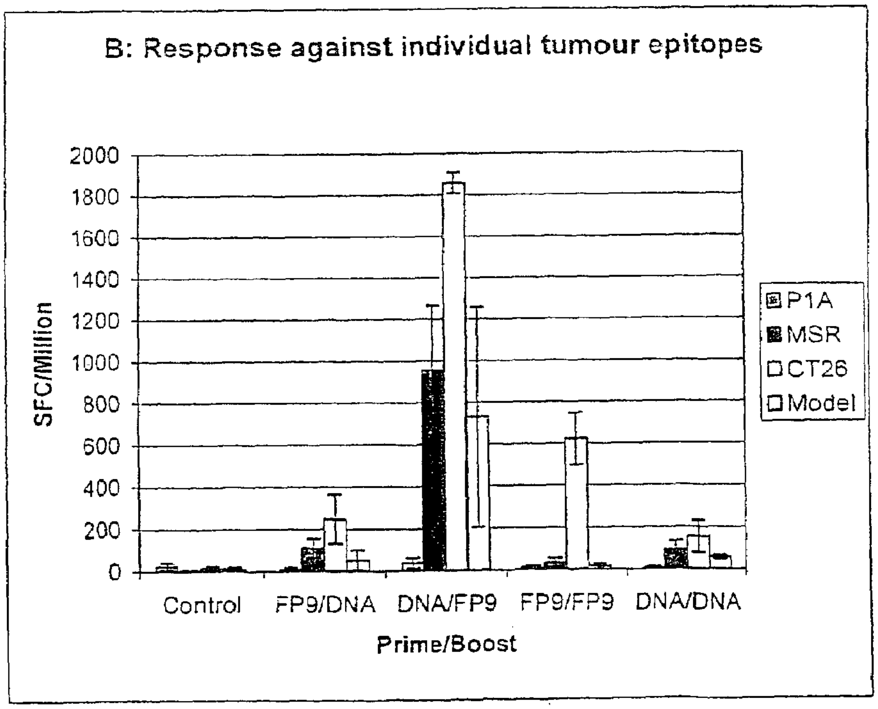

Immunisation of BALB/c mice using pSG2.ME1 and/or FP9.ME1 elicited IFNγ-secreting T cells against the tumour epitopes (H-$2^d$) (FIGS. 16A-16B), but not against the LCMV epitopes (H-$2^b$). The total frequency of IFNγ-secreting T cells elicited against the tumour epitopes was significantly (P<0.004) higher following heterologous prime/boost immunisation with pSG2.MEl/FP9.ME1 than other heterologous or homologous immunisation regimes (FIGS. 16A-16B). Immunisation with other regimes elicited T cell responses that were significantly higher than immunisation with control constructs, but not significantly different (P>0.05) from each other. Importantly, prime/boost immunisation with pSG2.ME1/FP9.ME1 elicited substantial T cell responses against the immunodominant epitope from CT26, the MSR epitope from P815 and a model $L^d$-restricted epitope from beta-galactosidase. Among these epitopes, response against the CT26 epitope was most substantial and exceeded the limit of detection (2000 sfc/million) of the IFN-γ ELISPOT assay used in this experiment. These results indicate that prime/boost immunisation using pSG2.ME1/FP9.ME1 is likely to elicit a protective immune response against CT26 colorectal carcinoma in BALB/c mice (See above).

Figure 17A:
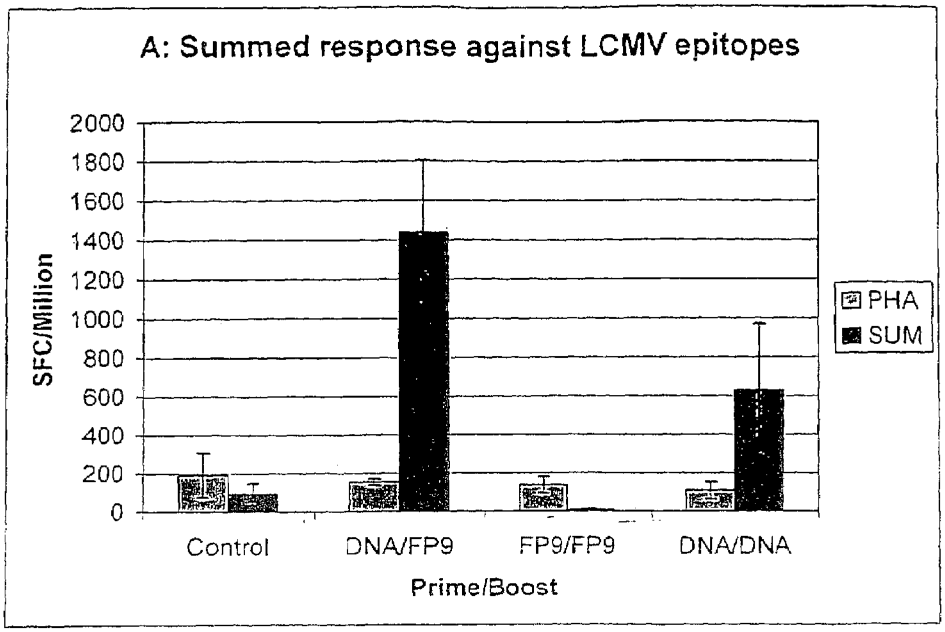
FIGS. 17A-17B show specific immune responses in C57BL/6 mice following prime/boost immunisation with pSG2.ME1 and FP9.ME1. C57BL/6 mice were immunised im. with pSG2.ME1 (DNA) or iv. with FP9.ME1 (FP9) and boosted 14 days later in a similar manner. Control animals were immunised with identical vectors encoding irrelevant antigens. Fourteen days after the booster immunisation the T cell response elicited against the tumour epitopes were determined in splenocytes using the IFNγELISPOT assay. Columns represent the antigen-specific IFNγsfc/million splenocytes±1 SD for four mice per group.
Figure 17B:
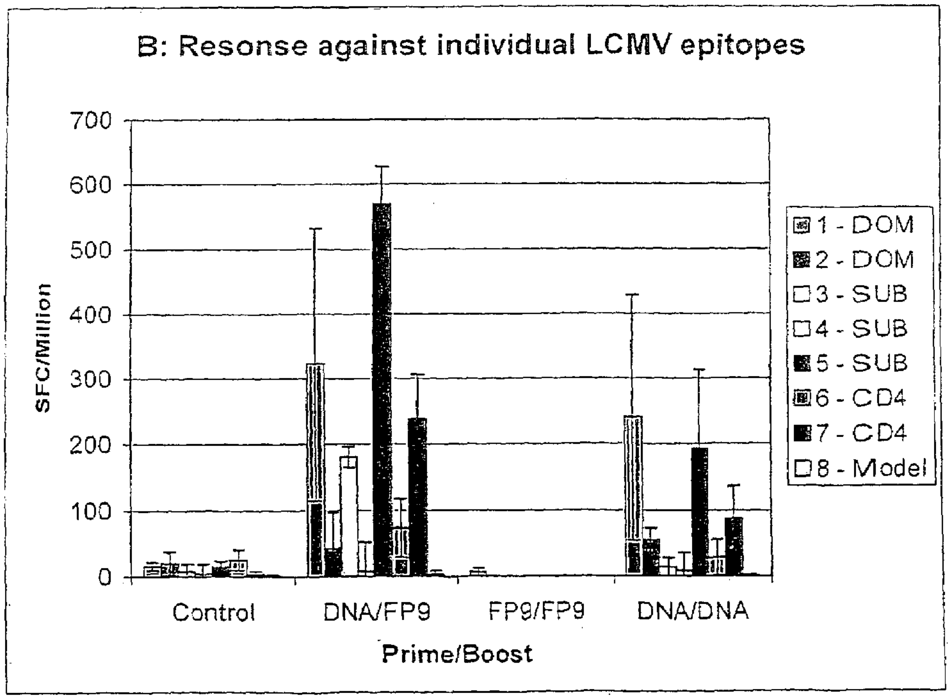

Immunisation of C57BL/6 mice using pSG2.ME1 and/or FP9.ME1 elicited IFNγ-secreting T cells against the LCMV epitopes (H-$2^b$), but not against the tumour epitopes (H-$2^b$) (FIGS. 17A-17B). The total frequency of IFNγ-secreting T cells elicited against LCMV epitopes by prime/boost immunisation with pSG2.ME1/FP9.ME1 was significantly higher than that elicited by homologous immunisation with FP9.ME1 (P w 0.003) alone or pSG2.ME 1 (P=0.016) alone.

Interestingly, heterologous prime/boost immunization regimes using pSG2.ME1 and FP9.ME1 elicited greatly enhanced immune responses against CD8+ epitopes characterised as dominant and subdominant, and those recognised by CD4+ T cells when compared to the homologous immunisation regimes using pSG2.ME1 and FP9.ME1 alone. Thus, this prime/boost immunisation regimes is likely to be even more efficacious against LCMV infection in C57BL/6 mice than the homologous prime/boost immunisation regimes (See above).

All publications mentioned in the above specification are herein incorporated by reference. Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in chemistry, biology or related fields are intended to be within the scope of the following claims.

While this invention has been particularly shown and described with references to preferred embodiments thereof, it will be understood by those skilled in the art that various changes in form and details may be made therein without departing from the scope of the invention encompassed by the appended claims.

What is claimed is:

1. A method for eliciting an immune response to a target disease-associated antigen in a subject which comprises the step of administering (i) a first composition which comprises a first non replicating viral vector; and (ii) a second composition which comprises a second non replicating viral vector to the subject in either order; wherein the first non-replicating viral vector comprises a fowlpox viral genome in which a nucleotide sequence encoding one or more epitopes of said target disease-associated antigen is inserted into the nucleotide sequence of SEQ ID NO: 1 at a site that is nonessential for replication of said fowlpox viral genome, and the second non replicating viral vector comprises a nucleotide sequence encoding one or more epitopes of said target disease-associated antigen; thereby eliciting an immune response to said target disease-associated antigen.

2. The method according to claim 1 wherein said second non replicating viral vector is a poxvirus vector.

3. The method according to claim 2 wherein said first non replicating viral vector and said second non replicating viral vector are from different poxvirus genera.

4. The method according to claim 3 wherein said second non-replicating viral vector is an orthopox virus.

5. The method according to claim 1 wherein the one or more epitopes of said target antigen are T cell epitopes.

6. The method according to claim 5 wherein the one or more T cell epitopes are under the control of a poxvirus promoter.

7. The method according to claim 5 wherein the one or more T cell epitopes are epitopes of an antigen from *Plasmodium berghei, Plasmodium falciparum, Plasmodium cynomolgi, Plasmodium vivax, Mycobacterium tuberculosis* or *Theileria parva.*

8. The method according to claim 4 wherein the first composition is administered as a boosting composition.

9. The method according to claim 4 wherein the first composition is administered as a priming composition.

10. The method according to claim 1 wherein the subject is a primate.

11. The method according to claim 10 wherein the primate is a human.

12. The method of claim 1, wherein the target disease-associated antigen is selected from the group consisting of a tuberculosis antigen, a malaria antigen, a viral antigen and a cancer antigen.

13. The method of claim 1, wherein the target disease-associated antigen is Ag85A or ESAT6 from *Mycobacterium tuberculosis.*

14. The method of claim 1, wherein the target disease-associated antigen is TRAP from *Plasmodium falciparum.*

15. The method of claim 1, wherein the target disease-associated antigen is CSP or Pb9 from *Plasmodium berghei.*

16. The method of claim 1, wherein the target disease-associated antigen is selected from the group consisting of a tumor antigen and a viral antigen.

17. The method of claim 16, wherein the viral antigen is an LCMV antigen.

18. A method for eliciting a protective immune response to a target disease-associated antigen in a subject, wherein the target disease-associated antigen is the TRAP antigen from *Plasmodium falciparum*, comprising the step of administering (i) a first composition which comprises a first non-replicating viral vector; and (ii) a second composition which comprises a second non-replicating viral vector to the subject in either order; within the first non-replicating viral vector comprises a fowlpox viral genome in which a nucleotide sequence encoding one or more epitopes of said target disease-associated antigen is inserted into the nucleotide sequence of SEQ ID NO: 1 at a site that is nonessential for replication of said fowlpox viral genome; and the second non replicating viral vector comprises a nucleotide sequence encoding one or more epitopes of said target disease-associated antigen; thereby eliciting a protective immune response to said target disease-associated antigen.

19. A method for eliciting a protective immune response to a target disease-associated antigen in a subject, wherein the target disease-associated antigen is the CSP or Pb9 antigen from *Plasmodium berghei*, comprising the step of administering (i) a first composition which comprises a first non-replicating viral vector; and (ii) a second composition which comprises a second non-replicating viral vector to the subject in either order; wherein the first non-replicating viral vector comprises a fowlpox viral genome in which a nucleotide sequence encoding one or more epitopes of said target disease-associated antigen is inserted into the nucleotide sequence of SEQ ID NO: 1 at a site that is nonessential for replication of said fowlpox viral genome, and the second non replicating viral vector comprises a nucleotide sequence encoding one or more epitopes of said target disease-associated antigen;thereby eliciting a protective immune response to said target disease-associated antigen.

20. The method according to claim 1, wherein the nucleotide sequence encoding one or more epitopes of the target disease-associated antigen is inserted into the fowlpox viral vector by homologous recombination.

* * * * *